(12) United States Patent
Corrao et al.

(10) Patent No.: US 11,779,318 B2
(45) Date of Patent: *Oct. 10, 2023

(54) INSERTION INSTRUMENT FOR ANCHOR ASSEMBLY

(71) Applicant: DePuy Synthes Products, Inc., Raynham, MA (US)

(72) Inventors: Ernie Corrao, Bethel, CT (US); Ron George Litke, Jr., Sandy Hook, CT (US); Wamis Singhatat, Malvern, PA (US); Scott Larsen, Spring City, PA (US); Stephen Joseph Snyder, Encino, CA (US); Nicolas Bouduban, Biel/Bienne (CH); Robert L. Richards, Minneapolis, MN (US)

(73) Assignee: DePuy Synthes Products, Inc., Raynham, MA (US)

( * ) Notice: Subject to any disclaimer, the term of this patent is extended or adjusted under 35 U.S.C. 154(b) by 667 days.

This patent is subject to a terminal disclaimer.

(21) Appl. No.: 16/787,309

(22) Filed: Feb. 11, 2020

(65) Prior Publication Data
US 2020/0178947 A1     Jun. 11, 2020

Related U.S. Application Data

(60) Division of application No. 15/627,698, filed on Jun. 20, 2017, now Pat. No. 10,595,839, which is a
(Continued)

(51) Int. Cl.
*A61B 17/10* (2006.01)
*A61B 17/00* (2006.01)
(Continued)

(52) U.S. Cl.
CPC ...... *A61B 17/0057* (2013.01); *A61B 17/0401* (2013.01); *A61B 17/0469* (2013.01);
(Continued)

(58) Field of Classification Search
CPC ............ A61B 17/0057; A61B 17/0401; A61B 17/0469; A61B 17/0482; A61B 17/0483;
(Continued)

(56) References Cited

U.S. PATENT DOCUMENTS 233,475 A    10/1880   Cook et al.
261,501 A    7/1882   Wandermark
(Continued)

FOREIGN PATENT DOCUMENTS

CN        1891172 A      1/2007
CN     101056587 A    10/2007
(Continued)

OTHER PUBLICATIONS

Smith & Nephew Endoscopy, "Fast-Fix Meniscal Repair System: Technique Information," http://endo.smith-nephew.com/no/node.asp?NodeId=3045, Accessed Apr. 26, 2011, 3 pages.
(Continued)

*Primary Examiner* — Diane D Yabut
*Assistant Examiner* — Christina C Lauer
(74) *Attorney, Agent, or Firm* — BakerHostetler

(57) ABSTRACT

An insertion instrument is configured to eject at least one anchor body into respective target locations, and subsequently apply a predetermined tensile force at least one actuation member of the at least one anchor member so as to actuate the at least one anchor body from a first configuration to a second expanded configuration. The insertion instrument can include a tension assembly that applies the predetermined tensile force to the at least one actuation member. The predetermined tensile force can be defined by a distance of travel, a predetermined failure force of a fuse, or a combination of distance of travel and a predetermined failure force of a fuse.

20 Claims, 155 Drawing Sheets

Related U.S. Application Data division of application No. 13/283,063, filed on Oct. 27, 2011, now Pat. No. 9,724,080, which is a continuation-in-part of application No. 13/172,619, filed on Jun. 29, 2011, now Pat. No. 9,451,938, which is a continuation-in-part of application No. 13/095,192, filed on Apr. 27, 2011, now Pat. No. 9,173,645.

(60) Provisional application No. 61/443,142, filed on Feb. 15, 2011, provisional application No. 61/443,142, filed on Feb. 15, 2011, provisional application No. 61/461,490, filed on Jan. 18, 2011, provisional application No. 61/461,490, filed on Jan. 18, 2011, provisional application No. 61/432,755, filed on Jan. 14, 2011, provisional application No. 61/432,755, filed on Jan. 14, 2011, provisional application No. 61/398,699, filed on Jun. 29, 2010, provisional application No. 61/398,699, filed on Jun. 29, 2010, provisional application No. 61/328,251, filed on Apr. 27, 2010.

(51) Int. Cl.
*A61B 17/04* (2006.01)
*A61B 17/84* (2006.01)
*A61B 17/06* (2006.01)
*A61B 17/29* (2006.01)

(52) U.S. Cl.
CPC ...... *A61B 17/0482* (2013.01); *A61B 17/0483* (2013.01); *A61B 17/0467* (2013.01); *A61B 17/0487* (2013.01); *A61B 17/842* (2013.01); *A61B 2017/00477* (2013.01); *A61B 2017/00623* (2013.01); *A61B 2017/00663* (2013.01); *A61B 2017/0406* (2013.01); *A61B 2017/0409* (2013.01); *A61B 2017/0414* (2013.01); *A61B 2017/0417* (2013.01); *A61B 2017/0419* (2013.01); *A61B 2017/0464* (2013.01); *A61B 2017/0475* (2013.01); *A61B 2017/0477* (2013.01); *A61B 2017/0496* (2013.01); *A61B 2017/06042* (2013.01); *A61B 2017/06052* (2013.01); *A61B 2017/06176* (2013.01); *A61B 2017/292* (2013.01); *A61B 2017/2917* (2013.01)

(58) Field of Classification Search
CPC .... A61B 2017/0419; A61B 2017/0417; A61B 2017/0409
See application file for complete search history.

(56) References Cited

U.S. PATENT DOCUMENTS

| | | | |
|---|---|---|---|
| 330,087 | A | 11/1885 | Binns |
| 400,743 | A | 4/1889 | Brown |
| 2,490,364 | A | 12/1949 | Livingston |
| 3,580,256 | A | 5/1971 | Wilkinson et al. |
| 3,867,728 | A | 2/1975 | Stubstad et al. |
| 3,908,677 | A | 9/1975 | Beach |
| 3,987,806 | A | 10/1976 | Gilbert |
| 4,006,747 | A | 2/1977 | Kronenthal et al. |
| 4,235,238 | A | 11/1980 | Ogiu et al. |
| 4,669,473 | A | 6/1987 | Richards et al. |
| 4,741,330 | A | 5/1988 | Hayhurst |
| 4,778,990 | A | 10/1988 | Laughlin |
| 4,788,990 | A | 12/1988 | Wisegerber |
| 4,994,028 | A | 2/1991 | Leonard et al. |
| 4,994,069 | A | 2/1991 | Ritchart et al. |
| 5,021,059 | A | 6/1991 | Kensey et al. |
| 5,041,129 | A | 8/1991 | Hayhurst et al. |
| 5,053,046 | A | 10/1991 | Janese |
| 5,062,344 | A | 11/1991 | Gerker |
| 5,120,596 | A | 6/1992 | Yamada |
| 5,129,912 | A | 7/1992 | Noda et al. |
| 5,156,616 | A | 10/1992 | Meadows et al. |
| 5,269,809 | A | 12/1993 | Hayhurst et al. |
| 5,281,238 | A | 1/1994 | Chin et al. |
| 5,403,348 | A | 4/1995 | Bonutti |
| 5,417,691 | A | 5/1995 | Hayhurst |
| 5,464,426 | A | 11/1995 | Bonutti |
| 5,478,353 | A | 12/1995 | Yoon |
| 5,507,754 | A | 4/1996 | Green et al. |
| 5,522,846 | A | 6/1996 | Bonutti |
| 5,527,343 | A | 6/1996 | Bonutti |
| 5,540,703 | A | 7/1996 | Barker et al. |
| 5,549,630 | A | 8/1996 | Bonutti |
| 5,562,684 | A | 10/1996 | Kammerer |
| 5,562,736 | A | 10/1996 | Ray et al. |
| 5,571,189 | A | 11/1996 | Kuslich |
| 5,584,862 | A | 12/1996 | Bonutti |
| 5,601,557 | A | 2/1997 | Hayhurst |
| 5,626,614 | A | 5/1997 | Hart |
| 5,628,756 | A | 5/1997 | Barker et al. |
| 5,643,319 | A | 7/1997 | Green et al. |
| 5,649,945 | A | 7/1997 | Ray et al. |
| 5,699,657 | A | 12/1997 | Paulson |
| 5,702,462 | A | 12/1997 | Oberlander |
| 5,728,109 | A | 3/1998 | Schulze et al. |
| 5,733,306 | A | 3/1998 | Bonutti |
| 5,824,093 | A | 10/1998 | Ray et al. |
| 5,906,626 | A | 5/1999 | Carrillo |
| 5,941,900 | A | 8/1999 | Bonutti |
| 5,944,739 | A | 8/1999 | Zlock et al. |
| 5,948,002 | A | 9/1999 | Bonutti |
| 5,951,590 | A | 9/1999 | Goldfarb |
| 5,957,953 | A | 9/1999 | Dipoto et al. |
| 5,970,697 | A | 10/1999 | Jacobs et al. |
| 5,989,252 | A | 11/1999 | Fumex |
| 6,056,773 | A | 5/2000 | Bonutti |
| 6,068,648 | A * | 5/2000 | Cole ............ A61B 17/82 606/232 |
| 6,077,292 | A | 6/2000 | Bonutti |
| 6,110,183 | A | 8/2000 | Cope |
| 6,113,611 | A | 9/2000 | Allen et al. |
| 6,146,422 | A | 11/2000 | Lawson |
| 6,179,860 | B1 | 1/2001 | Fulton et al. |
| 6,187,048 | B1 | 2/2001 | Milner et al. |
| 6,209,550 | B1 | 4/2001 | Powell, Jr. |
| 6,224,630 | B1 | 5/2001 | Bao et al. |
| 6,245,107 | B1 | 6/2001 | Ferree |
| 6,287,325 | B1 | 9/2001 | Bonutti |
| 6,296,659 | B1 | 10/2001 | Foerster |
| 6,306,159 | B1 | 10/2001 | Schwartz et al. |
| 6,325,816 | B1 | 12/2001 | Fulton et al. |
| 6,409,742 | B1 | 6/2002 | Fulton et al. |
| 6,432,123 | B2 | 8/2002 | Schwartz et al. |
| 6,482,235 | B1 | 11/2002 | Lambrecht et al. |
| 6,508,839 | B1 | 1/2003 | Lambrecht et al. |
| 6,511,498 | B1 | 1/2003 | Fumex |
| 6,530,933 | B1 | 3/2003 | Yeung et al. |
| 6,579,291 | B1 | 6/2003 | Keith et al. |
| 6,592,625 | B2 | 7/2003 | Cauthen |
| 6,638,291 | B1 | 10/2003 | Ferrera et al. |
| 6,656,182 | B1 | 12/2003 | Hayhurst |
| 6,689,125 | B1 | 2/2004 | Keith et al. |
| 6,719,797 | B1 | 4/2004 | Ferree |
| 6,758,855 | B2 | 7/2004 | Fulton et al. |
| 6,964,674 | B1 | 11/2005 | Matsuura et al. |
| 6,972,027 | B2 | 12/2005 | Fallin et al. |
| 6,984,247 | B2 | 1/2006 | Cauthen |
| 6,986,775 | B2 | 1/2006 | Morales et al. |
| 6,991,643 | B2 | 1/2006 | Saadat |
| 6,997,956 | B2 | 2/2006 | Cauthen |
| 7,004,970 | B2 | 2/2006 | Cauthen et al. |
| 7,033,393 | B2 | 4/2006 | Gainor et al. |
| 7,033,395 | B2 | 4/2006 | Cauthen |
| 7,041,052 | B2 | 5/2006 | Saadat et al. |
| 7,048,754 | B2 | 5/2006 | Martin et al. |
| 7,052,516 | B2 | 5/2006 | Cauthen et al. |
| 7,128,708 | B2 | 10/2006 | Saadat et al. |

(56) References Cited

U.S. PATENT DOCUMENTS

| | | |
|---|---|---|
| 7,153,312 B1 | 12/2006 | Torrie et al. |
| 7,189,235 B2 | 3/2007 | Cauthen |
| 7,285,124 B2 | 10/2007 | Foerster |
| 7,303,575 B2 | 12/2007 | Ogle |
| 7,326,221 B2 | 2/2008 | Sakamoto et al. |
| 7,329,279 B2 | 2/2008 | Haug et al. |
| 7,335,221 B2 | 2/2008 | Collier et al. |
| 7,347,863 B2 | 3/2008 | Rothe et al. |
| 7,390,332 B2 | 6/2008 | Selvitelli et al. |
| 7,468,074 B2 | 12/2008 | Caborn et al. |
| 7,491,212 B2 | 2/2009 | Sikora et al. |
| 7,494,496 B2 | 2/2009 | Swain et al. |
| 7,601,165 B2 | 10/2009 | Stone |
| 7,615,076 B2 | 11/2009 | Cauthen et al. |
| 7,621,925 B2 | 11/2009 | Saadat et al. |
| 7,651,509 B2 | 1/2010 | Bojarski et al. |
| 7,658,750 B2 | 2/2010 | Li |
| 7,666,193 B2 | 2/2010 | Starksen et al. |
| 7,670,379 B2 | 3/2010 | Cauthen |
| 7,670,380 B2 | 3/2010 | Cauthen, III |
| 7,678,135 B2 | 3/2010 | Maahs et al. |
| 7,731,732 B2 | 6/2010 | Ken |
| 7,736,379 B2 | 6/2010 | Ewers et al. |
| 7,749,250 B2 | 7/2010 | Stone et al. |
| 7,749,273 B2 | 7/2010 | Cauthen et al. |
| 7,753,941 B2 | 7/2010 | Keith et al. |
| 7,776,096 B2 | 8/2010 | Cauthen |
| 7,828,850 B2 | 11/2010 | Cauthen et al. |
| 7,846,208 B2 | 12/2010 | Cauthen et al. |
| 7,857,830 B2 | 12/2010 | Stone et al. |
| 7,905,904 B2 | 3/2011 | Stone et al. |
| 7,905,923 B2 | 3/2011 | Keith et al. |
| 7,909,851 B2 | 3/2011 | Stone et al. |
| 7,909,879 B2 | 3/2011 | Cauthen |
| 7,922,768 B2 | 4/2011 | Cauthen et al. |
| 7,935,147 B2 | 5/2011 | Wales |
| 7,951,201 B2 | 5/2011 | Cauthen et al. |
| 7,959,650 B2 | 6/2011 | Kaiser et al. |
| 7,963,992 B2 | 6/2011 | Cauthen et al. |
| 7,985,257 B2 | 7/2011 | Cauthen et al. |
| 7,993,405 B2 | 8/2011 | Cauthen et al. |
| 7,998,108 B2 | 8/2011 | Nazzaro et al. |
| 8,034,112 B2 | 10/2011 | Cauthen et al. |
| 8,048,160 B2 | 11/2011 | Cauthen |
| 8,083,768 B2 | 12/2011 | Ginn et al. |
| 8,088,130 B2 | 1/2012 | Kaiser et al. |
| 8,088,165 B2 | 1/2012 | Cauthen et al. |
| 8,100,914 B2 | 1/2012 | Cauthen et al. |
| 8,118,836 B2 | 2/2012 | Denham et al. |
| 8,128,640 B2 | 3/2012 | Harris et al. |
| 8,128,658 B2 | 3/2012 | Kaiser et al. |
| 8,128,698 B2 | 3/2012 | Bentley et al. |
| 8,137,382 B2 | 3/2012 | Denham et al. |
| 8,216,253 B2 | 7/2012 | Saadat et al. |
| 8,216,260 B2 | 7/2012 | Lam et al. |
| 8,298,291 B2 | 10/2012 | Ewers et al. |
| 8,696,716 B2 | 4/2014 | Kartalian et al. |
| 8,814,903 B2 | 8/2014 | Sengun et al. |
| 8,828,053 B2 | 9/2014 | Sengun et al. |
| 8,920,436 B2 | 12/2014 | Lam et al. |
| 8,926,634 B2 | 1/2015 | Rothe et al. |
| 9,023,081 B2 | 5/2015 | Maiorino et al. |
| 9,149,266 B2 * | 10/2015 | Lamson ............ A61B 17/0401 |
| 9,173,645 B2 | 11/2015 | Overes et al. |
| 9,724,080 B2 * | 8/2017 | Corrao ............... A61B 17/0469 |
| 2002/0029782 A1 | 3/2002 | Linderoth |
| 2002/0065536 A1 | 5/2002 | Hart et al. |
| 2002/0115999 A1 | 8/2002 | Mcdevitt et al. |
| 2002/0143359 A1 | 10/2002 | Fulton et al. |
| 2002/0188301 A1 | 12/2002 | Dallara et al. |
| 2003/0060835 A1 | 3/2003 | Wenstrom |
| 2003/0167071 A1 | 9/2003 | Martin et al. |
| 2004/0097980 A1 | 5/2004 | Ferree |
| 2004/0122473 A1 | 6/2004 | Ewers et al. |
| 2004/0153074 A1 | 8/2004 | Bojarski et al. |
| 2004/0153704 A1 | 8/2004 | Bragulla et al. |
| 2004/0162618 A1 | 8/2004 | Mujwid et al. |
| 2004/0225183 A1 | 11/2004 | Michlitsch et al. |
| 2004/0225359 A1 | 11/2004 | Bojarski et al. |
| 2004/0243171 A1 | 12/2004 | Fulton et al. |
| 2004/0267257 A1 | 12/2004 | Bourne et al. |
| 2005/0080422 A1 | 4/2005 | Otte et al. |
| 2005/0228406 A1 | 10/2005 | Bose |
| 2005/0228448 A1 | 10/2005 | Li |
| 2005/0251157 A1 | 11/2005 | Saadat et al. |
| 2005/0251159 A1 | 11/2005 | Ewers et al. |
| 2005/0251177 A1 | 11/2005 | Saadat et al. |
| 2005/0251202 A1 | 11/2005 | Ewers et al. |
| 2005/0251205 A1 | 11/2005 | Ewers et al. |
| 2005/0251206 A1 | 11/2005 | Maahs et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0256582 A1 | 11/2005 | Ferree |
| 2005/0277966 A1 | 12/2005 | Ewers et al. |
| 2005/0277981 A1 | 12/2005 | Maahs et al. |
| 2005/0283192 A1 | 12/2005 | Torrie et al. |
| 2005/0283246 A1 | 12/2005 | Cauthen et al. |
| 2006/0064126 A1 | 3/2006 | Fallin et al. |
| 2006/0178680 A1 | 8/2006 | Nelson et al. |
| 2006/0190042 A1 | 8/2006 | Stone et al. |
| 2006/0206119 A1 | 9/2006 | Chu |
| 2006/0224166 A1 | 10/2006 | Weisenburgh et al. |
| 2006/0259076 A1 | 11/2006 | Burkhart et al. |
| 2006/0265008 A1 | 11/2006 | Maruyama et al. |
| 2006/0271073 A1 | 11/2006 | Lam et al. |
| 2006/0271074 A1 | 11/2006 | Ewers et al. |
| 2007/0010857 A1 | 1/2007 | Sugimoto et al. |
| 2007/0027476 A1 | 2/2007 | Harris et al. |
| 2007/0073320 A1 | 3/2007 | Mikkaichi et al. |
| 2007/0083236 A1 | 4/2007 | Sikora et al. |
| 2007/0100348 A1 | 5/2007 | Cauthen et al. |
| 2007/0129804 A1 | 6/2007 | Bentley et al. |
| 2007/0142846 A1 * | 6/2007 | Catanese, III ........ A61F 2/0063 606/142 |
| 2007/0156245 A1 | 7/2007 | Cauthen et al. |
| 2007/0162054 A1 | 7/2007 | Horaguchi |
| 2007/0162120 A1 | 7/2007 | Bouffier |
| 2007/0185532 A1 | 8/2007 | Stone et al. |
| 2007/0255285 A1 | 11/2007 | Trieu |
| 2007/0276433 A1 | 11/2007 | Huss |
| 2008/0009888 A1 | 1/2008 | Ewers et al. |
| 2008/0015635 A1 | 1/2008 | Olsen et al. |
| 2008/0015636 A1 | 1/2008 | Olsen et al. |
| 2008/0033487 A1 | 2/2008 | Schwartz et al. |
| 2008/0039873 A1 | 2/2008 | Bonutti et al. |
| 2008/0086155 A1 | 4/2008 | Rothe et al. |
| 2008/0097484 A1 | 4/2008 | Lim et al. |
| 2008/0097522 A1 | 4/2008 | Chopra |
| 2008/0140092 A1 | 6/2008 | Stone et al. |
| 2008/0140093 A1 | 6/2008 | Stone et al. |
| 2008/0147086 A1 | 6/2008 | Pfister et al. |
| 2008/0147102 A1 | 6/2008 | Rotella et al. |
| 2008/0167658 A1 | 7/2008 | Kerr et al. |
| 2008/0177302 A1 | 7/2008 | Shurnas |
| 2008/0177304 A1 | 7/2008 | Westra et al. |
| 2008/0188893 A1 | 8/2008 | Selvitelli et al. |
| 2008/0195145 A1 | 8/2008 | Bonutti et al. |
| 2008/0200930 A1 | 8/2008 | Saadat et al. |
| 2008/0208225 A1 | 8/2008 | Seibold et al. |
| 2008/0208226 A1 | 8/2008 | Seibold et al. |
| 2008/0228198 A1 | 9/2008 | Traynor et al. |
| 2008/0228265 A1 | 9/2008 | Spence et al. |
| 2008/0228266 A1 | 9/2008 | Mcnamara et al. |
| 2008/0228267 A1 | 9/2008 | Spence et al. |
| 2008/0243151 A1 | 10/2008 | Binmoeller et al. |
| 2008/0269781 A1 | 10/2008 | Funamura et al. |
| 2008/0281355 A1 | 11/2008 | Mayer et al. |
| 2008/0294193 A1 | 11/2008 | Schwartz et al. |
| 2008/0312689 A1 | 12/2008 | Denham et al. |
| 2008/0319524 A1 | 12/2008 | Yachia et al. |
| 2009/0018561 A1 | 1/2009 | Schwartz et al. |
| 2009/0030522 A1 | 1/2009 | Cauthen et al. |

(56) References Cited

U.S. PATENT DOCUMENTS

| | | |
|---|---|---|
| 2009/0036937 A1 | 2/2009 | Cauthen et al. |
| 2009/0036989 A1 | 2/2009 | Cauthen et al. |
| 2009/0036990 A1 | 2/2009 | Cauthen et al. |
| 2009/0062846 A1 | 3/2009 | Ken |
| 2009/0062847 A1 | 3/2009 | Ken |
| 2009/0062848 A1 | 3/2009 | Ken |
| 2009/0062850 A1 | 3/2009 | Ken |
| 2009/0062854 A1 | 3/2009 | Kaiser et al. |
| 2009/0069823 A1 | 3/2009 | Foerster et al. |
| 2009/0076547 A1 | 3/2009 | Sugimoto et al. |
| 2009/0082805 A1 | 3/2009 | Kaiser et al. |
| 2009/0157184 A1 | 6/2009 | Cauthen et al. |
| 2009/0228042 A1 | 9/2009 | Koogle et al. |
| 2009/0259260 A1 | 10/2009 | Bentley et al. |
| 2009/0306711 A1 | 12/2009 | Stone et al. |
| 2010/0049212 A1 | 2/2010 | Caborn et al. |
| 2010/0069923 A1 | 3/2010 | Nguyen et al. |
| 2010/0094337 A1 | 4/2010 | Maiorino |
| 2010/0094425 A1 | 4/2010 | Bentley et al. |
| 2010/0121376 A1 | 5/2010 | Li |
| 2010/0292731 A1 | 11/2010 | Gittings et al. |
| 2011/0022083 A1 | 1/2011 | Dimatteo et al. |
| 2011/0022084 A1 | 1/2011 | Sengun et al. |
| 2011/0077667 A1 | 3/2011 | Singhatat et al. |
| 2011/0082472 A1 | 4/2011 | Harris et al. |
| 2011/0106151 A1 | 5/2011 | Mcdevitt et al. |
| 2011/0172701 A1 | 7/2011 | Wales et al. |
| 2011/0270278 A1 | 11/2011 | Overes et al. |
| 2012/0004669 A1 | 1/2012 | Overes et al. |
| 2012/0013422 A1 | 1/2012 | Tenno et al. |
| 2012/0035654 A1 | 2/2012 | Belson |
| 2012/0046693 A1 | 2/2012 | Denham et al. |
| 2012/0053630 A1 | 3/2012 | Denham et al. |
| 2012/0109156 A1 | 5/2012 | Overes et al. |
| 2012/0130422 A1 | 5/2012 | Hootstein |
| 2012/0143215 A1 | 6/2012 | Corrao et al. |
| 2012/0150223 A1 | 6/2012 | Manos et al. |
| 2012/0197271 A1 | 8/2012 | Astorino et al. |
| 2012/0215257 A1 | 8/2012 | Mcdevitt et al. |
| 2013/0110165 A1 | 5/2013 | Burkhart et al. |
| 2014/0074157 A1 | 3/2014 | Hirotsuka et al. |
| 2014/0243859 A1 | 8/2014 | Robinson |
| 2014/0336703 A1 | 11/2014 | Sengun et al. |
| 2015/0038992 A1 | 2/2015 | Dimatteo et al. |
| 2015/0173740 A1 | 6/2015 | Sugimoto et al. |

FOREIGN PATENT DOCUMENTS

| | | |
|---|---|---|
| DE | 4207854 A1 | 9/1993 |
| EP | 0834281 A1 | 4/1998 |
| EP | 0838197 A2 | 4/1998 |
| EP | 1741400 | 1/2007 |
| EP | 1804683 A2 | 7/2007 |
| EP | 1938760 A1 | 7/2008 |
| EP | 1964520 A2 | 9/2008 |
| EP | 2238944 A2 | 10/2010 |
| EP | 2663240 A1 | 11/2013 |
| EP | 2663242 A1 | 11/2013 |
| JP | 2006-516468 A | 7/2006 |
| JP | 2007-536007 A | 12/2007 |
| JP | 2009-500105 A | 1/2009 |
| JP | 2010-165577 A | 7/2010 |
| JP | 2011-025035 | 2/2011 |
| JP | 2013-525023 | 6/2013 |
| WO | 92/11810 A1 | 7/1992 |
| WO | 99/22648 A1 | 5/1999 |
| WO | 03/96910 | 11/2003 |
| WO | 2004/071307 A2 | 8/2004 |
| WO | 2005/011463 A2 | 2/2005 |
| WO | 2005/065553 A1 | 7/2005 |
| WO | 2006/037639 A1 | 4/2006 |
| WO | 2006/039296 A2 | 4/2006 |
| WO | 2006/117398 A2 | 11/2006 |
| WO | 2007/005394 A1 | 1/2007 |
| WO | 2007/037326 A1 | 4/2007 |
| WO | 2008/010738 A2 | 1/2008 |
| WO | 2008/048667 A1 | 4/2008 |
| WO | 2009/126781 A1 | 10/2009 |
| WO | 2009/146402 A1 | 12/2009 |
| WO | 2010/045179 A1 | 4/2010 |
| WO | 2010/088561 A2 | 8/2010 |
| WO | 2011/137159 A1 | 11/2011 |
| WO | 2012/006161 A2 | 1/2012 |
| WO | 2012/096706 | 7/2012 |
| WO | 2012/096707 A1 | 7/2012 |

OTHER PUBLICATIONS

Snyder, "Shoulder Arthroscopy: Arthroscopic Treatment of the Acromioclavicular Joint", Chapter 13, 2nd Edition, 2003, 167-183.

Southwick et al., "Prosthetic Replacement of Chest-Wall Defects: An Experimental and Clinical Study", A. M.A. Archives of Surgery, 1956, 72, 901-907.

The Free Dictionary, definition of "knot", http://medical-dictionary.thefreedictionary.com/knot as accessed on Jun. 21, 2016.

U.S. Non-Provisional Application filed on Dec. 2, 1999 by Paul Alexander Torrie et al., entitled "Wound Closure Devices and Methods", U.S. Appl. No. 09/453,120.

U.S. Non_provisional Application Filed on Jan. 18, 2000 by Joseph C. Cauthen, entitled "Spinal Disc Annulus Reconstruction Method And Spinal Disc Annulus Stent", U.S. Appl. No. 09/484,706.

U.S. Appl. No. 12/509,112: Non-Final Office Action, dated Jul. 12, 2012, 8 pages.

U.S. Appl. No. 12/509,112: Restriction Requirement, dated Apr. 10, 2012, 6 pages.

U.S. Appl. No. 12/509,112: Restriction Requirement, dated Nov. 17, 2011, 8 pages.

U.S. Appl. No. 13/095,192: Restriction Requirement, dated Sep. 6, 2012, 10 pages.

U.S. Provisional Application Filed on Apr. 27, 2010 by Tom Overes, entitled "Elongated Suturing Element and Method of Using the Same", U.S. Appl. No. 61/328,251.

U.S. Provisional Application filed on Aug. 13, 1999 by Bret A. Ferree, entitled "Spinal Disc and Nucleus Repair/Augmentation Methods and Apparatus", U.S. Appl. No. 60/148,913.

U.S. Provisional Application filed on Aug. 18, 1999 by Gregory H. Lambrecht, entitled "Devices and Methods of Intervertebral Disc Augmentation", U.S. Appl. No. 60/149,490.

U.S. Provisional Application filed on Dec. 23, 1998 by Herbert E. Schwartz, entitled "Meniscal Repair Device", U.S. Appl. No. 60/113,548.

U.S. Provisional Application Filed on Feb. 15, 2011 by Tom Overes, entitled "Anchor Body", U.S. Appl. No. 61/443,142.

U.S. Provisional Application Filed on Jan. 14, 2011 by Kevin Henrichsen et al., entitled "Multi-Fire Knot Anchor Deployment System", U.S. Appl. No. 61/432,755.

U.S. Provisional Application Filed on Jan. 18, 2011 by Kevin Henrichsen et al., entitled "Multi-fire knot anchor deployment system", U.S. Appl. No. 61/461,490.

U.S. Provisional Application filed on Jan. 22, 2001 by Peter T. Keith et al., entitled "Devices and methods for the reatment of spinal disorders",, U.S. Appl. No. 60/263,343.

U.S. Provisional Application Filed on Jun. 29, 2010 by Tom Overes et al., entitled "Knot anchor implant", U.S. Appl. No. 61/398,699.

U.S. Provisional Application filed on Oct. 20, 1999 by Joseph C. Cauthen, entitled "Spinal Disc Annulus Reconstruction Method and Spinal Disc Annulus Stent", U.S. Appl. No. 60/160,710.

U.S. Provisional Application filed on Oct. 25, 1999 by Gregory Herbert Lambrecht, entitled "Methods and Devices for Intervertebral Disc Repair", U.S. Appl. No. 60/161,085.

U.S. Provisional Application filed on Sep. 20, 1999 by David G. Matsuura et al., entitled "Annulotomy Closure Device", U.S. Appl. No. 60/154,969.

Unipoint Industries, Inc., "Polyvinyl Alcohol Foam for Surgical and Industrial Use: Data Sheets," Jul. 15, 1989, 6 pages.

Urbaniak et al., "Replacement of intervertebral discs in chimpanzees by silicone-dacron implants: a preliminary report," J. Biomed. Mater. Res. Symposium, May 1973, 7(4), 165-186.

(56) References Cited

OTHER PUBLICATIONS

Vuono-Hawkins et al., "Mechanical Evaluation of a Canine Intervertebral Disc Spacer: In Situ and In Vivo Studies", Journal of Orthopaedic Research, Jan. 1994, 119-127.
Wageck et al., "Arthroscopic meniscal suture with the "double-loop technique"," Arthroscopy: The Journal of Arthroscopic and Related Surgery, Feb. 1997, 13(1), 120-123.
Yasargil, M. G., "Microsurgical Operation of Herniated Lumbar Disc," Advances in Neurosurgery, Lumbar Disc Adult Hydrocephalus, Springer-Verlag, 1977, 4(81), p. 81.
Abstracts of the 7th Annual Meeting of the Japanese Society of Microsurgery, Oct. 1980, Niigata, Japan, 8 pages.
Ahlgren et al., "Annular incision technique on the strength and multidirectional flexibility of the healing intervertebral disc," Spine, Apr. 15, 1994, 19(8) 948-954.
Ahlgren et al., "Effect of Annular Repair on the Healing Strength of the Intervertebral Disc", Spine, Sep. 2000, vol. 25, No. 17, 2165-2170.
Arthrex, Inc., "Arthroscopic Meniscal Repair using the Meniscal Cinch: Surgical Technique," www.arthrex.com, copyrights 2008, 6 pages.
Barrett et al., "T-Fix endoscopic meniscal repair: technique and approach to different types of tears," Arthroscopy: The Journal of Arthroscopic and Related Surgery, Apr. 1995, 11(2), 245-251.
Biomet Maxfire Technique Guide, Meniscal Repair, 1994, 16 pages.
Brinckmann et al., "A laboratory model of lumbar disc protrusion", Fissure and Fragment Institut fur Experimentelle Biomechanik, Universitat, Munster, German, Spine (Phila., PA 1976) Jan. 15, 1994,19(2): 228-235.
Burg et al., "Modulation of Surface and Bulk Properties of Biomedical Polymers," Annals of the New York Academy of Sciences, Dec. 1997, 831, 217-222.
Caborn, D., "Meniscal Repair with the Fast T-Fix Suture System," Smith & Nephew Technique Plus Illustrated Guide, Mar. 2002, 10 pages.
Cauthen, J., "Annulotomy Study Table", Feb. 8, 1999, 1 page.
Cauthen, J., "Microsurgical Annular Reconstruction (Annuloplasty) Following Lumbar Microdiscectomy: A New Technique," Abstract, AANS CNS Section on Disorders of the Spine and Peripheral Nerves Annual Meeting, 1999, 2 pages.
Cauthen, J., "Microsurgical Annular Reconstruction (Annuloplasty) Following Lumbar Microdiscectomy: A New Technique," Draft Abstract, Sep. 4, 1998, 4 pages.
Cayenne Medical, "Crossfix Meniscal Repair System, Surgical Technical Guide", July 209, 4 pages.
Clifford Ashley "The Ashley Book of Knots" 1944.
Cobey, M., "Arthroplasties using compressed ivalon sponge ("intramedic sponge") long-term follow-up studies in 109 cases," Clinical Orthopaedics and Related Research, Sep.-Oct. 1967, 54, 139-144.
Coen et al., "An anatomic evaluation of T-Fix suture device placement for arthroscopic all-inside meniscal repair," Arthroscopy: The Journal of Arthroscopic and Related Surgery, Apr. 1999, 15(3), 275-280.
Dodge, Jr. et al., "Use of Polyvinyl Sponge in Neurosurgery," Journal of Neurosurgery, May 1954, 11(3), 258-261.
Edgerton et al., "Augmentation Mammaplasty: Psychiatric Implications and Surgical Indications," Plastic & Reconstructive Surgery, Apr. 1958, 21(4), 279-305.
European Patent Application No. 05802651.9: European Search Report, dated Aug. 31, 2009, 7 pages.
European Patent Application No. 10251328.0 ; European Search Report dated Oct. 29, 2010.
Hampton et al., "Healing Potential of the Anulus Fibrosus," Spine, Apr. 1989,14(4), 398-401.
Hoffman et al., "Arthroscopic shoulder stabilization using Mitek anchors", Knee Surg., Sports Traumatol., Arthroscopy, Mar. 1995, vol. 3, Issue 1, 50-54.
International Patent Application No. PCT/US2011/034084: International Search Report and Written Opinion dated Jul. 1, 2011, 5 pages.

International Patent Application No. PCT/US2011/034085: International Search Report and Written Opinion dated Jul. 1, 2011, 5 pages.
International Patent Application No. PCT/US2011/042384: International Search Report and Written Opinion dated Feb. 6, 2012, 26 pages.
International Patent Application No. PCT/US2011/058065: International Search Report and Written Opinion dated Apr. 5, 2012, 23 pages.
International Patent Application No. PCT/US2011/058071: International Search Report and Written Opinion dated Feb. 6, 2012, 14 pages.
International Patent Application No. PCT/US2005/034495: International Search Report, dated Apr. 7, 2007, 2 pages.
Kambin et al., "Development of degenerative spondylosis of the lumbar spine after partial discectomy. Comparison of aminotomy, discectomy, and posterolateral discectomy," Spine, Mar. 1, 1995, 20(5), 599-607.
Klinger, "Proceedings of the 1976 Meeting of the Deutsche Gesellschaft for Neurochirurgica in Berlin", Acta Neurochirurgica, Sep. 1977, vol. 36, Issue 3-4, 265-294.
Kotilainen et al., "Microsurgical treatment of lumbar disc herniation: Follow-up of 237 patients," Acta Neurochirurgica, 1993, 120(3-4) 143-149.
Kroschwitz, J. I., "Concise Encyclopedia of Polymer Science and Engineering: Vinyl Alcohol Polymers," Wiley & Sons, 1990, 1233-1236.
Kusaka et al., "The Effect of Annulus Fibrosus Perforation on the Intradiscal Matrix Strain of the Axially Loaded Intervertebral Disc," Transactions of the 44th Annual Meeting, Orthopaedic Research Society, Mar. 16-19, 1998, New, Orleans, Louisiana, 23(1), p. 190-32 (Abstract).
Lehmann et al., "Refinements in technique for open lumbar discectomy," International Society for the Study of the Lumbar Spine, 1997, 2 pages.
Liu et al., "Morphologic Characterization of Polyvinyl Sponge (Ivalon) Breast Prosthesis," Archives of Pathol. & Lab. Medicine, Sep. 1996, 120(9), 876-878.
Malemud, C. J., "The Role of Growth Factors in Cartilage Metabolism," Rheum. Dis. Clin. North Am., Aug. 1993, 19(3), 569-580.
Maroon et al., "Microdiscectomy versus Chemonucleolysis", Neurosurgery, vol. 16(5), 644-649, May 1985.
Mayer et al., "Endoscopic Discectomy in Pediatric and Juvenile Lumbar Disc Herniation's", Journal of the Pediatric Orthopaedics, Part B, Jan. 1996, 39-43.
Mayer et al., "Percutaneous Endoscopic Lumbar Discectomy (PELD)", Neurosurg., Rev., Jun. 1993, 115-120.
Mitek Brochure, Rapid Loe, "Surgical Technique Guide for Repair of Meniscal Tears", 2001, 6 pages.
Ordway et al., "Failure Properties of a Hydrogel Nucleus in the Intervertebral Disc," North American Spine Society, Oct. 22-25, 1997, 168-169.
Osti et al., "1990 Volvo Award in Experimental Studies: Anulus Tears and Intervertebral Disc Degeneration: An Experimental Study Using an Animal Model," Spine, Aug. 1990,15(8), 762-767.
Osti et al., "Annular Tears and Disc Degeneration in the Lumbar Spine. A post-mortem study of 135 discs," The Journal of Bone and Joint Surgery, Sep. 1992, 74(5), 678-682.
Panjabi et al., "Intrinsic Disc Pressure as a Measure of Integrity of the Lumbar Spine," Spine, Aug. 1988, 13(8), 313-917.
Peters et al., "Ivalon Breast Prostheses: Evaluation 19 Years after Implantation," Plastic and Reconstructive Surgery, Apr. 1981, 67(4), 514-518.
PR Newswire, "Smith & Nephew Launches Fast-Fix (Trademarsk) AB Meniscal Repair System," http://www.prnewswire.com/news-releases/smith-nephew-launches-fast-fixtm-ab-menis . . . , Accessed Aug. 23, 2010, 1 page.
Ray, C. D., "Prosthetic Disc Nucleus Implants: Update," North American Spine Society 13th Annual Meeting, 1999, 252-253.
Sgaglione et al., "All-Inside Meniscal Repair with the Ultra Fast-Fix TM Meniscal Repair System," Smith & Nephew Knee Series Technique Guide, Feb. 2008,12 pages.

(56) References Cited

OTHER PUBLICATIONS

Silver et al., "Cartilage Wound Healing: An Overview," Otolaryngol. Clin. North Am., Oct. 1995, 28(5), 847-863.
Smith & Nephew Endoscopy, "Endoscopic Meniscal Repair Using the T-Fix TM" Smith & Nephew, May 1996, 16 pages.

* cited by examiner

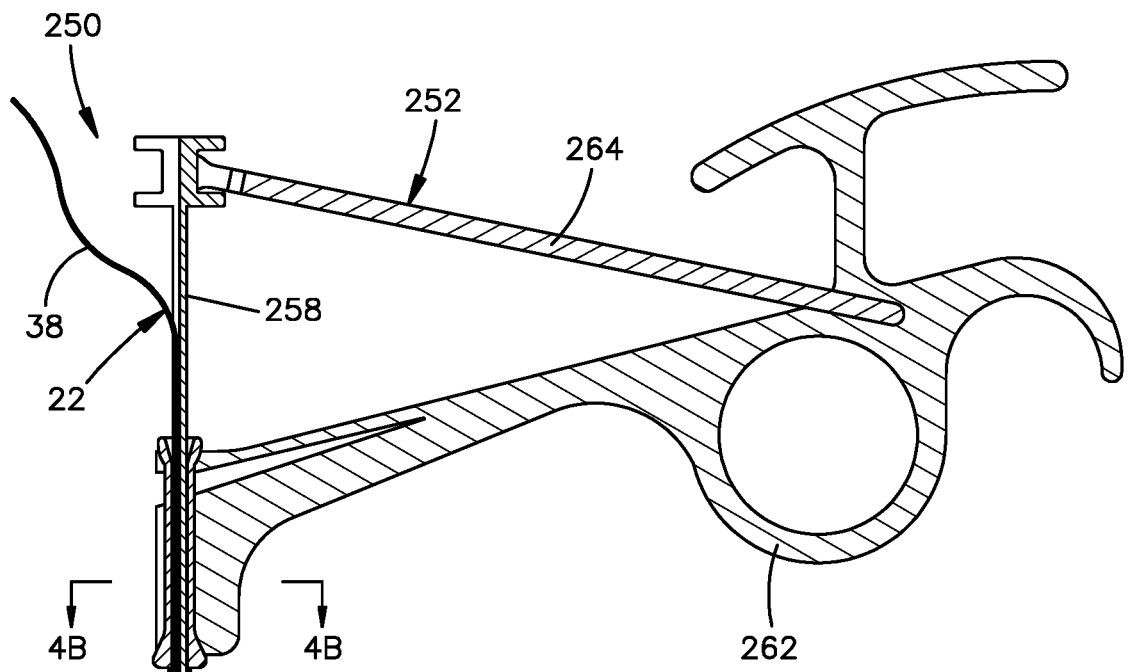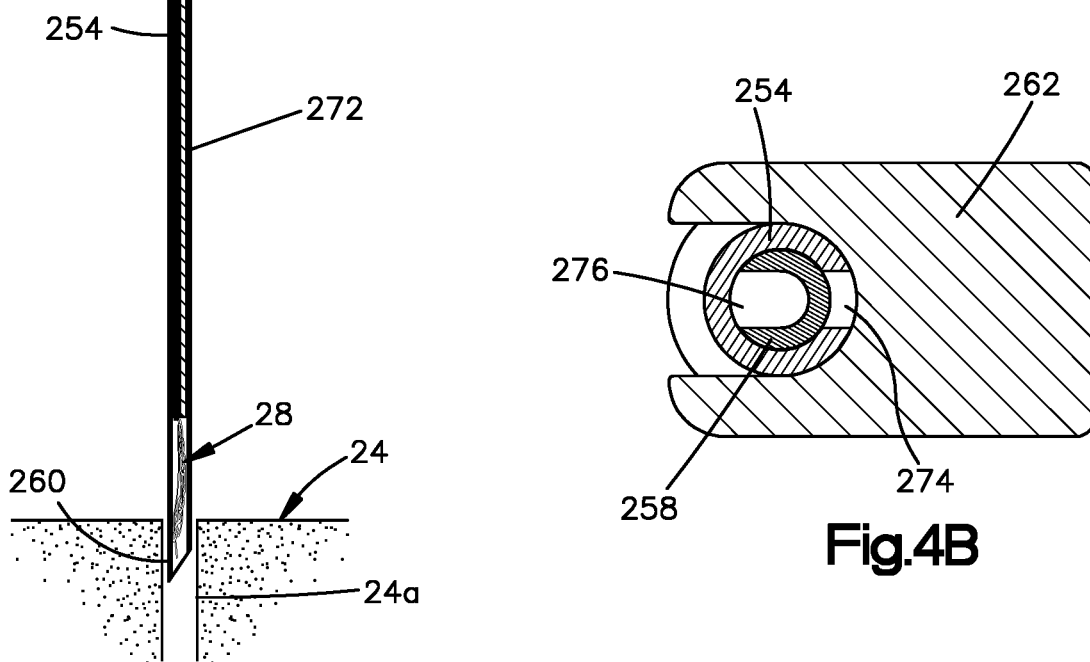

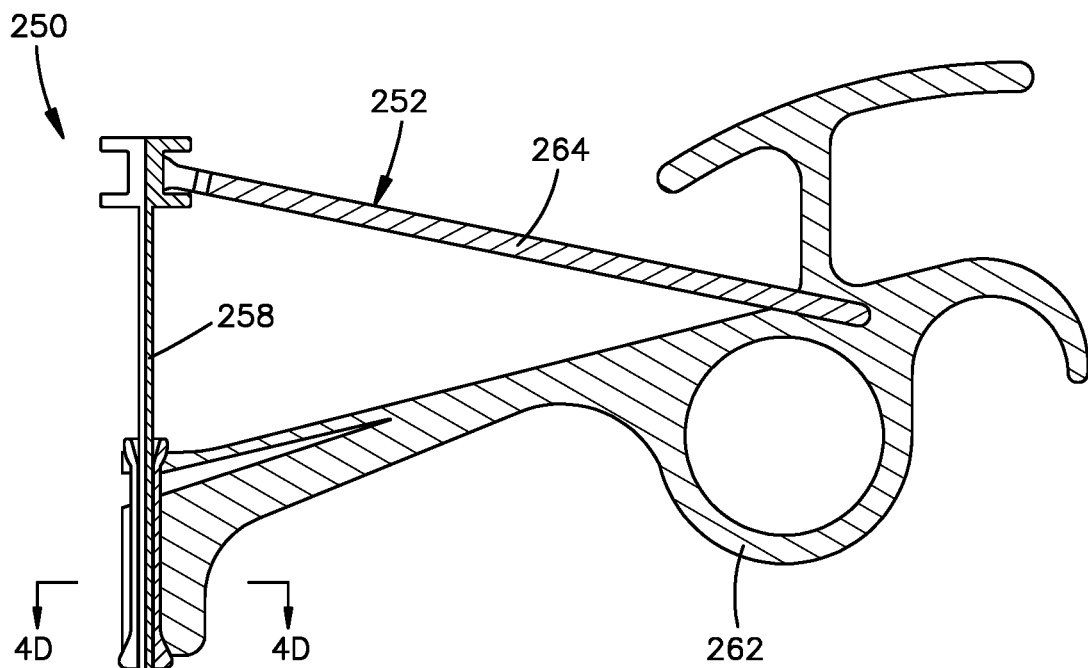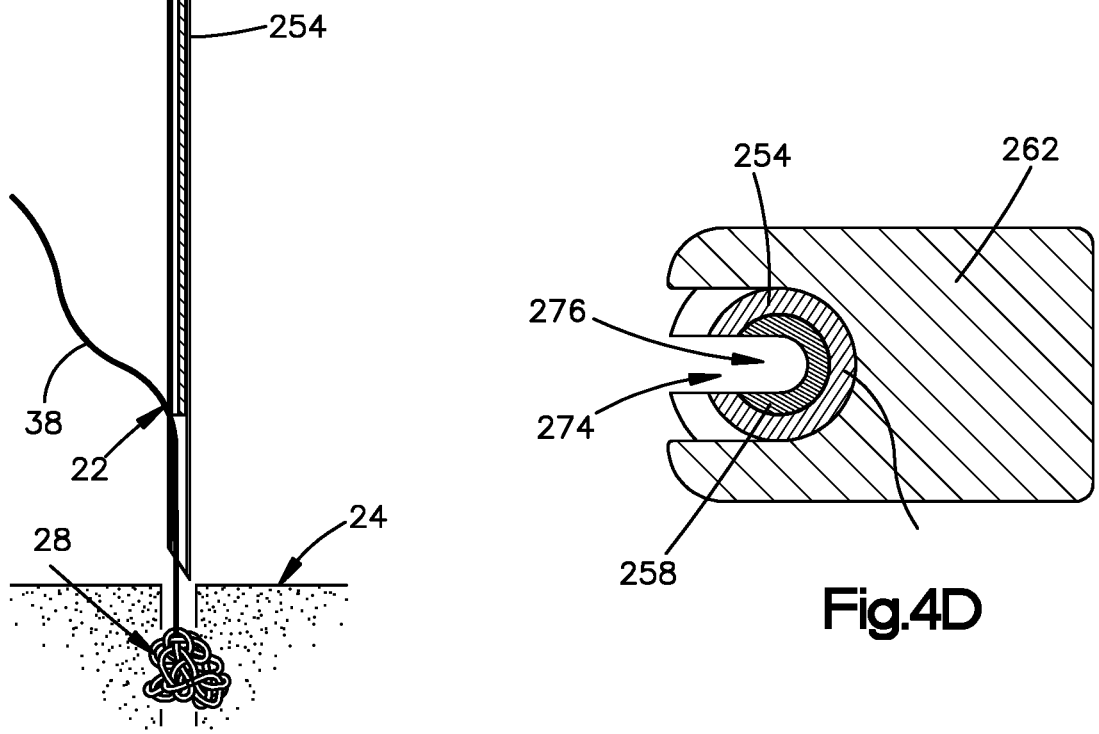

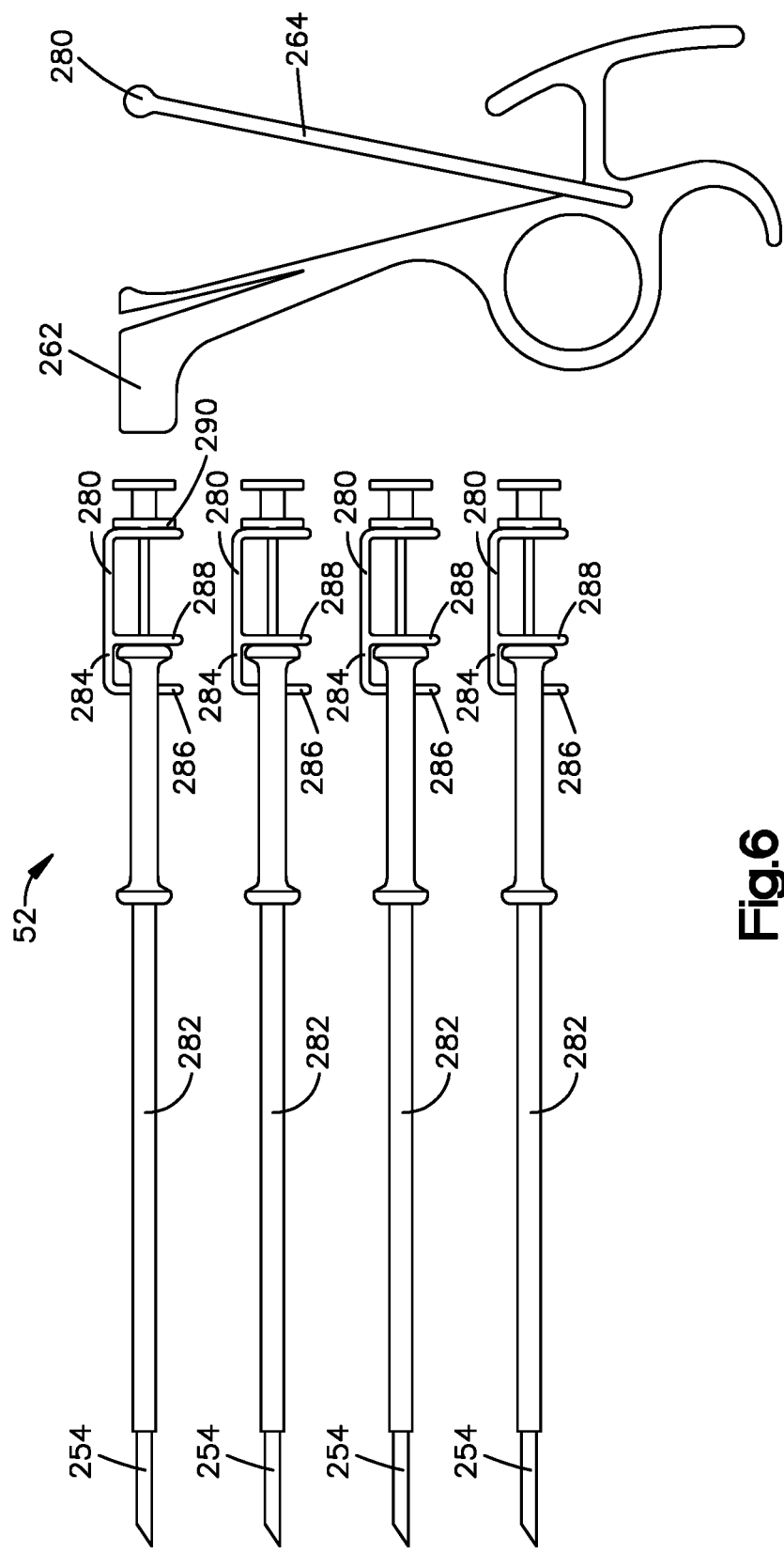

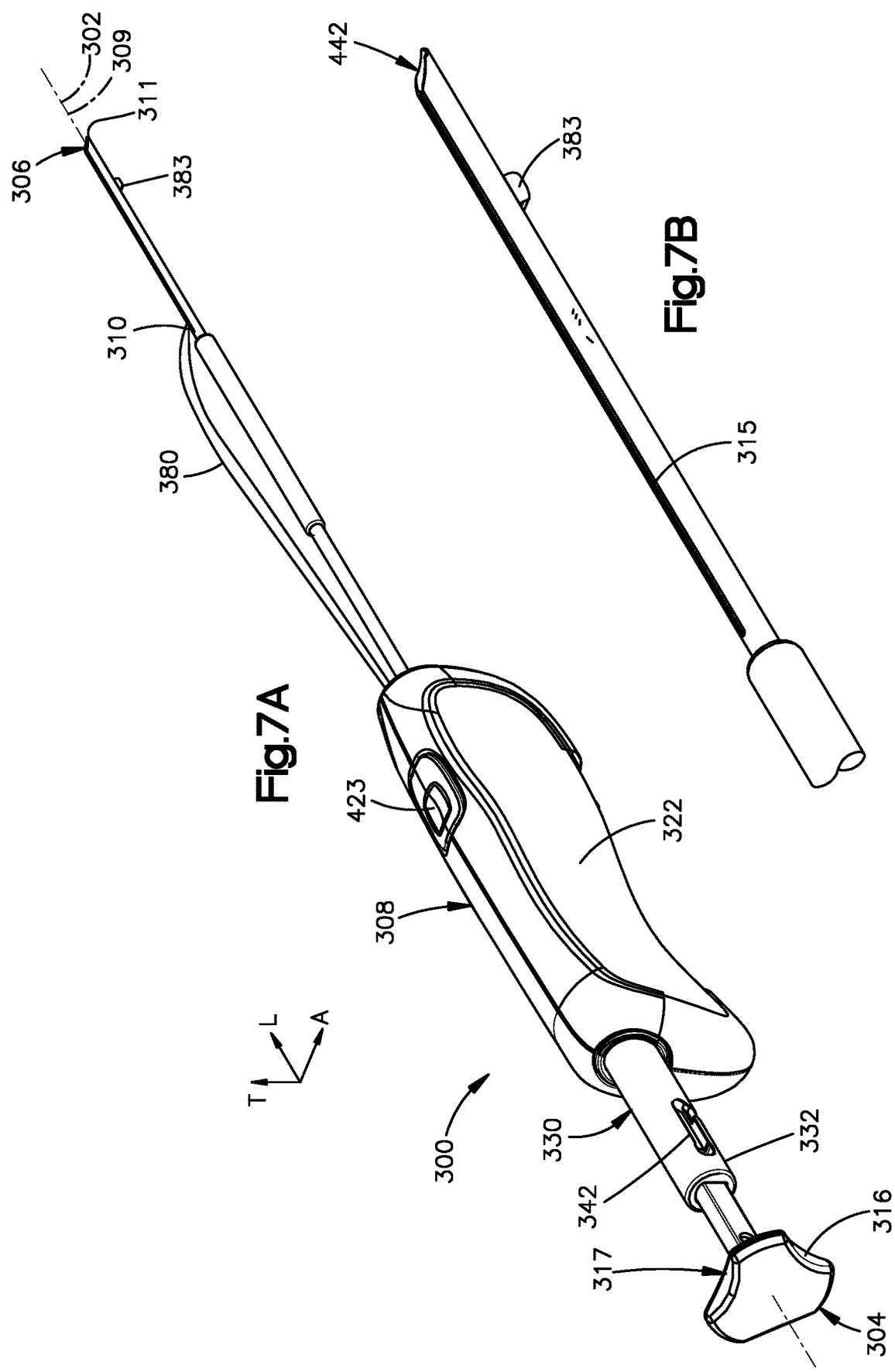

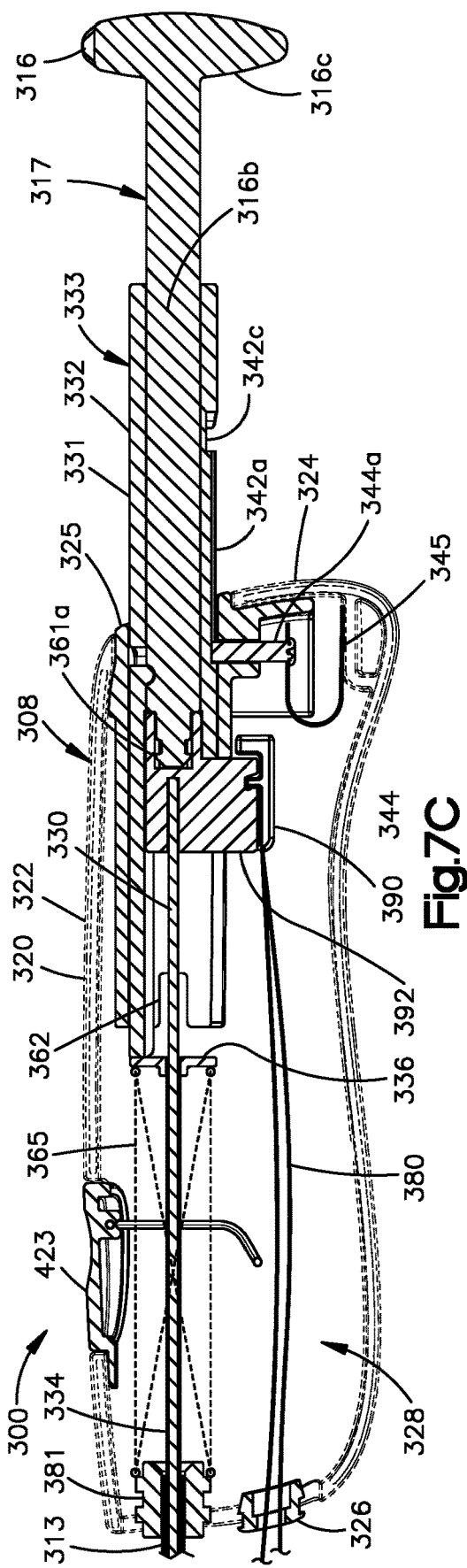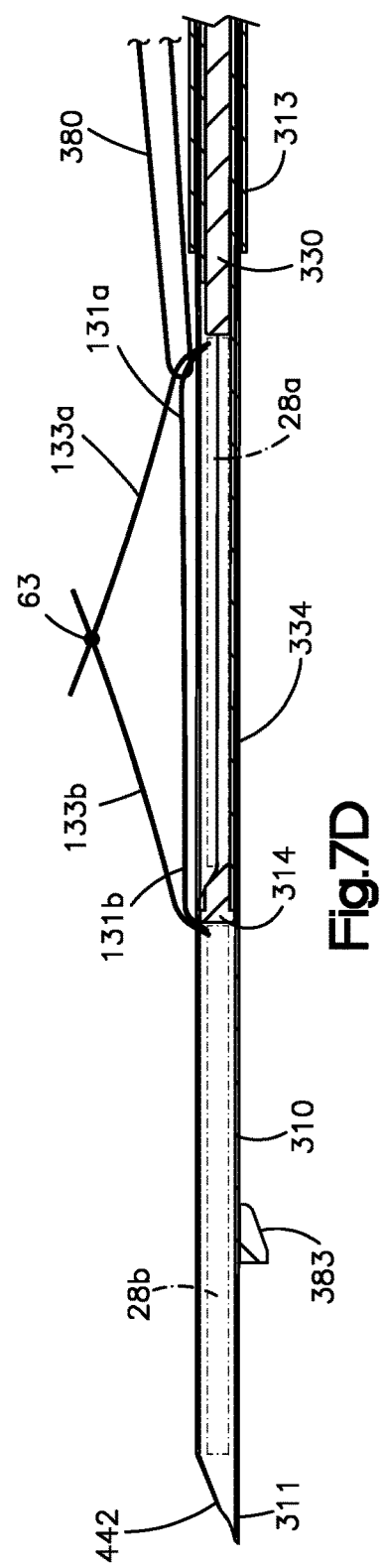

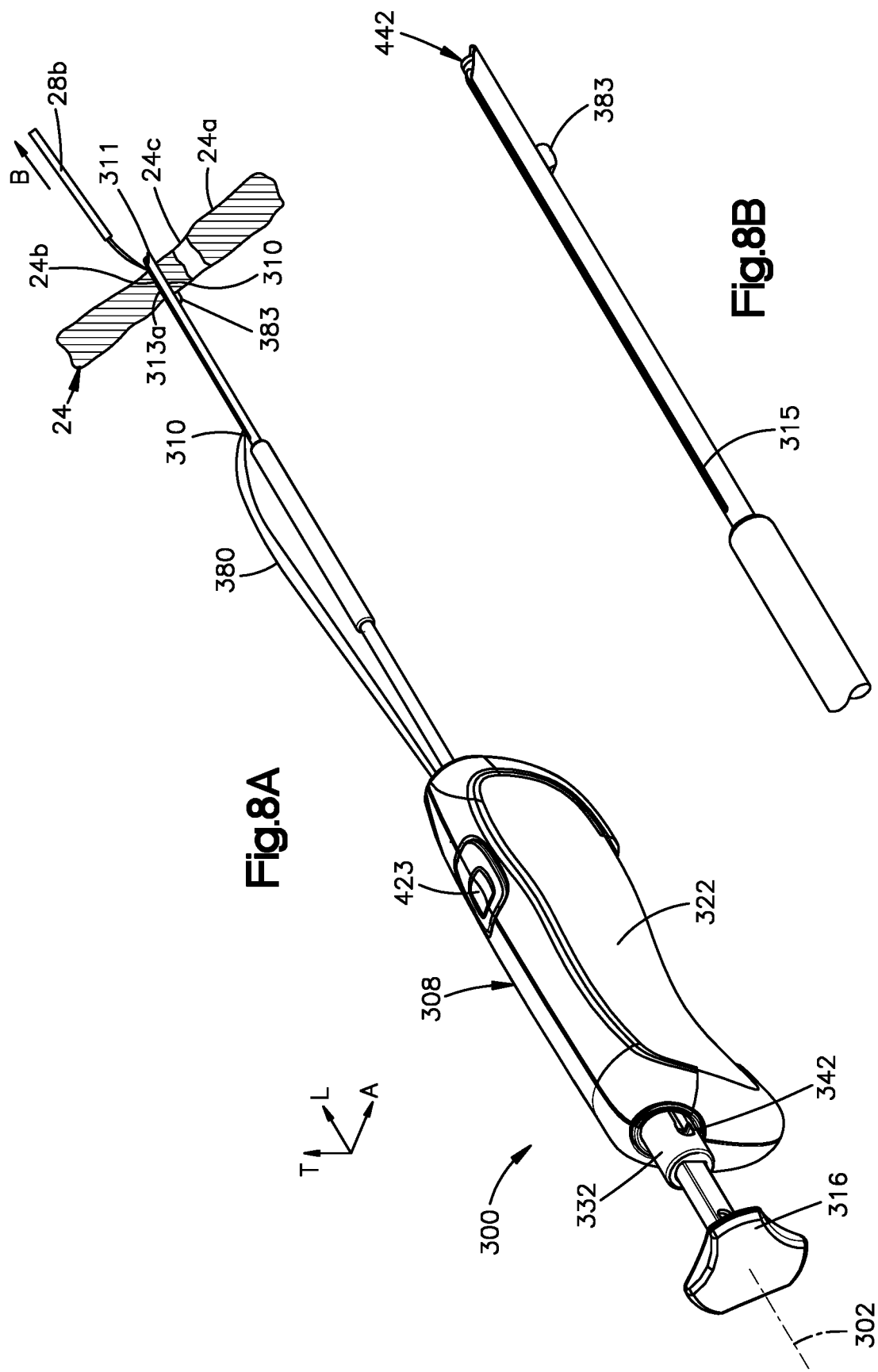

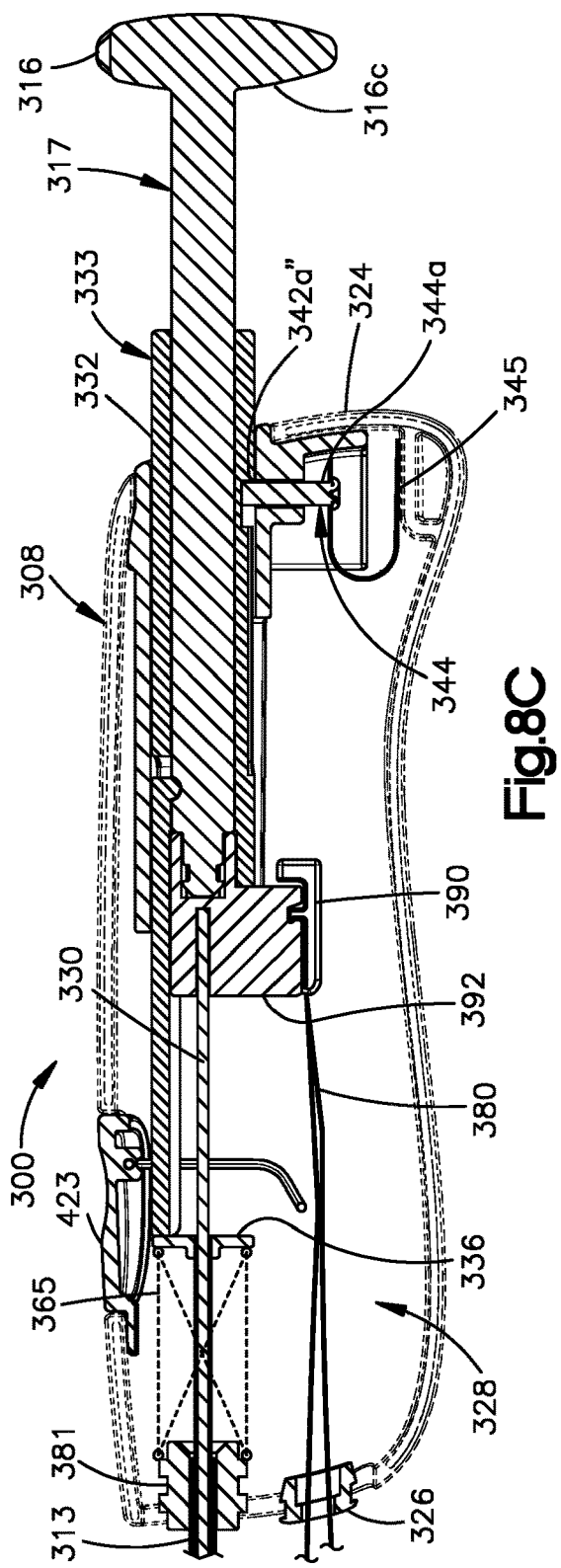
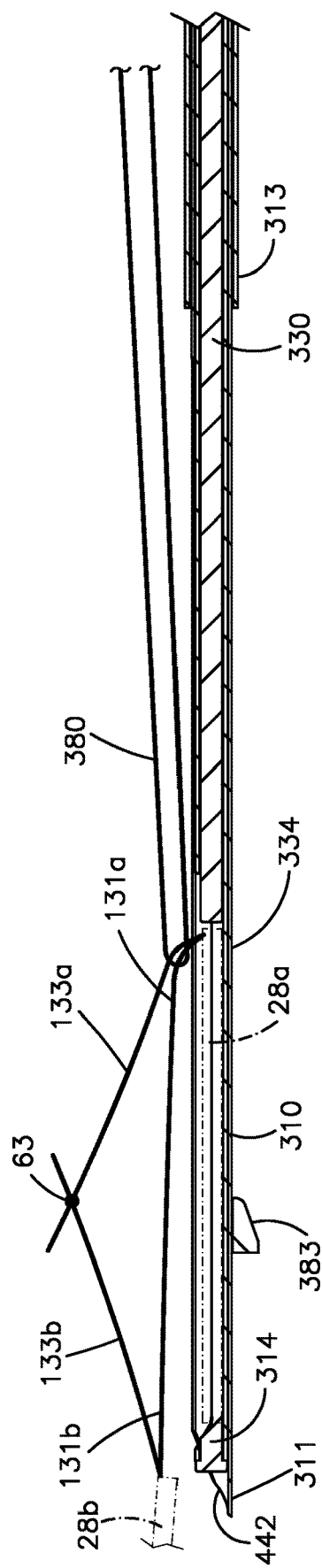
Fig.8C
Fig.8D

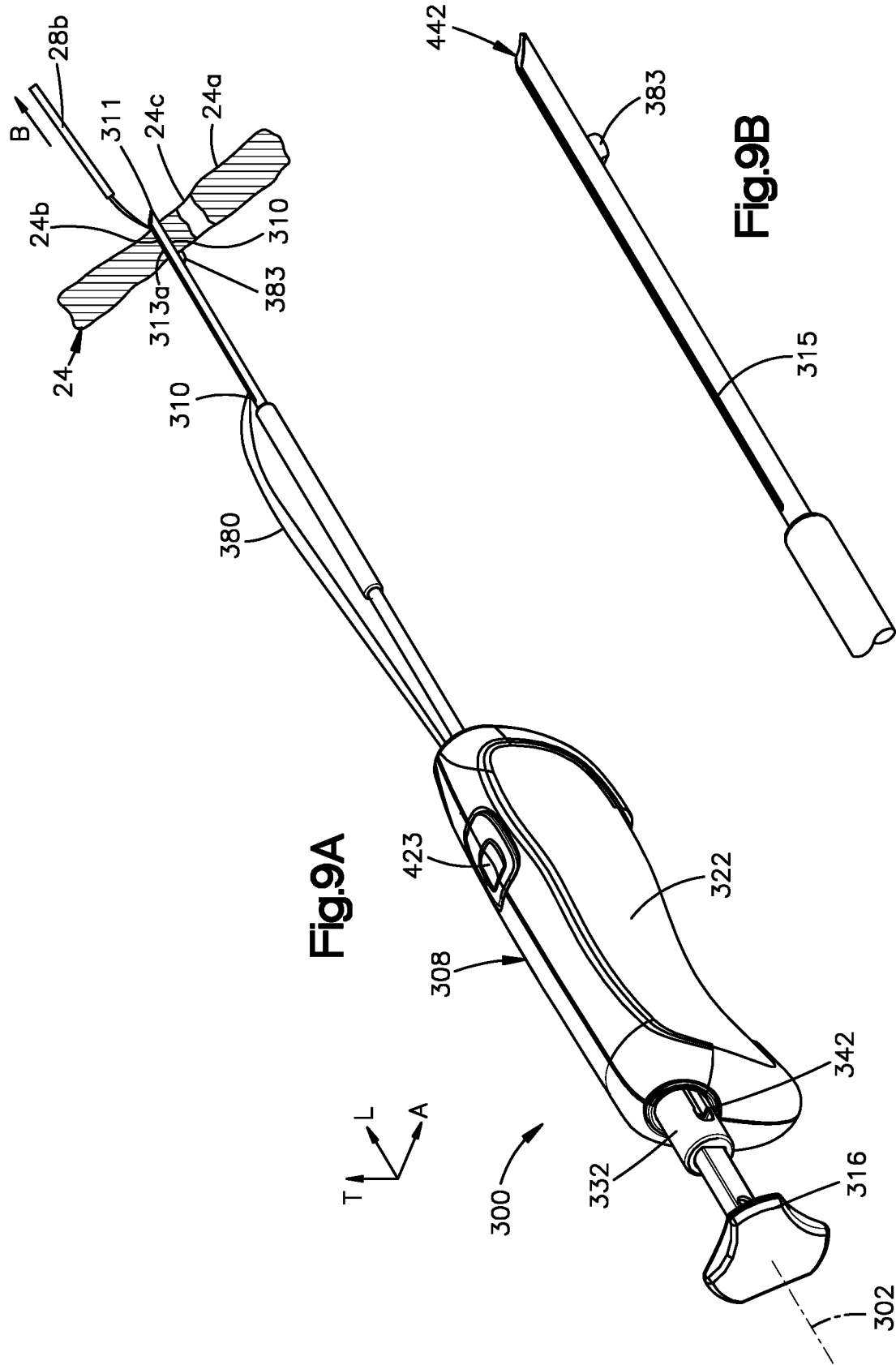

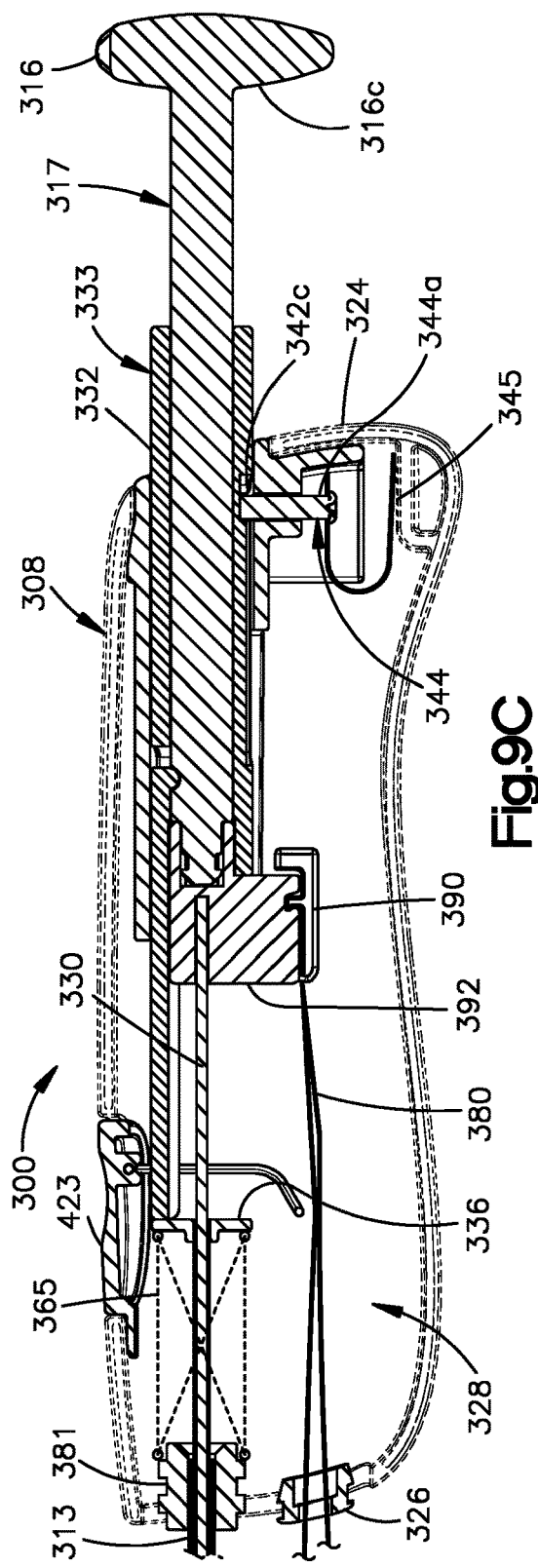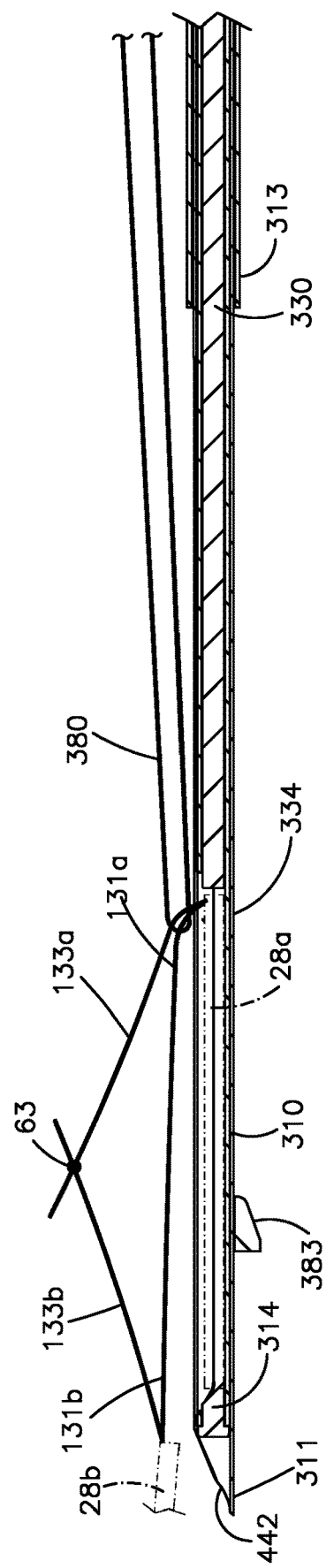

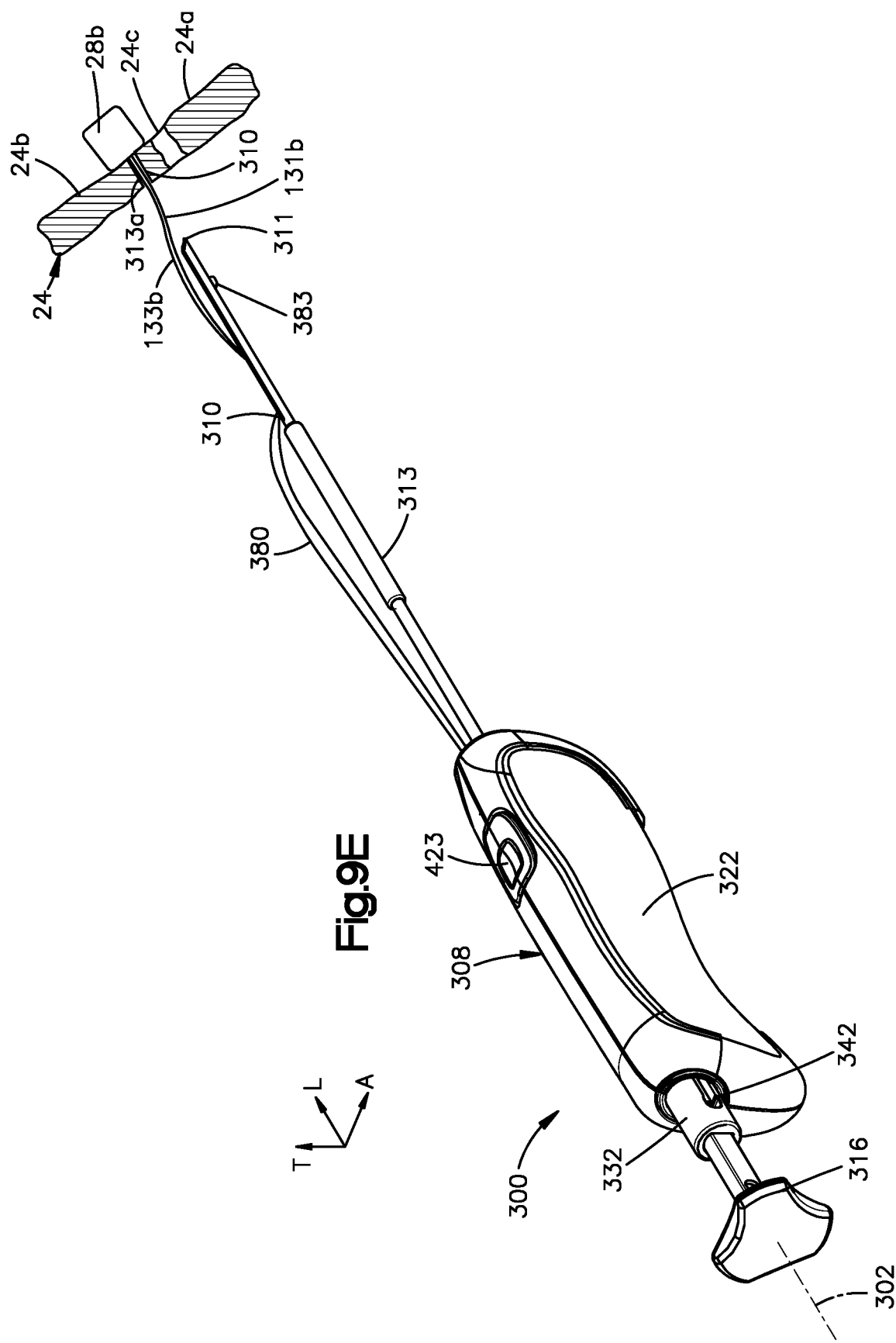

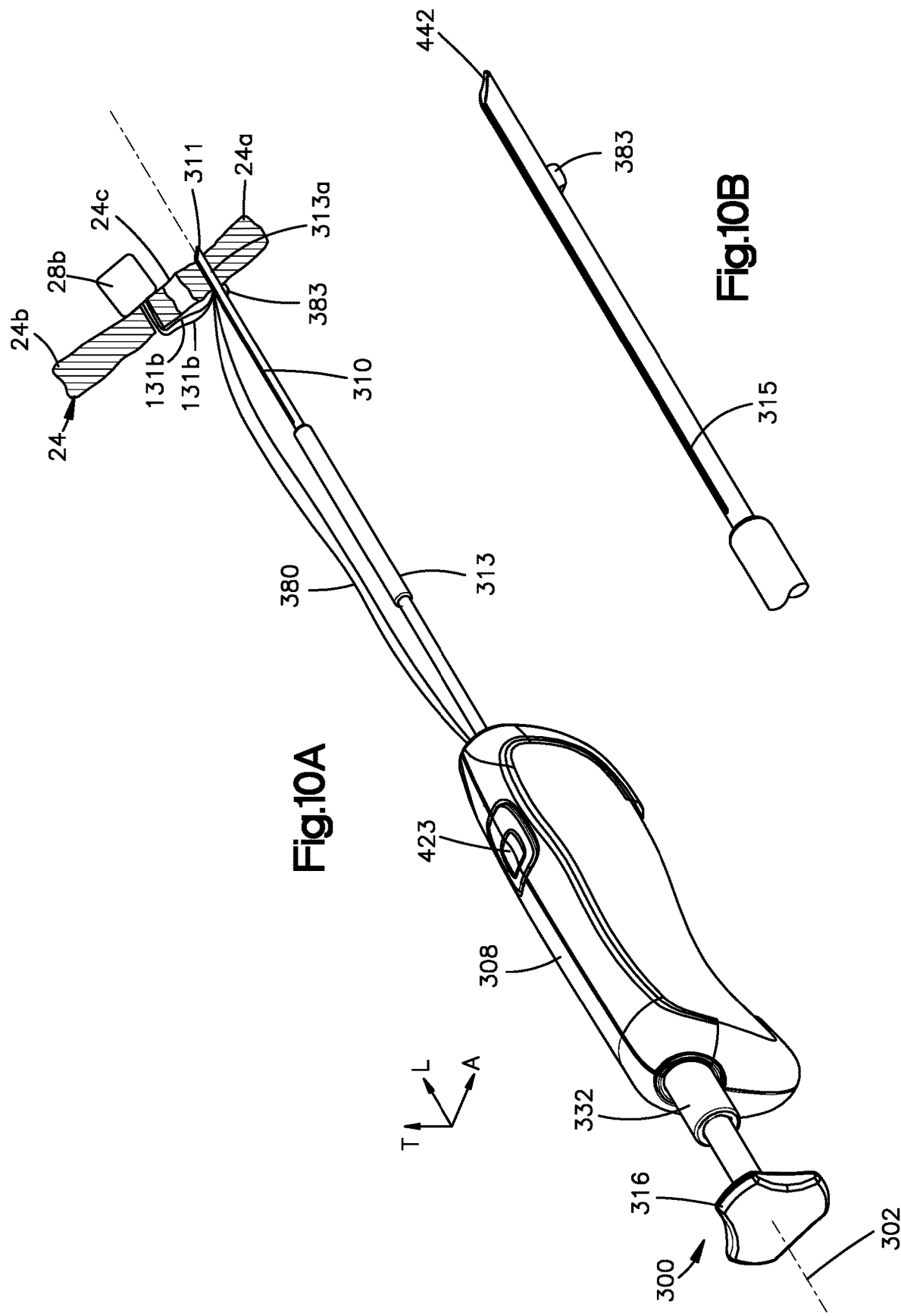

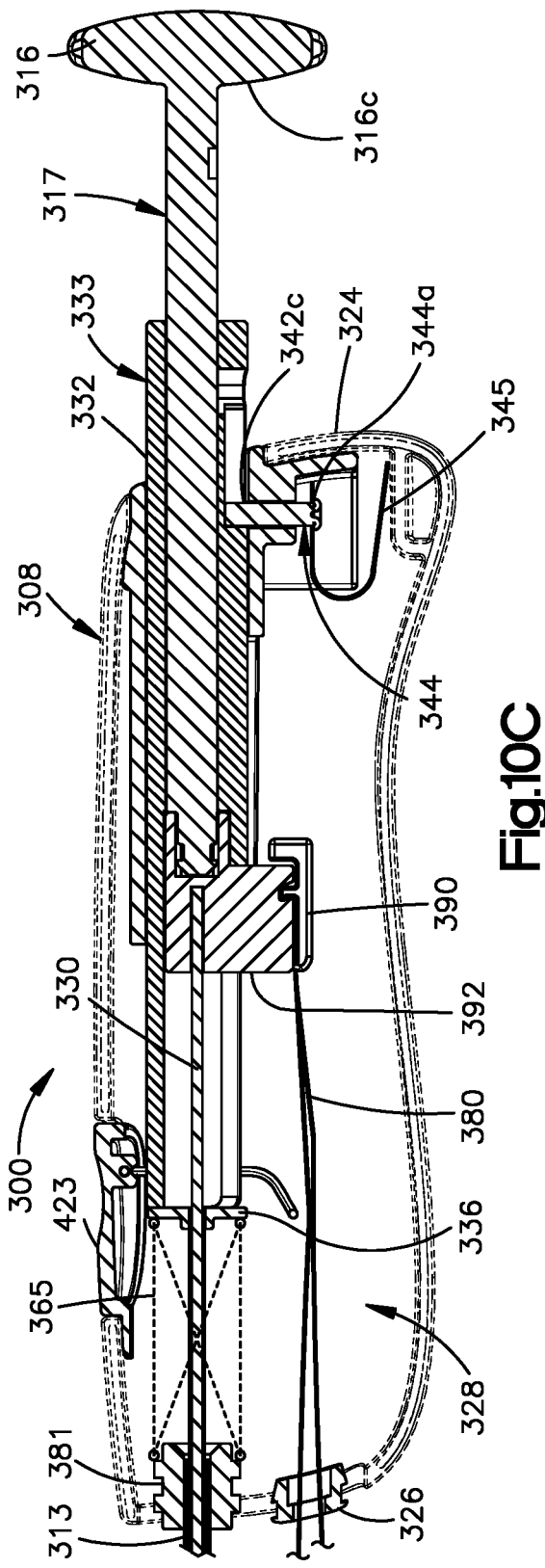
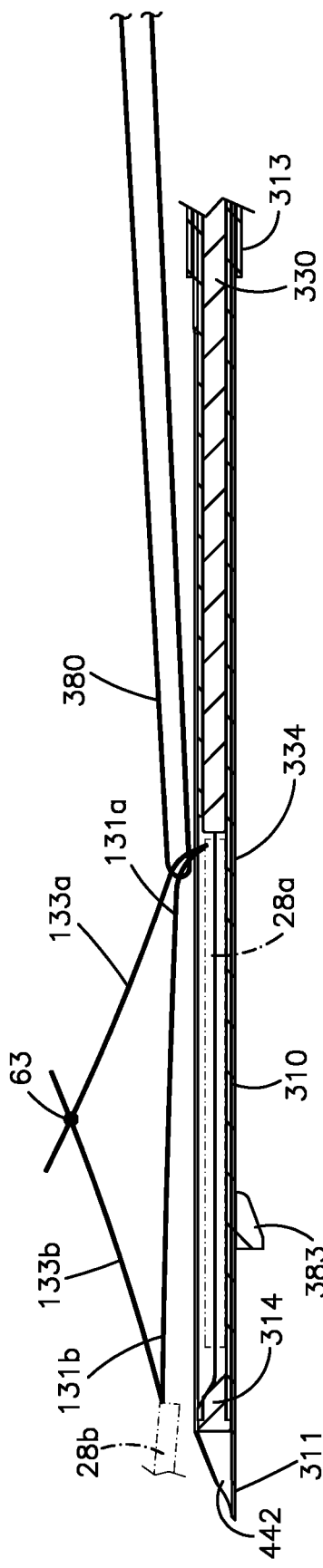
Fig.10C
Fig.10D

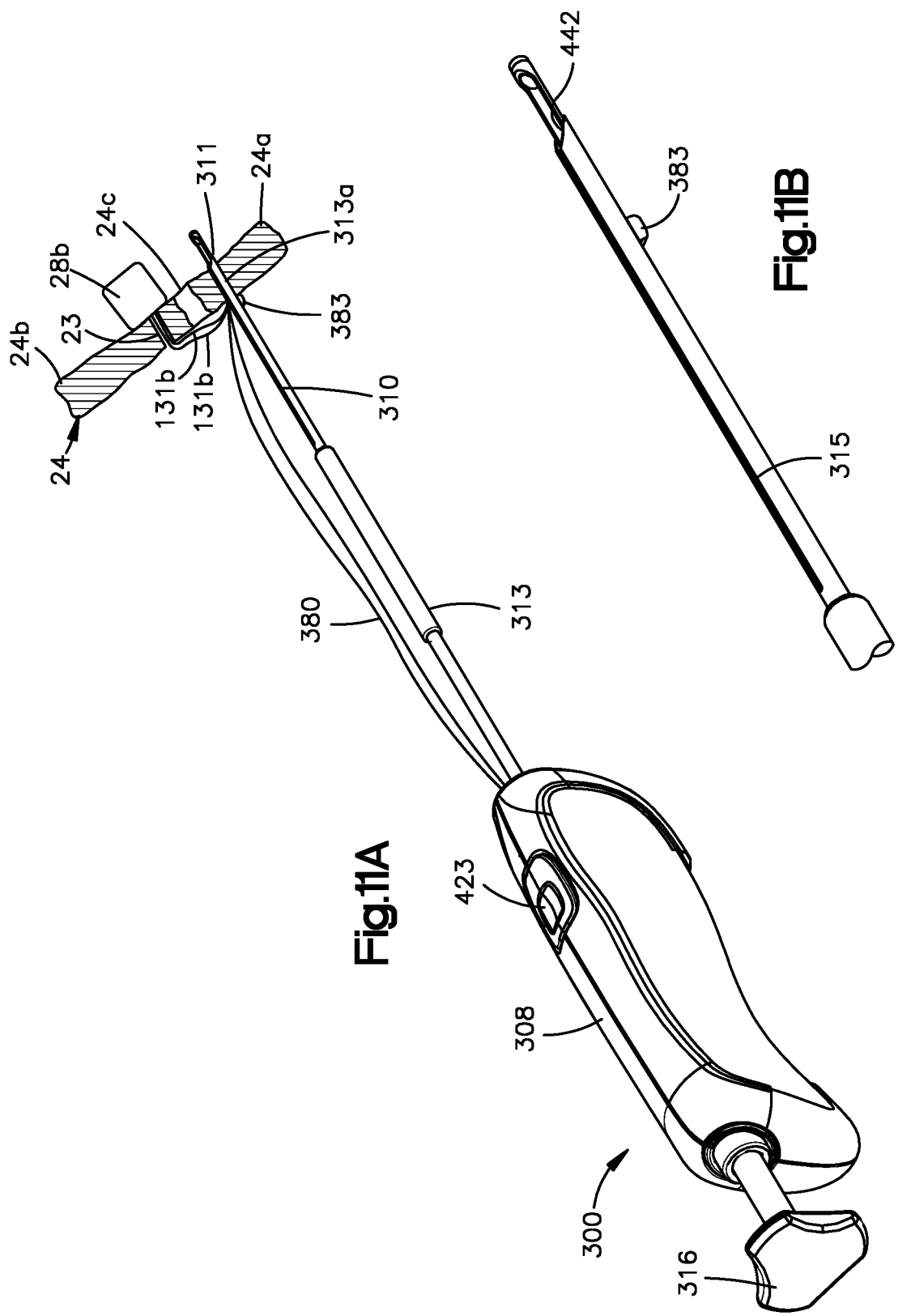

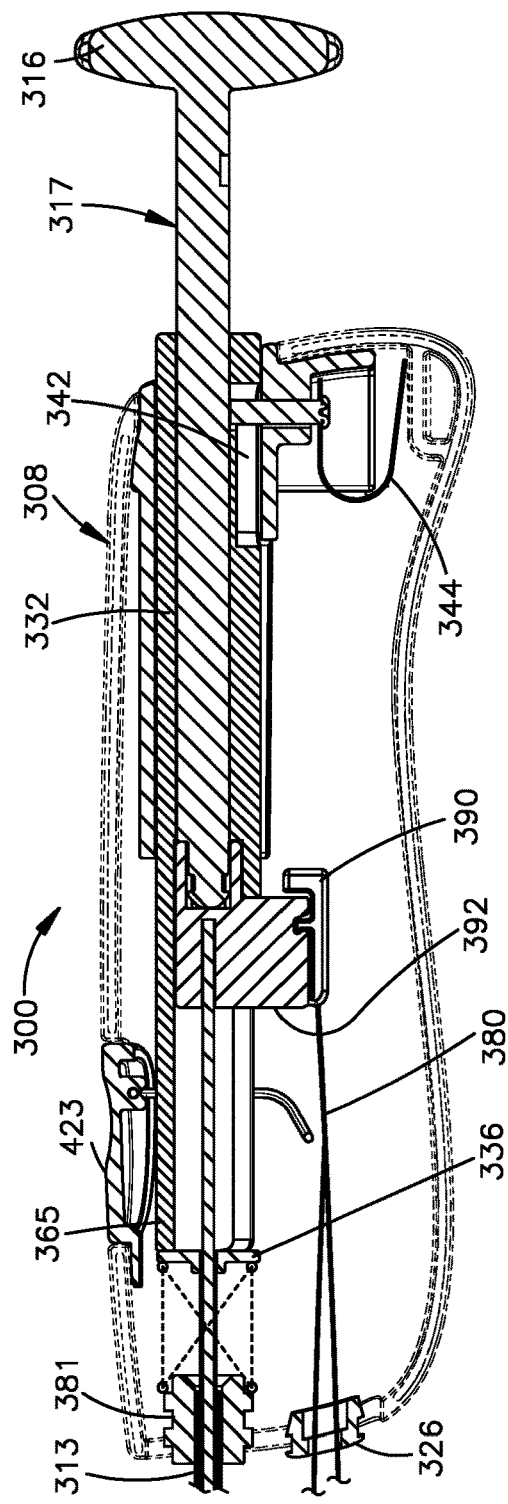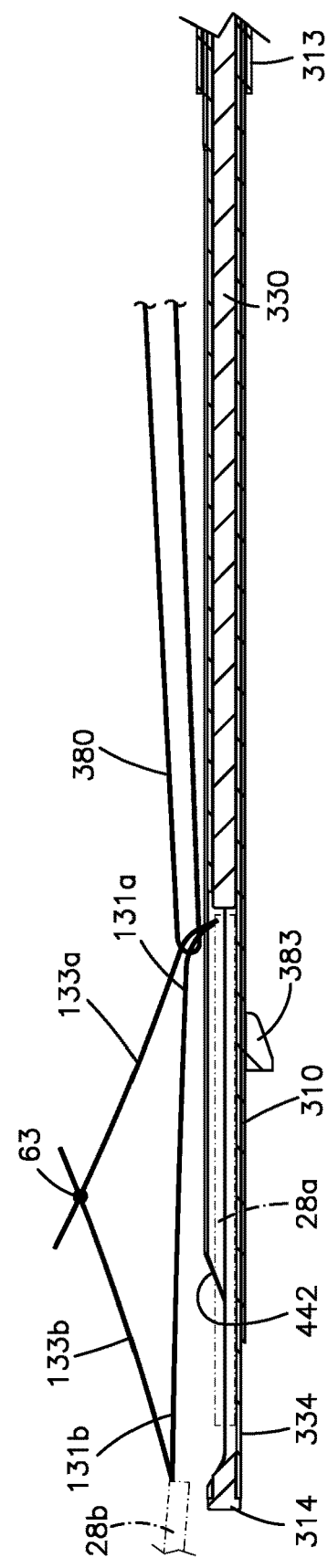

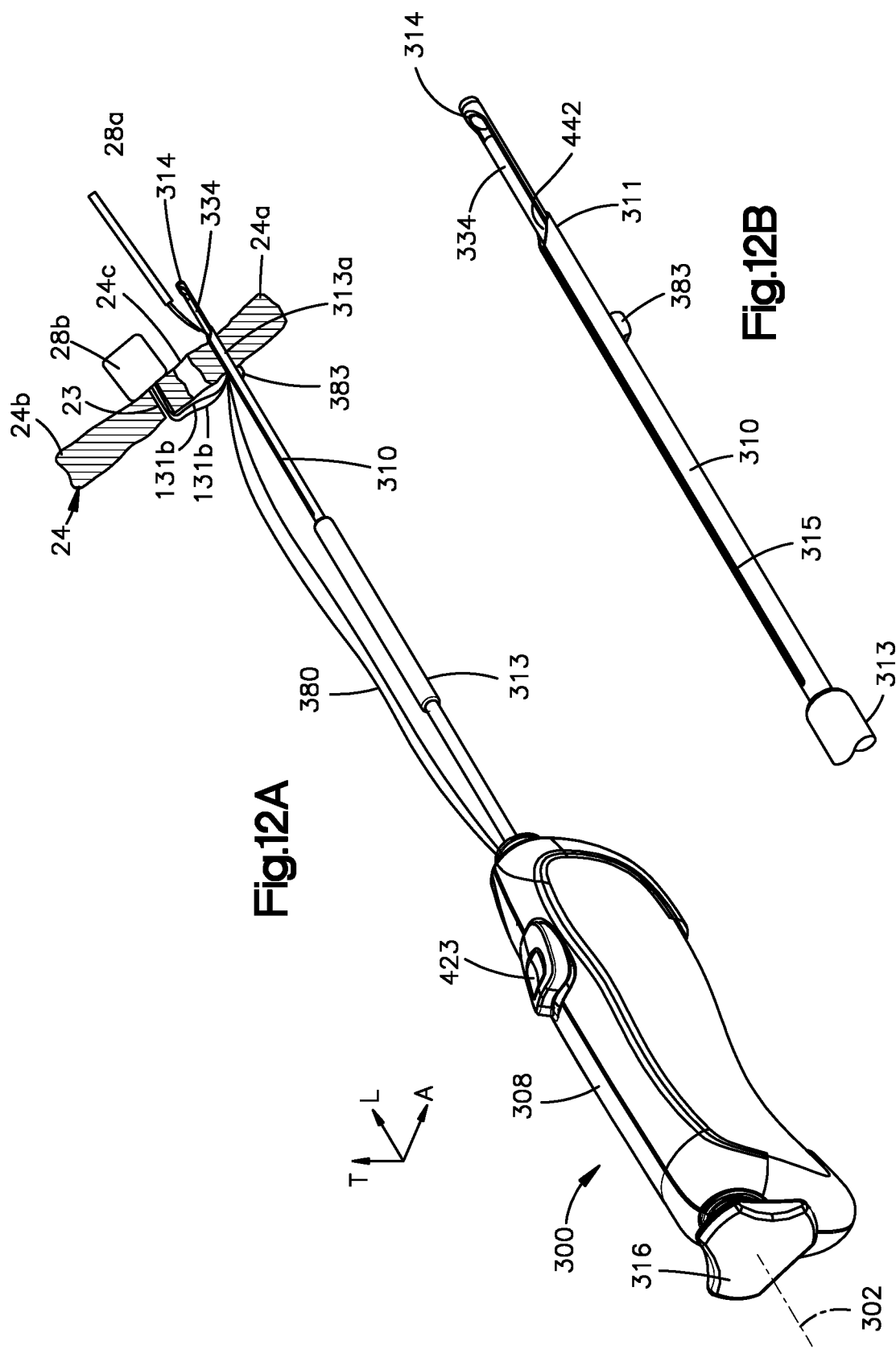

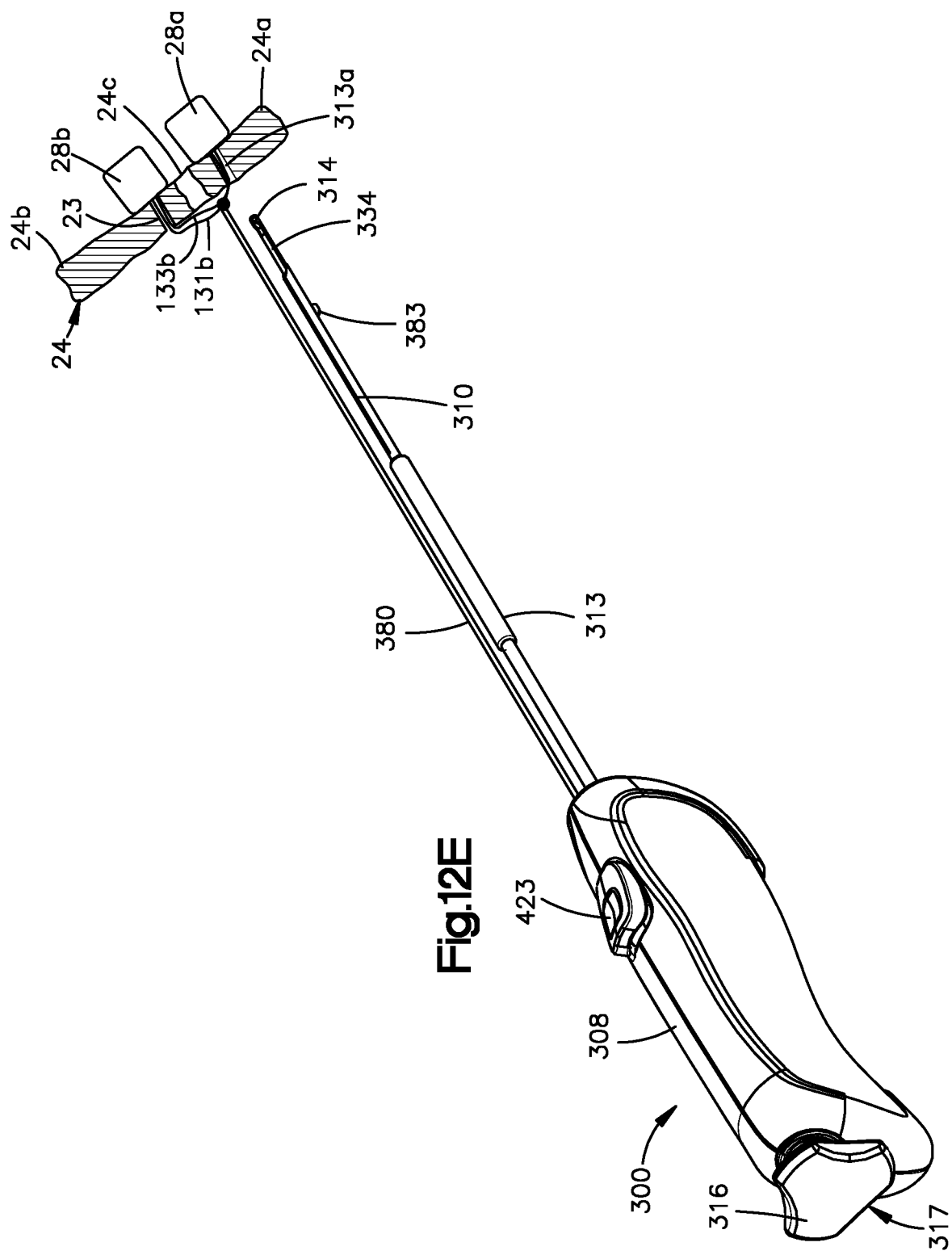

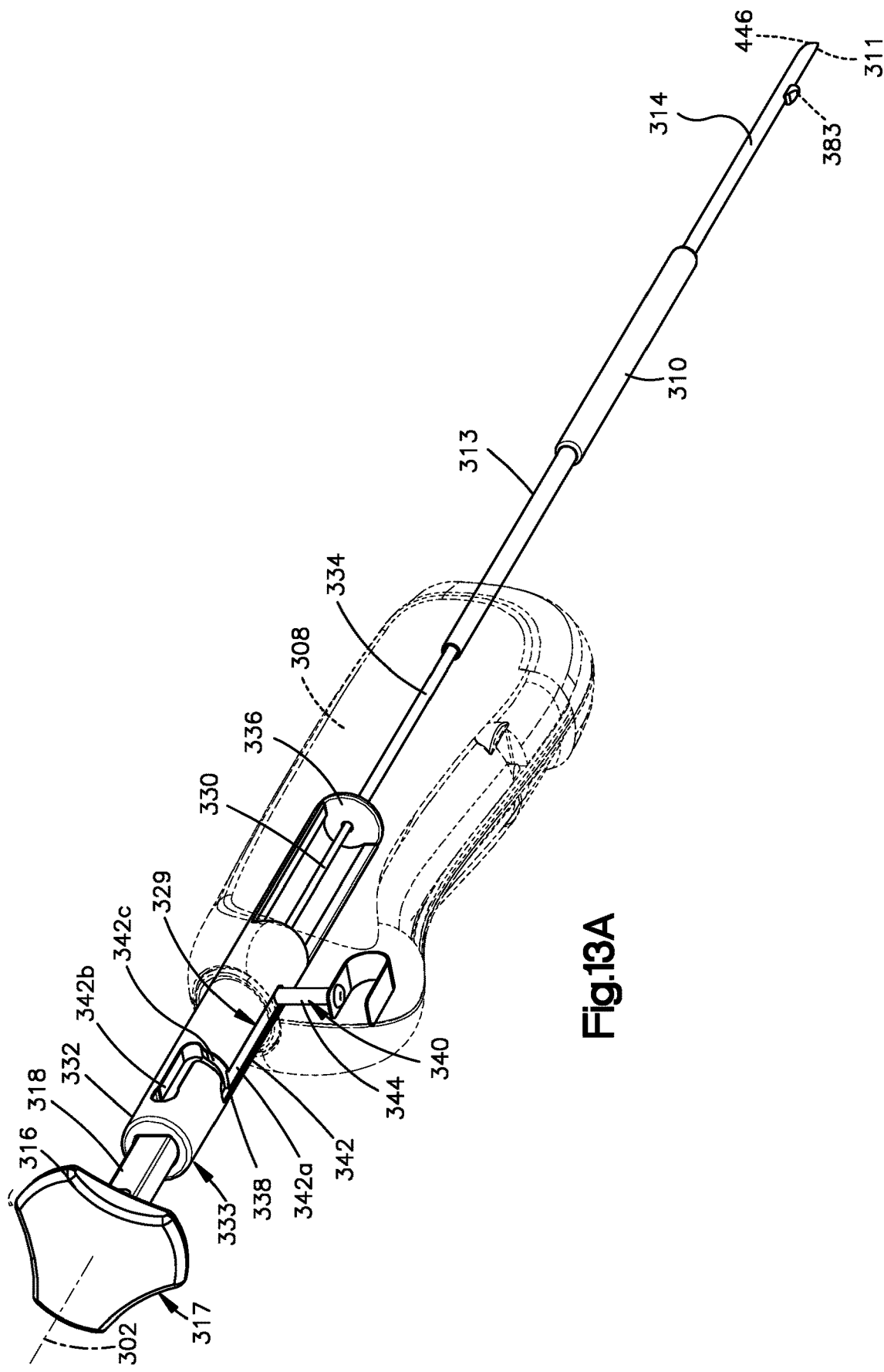

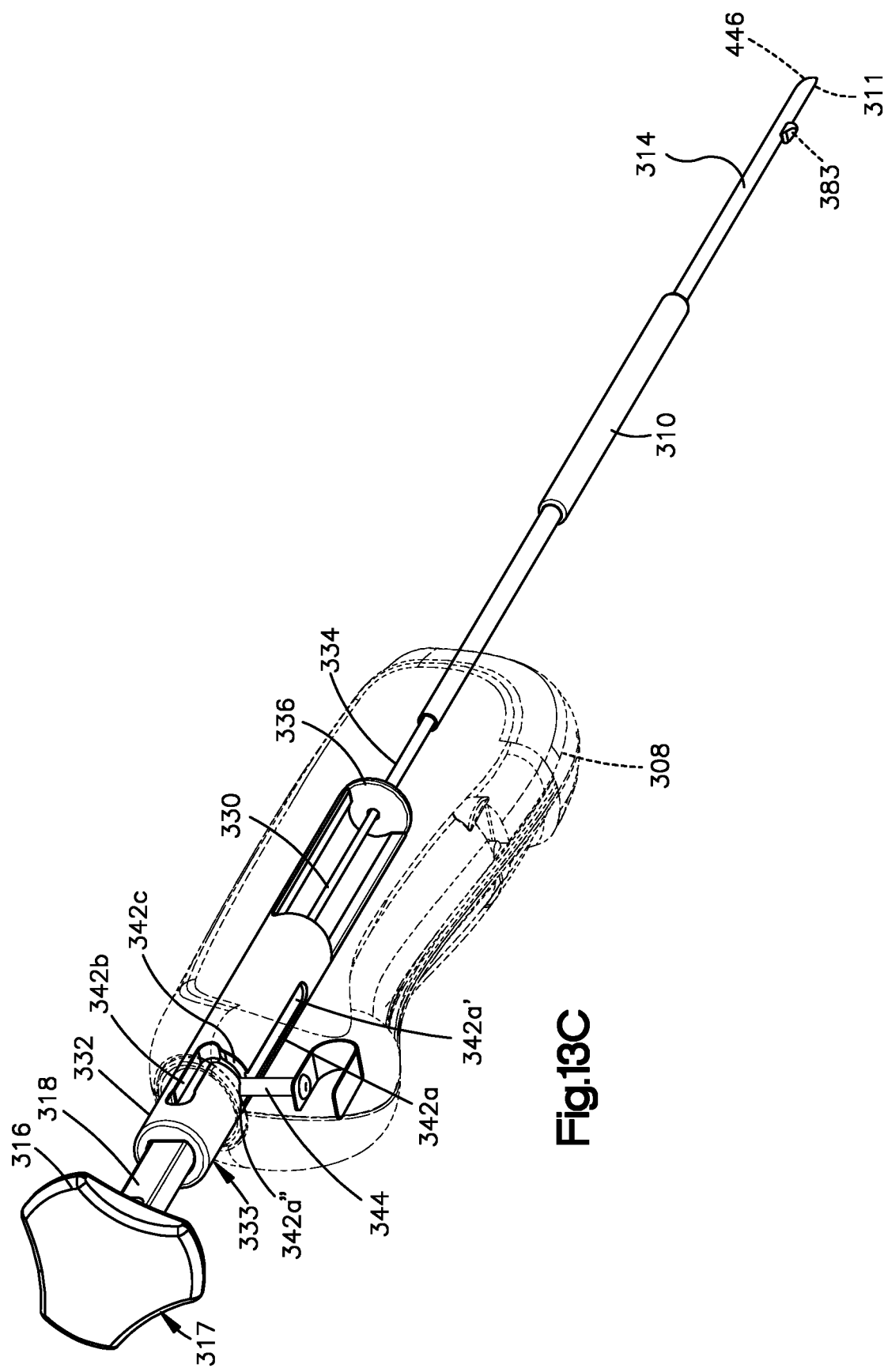

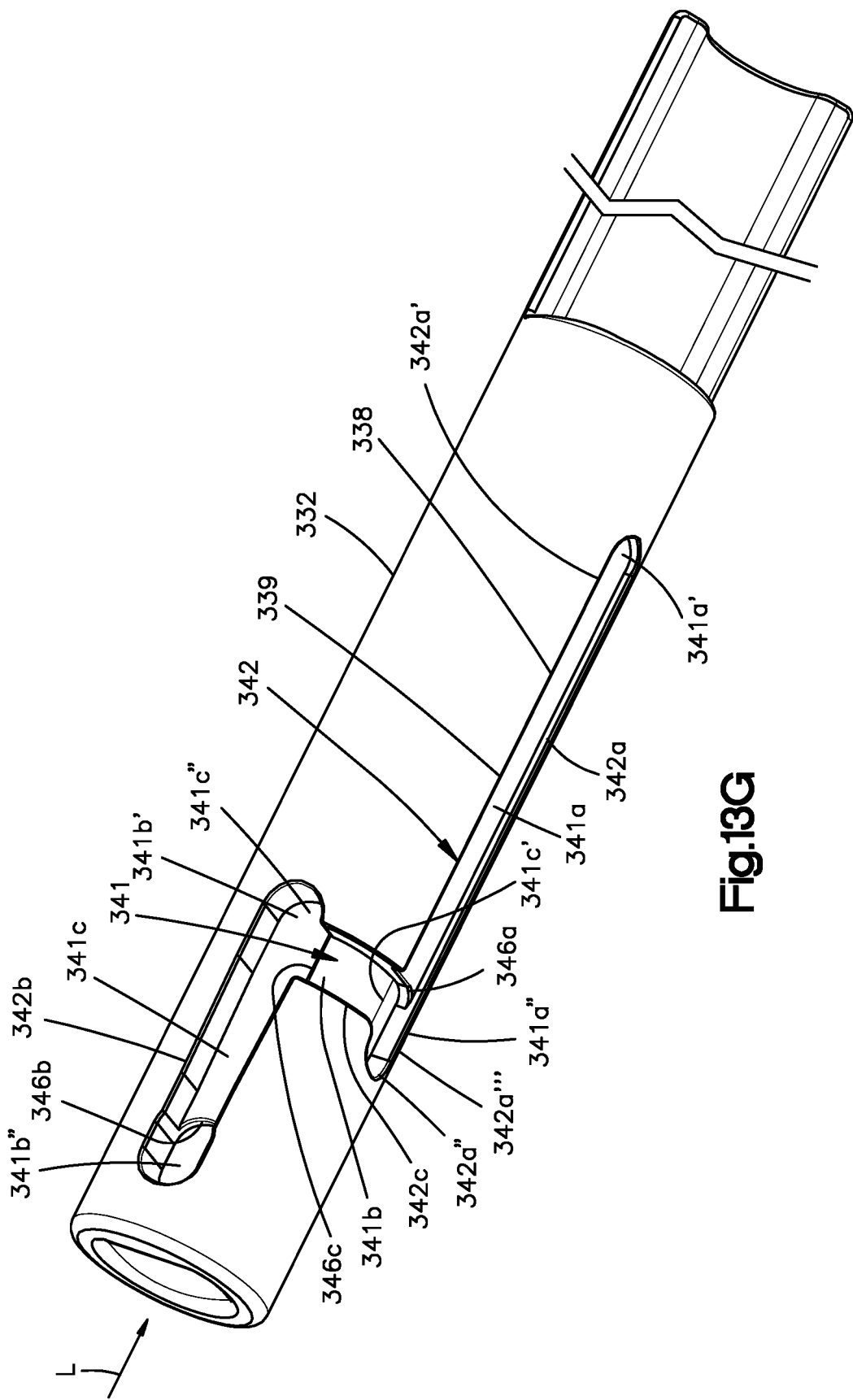

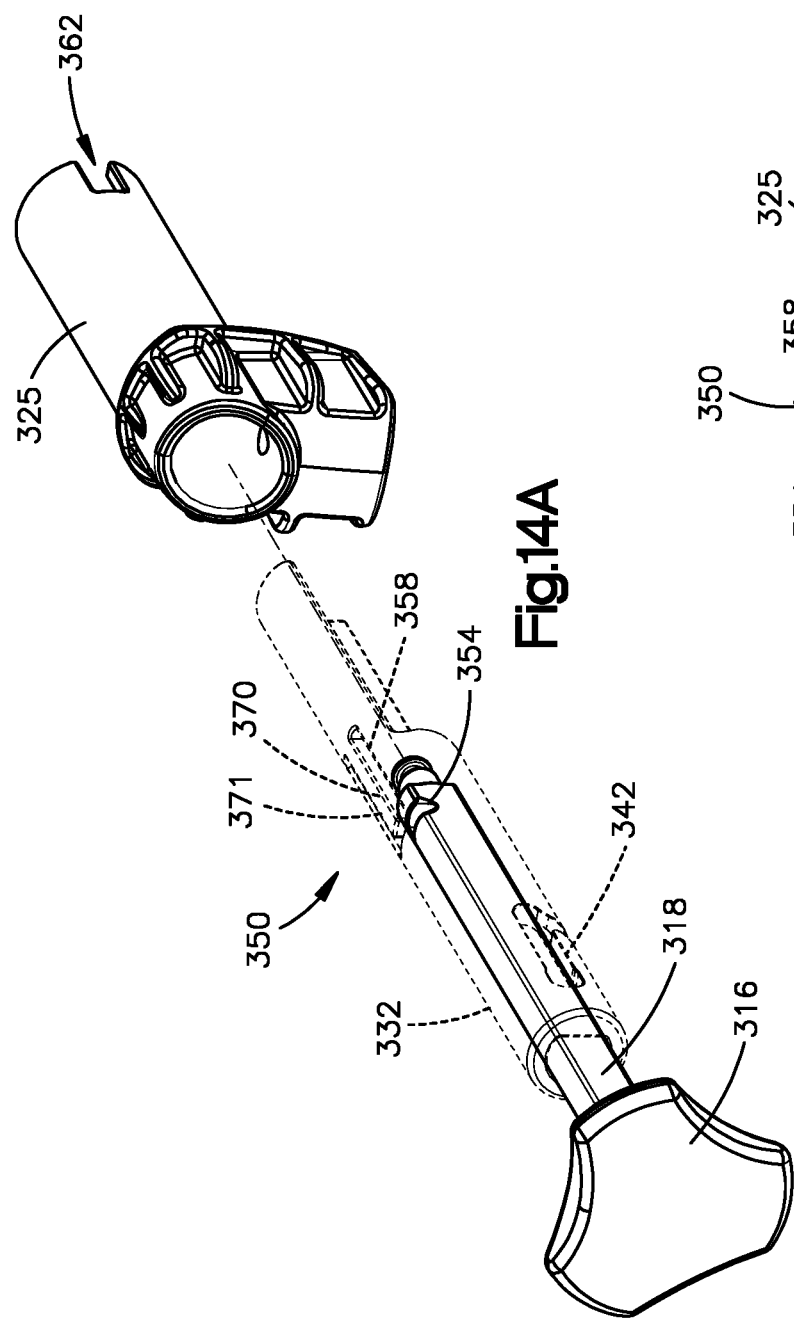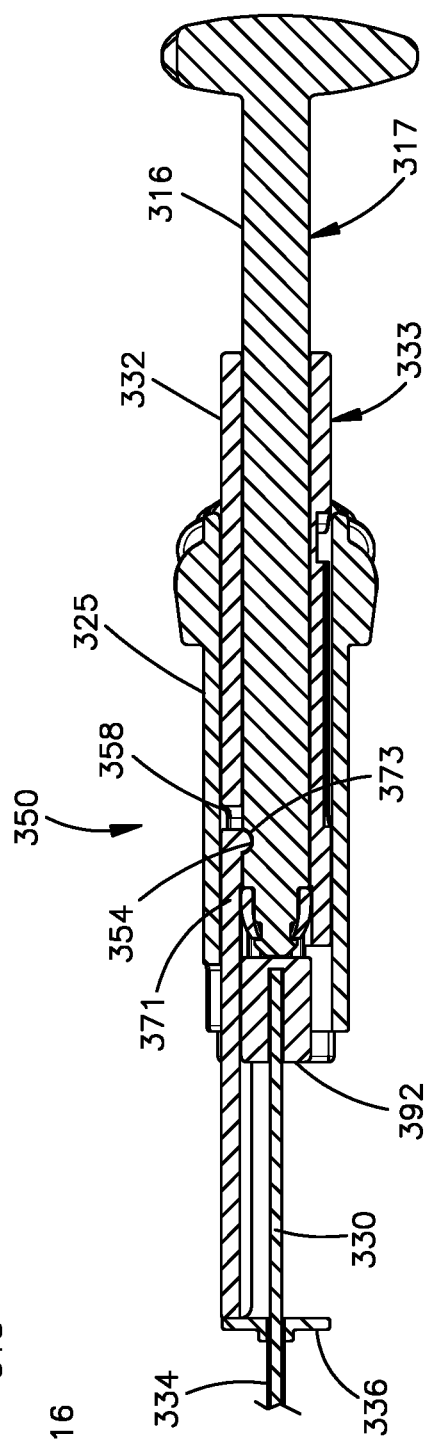

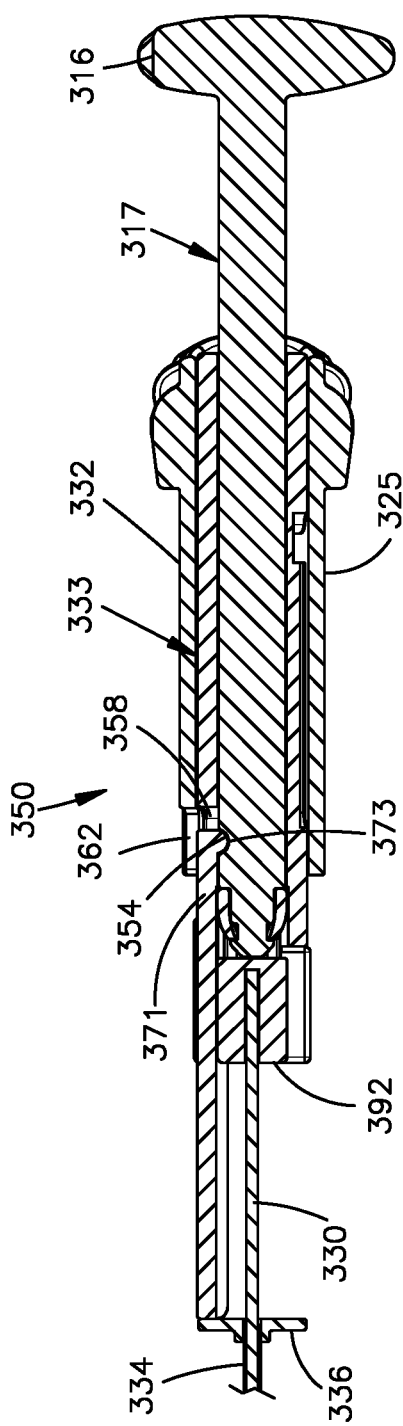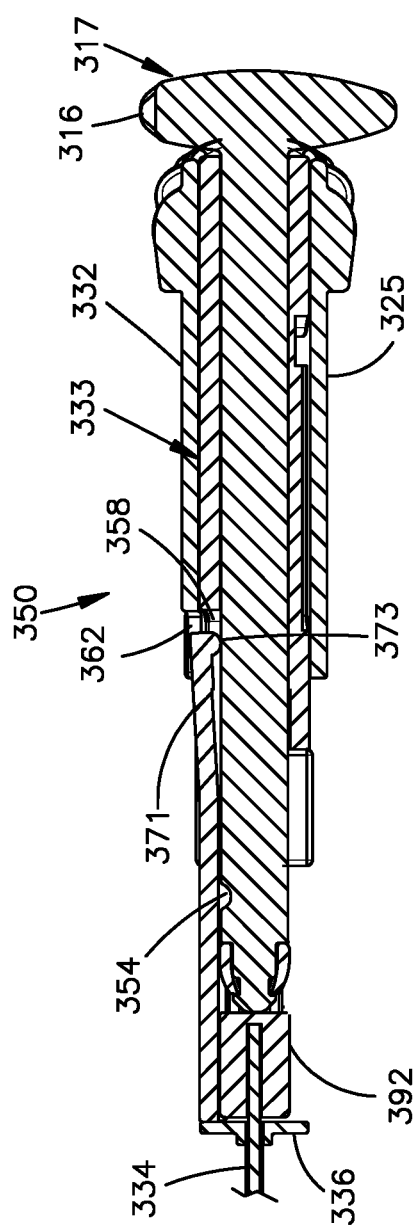

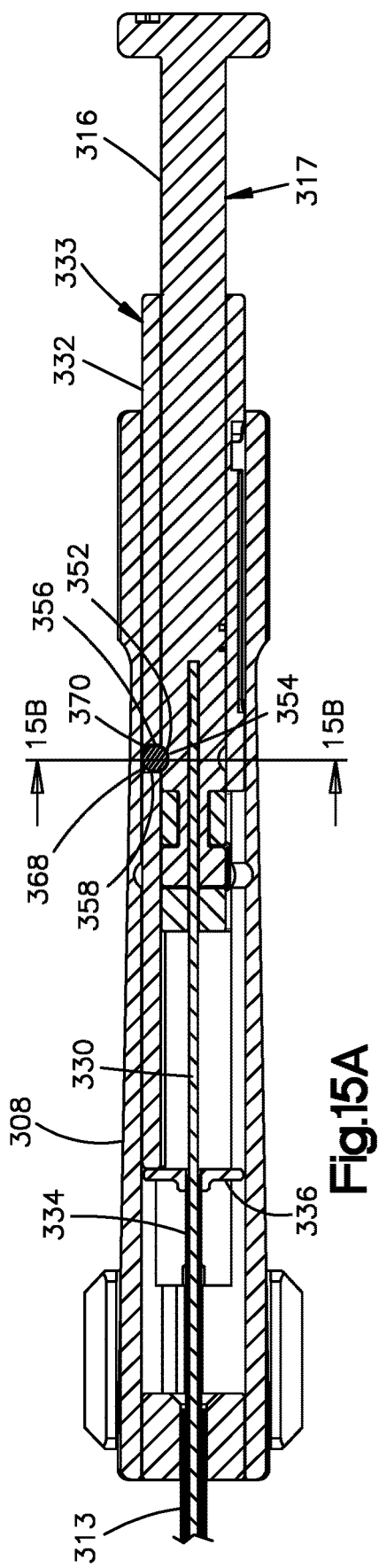
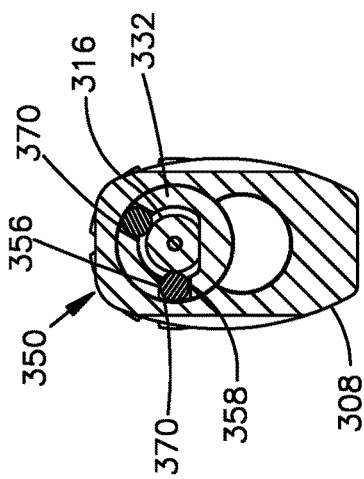
Fig.15A
Fig.15B

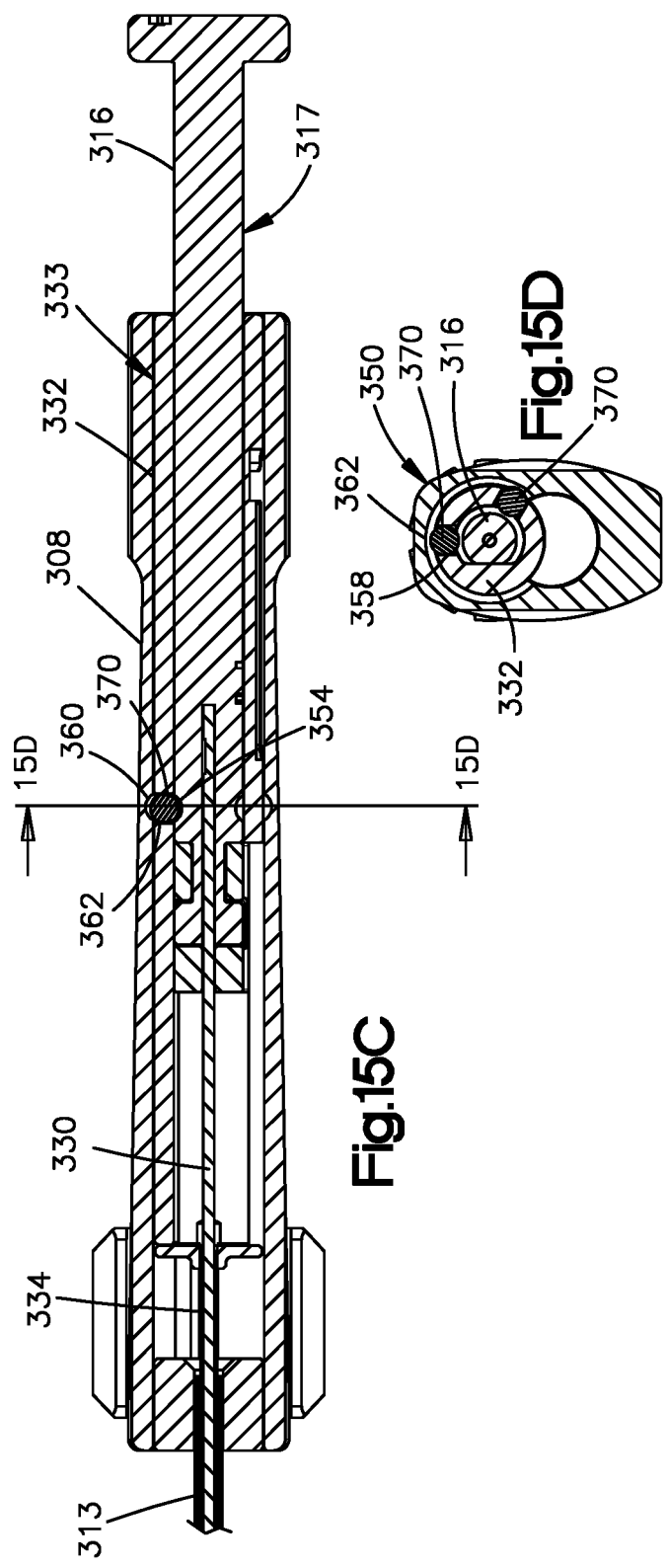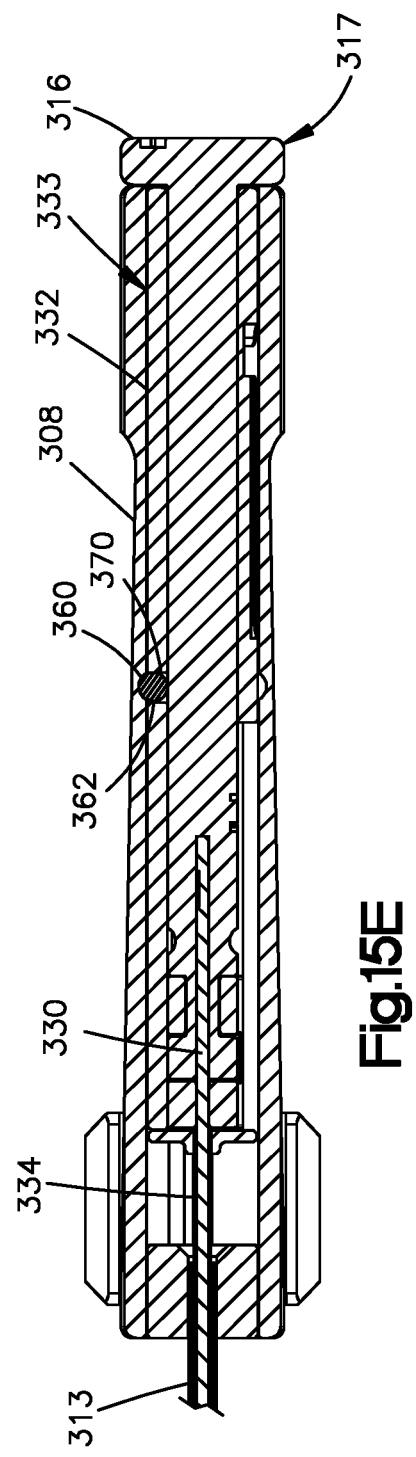

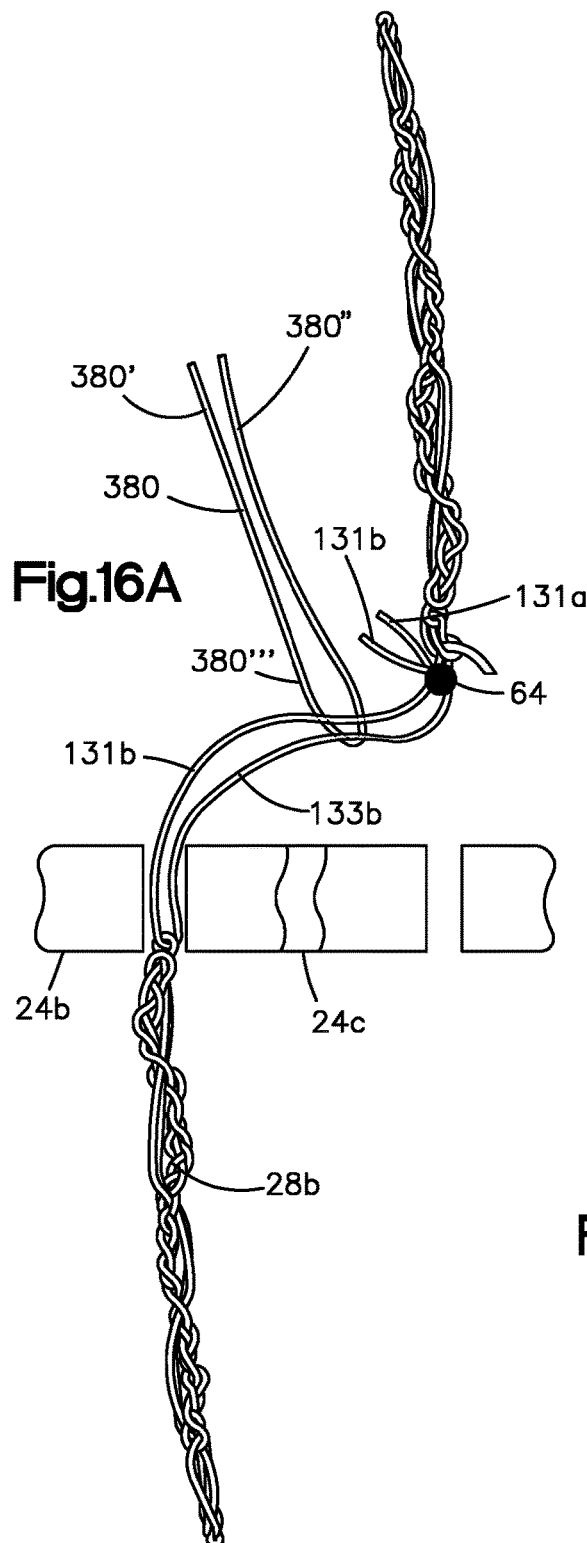
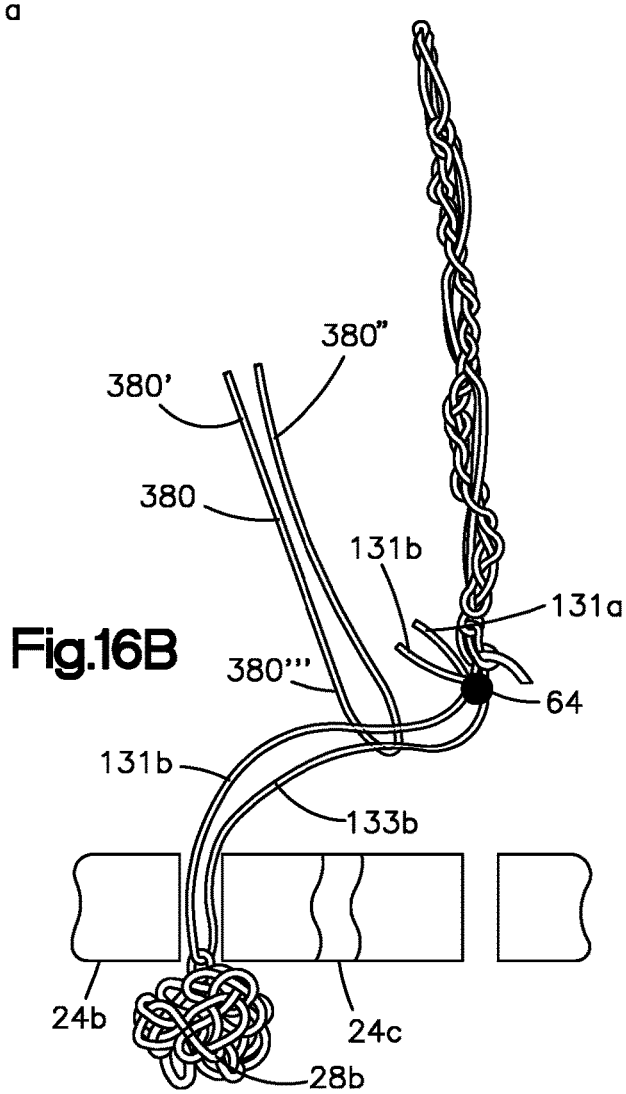

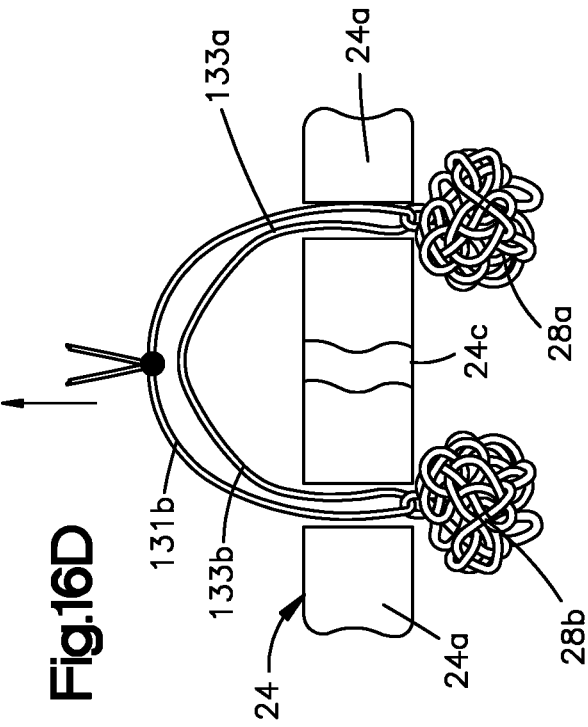
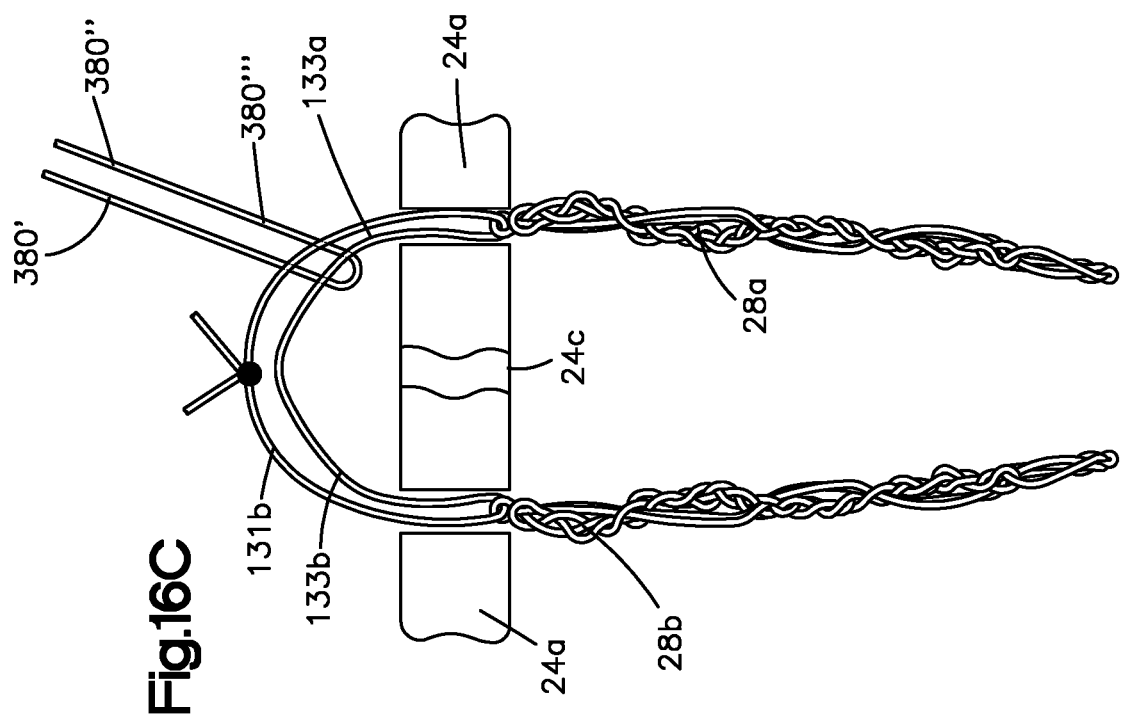

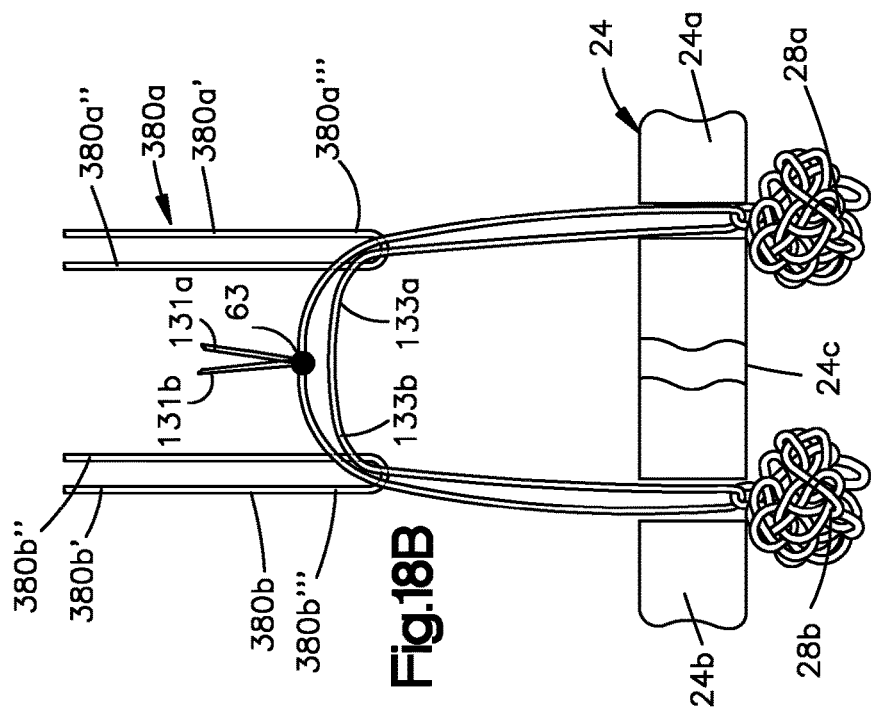
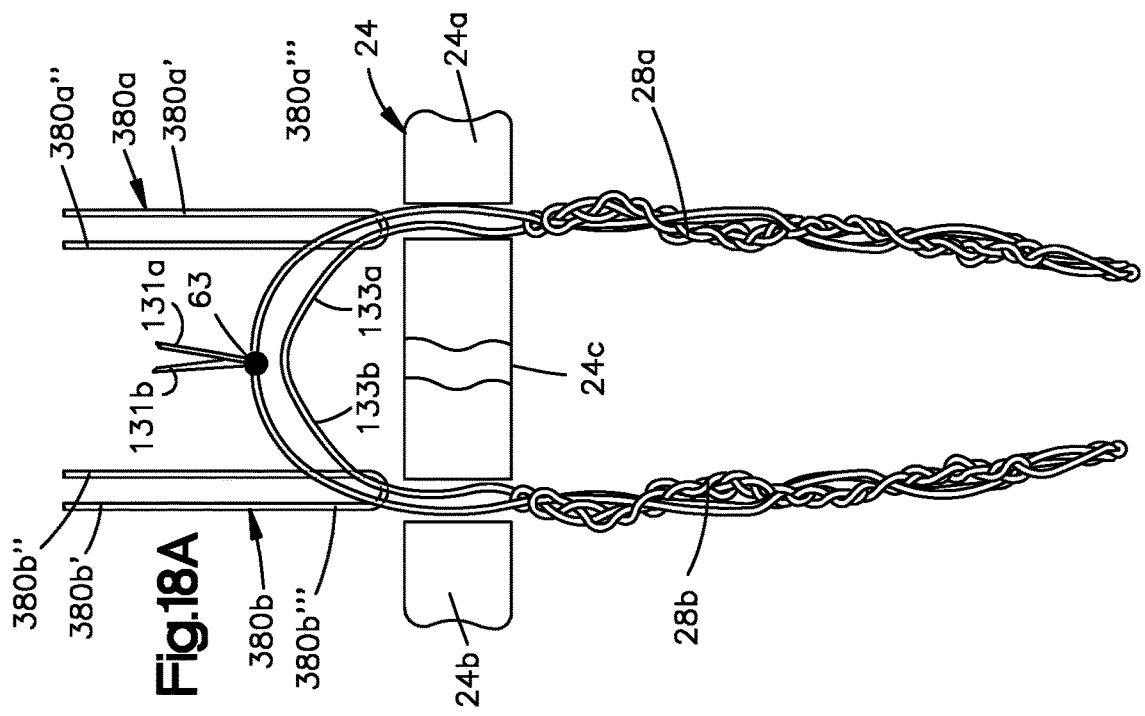

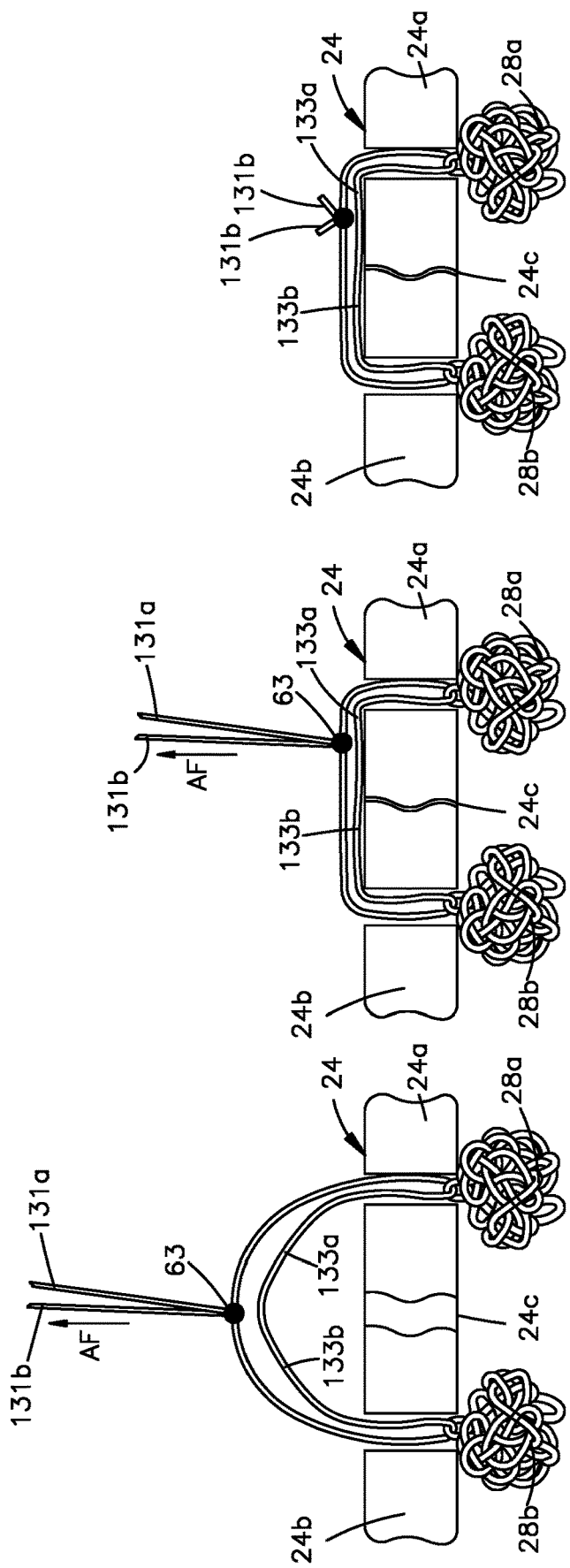

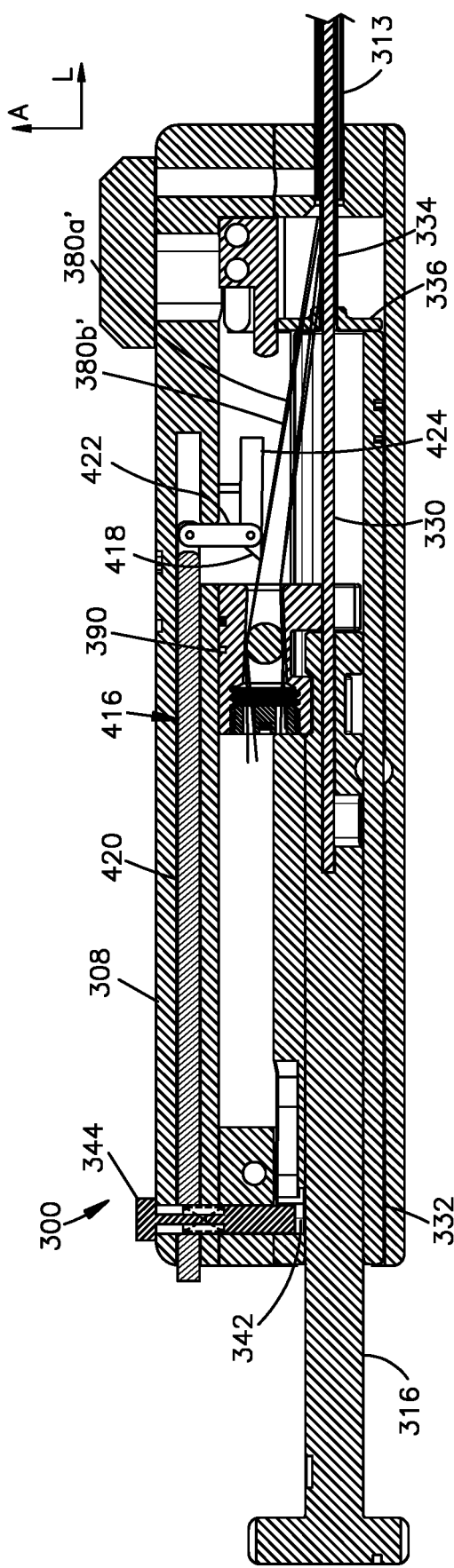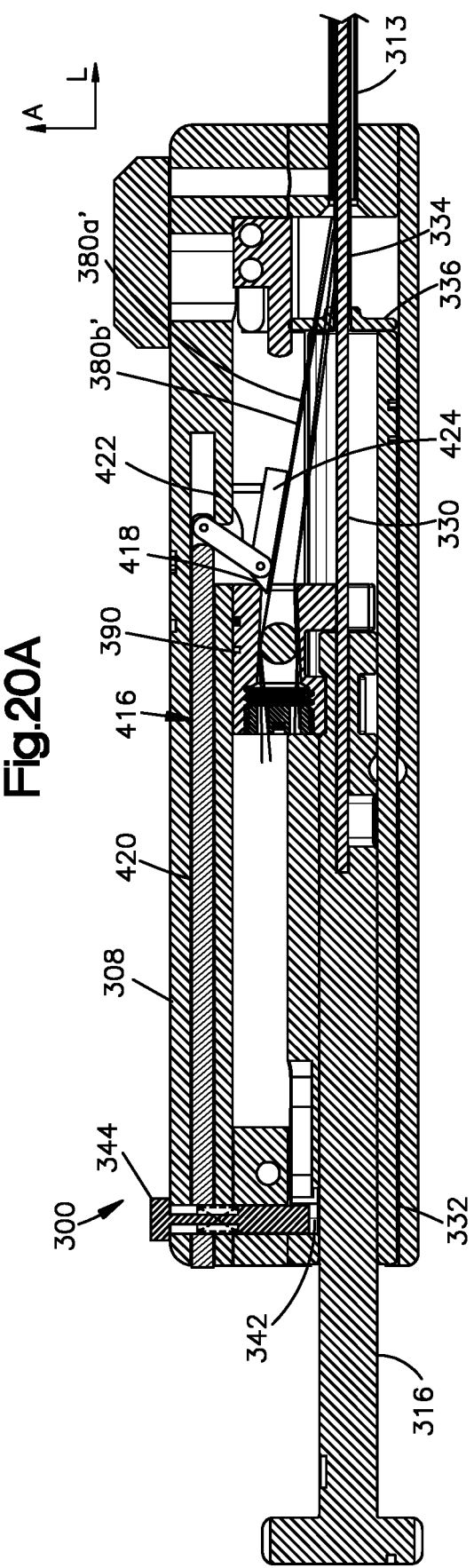

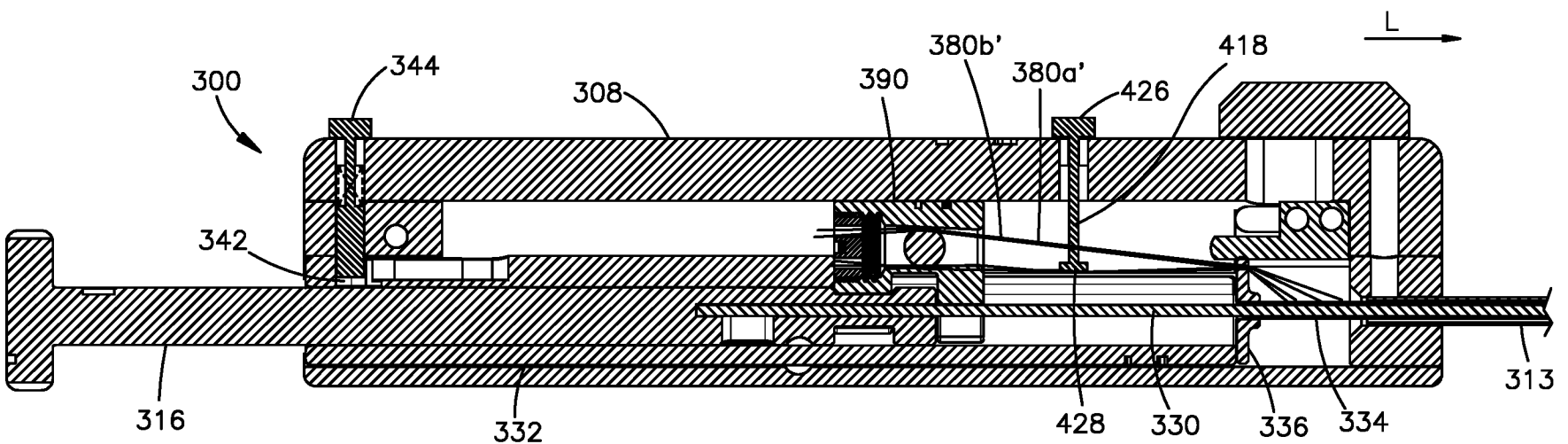

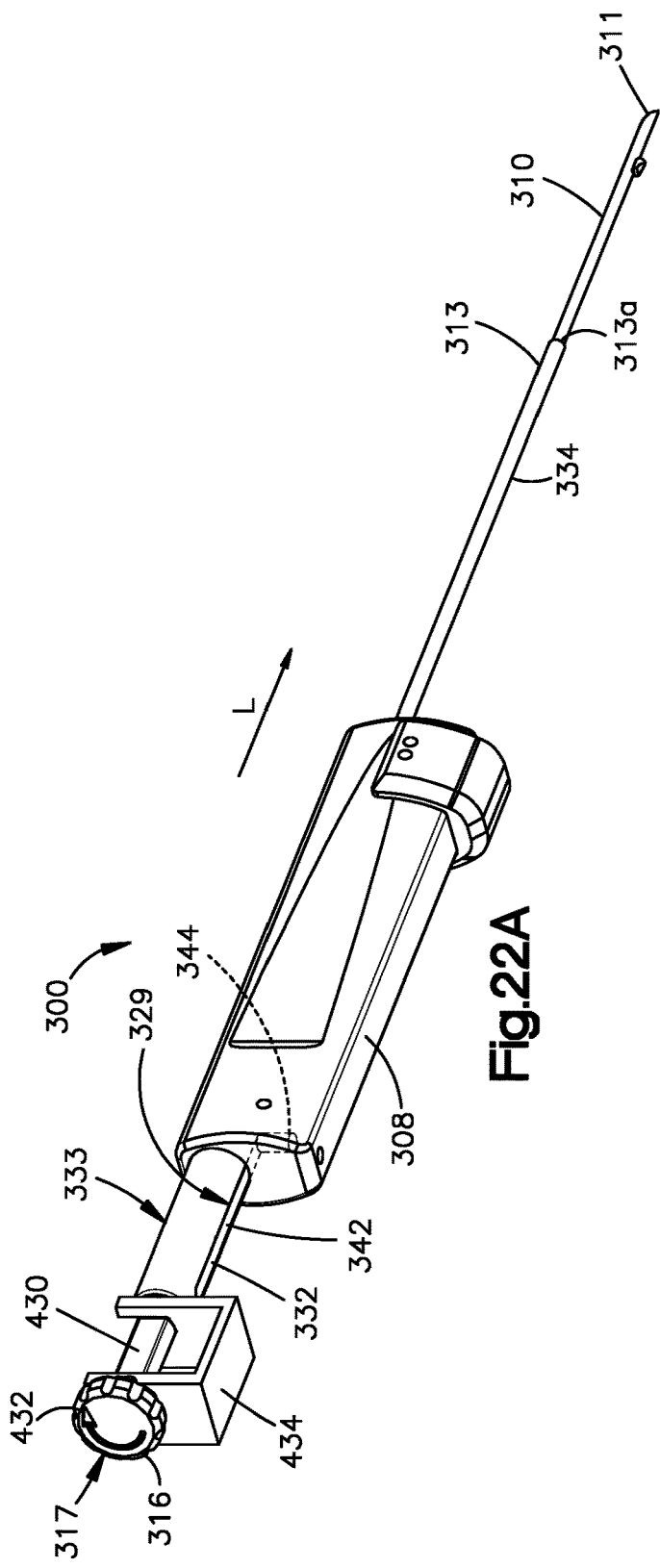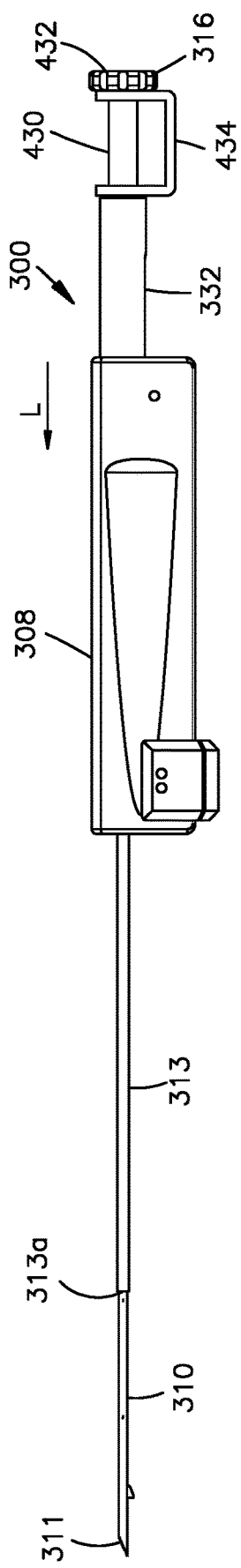

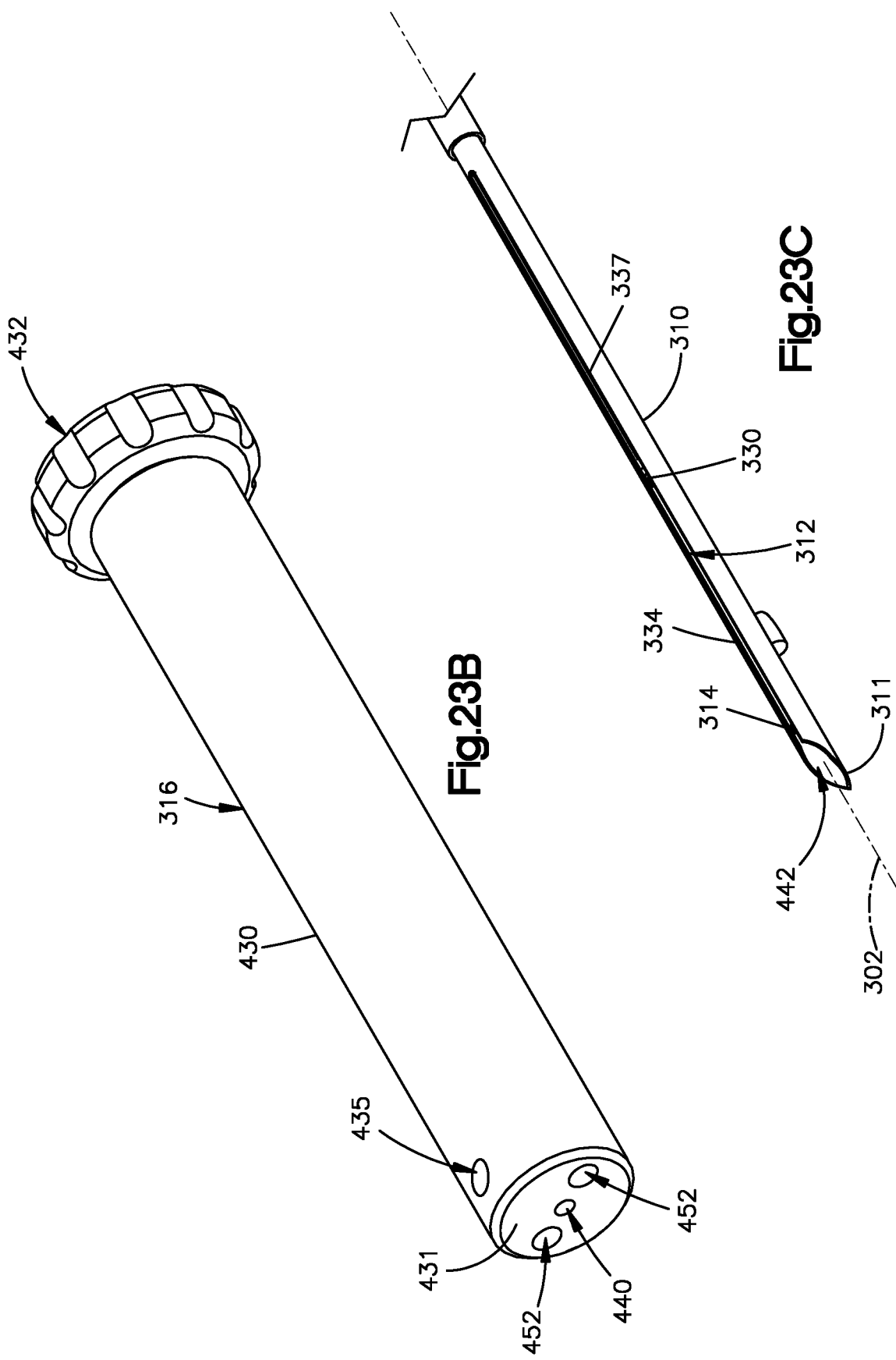

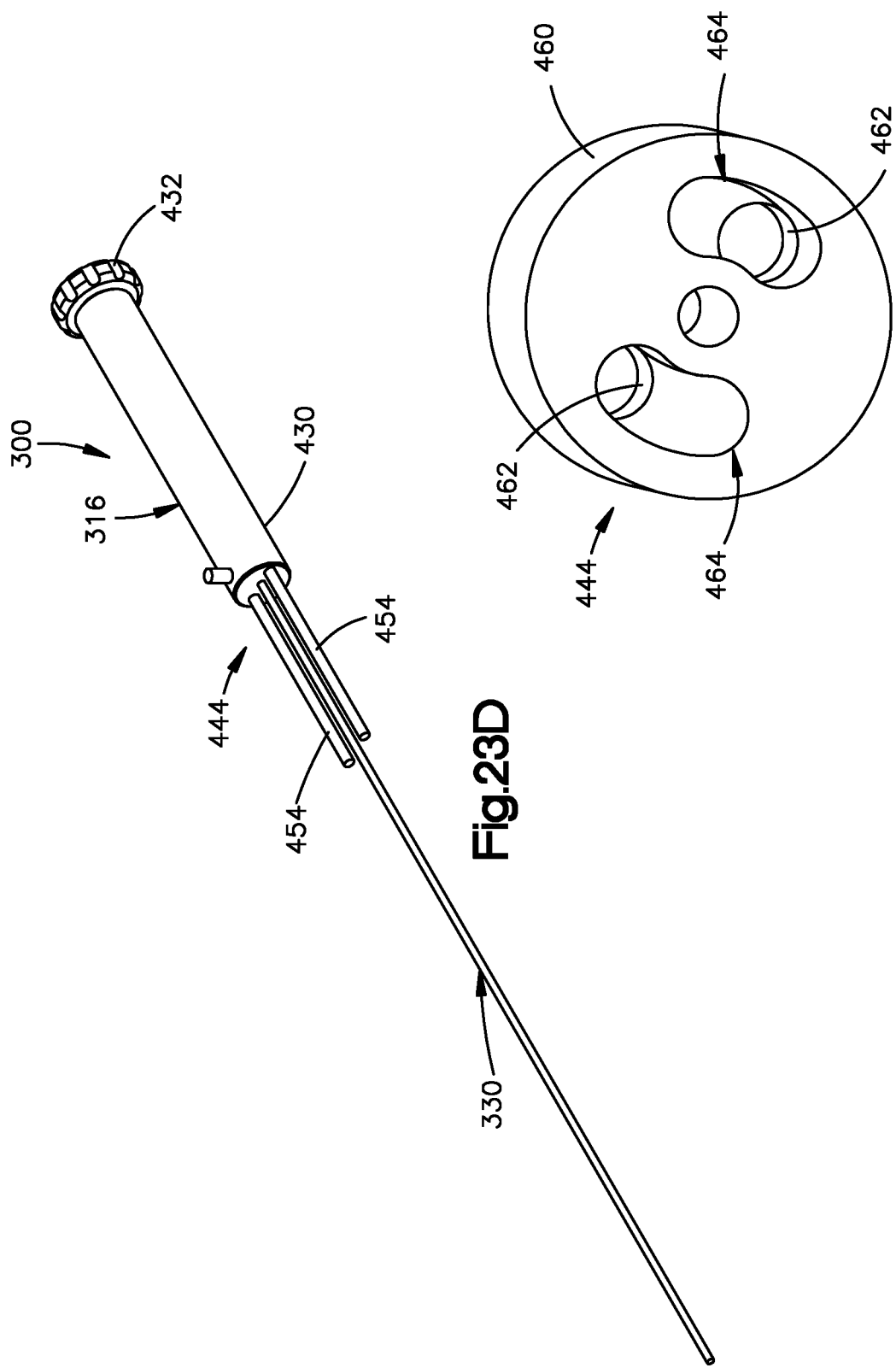

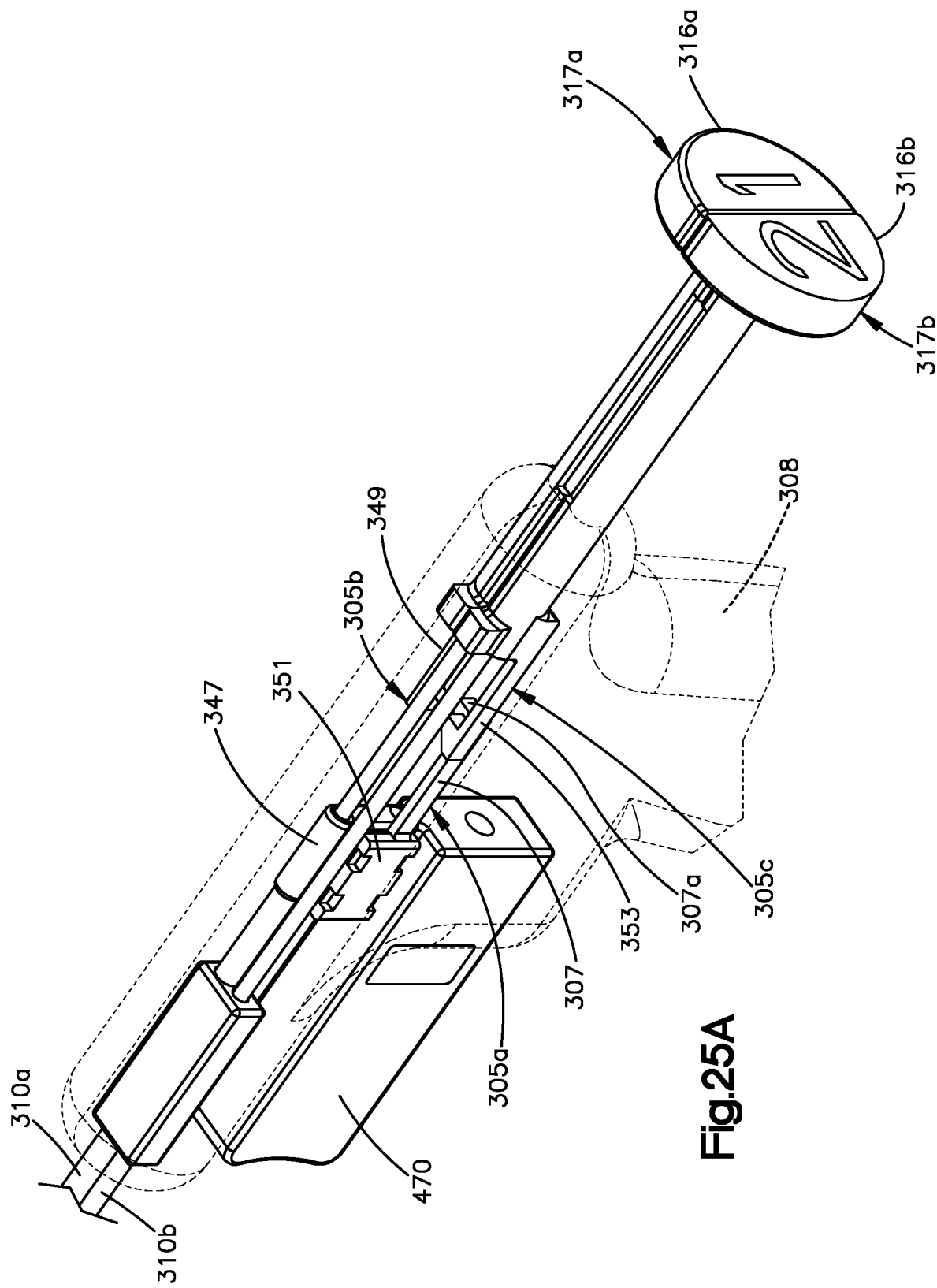

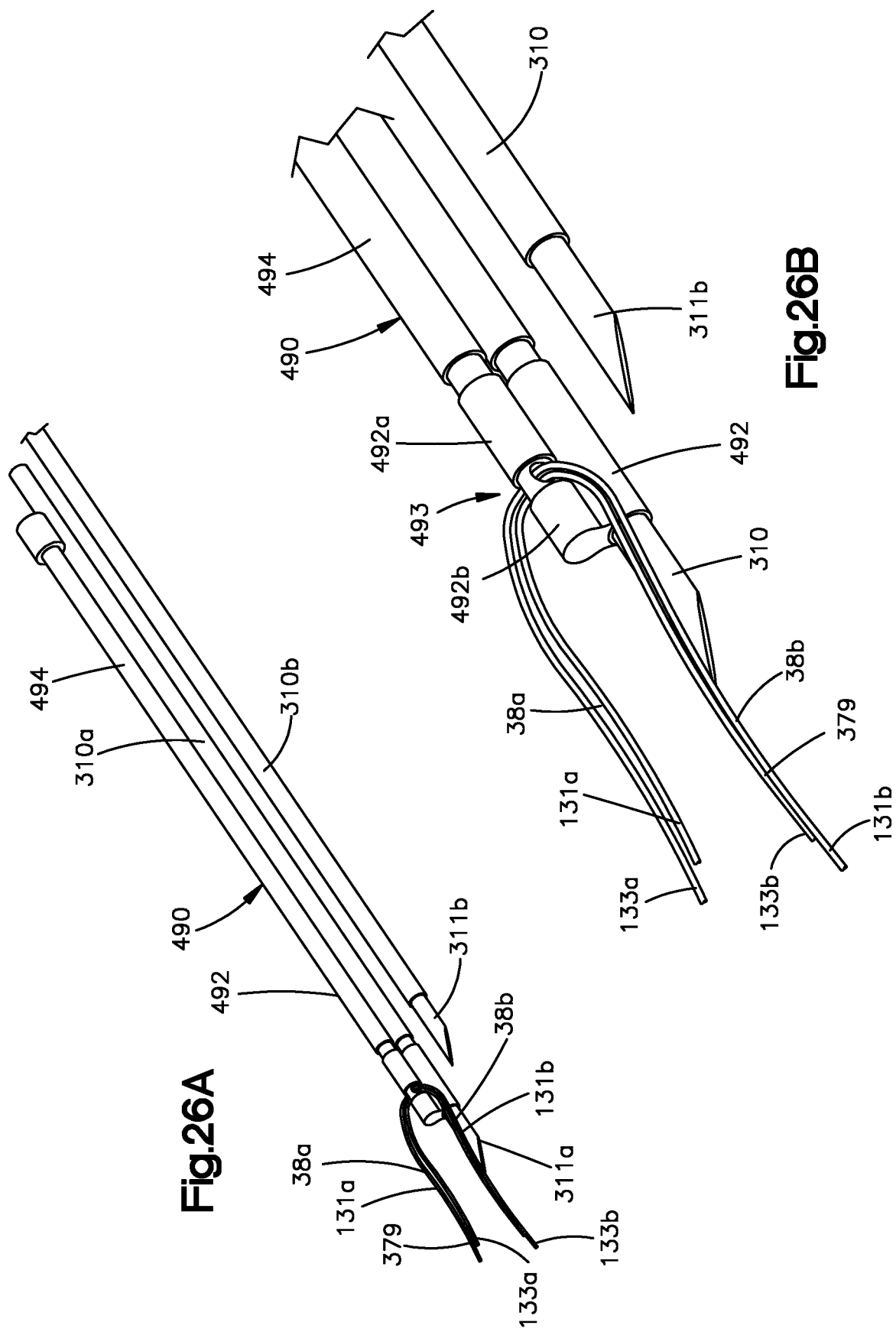

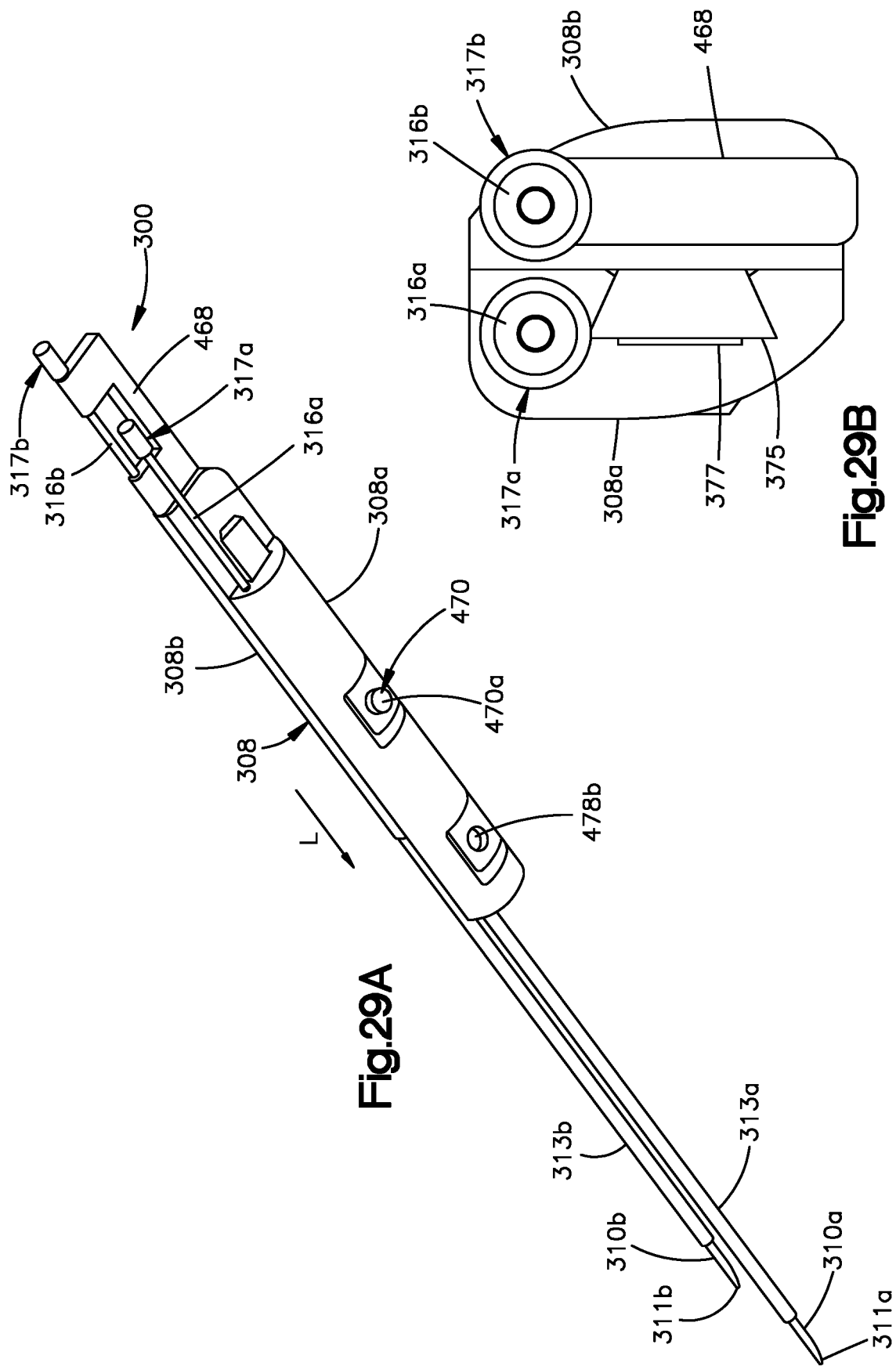

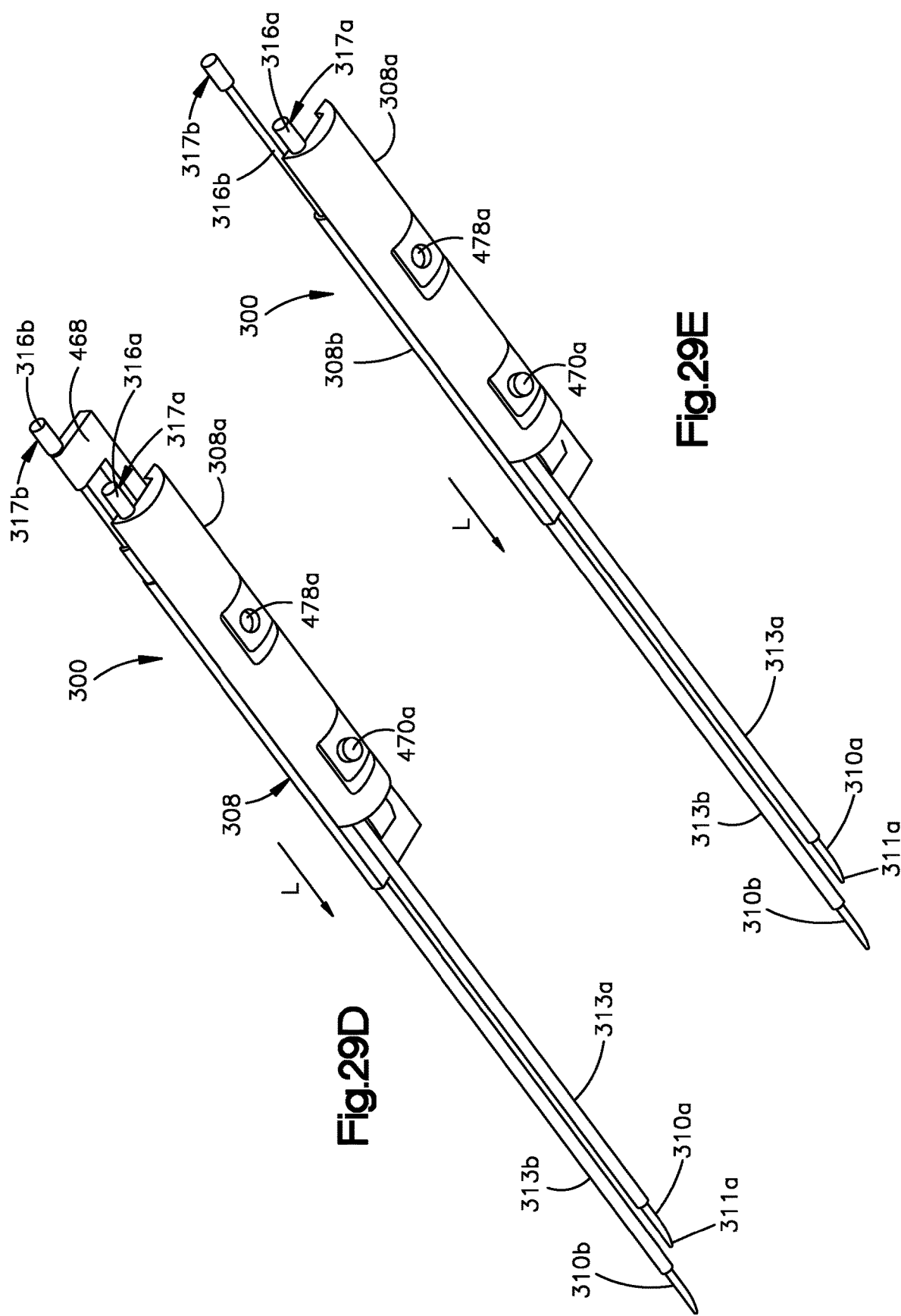

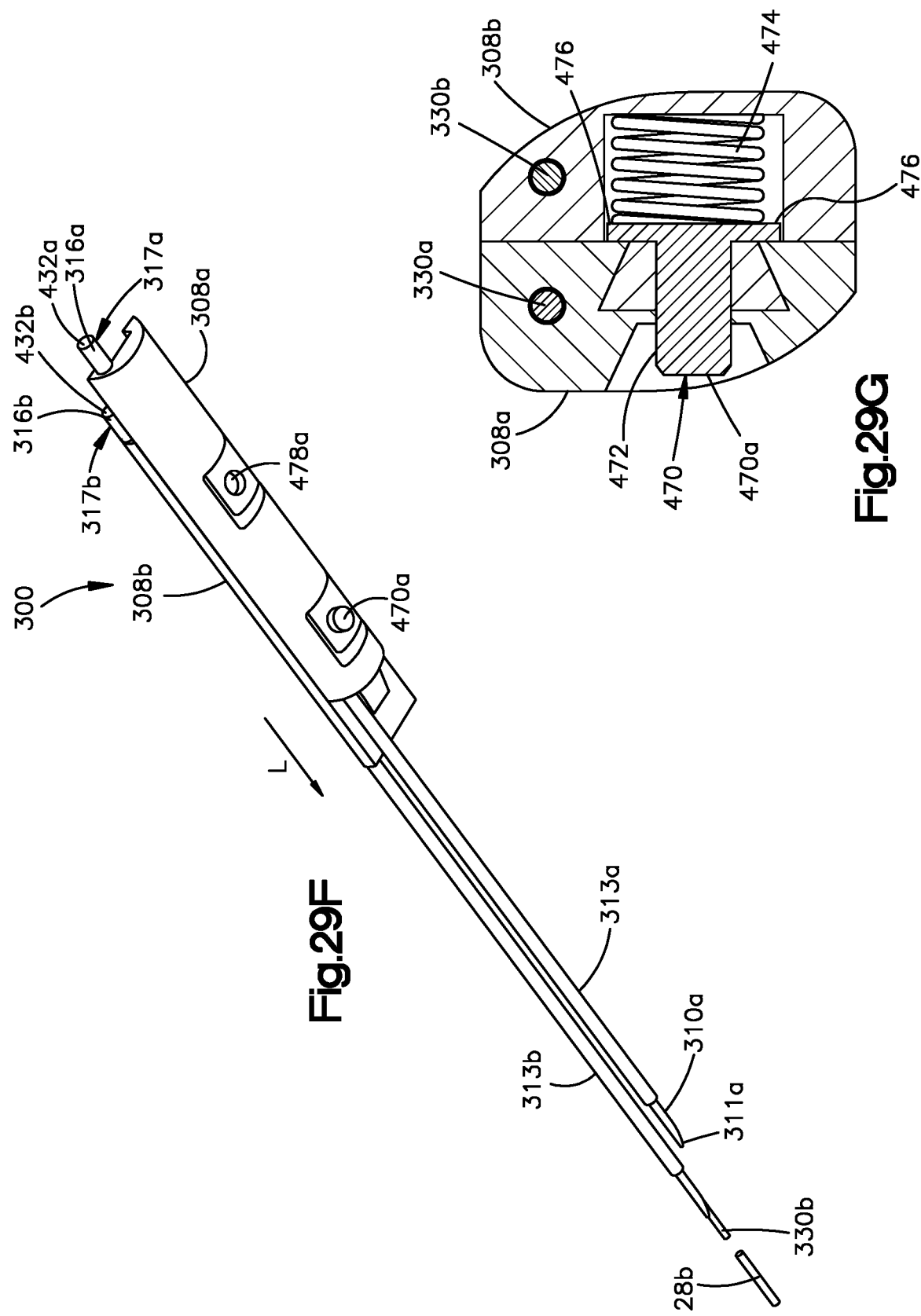

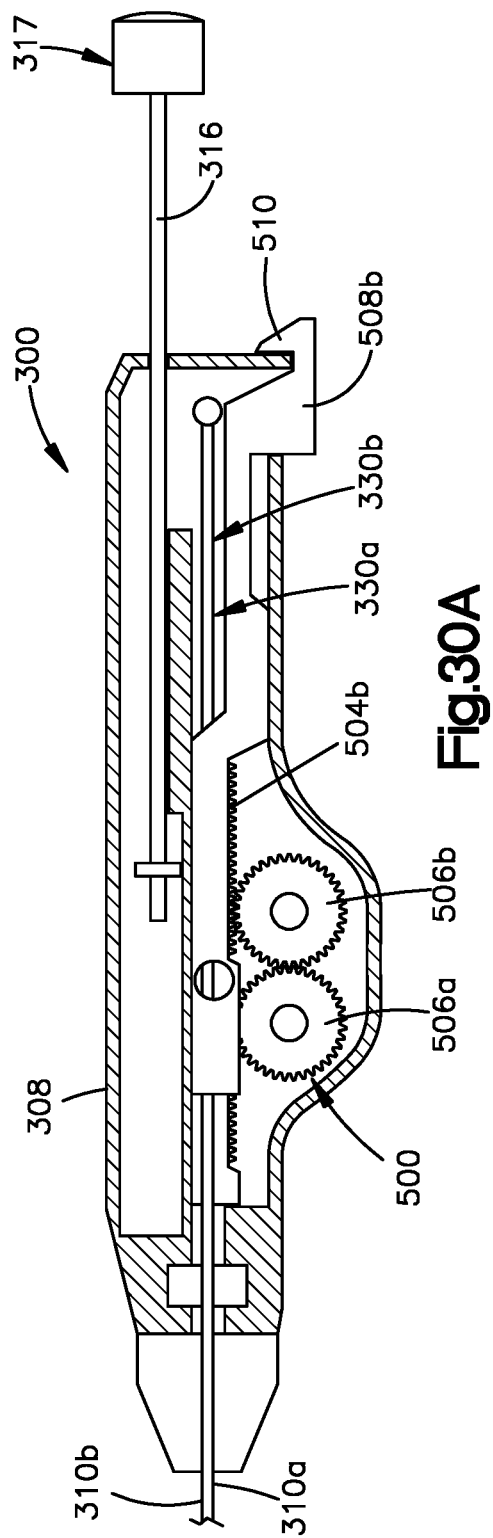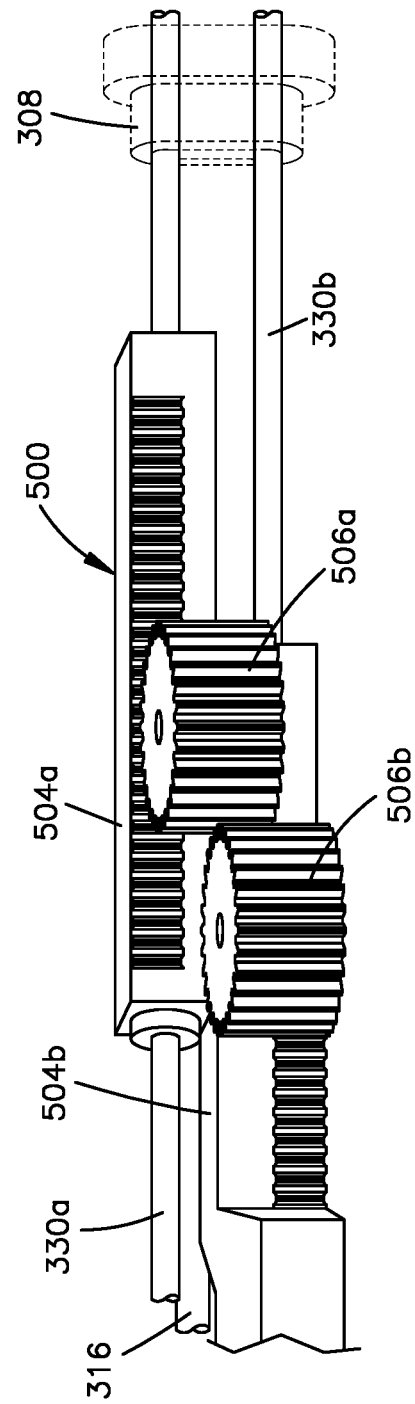

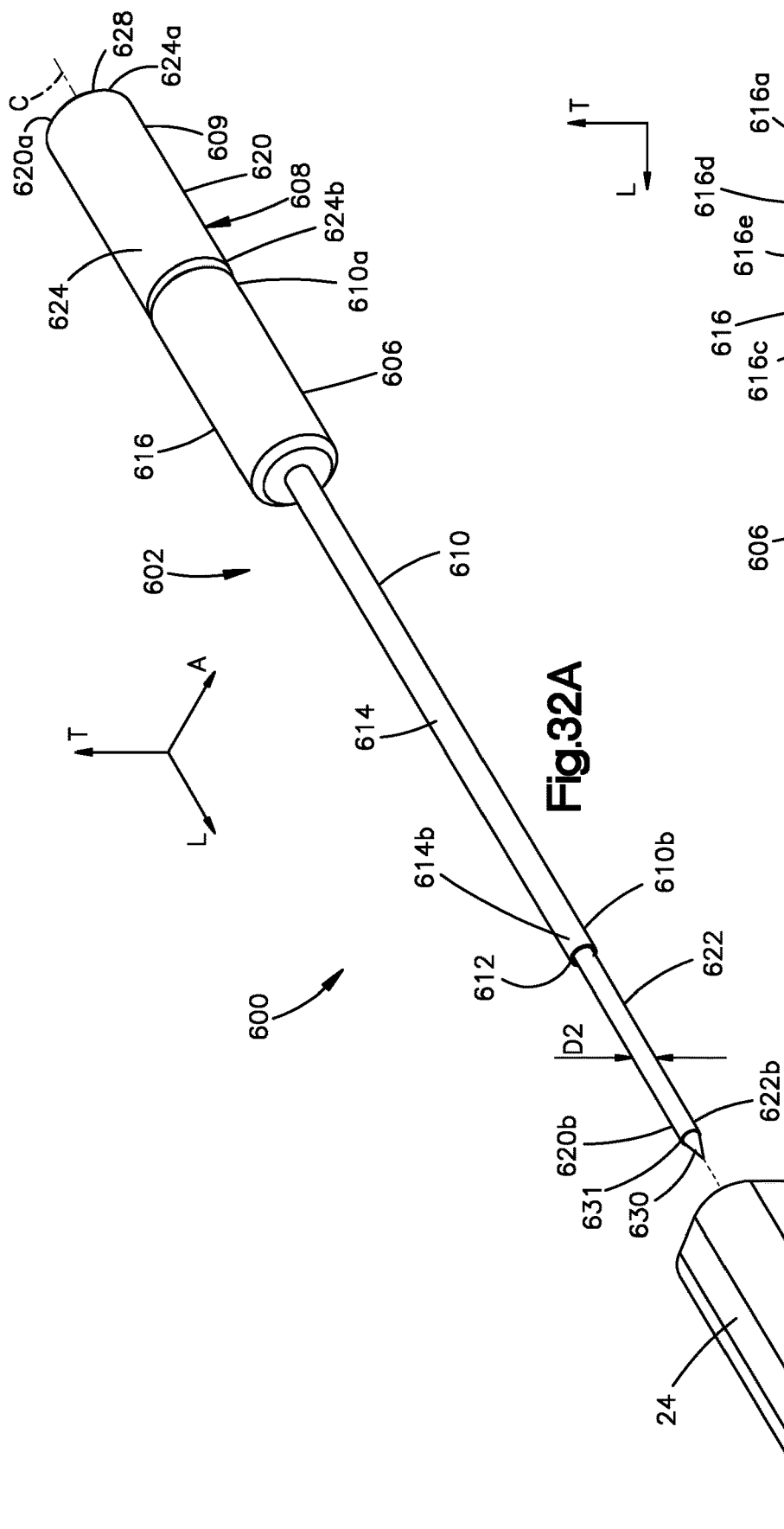
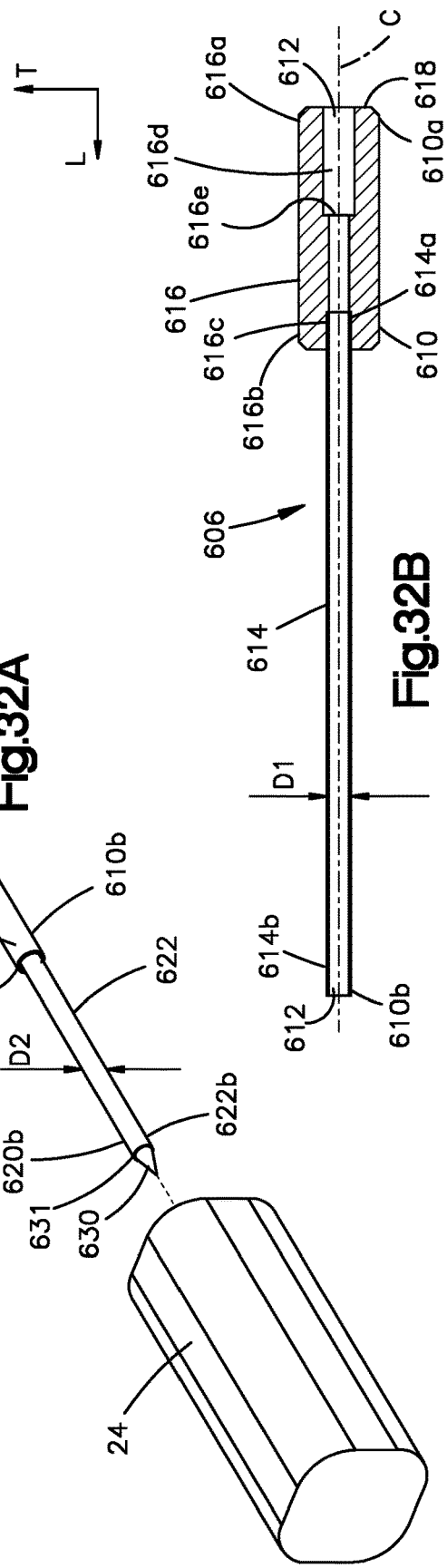

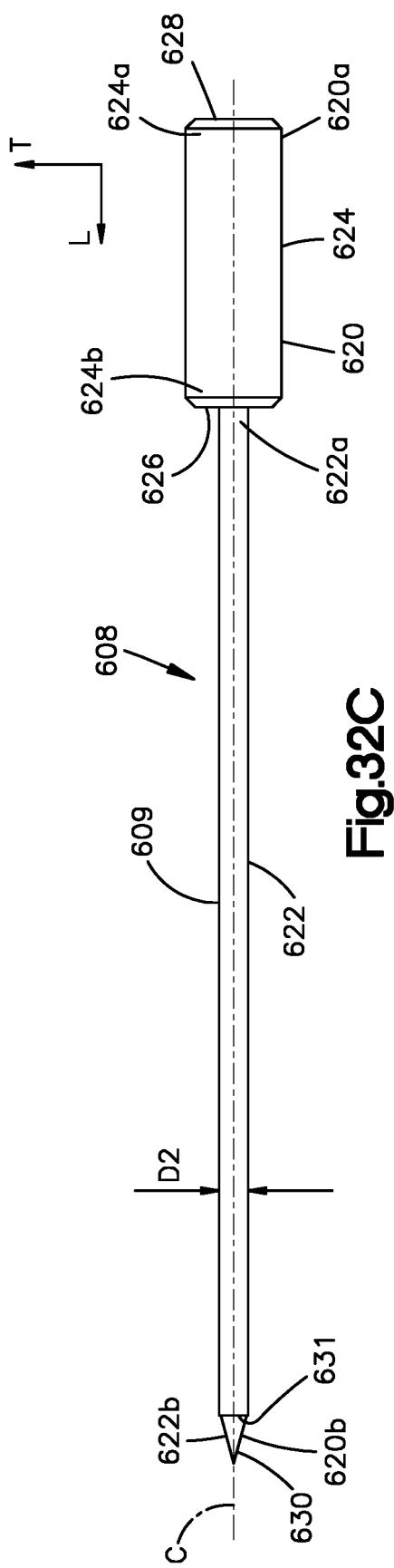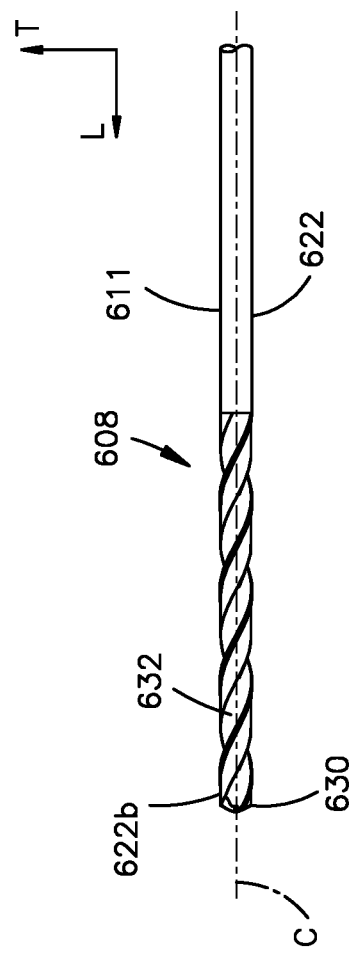
Fig.32C
Fig.32D

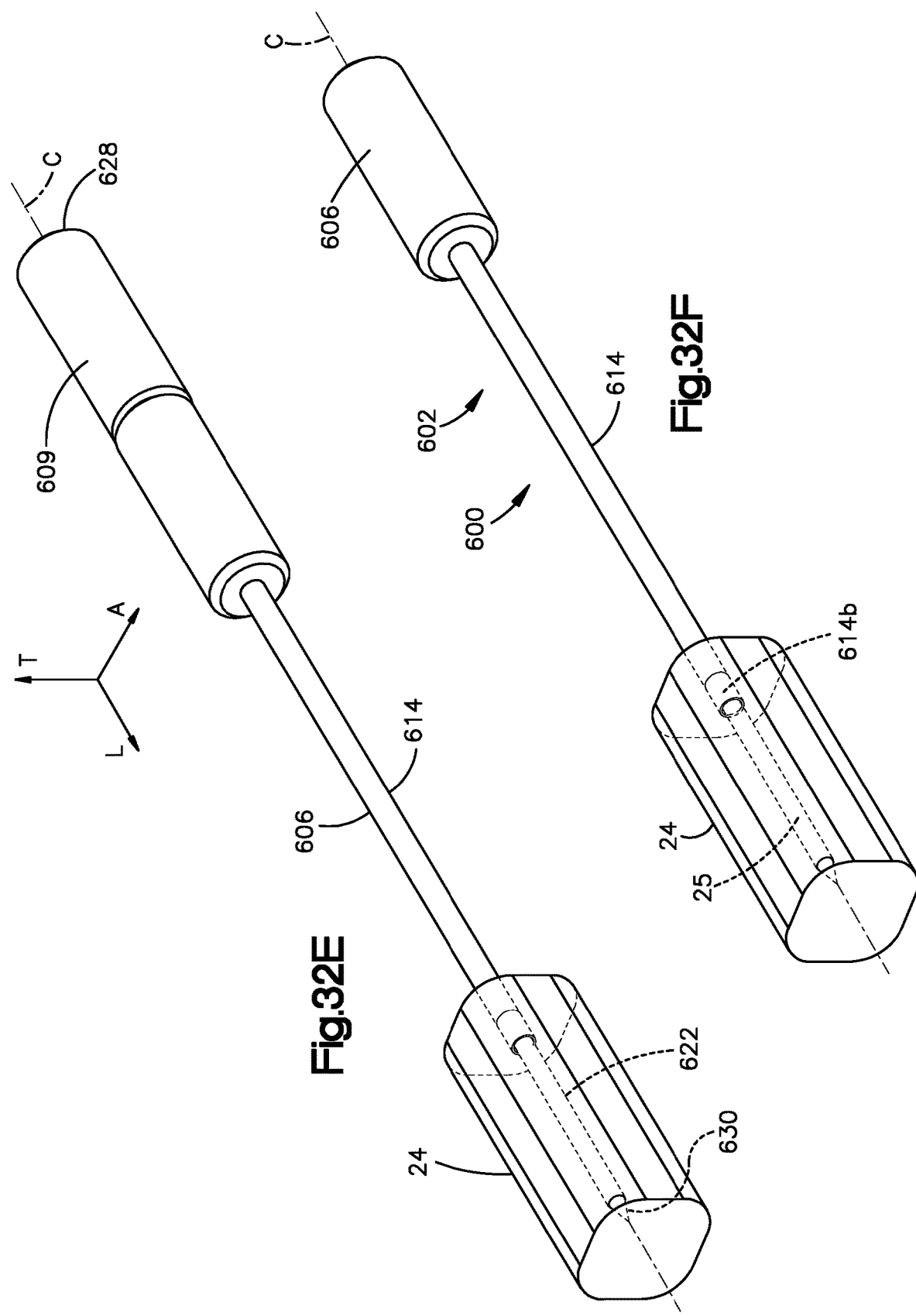

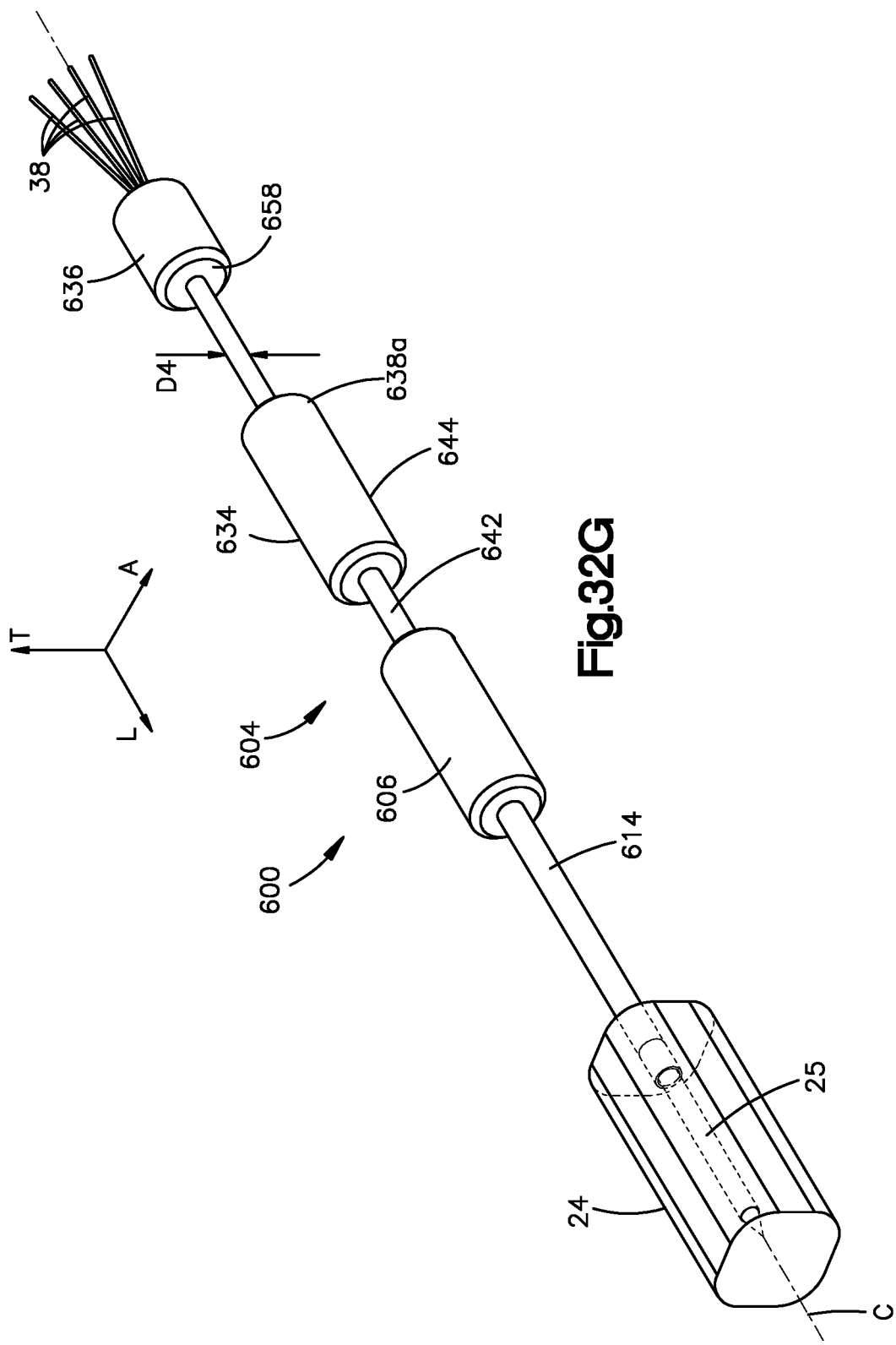

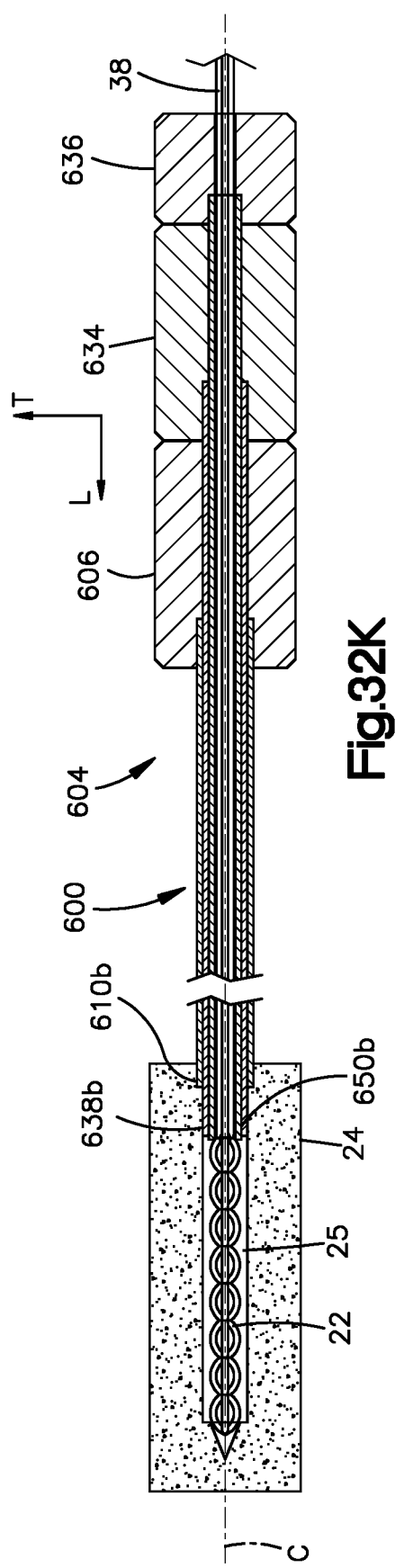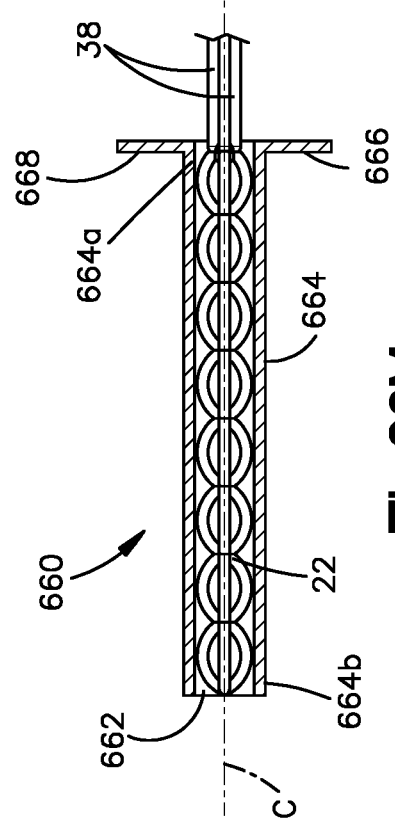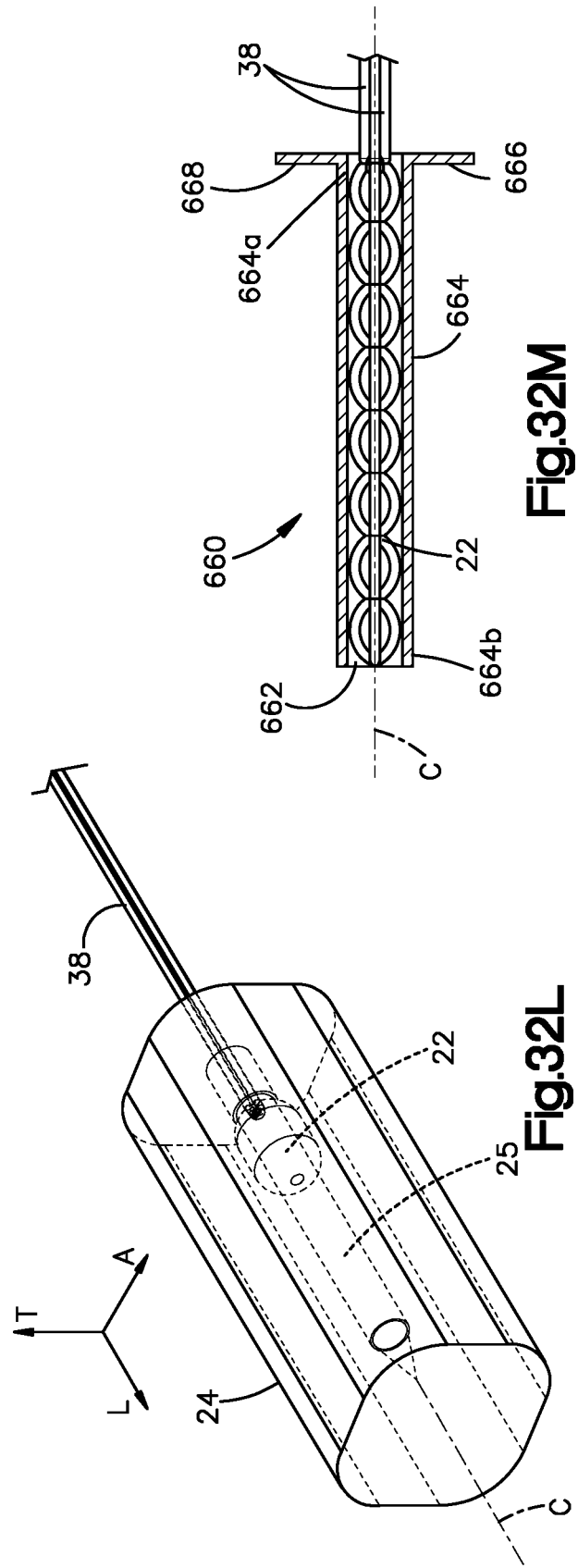

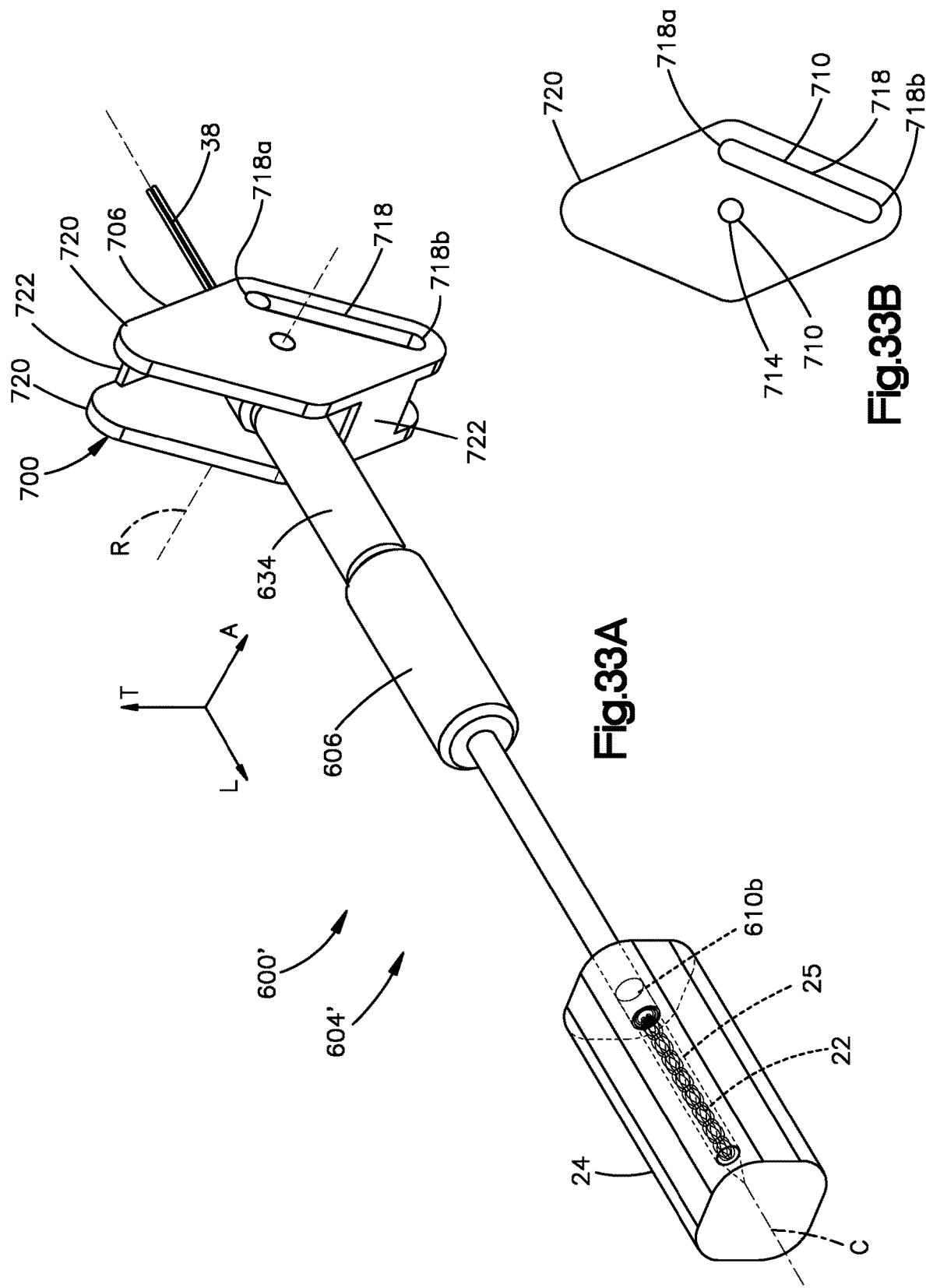

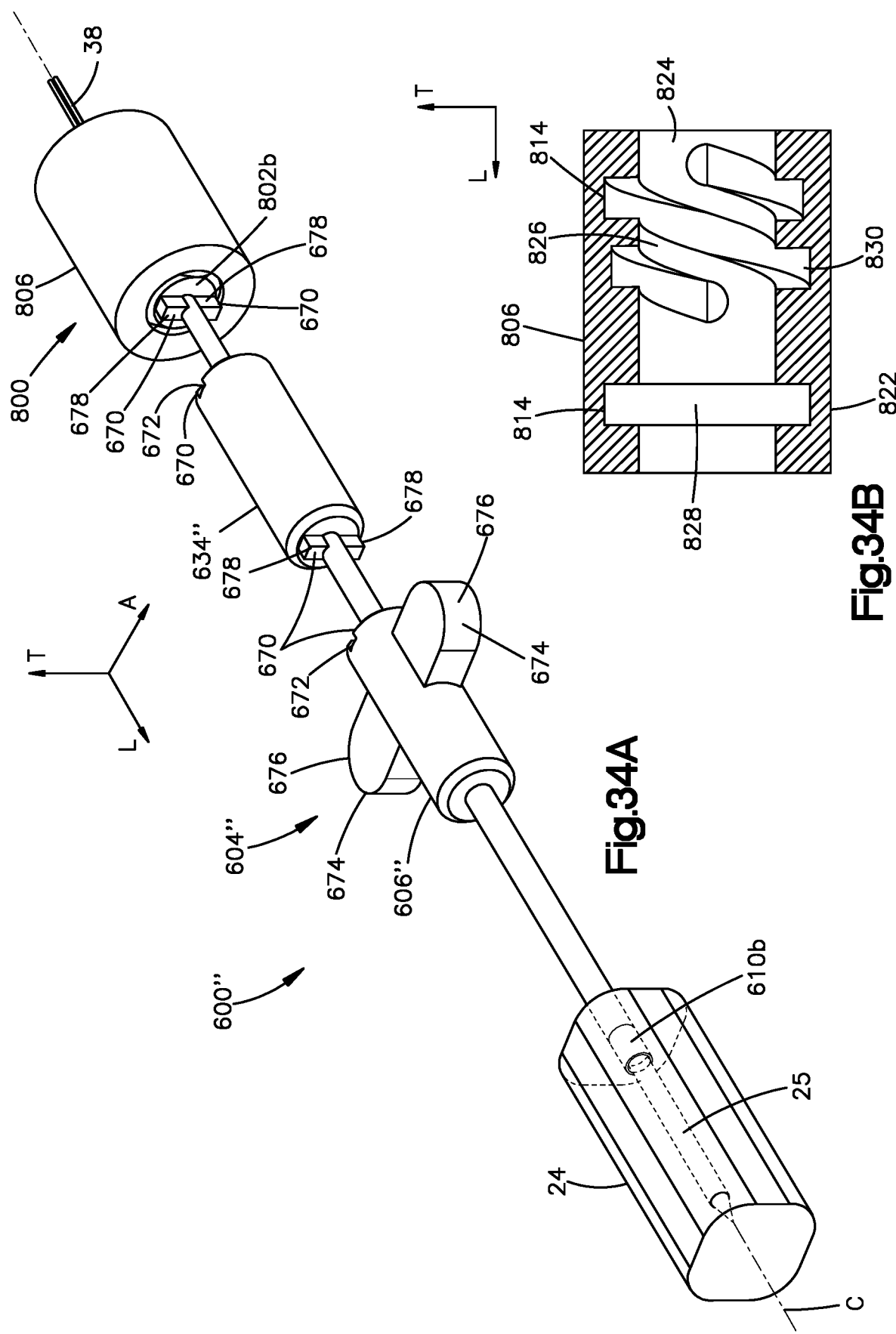

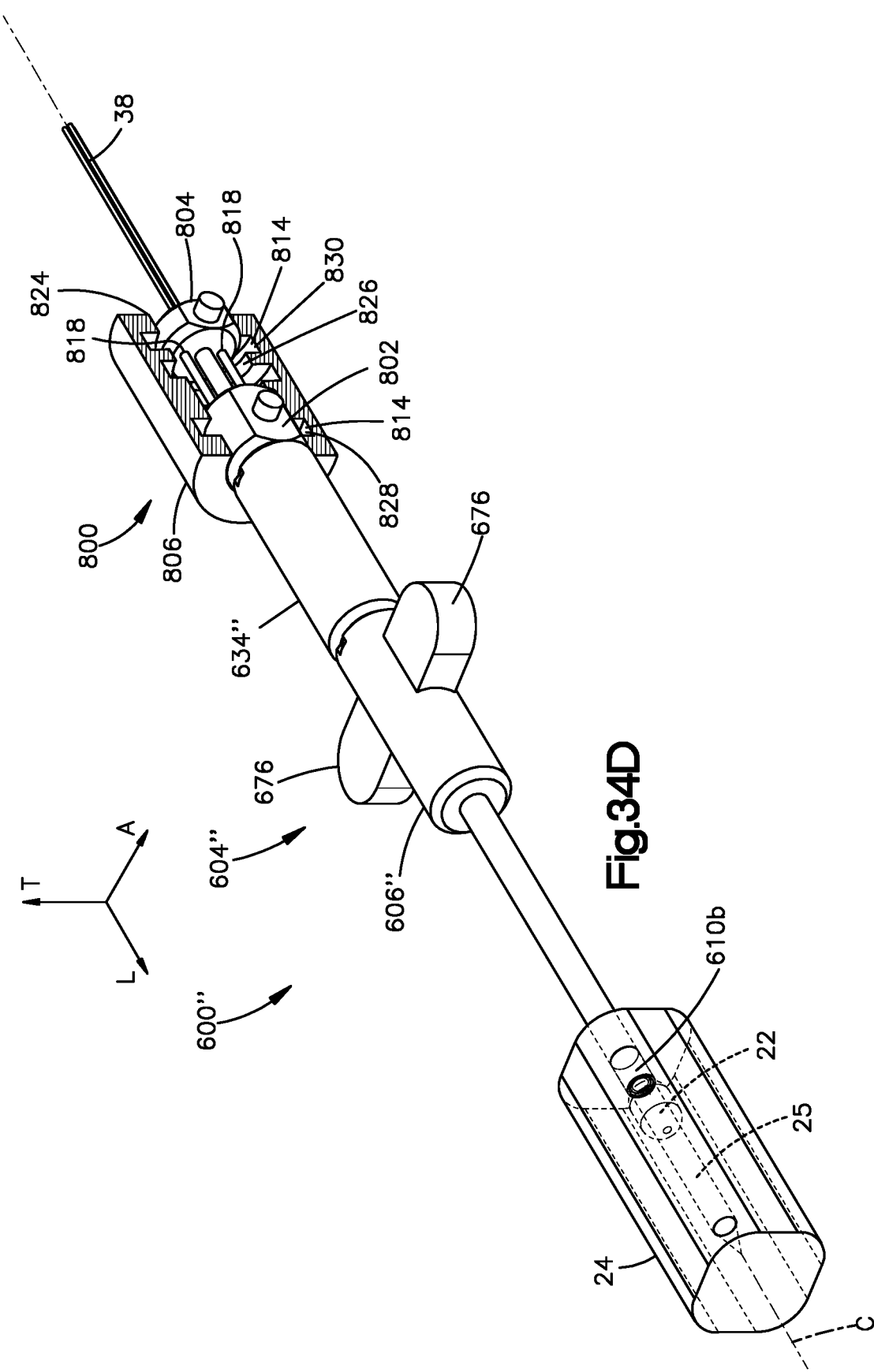

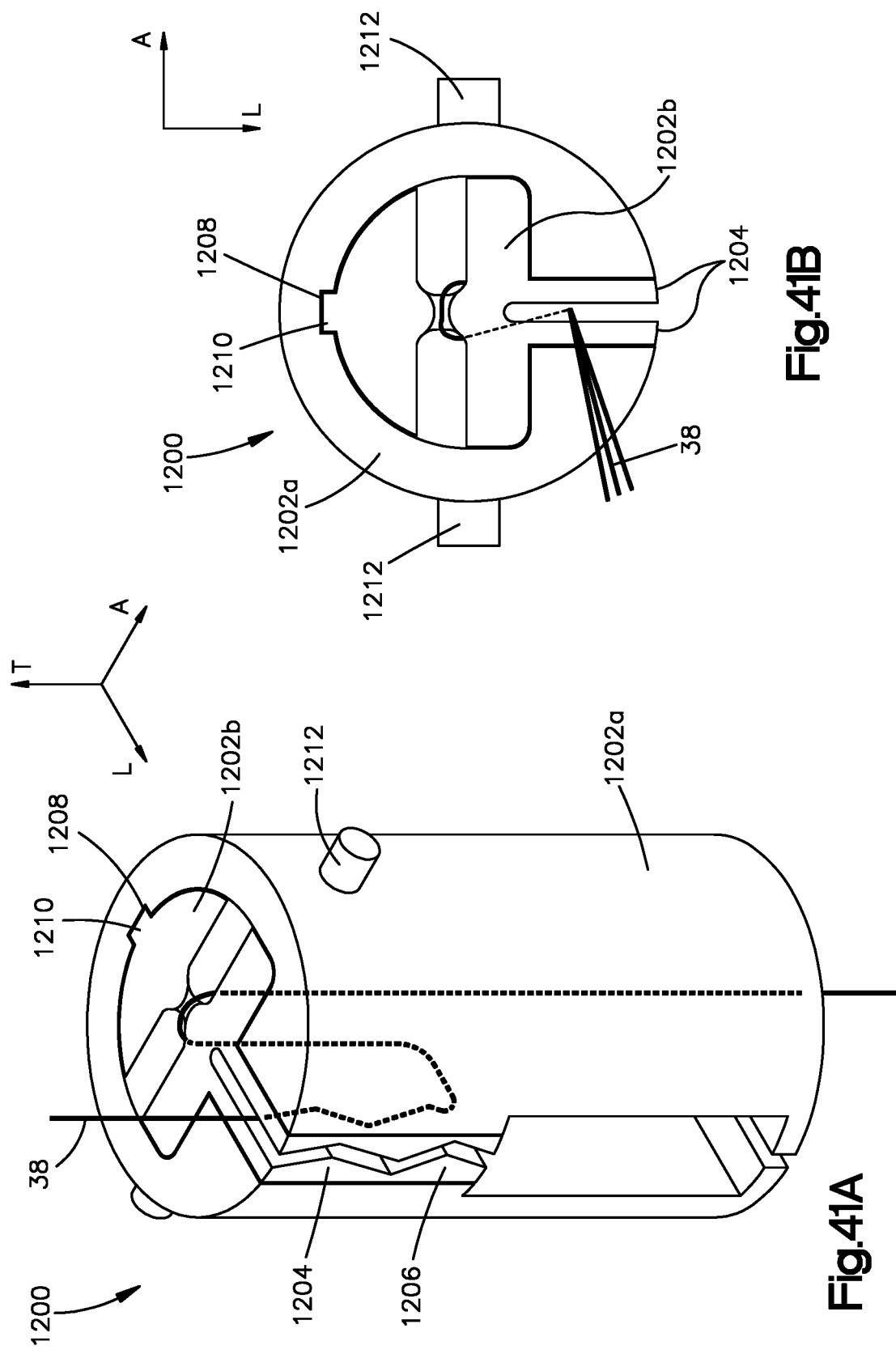

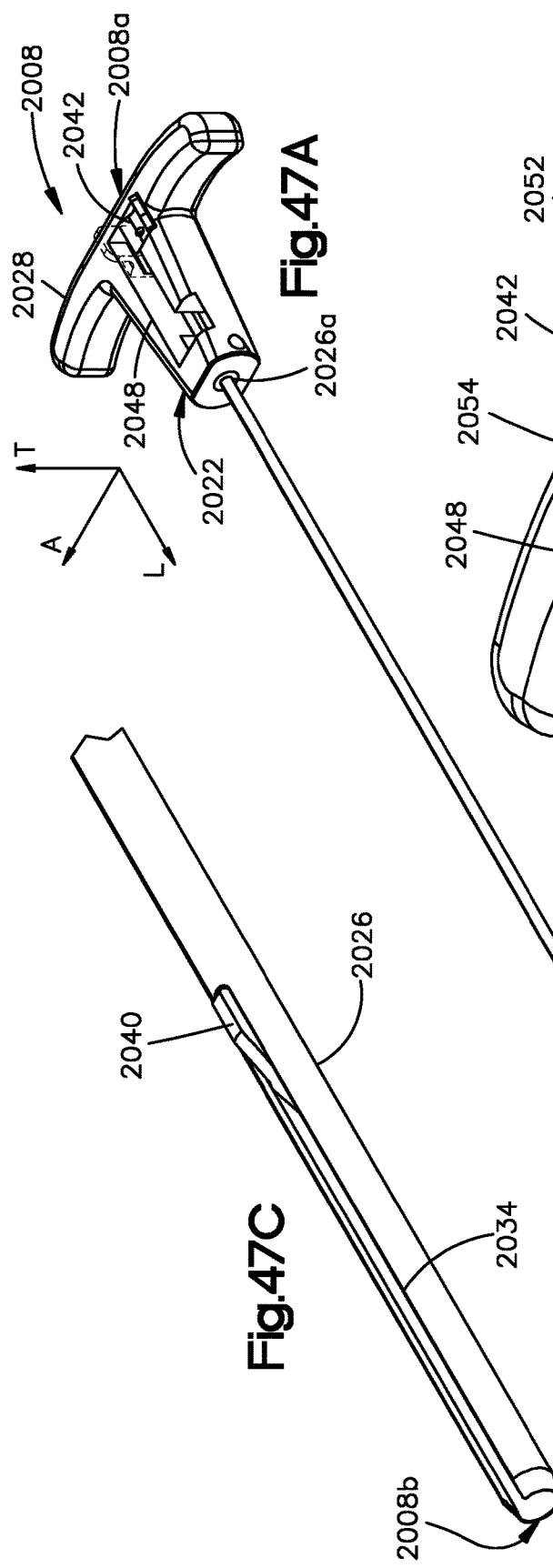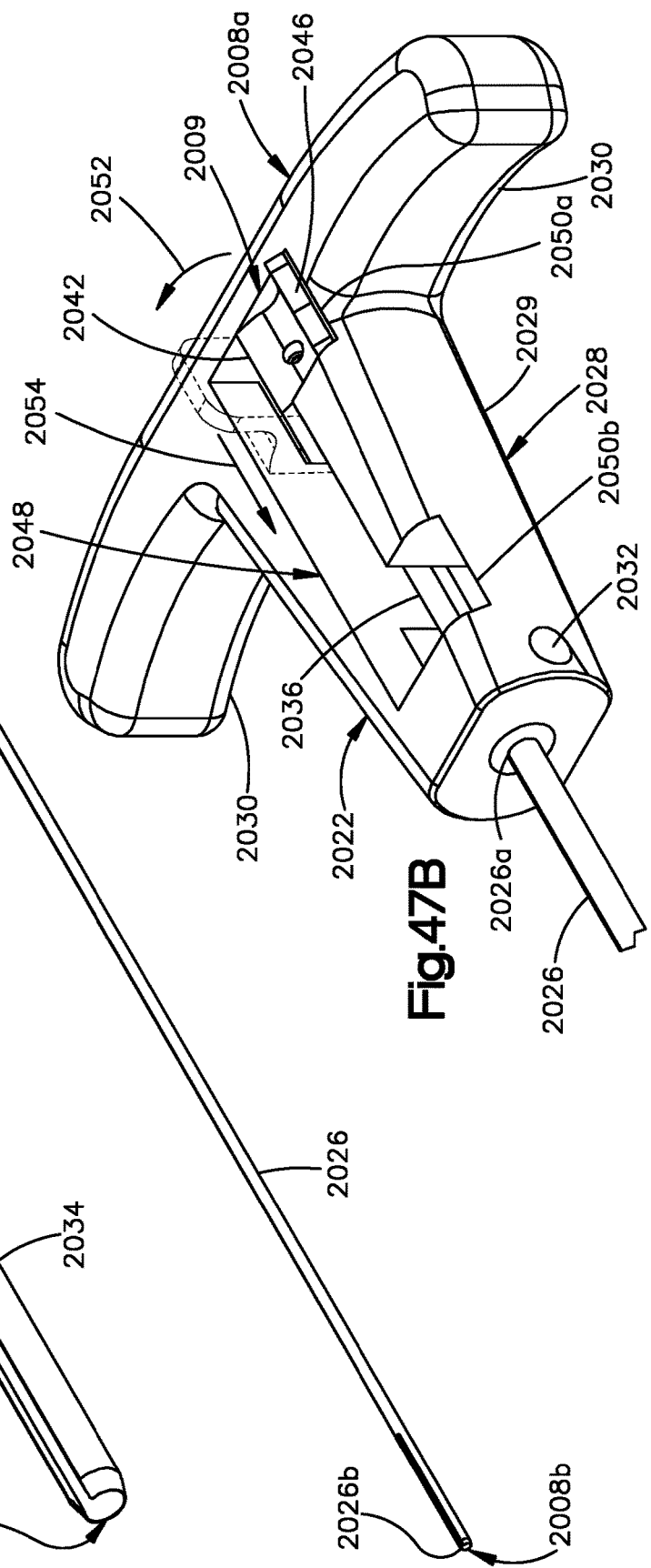

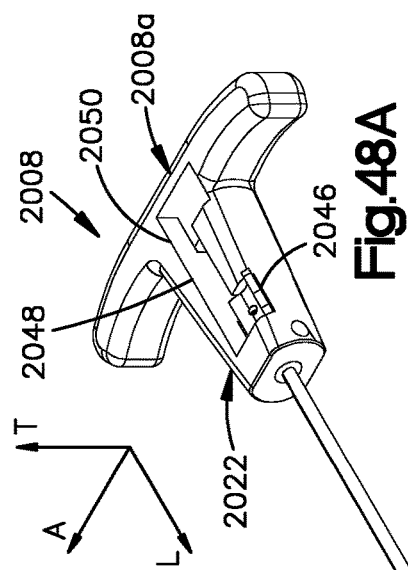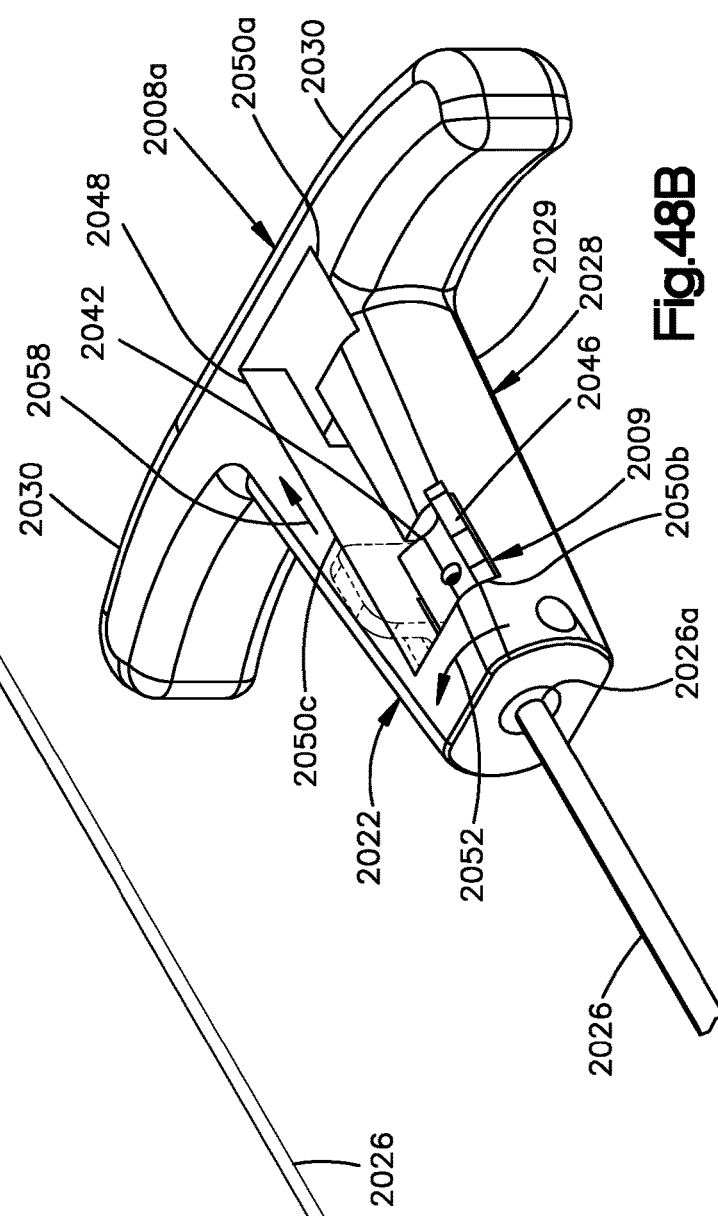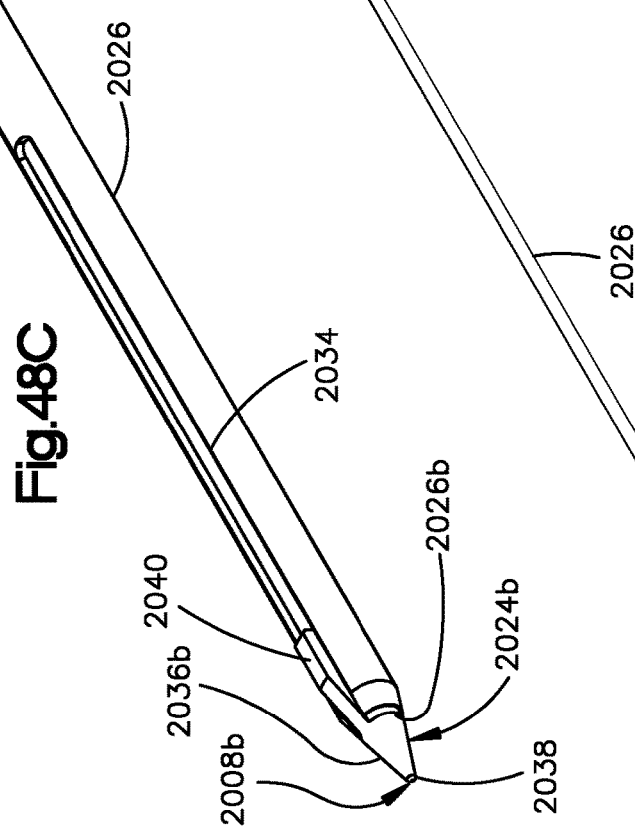

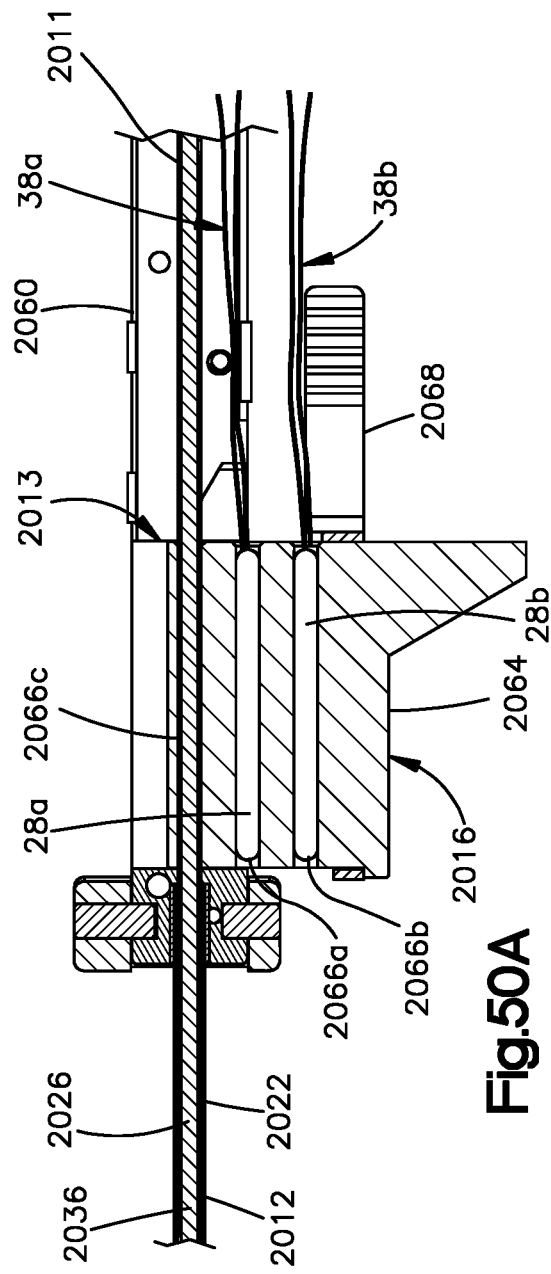
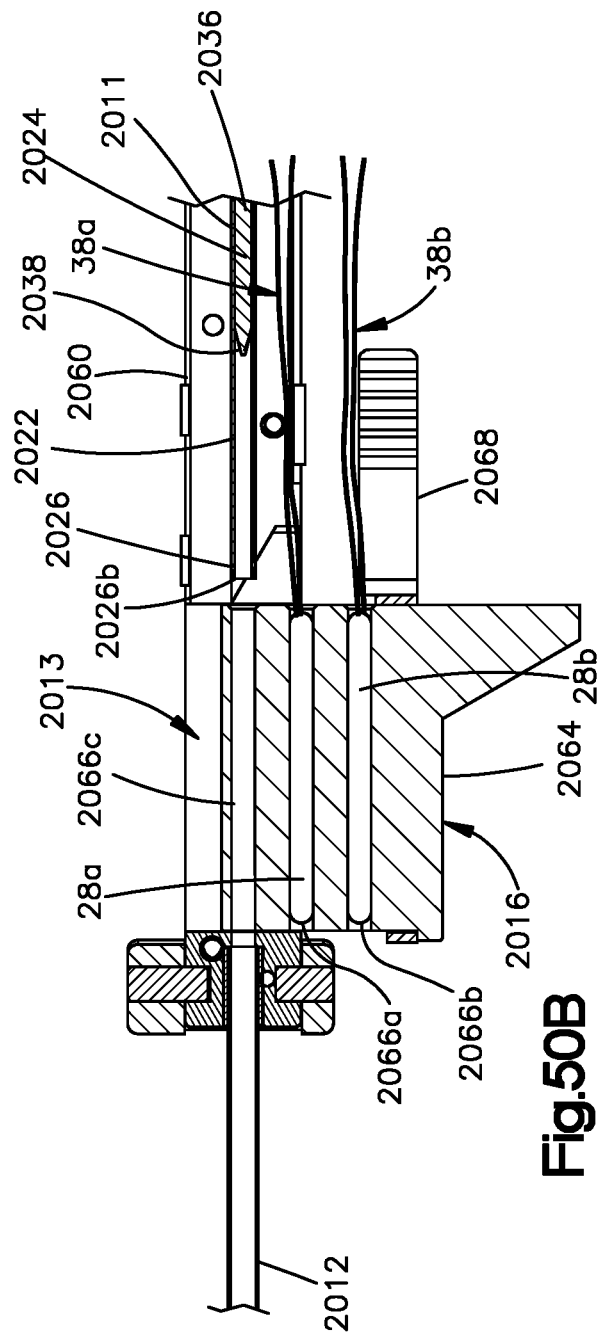

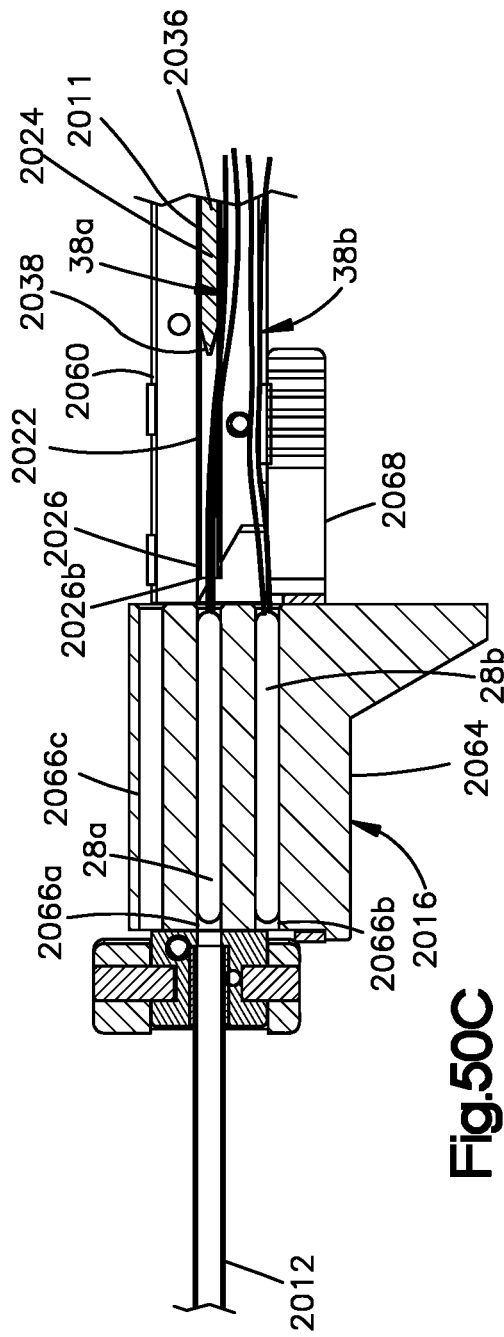
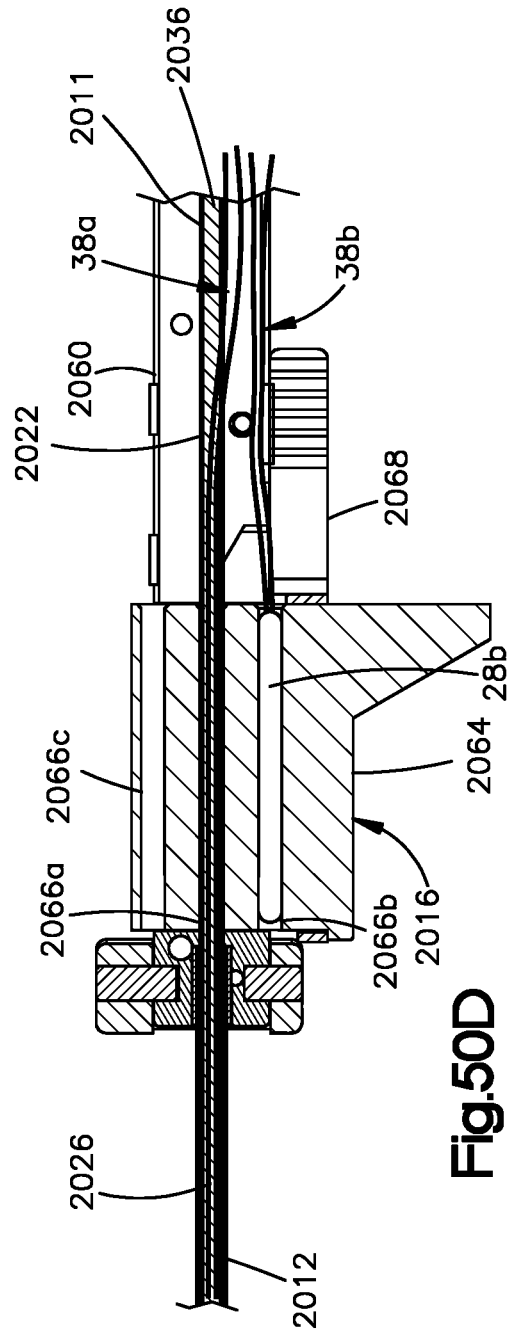

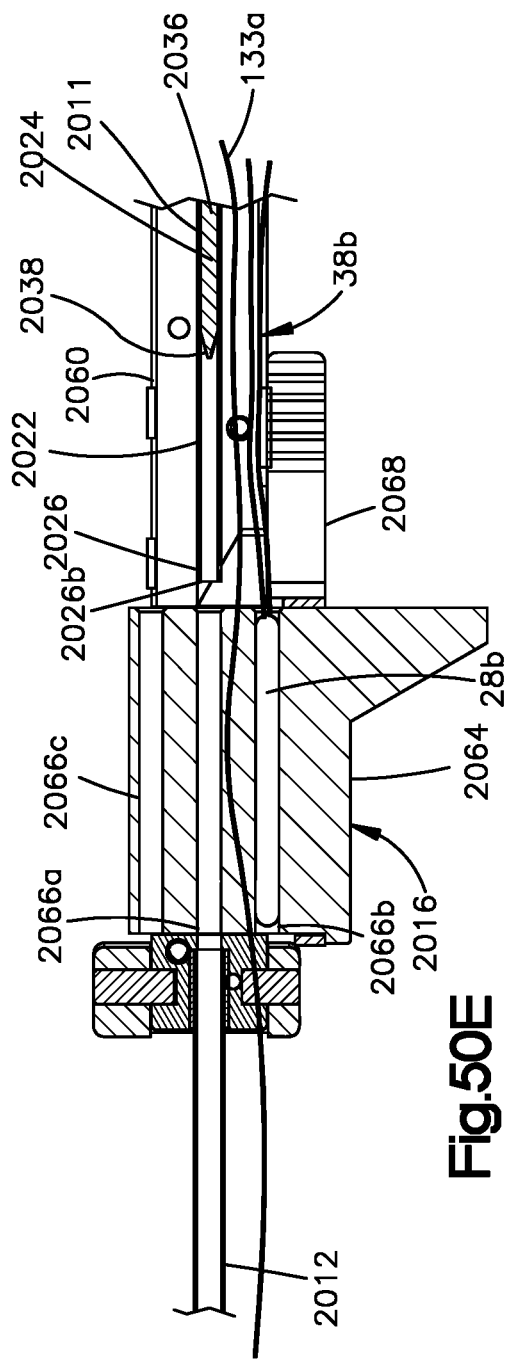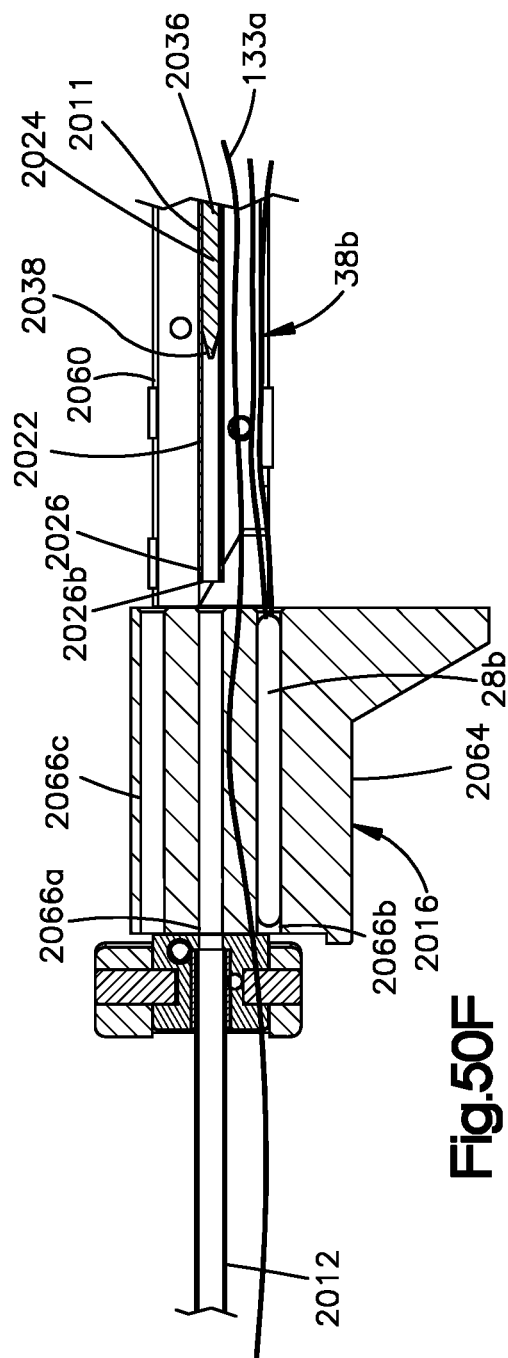

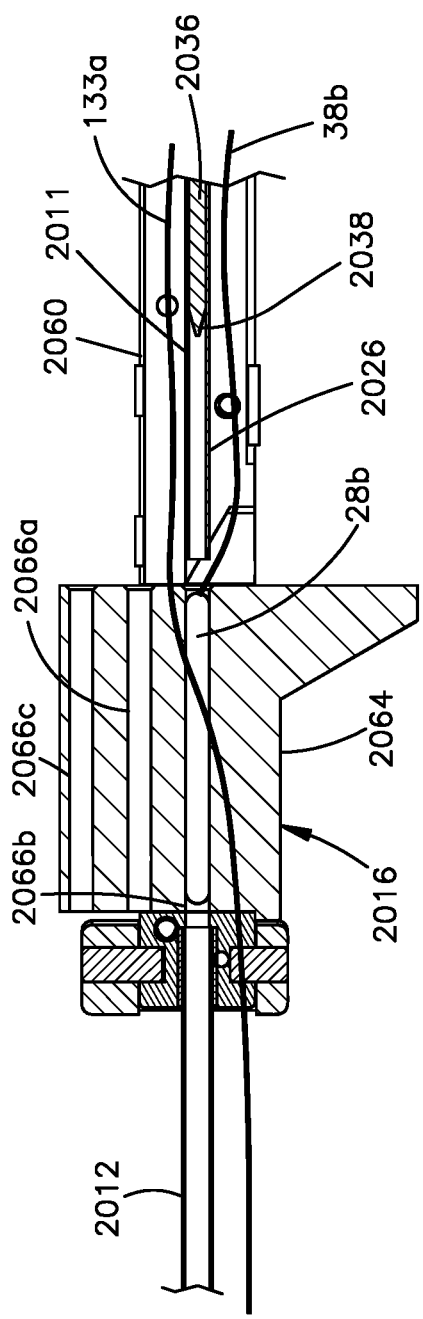
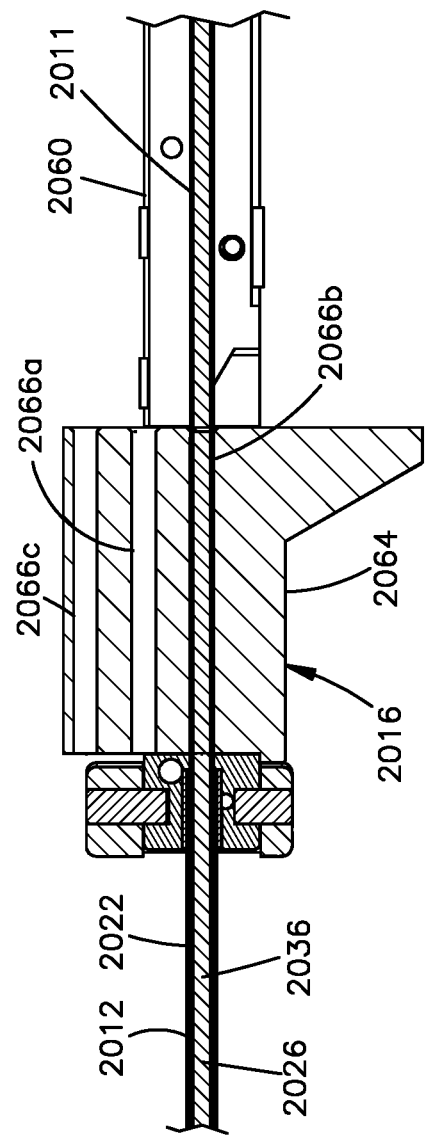
Fig.50G
Fig.50H

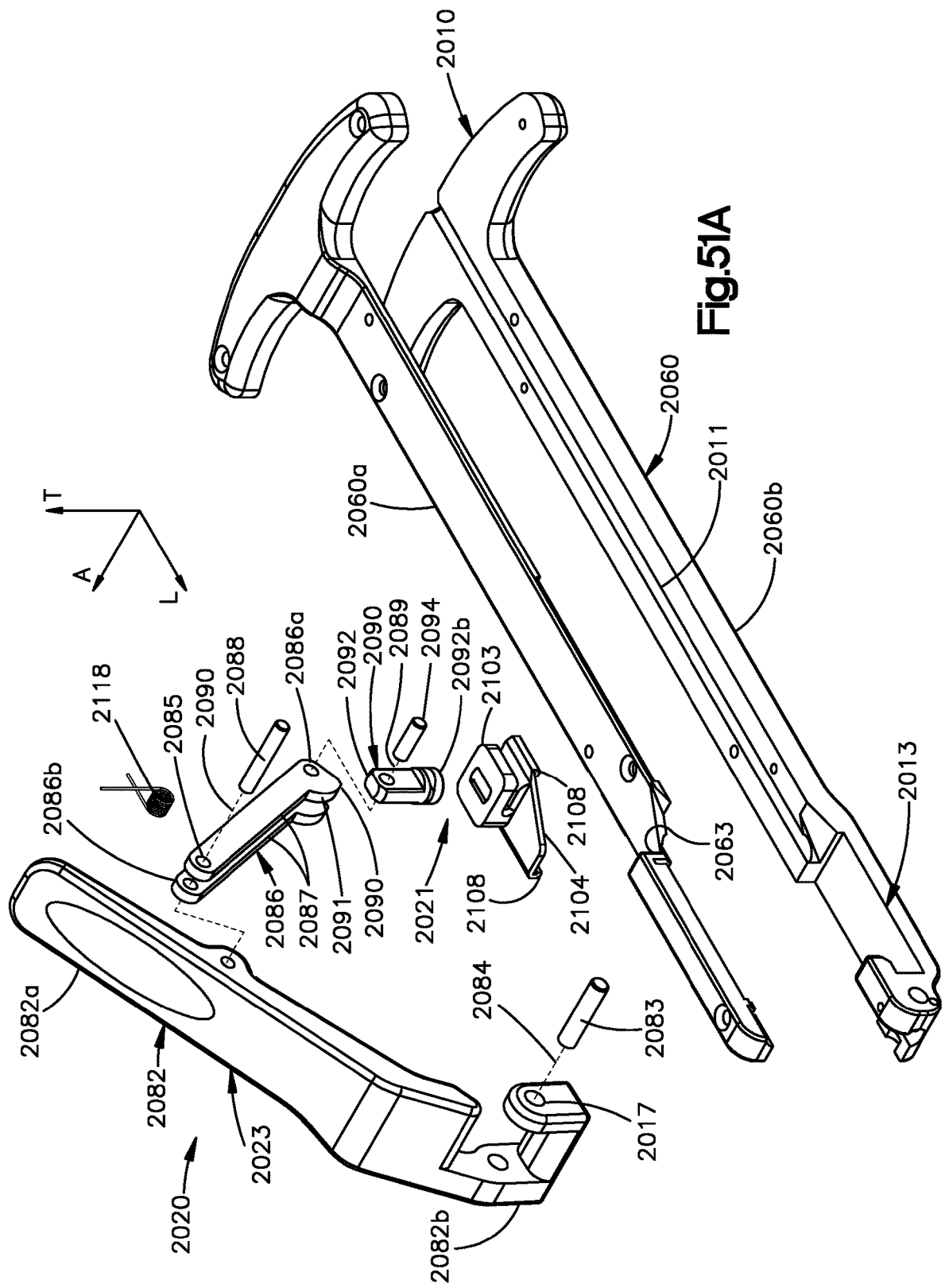

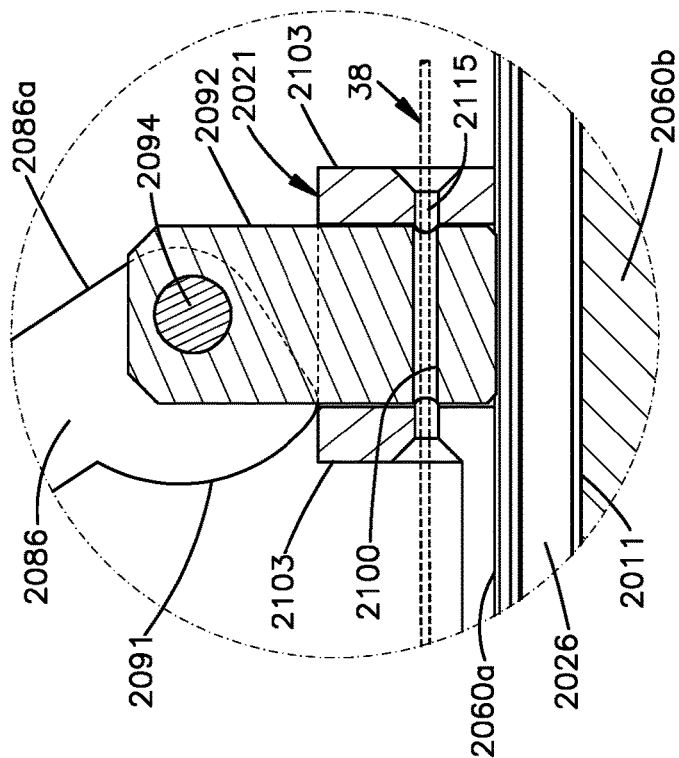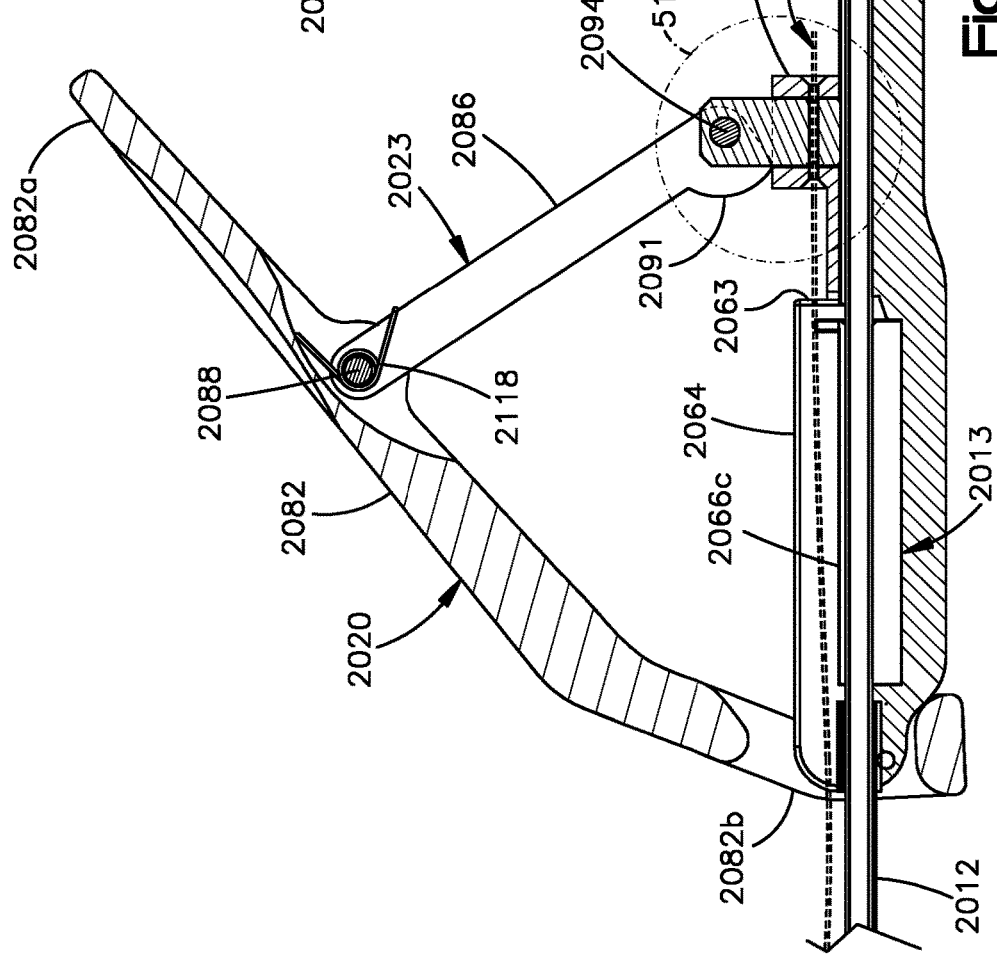

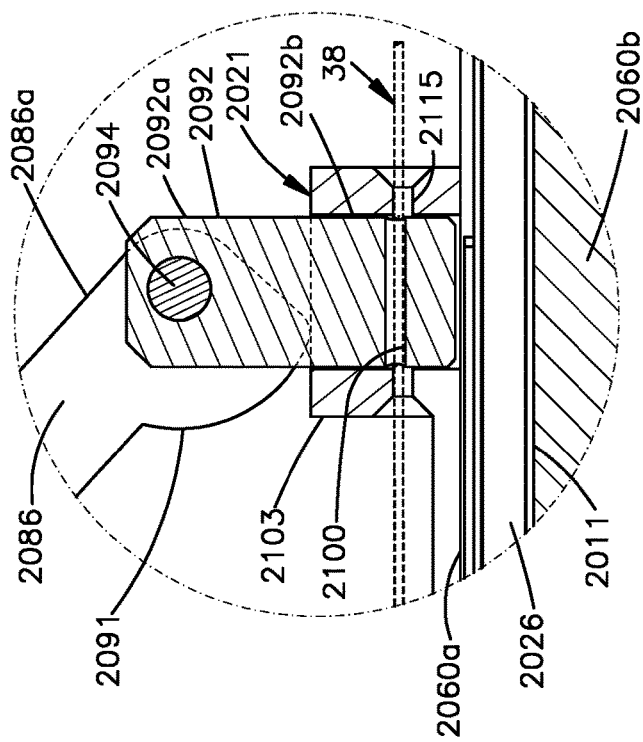
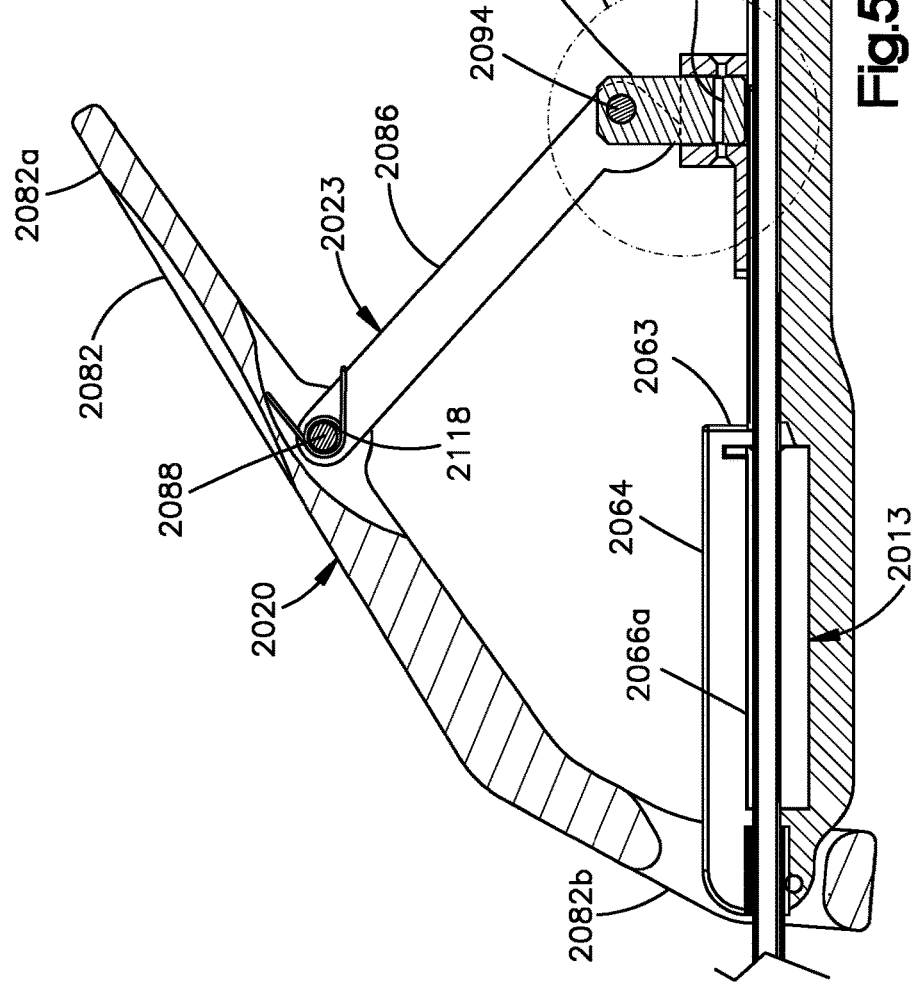
Fig.51F
Fig.51E

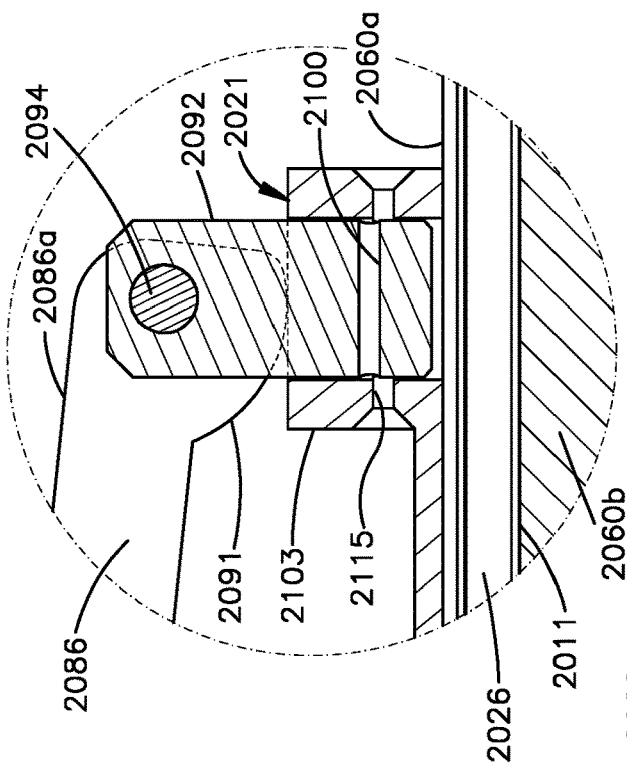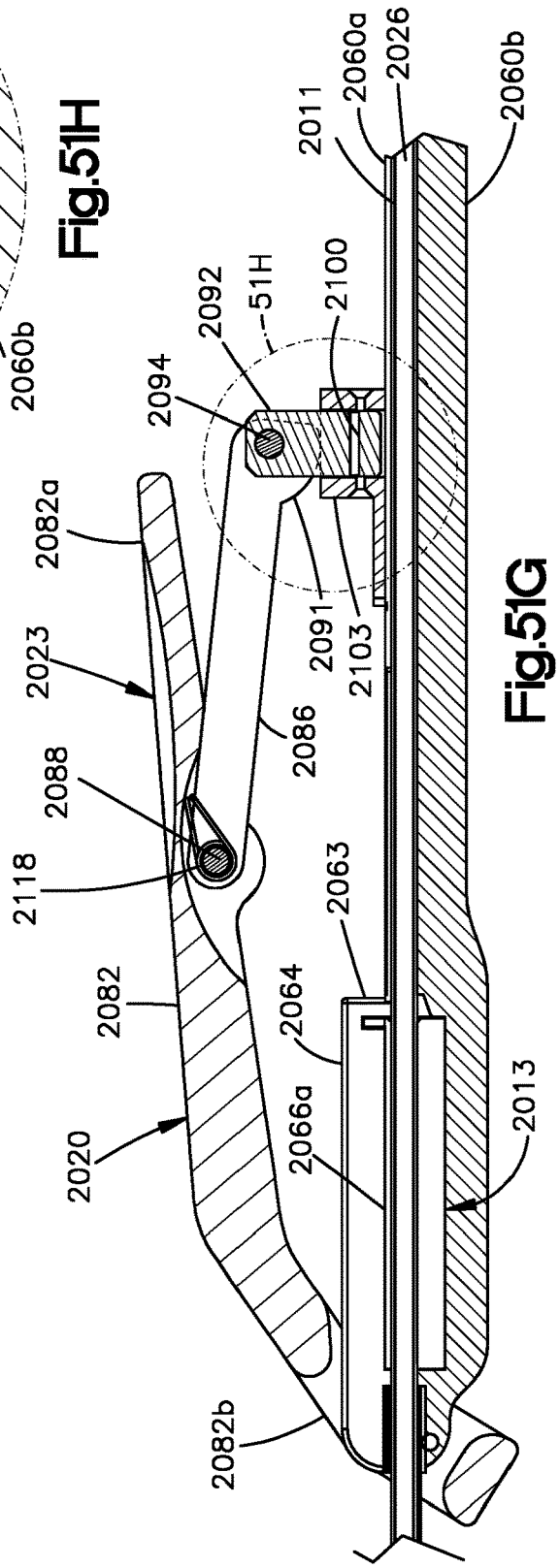

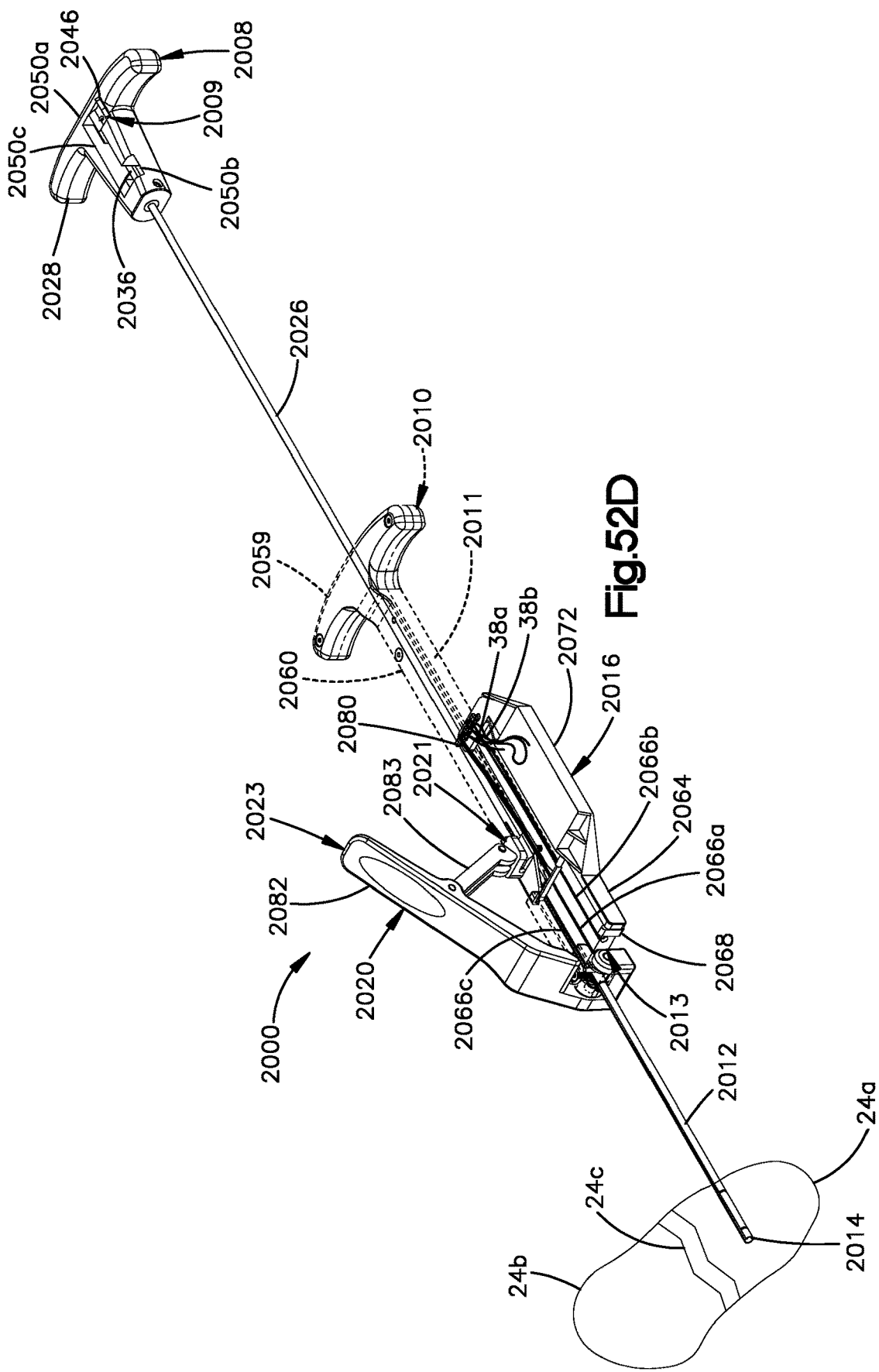

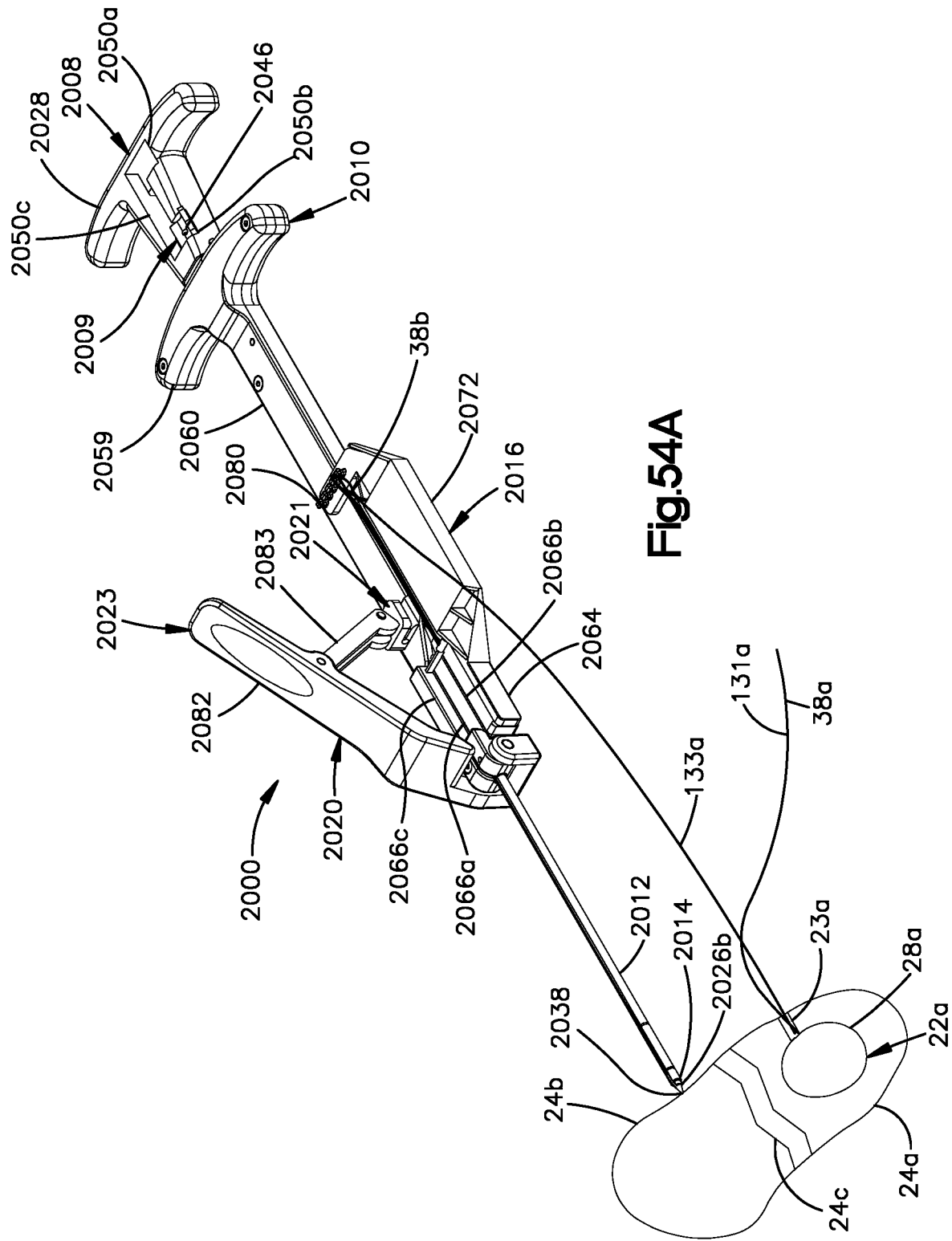

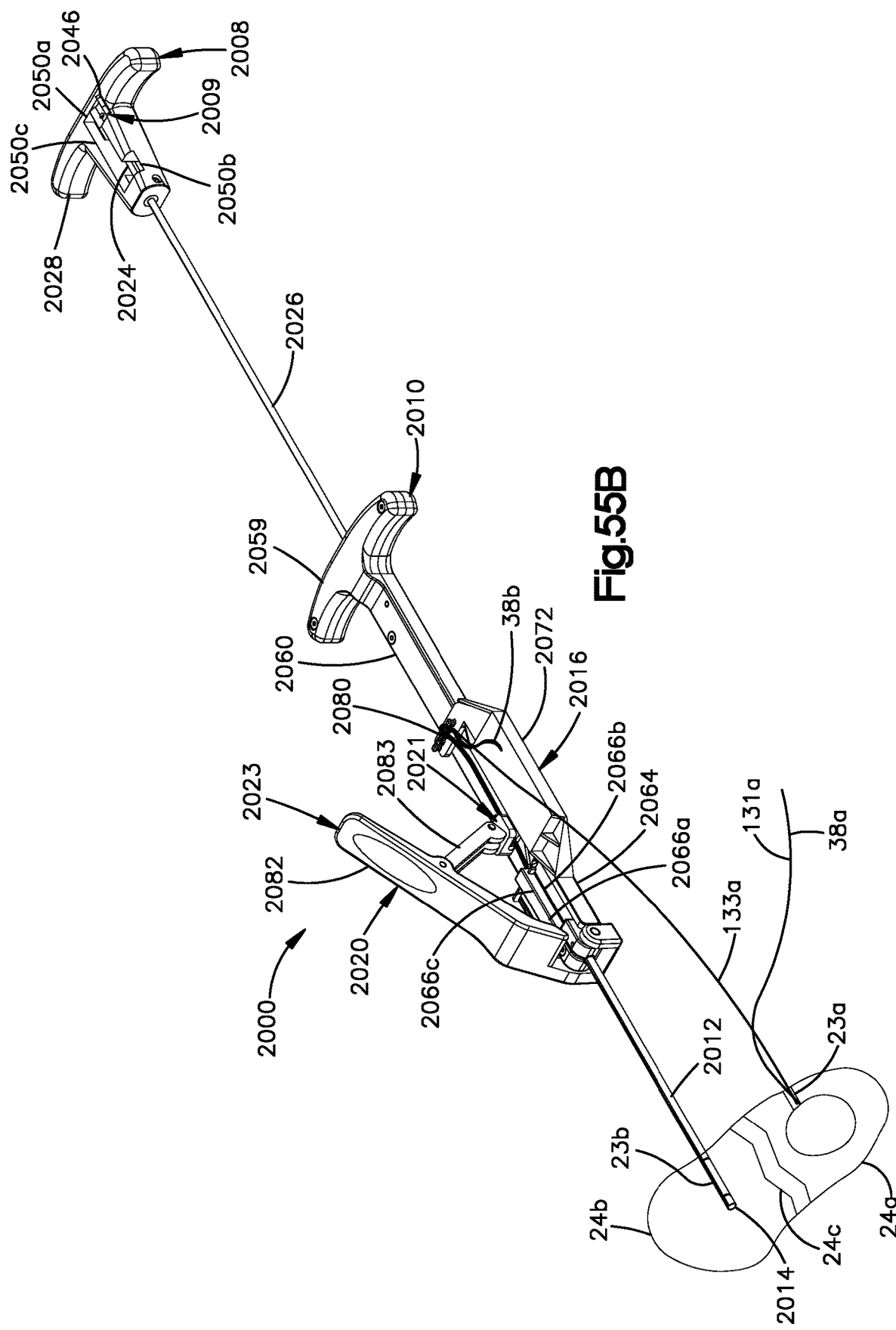

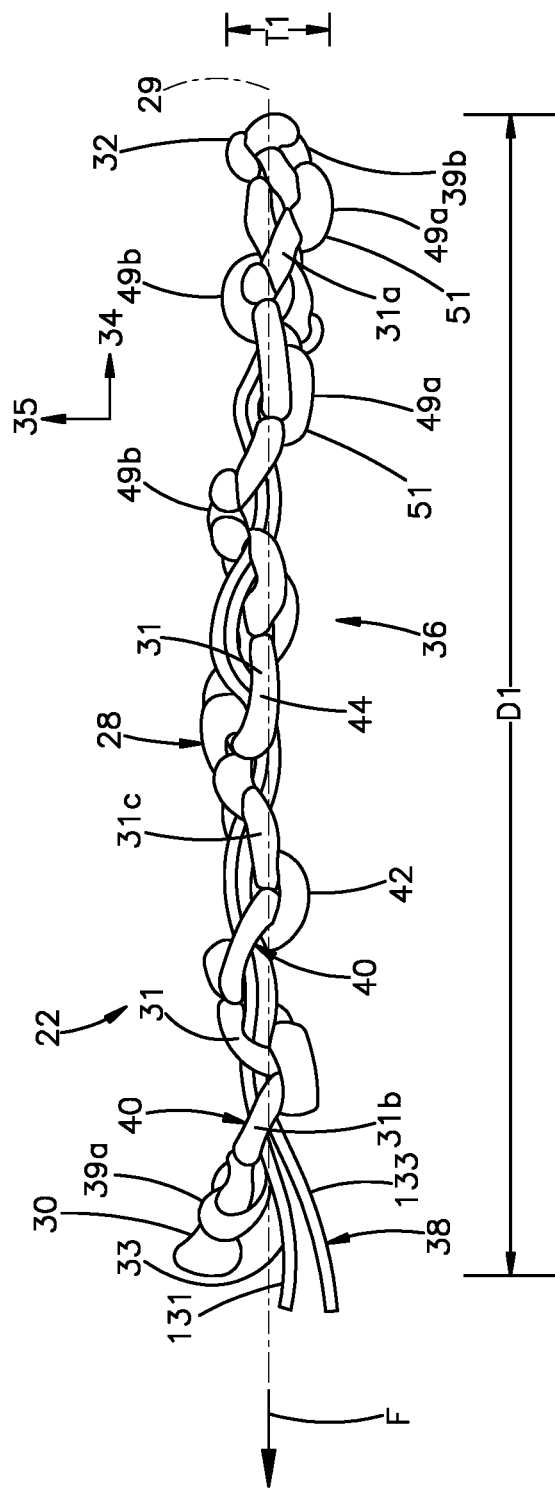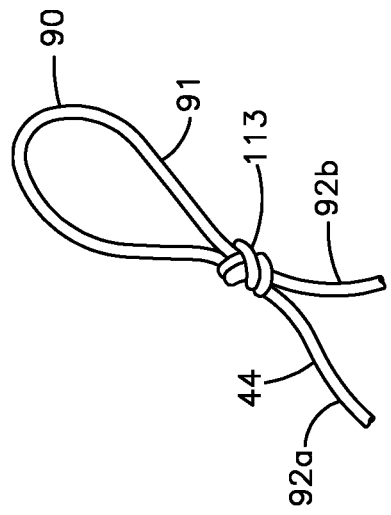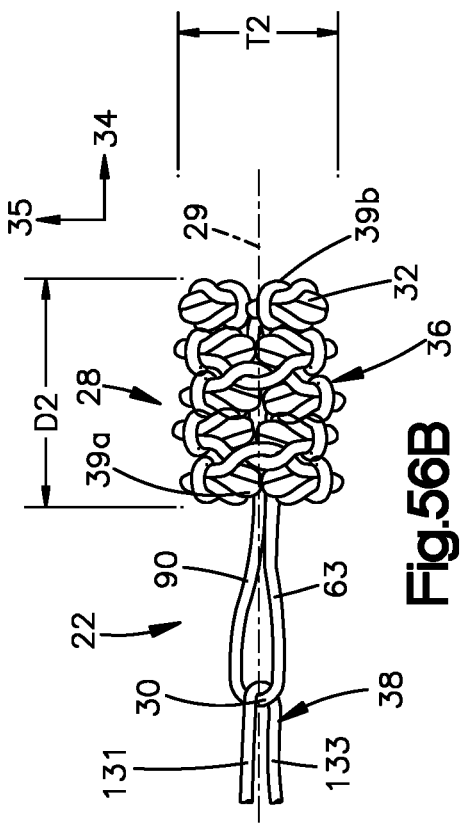

INSERTION INSTRUMENT FOR ANCHOR ASSEMBLY

CROSS-REFERENCE TO RELATED APPLICATIONS

This application is a divisional of U.S. patent application Ser. No. 15/627,698, filed Jun. 20, 2017, which is a divisional of U.S. patent application Ser. No. 13/283,063, filed Oct. 27, 2011 (now U.S. Pat. No. 9,724,080, issued Aug. 8, 2017), which is a continuation-in-part of U.S. patent application Ser. No. 13/172,619, filed Jun. 29, 2011, (now U.S. Pat. No. 9,451,938, issued Sep. 27, 2016), which is a continuation-in-part of U.S. patent application Ser. No. 13/095,192, filed Apr. 27, 2011 (now U.S. Pat. No. 9,173,645, issued Nov. 3, 2015). U.S. patent application Ser. No. 13,172,619 further claims the benefit of U.S. Patent Application Ser. No. 61/398,699 filed on Jun. 29, 2010 (Overes, et al.), U.S. Patent Application Ser. No. 61/432,755 filed on Jan. 14, 2011 (Henrichsen, et al.), U.S. Patent Application Ser. No. 61/461,490 filed on Jan. 18, 2011 (Henrichsen, et al.), and U.S. Patent Application Ser. No. 61/443,142 filed on Feb. 15, 2011 (Overes). U.S. patent application Ser. No. 13/095,192 claims the benefit of U.S. Patent Application Ser. No. 61/328,251 filed on Apr. 27, 2010 (Overes), U.S. Patent Application Ser. No. 61/398,699 filed on Jun. 29, 2010 (Overes, et al.), U.S. Patent Application Ser. No. 61/432,755 filed on Jan. 14, 2011 (Henrichsen, et al.), U.S. Patent Application Ser. No. 61/461,490 filed on Jan. 18, 2011 (Henrichsen, et al.), and U.S. Patent Application Ser. No. 61/443,142 filed on Feb. 15, 2011 (Overes). The disclosure of each of the above identified patent applications is incorporated by reference as if set forth in its entirety herein. The disclosure of U.S. patent application Ser. No. 13/283,198 filed on Oct. 27, 2011 (now U.S. Pat. No. 9,597,064, issued Mar. 21, 2017) and entitled "Method for Approximating a Tissue Defect Using an Anchor Assembly" is hereby incorporated by reference as if set forth in its entirety herein. The disclosure of U.S. patent application Ser. No. 13/283,002 filed on Oct. 27, 2011 (now U.S. Pat. No. 9,743,919, issued Aug. 29, 2017) and entitled "Stitch Lock for Attaching Two or More Structures" is hereby incorporated by reference as if set forth in its entirety herein.

BACKGROUND

Orthopaedic surgical procedures often involve the use of a fixation device. Usually an access hole is produced in a bone or soft tissue wherein a suitable fixation device can be fastened. Apart from screws, expandable fixations devices can be used which are inserted into the hole in a collapsed state and transformed into an expanded state once being correctly positioned.

In one example orthopaedic surgical procedure, such as a lumbar microdiscectomy, radiculopathy is treated by surgically removing the herniated nucleus pulposus to achieve neural decompression. The lumbar microdiscectomy is one of the most common spinal surgeries performed today. Many patients find relief with this procedure, but for others, the disc could re-herniate through the opening in the annulus resulting in continuing pain and potentially requiring additional surgery. Currently, the standard microdiscectomy technique does not involve closing the annular defect and presents the surgeon with a dilemma. The surgeon may elect to remove the herniated portion of the nucleus impinging on the nerves, which treats radiculopathy, but may increase the risk of post-operative reherniation of the remaining nucleus through the existing defect of the annulus. Alternately, the surgeon may elect to perform extensive debulking, in which most of the remaining nucleus material is removed in addition to the herniated portion to minimize the risk of post-operative reherniation. However, the risk of post-operative disc height collapse and subsequent progression to lower back pain increases.

Conventional expandable implants include a sleeve with an expandable portion having plurality of fingers or expandable parts formed by intermediate slots or holes in the peripheral wall of the sleeve and a compression element extending through the central bore of the sleeve. The compression element can be coupled to the front end of the sleeve so that upon pulling said compression element towards the rear end of the sleeve said fingers or expandable parts are bent radially outwards so as to transform said expandable portion from its collapsed state to its expanded state.

SUMMARY

In accordance with one embodiment, an insertion instrument is configured to eject at least one anchor at a target location. The anchor includes an anchor body that extends substantially along a direction of elongation, and an actuation member that extends from the anchor body substantially along the direction of elongation. The insertion instrument can include an access member elongate along a longitudinal direction, the access member defining a distal end that is configured to be at least partially inserted into the target location, an anchor housing that releasably carries the at least one anchor. The anchor housing is configured to be aligned with the access member. The insertion instrument can further include a pusher member configured to be inserted into the anchor housing and to eject the at least one anchor from the anchor housing and out the distal end of the access member.

BRIEF DESCRIPTION OF THE DRAWINGS

The foregoing summary, as well as the following detailed description of an example embodiment of the application, will be better understood when read in conjunction with the appended drawings, in which there is shown in the drawings example embodiments for the purposes of illustration. It should be understood, however, that the application is not limited to the precise arrangements and instrumentalities shown. In the drawings:

FIG. 4A is a sectional elevation view of a fixation kit constructed in accordance with an alternative embodiment, shown in a first rotative state;

FIG. 4B is a sectional side elevation view of the kit illustrated in FIG. 4A, taken along line 4B-4B;

FIG. 4C is a sectional side elevation view of the fixation kit as illustrated in FIG. 4A, but shown in a second rotative state whereby a pair of apertures is aligned;

FIG. 4D-sectional side elevation view of the fixation kit illustrated in FIG. 4C, taken along line 4D-4D;

FIG. 6 is a side elevation view of the fixation kit constructed in accordance with another embodiment;

FIG. 7A is a perspective view of a fixation kit including an insertion instrument constructed in accordance with an alternative embodiment including a casing and a cannula extending from the casing, the instrument shown in a first configuration with first and second anchor bodies loaded in the insertion instrument;

FIG. 7B is an enlarged perspective view of the cannula of the insertion instrument illustrated in FIG. 7A;

FIG. 7C is a sectional side elevation view of the casing of the insertion instrument illustrated in FIG. 7A;

FIG. 7D is an enlarged sectional side elevation view of the cannula of the insertion instrument illustrated in FIG. 7A;

FIG. 8A is a perspective view of the fixation kit illustrated in FIG. 7A, showing the insertion instrument in the second position so as to eject the second anchor body from the insertion instrument, the second anchor body shown in a first configuration FIG. 8B is an enlarged perspective view of the cannula of the insertion instrument illustrated in FIG. 8A;

FIG. 8C is a sectional side elevation view of the casing illustrated in FIG. 8A;

FIG. 8D is a sectional side elevation view of the cannula illustrated in FIG. 8A;

FIG. 9A is a perspective view of the fixation kit illustrated in FIG. 8A, showing the insertion instrument in an offset position;

FIG. 9B is an enlarged perspective view of the cannula of the insertion instrument illustrated in FIG. 9A FIG. 9C is a sectional side elevation view of the casing of the insertion instrument illustrated in FIG. 9A;

FIG. 9D is a sectional side elevation view of the cannula of the insertion instrument illustrated in FIG. 9A;

FIG. 9E is a perspective view of the fixation kit illustrated in FIG. 9A, showing the second anchor body in an expanded configuration;

FIG. 10A is a perspective view of the fixation kit illustrated in FIG. 9A, showing the insertion instrument in an intermediate position upon completion of an intermediate stroke;

FIG. 10B is an enlarged perspective view of the cannula of the insertion instrument illustrated in FIG. 10A FIG. 10C is a sectional side elevation view of the casing of the insertion instrument illustrated in FIG. 10A;

FIG. 10D is a sectional side elevation view of the cannula of the insertion instrument illustrated in FIG. 10A FIG. 11A is a perspective view of the fixation kit illustrated in FIG. 10A, showing the insertion instrument upon completion of a first portion of a second stroke after the intermediate stroke;

FIG. 11B is an enlarged perspective view of the cannula of the insertion instrument illustrated in FIG. 11A FIG. 11C is a sectional side elevation view of the casing of the insertion instrument illustrated in FIG. 11A;

FIG. 11D is a sectional side elevation view of the cannula of the insertion instrument illustrated in FIG. 11A;

FIG. 12A perspective view of the fixation kit illustrated in FIG. 11A, showing the insertion instrument in a third position upon completion of a second portion of the second stroke, ejecting a first anchor body from the insertion instrument, the first anchor body shown in a first configuration;

FIG. 12B is an enlarged perspective view of the cannula of the insertion instrument illustrated in FIG. 12A;

FIG. 12E is a perspective view of the fixation kit similar to FIG. 12A, but showing the first anchor body in an expanded configuration;

FIG. 13A is a perspective view of the insertion instrument illustrated in FIG. 7A, with portions removed so as to illustrate a guide system when the instrument is in the first position;

FIG. 13C is a perspective view of the insertion instrument illustrated in FIG. 9A, with portions removed so as to illustrate the guide system when the insertion instrument is in the offset position;

FIG. 13G is a perspective view of a guide track of the guide system illustrated in FIG. 13A;

FIG. 14A is a perspective view of a coupling assembly constructed in accordance with one embodiment, FIG. 14B is a sectional side elevation view of the coupling assembly illustrated in FIG. 14A, shown in a first mode of operation;

FIG. 14C is a sectional side elevation view of the coupling assembly illustrated in FIG. 14B, shown in a transition between the first mode of operation and a second mode of operation;

FIG. 14D is a sectional side elevation view of the coupling assembly illustrated in FIG. 14C, shown in the second mode of operation.

FIG. 15A is a sectional side elevation view of the insertion instrument constructed in accordance with another embodiment, showing a coupling assembly disposed in a first mode of operation;

FIG. 15B is a sectional end elevation view of the coupling assembly illustrated in FIG. 15A, taken along line 15B-15B;

FIG. 15C is a sectional side elevation view of the insertion instrument illustrated in FIG. 15A, but showing the coupling assembly transitioning from the first mode of operation to a second mode of operation;

FIG. 15D is a sectional end elevation view of the coupling assembly illustrated in FIG. 15C, taken along line 15D-15D;

FIG. 15E is a sectional side elevation view of the insertion instrument illustrated in FIG. 15C, but showing the coupling assembly in the second mode of operation;

FIG. 16A is a schematic side elevation view of the anchor assembly as illustrated in FIG. 1G, including a tensioning strand in accordance with an alternative embodiment, showing on of the anchor bodies implanted in the first configuration;

FIG. 16B is a schematic side elevation view of the anchor assembly as illustrated in FIG. 16A, but showing the implanted anchor body in the expanded configuration;

FIG. 16C is a schematic side elevation view of the anchor assembly as illustrated in FIG. 16B, showing the other anchor body implanted in the first configuration;

FIG. 16D is a schematic side elevation view of the anchor assembly as illustrated in FIG. 16C, showing the other anchor body in the expanded configuration;

FIG. 18A is a schematic side elevation view of the anchor assembly as illustrated in FIG. 1G, including a pair of tensioning strands in accordance with an alternative embodiment, showing the anchor bodies in the first configuration;

FIG. 18B is a schematic side elevation view of the anchor assembly as illustrated in FIG. 18A, but showing the anchor bodies in the expanded configuration;

FIG. 18C is a schematic side elevation view of the anchor assembly as illustrated in FIG. 18B, showing actuation of a locking member and approximation of an anatomical gap;

FIG. 18D is a schematic side elevation view of the anchor assembly as illustrated in FIG. 18C, showing locking of the locking member;

FIG. 18E is a schematic side elevation view of the anchor assembly as illustrated in FIG. 18D, show in a final assembled configuration;

FIG. 20A is a sectional side elevation view of the insertion instrument including a cutting assembly in accordance with another embodiment, showing the cutting assembly in a disengaged position;

FIG. 20B is a sectional side elevation view of the insertion instrument as illustrated in FIG. 20A, but showing the cutting assembly in an engaged position;

FIG. 21A is a sectional side elevation view of the insertion instrument as illustrated in FIG. 20A, but including a cutting assembly constructed in accordance with another embodiment, shown in a disengaged position;

FIG. 21B is a sectional side elevation view of the insertion instrument as illustrated in FIG. 21A, but showing the cutting assembly in an engaged position;

FIG. 22A is a perspective view of the insertion instrument illustrated in FIG. 7A, but constructed in accordance with an alternative embodiment, shown in the first position;

FIG. 22B is a side elevation view of the insertion instrument as illustrated in FIG. 22A;

FIG. 23B is a perspective view of a plunger of the insertion instrument illustrated in FIG. 23A;

FIG. 23C is a perspective view of a distal end of the insertion instrument illustrated in FIG. 23A;

FIG. 23D is a perspective view of various components of the insertion instrument illustrated in FIG. 23A, including the plunger illustrated in FIG. 23B, a push rod, and a pair of first coupling members;

FIG. 23E is a perspective view of a second coupling member configured to engage the first coupling members illustrated in FIG. 23D;

FIG. 25A is a perspective view of components of the insertion instrument illustrated in FIG. 24A, showing each of the first and second pusher assemblies in the first position;

FIG. 26A is a perspective view of a retention assembly constructed in accordance with one embodiment;

FIG. 26B is an enlarged perspective view of a portion of the retention assembly illustrated in FIG. 26A;

FIG. 29A is a perspective view of an insertion instrument constructed in accordance with another embodiment, the insertion instrument including first and second pusher assemblies disposed in a side-by-side relationship, showing each of the pusher assemblies in a first position;

FIG. 29B is an end elevation view of the insertion instrument illustrated in FIG. 29A;

FIG. 29D is a perspective view of the insertion instrument illustrated in FIG. 29C, after actuation of a swap actuator from a first position to a second position;

FIG. 29E is a perspective view of the insertion instrument illustrated in FIG. 29D, after removal of a lockout tab from the second pusher assembly;

FIG. 29F is a perspective view of the insertion instrument illustrated in FIG. 29E, showing the second pusher assembly in a second position;

FIG. 29G is a schematic sectional end elevation view of the insertion instrument illustrated in FIG. 29D, showing a portion of the swap actuator;

FIG. 30A is a perspective view of an insertion instrument constructed in accordance with another embodiment, the insertion instrument including first and second reciprocally movable cannulas, the drawing showing a portion of the casing cut away so as to expose internal components of the insertion instrument;

FIG. 30B is a perspective view of a reciprocal motion assembly of the insertion instrument illustrated in FIG. 30A, the reciprocal motion assembly configured to reciprocally drive the first and second cannulas;

FIG. 30C is a perspective view of a drive member of the reciprocal motion assembly illustrated in FIG. 30B;

FIG. 30D is a perspective view of a selective plunger engagement assembly configured to selectively move the plunger between operably communication with the first and second cannulas;

FIG. 31 is a perspective view of an insertion instrument, wherein the cannula defines a side ejection port in accordance with another embodiment;

FIG. 32A is a perspective view of an access assembly in accordance with an embodiment, the access assembly comprising an access member and an opening creating member;

FIG. 32B is a side section view of the access member illustrated in FIG. 32A;

FIG. 32C is a side elevation view of the awl illustrated in FIG. 32A;

FIG. 32D is a side elevation view of a portion of the awl illustrated in FIG. 32C, in accordance with an alternative embodiment;

FIG. 32E is a perspective view of the access assembly inserted into a target anatomical location;

FIG. 32F is a perspective view of the access member inserted into the target anatomical location;

FIG. 32G is a perspective view of an anchor inserter assembly in accordance with an embodiment, the anchor inserter assembly comprising the access member, an anchor housing carrying an anchor, and a pusher member;

Figure 32H:
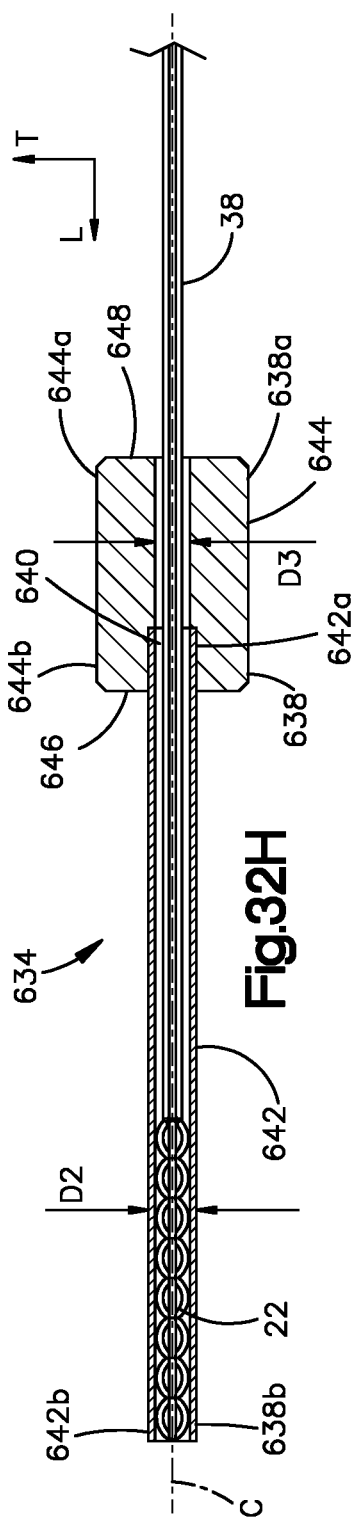
Figure 32I:
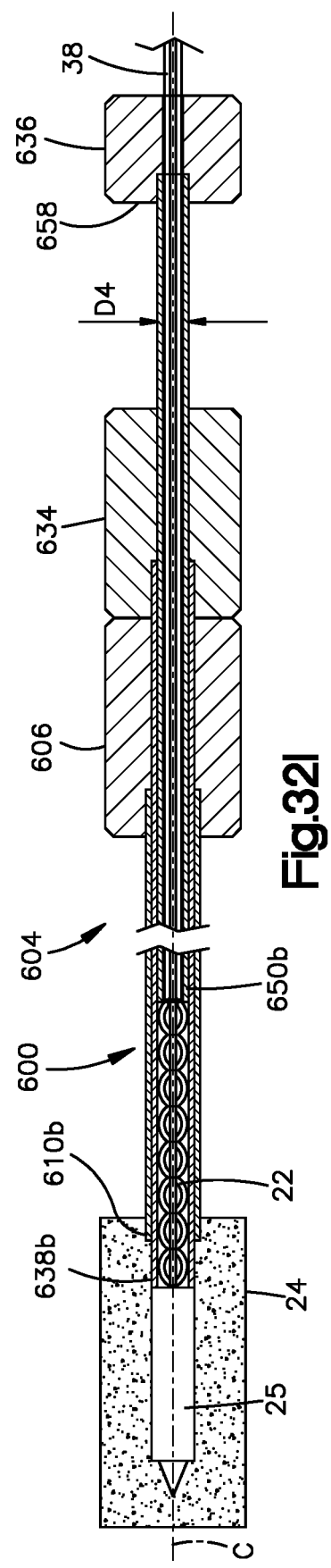
Figure 32J:
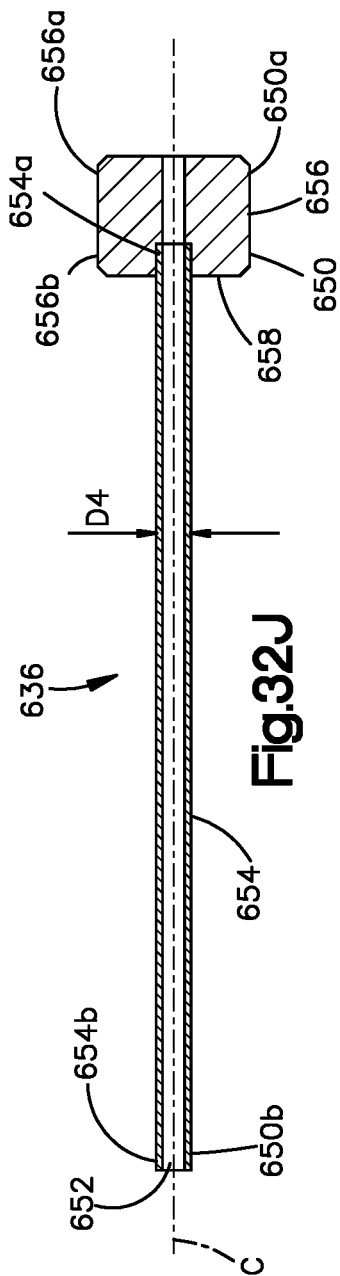
Figure 33C:
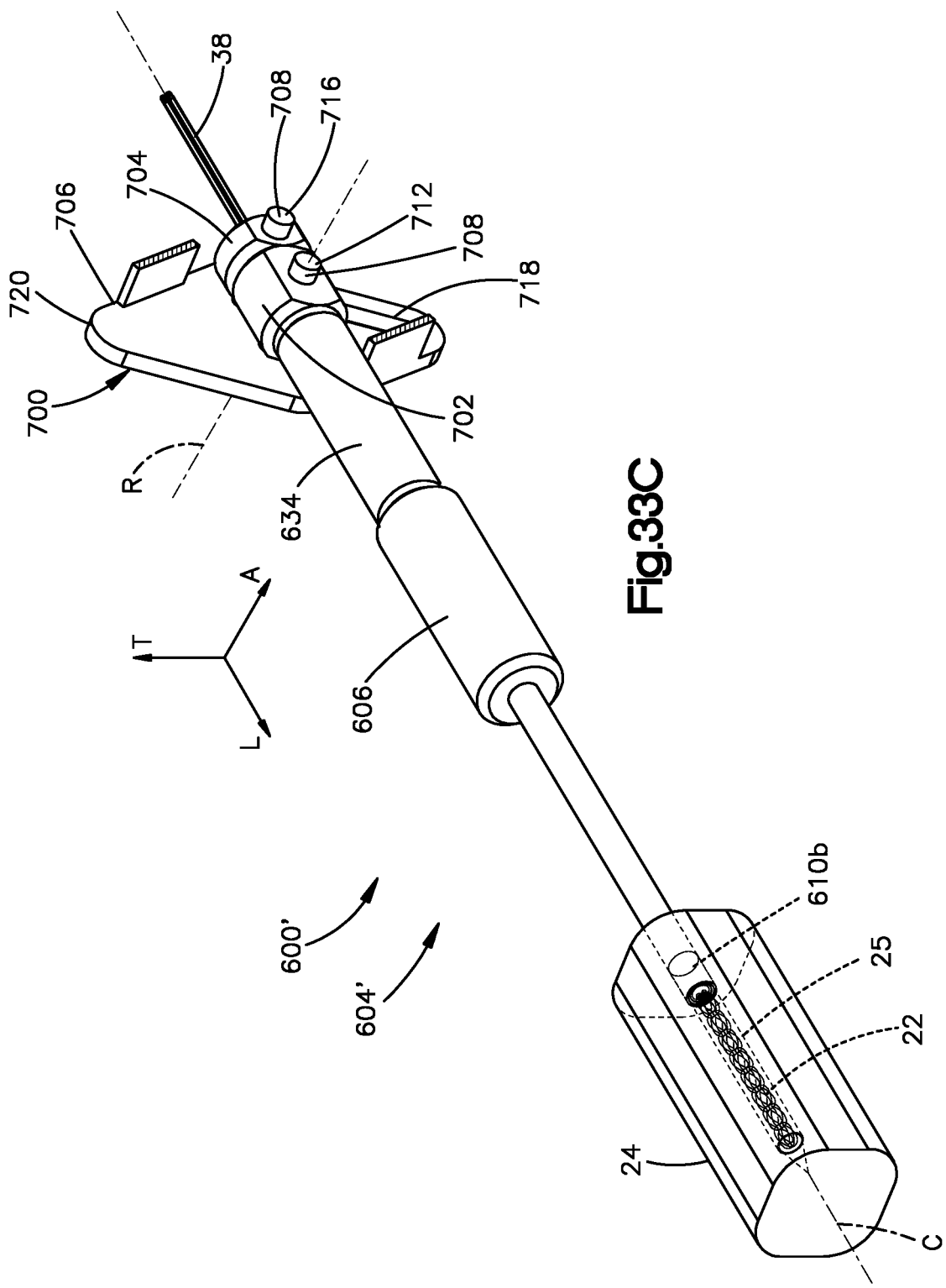
Figure 33D:
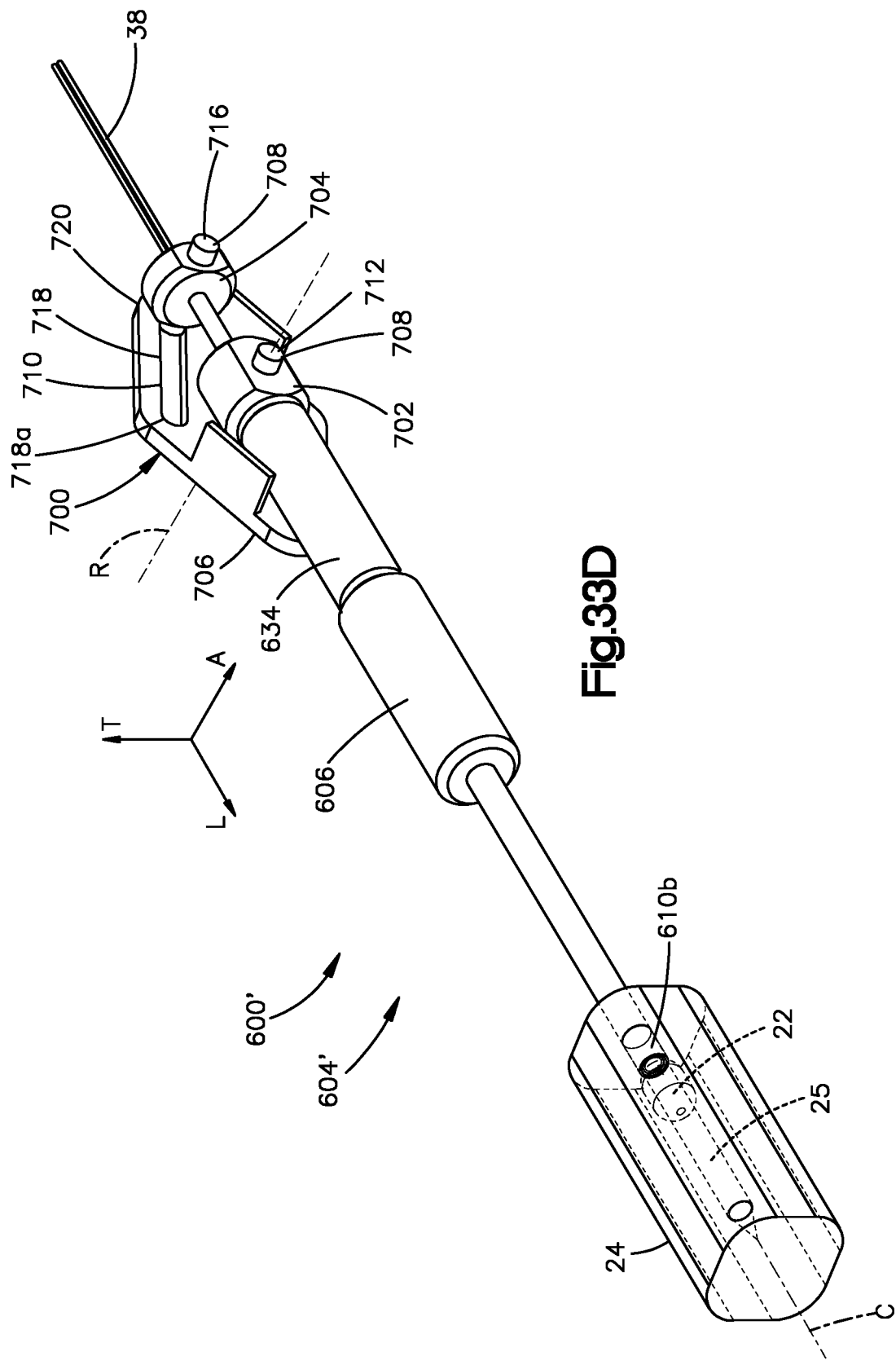
Figure 34C:
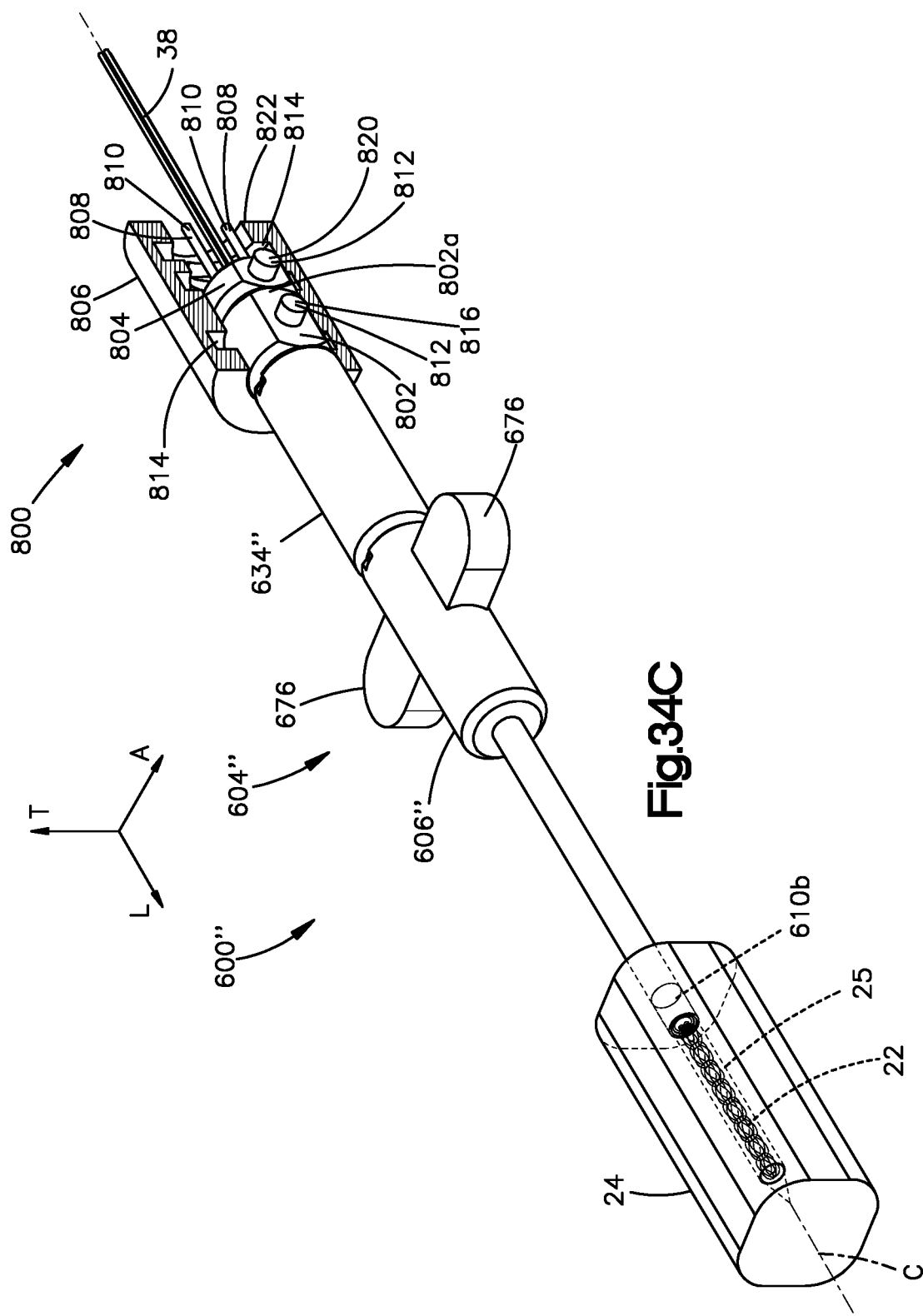
Figure 35A:
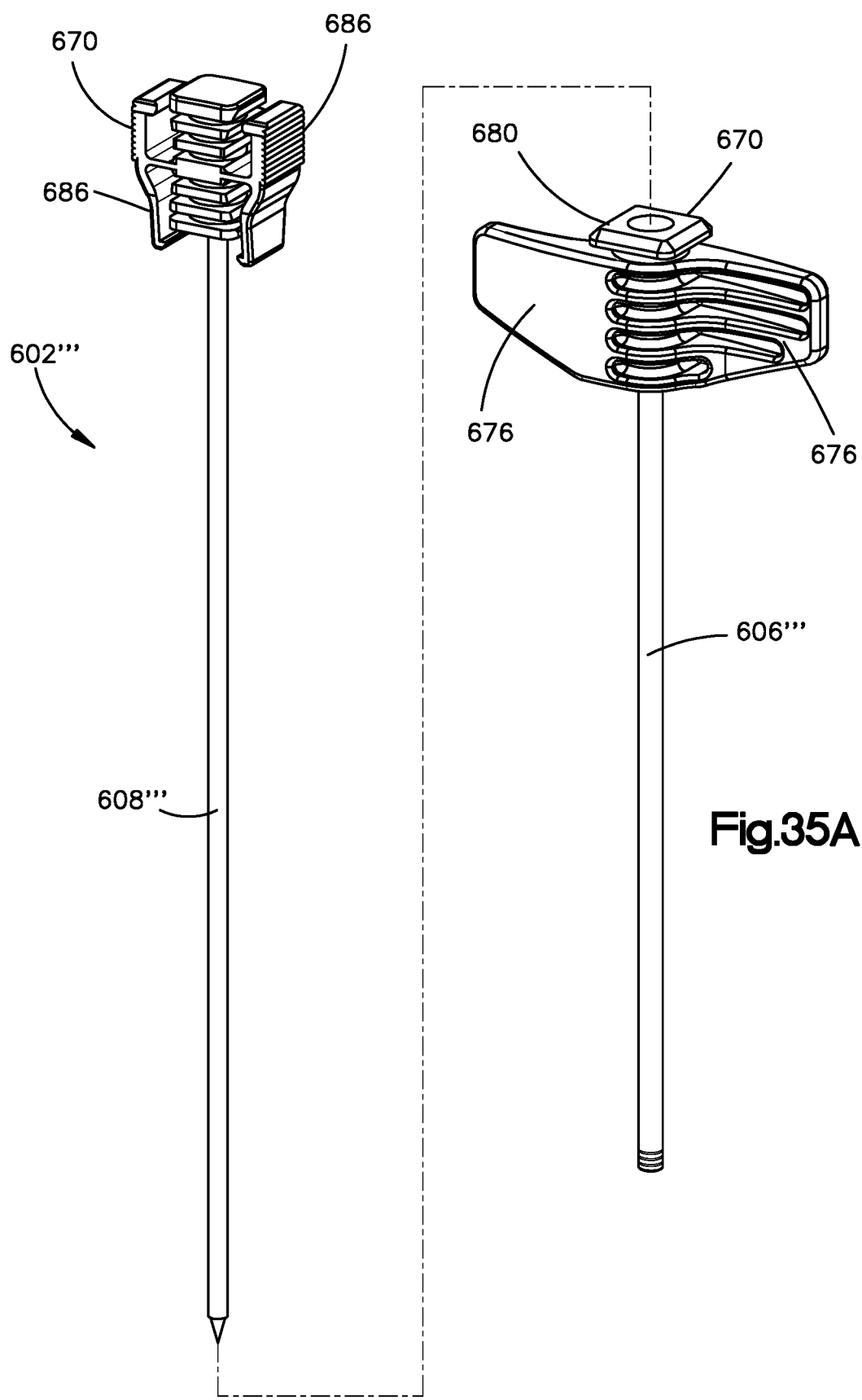
Figure 35B:
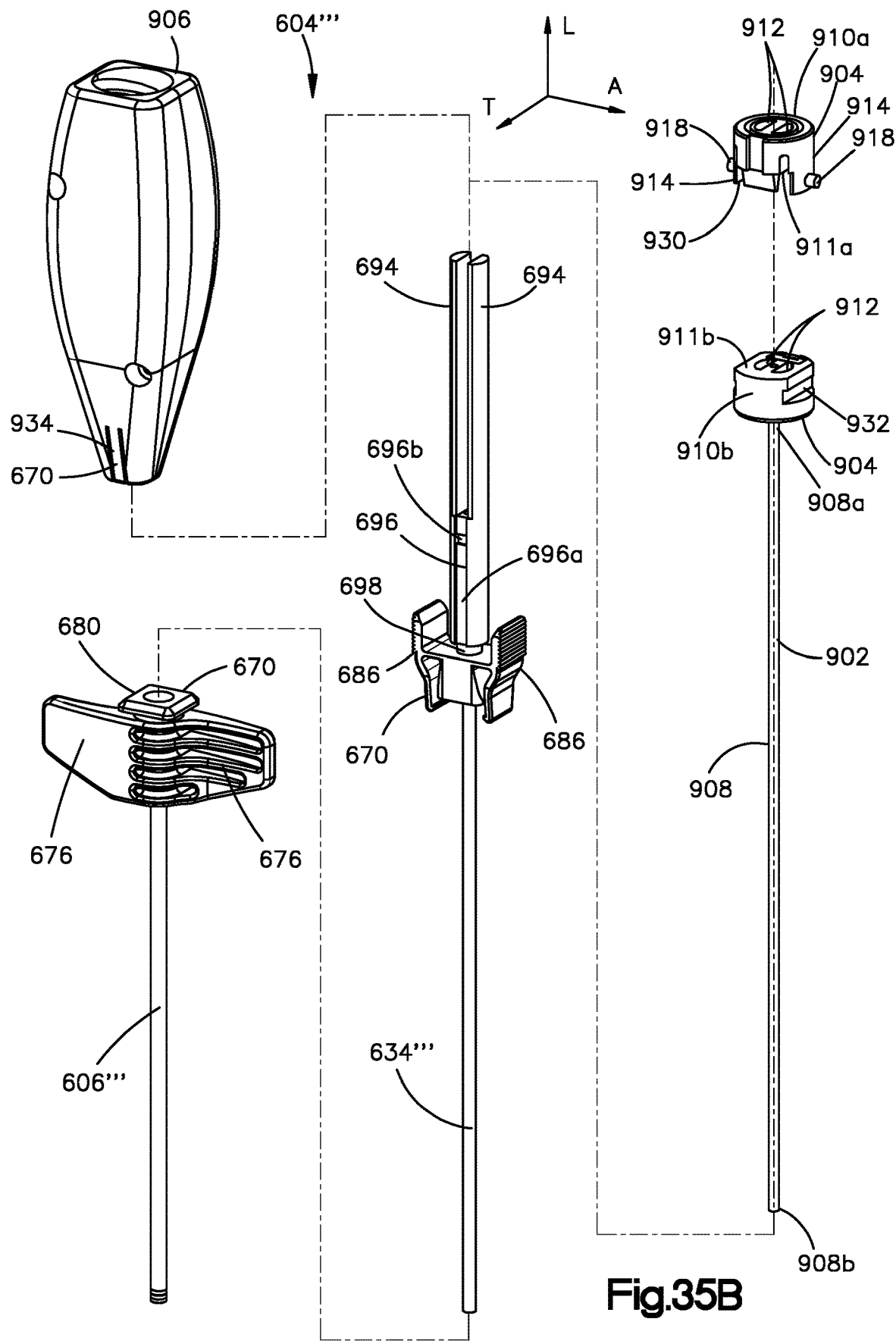
Figure 36A:
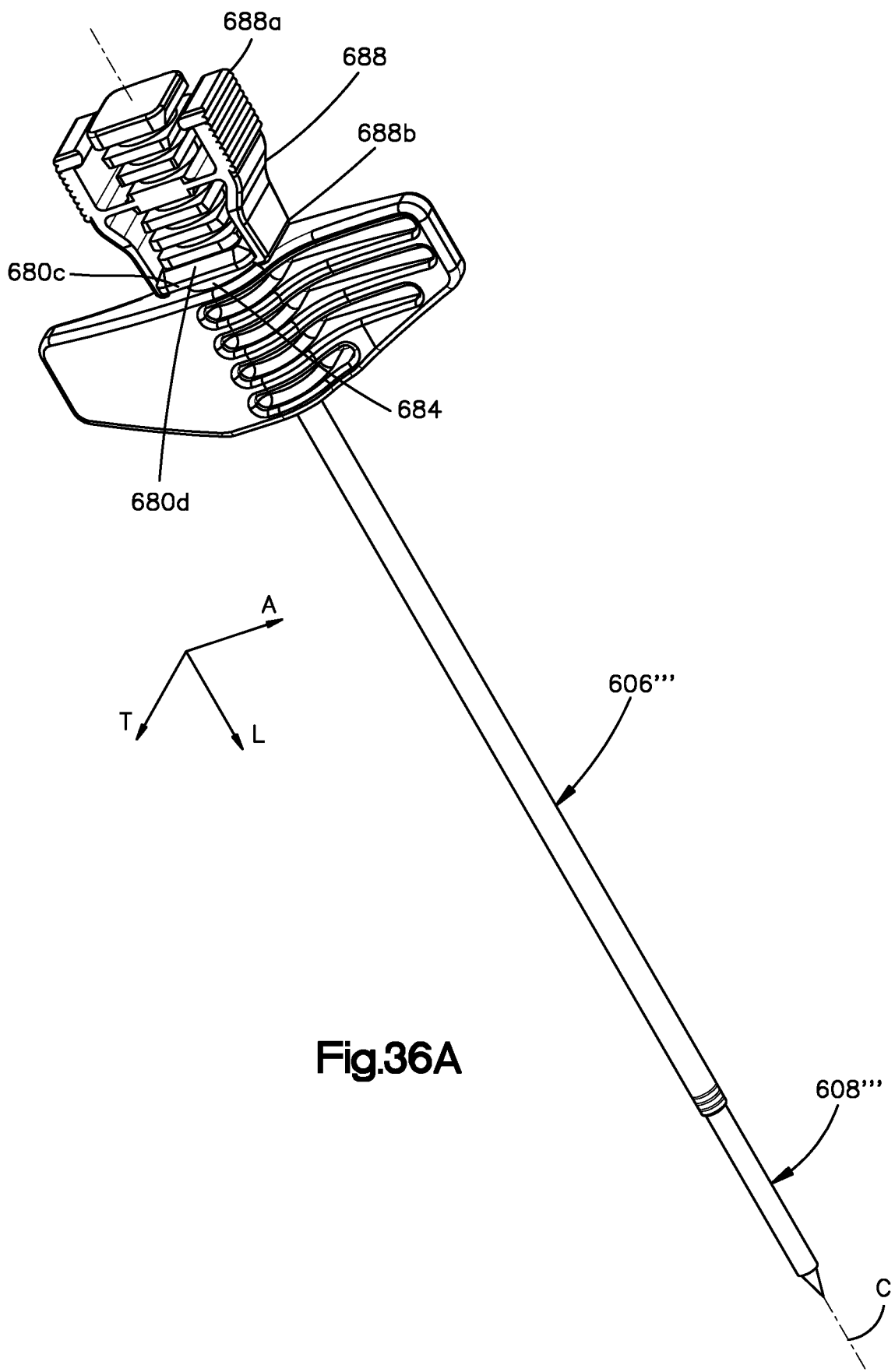
Figure 36B:
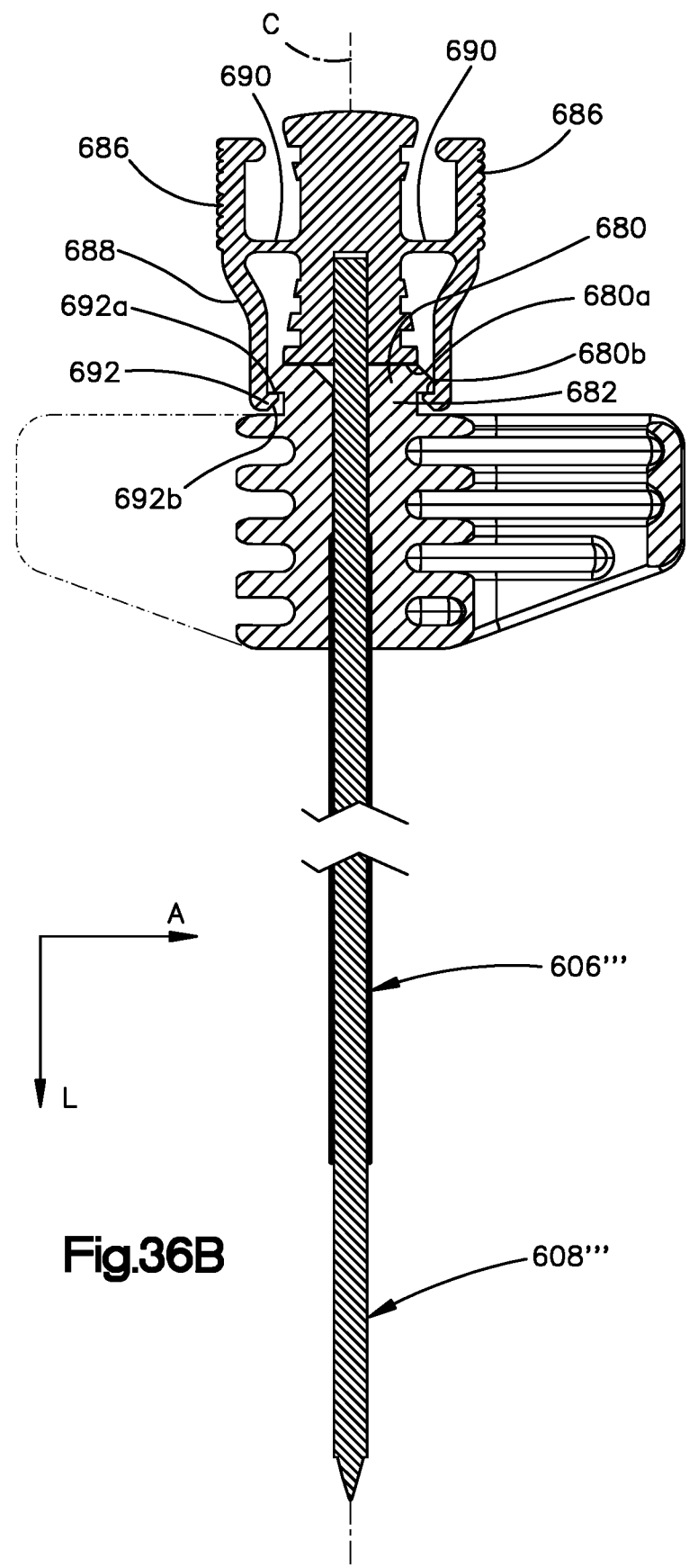
Figure 37A:
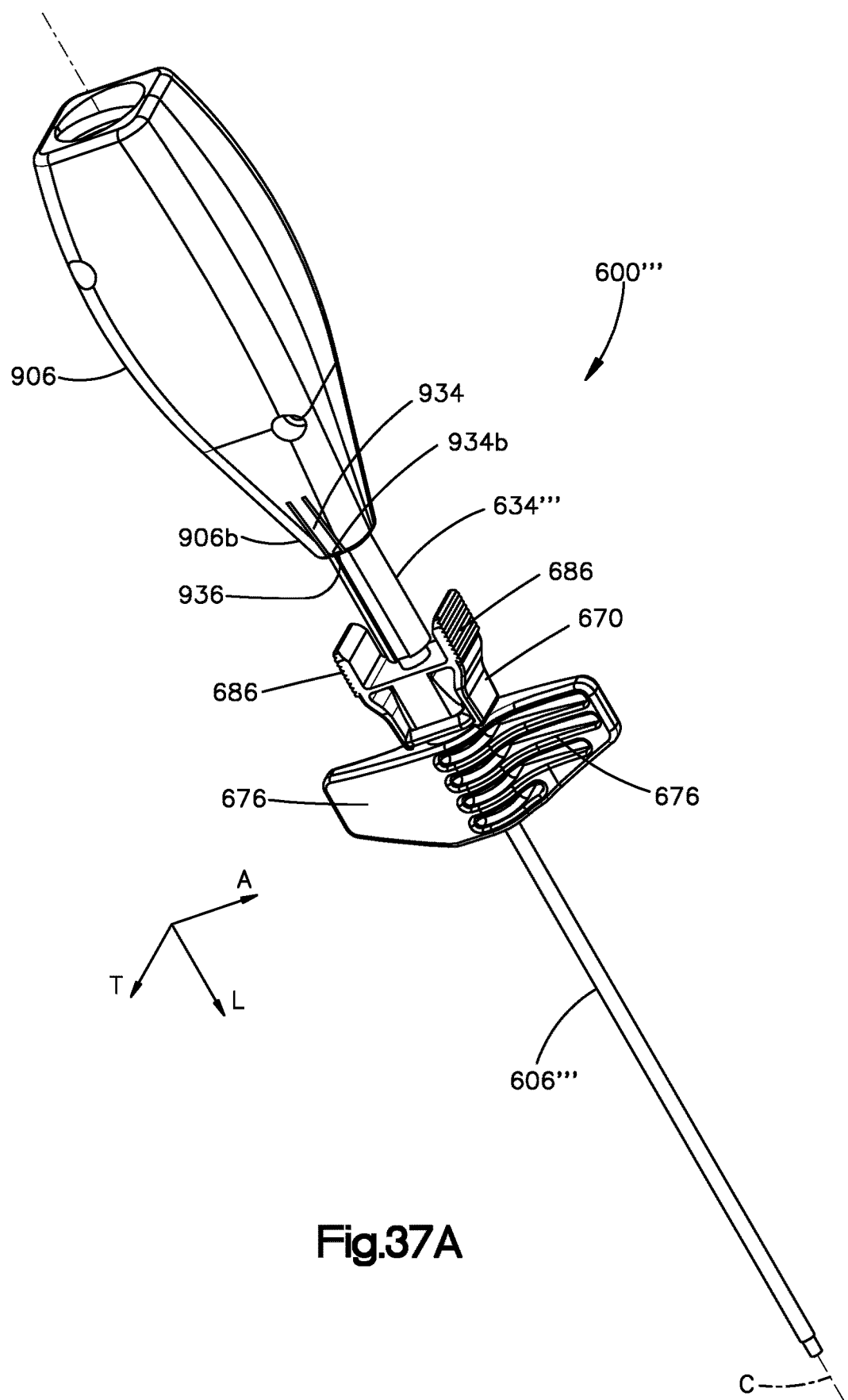
Figure 37B:
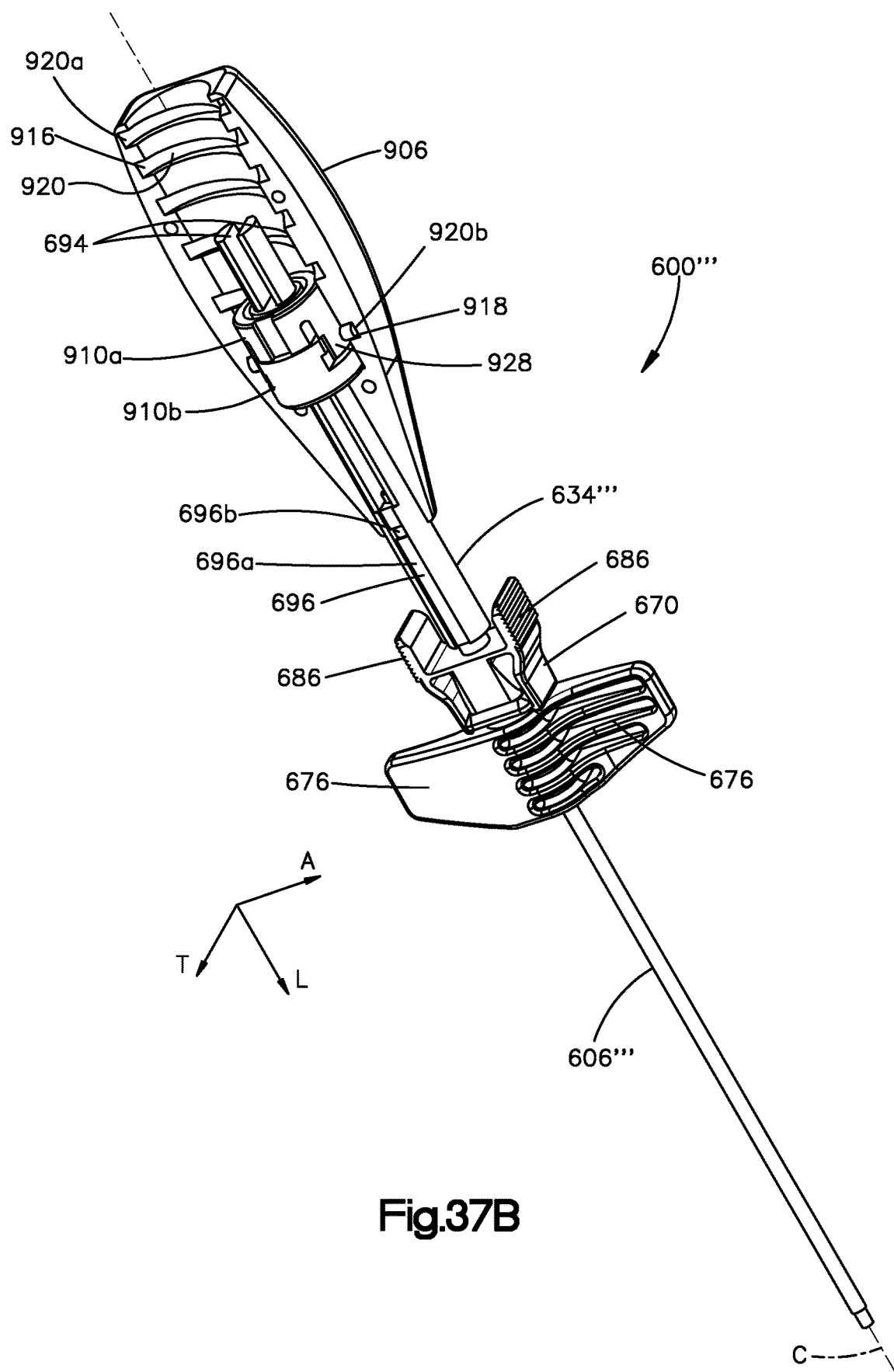
Figure 38:
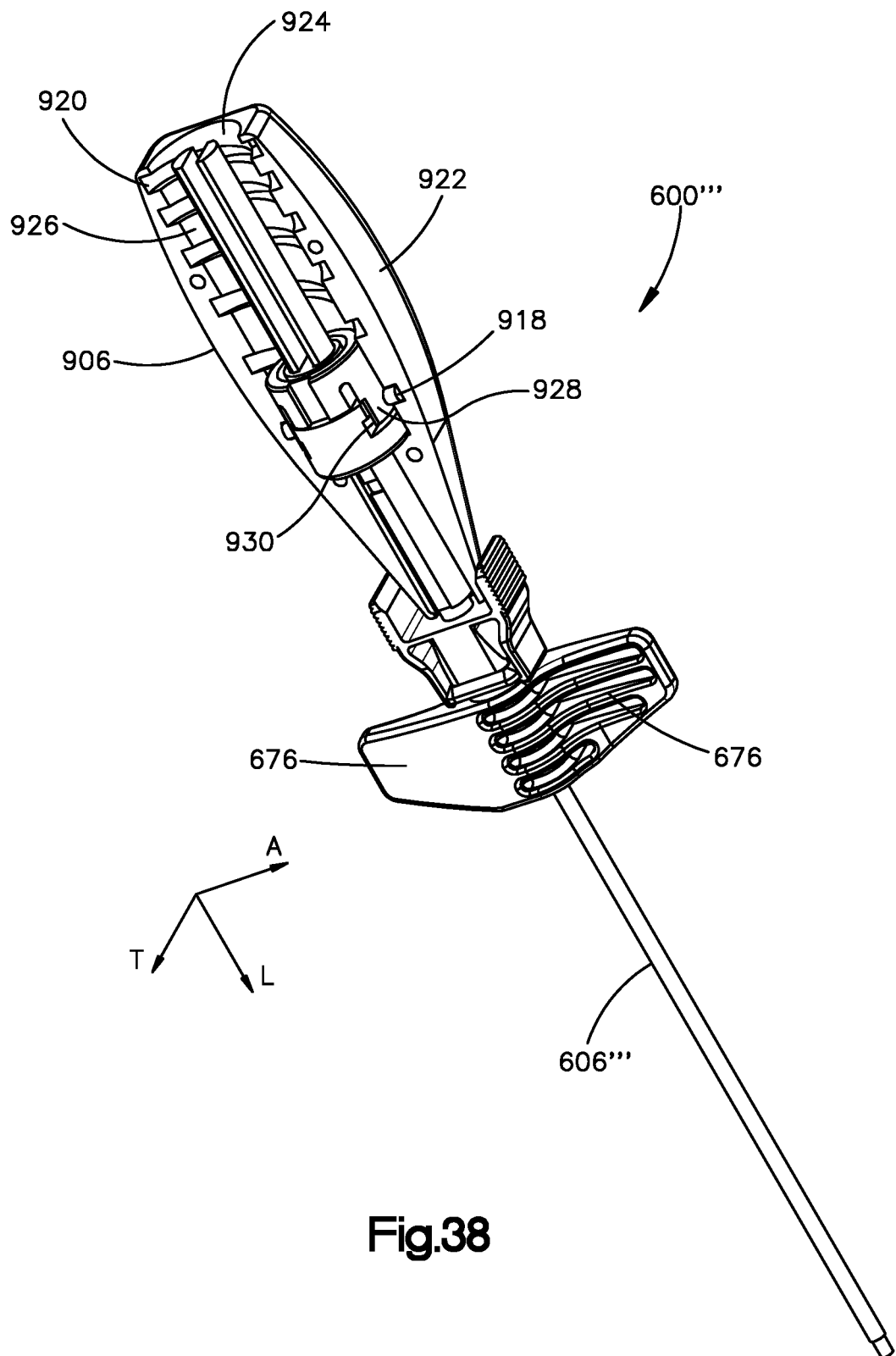
Figure 39:
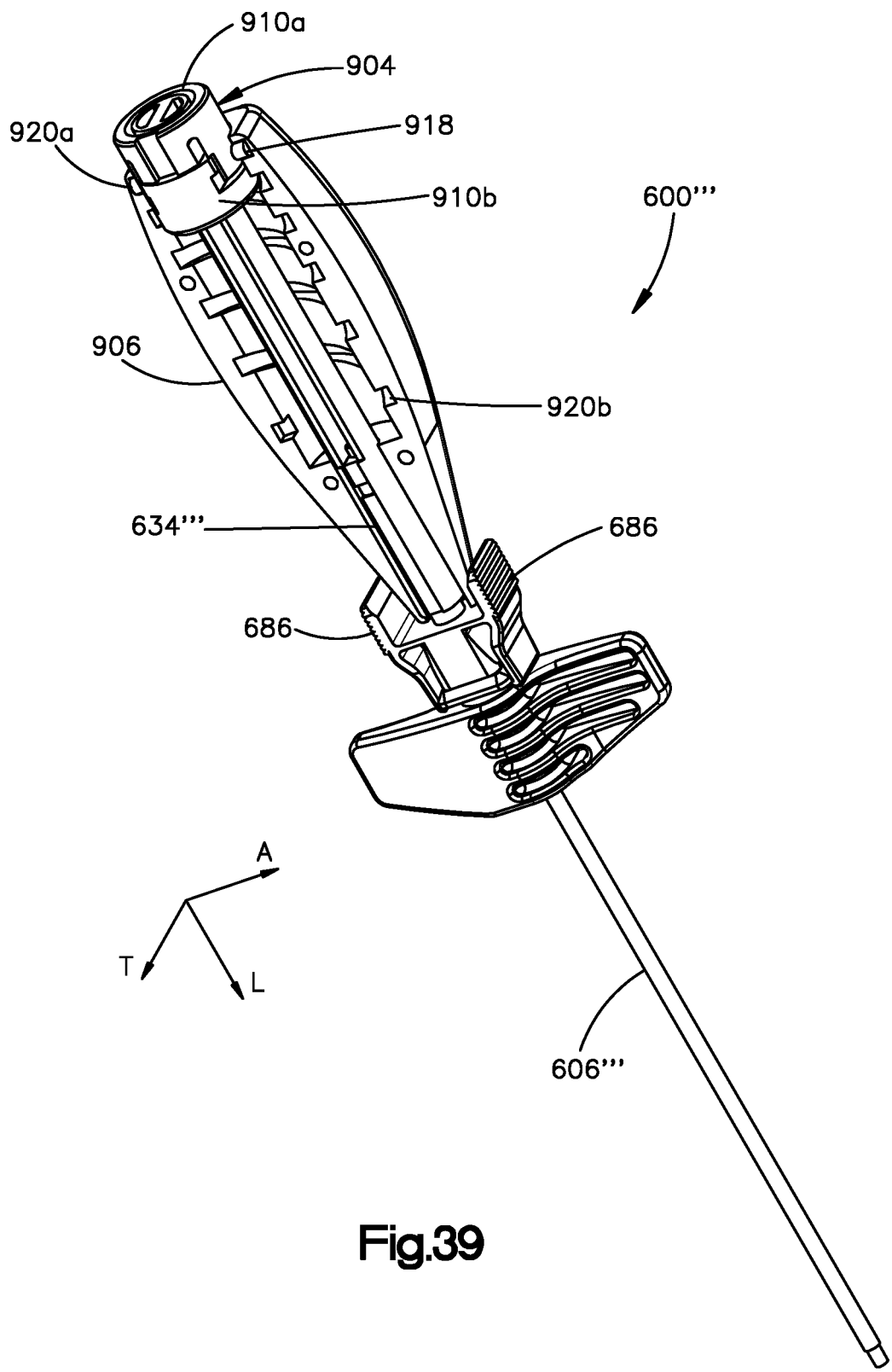
Figure 40B:
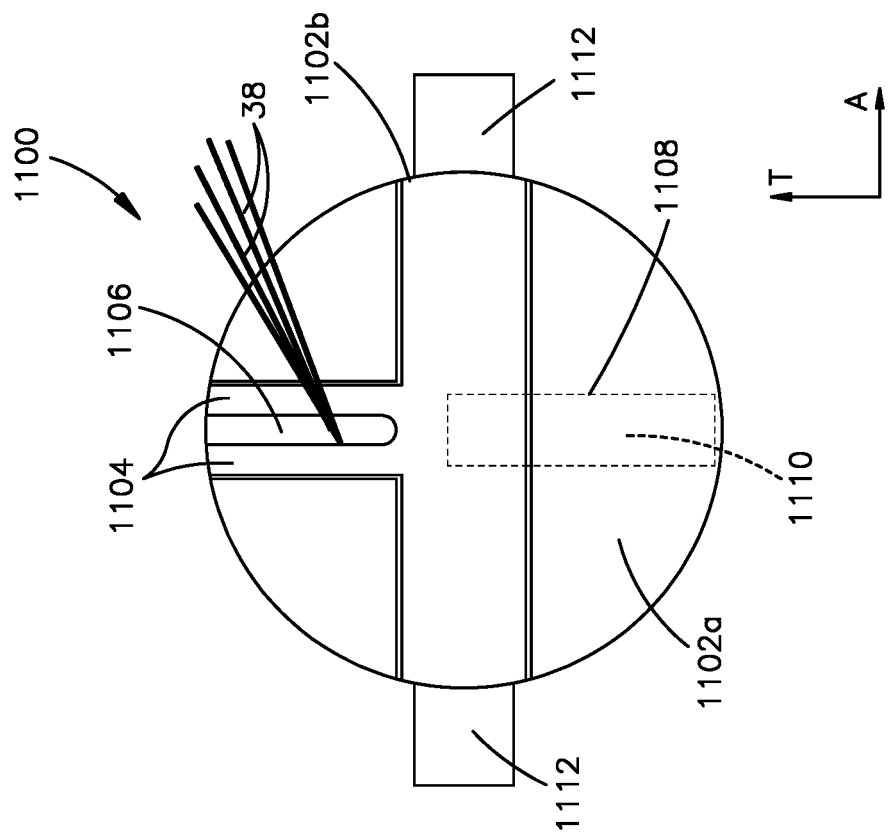
Figure 40A:
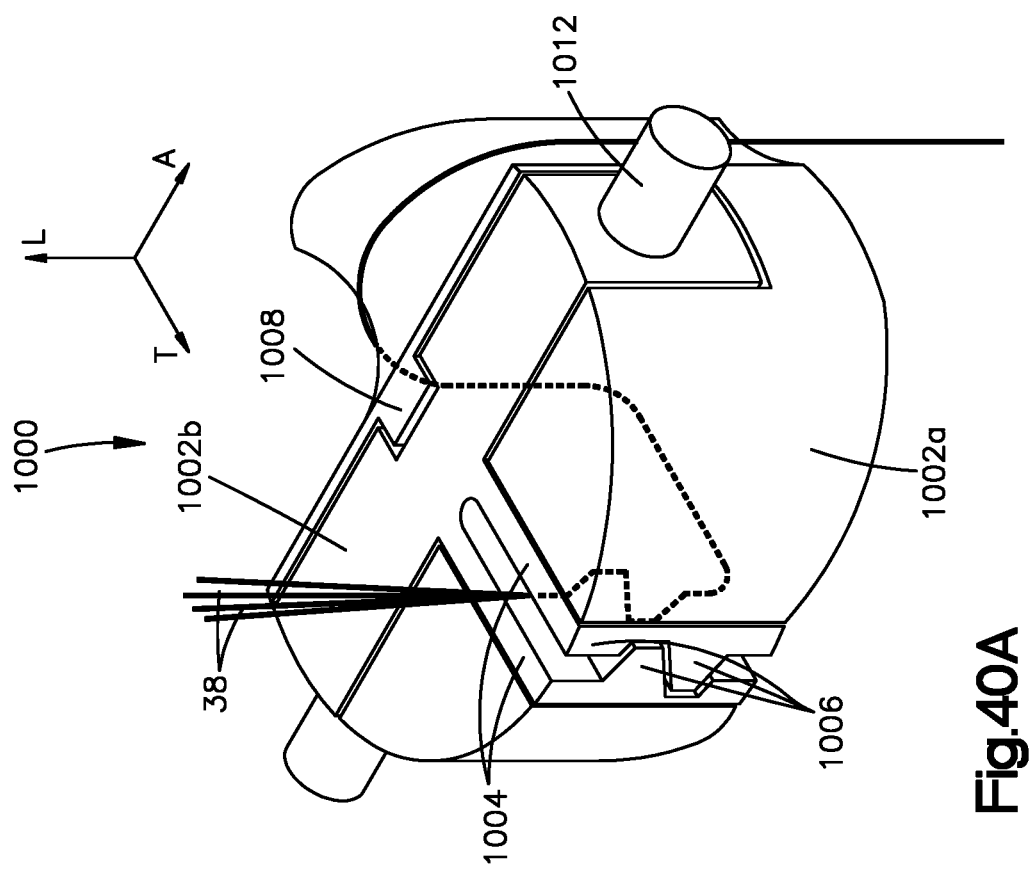
Figure 42:
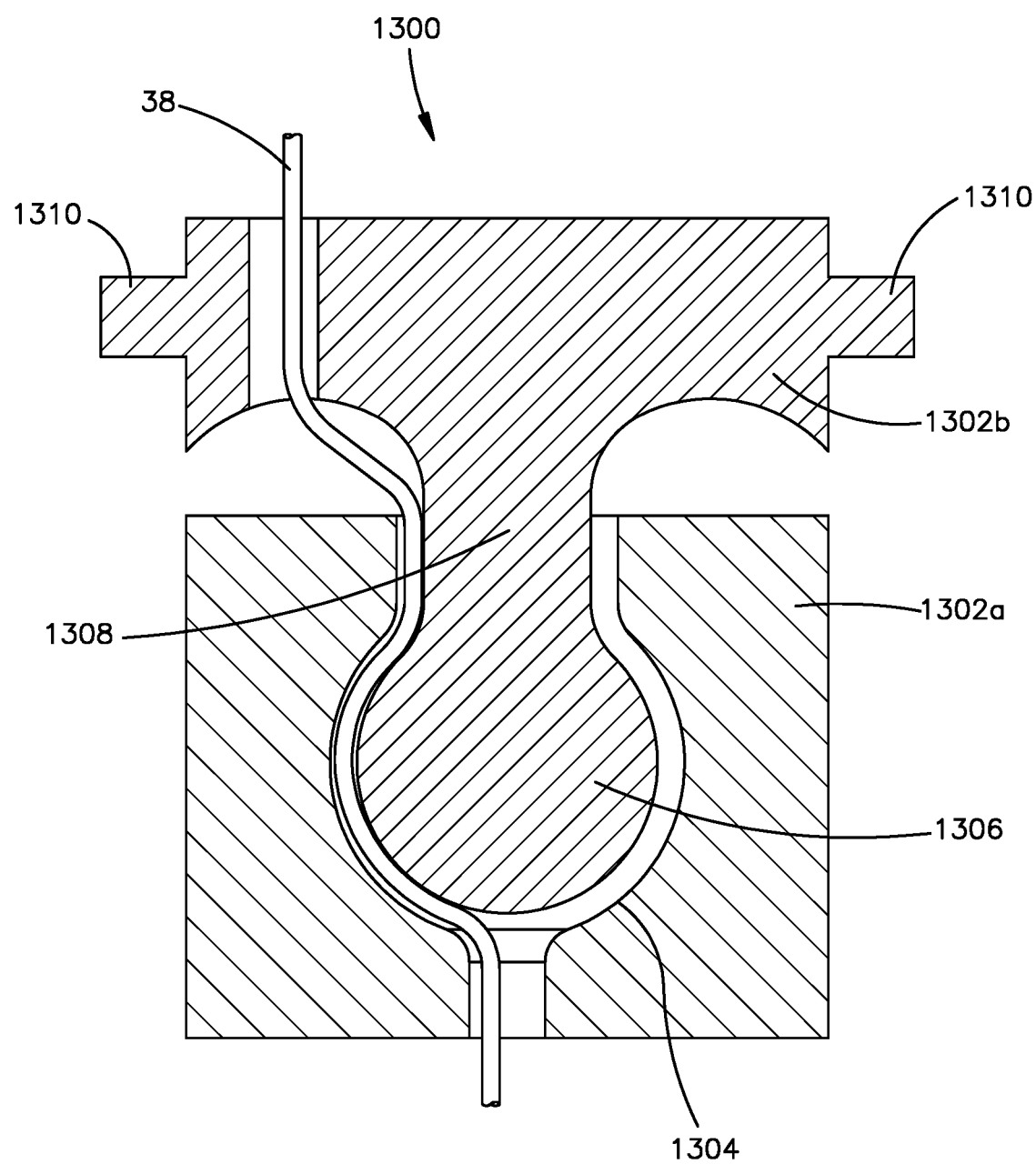
Figure 43:
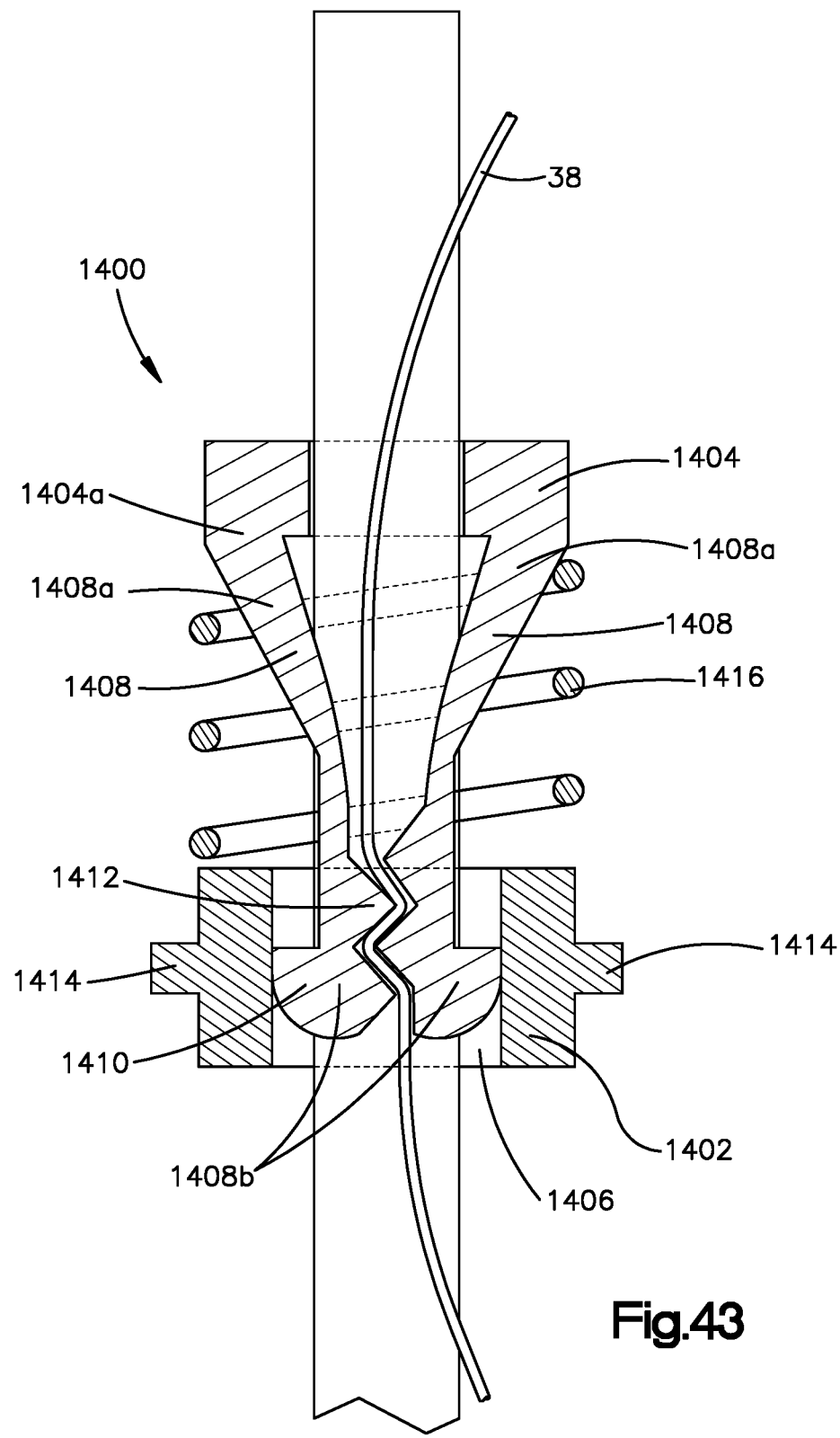
Figure 44A:
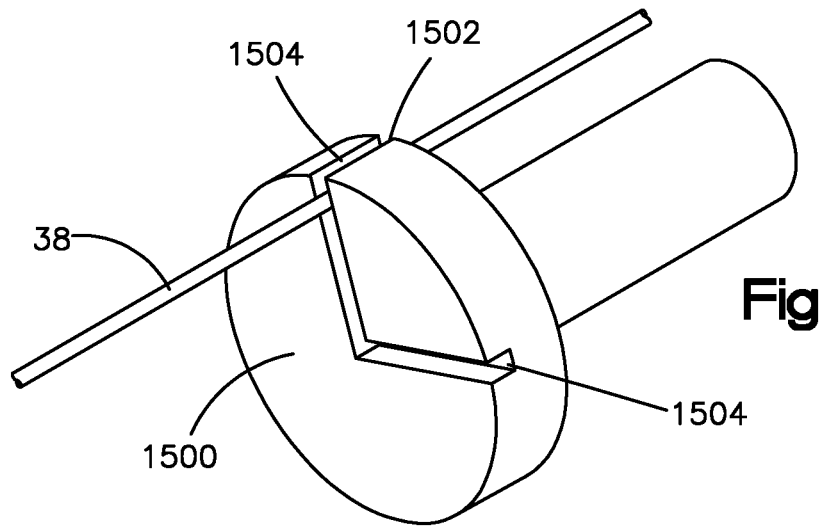
Figure 44B:
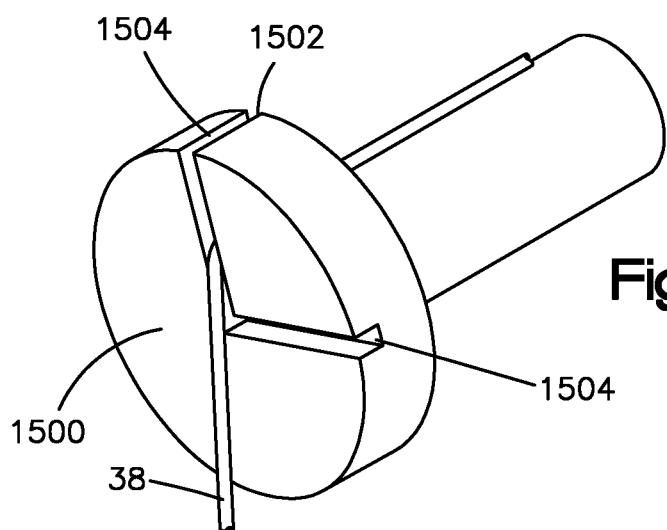
Figure 44C:
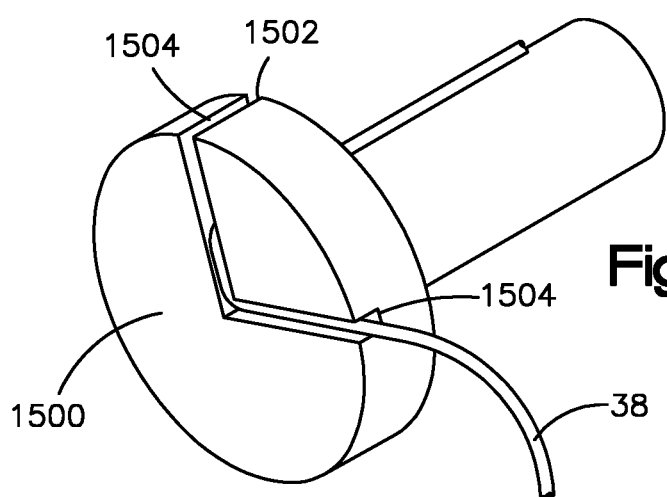
Figure 45:
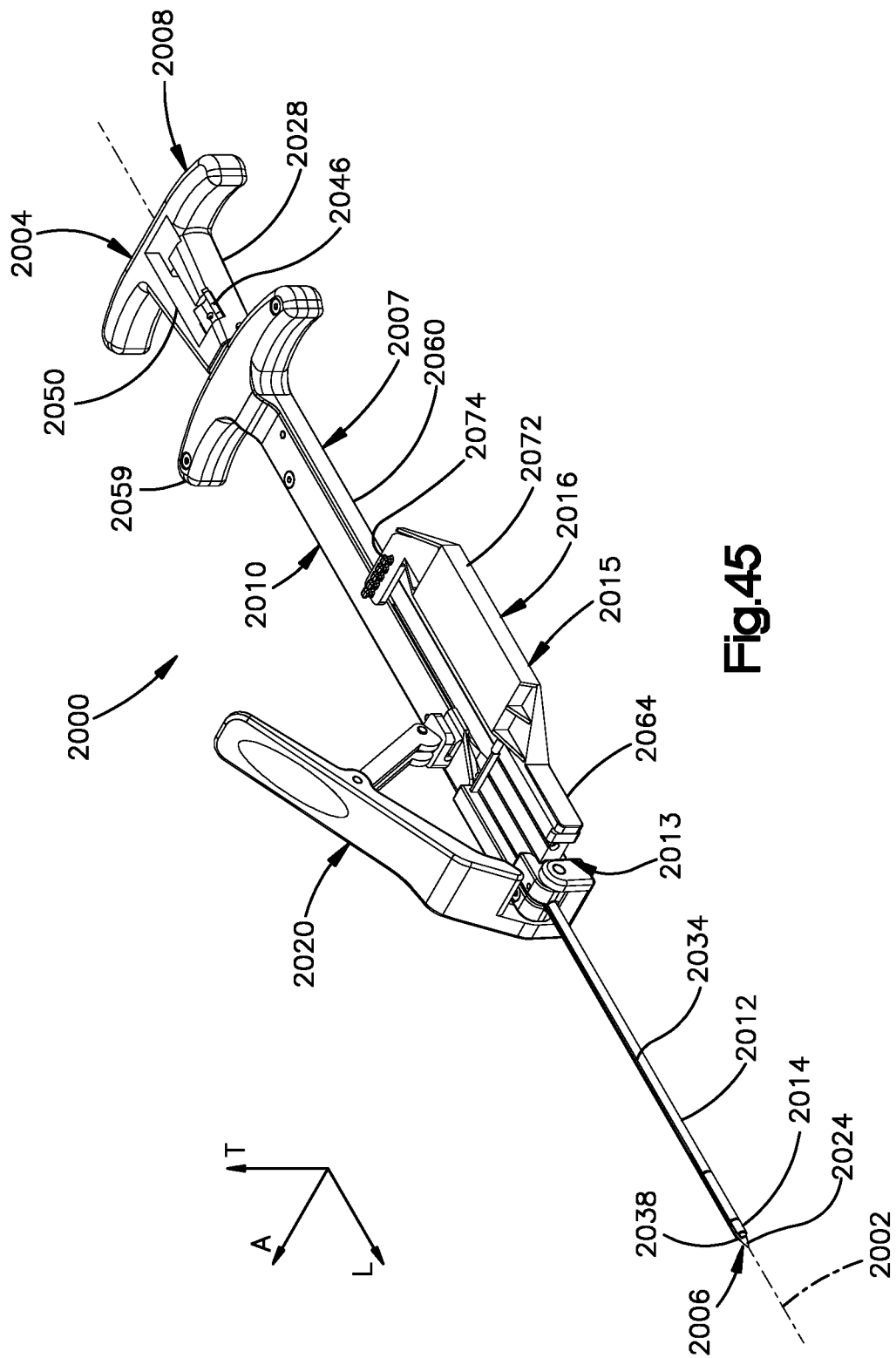
Figure 46:
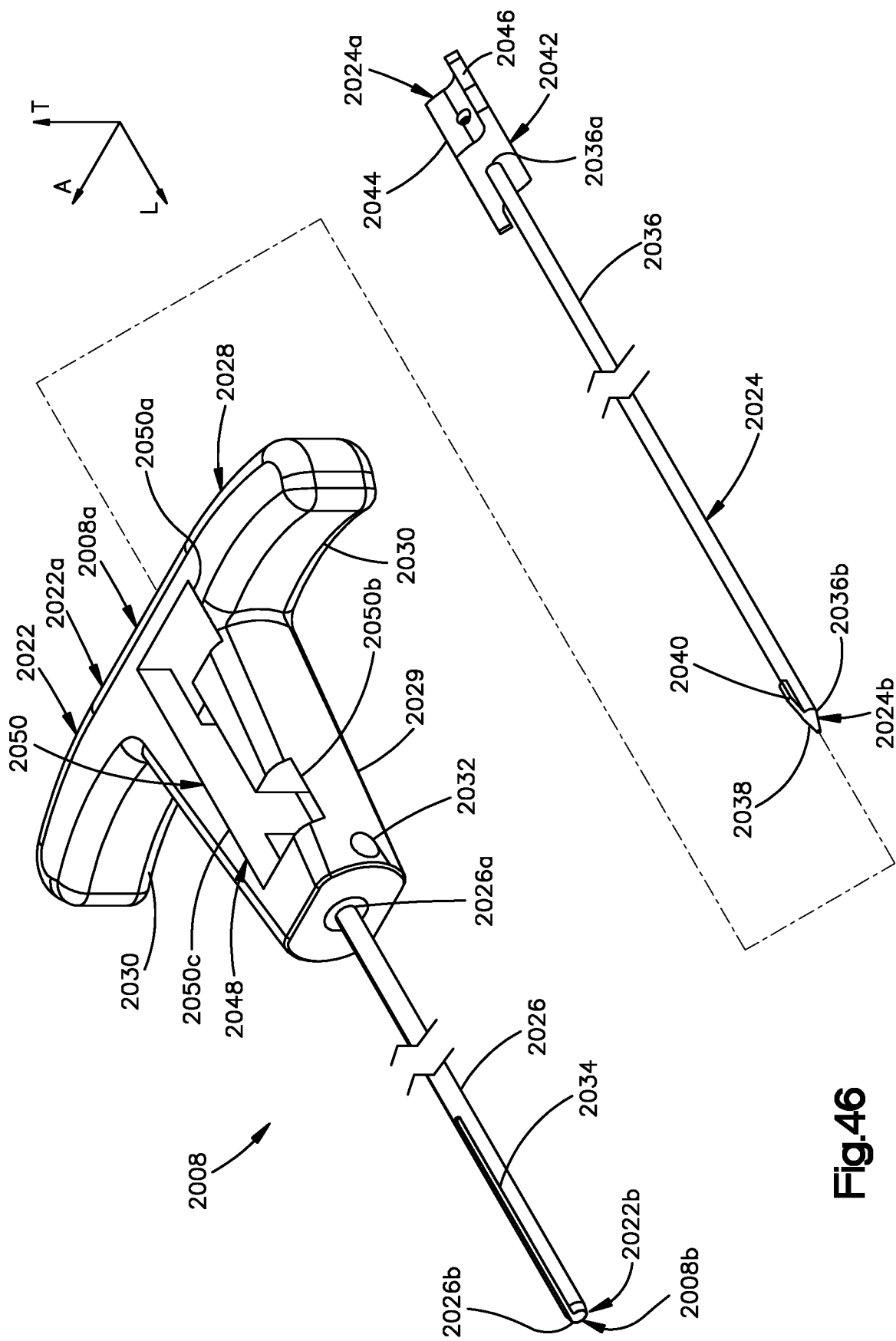
Figure 49A:
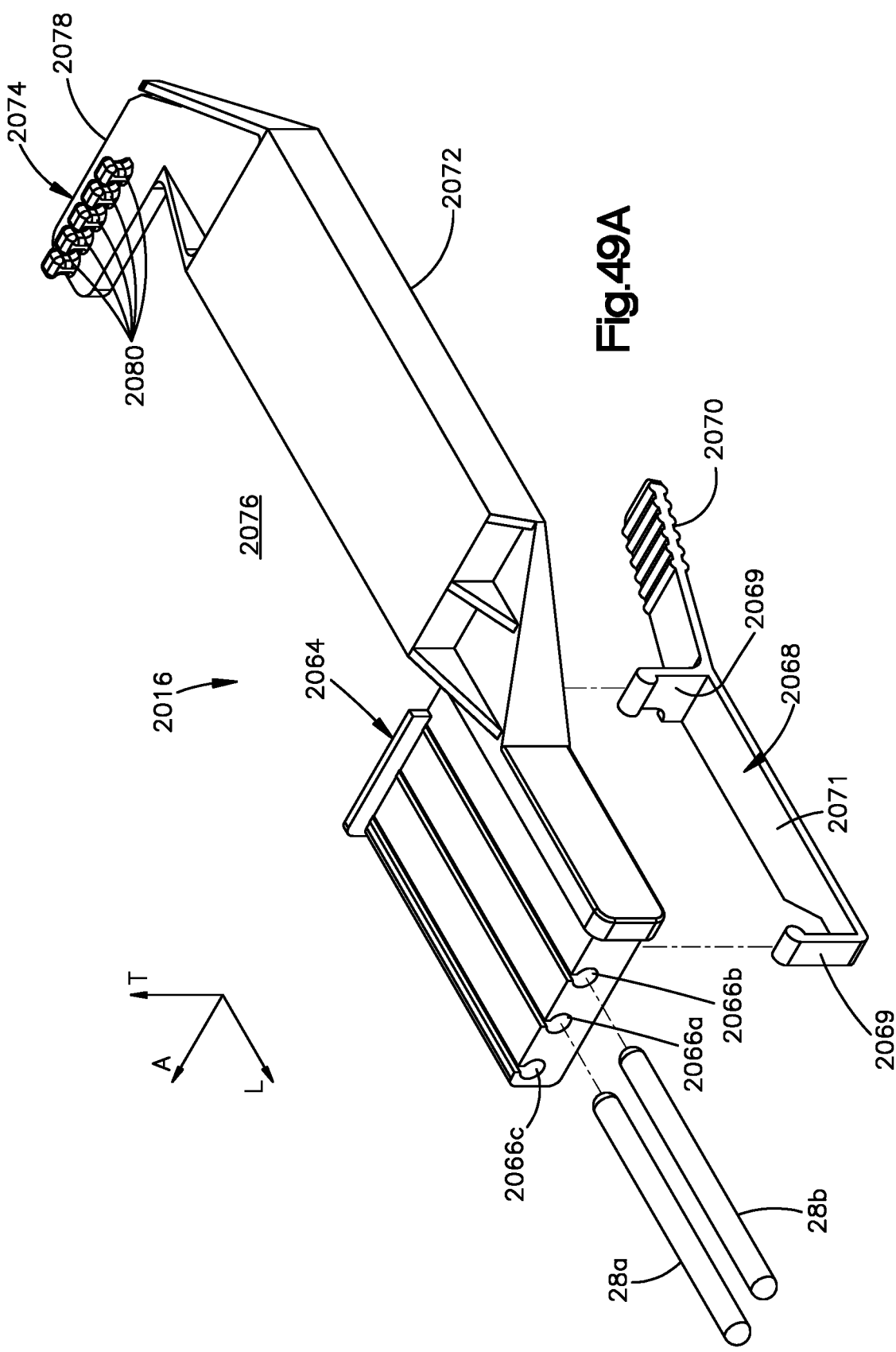
Figure 49B:
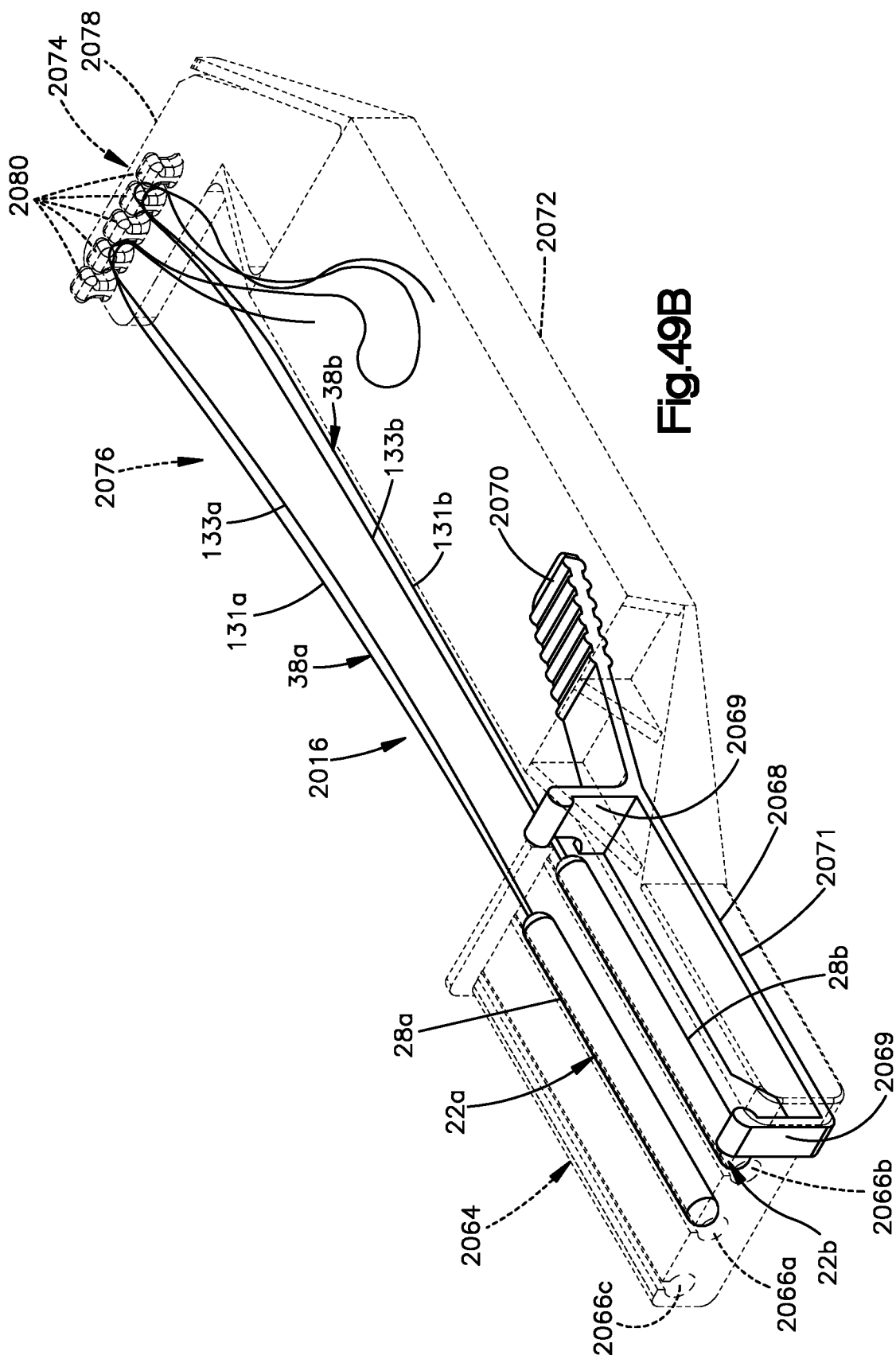
Figure 51D:
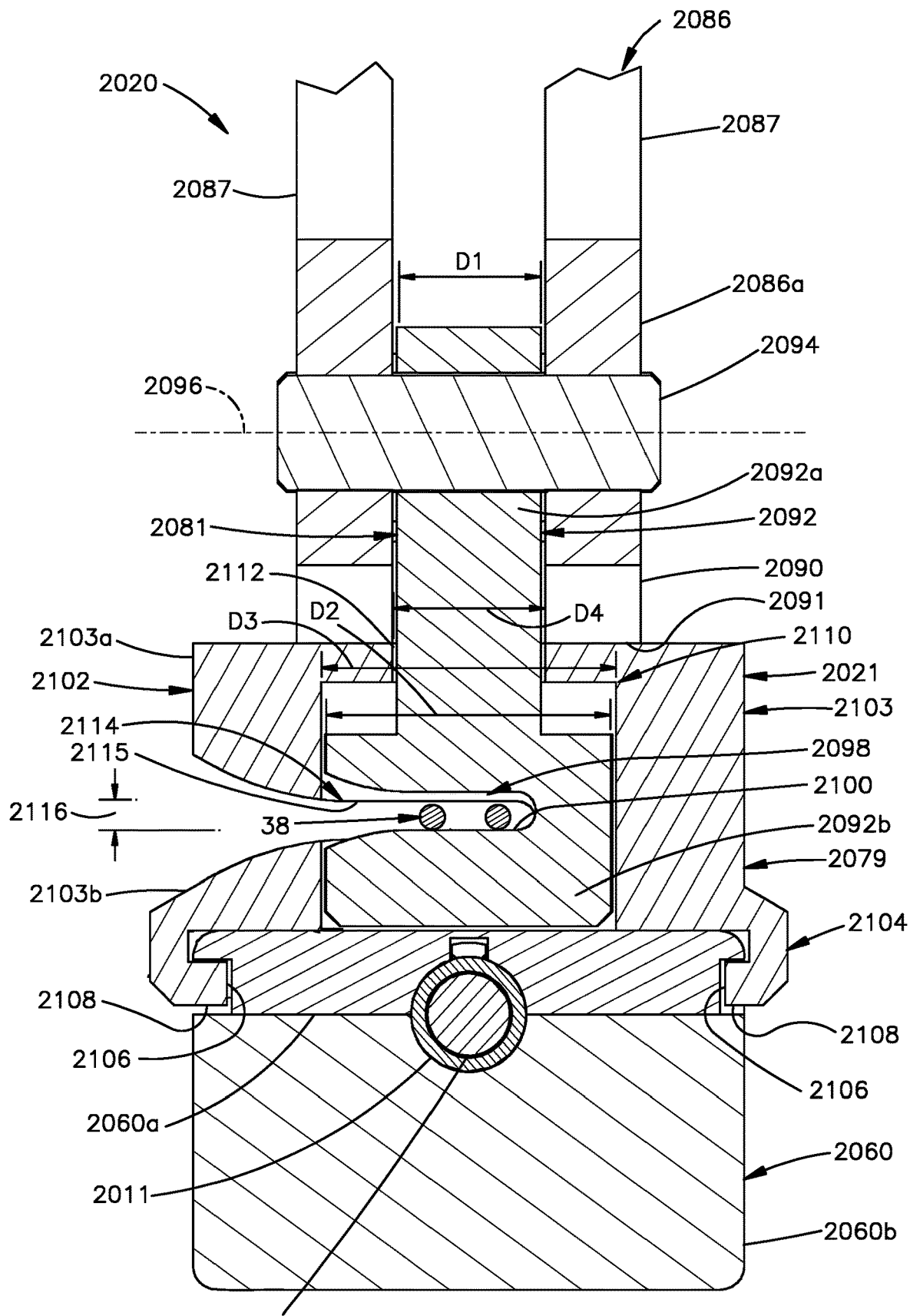
Figure 51:
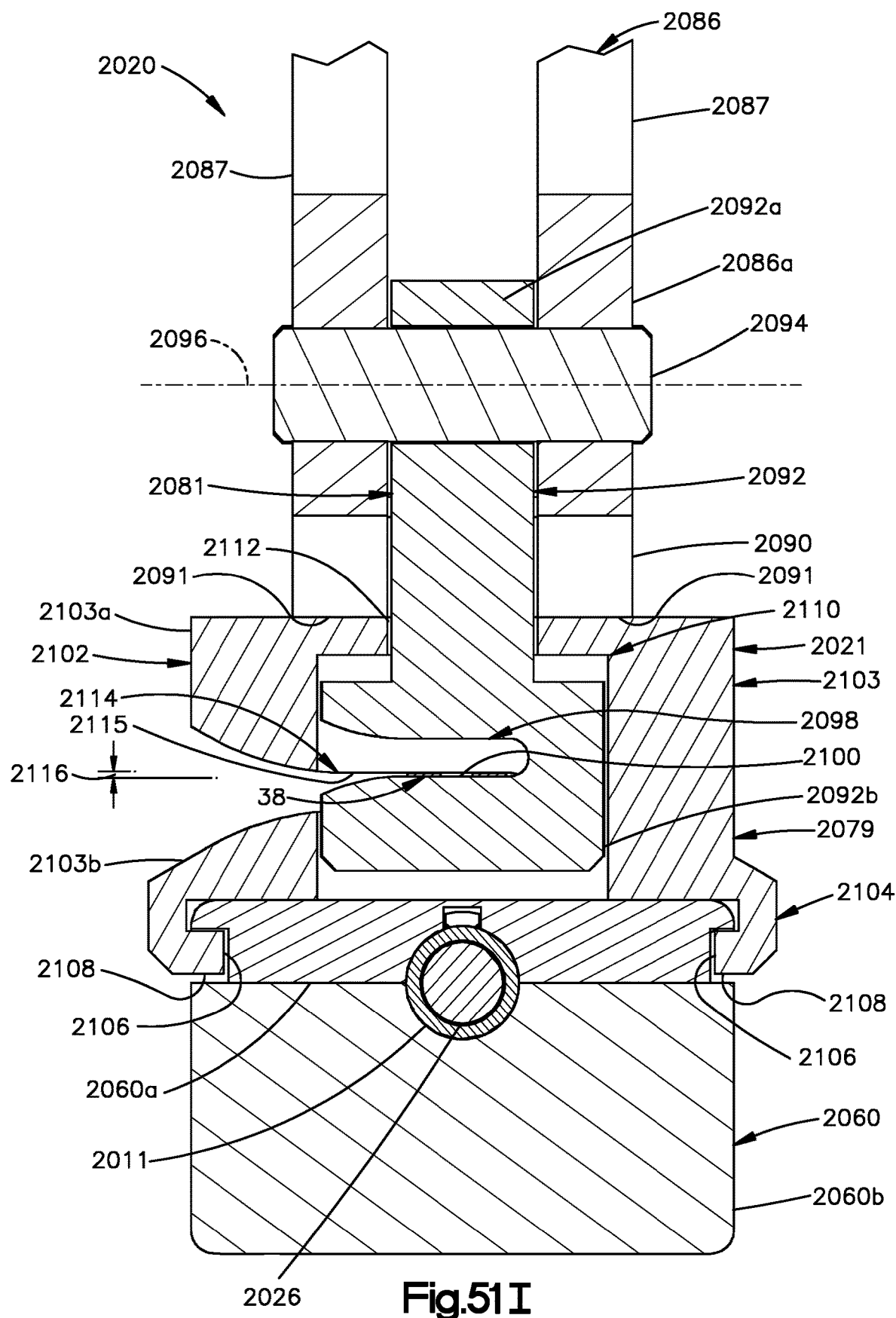
Figure 52A:
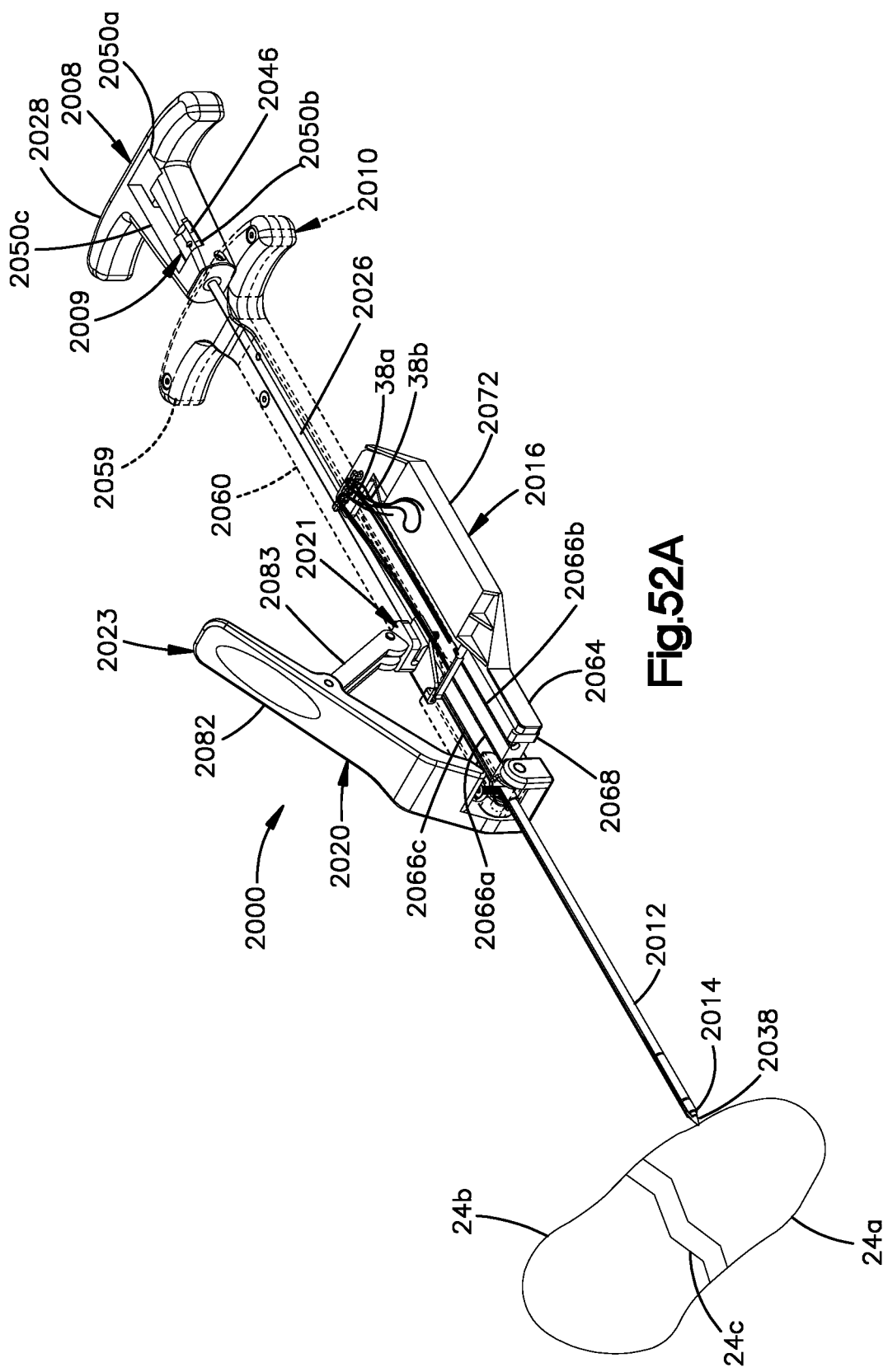
Figure 52B:
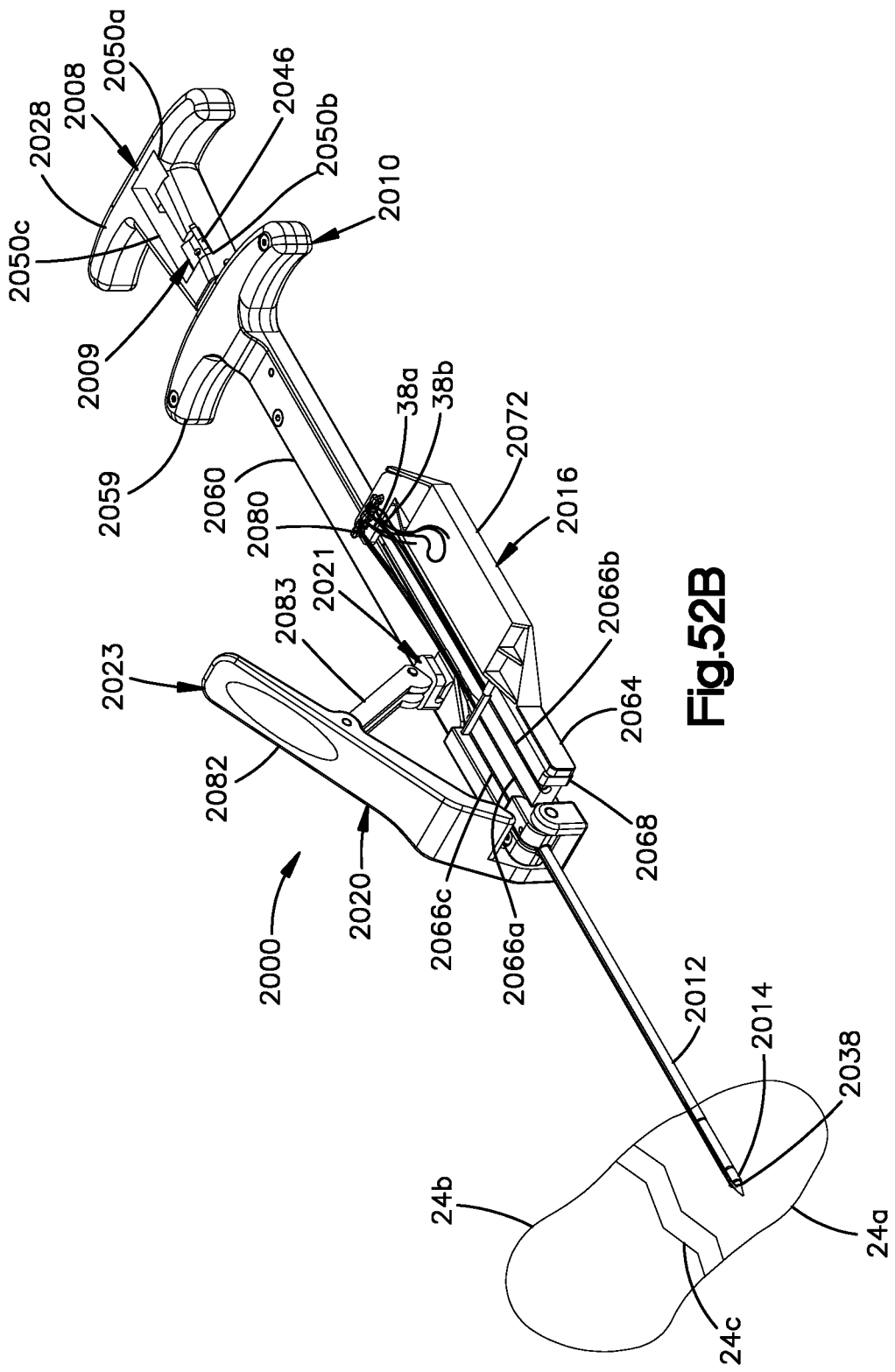
Figure 52C:
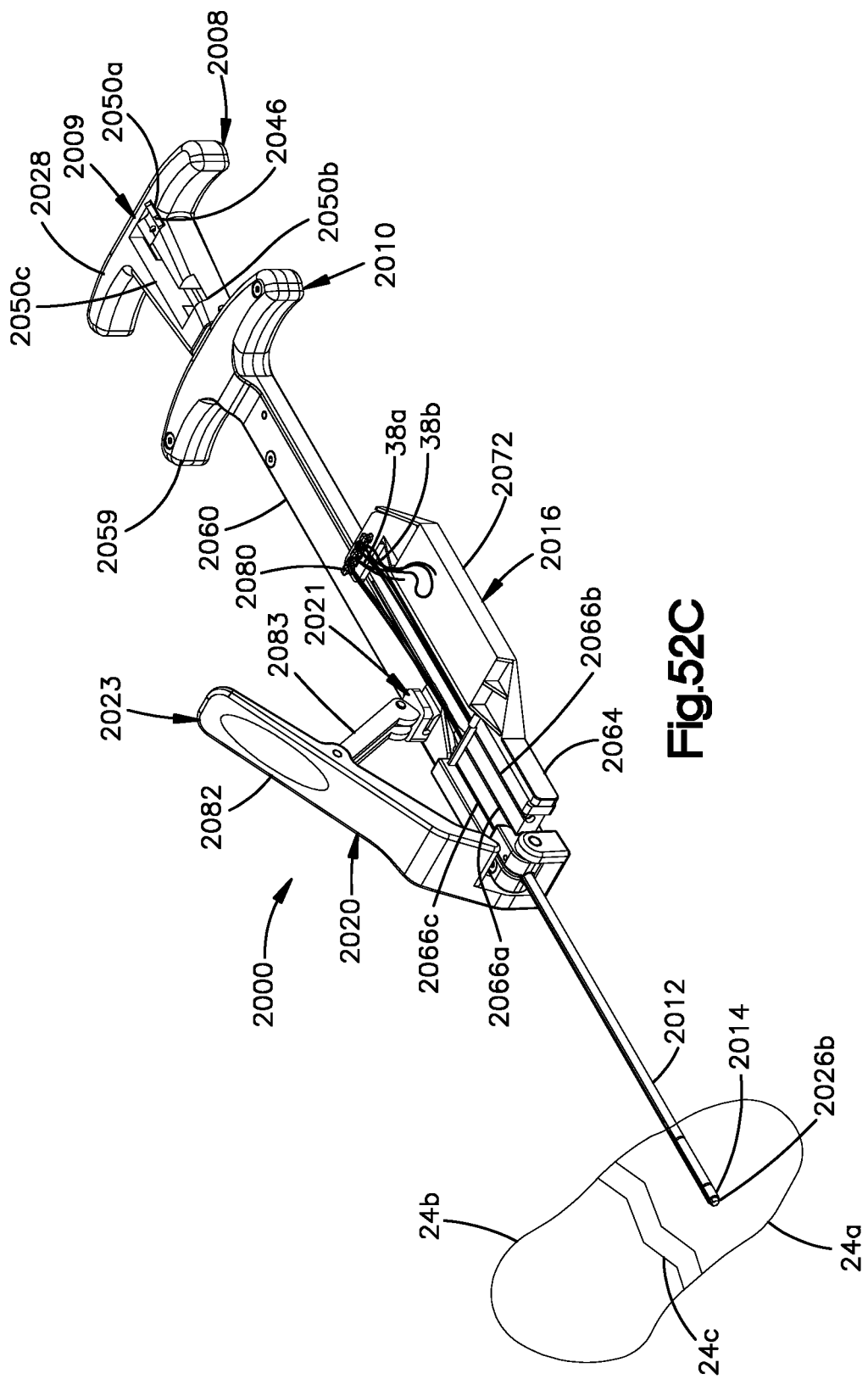
Figure 53A:
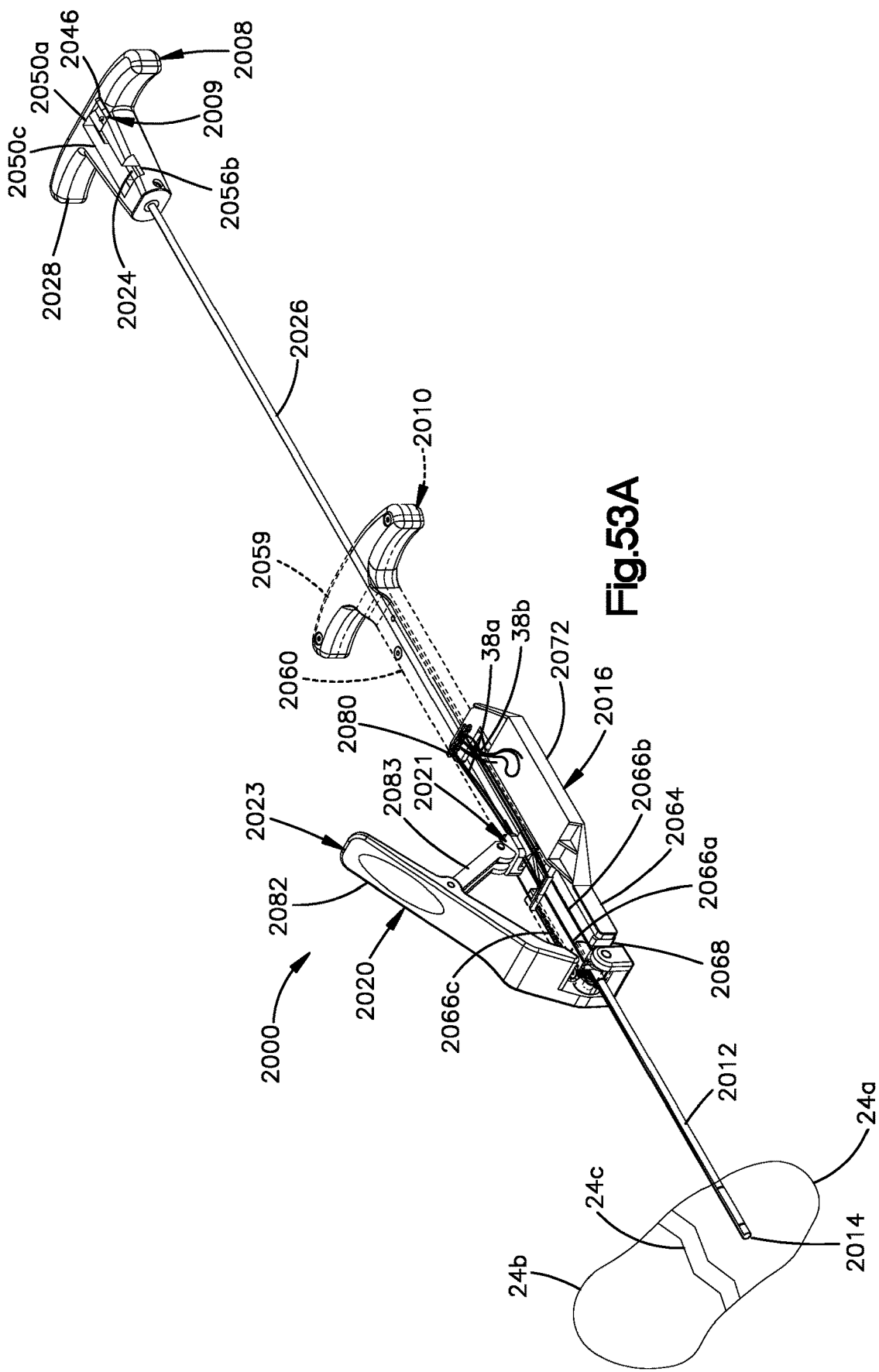
Figure 53B:
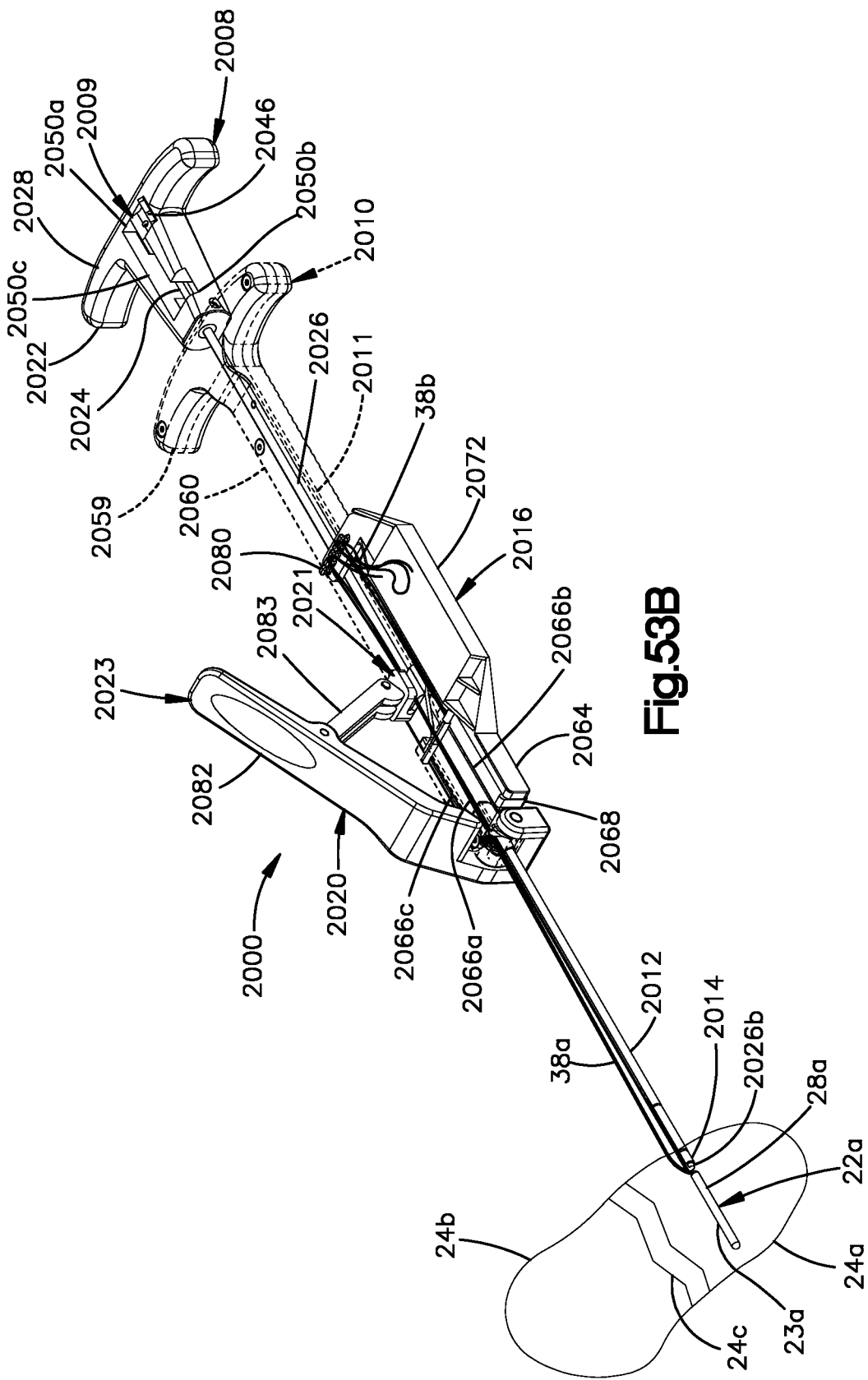
Figure 53C:
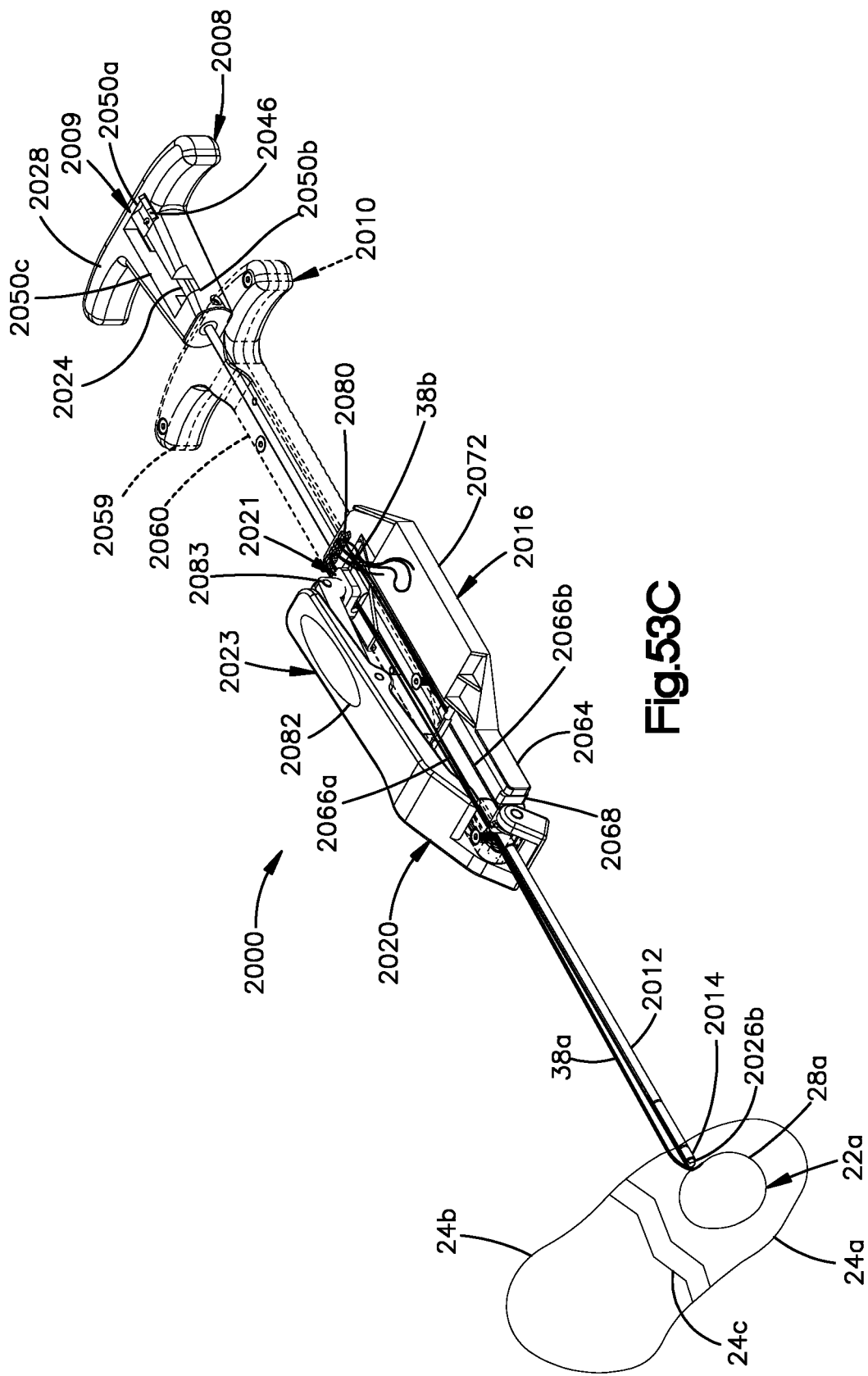
Figure 53D:
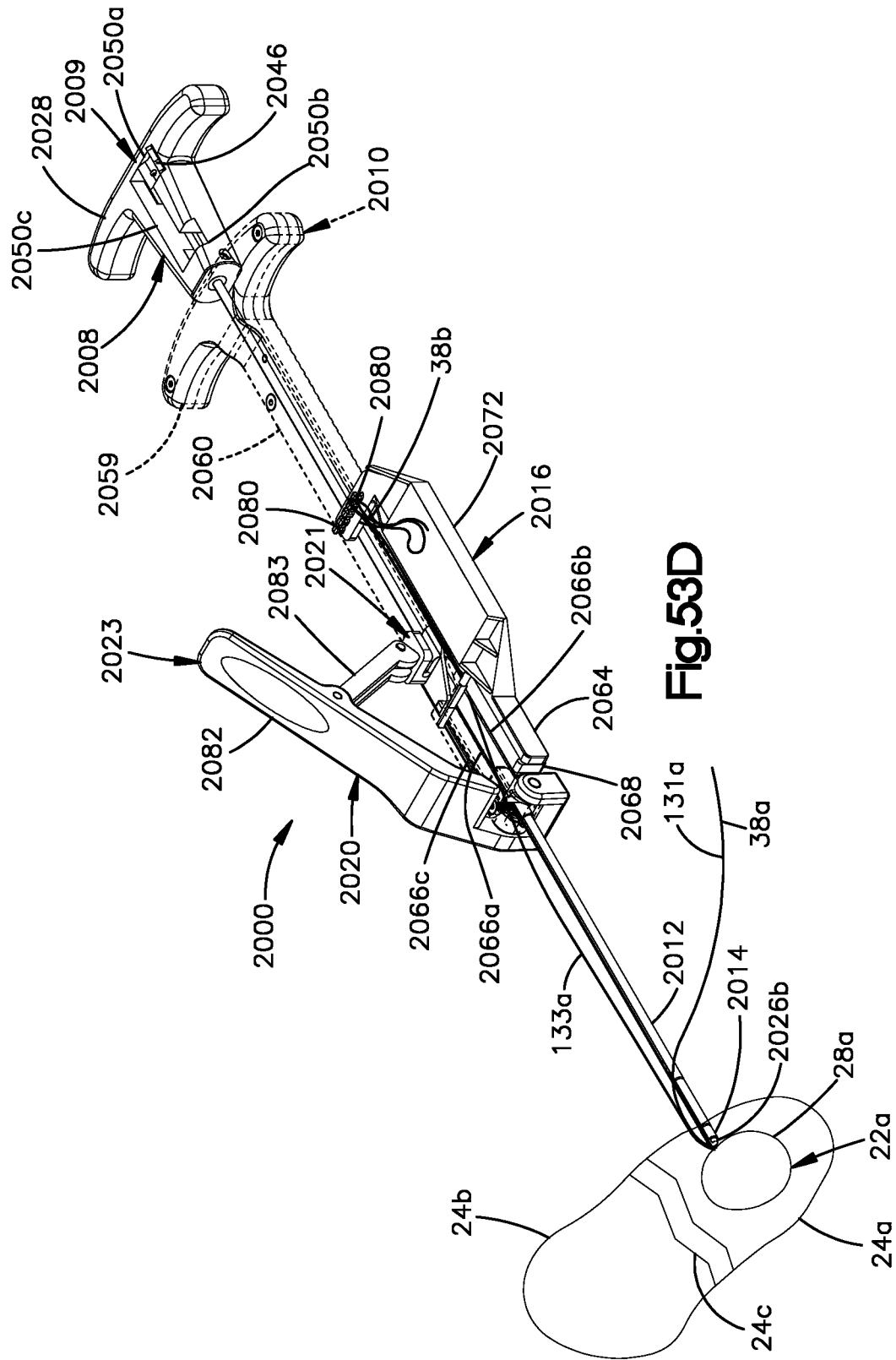
Figure 53E:
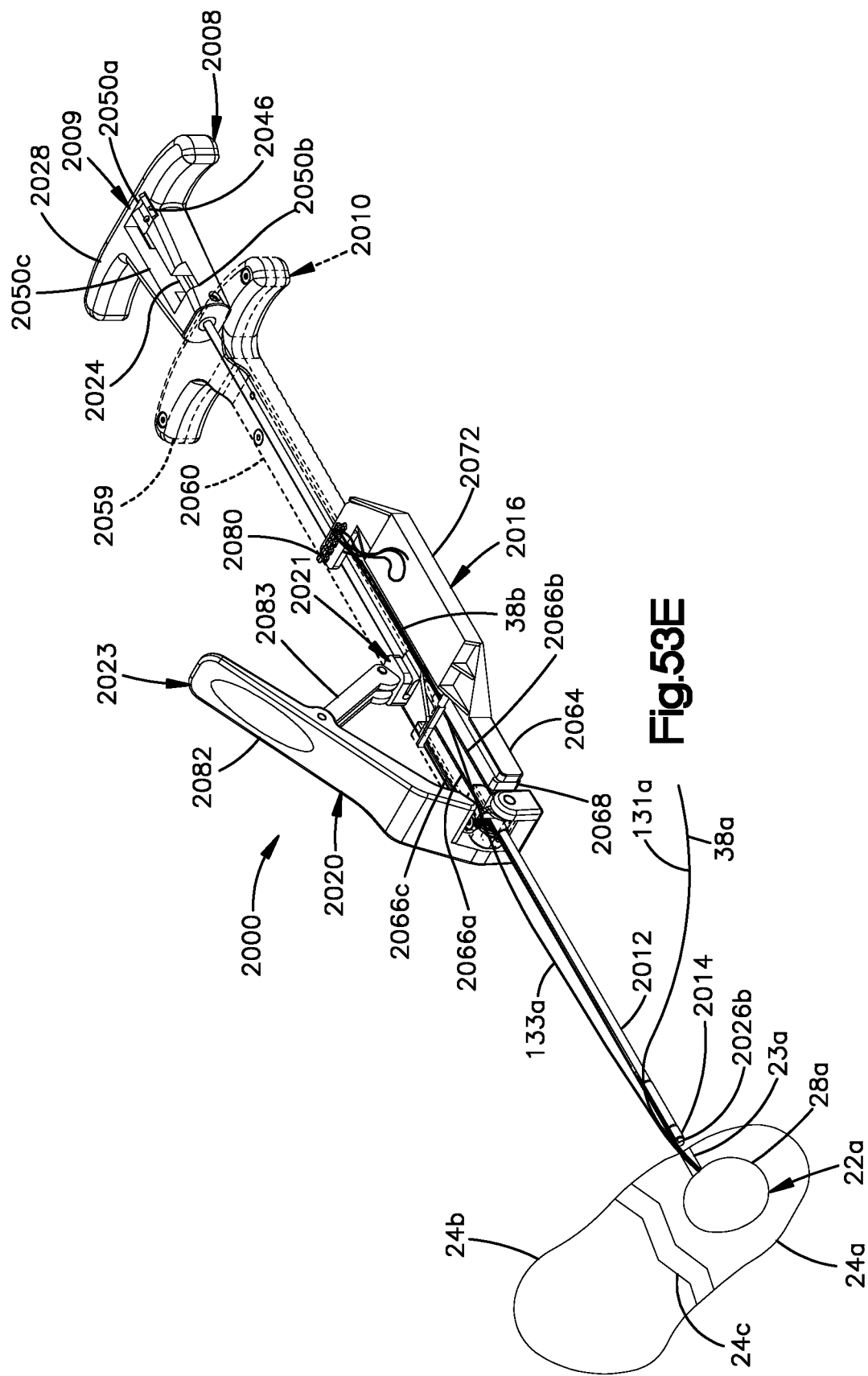
Figure 54B:
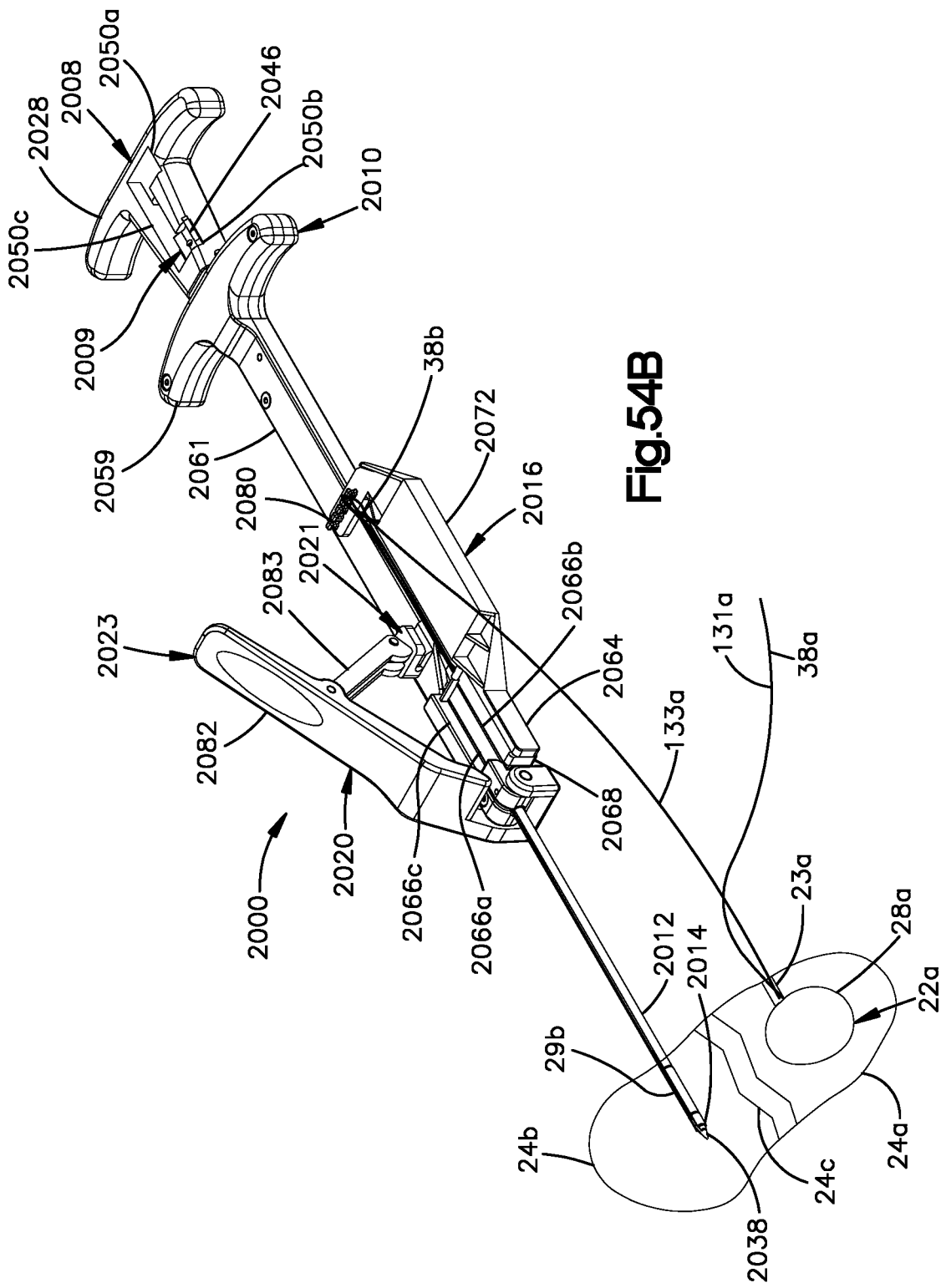
Figure 54C:
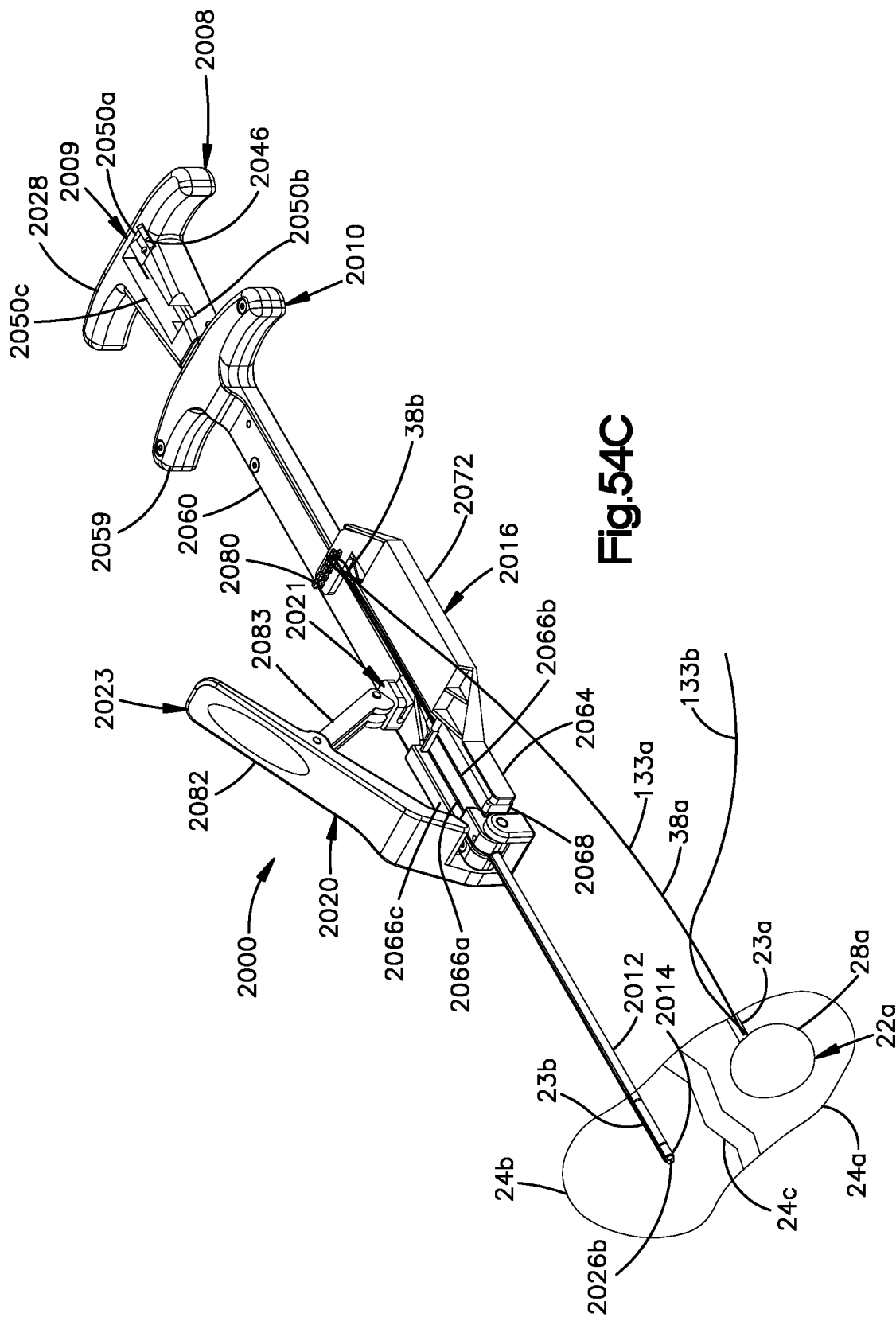
Figure 54D:
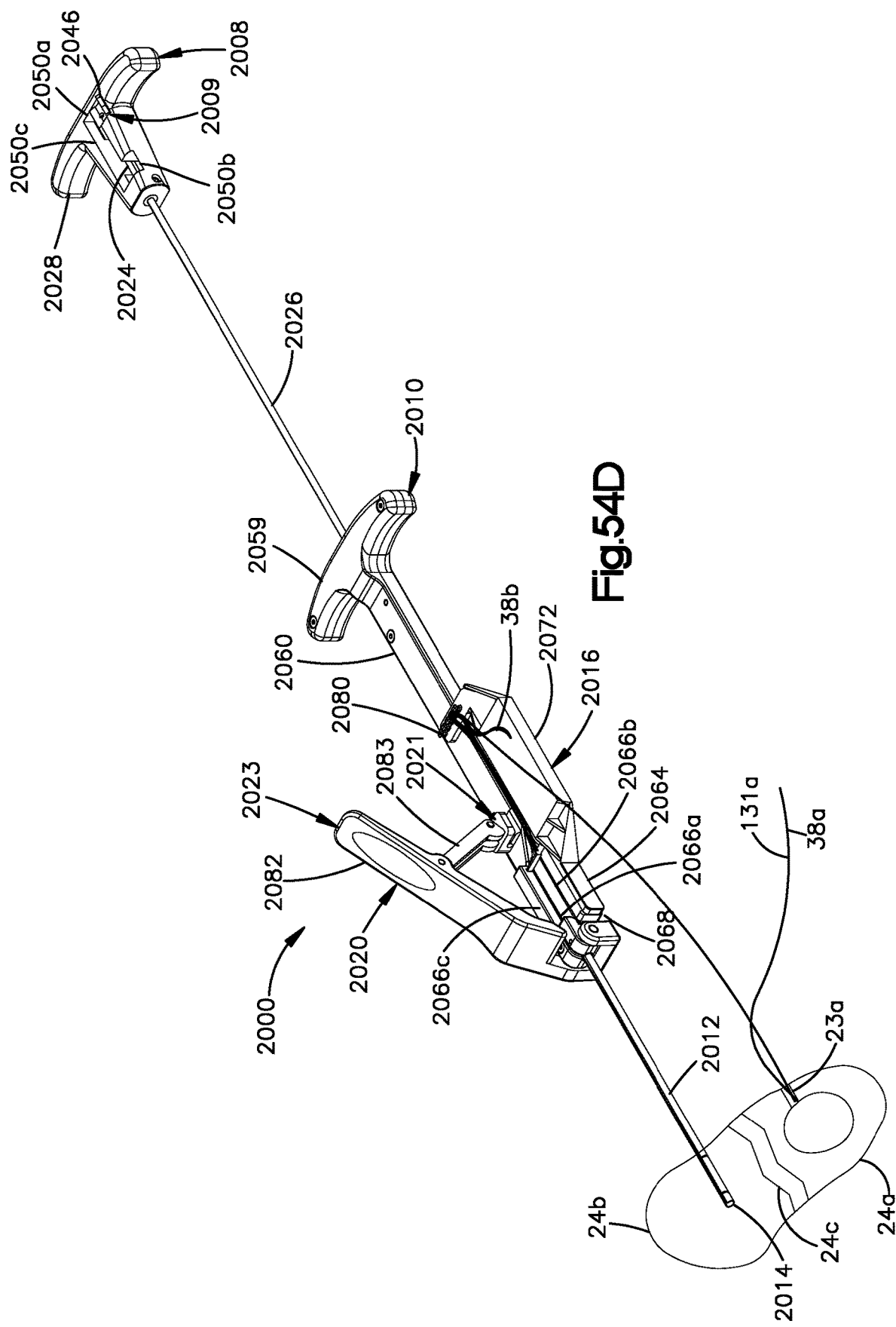
Figure 55A:
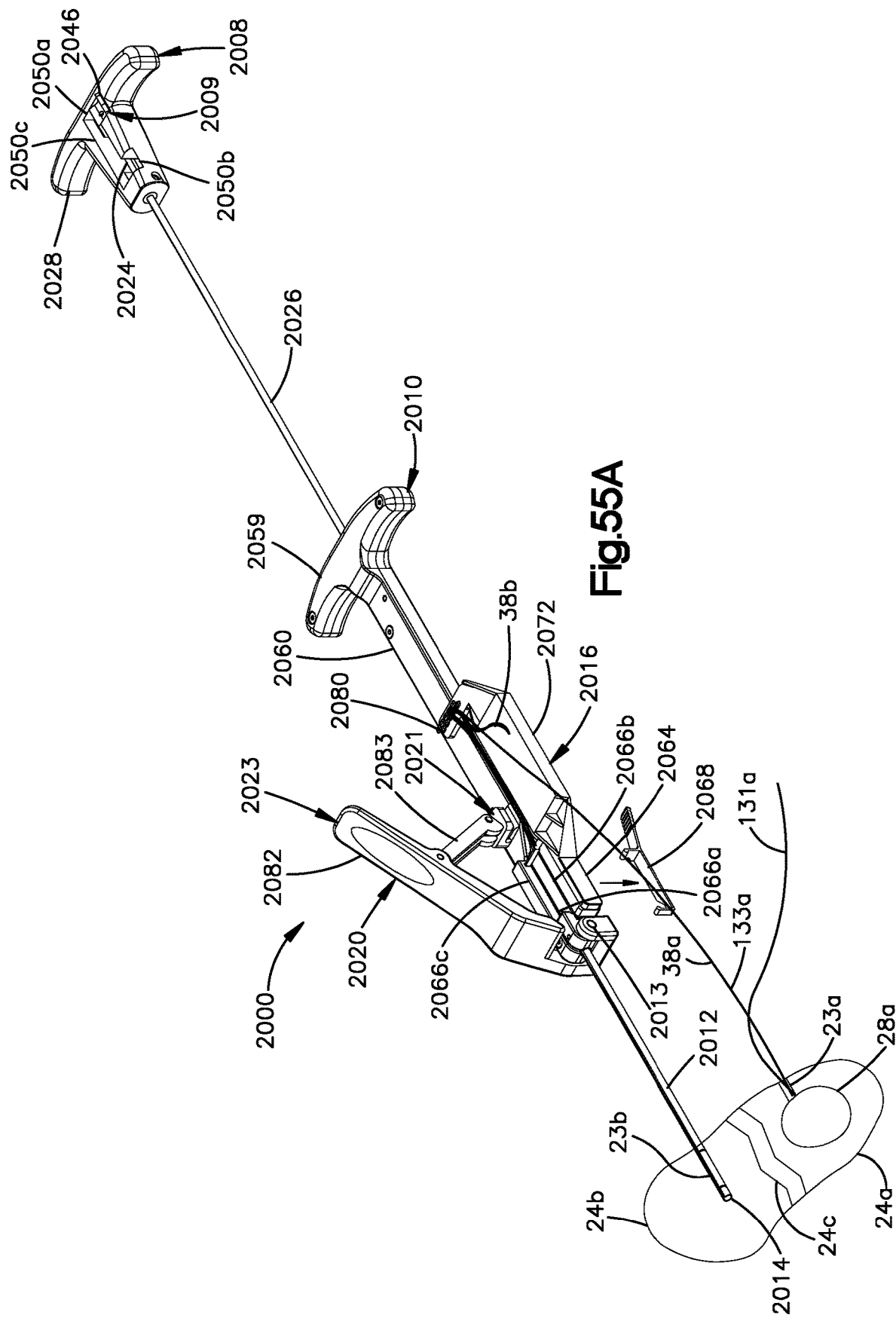
Figure 55C:
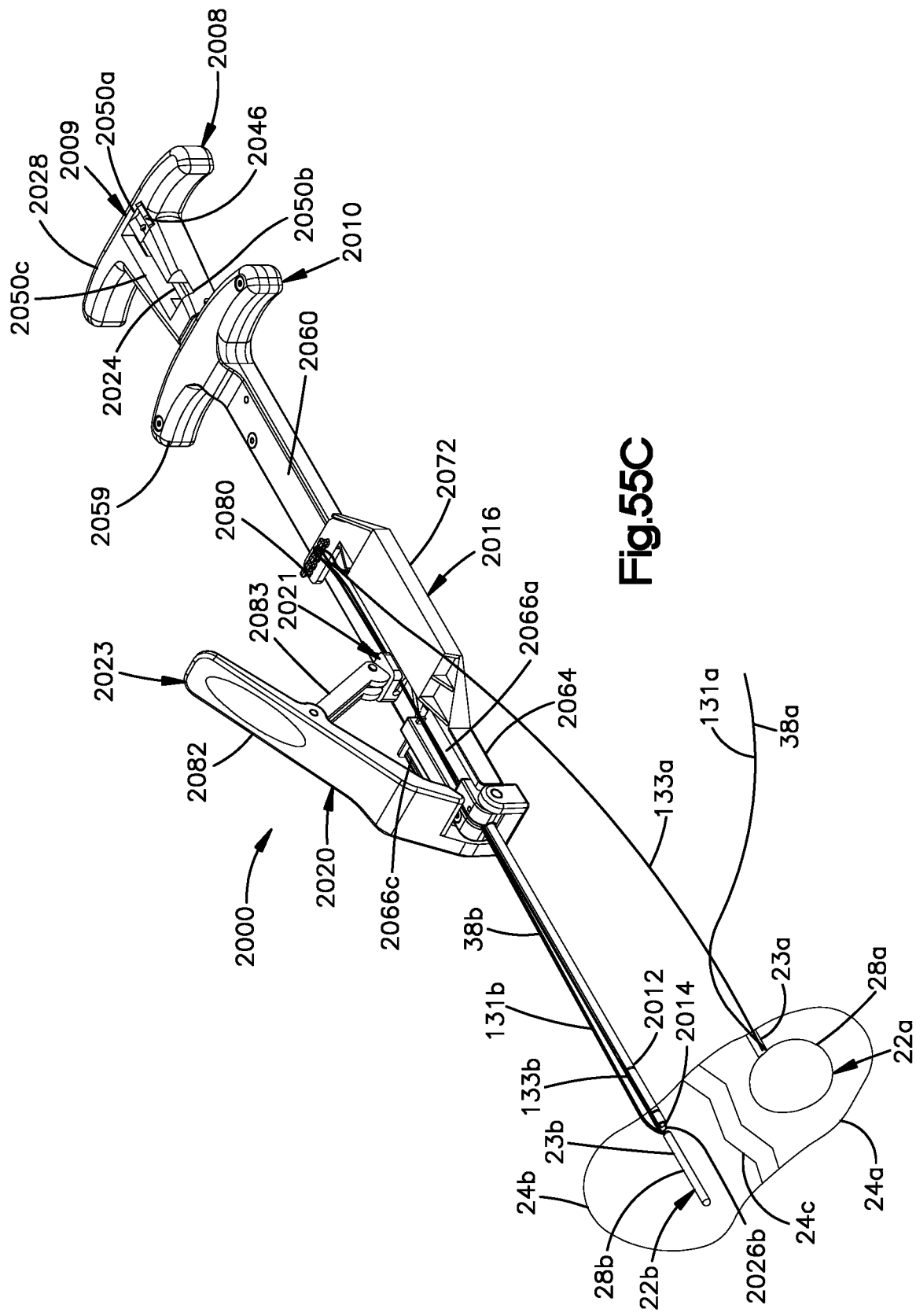
Figure 55D:
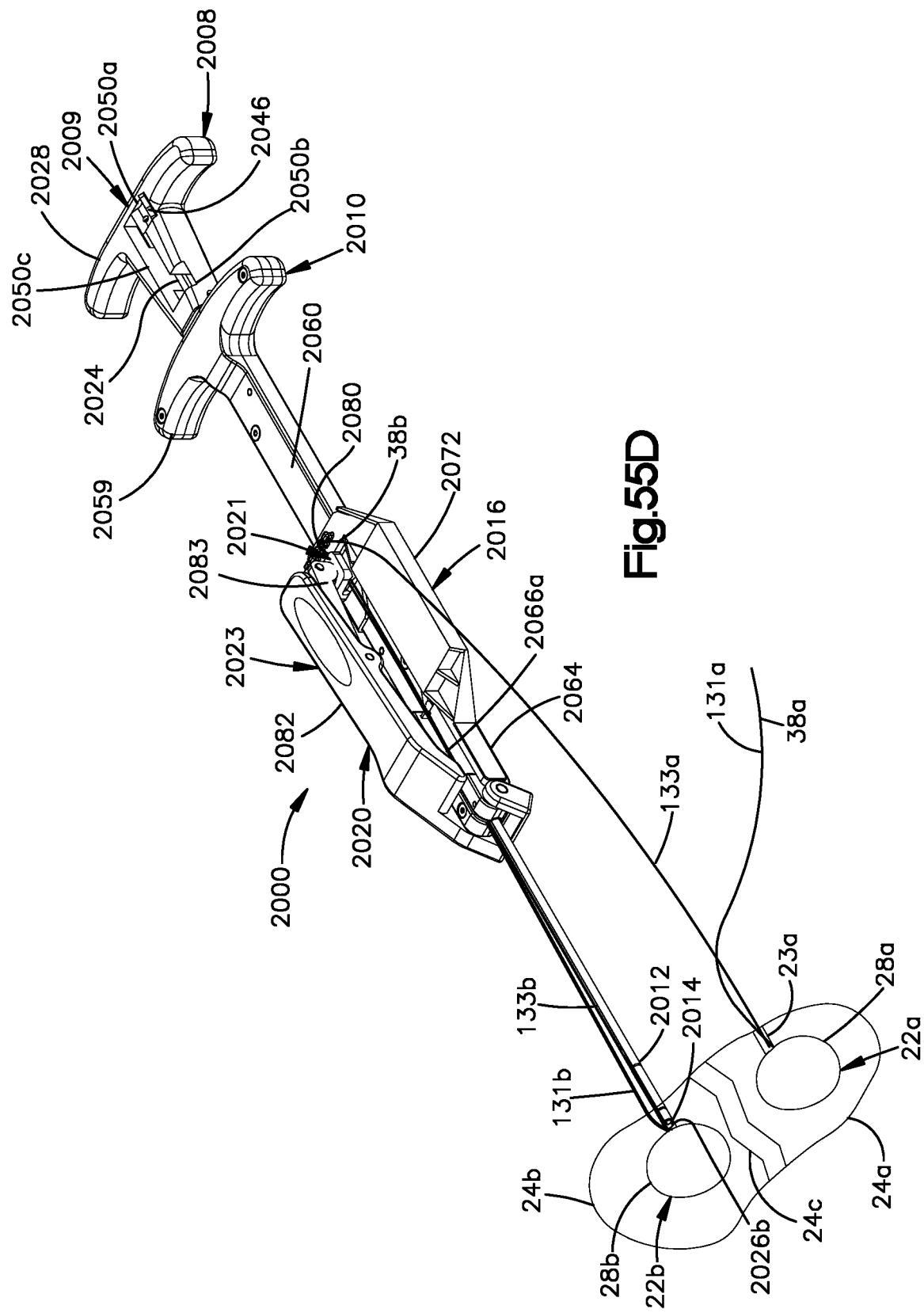
Figure 55E:
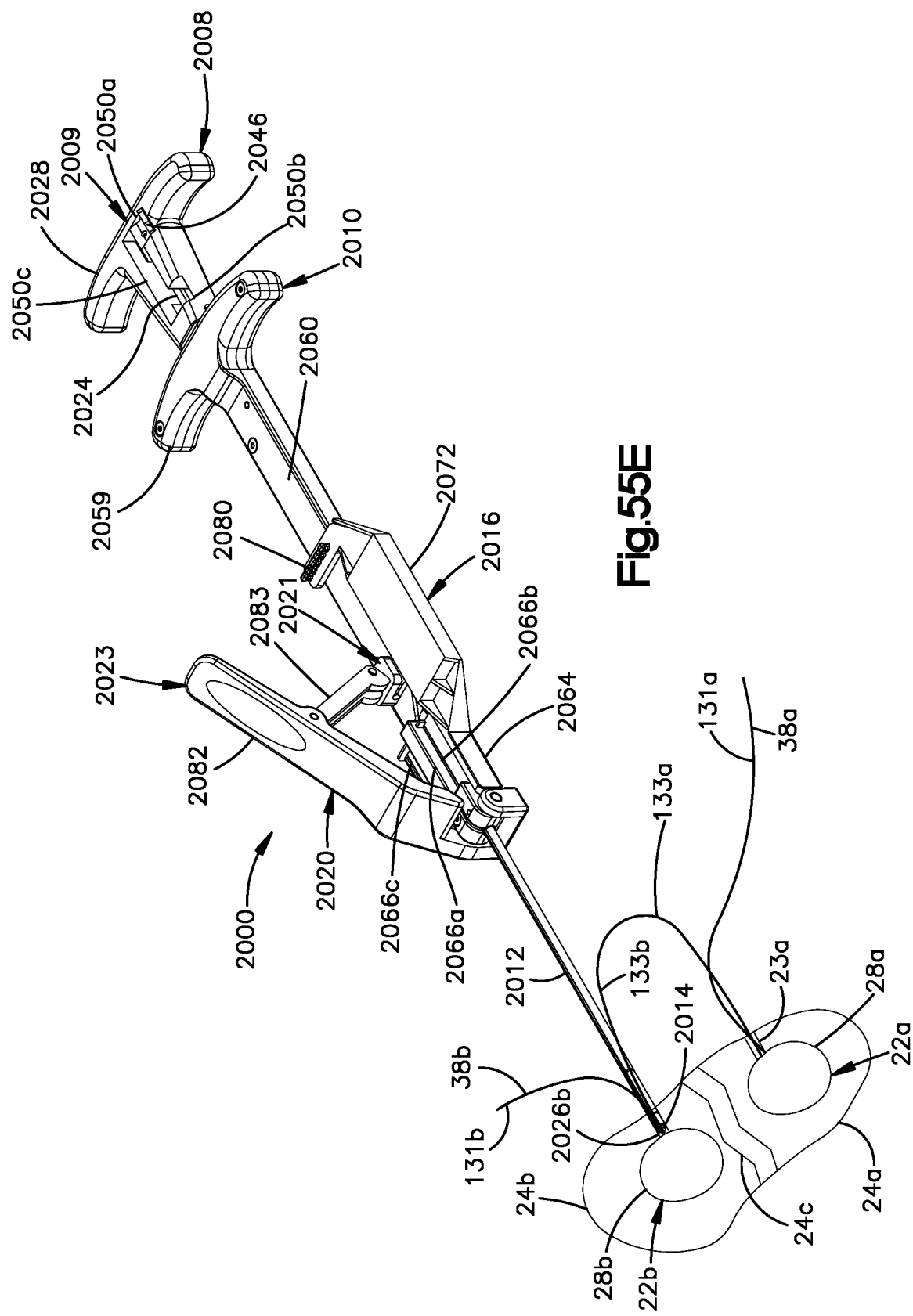
Figure 55F:
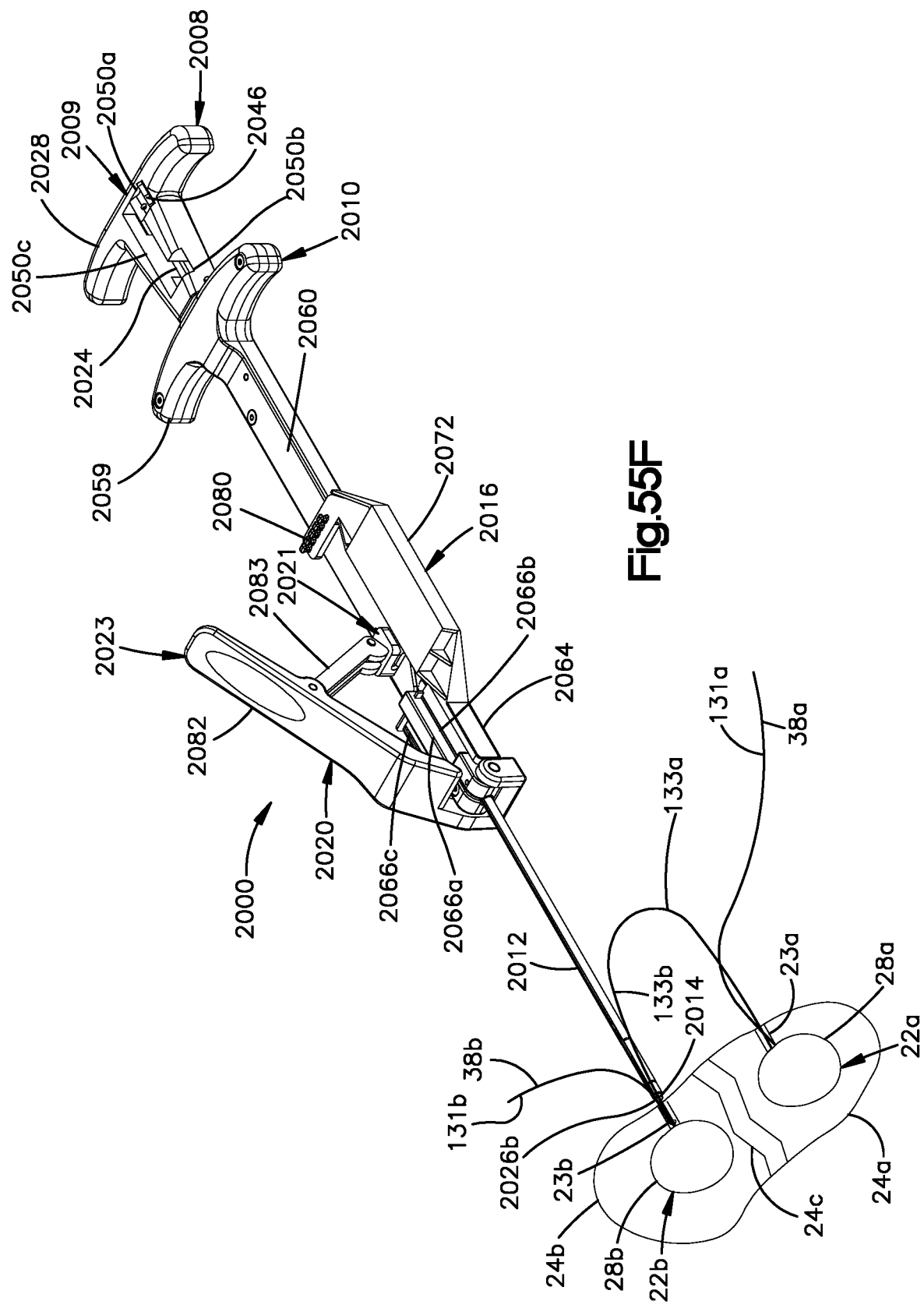
Figure 57B:
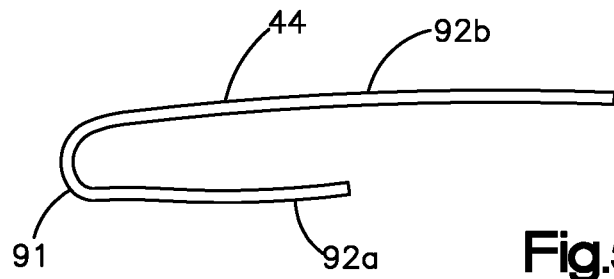
Figure 57C:
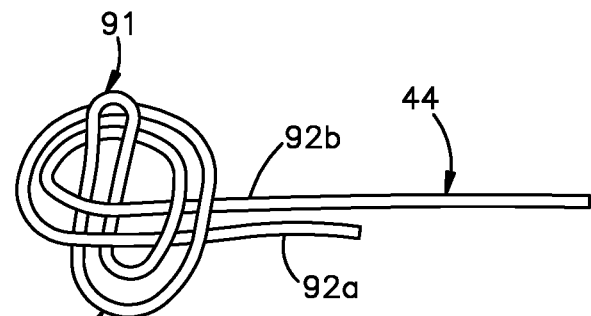
Figure 57D:
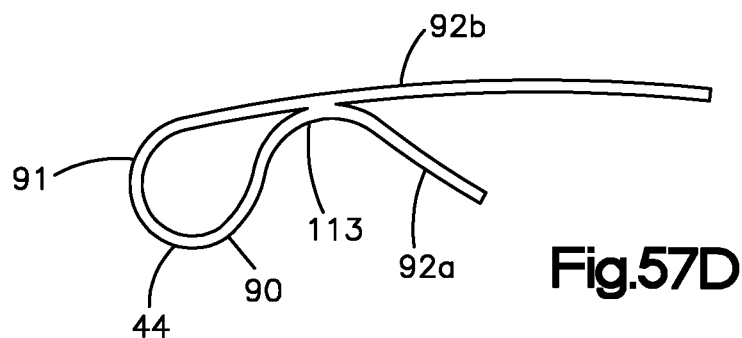
Figure 57E:
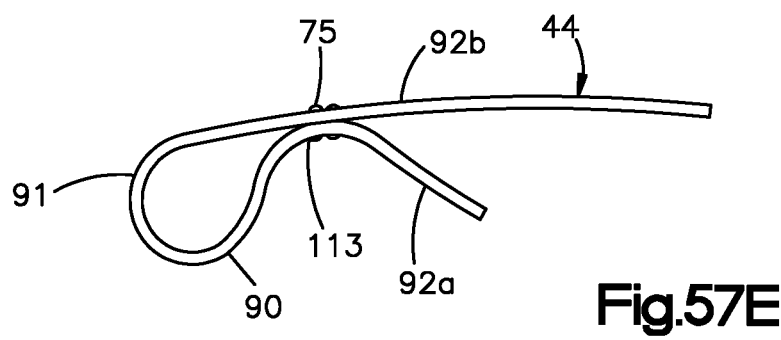
Figure 57F:
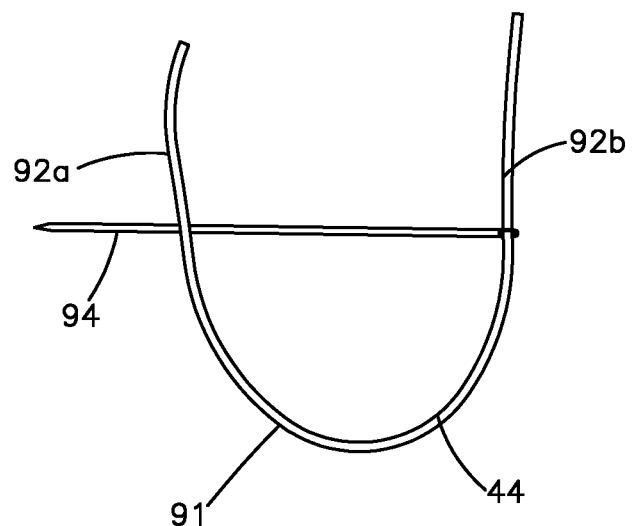
Figure 58B:
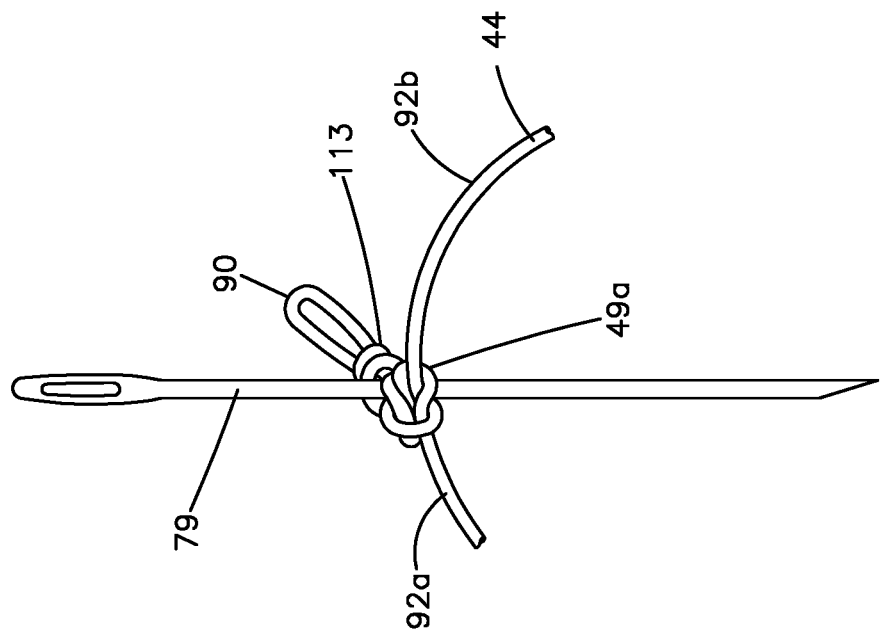
Figure 58A:
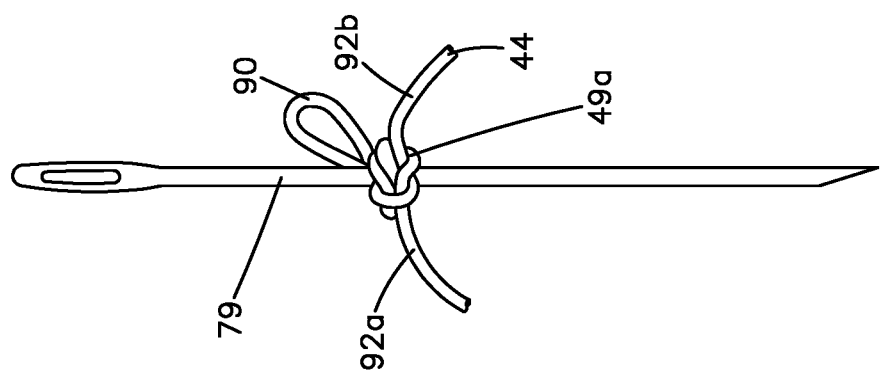
Figure 58C:
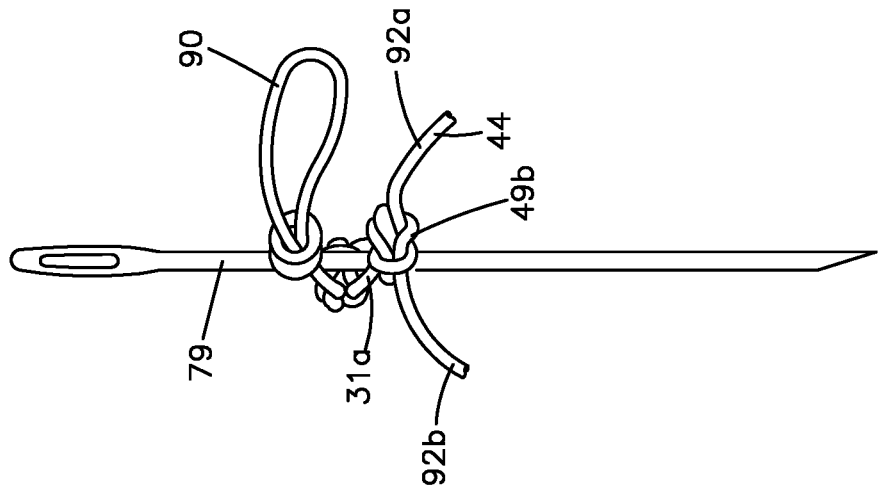
Figure 58D:
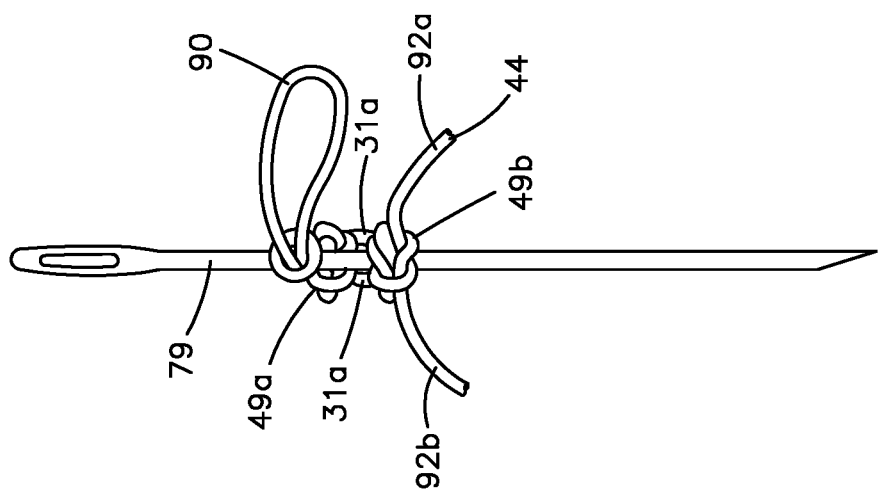
Figure 58F:
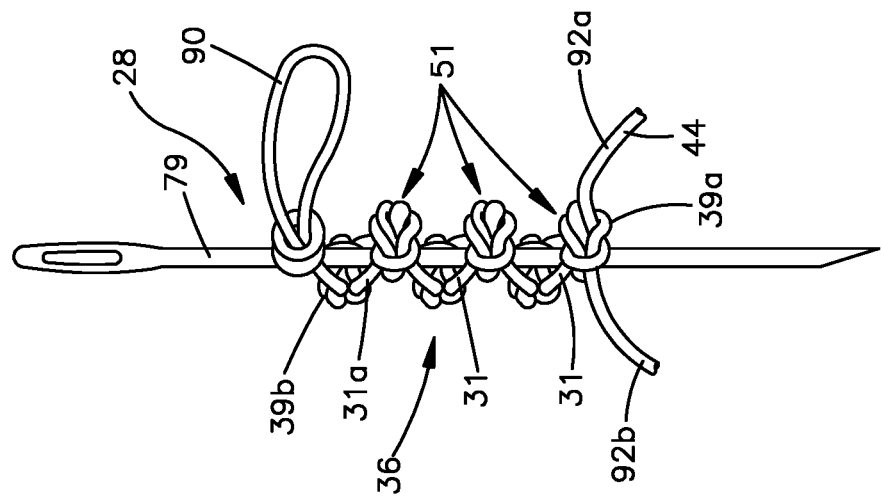
Figure 58E:
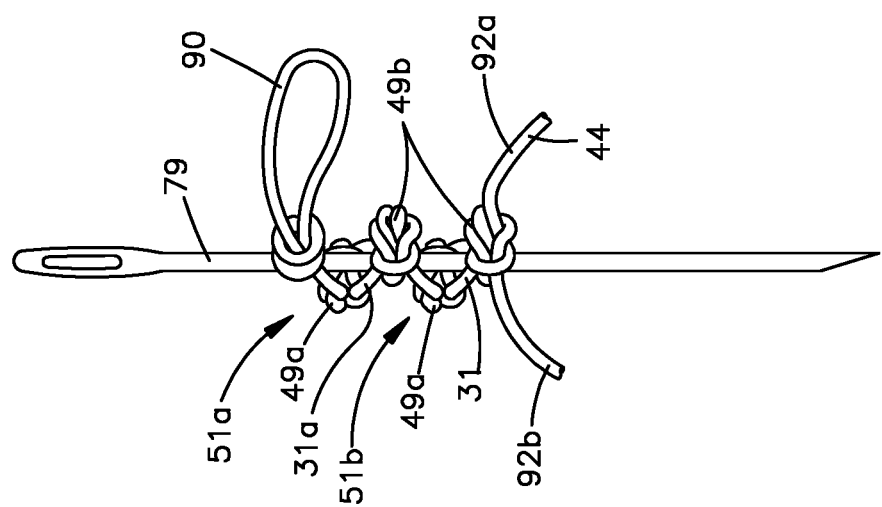
Figure 58H:
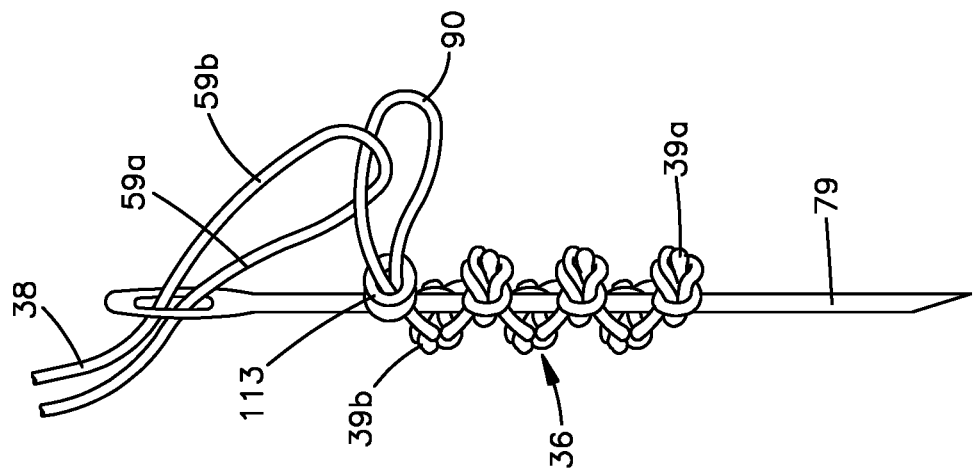
Figure 58G:
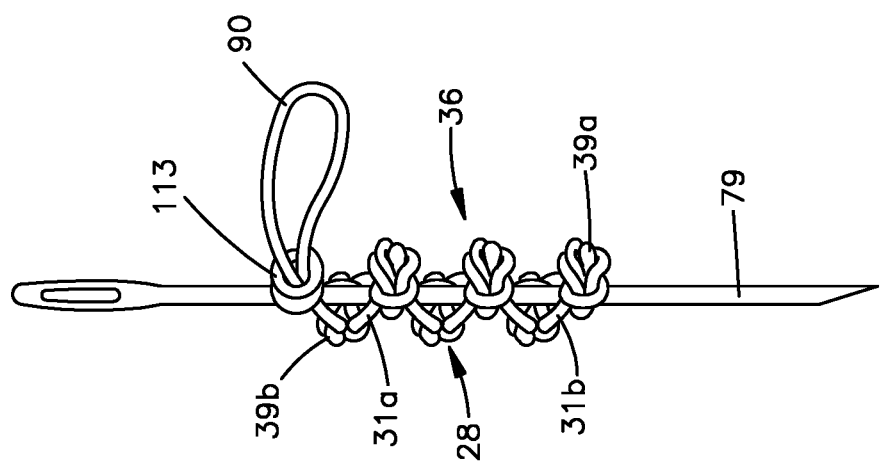
Figure 58I:
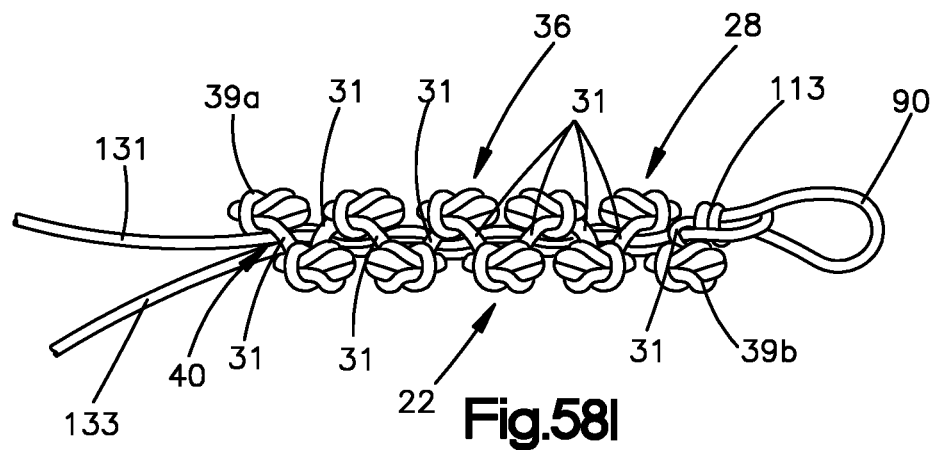
Figure 58J:
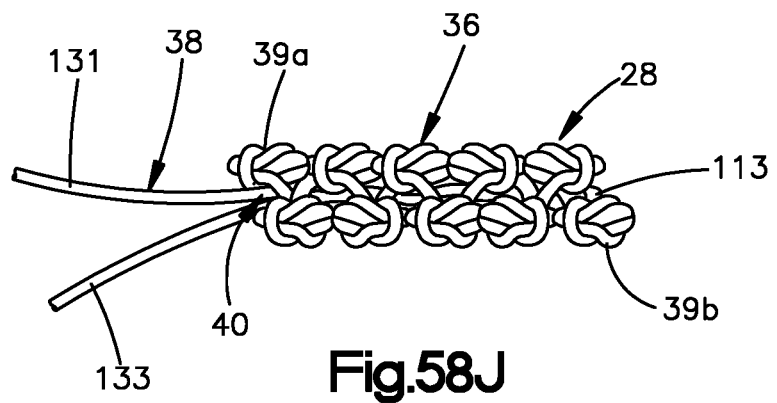
Figure 59:
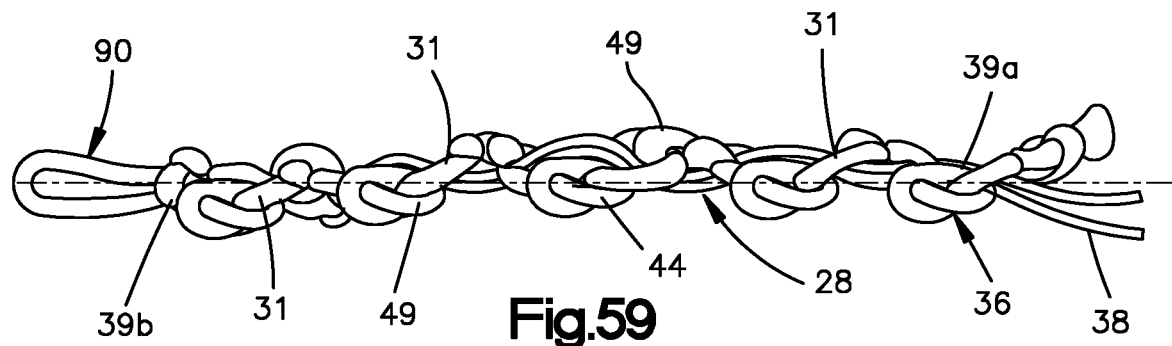
Figure 60A:
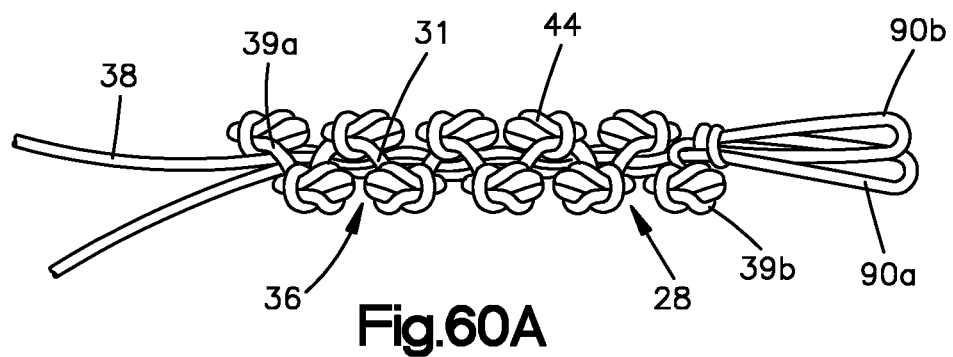
Figure 60B:
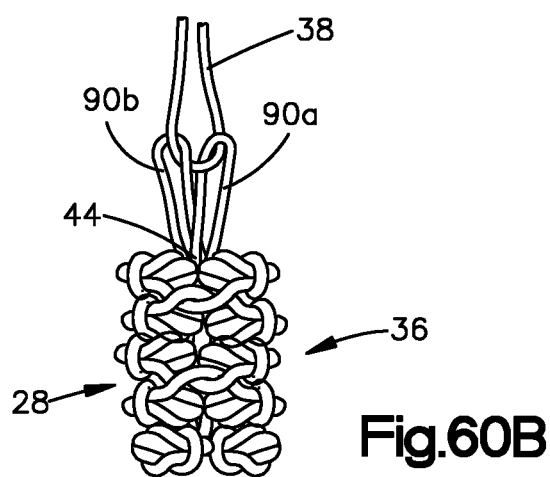
Figure 60C:
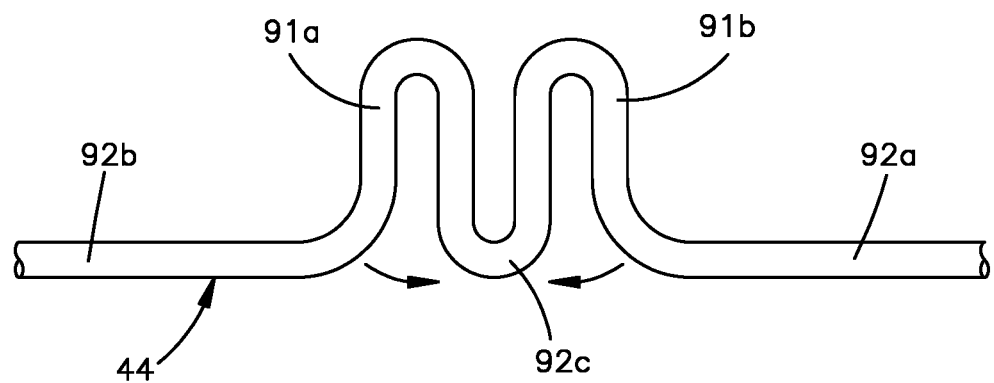
Figure 60D:
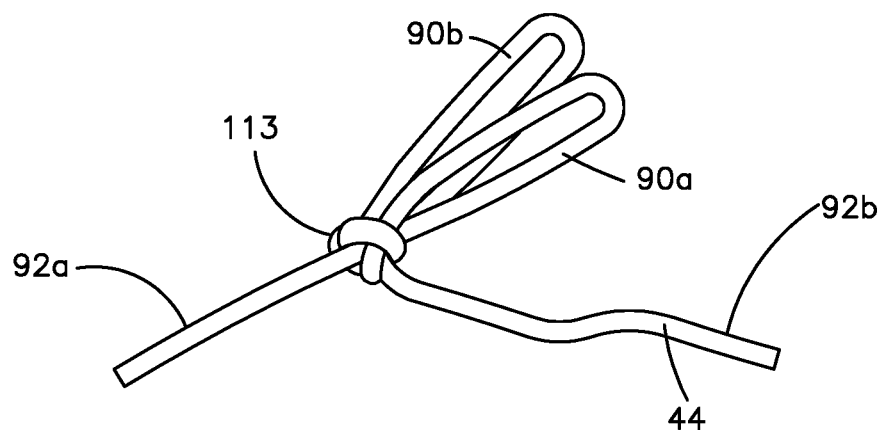

FIG. 32H is a side section view of the anchor housing illustrated in FIG. 32G;

FIG. 32I is a side section view of the anchor inserter assembly illustrated in FIG. 32G, with the anchor not yet ejected from the access member;

FIG. 32J is a side section view of the pusher member illustrated in FIG. 32G;

FIG. 32K is a side section view of the anchor inserter assembly illustrated in FIG. 32G, with the pusher member advanced such that the anchor is ejected from the access member;

FIG. 32L is a perspective view of the anchor expanded with the target anatomical location;

FIG. 32M is a side section view of the anchor assembly, constructed in accordance with an alternative embodiment;

FIG. 33A is a perspective view of an anchor inserter assembly in accordance with an alternative embodiment, the anchor inserter assembly comprising an access member, an anchor housing carrying an anchor, and a tension assembly;

FIG. 33B is a side elevation view of a component of the tension assembly illustrated in FIG. 33A;

FIG. 33C is a perspective view depicting components of the tension assembly illustrated in FIG. 33A, before the tension assembly is operated to expand the anchor;

FIG. 33D is a perspective view depicting components of the tension assembly illustrated in FIG. 33A, after the tension assembly has been operated to expand the anchor;

FIG. 34A is a perspective view of an anchor inserter assembly in accordance with still another alternative embodiment, the anchor inserter assembly comprising an access member, an anchor housing carrying an anchor, and a tension assembly;

FIG. 34B is a side section view of a component of the tension assembly;

FIG. 34C is a perspective partial cutaway view depicting components of the tension assembly illustrated in FIG. 34A, before the tension assembly is operated to expand the anchor;

FIG. 34D is a perspective partial cutaway view depicting components of the tension assembly illustrated in FIG. 34A, after the tension assembly has been operated to expand the anchor;

FIG. 35A is a perspective exploded view of an access assembly in accordance with still another alternative embodiment, the anchor inserter assembly comprising an awl and an access member;

FIG. 35B is a perspective exploded view of an anchor inserter assembly in accordance with the alternative embodiment illustrated in FIG. 35A, the anchor inserter assembly comprising the access member, an anchor housing carrying an anchor, and a tension assembly;

FIG. 36A is a perspective view of an access assembly including the awl and the access member illustrated in FIG. 35;

FIG. 36B is a side section view of the access assembly illustrated in FIG. 36A;

FIG. 37A is a perspective view of an anchor inserter assembly including the access member, the anchor housing carrying an anchor, and the tension assembly illustrated in FIG. 35, the anchor inserter assembly configured for operation in a first mode;

FIG. 37B is a perspective cutaway view of the anchor inserter assembly illustrated in FIG. 37A;

FIG. 38 is a perspective view of the anchor inserter assembly illustrated in FIG. 37A, configured for operation in an anchor expanding mode with a translating member in a neutral position;

FIG. 39 is a perspective view of the anchor inserter assembly illustrated in FIG. 38, with the translating member in an extended position;

FIG. 40A is a perspective view of a translating member constructed in accordance with an alternative embodiment;

FIG. 40B is an elevation view of a translating member constructed in accordance with another alternative embodiment;

FIG. 41A is a perspective view of a translating member constructed in accordance with another alternative embodiment;

FIG. 41B is an elevation view of the translating member illustrated in FIG. 41A;

FIG. 42 is a section elevation view of a translating member constructed in accordance with another alternative embodiment;

FIG. 43 is a section elevation view of a translating member constructed in accordance with another alternative embodiment;

FIGS. 44A-44C illustrate various views of a cleat that is configured to secure an actuation member to a translating member;

FIG. 45 is a perspective view of an insertion instrument constructed in accordance with another embodiment, configured to insert and expand a pair of anchor bodies at respective target locations, the insertion instrument including a housing that, in turn, includes a first body and a second body;

FIG. 46 is an exploded perspective view of the first body, including a pusher member and an opening creating member;

FIG. 47A is a perspective view of the first body illustrated in FIG. 46, shown in a retracted configuration;

FIG. 47B is a perspective view of an actuator of the first body illustrated in FIG. 47A, showing the actuator in a first position;

FIG. 47C is a perspective view of a distal end of the first body illustrated in FIG. 47A;

FIG. 48A is a perspective view of the first body illustrated in FIG. 46, shown in an extended configuration;

FIG. 48B is a perspective view of an actuator of the first body illustrated in FIG. 48A, showing the actuator in a second position;

FIG. 48C is a perspective view of a distal end of the first body illustrated in FIG. 48A;

FIG. 49A is a perspective view of an anchor cartridge constructed in accordance with one embodiment;

FIG. 49B is another perspective view of the anchor cartridge illustrated in FIG. 49A with portions hidden so as to illustrate a pair of anchors supported by the anchor cartridge;

FIG. 50A is a top plan view of a portion of the insertion instrument illustrated in FIG. 45, showing the anchor cartridge illustrated in FIG. 49B in an initial position and an opening creating member extended through the anchor cartridge;

FIG. 50B is a top plan view of the portion of the insertion instrument illustrated in FIG. 50A, but showing the opening creating member retracted;

FIG. 50C is a top plan view of the portion of the insertion instrument illustrated in FIG. 50B, but showing the anchor cartridge disposed in a first position;

FIG. 50D is a top plan view of the portion of the insertion instrument illustrated in FIG. 50C, but showing a pusher member extended through the anchor cartridge;

FIG. 50E is a top plan view of the portion of the insertion instrument illustrated in FIG. 50D, but showing the pusher member retracted;

FIG. 50F is a top plan view of the portion of the insertion instrument illustrated in FIG. 50E, but showing a stop clip removed;

FIG. 50G is a top plan view of the portion of the insertion instrument illustrated in FIG. 50F, but showing the anchor cartridge in a second position;

FIG. 50H is a top plan view of the portion of the insertion instrument illustrated in FIG. 50G, but showing a pusher member extended through the anchor cartridge;

FIG. 51A is an exploded perspective view of a tension assembly of the insertion instrument illustrated in FIG. 45;

FIG. 51B is a sectional side elevation view of the tensioning assembly illustrated in FIG. 51A, shown in a first position;

FIG. 51C is an exploded sectional side elevation view of the tensioning assembly illustrated in FIG. 51B, taken at line 51C;

FIG. 51D is a sectional end elevation view of the tensioning assembly as illustrated in FIG. 51B;

FIG. 51E is a sectional side elevation view of the tensioning assembly illustrated in FIG. 51A, shown in a second position;

FIG. 51F is an exploded sectional side elevation view of the tensioning assembly illustrated in FIG. 51E, taken at line 51F;

FIG. 51G is a sectional side elevation view of the tensioning assembly illustrated in FIG. 51A, shown in a third position;

FIG. 51H is an exploded sectional side elevation view of the tensioning assembly illustrated in FIG. 51G, taken at line 51H;

FIG. 51I is a sectional end elevation view of the tensioning assembly as illustrated in FIG. 51G;

FIG. 52A is a perspective view of the insertion instrument illustrated in FIG. 45, configured to be inserted into a first target location;

FIG. 52B is a perspective view of the insertion instrument illustrated in FIG. 52A, shown inserted into the first target location so as to create a first opening;

FIG. 52C is a perspective view of the insertion instrument illustrated in FIG. 52B, but showing an opening tip retracted;

FIG. 52D is a perspective view of the insertion instrument illustrated in FIG. 52C, but showing a pusher member retracted;

FIG. 53A is a perspective view of the insertion instrument illustrated in FIG. 52D, but showing an anchor cartridge in a first position;

FIG. 53B is a perspective view of the insertion instrument illustrated in FIG. 53A, but showing a first anchor body inserted into the first opening;

FIG. 53C is a perspective view of the insertion instrument illustrated in FIG. 53B, but showing a tensioning assembly actuated so as to expand the inserted anchor body;

FIG. 53D is a perspective view of the insertion instrument illustrated in FIG. 53C, but showing the tensioning assembly in a first position;

FIG. 53E is a perspective view of the insertion instrument illustrated in FIG. 53D, shown removed from the first target location;

FIG. 54A is a perspective view of the insertion instrument illustrated in FIG. 53E, configured to be inserted into a second target location;

FIG. 54B is a perspective view of the insertion instrument illustrated in FIG. 54A, shown inserted into the second target location so as to create a second opening;

FIG. 54C is a perspective view of the insertion instrument illustrated in FIG. 54B, but showing an opening tip retracted;

FIG. 54D is a perspective view of the insertion instrument illustrated in FIG. 54C, but showing a pusher member retracted;

FIG. 55A is a perspective view of the insertion instrument illustrated in FIG. 54D, but showing a stop clip removed from an anchor cartridge;

FIG. 55B is a perspective view of the insertion instrument illustrated in FIG. 55A, but showing the anchor cartridge in a second position;

FIG. 55C is a perspective view of the insertion instrument illustrated in FIG. 55B. but showing a second anchor body inserted into the second opening;

FIG. 55D is a perspective view of the insertion instrument illustrated in FIG. 55C, but showing a tensioning assembly actuated so as to expand the inserted second anchor body;

FIG. 55E is a perspective view of the insertion instrument illustrated in FIG. 55D, but showing the tensioning assembly in a first position;

FIG. 55F is a perspective view of the insertion instrument illustrated in FIG. 55E, shown removed from the second target location;

FIG. 56A is a side elevation view of an expandable anchor constructed in accordance with another embodiment, the expandable anchor having an anchor body and an actuation strand, showing the anchor body in a first configuration FIG. 56B is a side elevation view of the expandable anchor illustrated in FIG. 56A, showing the anchor body in an expanded configuration;

FIG. 57A is side elevation view of a first method step to create the anchor body illustrated in FIG. 56A, showing construction of an eyelet;

FIGS. 57B-C illustrate method steps for creating the eyelet illustrated in FIG. 57A in accordance with one embodiment;

FIG. 57D illustrates a method step for creating the eyelet illustrated in FIG. 57A in accordance with one embodiment;

FIG. 57E illustrates a method step for creating the eyelet illustrated in FIG. 57A in accordance with one embodiment;

FIGS. 57F-L illustrate method steps of creating the eyelet illustrated in FIG. 57A in accordance with one embodiment;

FIG. 58A is a perspective view of a second method step to create the anchor body illustrated in FIG. 56A, showing a first knot that ties the eyelet illustrated in FIG. 57A around a mandrel;

FIG. 58B is another perspective view of the second method step illustrated in FIG. 58A;

FIG. 58C is a perspective view of a third method step to create the anchor body illustrated in FIG. 56A, showing a second knot that is opposite the first knot;

FIG. 58D is another perspective view of the third method step illustrated in FIG. 58D;

FIG. 58E is a perspective view of a method step to create the anchor body illustrated in FIG. 56A, showing a plurality of knots alternatingly tied on opposite each other;

FIG. 58F is another perspective view of the method step illustrated in FIG. 58E;

FIG. 58G is a perspective view of the anchor body illustrated in FIG. 56A, disposed about a mandrel;

FIG. 58H is a perspective view of the anchor body illustrated in FIG. 58G, showing an actuation strand inserted through the eyelet and through the mandrel;

FIG. 58I is a perspective view of the anchor body and actuation strand illustrated in FIG. 58H, showing the actuation strand driven through the anchor body;

FIG. 58J is a perspective view of the anchor body and actuation strand illustrated in FIG. 58I, showing the eyelet driven through the anchor body;

FIG. 59 is a perspective view of an expandable anchor similar to the expandable anchor illustrated in FIG. 56A, but showing the knots of the anchor body configured as overhand knots, shown prior to drawing the eyelet into the expandable portion of the anchor body;

FIG. 60A is a perspective view of an expandable anchor similar to the expandable anchor as illustrated in FIG. 56A, but showing the anchor body including a pair of eyelets prior to drawing the eyelets into the expandable portion of the anchor body; and FIG. 60B is a perspective view of the expandable anchor illustrated in FIG. 60A, showing the anchor body in an expanded configuration;

FIG. 60C is a perspective view of an anchor body strand of the expandable anchor illustrated in FIG. 60A, showing the anchor body strand at a phase in which the stand is prepared so as to define first and second loops; and FIG. 60D is a perspective view of the anchor body strand illustrated in FIG. 60C, showing the anchor body strand at a phase in which the stand is prepared to define first and second eyelets.

DETAILED DESCRIPTION

Figure 1A:
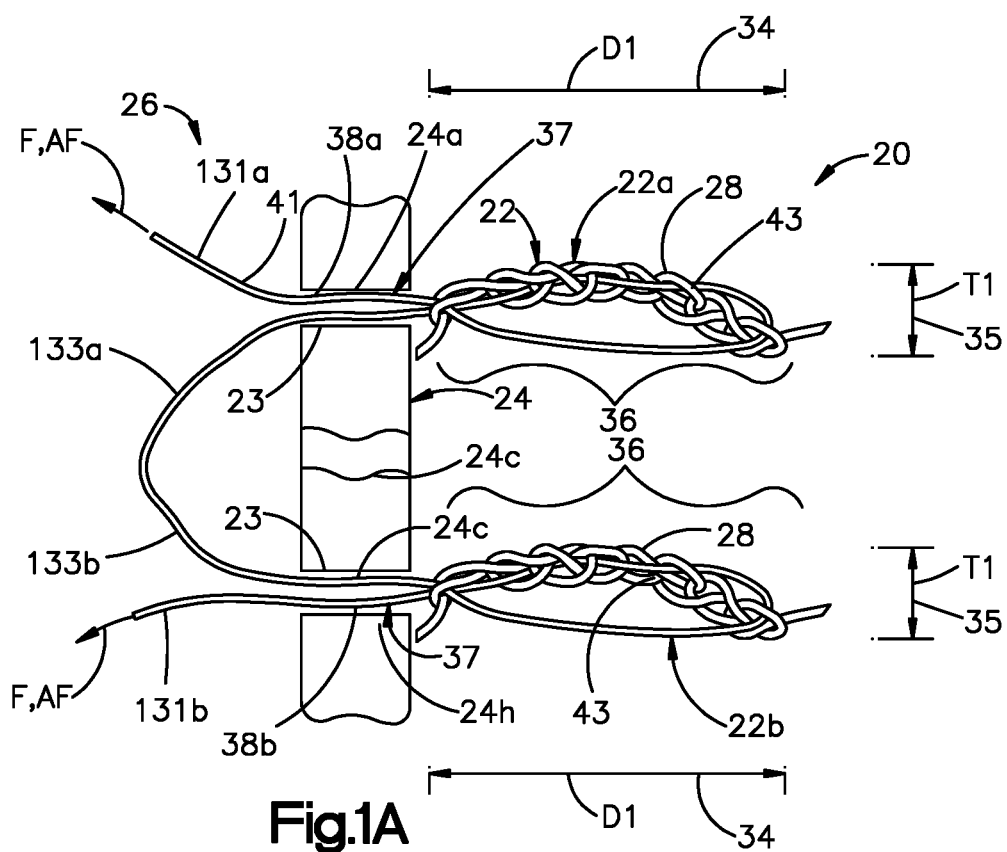
FIG. 1A is a schematic side elevation view of an anchor assembly including a pair of anchor bodies implanted across an anatomical defect and shown in a first configuration.
Figure 1B:
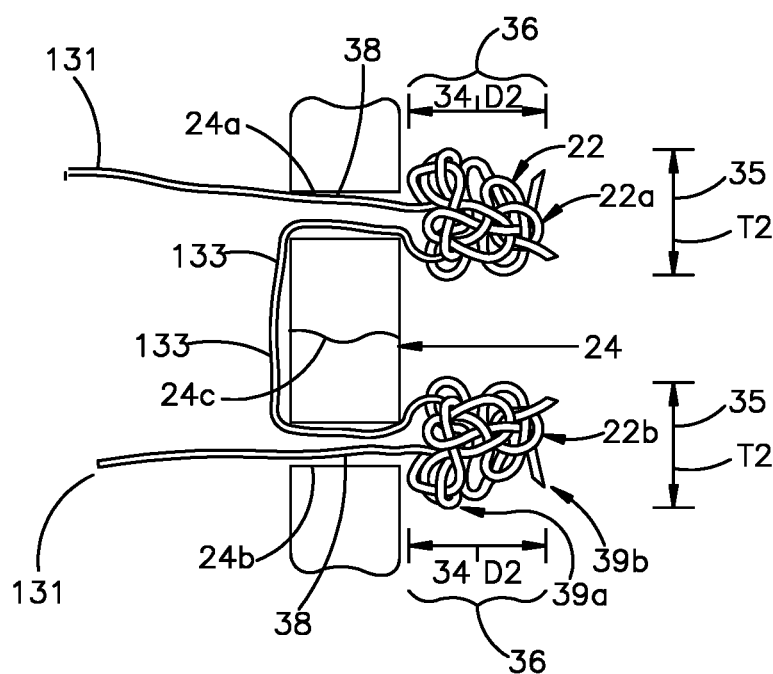
FIG. 1B is a schematic side elevation view of the anchor assembly illustrated in FIG. 1A, showing the anchor bodies in an expanded configuration and in an approximated position.

Referring initially to FIGS. 1A-B, an anchor assembly 20 can include at least one expandable anchor 22 such as a first expandable anchor 22a and a second expandable anchor 22b that, in turn, include respective anchor bodies 28a and 28b that are configured to be secured to an anatomical location, which can be defined by at least one anatomical structure 24. The anatomical structure 24 can be defined by, for instance, anatomy of a human or other animal, or an implant that is secured or configured to be secured to anatomy of a human or other animal. The anatomy can be defined by tissue that can include at least one of bone and soft tissue such as a tendon, a ligament, cartilage, the annulus of an intervertebral disc, or the like.

In accordance with one embodiment, the at least one anatomical structure 24 can define first and second target anatomical locations 24a and 24b on opposite sides of a gap, such as a gap 24c. Thus, the gap 24c can be disposed in an anatomical structure, and can for instance define an anatomical defect, or can be disposed between different anatomical structures. First and second anchors 22a and 22b can be injected or otherwise driven or inserted into the respective first and second target anatomical locations 24a and 24b on opposite sides of the gap 24c, and subsequently drawn toward each other so as to approximate the gap 24c. Alternatively or additionally still, the anchor assembly 20 can be configured to secure an auxiliary structure to the anatomical structure. In this regard, it should be further appreciated that the anchor assembly 20 can include any number of anchors 22 as desired.

Each anchor body 28a and 28b can include a respective expandable portion 36a and 36b, and an actuation member 37a and 37b, such as an actuation strand 38a and 38b, that is configured to actuate the respective expandable portion 36a and 36b, and thus the respective anchor body 28a and 28b, from a first configuration illustrated in FIG. 1A, whereby the anchor body 28a and 28b is initially placed at the target anatomical location, to an expanded configuration illustrated in FIG. 1B, whereby the respective anchor body 28a and 28b can be secured to the anatomical structure 24. Thus, the anchor bodies 28a and 28b of the anchors 22a and 22b can be inserted through an opening 23 at the respective target anatomical locations 24a and 24b that can be created, for example, when delivering the anchor bodies 28a and 28b to the respective target anatomical locations 24a and 24b, for instance by injecting the anchor bodies 28a and 28b to the respective target anatomical locations 24a and 24b.

The expandable portion 36 of the anchor body 28 extends along the direction of elongation 34 so as to define an initial distance D1 as measured from the proximal end 39a to the distal end 39b along the direction of elongation 34 when in the first configuration. The initial distance D1 can be any length as desired, such within a range having a lower end that can be defined by approximately 5 mm, alternatively approximately 10 mm, alternatively still approximately 20 mm, and alternatively still approximately 24.5 mm, and having an upper end that can be defined by approximately 50 mm, alternatively approximately 40 mm, alternatively still approximately 30 mm, and alternatively still approximately 25.5 mm.

Furthermore, when in the first configuration, the expandable portion 36 defines an initial maximum thickness T1 that extends in a second direction 35 that is substantially perpendicular, with respect to the direction of elongation 34. The initial maximum thickness T1 can be sized as desired. As illustrated in FIG. 1B, when the expandable portion 36 in the expanded configuration, the expandable portion 36 is collapsed, for instance compressed or tangled, along the direction of elongation 34 to a second distance D2 as measured from the proximal end 39a to the distal end 39b along the direction of elongation 34. The second distance D2 can be less than the initial distance D1. As the expandable portion 36 collapses along the direction of elongation, for instance as it is actuated from the first configuration to the expanded configuration, the expandable portion 36 expands along the second direction 35 to a second maximum thickness T2 that is greater than the initial maximum thickness T1. The second maximum thickness T2 extends along the second direction 35 which is substantially perpendicular to the direction of elongation 34.

The maximum thicknesses T1 and T2 in the second direction 35 can be defined such the anchor body 28 does not define a thickness in the second direction 35 that is greater than the maximum thicknesses T1 and T2, respectively. It should be appreciated that the proximal and distal ends 39a and 39b can change locations on the expandable portion 36 as the expandable portion 36 actuates to the expanded configuration, for instance due to configuration of the expandable portion 36 when in the expanded configuration. However, when the expandable portion 36 is in the expanded configuration, the proximal and distal ends 39a and 39b continue to define the proximal-most and distal-most ends of the expandable portion 36, such that the distance D2 along the direction of elongation 34 is defined linearly between the proximal and distal ends 39a and 39b of the expandable portion 36 when the expandable portion 36 is in the expanded configuration.

Each of the actuation strands 38 of the first and second anchors 22a and 22b can be attached to each other. For instance, the actuation strand 38 of the first anchor 22a can be integral with the actuation strand 38 of the second anchor 22b. Alternatively, as will be described in more detail below with reference to FIGS. 2A-C, the actuation strand 38 of the first anchor 22a can be separate from the actuation strand 38 of the second anchor 22a, such that the actuation strands 38 of the first and second anchors 22a and 22b are subsequently attached, directly or indirectly, using any suitable connector member 63. The connector member 63 can be integral with either or both of the actuation strands 38a and 38b or can be separately attached to each of the actuation strands 38a and 38b. In accordance with one embodiment, the actuation strands 38a and 38b of each of the first and second anchors 22a and 22b defines at least one respective actuation portion 131a and 131b and can further include at least one respective attachment portion 133a and 133b. The actuation portions 131a and 131b are each configured to receive an actuation force that causes the respective anchor 22a and 22b to actuate from the first configuration to the expanded configuration.

In accordance with the illustrated embodiment, the attachment portions 133a and 133b of the actuation strands 38a and 38b of the first and second anchors are configured to be attached to each other so as to span across the gap 24c and attach the first anchor body 28a to the second anchor body 28b. The attachment portions 133a and 133b can be integral with each other, or attached to each other using any suitable connector member. Furthermore, in accordance with the illustrated embodiment, the actuation portions 131a and 131b can also define attachment portions that are configured to be attached to each other in any suitable manner, either before or after the actuation force F is applied to the actuation portions 131a and 131b. Thus, the attachment portion 133a and 133b of a respective anchor 22a and 22b is configured to attach the respective anchor to another anchor, such as an attachment portion of the other anchor. Furthermore, the actuation portion 131a of the first anchor 22a is configured to attach the respective anchor 22a to the second anchor 22b. In accordance with the illustrated embodiment, the attachment portion 133a of the actuation strand 38a of the first anchor 22a is integral with the attachment portion 133b of the actuation strand 38b of the second anchor 22b, though it should be appreciated that the attachment portions 133a-b of the first and second anchors 22a-b can be separate from each other and attached to each other, as described in more detail below.

With continuing reference to FIGS. 1A-B, once the expandable portions 36a-b of the anchors 22a-b have actuated to the expanded configuration, the actuation strands 38a-b can be placed in tension. For instance, in accordance with one embodiment, an approximation Force AF can be applied to either or both of the actuation portion 131a-b of the actuation strands 38a-b of the first and second anchors 22a-b, thereby inducing a tension in the actuation strands 38a-b of the first and second anchors 22a-b so as to apply a biasing force that draws the first and second anchors 22a and 22b toward each other. Accordingly, if a gap 24c is disposed between the first and second anchors 22a and 22b, movement of the anchors 22a and 22b toward each other in response to the biasing force approximates the gap 24c which, in certain embodiments, can be an anatomical defect, such as a tissue defect as described above.

Furthermore, when the actuation strands 38a-b are maintained in tension after the defect 24 has been approximated, the anchor bodies 28a-b are prevented from backing out from the anatomy through the respective target locations 24a-b, which could allow the gap 24c to open. Thus, once the gap 24c has been approximated, the actuation strand 38a of the first anchor 22a can be attached to the actuation strand 38b of the second anchor 22b so as to maintain tension between the first and second anchors 22a and 22b and prevent the first and second anchors 22a and 22b from separating.

The anchor bodies 28a and 28b can be constructed by weaving any suitable substrate, such as a strand, for instance a strand of suture, in any manner desired so as to produce a plurality of openings 43 that extend through the respective anchor bodies 28a and 28b. The first and second actuation strands 38a and 38b can be woven through at least two of the openings 43 along the direction of elongation 34 of the anchor bodies 28a and 28b.

In accordance with the embodiment illustrated in FIGS. 1A-1F, the first and second actuation strands 38a and 38b are integral with the respective first and second anchor bodies 28a and 28b. In accordance with other embodiments, the first and second actuation strands 38a and 38b are illustrated as separate from and attached to the respective first and second anchor bodies 28a and 28b (see FIG. 2C). In accordance with still other embodiments, one of the first and second actuation strands 38a and 38b is integral with the respective anchor body and the other of the first and second actuation strands 38a and 38b is separate from and attached to the respective anchor body. In accordance with embodiments whereby the first and second actuation strands 38a and 38b are illustrated and described as integral with the respective first and second anchor bodies 28a and 28b, it should be appreciated that the first and second actuation strands 38a and 38b can alternatively be separate from and attached to the respective first and second anchor bodies 28a and 28b, unless otherwise indicated. Furthermore, in accordance with embodiments whereby the first and second actuation strands 38a and 38b are illustrated and described as separate from and attached to the respective first and second anchor bodies 28a and 28b, it should be appreciated that the first and second actuation strands 38a and 38b can alternatively be integral with the respective first and second anchor bodies 28a and 28b, unless otherwise indicated.

Referring to FIGS. 1C-1F, the anchor assembly 20 can include at least one connector member 63 that is configured to join the anchors 22 and allow a biasing force to be applied to at least one of the anchors 22a and 22b that draws the anchors 22a and 22b together, thereby approximating the anatomical defect 24. The connector member 63 can be integral with one or both of the first and second anchors 22a and 22b, for instance integral with one or both of the first and second actuation strands 38a and 38b, can be integral with one or both of the first and second anchor bodies, or can be separate from and attached (directly or indirectly) to one or both of the first and second anchors 22a and 22b. For instance, the connector member 63 can be separate from and attached between the first and second anchors 22a and 22b, as will be described in more detail below. While connector members 63 are described herein in accordance with various embodiments, it should be appreciated that the anchor assembly 20 can alternatively include any suitable connector member configured to attach the first anchor 22a to the second anchor 22b.

Figure 2A:
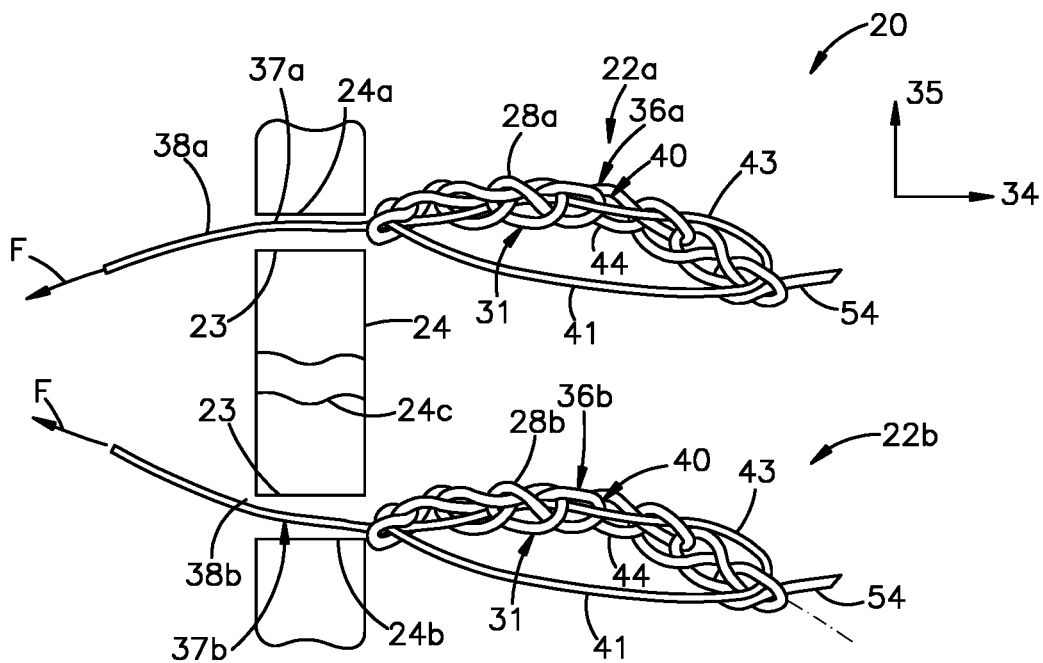
FIG. 2A is a side elevation view of an anchor assembly including first and second anchors implanted in an anatomical structure on opposed sides of an anatomical defect and shown in a first configuration.

The anchor assembly 20 can include a connector member 63 that is integral with the corresponding actuation strands 38a and 38b. As described above, each of the first and second anchor bodies 28a and 28b can be implanted at respective first and target anatomical locations 24a and 24b that are disposed on opposite sides of a gap 24c as illustrated in FIG. 2A. Each of the first and second actuation strands 38a and 38b can receive an actuation force F substantially along the direction of elongation 34 that causes the respective first and second anchor bodies 28a and 28b, and in particular the respective expandable portions 36a and 36b, to actuate from the first configuration to the expanded configuration so as to fix the first and second anchor bodies 28a and 28b at the respective first and second target anatomical locations 24a and 24b. The actuation force F applied to each of the actuation strands 38a and 38b can be in the form of different actuation forces, or can be the same actuation force.

Figure 1C:
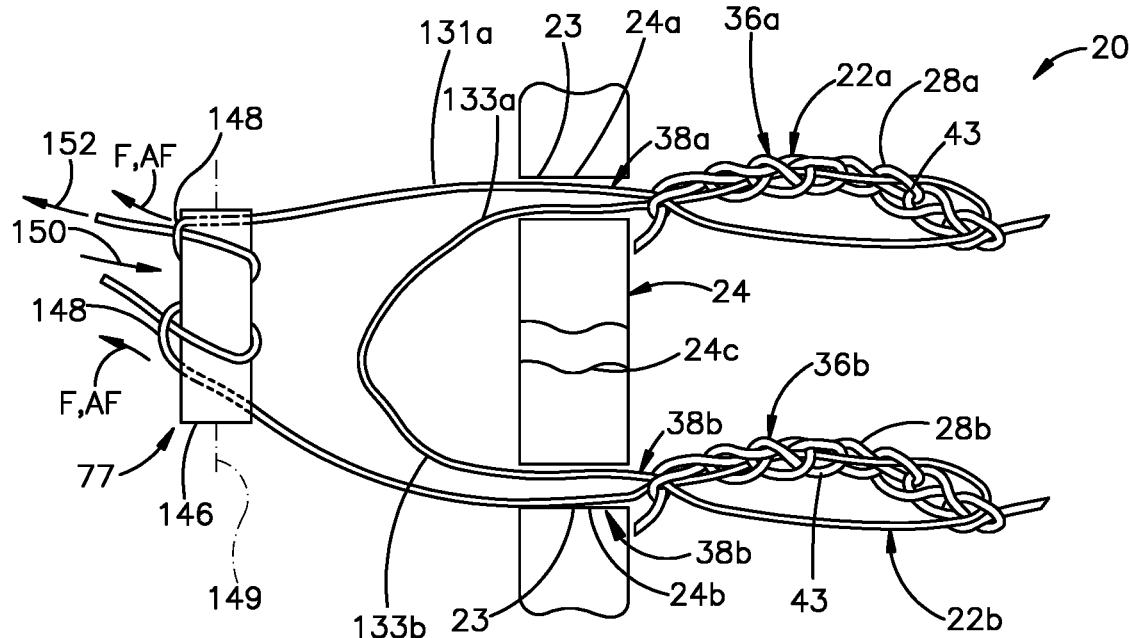
FIG. 1C is a side elevation view of an anchor assembly including the anchor bodies illustrated in FIG. 1A and a connector member configured to attach actuation portions of the anchor bodies, showing the anchor bodies in the first configuration.
Figure 1D:
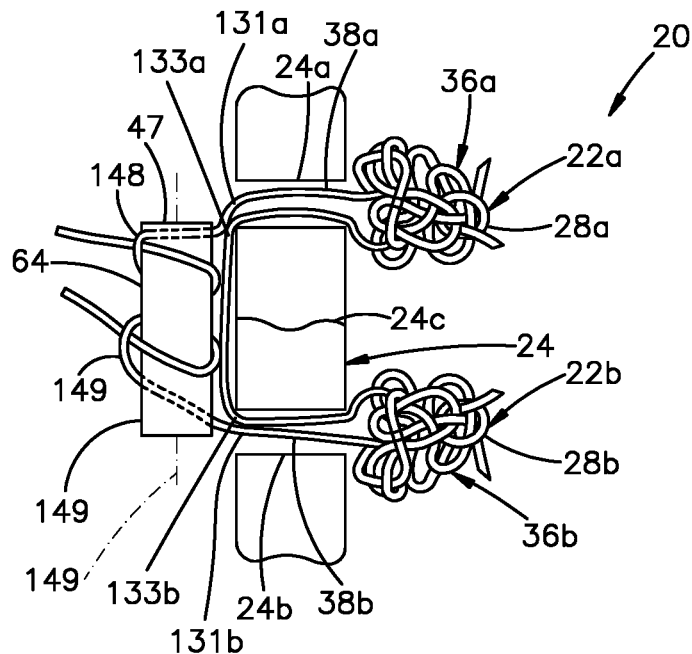
FIG. 1D is a side elevation view of the anchor assembly illustrated in FIG. 1C, showing the connector member tightened with the anchor bodies in the expanded configuration.

For instance, referring to FIGS. 1C-1D, the connector member 63 can be configured as an auxiliary connector member 77, that is a connector member that is separate from one or both of the first and second actuation strands 38*a* and 38*b* and configured to attach to the first and second actuation strands 38*a* and 38*b* to each other. For instance, the auxiliary connector member 77 can be made from any suitable metal, plastic, or any alternative biocompatible material, and can be configured as a body 146, which can be flexible or rigid, that is configured to attach to either or both of the first actuation strands 38*a* and 38*b*, and in particular to the actuation portions 131*a-b*, at a location between the anchors 22*a* and 22*b*. For instance, each of the first and second actuation portions 131*a-b* can be stitched through the body 146 and tied about the body 146 so as to define a knot 148 that can be actuated from an unlocked configuration to a locked configuration. The first and second actuation portions 131*a-b* are slidable with respect to the body 146 when the knots 148 are in the unlocked configuration, and fixed with respect to sliding movement relative to the body 146 when the knots 148 are in the locked configuration. The body 146 can define any shape as desired, such as substantially cylindrical, and can be flexible or substantially rigid as desired.

During operation, the actuation portions 131*a-b* can be stitched through the body 146 along a direction away from the anatomical structure 24 and tied about the body 146 such that the respective knots 148 are in the unlocked configuration. The body 146 can be oriented such that its long axis 149 is oriented substantially parallel to the anatomical structure 24. The body 146 can be translated along the first and second actuation strands 38*a* and 38*b* along the direction of Arrow 150 toward the anatomical structure 24 while the actuation strands 38*a* and 38*b* are under tension, which causes the actuation strands 38*a* and 38*b* to translate relative to the body 146 along an opposite direction indicated by Arrow 152. As the body 146 translates along the actuation strands 38*a* and 38*b* toward the gap 24*c*, the body 146 applies the actuation force F to the actuation strands 38*a* and 38*b*, thereby causing the anchors 22*a* and 22*b* to actuate from the first configuration to the expanded configuration.

As the body 146 further translates toward the gap 24*c* after the anchors 22*a* and 22*b* have been actuated to their expanded configuration, the body 146 applies the approximation force AF to at least one or both of the actuation strands 38*a* and 38*b* that draws at least one or both of the anchors 22*a* and 22*b* inward toward the other, thereby approximating the gap 24*c*. In this regard, it should be appreciated that the approximation force AF can be a continuation of the actuation force F. Alternatively, the actuation force F can be applied to the actuation strands 38*a* and 38*b* at a location upstream of the body 146, or prior to attaching the actuation strands 38*a* and 38*b* to the body 146. The knot 148 can then be tightened so as to secure the first and second actuation strands 38*a* and 38*b* to the body 146, and therefore also to each other so as to prevent separation of the first and second anchors 22*a* and 22*b*. Once the gap 24*c* has been approximated, the body 146, and thus the knots 148, can be disposed along the outer surface of the anatomical structure 24. Alternatively, the body 146 can be sized such that a portion of the body 146, and thus the knots 148, is disposed in the opening 23 that receives the anchor bodies 28*a* and 28*b* once the gap 24*c* has been approximated. Accordingly, the knots 148 can be disposed behind the anatomical structure 24, or can be embedded in the anatomical structure 24.

The body 146 can thus define a sliding member 47 that allows one of the first and second actuation strands 38*a* and 38*b* to slide with respect to the other of the first and second actuation strands 38*a* and 38*b* so as to approximate the gap 24*c*, and can further define a locking member 64 that secures the first and second actuation strands 38*a* and 38*b* to each other, for example with respect with respect to relative movement that would allow the first and second anchor bodies 28*a* and 28*b* to separate.

Figure 1E:
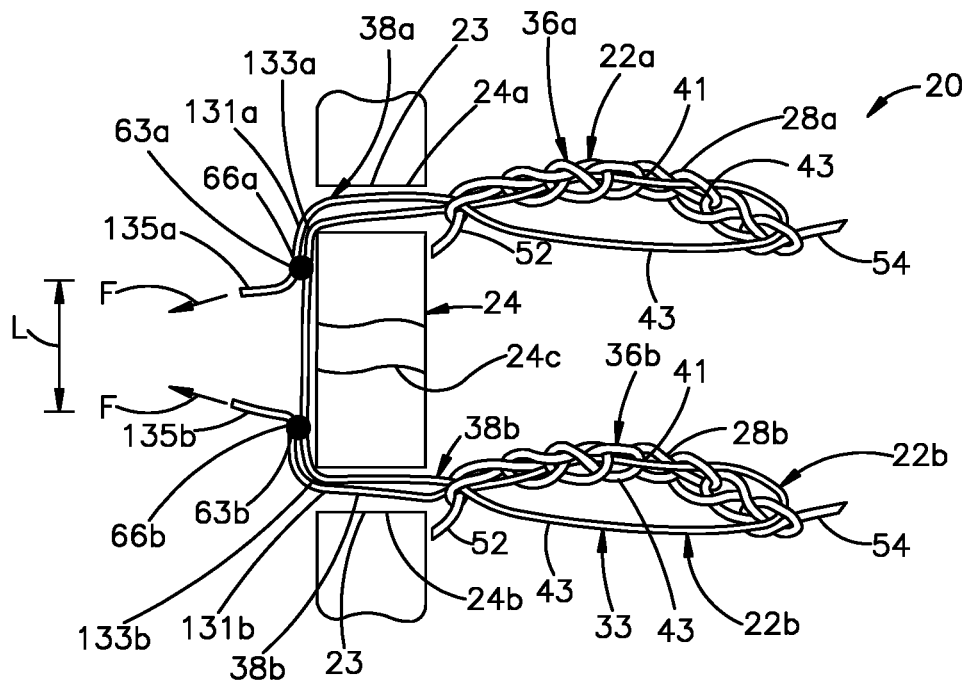
FIG. 1E is a side elevation view of an anchor assembly similar to FIG. 1C, but including an integral connector member.
Figure 1F:
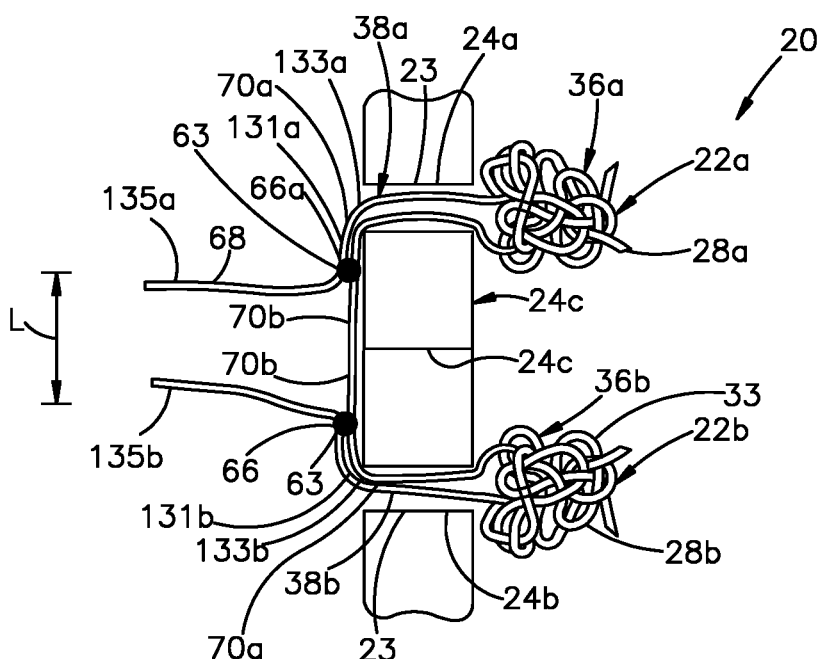
FIG. 1F is a side elevation view of the anchor assembly illustrated in FIG. 1E, showing the connector member tightened with the anchor bodies in the expanded configuration.

Referring now to FIGS. 1E-1F, the anchor assembly 20 can include a pair of connector members 63*a* and 63*b* configured to attach at least one or both of the actuation portions 131*a* and 131*b* to the respective attachment portions 133*a* and 133*b*. In accordance with the illustrated embodiment, the actuation strands 38*a* and 38*b* are defined by a common actuation member, such as a common strand, which can be an auxiliary strand 33 that is separate from, and woven through, at least one such as a pair or a plurality of openings of both the first and second anchor bodies 28*a-b*, such that the respective attachment portions 133*a* and 133*b* are integral with each other. Thus, in accordance with the illustrated embodiment, the first and second actuation strands 38*a* and 38*b* are integral with each other. The anchor assembly 20 can include first and second connector members 63*a* and 63*b* that are defined by the actuation strands 38*a* and 38*b*, and are configured to attach the actuation portions 131*a* and 131*b* to other locations of the common strand, and thus to each other. In accordance with the illustrated embodiment, the first and connector member 63*a* can attach the corresponding first actuation portion 131*a* to another location of the auxiliary strand 33 that is spaced from the first actuation portion 131*a*. Likewise, the second and connector member 63*b* can attach the corresponding second first actuation portion 131*b* to another location of the auxiliary strand 33 that is spaced from the second first actuation portion 131*b*. For instance, in accordance with the illustrated embodiment, the first connector member 63*a* attaches the first actuation portion 131*a* to the first attachment portion 133*a*, and the second connector member 63*b* attaches the second actuation portion 131*b* to the second attachment portion 133*b*.

Thus, it can be said that at least one connector member, such as the first and second connector members 63*a* and 63*b*, can attach the first and second actuation portions 131*a* and 131*b* to respective other locations of the auxiliary strand 33 so as to attach the first and second actuation portions 131*a* and 131*b* to each other, for instance indirectly through at least one or both of the attachment portions 133*a* and 133*b*. It can further be said that the first connector member 63*a* operably attaches one portion of the first actuation strand 38*a* to another location of the actuation strand 38*a*, and the second connector member 63*b* operably attaches one portion of the second actuation strand 38*b* to another location of the second actuation strand 38*b*. Alternatively, it should be appreciated that the first and second connector members 63*a* and 63*b* can attach the respective first and second actuation portions 131*a* and 131*b* to the anchor body 28, such as at respective first and second end portions 52 and 54. While the actuation strands 38*a* and 38*b* are illustrated as separate from each other, the actuation strands 38*a* and 38*b* can alternatively be attached to each other, for instance via any suitable connector member 63 of the type described herein, so as to define an outer connector strand.

In accordance with the illustrated embodiment, each of the first and second connector members 63*a* and 63*b* can be configured as respective knots 66*a* and 66*b* that are defined by the auxiliary strand 33. In accordance with the illustrated embodiment, the first knot 66*a* includes a post end 68, which can be defined by the actuation portion 131*a* of the first actuation strand 38*a*, and a free end, which can include a static portion 70*a* that is defined by a first end 137*a* of the first attachment portion 133*a* and a free portion 70*b* that is defined by a second end 139*a* of the first attachment portion 133*a*. The first end 137*a* can be disposed between the knot 66*a* and the first anchor body 28*a*, and the second end 139*a* can be disposed between the knot 66*a* and the second connector member 63*b*. Alternatively, the free portion 70*b* can be defined by the attachment portion 133*b* of the second actuation strand 38*b*.

In accordance with one embodiment, the second knot 66*a* includes a post end 68, which can be defined by the actuation portion 131*b* of the second actuation strand 38*b*, and a free end, which can include a static portion 70*a* that is defined by a first end 137*b* of the second attachment portion 133*b* and a free portion 70*b* that is defined by a second end 139*b* of the second attachment portion 133*b*. The first end 137*b* can be disposed between the knot 66*b* and the second anchor body 28*b*, and the second end 139*b* can be disposed between the knot 66*b* and the first connector member 63*a*. Alternatively, the free portion 70*b* can be defined by the attachment portion 133*a* of the first actuation strand 38*a*. The attachment portions 133*a* and 133*b* are illustrated as being integral with each other, though it should be appreciated that the attachment portions 133*a* and 133*b* can be separate and attached to each other as desired.

Each of the first and second knots 66*a* and 66*b* can define respective sliding members 47 that allow the respective post ends 68 to translate therethrough relative to the free ends. Thus, the sliding members 47 allow the first and second actuation portions 131*a* and 131*b* to translate relative to the first and second attachment portions 133*a* and 133*b*, for instance in response to the applied actuation force F when the knots 66*a* and 66*b* are in unlocked configurations, thereby actuating the respective anchor body 28*a* and 28*b* from the first configuration to the expanded configuration. Each knot 66 further defines a locking member 64 that can be actuated to a locked configuration so as to secure the at least one or both of the anchors 22*a* and 22*b* in their respective biased positions. For instance, a tensile locking force can be applied to the free portions 70*b* of the free ends of the knots 66*a* and 66*b* so as to prevent the actuation portions 131*a* and 131*b* from translating through the knots 66*a* and 66*b* relative to the attachment portions 133*a* and 133*b*.

The first and second knots 66*a* and 66*b* can be spaced apart a fixed distance L along the auxiliary strand 33, such that the gap 24*c* is maintained approximated when the anchor bodies 22*a* and 22*b* are inserted into the respective target anatomical locations 24*a* and 24*b*. For instance, the gap 24*c* can be approximated prior to injecting the knots 66*a* and 66*b* into the respective target anatomical locations 24*a* and 24*b*. During operation, once the first and second anchors 22*a* and 22*b* are implanted at the respective first and second target anatomical locations 24*a* and 24*b*, the knots 66*a*-*b* can be in an unlocked configuration such that application of the actuation force F to the respective actuation strands 38*a*-*b*, for instance the actuation portions 131*a*-*b*, causes the respective anchor bodies 28*a*-*b* to actuate from the first configuration to the expanded configuration. Next, a tensile locking force can be applied to the respective attachment portions 133*a*-*b* against the corresponding knots 66*a*-*b*, so as to actuate the knots 66*a*-*b* to their locked configurations and maintain the anchor 22*a*-*b* in their expanded configurations.

The distance L between the first and second knots 66*a* and 66*b* can be substantially equal to or less than the distance between the target anatomical locations 24*a* and 24*b*, such that the gap 24*c* is approximated when the first and second anchors 22*a* and 22*b* are expanded behind the anatomy and joined by the auxiliary strand 33, such that tension induced in the actuation strands 38*a* and 38*b* maintains the approximation of the gap 24*c*. While the first and second connector members 63*a*-*b* can be configured as respective knots 66, it should be appreciated that either or both of the first and second connector members 63*a* and 63*b* can be alternatively configured as any suitable locking member 63 of any type described herein or any suitable alternatively constructed locking member. For instance, at least one or both of the connector members 63*a*-*b* can define a splice, whereby the respective actuation strands 38*a*-*b* can be spliced through the other of the actuation strands 38*a*-*b* or itself, and the connector strand is placed in tension after actuation of the anchors 22*a* and 22*b* so as to apply a compressive force that prevents translation of the anchor strands 38*a*-*b*.

It should be appreciated that the anchor bodies 28*a* and 28*b* can be constructed in accordance with any suitable embodiment as desired. For instance, referring now to FIGS. 1G-1H, each of the anchor bodies 28*a* and 28*b* can include an eyelet 90 that extends from a distal end of the respective expandable portions 36*a* and 36*b*. The actuation strand 38 can be configured as an auxiliary strand 33 that is separate from the anchor bodies 28. The actuation strand can be woven through the anchor bodies 28*a* and 28*b*, and can extend through the respective eyelets 90*a* and 90*b* so as to define a path for the eyelets 90*a* and 90*b* to travel through the respective anchor bodies 28*a* and 28*b* when the anchor bodies 28*a* and 28*b* are actuated from the first configuration to the expanded configuration. The auxiliary strand 33 can thus attach the first anchor body 28*a* to the second anchor body 28*b*, and can further be configured to receive the actuation force F that cases the anchor bodies 28*a* and 28*b* to actuate from the first configuration to the expanded configuration once implanted in the respective target anatomical locations 24*a* and 24*b*.

As described above, the anchor assembly 20 can include any suitable connector member 63 that can be configured to attach to the first and second actuation portions 131*a* and 131*b*, thereby attaching the first and second actuation strands 38*a* and 38*b* to each other, and also attaching the anchors 22*a* and 22*b* to each other. The first and second actuation strands 38*a* and 38*b* are illustrated as integral with each other, and thus define a common actuation strand. Alternatively, the first and second actuation strands 38*a* and 38*b* can be separate from each other and attached to each other in any manner desired.

Figure 1G:
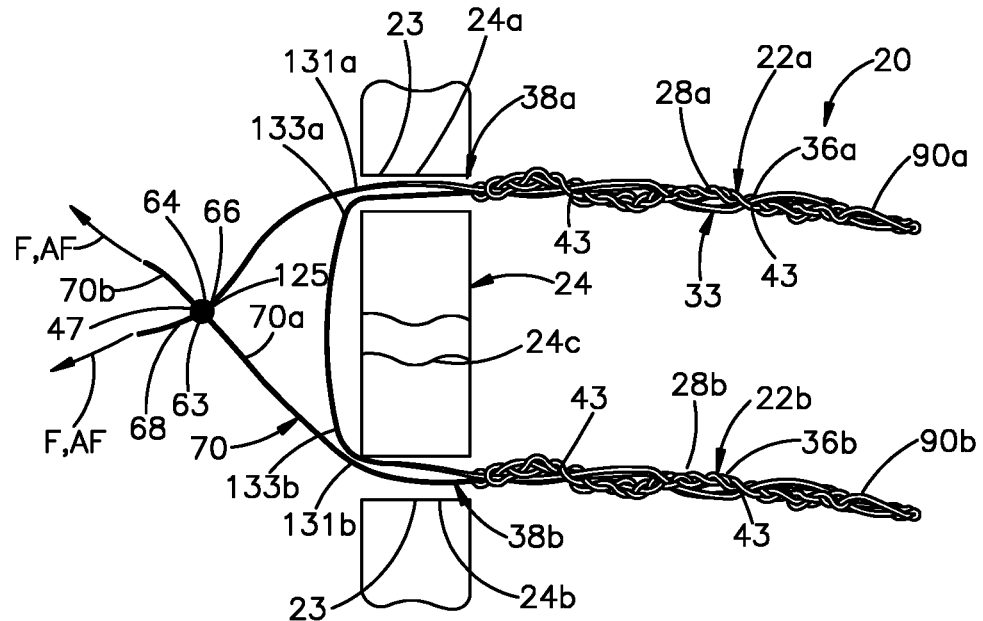
FIG. 1G is a schematic side elevation view of an anchor assembly including a pair of anchor bodies constructed in accordance with an alternative embodiment, shown implanted across an anatomical defect and shown in a first configuration.
Figure 1H:
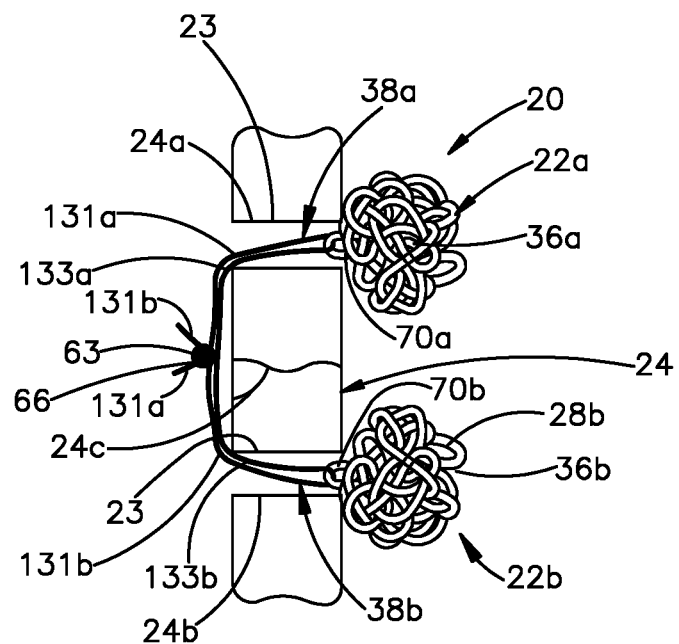
FIG. 1H is a schematic side elevation view of the anchor assembly illustrated in FIG. 1G, showing the anchor bodies in an expanded configuration and in an approximated position.

In accordance with the embodiment illustrated in FIGS. 1G-H, the connector member 63 is defined by and integral with the first and second actuation strands 38*a* and 38*b*. Thus, the actuation portions 131*a* and 131*b* of the actuation strands 38*a* and 38*b* are attached directly to each other. The connector member 63 can define a sliding member 47 and a locking member 64 at a junction 125. For instance, the connector member 63 can define a knot 66 that can be constructed as desired, and can be defined by one or both of the actuation strands 38*a* and 38*b*. Thus, at least a portion of the connector member 63 can be integral with at least one or both of the actuation strands 38*a* and 38*b*.

One of the first and second actuation strands 38*a* and 38*b* can define the post end 68 of the knot 66, and the other of the first and second actuation strands 38*a* and 38*b* can define the free end 70 of the knot 66. In accordance with the illustrated embodiment, the first actuation strand, such as the first actuation portion 131a, defines the post end 68 and the second actuation strand 38b, such as the second actuation portion 131b, defines the free end 70.

The first and second actuation strands 38a and 38b can be tied into the knot 66 prior to applying tension to the actuation strands 38a and 38b that biases the first and second anchors 22a and 22b toward each other and approximates the gap 24c. Once the knot 66 is formed, and when the knot 66 is in an unlocked configuration, the actuation force F can be applied to the actuation strands 38a and 38b, and in particular to the actuation portions 131a-b, so as to actuate the respective expandable portions 36 from the first configuration to the expanded configuration. Next, the approximation force AF can be applied to the terminal portion 135a of the first actuation strand 38a, which defines the post strand 68, thereby causing the post end 68 to slide through the knot 66 and draw the respective anchor, such as the first anchor 22a, toward the other anchor, such as the second anchor 22b. Once the gap 24c has been approximated, the free strand 70b of the free end 70, for instance defined by the terminal portion 135b of the second actuation strand 38b, can be placed in tension so as to lock knot 66 and prevent the first actuation strand 38a from translating through the knot 66, thereby fixing the actuation strands 38a and 38b in tension. While the connector member 63 can be configured as the knot 66, it should be appreciated that the connector member 63 can alternatively be configured in accordance with any embodiment described herein or any suitable alternative connector as desired.

Figure 2B:
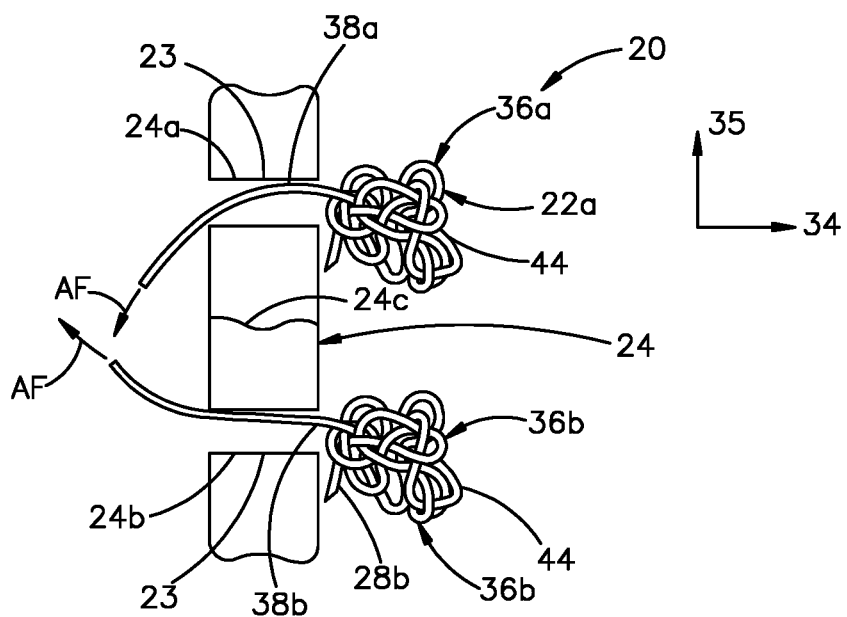
FIG. 2B is a side elevation view of the anchor assembly illustrated in FIG. 2A, showing the first and second anchors in respective expanded configurations.
Figure 2C:
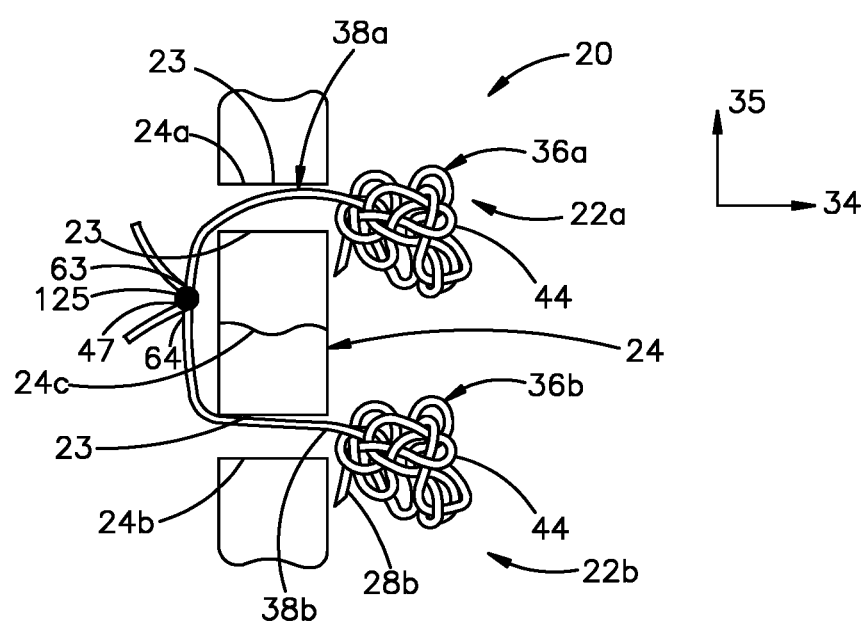
FIG. 2C is a side elevation view of the anchor assembly illustrated in FIG. 2A, including a connector member that attaches the first anchor to the second anchor.

Referring now to FIGS. 2A-C, and as generally described above with respect to FIGS. 1A-B, the anchor assembly 20 can include first and second anchors 22a and 22b. The first anchor 22a includes a first anchor body 28a that extends substantially along the direction of elongation 34 and defines a first plurality of openings 40a that extend through the first anchor body 28a. The first anchor 22a further includes a first actuation strand 38a that extends through at least one of the openings 40a, such as a plurality of the openings, and is configured to receive an actuation force F that causes the first anchor body 28a to actuate from the first configuration to the expanded configuration in the manner described above. The first actuation strand 38a can be separate from and attached to, for instance woven through openings of, the first anchor body 28a, or can be integral with the first anchor body 28a and extend through openings of the first anchor body 28a.

The second anchor 22b includes a second anchor body 28b that extends substantially along the direction of elongation 34 and defines a second plurality of openings 40b that extend through the second anchor body 28b. The second anchor 22b further includes a second actuation strand 38b that extends through at least one of the openings 40b, such as a plurality of the openings, and is configured to receive an actuation force F that causes the second anchor body 28b to actuate from the first configuration to the expanded configuration in the manner described above. The second actuation strand 38b can be separate from and attached to, for instance woven through openings of, the second anchor body 28b, or can be integral with the second anchor body 28b and extend through openings of the second anchor body 28b.

In accordance with the embodiment illustrated in FIGS. 2A-B, the first and second actuation strands 38a and 38b are integral with the respective first and second anchor bodies 28a and 28b. In accordance with other embodiments, the first and second actuation strands 38a and 38b are illustrated as separate from and attached to the respective first and second anchor bodies 28a and 28b. In accordance with still other embodiments, one of the first and second actuation strands 38a and 38b is integral with the respective anchor body and the other of the first and second actuation strands 38a and 38b is separate from and attached to the respective anchor body. In accordance with embodiments whereby the first and second actuation strands 38a and 38b are illustrated and described as integral with the respective first and second anchor bodies 28a and 28b, it should be appreciated that the first and second actuation strands 38a and 38b can alternatively be separate from and attached to the respective first and second anchor bodies 28a and 28b, unless otherwise indicated. Furthermore, in accordance with embodiments whereby the first and second actuation strands 38a and 38b are illustrated and described as separate from and attached to the respective first and second anchor bodies 28a and 28b, it should be appreciated that the first and second actuation strands 38a and 38b can alternatively be integral with the respective first and second anchor bodies 28a and 28b, unless otherwise indicated.

With continuing reference to FIG. 2C, the anchor assembly 20 can include at least one connector member 63 that is configured to join the anchors 22 and allow a biasing force to be applied to at least one of the anchors 22a and 22b that draws the anchors 22a and 22b together, thereby approximating the anatomical defect 24. The connector member 63 can be integral with one or both of the first and second anchors 22a and 22b, for instance integral with one or both of the first and second actuation strands 38a and 38b, can be integral with one or both of the first and second anchor bodies, or can be separate from and attached (directly or indirectly) to one or both of the first and second anchors 22a and 22b. For instance, the connector member 63 can be separate from and attached between the first and second anchors 22a and 22b, as will be described in more detail below. While connector members 63 are described herein in accordance with various embodiments, it should be appreciated that the anchor assembly 20 can alternatively include any suitable connector member configured to attach the first anchor 22a to the second anchor 22b. At least one or both of the actuation strands 38a-b can be configured to receive an approximation force AF that biases at least one of the first and second anchors 22a and 22b toward the other so as to approximate the gap 24c.

The anchor assembly 20 can include a connector member 63 that is integral with the corresponding actuation strands 38a and 38b. As described above, each of the first and second anchor bodies 28a and 28b can be implanted at respective first and target anatomical locations 24a and 24b that are disposed on opposite sides of a gap 24c as illustrated in FIG. 2A. Each of the first and second actuation strands 38a and 38b can receive an actuation force F substantially along the direction of elongation 34 that causes the respective first and second anchor bodies 28a and 28b, and in particular the respective expandable portions 36a and 36b, to actuate from the first configuration to the expanded configuration so as to fix the first and second anchor bodies 28a and 28b at the respective first and second target anatomical locations 24a and 24b. The actuation force F applied to each of the actuation strands 38a and 38b can be in the form of different actuation forces, or, as is described in more detail below, can be the same actuation force.

Referring now to FIG. 2B, once the first and second anchor bodies 28a and 28b are secured to the respective first and second target anatomical locations 24a and 24b, an approximation force AF can be applied to at least one or both of the first and second actuation segments 38a and 38b substantially along a direction toward the other of the respective first and second anchor bodies 28a and 28b, which can also be toward the respective gap 24c. Thus the approximation force AF can have a directional component that is toward the other of the respective first and second anchor bodies 28a and 28b, for instance can be directed purely toward the other of the first and second anchor bodies 28a and 28b. Likewise, the approximation force AF can have a directional component that is directed toward the gap 24c, for instance directed purely toward the gap 24c. Accordingly, the approximation force AF biases at least one or both of the anchor bodies 28a and 28b toward the other of the anchor bodies 28a and 28b to respective biased positions that to approximate the gap 24c.

Referring again to FIG. 2C, the connector member 63 that can define at least one or both of a sliding member 47 and a locking member 64 that attaches the first and second connector actuation strands 38a and 38b together, for instance at a junction 125. Thus, it should be appreciated that the at least one of the sliding member 47 and locking member 64 can likewise attach the first actuation strand 38a to the second actuation strand 38b. In accordance with one embodiment, the connector member 63 can attach the first and second actuation strands 38a and 38b after the first and second actuation strands 38a and 38b have been put under tension so as to maintain the gap 24c in an approximated state. The member 63 can be actuated to the locked configuration so as to prevent or resist separation of the first and second anchors 22a and 22b that would cause the gap 24c to open from the approximated state. Alternatively or additionally, the connector member 63 can attach the first and second actuation strands 38a and 38b to each other prior to applying the approximation force AF to the actuation strands 38a and 38b, and placing the actuation strands 38a and 38b under tension, and therefore prior to approximating the gap 24c.

In accordance with certain embodiments, the connector member 63 is defined by, and integral with, the first and second actuation strands 38a and 38b, and can be configured as a sliding and locking knot that can iterate from an unlocked configuration, whereby one of the actuation strands 38a and 38b to slide relative to the other so as to approximate the gap 24c, and a locked configuration, whereby the actuation strands 38a and 38b are prevented from sliding relative to each other through the knot. The connector member 63 defines the at least one of the sliding member 47 and the locking member 64 at the junction 125. Thus, it can be said that the connector member 63 can directly or indirectly attach the first and second actuation strands 38a and 38b together.

Figure 3A:
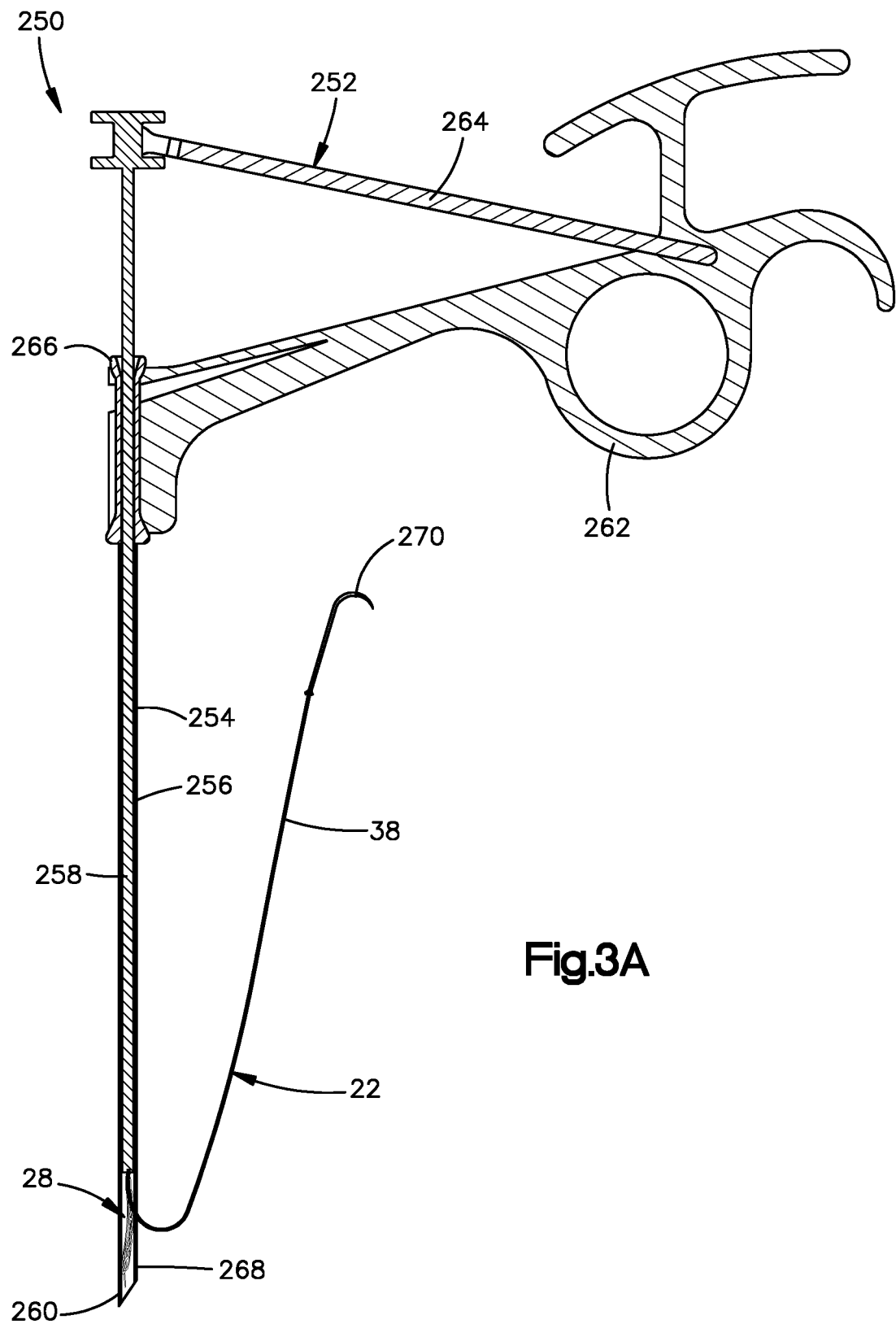
FIG. 3A is a side elevation view of a fixation kit including at least one anchor and an insertion instrument.

Referring now to FIG. 3A, a fixation assembly 250 can include the anchor assembly 20, such as at least one anchor 22, and an insertion instrument 252 configured to inject the anchor 22 in the anatomical structure 24 as illustrated in FIGS. 1A-B. It should be appreciated that the fixation kit 250 can include at least one or more up to all of the anchors 22 described herein alone, attached to each other, or configured to be attached to each other in accordance with any of the embodiments describer herein. The insertion instrument 252 can include a cannula 254 with a central opening 256 and a first pusher member such as a plunger or push rod 258 which is coaxially insertable into the central opening 256. the cannula 254 has an acuminated tip 260 and a slot 268 extending axially from the tip 260. The cannula 254 can extends substantially straight as illustrated, or can be curved or define any suitable shape as desired so as to eject an anchor body 28.

Further, the insertion instrument 252 comprises a handle 262 with an operating lever 264. One end of the handle 262 is detachably attached to the cannula 254 and the operating lever 264 is detachably attached to the plunger 258. The outer diameter of the plunger 258 corresponds to the inner diameter of the central opening 256 of the cannula 254. At the rear end the central opening of the cannula 254 is conically configured in such a manner that it enlarges towards the rear end of the cannula 254 at an inlet 266. Thus, the anchor body 28 of the anchor 22 can be inserted in its first configuration through the conical inlet 266 and into the central opening 256 of the cannula 254, such that the anchor body 28 can be compressed.

When the anchor body 28 is pressed out of the cannula 254 by pressing the plunger 258 forward the anchor body 28 can radially expand, for instance in the second direction 35 (see FIGS. 1A-B) in such a manner that it can be retained by the front face of the cannula 254 when a tensile force is exerted onto the actuation strand 38 in order to tighten the anchor body 28. the actuation strand 38 is led through the slot 268 so that it can be led alongside the cannula 254 when the cannula 254 is inserted into the anatomical structure 24. At the free end of the actuation strand 38 a needle 270 is attached that can be used for finishing a surgical procedure when the anchor body 28 of the anchor 22 has been actuated to the expanded configuration and secured to the anatomical structure 24.

Figure 3B:
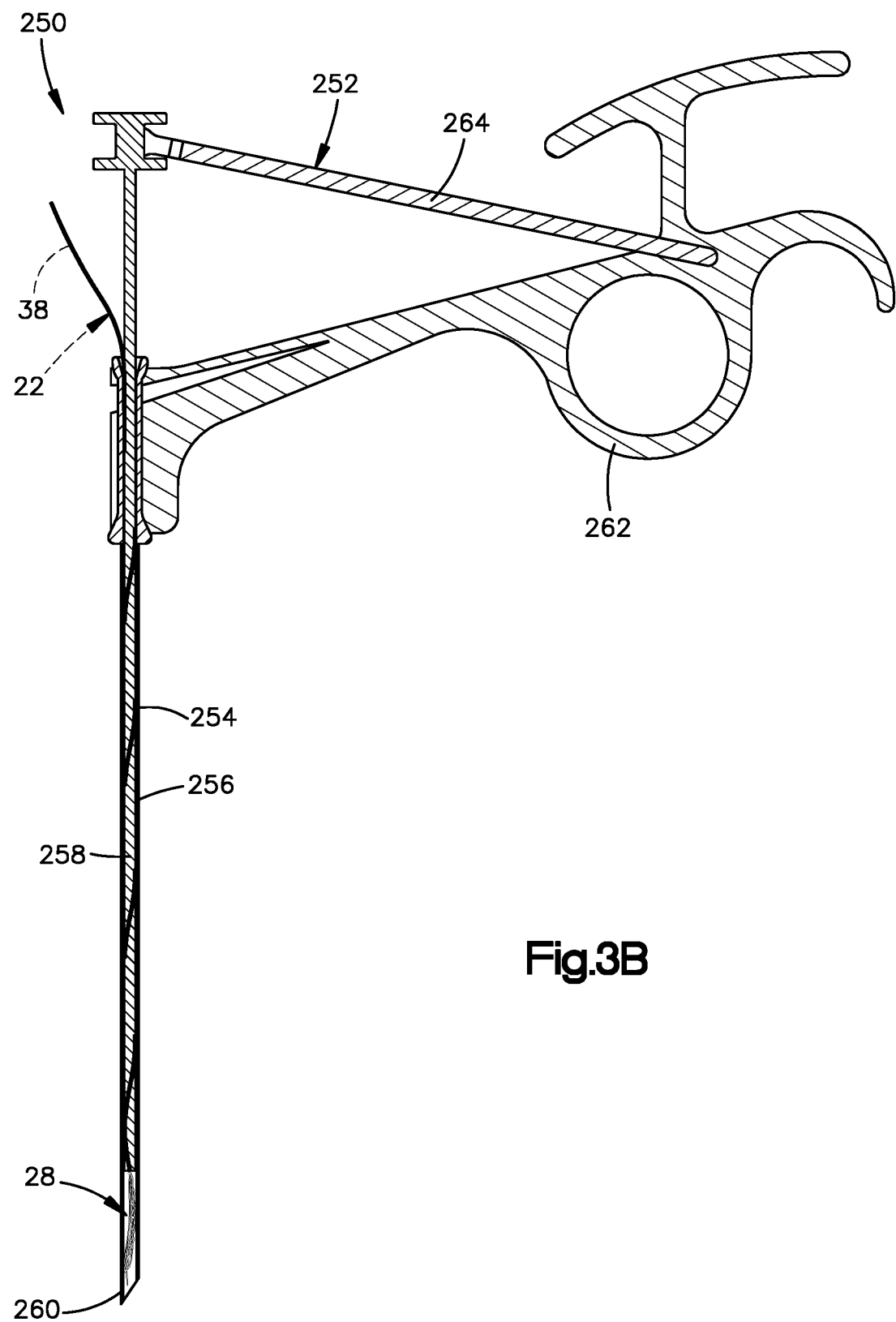
FIG. 3B is a sectional side elevation view of the fixation kit illustrated in FIG. 3A.
Figure 5A:
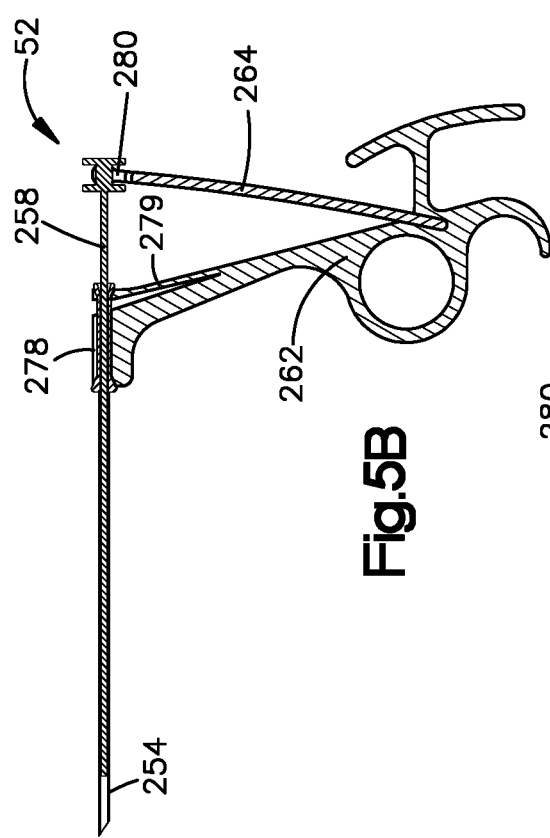
FIG. 5A is a sectional side elevation view of an insertion instrument during assembly.
Figure 5B:
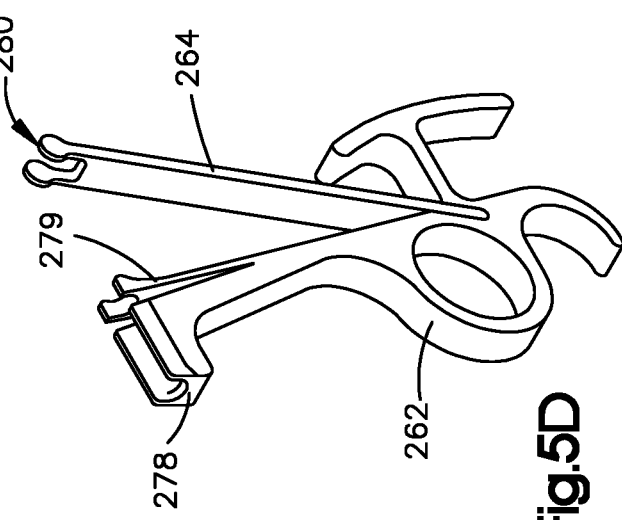
FIG. 5B is a sectional side elevation view of the insertion instrument illustrated in FIG. 5A, but shown assembled.
Figure 5C:
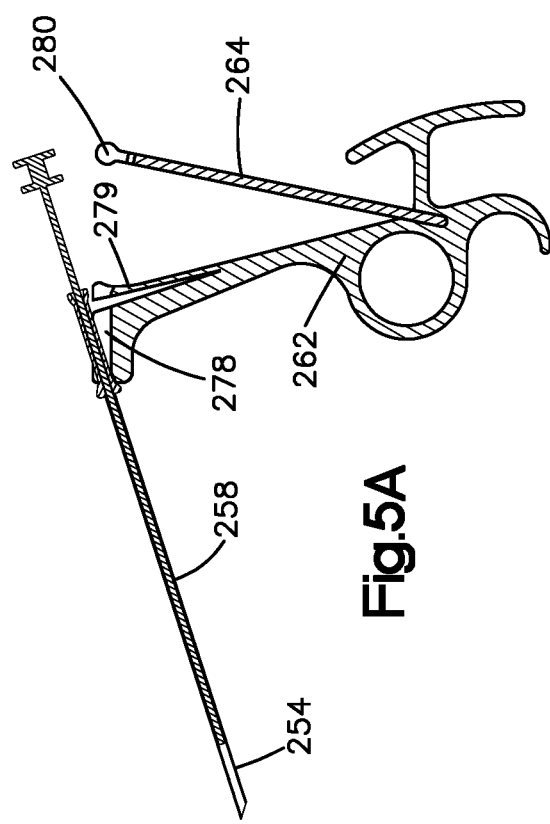
FIG. 5C is a sectional side elevation view of a handle of the insertion instrument illustrated in FIG. 5B.
Figure 5D:
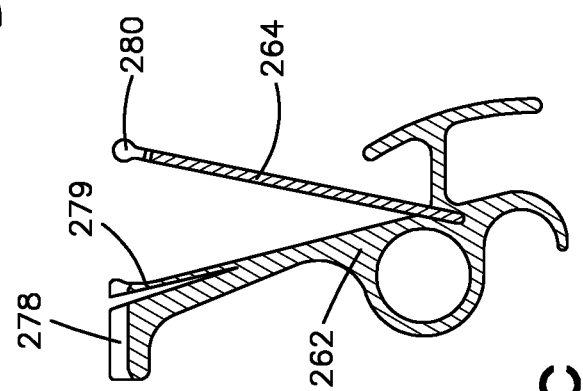
FIG. 5D is a perspective view of the handle illustrated in FIG. 5C.

Referring to FIG. 3B, the plunger 258 can have an outer diameter or alternative cross-sectional dimension that is less than the inner diameter or cross-sectional dimension of the central opening 256 of the cannula 254. The actuation strand 38 of the anchor 22 can thus be led through the central opening 256 of the cannula 254 when the plunger 258 is inserted in the central opening 256 of the cannula 254. By actuating the operating lever 264 at the handle 262, the plunger 258 can push the anchor 22 forward in the cannula 254 as far as the anchor body 28 exits from the central opening 256 at the tip 260 of the cannula 254. Once the anchor body 28 is positioned in the central opening 256 the actuation strand 38 can be pulled backward at the rear end of the cannula 254 so that the anchor body 28 can be actuated in the cavity 256 to its expanded configuration.

Referring to FIGS. 4A-D, the plunger 258 can define a central bore 272 where the actuation strand 38 of the anchor 22 can be led through. Further, the cannula 254 has a first longitudinal aperture 274 extending between the tip 260 and the rear end of the cannula 254 so that the cannula 254 is slotted over its entire length. A second longitudinal aperture 276 extends on the plunger 258 between the front end and the rear end of the plunger 258 so that the plunger 258 is slotted over its entire length as well. As shown in FIG. 4B when the cannula 254 is in a first rotative position relative to the plunger 258 the first longitudinal aperture 274 of the cannula 254 is diametrically opposite to the second longitudinal aperture 276 of the plunger 258. In the first rotative position of the cannula 254 the actuation strand 38 of the anchor 22 is retained by the central bore 272. Once the anchor body 28 of the anchor 22 has been fixed in a cavity of a patient's body by pulling the actuation strand 38 of the anchor 22 backward the cannula 254 can be rotated into a second rotative position relative to the plunger 258 (FIG. 4D). In this second rotative position of the cannula 254 the first longitudinal aperture 274 of the cannula 254 is aligned with the second longitudinal aperture 276 of the plunger 258 and the insertion instrument 252 can be released from the actuation strand 38 of the anchor 22.

FIGS. 5A-D illustrate the handle 262 and the attachment of the cannula 254 to the handle 262 of an embodiment of the insertion instrument 252 of FIGS. 3A to 4D. The upper end portion of the handle 262 comprises a groove 278 into which the cannula 254 can be inserted and a spring member such as a leaf spring 279 so as to provide a releasable snap lock configured to releasably attach the cannula 254 to the handle 262. The rear end of the plunger 258 can be snapped into a resilient fork 280 arranged at the upper end of the operating lever 264.

Referring to FIG. 6, the insertion instrument 52 can include a depth control tube 282 slid over the cannula 254 and a clamping element 284. The insertion instrument 52 is pre-operatively prepared by inserting the anchor 22 into the cannula 254 and inserting the plunger 258. Once the anchor 22 and the plunger 258 have been inserted any one of a plurality of clamping elements 284 is attached to the rear end of the insertion instrument 252 by snapping a first tab 286 onto the rear portion of the cannula 254. To prevent an unintended displacement of the plunger 258 relative to the cannula 254 the clamping element 284 comprises a second tab 288 which abuts the rear end of the cannula 254 and a third tab 290 which abuts an enlarged portion at the rear end of the plunger 258. Before using the insertion instrument 252, the clamping element 284 is removed from the cannula 254 and the handle 262 is attached to the cannula 254, and the insertion instrument 252 can be operated in the manner described herein.

Referring now to FIGS. 1A and 7A-D, an insertion instrument 300 constructed in accordance with an alternative embodiment is configured to deliver at least one anchor knot, such as the first and second anchor knots 22a and 22b, to a respective target location, such as target locations 24a and 24b (FIG. 1A). The insertion instrument 300 is illustrated as elongate along a longitudinal axis 302 that extends substantially along a longitudinal direction L, and defines a proximal end 304 and an opposed distal end 306 that is spaced from the proximal end 304 along the longitudinal axis 302. Thus, it should be appreciated that the terms "distal" and "proximal" and derivatives thereof refer to a spatial orientation closer to the distal end 306 and the proximal end 304, respectively. Furthermore, the directional term "downstream" and "upstream" and derivatives thereof refer to a direction that extends from the proximal end 304 toward the distal end 306, and a direction that extends from the distal end 306 toward the proximal end 304, respectively. The insertion instrument 300 further extends along a lateral direction A that is substantially perpendicular to the longitudinal direction L, and a transverse direction T that is substantially perpendicular to the longitudinal direction L and the lateral direction A. It can also be said that the lateral and transverse directions A and T extend radially with respect to the longitudinal axis 302. Thus, the terms "radially outward" and "radially inward" and derivatives thereof refer to a direction away from and toward the longitudinal axis 302, respectively, and can be used synonymously with laterally and transversely as desired.

The insertion instrument 300 includes a casing 308 that can provide a handle, and a cannula 310 that is supported by the casing 308 and extends distally out from the casing 308 along a central axis 309. The cannula 310 can be fixed to the casing 308 with respect to translation. The central axis 309 can extend longitudinally and can thus be inline with the longitudinal axis 302 of the insertion instrument 300, or can be offset with respect to the longitudinal axis 302 of the insertion instrument 300. The cannula 310 extends substantially straight as illustrated, but can alternatively be curved or define any suitable alternative shape as desired. The cannula 310 defines an elongate opening 312, which can be elongate longitudinally or along any other direction or combination of directions as desired, that is sized to receive the at least one anchor knot, such as the first and second anchor knots 22a and 22b. The insertion instrument 300 can further include a biasing member such as a plug 314 that is disposed in the elongate opening 312, such that the first knot anchor body 28a is disposed in the cannula 310 at a location upstream of the plug 314, and the second knot anchor 28b is disposed in the cannula 310 at a location downstream of the plug 314. Thus, the plug 314 can further provide a divider that separates the first anchor body 28a from the second anchor body 28b along the longitudinal direction. The first and second anchor bodies 28a and 28b are stacked in the instrument 300 along the longitudinal axis 302. The cannula 310 defines a distal tip 311 that is configured to pierce tissue at a target location so as to deliver at least one anchor to the target location.

The insertion instrument 300 further includes a plunger 316 that is supported by the casing 308, and extends proximally out from the casing 308. The plunger 316 is configured to translate distally from an initial or first position illustrated in FIGS. 7A-D along a first stroke to a second position illustrated in FIGS. 8A-D, thereby causing the plug 314 to bias the second anchor 22b distally so as to eject the second anchor 22b out the cannula 310, for instance out a distal ejection port 442 that extends substantially longitudinally through the tip 311.

Figure 12C:
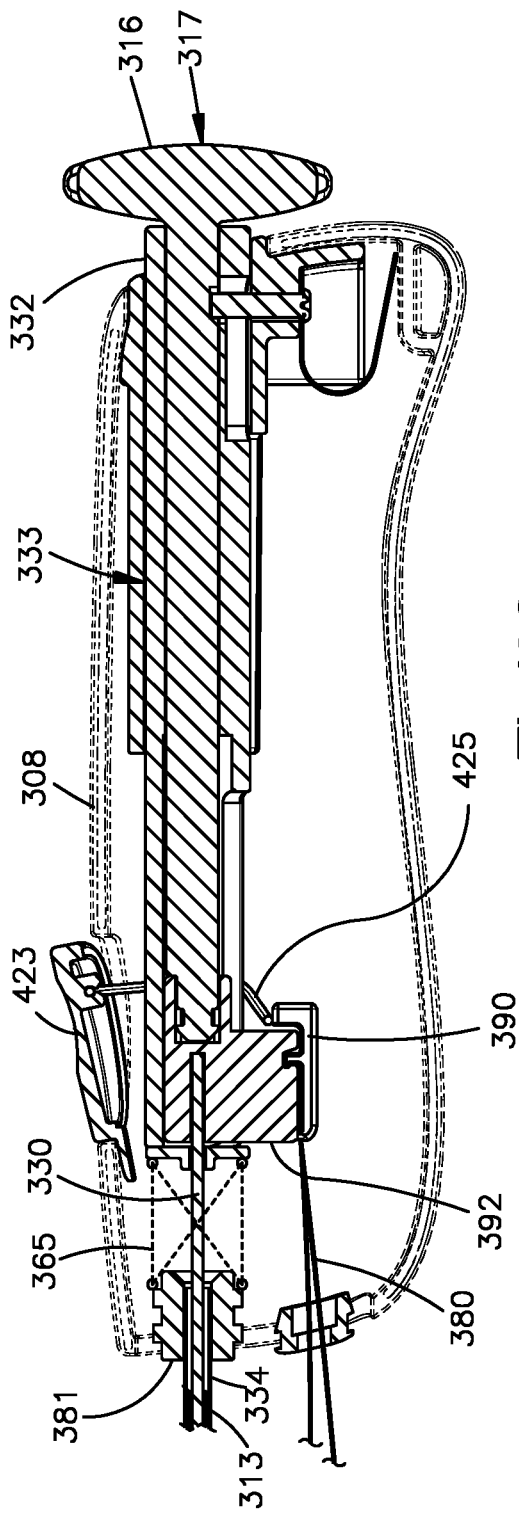
FIG. 12C is a sectional side elevation view of the casing of the insertion instrument illustrated in FIG. 12A.
Figure 12D:
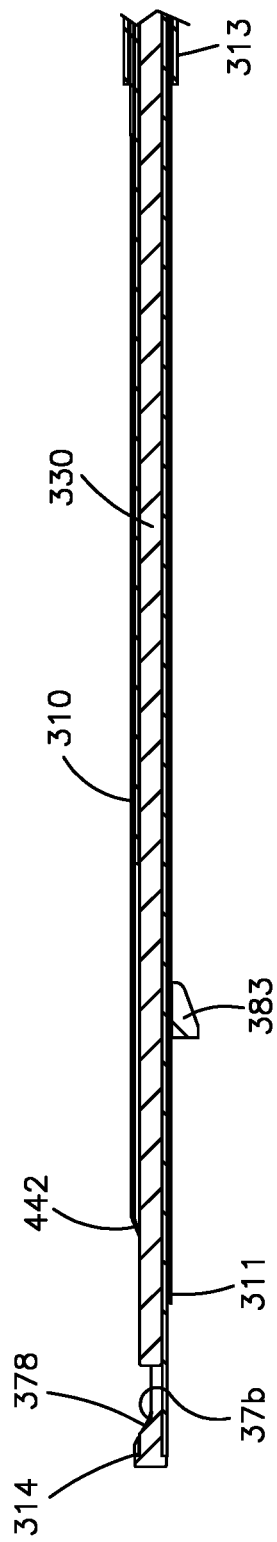
FIG. 12D is a sectional side elevation view of the cannula of the insertion instrument illustrated in FIG. 12A.
Figure 12F:
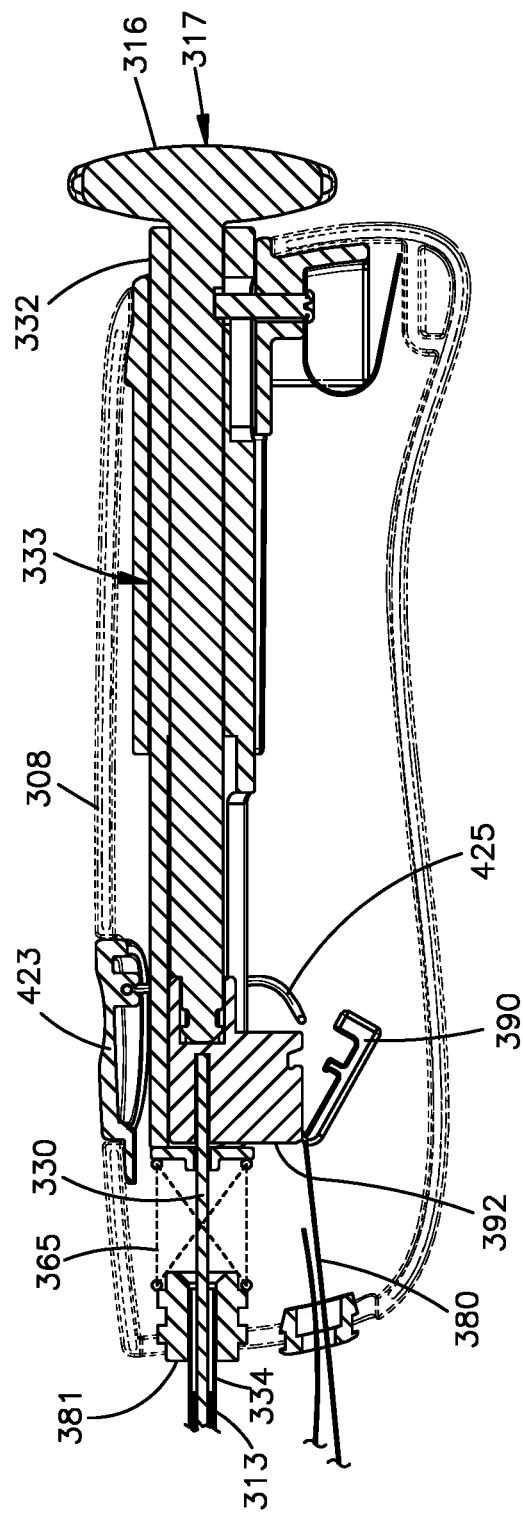
FIG. 12F is a sectional side elevation view of the casing of the insertion instrument illustrated in FIG. 12A, after release of a strand retention mechanism.

Once the second anchor 22b has been ejected out the ejection port 442, the plunger 316 is configured to translate further distally along a first portion of a second stroke illustrated in FIGS. 11A-C, and along a second portion of the second stroke illustrated in FIGS. 12A-C, such that a push rod 330 (see FIG. 7C) biases the first anchor body 28a distally so as to eject the first anchor 22a out the cannula 310, for instance out the ejection port 442, into the first target anatomical location 22a. Alternatively, as described in more detail below, the cannula 310 can define a side ejection port 318 (described below with reference to FIG. 31) that is configured to eject the first and second anchor bodies 28a and 28b out the cannula 310 along a direction angularly offset with respect to the central axis 309.

The insertion instrument 300 can be configured such that the plunger 316 moves distally from the second position to an offset position as illustrated in FIGS. 9A-D before moving along an intermediate stroke from the offset position to an intermediate position as illustrated in FIGS. 10A-D. Accordingly, the plunger 316 can move from the second position, to the offset position, to the intermediate position, and finally to the third position illustrated in FIGS. 12A-D. In accordance with the illustrated embodiment, the plunger 316 is rotated from the second position to the intermediate position prior to translating along the second stroke to the third position. For instance, the plunger 316 can move along a first portion of the second stroke as illustrated in FIGS. 11A-D prior to moving along a second portion of the second stroke as illustrated in FIGS. 12A-D. An actuation force can be applied to the actuation portion 131a and 131b of the first and second anchors 22a and 22b, respectively, after each anchor has been ejected, or can alternatively be applied after both anchors 22a and 22b have been ejected. The anchors 22a and 22b can be attached to each other in any manner as desired, for instance across the gap 24c.

Referring now to FIGS. 7A-C in particular, the casing 308 defines a body 320 that defines at least one radially outer side wall 322, such as a plurality of joined walls that can be of any size and shape, and further defines a proximal wall 324 and an opposed distal wall 326. The at least one outer wall 322, the proximal wall 324, and the distal wall 326 at least partially define an interior 328 that can be in fluid communication with the elongate opening 312 of the cannula 310. The cannula 310 is attached to the distal wall 326 of the casing 308 and is thus fixed to the casing 308. The cannula 310 extends distally from the casing 308 to the tip 311. The tip 311 can be tapered distally, such that the cannula 310 defines a tapered distal end. For instance, the tip 311 can be conical, that is the tip 311 can define a portion that is conical, and can define the shape of a cone or any suitable alternative shape as desired. The insertion instrument 300 can further include a support sleeve 313 that at least partially surrounds the cannula 310 at the interface with the casing 308, and extends distally along a portion of the length of the cannula 310. The support sleeve 313 provides structural support and rigidity to the cannula 310.

The plunger 316 defines a distal end 316a that is disposed in the interior 328, a body portion 316b that extends proximally from the distal end 316a and out the proximal wall 324 of the casing 308, and a proximal end 316c that can define a grip that is disposed outside the casing 308. The insertion instrument 300 further includes a first pusher assembly 317 that can include the plunger 316 and a first pusher member, such as a push rod 330 that is attached, directly or indirectly, to the distal end 316a of the plunger 316. The push rod 330 can be attached to the plunger 316 (for instance integral with the plunger 316 or separately attached to the plunger 316 via any suitable fastener or intermediate apparatus as desired). For instance, in accordance with the illustrated embodiment, the distal end 316a of the plunger is attached to a retention housing 392 as is described in more detail below with reference to FIG. 17. The push rod 330 is attached to the retention housing 392, and is thus attached to the plunger 316. The push rod 330 can extend distally from the plunger 316 into the opening 312 of the cannula 310 and out the distal wall 326 of the casing 308. It should be appreciated that reference to at least one or both of the plunger 316 and the push rod 330 can be applicable to the first pusher assembly 317. For instance, description with respect to the structure that is fixed or coupled to at least one or both of the plunger 316 and the push rod 330 can be said to be fixed or coupled, respectively, to the first pusher assembly 317.

Because the push rod 330 is translatably fixed to the plunger 316, movement of the plunger 316 proximally and distally causes the push rod 330 to likewise move proximally and distally. The push rod 330 defines a distal end 330a disposed in the opening 312 of the cannula 310. Accordingly, the distal end 330a of the push rod 330 is configured to brace against the first anchor 22a when the insertion instrument 300 is in the first position as illustrated in FIGS. 7A-D. The distal end 330a of the push rod 330 is configured to brace against the first anchor 22a when the insertion instrument 300 is in the first position, and also as the plunger 316, and thus the push rod 330, translates distally from the first position to the second position, such that the push rod 330 ejects the first anchor 22a out the insertion instrument 300 and into the respective target location 24a. When a tensile force is applied to the respective actuation member 37a substantially along the direction of elongation of the anchor body 28a after the first anchor body 28a has been ejected and is braced against the anatomical structure 24, the anchor body 28a expands along the second direction 35 that is perpendicular with respect to the direction of elongation 34 of the anchor body 28a (see, for instance, FIGS. 1A-B).

The insertion instrument 300 can further includes a second pusher assembly 333 that includes an attachment member 331, such as a collar 332 that extends about the plunger 316 and can at least partially surround the plunger 316, and a second pusher member, such as a push tube 334 that extends distally from the collar 332 and at least partially surrounds the push rod 330. The push tube 334 can be attached to the collar 332 (for instance integral with the collar 332 or separately attached to the collar 332 via any suitable fastener as desired). Accordingly, description of at least one or both of the push tube and the collar 332 can be applicable to the second pusher assembly 333. For instance, description with respect to the structure that is fixed or coupled to at least one or both of the push tube 334 and the collar 332 can be said to be fixed or coupled, respectively, to the second pusher assembly 333.

The push tube 334 can include the plug 314 that can define the distal end of the push tube 334. The push tube 334 can be cannulated in accordance with the illustrated embodiment so as to define a longitudinally elongate opening 335, and the push rod 330 has an outer diameter that is less than that of the opening 335, such that the push rod 330 is disposed inside the elongate opening 335 of the push tube 334. It should be appreciated that structures described herein as defining a diameter can alternatively define any suitably configured cross section, which can be circular or alternatively shaped, and thus can define any cross-sectional dimension which can be a diameter or not. The cannula 310 can contain both the first and second anchor bodies 28a and 28b. For instance, the push tube 334 can contain the first anchor body 28a at a location upstream of the plug 314, and the cannula 310 can contain the second anchor body 28b at a location distal to the plug 314, and thus distal to the first anchor body 28a.

The insertion instrument 300 can include a force transfer member 336 that can extend radially inward from the distal end of the collar 332, such that the push rod 330 extends distally through or from force transfer member 336. The force transfer member 336 can abut the collar 332, or can be fixed to the distal end of the collar 332. The force transfer member 336 can further abut or be fixed to the proximal end of the push tube 334. If the force transfer member 336 abuts one or both of the collar 332 and the push tube 334, then 1) distal movement of the collar 332 biases the force transfer member 336 distally, which in turn biases the push tube 334, including the plug 314, distally, and 2) proximal movement of the collar 332 does not bias the push tube 334 proximally. If the force transfer member 336 is attached to the collar 332 and the push tube 334, then 1) distal movement of the collar 332 biases the force transfer member 336 distally, which in turn biases the push tube 334, including the plug 314, distally, and 2) proximal movement of the collar 332 biases the force transfer member 336 distally, which in turn biases the push tube 334, including the plug 314, distally. Whether the force transfer member 336 abuts or is fixed to the collar 332 and the push tube 334, it can be said that the collar 332 is translatably coupled to the push tube 334, such that distal translation of the collar 332 causes the push tube 334 to translate distally.

The collar 332, and thus the push tube 334, including the plug 314, is configured to be selectively coupled to and decoupled from the first pusher assembly 317 with respect to translation, and configured to be selectively coupled to and decoupled from the casing 308 with respect to translation.

For instance, in a first configuration, the collar 332 is translatably fixed to the plunger 316, and thus also to the push rod 330. Furthermore, in the first configuration, the collar 332 is translatably decoupled from the casing 308 and thus also translatably decoupled from the cannula 310. Accordingly, in the first configuration, proximal and distal movement of the plunger 316 and push rod 330 relative to the casing 308 and cannula 310 causes the collar 332 to correspondingly move proximally and distally relative to the casing 308 and cannula 310. It should be appreciated that in the first configuration, the push rod 330 is translatably coupled to the push tube 334, such that the push rod 330 and the push tube 334 translate in tandem, for instance during the first stroke, thereby causing the push tube 334 to eject the second anchor body 28b out the cannula 310, as will be described in more detail below. As described above, when a tensile force is applied to the respective actuation member 37b substantially along the direction of elongation of the second anchor body 28b after the second anchor body 28b has been ejected, the second anchor body 28b expands along the second direction 35 that is perpendicular with respect to the direction of elongation 34 of the anchor body 28b (see, for instance, FIGS. 1A-B).

In a second configuration, the collar 332 is translatably decoupled from the plunger 316, and thus the push rod 330, and is translatably coupled to the casing 308, and thus the cannula 310. Accordingly, in the second configuration, the plunger 316 and push rod 330 move proximally and distally relative to the collar 332 and the casing 308 and the cannula 310. It should be appreciated that in the second configuration, after the first stroke, the push rod 330 is translatably decoupled from the push tube 334, such that the push rod 330 translates distally relative to the push tube 334 and thus the plug 314, for instance during at least a portion of the second stroke, thereby causing the push rod 330 to eject the first anchor body 28a out the cannula 310, as will be described in more detail below.

Referring now to FIGS. 13A-G, the insertion instrument 300 includes a guide system 329 that operably couples the casing 308 and the push tube 334 so as to guide relative movement between the casing 308 and the push rod 330. In accordance with the illustrated embodiment, the guide system 329 includes complementary first and second guide members 338 and 340, respectively, that are coupled between the casing 308 and the collar 332. In accordance with the illustrated embodiment, during the first stroke and a first portion of the second stroke, the first and second guide members 338 and 340 cooperate to guide the movement of the plunger 316 (and push rod 330) and collar 332 (and push tube 334) in tandem relative to the casing 308. In that regard, it should be appreciated that the first and second guide members 338 and 340 are operably coupled between the plunger 316 and the collar 332 during the first stroke and a first portion of the second stroke. In accordance with the illustrated embodiment, during a second portion of the second stroke, the first and second guide members 338 and 340 cooperate to guide the movement of the plunger 316 and push rod 330 relative to both the collar 332 (and push tube 334) and the casing 308. In that regard, it should be appreciated that the first and second guide members 338 and 340 are operably coupled between the casing 308 and the collar 332 during the second portion of the second stroke.

In accordance with the illustrated embodiment, one of the first and second guide members 338 and 340 is provided as a guide track 342 that extends into one of the collar 332 and the casing 308, and the other of the guide members 338 and 340 is provided as a guide pin 344 that extends into the guide track 342, such that the guide pin 344 rides in the guide track 342, thereby operably coupling the collar 332 to the casing 308. In accordance with the illustrated embodiment, the first guide member 338 is provided as the guide track 342 that is carried, and defined, by the collar 332, and the second guide member 340 is provided as the guide pin 344 that is translatably fixed to the casing 308 and extends into the guide track 342. For instance, the guide pin 344 extends radially into or through the side wall 322 of the casing 308 and into the guide track 342. It should be appreciated in accordance with an alternative embodiment that the guide track 342 can be carried, and defined, by the casing 308 and the guide pin 344 can be translatably fixed to the collar 332.

In accordance with the embodiment illustrated in FIG. 13G, the track 342 defines a slot 339 that extends radially into the collar 332 but not through the collar 332, and a base 341 of the collar 332 that is located at the radially inner end of the slot 339. The guide track 342 defines a first guide portion such as a first track portion 342a, a second guide portion such as a second track portion 342b that is offset, for instance radially, with respect to the first track portion 342a, and an angled intermediate guide portion such as an angled intermediate track portion 342c that connects the first track portion 342a to the second track portion 342a. Accordingly, the guide pin 344 is configured to travel along the first track portion 342a during the first stroke as the plunger 316 is translated from the first position to the second position. In particular, the second track portion 342a defines a first or distal end 342a' an opposed second or proximal end 342a", and an offset position 342a''' between the distal end 342a and the proximal end 342a". The offset position 342a''' is aligned with an intermediate track portion 342c that extends between the first track portion 342a and the second track portion 342b. Once the guide pin 344 has translated from the proximal end 342a" to the offset position 342a''', the guide pin 344 can travel along the intermediate track portion 342c toward the second track portion 342b as the plunger 316 is rotated to the intermediate position. The guide pin 344 can subsequently travel distally along the second track portion 342b as the plunger 316 is further translated toward the third position.

Figure 13B:
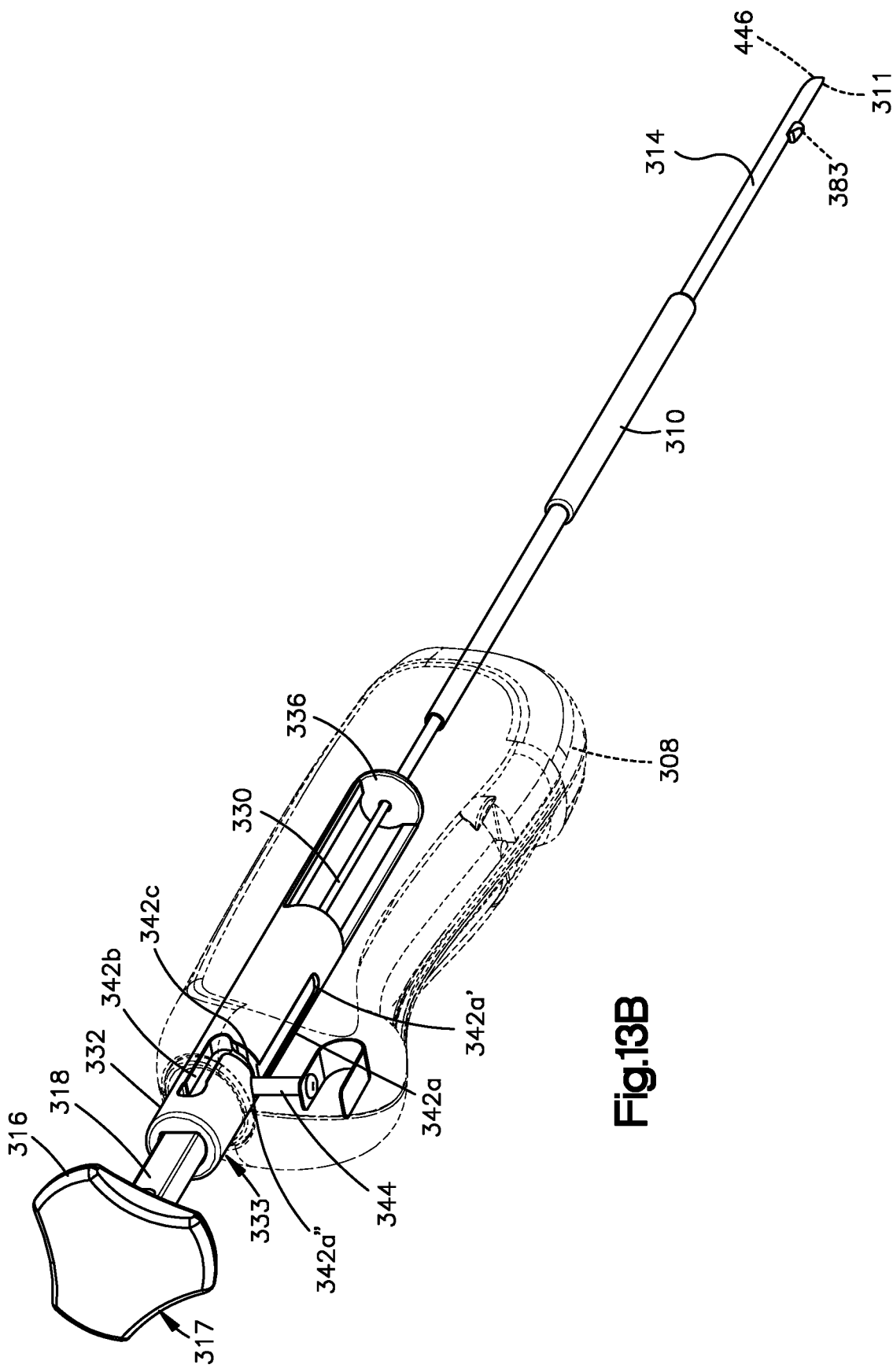
FIG. 13B is a perspective view of the insertion instrument illustrated in FIG. 8A, showing the guide system when the instrument is in the second position.

The first and second guide track portions 342a and 342b extend substantially longitudinally, such that distal translation of the collar 332 relative to the casing 308 during the first stroke causes the guide pin 344 and the guide track 342 to translate relative to each other. In accordance with the illustrated embodiment as shown in FIGS. 13A-B, the guide track 342 translates distally with respect to the guide pin 344, thereby causing the guide pin 344 to translate proximally along the first guide track portion 342a during the first stroke of the plunger 316 and the collar 332. Once the first stroke is completed, and the second anchor body 28b has been ejected from the cannula 310, the guide pin 344 is disposed at the proximal end 342a" of the first track portion 342a. The collar 332 defines a stop member at the proximal end of the first track portion 342a. Thus, the guide pin 344 interferes with the collar 332, thereby preventing the plunger 316 and collar 332 from further translating distally relative to the casing 308. Accordingly, the user is prevented from inadvertently ejecting the first anchor body 308a by continued distal translation of the plunger 316 after the second anchor body 28b has been ejected.

It should be appreciated during the first stroke that the guide pin 344 translates from the distal position 342a' (illustrated in FIG. 13A), past the offset position 342a''' (illustrated in FIG. 13C), to the proximal end 342a" (illustrated in FIG. 13B). When the guide pin 344 is at the offset position 342a''', the push tube 344 is slightly recessed proximally with respect to the distal ejection port 442 (see FIG. 9D). As the guide pin 344 moves to the proximal end 342a'', the push tube 344 translates distally with respect to the ejection port 442 (see FIG. 8D). As further illustrated in FIGS. 8A and 9A, the insertion instrument 300 includes a spring member 365, which can be a coil spring, that extends between a spring seat 381 that is secured to the casing 308, for instance at the distal wall 326 of the casing 308, and the force transfer member 336. Thus, the spring member 365 is operably coupled between the casing 308 and the second pusher assembly 333. When the second pusher assembly 333 is coupled to the first pusher assembly 317 with respect to translation, the spring member 365 is operably coupled between the casing 308 and the first pusher assembly 317.

The spring member 365 provides a force that biases the collar 332, and thus the plunger 316, proximally as the plunger 316 translates distally along the first stroke. Accordingly, referring to FIGS. 13B-C, once the guide pin 344 is in the second position at the proximal end 342a'' of the first track portion 342a, the spring force biases the collar 332 to move such that the guide pin 344 translates distally from the proximal end 342a'' of the first track portion 342a toward the distal end 342a' of the first track portion 342a. However, as is described in more detail below, the track 342 includes a base 341 that interferes with movement of the guide pin 344 along a distal direction from the offset position 342a''. When the guide pin 344 is in the offset position 342a''', the plug 314 of the push tube 334 is recessed proximally with respect to, or substantially aligned with, the distal ejection port 442 (see FIG. 9D) such that the plug 314 does not extend distally beyond the distal ejection port 442.

Figure 13D:
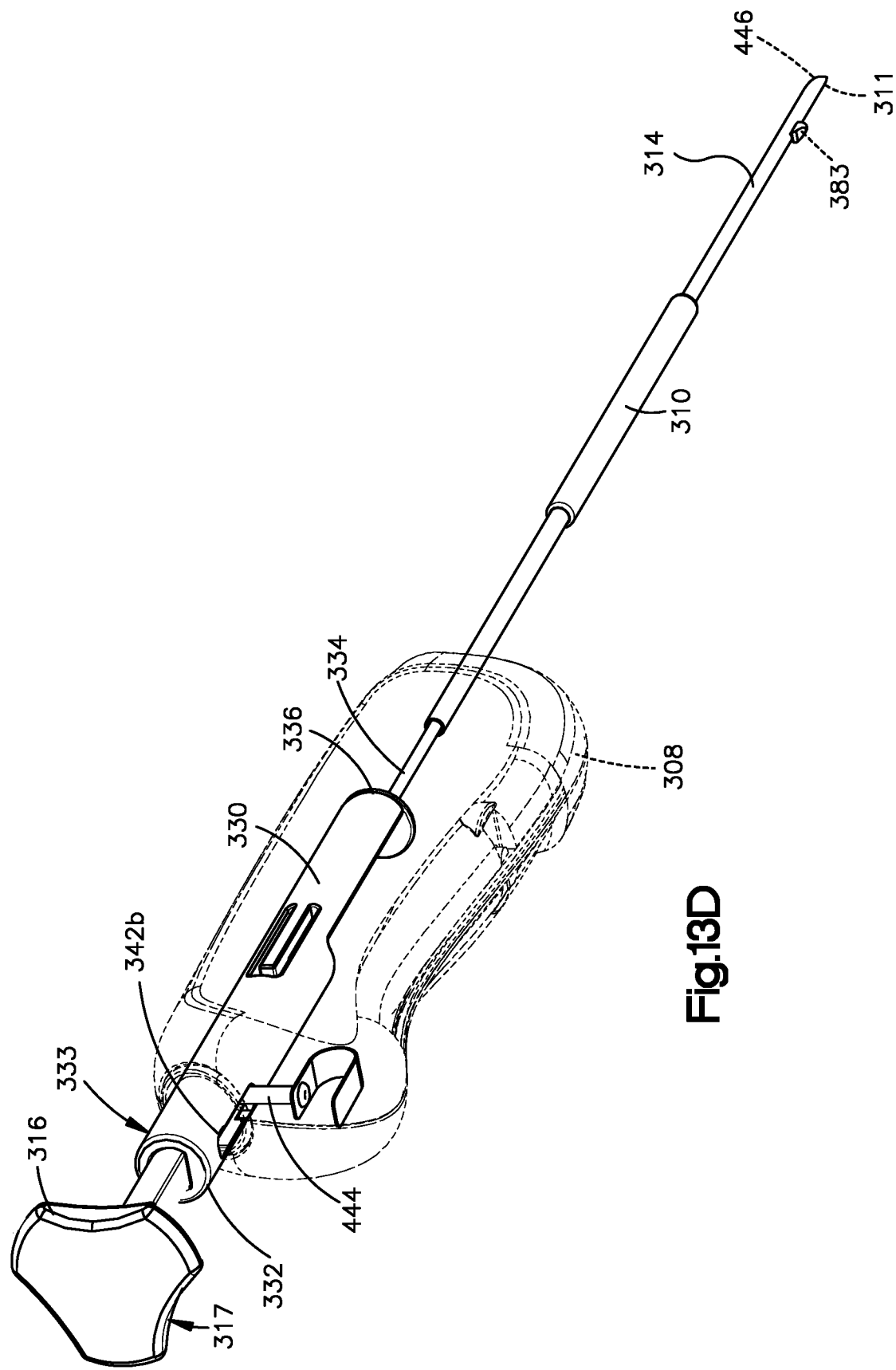
FIG. 13D is a perspective view of the insertion instrument illustrated in FIG. 10A, with portions removed so as to illustrate the guide system when the insertion instrument is in the intermediate position.
Figure 13E:
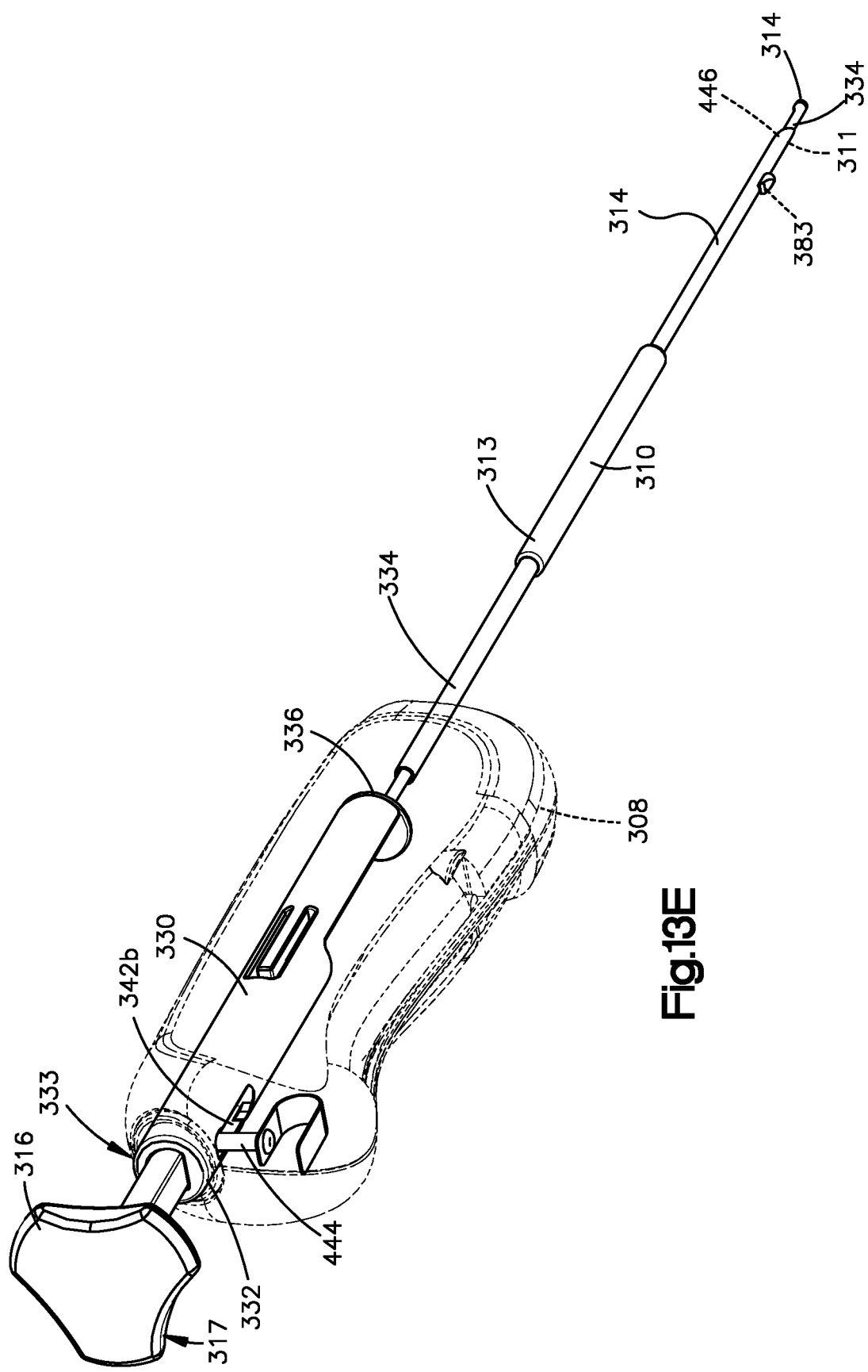
FIG. 13E is a perspective view of the insertion instrument illustrated in FIG. 11A, with portions removed so as to illustrate the guide system when the insertion instrument has completed the first portion of the second stroke.

Referring now to FIGS. 13C-D, the plunger 316 can be rotated along the direction of Arrow A as it travels along the intermediate stroke. The insertion instrument 300 defines a key 318 that rotatably couples the plunger 316 and the collar 332. In accordance with the illustrated embodiment, the key 318 is provided as complementary flat surfaces of the plunger 316 and the collar 332 that prevents defines the plunger 316 from rotating with respect to the collar 332. As a result, rotation of the plunger 316 along the direction of Arrow A causes the collar 332 to likewise rotate along the direction of Arrow A. Accordingly, upon completion of the first stroke, rotation of the plunger 316 causes the guide pin 344 to travel along the intermediate stroke from the first track portion 342a, along intermediate track portion 342c, and to the distal end of the second track portion 342b. Referring now to FIGS. 13D-E, once the guide pin 344 is disposed in the second track portion 342b, further translation of the plunger 316 and the collar 332 along a first portion of the second stroke causes the guide pin 344 to translate distally relative to the casing 308 until the guide pin 344 has traveled to the proximal end of the second track portion 342b. The collar 332 defines a stop member at the proximal end of the second track portion 342b that prevents the collar 332 from continuing to move distally with respect to the casing 308. It can be said that the collar 332 defines a stop member at the terminal ends of the first and second track portions 342a and 342b.

Figure 13F:
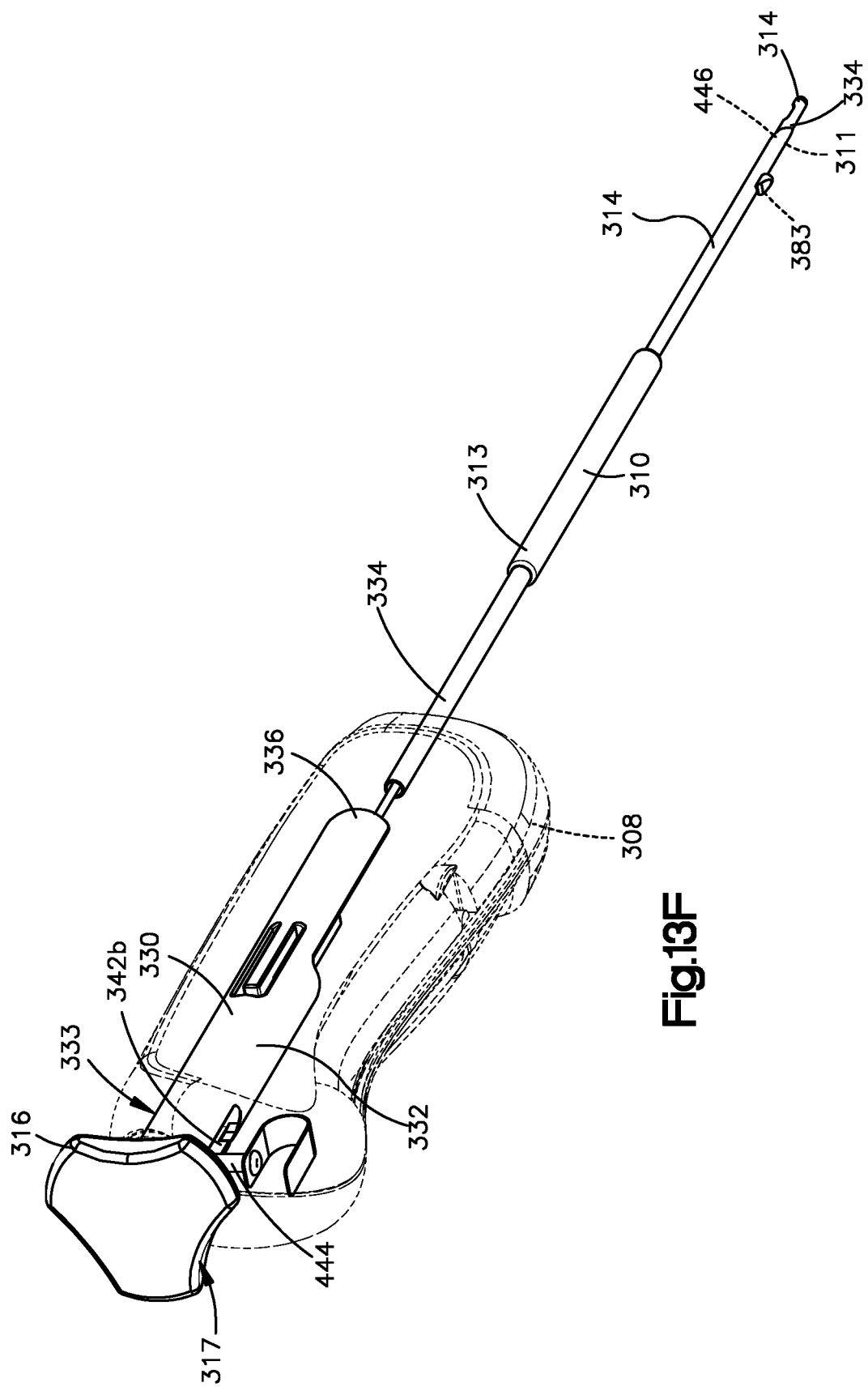
FIG. 13F is a perspective view of the insertion instrument illustrated in FIG. 12A, with portions removed so as to illustrate the guide system when the insertion instrument has completed the second portion of the second stroke.
Figure 16E:
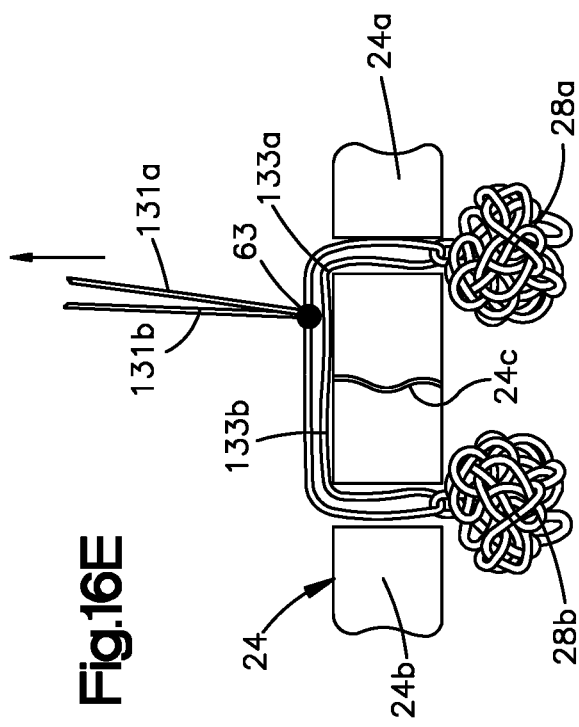
FIG. 16E is a schematic side elevation view of the anchor assembly as illustrated in FIG. 16D, showing locking of the locking member.
Figure 16F:
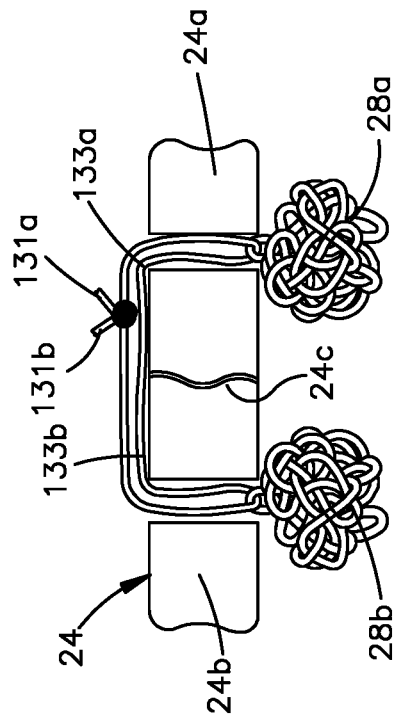
FIG. 16F is a schematic side elevation view of the anchor assembly as illustrated in FIG. 16E, show in a final assembled configuration.

Referring now to FIGS. 13E-F, and as is described in more detail below, once the guide pin 344 has traveled to the proximal end of the second track portion 342b, further distal translation of the plunger 316 along a second portion of the second stroke is decoupled from the collar 332, such that the plunger 316 and push rod 330 translate relative to the collar 332, the push tube 334, and the casing 308. The plunger 316 is configured to translate distally relative to the collar 332 and casing 308 during the second portion of the second stroke until the distal end 316c of the plunger abuts the casing 308, for instance at the proximal wall 324, thereby completing the second stroke and ejecting the second anchor body 28b out the cannula, as illustrated in FIGS. 12A-C.

Referring now to FIG. 13G in particular, the base 341 of the track 342 defines a first base portion 341a at the first track portion 342a, a second base portion 341b at the second track portion 342b, and an intermediate base portion 341c at the intermediate track portion 342c. The base 341 has portions that are deeper than others such that as the guide pin 344 rides along the track, at least one or both of audible and tactile feedback can be detected by the user to indicate that the collar 332, and in some instances the plunger 316, have completed a stroke or a portion of a stroke. The base 341 can further provide a stop that prevents the guide pin 344 from moving proximally along portions of the track 342. For instance, the first base portion 341a defines a first or distal first base portion 341a' and a second or proximal first base portion 341a'' that is deeper than the distal first base portion 341a'. The first base portion 341a defines an edge 346a that is disposed between the proximal first base portion 341a' and the distal first base portion 341a''. The edge 346a can extend radially, or along a direction having a radial component that extends toward the longitudinal axis 302.

The guide pin 344 can define a post 344a and a spring member 345 that is connected between the casing 308 and the post 344a, and biases the post 344a into the track 342 and against the base 341. Thus, as the guide pin 344 moves proximally relative to the first track portion 342a when the collar 332 and the plunger 316 move along the first stroke, the distal portion 344b of the guide pin 344 moves along the distal first base portion 341a' and over the edge 346a as the guide pin 344 travels to the distal first base portion 341a''. As the guide pin 344 travels over the edge 346a and is biased against the track 341 by a spring force of the spring member 345, at least one of a tactile and an audible feedback can be communicated to the user that the plunger 316 and the collar 332 have completed the first stroke. The edge 346a can be disposed at the offset position 342a''' of the first track portion, such that once the guide pin 344 has traveled along the first base portion 341a to the proximal end 342a'' of the first track portion 342a, the edge 346a prevents the force of the spring member 365 from causing the guide pin 344 to translate proximal with respect to the offset position 342a''' of the first track portion 342a. Rather, because the guide pin 344 abuts the edge 346a, the biasing force of the spring member 365 brings the guide pin 344 into alignment with the intermediate track portion 342c, and in position to be moved or rotated along the intermediate stroke.

With continuing reference to FIG. 13G, the intermediate base portion 341c defines a first or proximal intermediate base portion 341c' and a second or distal intermediate base portion 341c'' that is deeper than the proximal intermediate base portion 341c'. The distal intermediate base portion 341c'' can be aligned with the second base portion 341b. The intermediate base portion 341c defines an edge 346c that is disposed between the proximal intermediate base portion 341a' and the distal intermediate base portion 341a''. Alternatively, the intermediate base portion 341c can be devoid of the distal portion, such that the edge 346c is disposed between the intermediate base portion 341c and the second base portion 341b. The edge 346c can extend radially, or along a direction having a radial component that extends toward the longitudinal axis 302. As the distal portion 344b of the guide pin 344 travels over the edge 346c during a transition between the intermediate stroke and the second stroke, and is aligned with the second track portion 342b, at least one of a tactile and an audible feedback can be communicated to the user that the plunger 316 and the collar 332 have completed the intermediate stroke, and are in position to be moved along the first portion of the second stroke. Furthermore, the edge 346c prevents the plunger 316 from being rotated along a direction opposite the direction of Arrow A (FIG. 13C) once the guide pin 344 is positioned in the second track portion 342b.

The second base portion 341b defines a first or proximal second base portion 341b' and a second or distal second base portion 341b" that is deeper than the proximal second base portion 341b'. The distal second base portion 341b" can be disposed at the terminal distal end of the second track portion 342b. The second base portion 341b defines an edge 346b that is disposed between the proximal second base portion 341b' and the distal second base portion 341b". The edge 346b can extend radially, or along a direction having a radial component that extends toward the longitudinal axis 302. As the distal portion 344b of the guide pin 344 travels over the edge 346b, at least one of a tactile and an audible feedback can be communicated to the user that the plunger 316 and the collar 332 have completed the first portion of the second stroke. The feedback can indicate that the plunger 316 is decoupled from the collar 332, and can translate along the second portion of the second stroke independent of the collar 332, as will now be described. Furthermore, the edge 346b prevents the guide pin 344 from moving proximally along the second track portion 342b once the plunger 316 and the collar 332 have been decoupled.

Referring now to FIG. 7C and FIGS. 14A-D, the insertion instrument 300 includes a coupling assembly 350 that is configured to iterate between a first mode of operation and a second mode of operation. In the first mode of operation, the coupling assembly 350 translatably fixes the first pusher member, illustrated as the push rod 330, and the second pusher member, illustrated as the push tube 334 with respect to translation during the first stroke. In the first mode of operation, the coupling assembly 350 releasably translatably fixes the push rod 330 to the push tube 334, such that in a second mode of operation, the coupling assembly 350 decouples the push rod 330 from the push tube 334 such that the push rod 330 can translate distally relative to the push tube 334 after the first stroke, for instance during the second stroke. Furthermore, in the second mode of operation, the coupling assembly 350 can translatably fix the push tube 334 to the casing 308, such that a distal translation force applied to the plunger 316 causes the plunger 316, and thus the push rod 330, to translate distally relative to the push tube 334, and thus the collar 332. In accordance with the illustrated embodiment, the coupling assembly 350 is in the first mode of operation during the first stroke of the first pusher assembly 317, the intermediate stroke of the first pusher assembly 317, and the first portion of the second stroke of the first pusher assembly 317. In accordance with the illustrated embodiment, the coupling assembly 350 transitions to the second mode of operation, as the first pusher assembly 317 transitions between the first portion of the second stroke and the second portion of the second stroke. In accordance with the illustrated embodiment, the coupling assembly 350 is in the second mode of operation when the first pusher assembly 317 translates along the second portion of the second stroke and the second portion of the second stroke.

The coupling assembly 350 can include at least one first coupling member 352 illustrated as a first recess 354 that extends radially into the first pusher assembly 317, such as the plunger 316, in accordance with the illustrated embodiment. The coupling assembly 350 can further include at least one second coupling member 356 illustrated as a channel 358, that extends radially through the second pusher assembly 333, such as the collar 332, in accordance with the illustrated embodiment. The coupling assembly 350 can further include at least one third coupling member 360 illustrated as a second recess 362 that is carried by the casing 308. For instance, the insertion instrument 300 can include an inner housing 325 that is carried by the casing 308, for instance by the proximal wall 324 of the casing 308. The second recess 362 extends radially outward into the inner housing 325 in accordance with the illustrated embodiment. Alternatively, the second recess 362 could extend radially outward into the casing 308.

Furthermore, in accordance with the illustrated embodiment, the second recess 362 is disposed distal with respect to the channel 358 when the plunger 316 is in the first position illustrated in FIGS. 7C and 14B. The second recess 362 can further be radially offset with respect to the channel 358 when the plunger 316 is in the first position illustrated in FIGS. 7A and 13A. Alternatively, the second recess 362 can be radially aligned with respect to the second recess 362 (for instance if the track 342 does not include the intermediate track portion 342c, and can alternatively still be annular so as to circumscribe the radially inner surface of the casing 308 if desired.

The coupling assembly 350 can further include at least one fourth coupling member 368 illustrated as a latch 370 that is sized to partially fit in each of the first recess 354, the second recess 362. In accordance with the illustrated embodiment, the latch 370 is carried by the collar 332, and is configured as a leaf spring 371 that is disposed in the channel 358, which can be provided as a substantially U-shaped aperture or cut-out of the collar 332 so as to define the leaf spring 371. The leaf spring 371 carries a radially inward projection 373 that is sized to fit into the first recess of the plunger 316. The latch 370 can be further sized to be disposed in the channel 358, and is flexible radially inward and outward. Accordingly, the latch 370 can travel along the channel 358 between the first recess 354 (FIG. 14B) and the second recess 362 (FIG. 14D).

In accordance with the illustrated embodiment, the coupling assembly 350 is in the first mode of operation when the guide pin 344 is in the first track portion 342a, and remains in the first mode of operation when the guide pin 344 travels from the first track portion 342a to the intermediate track portion 342c, and further remains in the first mode of operation when the guide pin 344 travels along part of the second track portion 342b. In particular, the first recess 354 and the channel 358, and the projection 371 of the latch 370, can be positioned so as to be radially aligned when the guide pin 344 extends into the any of, and all of as illustrated, the first track portion 342a, the intermediate track portion 342c, and the portion of the second track portion 342b.

Accordingly, in the first mode of operation, the latch 370 is partially disposed in the first recess 354 of the plunger 316, and extends into the channel 358 of the collar 332. The latch projection 373 can be sized so as to be captured in the first recess 354, so as to couple the plunger 316 to the collar 332 with respect to translational movement. As a result, when the latch 370 is coupled to the plunger 316, the plunger 316 and the collar 332, and thus the first and second pusher assemblies 317 and 333, are coupled with respect to movement or translation along the longitudinal direction.

Referring now to FIGS. 14C-D, because the second recess 362 is sized to receive the latch 370 in accordance with the illustrated embodiment, when the latch 370 moves from the first recess 354 into the second recess 362, the latch 370 decouples the first pusher assembly 317 from the second pusher assembly 333, and couples the second pusher assembly 333, and in particular the collar 332, to the casing 308 with respect to at least translation and can also couple the collar 332 to the casing 308 with respect to rotation. As described above, the casing 308 is fixed to the cannula 310 with respect to at least translation, and can further be fixed to the cannula 310 with respect to translation. In accordance with the illustrated embodiment, when the plunger 316 is rotated from the second position to the intermediate position such that the guide pin 344 travels along the intermediate track portion 342*c* (see FIGS. 13C-D), the first recess 354 and the channel 358 are brought into longitudinal alignment with the second recess 362.

During the first portion of the second stroke (see FIG. 13E), the plunger 316 and the collar 332 translate longitudinally until the first recess 354 and the channel 358 are aligned with the second recess 362 of the casing 308. During the transition between the first and second portions of the second stroke (see also FIG. 13F), the latch 370 is driven (for instance cams) out of the first recess 352 and thus moves from the first recess 352 into the second recess 362, as illustrated in FIGS. 14C-D. In accordance with an alternative embodiment, the plunger 316 can include a spring member that biases the latch 370 radially outward from the first recess 352 and into the second recess 362. Alternatively still, the insertion instrument 300 can be configured such that the latch 370 can cam out of the first recess 352 and move from the first recess into the second recess 362 the as the plunger 316 and the collar 332 rotate past the second recess 362 of the casing 308. Once the latch 370 has moved out of the first recess 354 and into the second recess 362 while remaining attached to the collar 332, the plunger 316 can continue to translate distally relative to the collar 332 during the second portion of the second stroke (see FIG. 13F), which causes the push rod 330 to translate distally relative to the push tube 334.

Operation of the insertion instrument 300 will now be described with initial reference to FIGS. 7A-D, 13A, and FIGS. 14A-D. In particular, the insertion instrument 300 can be constructed such that when the plunger 316, and thus the push rod 330, is in the first position, the first and second anchor bodies 28*a* and 28*b* are disposed in the cannula 310. In accordance with the illustrated embodiment, the first anchor body 28*a* is disposed longitudinally between the ejection port 442 and the plug 314 of the push tube 334. When the first pusher assembly 317, including the plunger 316 and the push rod 330, and the second pusher assembly 333, including the collar 332 and the push tube 334, are in the first position, the coupling assembly releasably couples the first pusher assembly 317 and the second pusher assembly 333 with respect to longitudinal movement and rotational movement. In particular, the latch 370 extends in both the first recess 354 and the channel 358, thereby releasably coupling the plunger 316 and the collar 332 with respect to longitudinal movement and rotational movement.

Referring now to FIGS. 8A-D, 13A-B, and 14B in particular, the tip 311 can be injected into the anatomical structure 24, for instance at the second target anatomical location 24*b*, until at least a portion (such as a distal portion) of the ejection port 442 extends distal of, or behind, the anatomical structure 24. In accordance with the illustrated embodiment, the insertion instrument can include a depth stop 383 that extends radially out from the cannula 310, and is configured to abut the anatomical structure 24 and provides resistance to further insertion of the cannula 310 into the anatomical structure 24 once the cannula 310 has been injected to a desired depth, for instance such that the ejection port 442 is disposed behind the anatomical structure 24. In this regard, the depth stop 383 can provide tactile feedback to the user that the cannula 310 has been injected into the target structure 24 at the desired depth. When a distal force is applied to the plunger 316 while the casing 308 remains stationary, for instance when a user grips the casing 308 relatively stationary while applying a distal force to the plunger 316, the first and second pusher assemblies 317 and 333 translate distally with respect to the casing 308 along the first stroke. As the first and second pusher assemblies 317 and 333 travel distally relative to the casing 308, the guide pin 344 travels proximally along the first track portion 342*a* of the collar 332 until the guide pin 344 reaches the proximal end 342*a*" of the first track portion 342*a*. As the second pusher assembly 333 travels distally, the plug 314 biases the second anchor body 28*a* to translate distally toward the tip 311. Furthermore, because the first pusher assembly 317 translates distally with the second pusher assembly 333 relative to the casing 308, and thus also the cannula 310, the pusher rod 330 biases the first anchor body 28*b* downstream toward the tip 311 during the first stroke.

Once the guide pin 344 has reached the proximal end 342*a*" of the first guide track portion 342*a*, the plug 314 has translated distal with respect to the proximal end of the ejection port 442, and thus has biased the second anchor body 28*b* out the ejection port 442 to a location behind the anatomical structure 24, for instance at the second target anatomical location 24*b* (see FIG. 1A) along the direction of Arrow B. Thus, the first track portion 342*a* has a longitudinal length sufficient such that movement of the guide pin 344 along the first track portion 342*a* causes the push tube 334 to eject the second anchor body 28*b* from the insertion instrument 300. Once the plunger 316 and the collar 332 have completed the first stroke, the plug 314 can be spaced proximally from the tip 311. It should be appreciated that the collar 332 defines a stop at the proximal end 342*a*" of the first track portion 342*a* that prevents further distal translation of the collar 332, and thus of the push tube 334 and the push rod 330, before the latch 370 is coupled to the casing 308, as described above with respect to FIG. 14C.

Next, referring to FIGS. 9A-D, once the second anchor body 28*b* has been ejected out the insertion instrument 300, the distal force can be removed from the plunger 316, which causes the spring member 365 to bias the second pusher assembly 333, for instance the collar 332, and thus also the first pusher assembly 317, proximally until the guide pin 344 is aligned with the offset position 342*a*'" of the first track portion 342*a*, as described above. Once the guide pin is in the offset position 342*a*'", the guide pin 344 is aligned with the intermediate track portion 342*c*, and the plunger 316 can be rotated to the second track portion 342*b*.

At any time after completion of the first stroke and prior to ejection of the first anchor body 28*a*, the second anchor body 28*b* can be actuated to the expanded configuration illustrated in FIG. 1B. For instance, referring to FIG. 9E, the second anchor body 28*b* can be actuated by removing the insertion instrument from the target anatomy 24. As illustrated at FIG. 9B, and as described in more detail below with respect to, the insertion instrument 300 includes a strand retention assembly 390 that retains, for instance releaseably retains, at least one tensioning strand 380 that is operably coupled to the actuation portions 131*a* and 131*b* of the first and second anchor bodies 28*a* and 28*b*, extends proximally into the interior 328 of the casing 308 and is releasably connected to the retention assembly 390. The at least one tensioning strand 380 can be sized and positioned along the actuation strand 131 such that when tension is applied to the tensioning strand 380, for instance when removing the insertion instrument 300 proximally out of the anatomical structure 24, and in some embodiments translating the insertion instrument 310 further proximally after removal from the anatomical structure 24, the tensioning strand 380 communicates the tension to the actuation strand 131b, thereby actuating the second anchor body 28b to its expanded configuration. Alternatively still, a user can manually apply the actuation force to the respective actuation portion 131b as desired. The insertion instrument 300 can further define an elongate side slot 315 that extends through one radial side of the cannula 310 at a location proximal with respect to the ejection port 442. For instance, the slot 315 can extend from the ejection port 442 and proximally a sufficient distance and sized sufficiently such that the actuation portions 131a-b and attachment portions 133 can extends through the slot 315 and attach to the tensioning strand 380, which extends proximally into the casing 308. Alternatively, the at least one tensioning strand 380 can be attached to the actuation portions 131a-b inside the cannula 310, and can extend out the slot 315. Thus, the slot 315 can define a circumferential width that is greater than the thickness of the actuation strands 38a-b and the at least one tensioning strand 380, but less than the thickness of the anchor bodies 28a and 28b when the anchor bodies 28a and 28b are in their respective first configurations inside the cannula 310.

Referring now to FIGS. 10A-D, 13C-D, and FIGS. 14A-D, once the second anchor body 28b has been ejected and the guide pin 344 is at the offset position 342a''' of the first track portion 342a, and the insertion instrument 300 has been removed from the anatomical structure 24, the tip 311 of the insertion instrument 300 can be injected into the anatomical structure 24 at the first target anatomical location 24a in the manner described above with respect to the second target anatomical location 24b. The plunger 316 can be rotated along the direction of Arrow A before or after the tip 311 has been injected at the first target anatomical location 24a so as to travel along the intermediate stroke, which causes the guide pin 344 to translate along the intermediate track portion 342c toward the second track portion 342b. The plunger 316 can be rotated along the direction of Arrow A until the plunger 316 is in the intermediate position, whereby the guide pin 344 is longitudinally aligned with the second track portion 342b. Once the plunger 316 and collar 332 have rotated to the intermediate position, the plunger 316 and the collar 332 are again able to translate distally with respect to the casing 308, and the latch 370 is longitudinally aligned with the second recess 362.

Referring now to FIGS. 11A-D, 13D-E, and 14D, if the insertion instrument 300 was not injected into the first target anatomical location 24a prior to driving the plunger 316 to travel along the intermediate stroke, the insertion instrument 300 can be injected into the first target anatomical location 24a after driving the plunger 316 to travel along the intermediate stroke, but before driving the plunger 316 to translate along the second stroke. As the plunger 316 and the collar 332 are further driven distally with respect to the casing 308, the first and second pusher assemblies 317 and 333 translate distally with respect to the casing 308 along a first portion of the second stroke. Translation of the plunger 316 along the first portion of the second stroke causes the guide pin 344 to translate proximally from the intermediate portion to a location between the proximal and distal ends of the second track portion 342b.

As the plunger 316 translates distally with respect to the casing 308, the coupling assembly 350 causes the collar 332, and thus the push tube 334 including the plug 314, to correspondingly translate distally with respect to the casing 308 and cannula 310 until the first recess 354 becomes radially aligned with the second recess 362. Thus, it can be said that movement of the guide pin 344 along the second track portion 342b causes the latch 370 to move in alignment with the second recess 362. The second recess 362 can be positioned such that the latch 370 is radially aligned with the second recess 362 once the plug 314 has translated to a position distal with respect to the tip 311, and thus distal with respect to the ejection port 442, which can occur once the plunger 316 has translated along the first portion of the second stroke. Because the plug 314 has translated distal to the ejection port 442, the plug 314 is removed from interference with the first anchor body 28a as the first anchor body 28a is ejected out the cannula 310. Furthermore, because the push rod 330 and the push tube 334 translate together along the first portion of the second stroke, the push rod 330 continues to bias the first anchor body 28b downstream in the elongate opening 312 of the cannula 310 toward the tip 311. As the first and second recesses 354 and 362 become radially aligned at the transition between the first and second portions of the second stroke, the latch 370 is driven from the first recess 354 into the second recess 362.

Referring now to FIGS. 12A-D, 13E-F, and 14D, once the latch 370 is disposed in second recess 352, the second pusher assembly 333 becomes coupled to the casing 308 with respect to translation. Because the latch 370 is removed from the first recess 354, the first pusher assembly 317 is decoupled from the second pusher assembly 333 with respect to translation. Accordingly, the first pusher assembly 317 can translate with respect to the second pusher assembly 333 and the casing 308, and thus also with respect to the cannula 310. Thus, it can be said that the latch 370 moves into the second recess 362 so as to translatably decouple the push rod 330 and the push tube 334, such that the push rod 330 is translatable independently of the push tube 344 so as to eject the first anchor body 28a from the insertion instrument 330.

In accordance with the illustrated embodiment, as the first pusher assembly 317 is further biased distally with respect to the second pusher assembly 333 during the second portion of the second stroke, the plunger 316 and the push rod 330 translate distally with respect to the casing 308, and thus also the cannula 310. As a result, the push rod 330, for instance at its distal end, biases the second anchor body 28b to move distally relative to the plug 314. The plug 314 can define a ramp 376 at its proximal end. The ramp 376 can thus be disposed distal of the ejection port 442 and positioned along the longitudinal axis 302, and thus aligned with the first anchor body 28a as the pusher rod 330 translates along the longitudinal direction and ejects the first anchor body 28a out the cannula 310 along the longitudinal direction. The ramp 376 can define a tapered ejection surface 378 that is angled radially outward as it extends distally. Accordingly, as the pusher rod 330 biases the first anchor body 28a to translate distally from the ejection port 442 onto the ejection surface 378 as the pusher rod 330 translates relative to the plug 314, the first anchor body 28a rides along the ejection surface 378, which directs the first anchor body 28a away from the insertion instrument 300 at the first target anatomical location 24a. Thus, the second track portion 342b has a longitudinal length so as to allow the plug 314 to translate to a location distal of the tip 311, such that distal translation of the push rod 330 ejects the first anchor body 28*a* out the insertion instrument.

While the coupling assembly 350 is configured such that the collar 332 moves along the first stroke with the plunger 316, moves along the intermediate stroke with the plunger 316, and moves along a first portion of the second stroke with the plunger 316, it should be appreciated in accordance with alternative embodiments that the coupling assembly 350 can be configured such that the collar 332 translatably decouples from the plunger 316 after or during the first stroke, or after or during the intermediate stroke.

Referring now to FIG. 12E, once the first anchor body 28*a* has been injected to the first target location 24*a* at a location behind the anatomical structure 24, the first anchor body 28*a* can be actuated to its expanded configuration. For instance, the first anchor body 28*a* can be manually expanded by the user applying the actuation force F (FIG. 1A) to the respective actuation portion 131*a*. In accordance with the illustrated embodiment, the actuation strands 38*a* and 38*b* of the first and second anchor bodies 28*a* and 28*b*, respectively, can be a common strand. Accordingly, the actuation portion 131*a* is integral with the actuation portion 131*b*, and proximal translation of the insertion instrument 300, for instance upon removal of the insertion instrument 300 from the anatomical structure 24, can cause the insertion instrument 300 to apply a proximal tensile force onto the tensioning strand 380, which communicates the tensile force to the second anchor body 28*b*, thereby actuating the second anchor body 28 to its expanded configuration.

Referring now to FIGS. 15A-E, the coupling assembly 350 can be constructed in accordance with another embodiment, and can include at least one first coupling member 352 illustrated as a first recess 354 that extends radially into the first pusher assembly 317, such as the plunger 316, in accordance with the illustrated embodiment. The coupling assembly 350 can further include at least one second coupling member 356 illustrated as a channel 358, that extends radially through the second pusher assembly 333, such as the collar 332, in accordance with the illustrated embodiment. The coupling assembly 350 can further include at least one third coupling member 360 illustrated as a second recess 362 (FIG. 15C), that extends radially outward into the casing 308 in accordance with the illustrated embodiment. Furthermore, in accordance with the illustrated embodiment, the second recess 362 is disposed distal with respect to the channel 358 when the plunger 316 is in the first position illustrated in FIGS. 7A and 13A. The second recess 362 can further be radially offset with respect to the channel 358 when the plunger 316 is in the first position illustrated in FIGS. 7A and 13A. Alternatively, the second recess 362 can be radially aligned with respect to the second recess 362 (for instance if the track 342 does not include the intermediate track portion 342*c*, and can alternatively still be annular so as to circumscribe the radially inner surface of the casing 308 if desired.

The coupling assembly 350 can further include at least one fourth coupling member 368 illustrated as a latch 370 that is sized to partially fit in each of the first recess 354, the second recess 362. In accordance with the illustrated embodiment, the latch 370 is substantially spherical, and each of the first recess 354 and the second recess 362 can be substantially partially spherical, though it should be appreciated that the latch 370 and each of the first recess 354 and the second recess 362 can define any suitable shape as desired. The latch 370 can be further sized to be disposed in the channel 358, which can be in the form of a slot that is defined by a longitudinal dimension substantially equal to that of the latch 370, and is further defined by a radial dimension that is substantially equal to that of the latch 370. Accordingly, the latch 370 can travel along the channel 358 between the first recess 354 (FIGS. 15A-B) and the second recess 362 (FIGS. 15D-E).

In accordance with the illustrated embodiment, the coupling assembly 350 is in the first mode of operation when the guide pin 344 is in the first track portion 342*a*, and remains in the first mode of operation when the guide pin 344 travels from the first track portion 342*a* to the intermediate track portion 342*c*, and further remains in the first mode of operation when the guide pin 344 travels along part of the second track portion 342*b*. In particular, the first recess 354 and the channel 358 can be positioned so as to be radially aligned when the guide pin 344 extends into the any of, and all of as illustrated, the first track portion 342*a*, the intermediate track portion 342*c*, and the portion of the second track portion 342*b*. Further, the latch 370 defines a radial dimension substantially equal to that of the first recess 354 and the channel 358 combined, which is substantially equal to that of the channel 358 and the second recess 362, combined. Thus, the radial dimension of the latch 370 is also substantially equal to that of the channel 358 and the second recess 362 combined. It should also therefore be appreciated that the first recess 354 and the second recess 362 can define substantially the same radial dimension.

Accordingly, in the first mode of operation, the latch 370 is partially disposed in the first recess 354 of the plunger 316, and extends into the channel 358 of the collar 332. The latch 370 can be sized so as to be captured between the casing 308 and the plunger 316, and to extend through the collar 332 in the channel 358. Because the first recess 354 is shaped substantially equal to a portion of the latch 370 in the longitudinal and circumferential directions, longitudinal and rotational motion of the plunger 316 correspondingly causes the latch 370 to move longitudinally and rotationally, respectively, along with the plunger 316 when the latch 370 is disposed in the first recess 354. Furthermore, because the channel 358 is dimensioned substantially equal to that of the latch 370 in both the longitudinal and circumferential directions, longitudinal and rotational motion of the latch 370 correspondingly causes the collar 332 to move longitudinally and rotationally, respectively. As a result, when the latch 370 is disposed in the first recess 354 and the channel 358, the plunger 316 and the collar 332, and thus the first and second pusher assemblies 317 and 333, are coupled with respect to movement or translation along the longitudinal direction, and are further coupled with respect to rotation or movement in the radial direction.

Referring now to FIGS. 15C-E, because the second recess 362 is shaped substantially equal to a portion of the latch 370 in accordance with the illustrated embodiment, when the latch 370 moves from the first recess 354 into the second recess 362, the latch 370 decouples the first pusher assembly 317 from the second pusher assembly 333, and couples the second pusher assembly 333, and in particular the collar 332, to the casing 308 with respect to at least translation and can also couple the collar 332 to the casing 308 with respect to rotation. As described above, the casing 308 is fixed to the cannula 310 with respect to at least translation, and can further be fixed to the cannula 310 with respect to translation. In accordance with the illustrated embodiment, when the plunger 316 is rotated from the second position to the intermediate position such that the guide pin 344 travels along the intermediate track portion 342*c* (see FIGS. 13C-

D), the first recess 354 and the channel 358 are brought into longitudinal alignment with the second recess 362.

During the first portion of the second stroke (see FIG. 13E), the plunger 316 and the collar 332 translate longitudinally until the first recess 354 and the channel 358 are aligned with the second recess 362 of the casing 308. During the transition between the first and second portions of the second stroke (see also FIG. 13F), the latch 370 is driven (for instance cams) out of the first recess 352 and thus moves from the first recess 352 into the second recess 362. In accordance with an alternative embodiment, the plunger 316 can include a spring member that biases the latch 370 radially outward from the first recess 352 and into the second recess 362. Alternatively still, the insertion instrument 300 can be configured such that the latch 370 can cam out of the first recess 352 and move from the first recess into the second recess 362 the as the plunger 316 and the collar 332 translate past the second recess 362 of the casing 308. Once the latch 370 has moved out of the first recess 354 and into the second recess 362 while remaining disposed in the channel 358 of the collar 332, the plunger 316 can continue to translate distally relative to the collar 332 during the second portion of the second stroke (see FIG. 13F), which causes the push rod 330 to translate distally relative to the push tube 334.

Referring now to FIGS. 16A-17D, the anchor assembly 20 can include at least one tensioning member, such as a tensioning strand 380 that can be stitched through the first and second actuation strands 38a and 38b, respectively, of the first and second anchor bodies 28a and 28b. The anchor assembly 20 can include as many tensioning strands as desired that extend through one or both of the first and second actuation strands 38a and 38b. The tensioning strand 380 defines a first end 380', a second end 380", and a middle portion 380'" that extends between the first and second ends 380' and 380".

The tensioning strand 380 can be stitched through the first actuation strand of at least one of the anchor bodies 28a and 28b. In accordance with the illustrated embodiment, the tensioning strand 380 is stitched through the first actuation strand, and in particular through the first actuation portion 131a and the first attachment portion 133a of the first anchor body 28a. For instance, the first tensioning stand 380a can be threaded onto a needle, which is driven through the first actuation strand 38a, so as to insert the tensioning strand 380 through the actuation strand 38a, such that the tensioning strand 380 is connected to the actuation strand 38a at a location closer to the first anchor body 28a than the second anchor body 28b.

Referring now to FIGS. 7C and 17A-D the insertion instrument 300 can include a retention assembly, such as a strand retention assembly 390, that is configured to retain the at least one tensioning strand 380, and in particular the first and second ends 380a' and 380" of the tensioning strand 380. In accordance with one embodiment, the retention assembly releasably retains the tensioning strands 380. As will now be described, the retention assembly 390 is translatably fixed to the first pusher assembly 317, and thus moves proximally and distally along the longitudinal direction L along with the plunger 316. Accordingly, the tensioning strand 308 provides sufficient slack for the implantation of the first and second anchor bodies 28a and 28b in the respective target anatomical locations 24a and 24b. After the second anchor body 28b has been ejected from the cannula 310, proximal movement of the insertion instrument 300, for instance when removing the instrument from the anatomical structure 24, causes the retention assembly 390 to move in the proximal direction, thereby applying the tensile actuation force to the second tensioning strand 380, which communicates the actuation force to the second actuation portion 131b of the second actuation strand 38b, and causes the second anchor body 28b to expand. Similarly, after the first anchor body 28a has been ejected from the cannula 310, proximal movement of the insertion instrument 300, for instance when removing the instrument from the anatomical structure 24, causes the retention assembly 390 to move in the proximal direction, thereby applying the tensile actuation force to the tensioning strand 380, which communicates the actuation force to the first actuation portion 131a of the first actuation strand 38a, and causes the first anchor body 28a to expand.

The retention assembly 390 includes a retention housing 392 having a housing body 394 that is supported, directly or indirectly, by the plunger 316 is coupled to the distal end 316a of the plunger 316 in accordance with the illustrated embodiment. The housing body 394 is further coupled to the push rod 330, which extends distally from the retention assembly 390. The retention housing 392 includes a first locking member 400 and a second locking member 402 that extend from opposite, for instance laterally opposite, ends of the housing body 394. The first and second locking members 400 and 402 are configured to retain the respective first and second opposed ends 380' and 380" of the tensioning strand 380. The first locking member 400 is configured to be disengaged so as to release the first end 380'. The second locking member 402 is configured to retain the second end 380" of the tensioning strand 380 when the first locking member 400 is released.

In accordance with the illustrated embodiment, the first locking member 400 includes a locking body 407, and a clip 409 that is configured to be removably secured to the locking body 407. For instance, the clip 409 can be hingeably attached to the locking body 407, or otherwise movably attached to the locking body 407 as desired. The retention housing 392 can define a retention channel 411 disposed between the locking body 407 and the clip 409. The retention channel 411 can have any suitable shape as desired, and defines a serpentine shape in accordance with the illustrated embodiment. When the clip 409 is secured to the locking body 407, the retention channel 411 has a thickness less than that of the first end 380' of the tensioning strand 380. The clip 409 includes an outwardly projecting release tab 413 that is configured to receive a release force so as to release the clip 409 from the locking body 407, thereby freeing the first end 380' of the retention strand 380 from the retention assembly 39, as is described in more detail below.

In accordance with the illustrated embodiment, the second locking member 402 includes a second locking body 415, and a second clip 417 that is configured to be secured to the second locking body 415. The retention housing 392 can define a second retention channel 419 disposed between the second locking body 415 and the second clip 417. The second retention channel 419 can have any suitable shape as desired, and defines a serpentine shape in accordance with the illustrated embodiment. When the second clip 417 is secured to the second locking body 415, the second retention channel 419 has a thickness less than that of the second end 380" of the tensioning strand 380.

Thus, during operation, the first end 380' of the tensioning strand 380 can extend through the first retention channel 411 and the clip 409 can be secured to the locking body 407, thereby releasably locking the first end 380' of the tensioning strand 380 in the first locking member 400. Similarly, the second end 380" of the tensioning strand 380 can extend through the second retention channel 419 and the second clip 417 can be secured to the second locking body 415, thereby releasably locking the second end 380" of the tensioning strand 380 in the second locking member 402. When the first and second ends 380' and 380" are secured to the retention assembly, the insertion instrument can translate proximally once the first and second anchors 28a and 28b have been implanted to thereby deliver the tensile actuation force to the tensioning strand 380, which communicates the tensile actuation force to the respective actuation portions of the anchor bodies, thereby causing the anchor bodies to expand in the manner described above.

The retention assembly 490 further includes an actuator assembly 421 that is configured to release the first locking member 400. In particular, the actuator assembly 421 can include an actuator or button 423 that is carried by the casing 308 (see FIG. 7C), and at least one biasing member, such as a pair of arms 425 that extend into the interior 328 of the casing 308 from the button 423. It is recognized that the first anchor body 28a is ejected from the instrument 300 once the plunger 316 has completed the second stroke. Accordingly, the actuator assembly 421 is positioned such that the arms contact the retention housing 492 once the plunger 316 has reached the end of the second stroke.

Figure 17A:
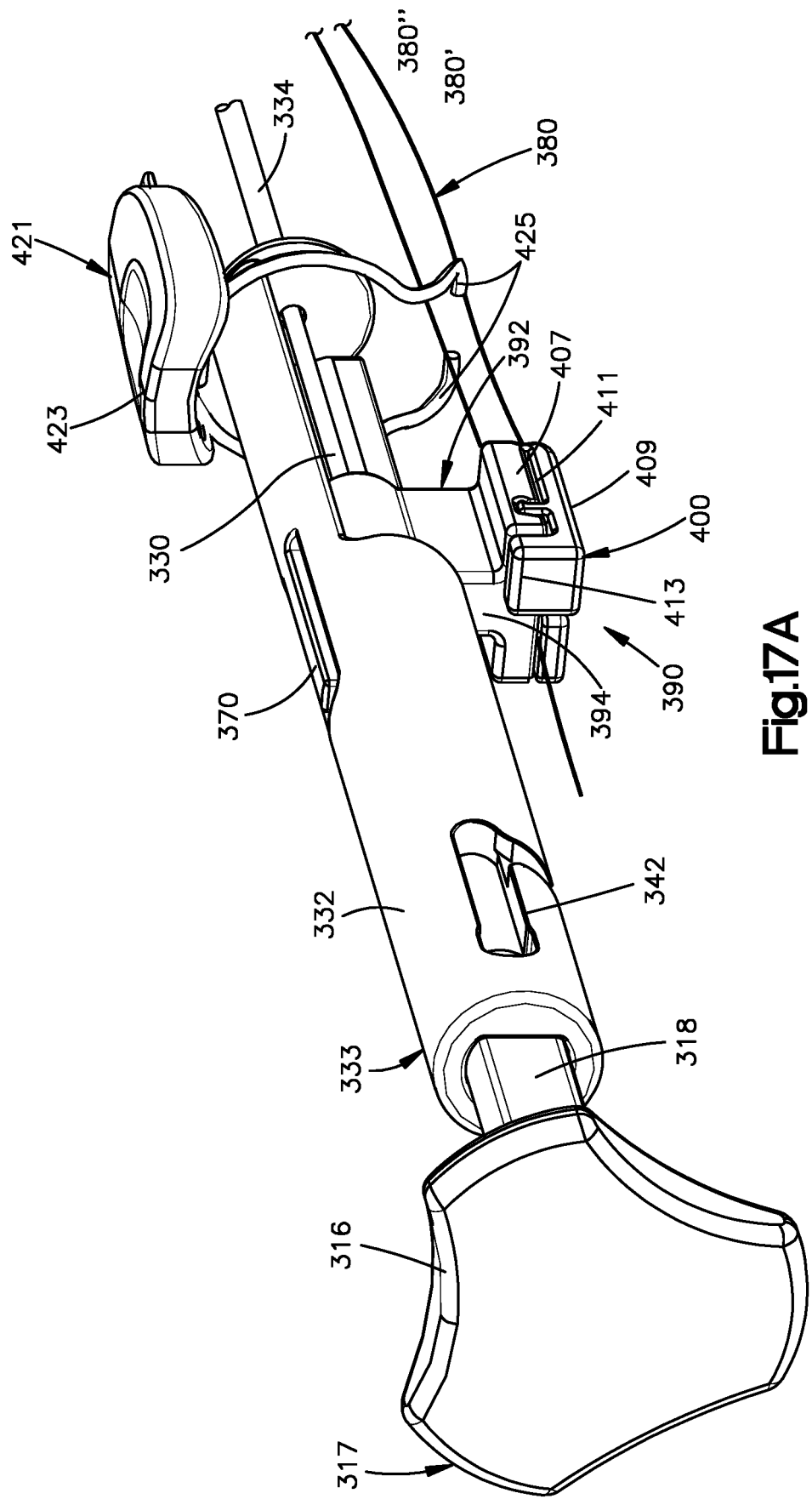
FIG. 17A is a perspective view of a strand retention assembly constructed in accordance with one embodiment, showing a releasable locking member.
Figure 17B:
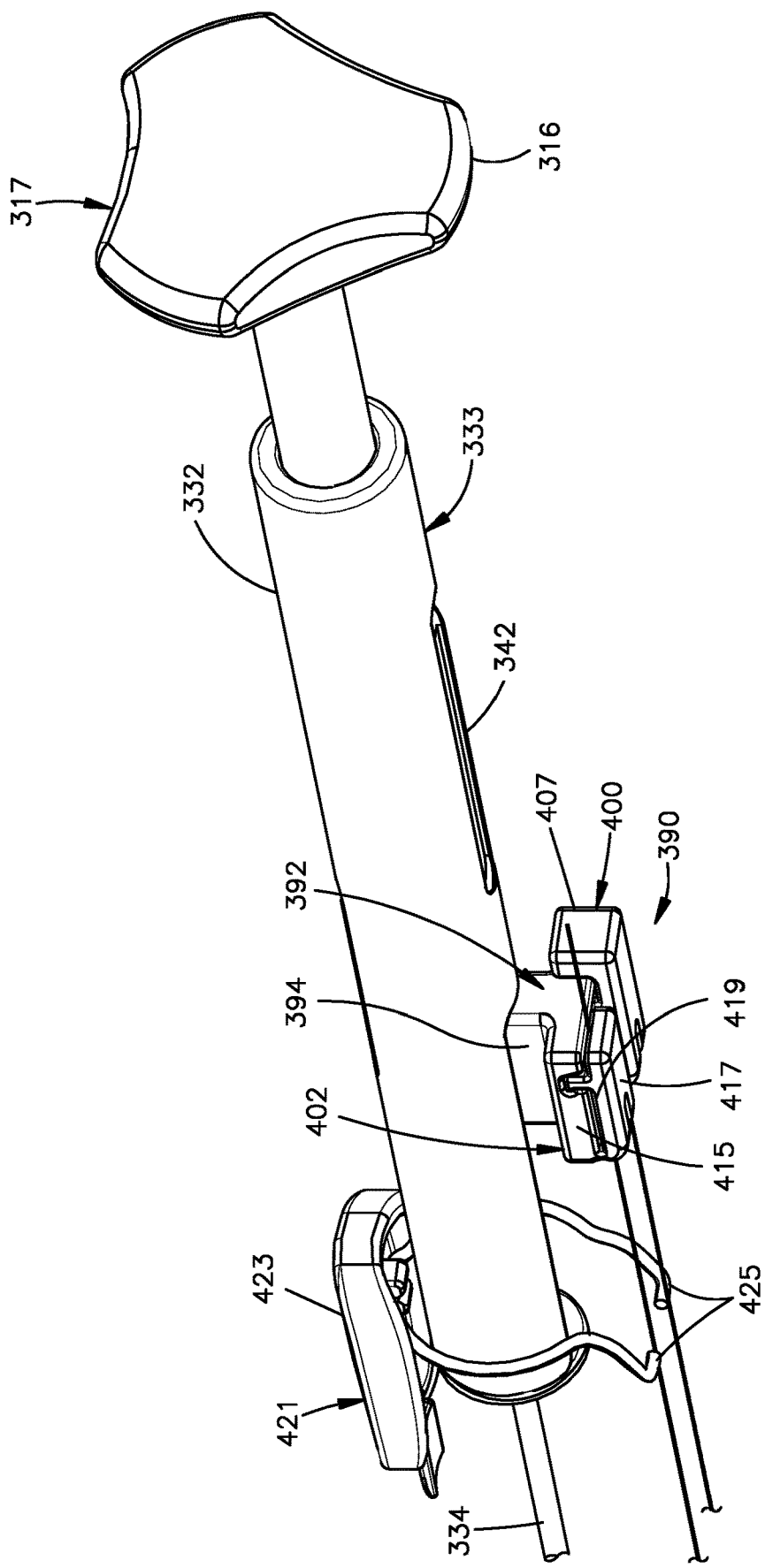
FIG. 17B is a perspective view of the strand retention assembly illustrated in FIG. 17A, showing a fixed locking member.
Figure 17C:
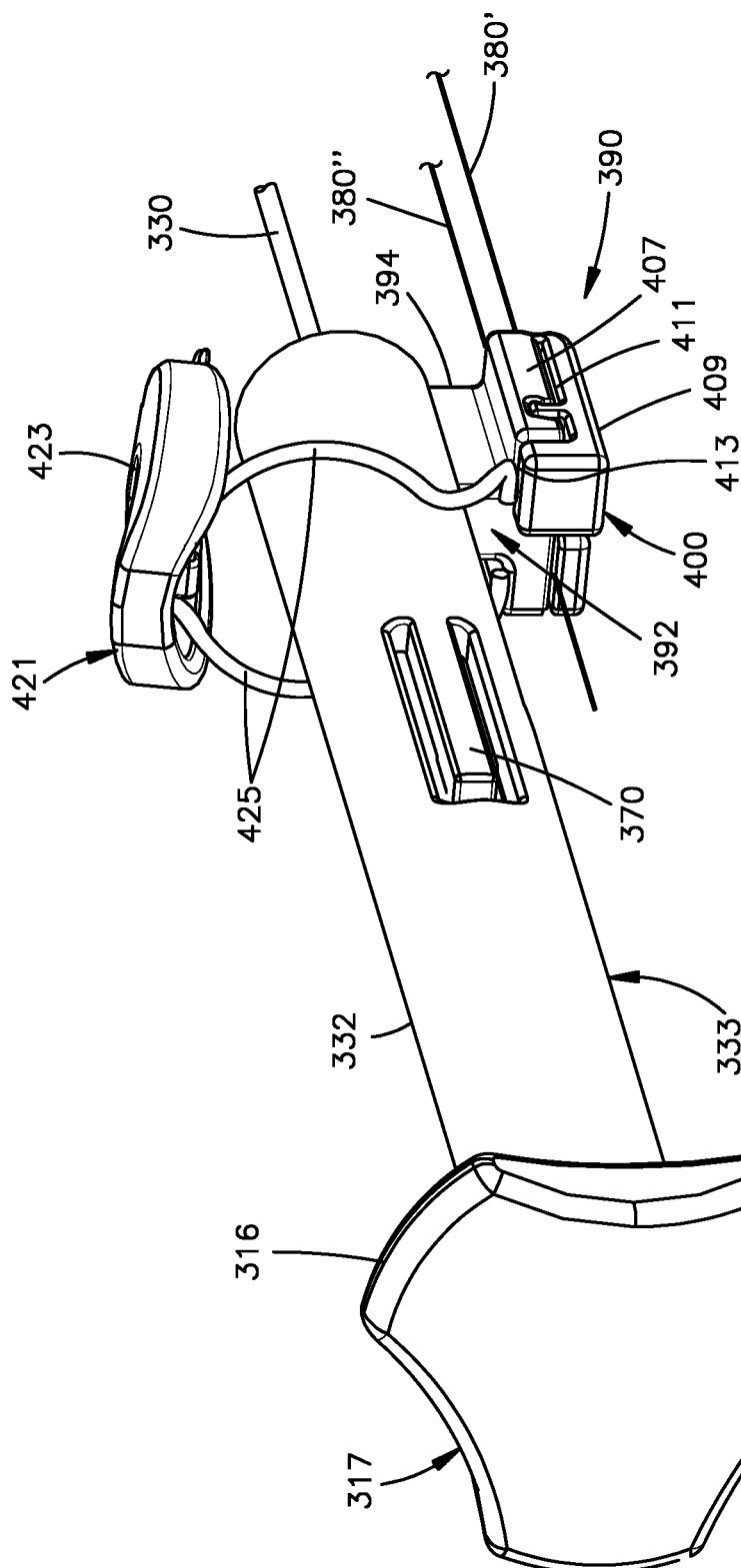
FIG. 17C is a perspective view of the strand retention assembly illustrated in FIG. 17A, operably coupled to an actuator.
Figure 17D:
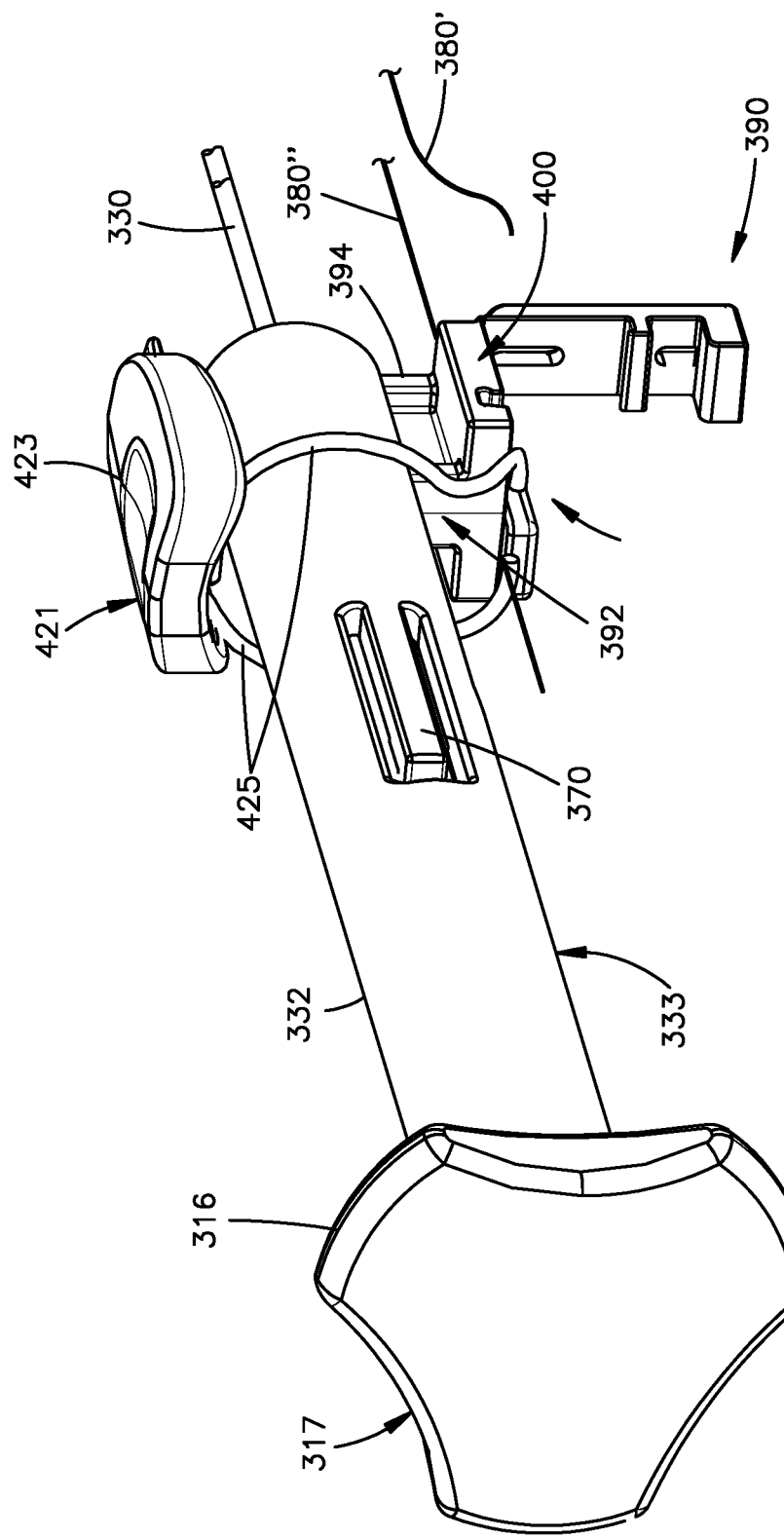
FIG. 17D is a perspective view of the strand retention assembly illustrated in FIG. 17C, shown in a released position.

Referring to FIGS. 12C and 17C, As the plunger 316 reaches the end of the second stroke, the arms 425 ride along outer surfaces of the first and second locking bodies 407 and 415, respectively, which causes the button 423 to raise radially outwardly from an unloaded position to a loaded position. Once the plunger 316 has reached the end of the second stroke, one of the arms is aligned with the release tab 413. Accordingly, the button 423 can be depressed, which causes one of the arms 425 to drive the release tab 413 away from the first locking body 407, which causes the clip 409 to move into an unlocked position whereby the clip 409 is removed from the locking body 407 a sufficient amount such that the retention channel 411 is thicker than the first end 380' of the tensioning strand 380. As a result, the first end 380' becomes unlocked from the retention assembly 390, and the instrument can be moved proximally so as to draw the tensioning strand 380 through the actuation strands of the anchor bodies.

Referring now to FIG. 18A, the anchor assembly 20 can alternatively include a pair of tensioning members, such as a first tensioning strand 380a and a second tensioning strand 380b that can be stitched through the first and second actuation strands 38a and 38b, respectively, of the first and second anchor bodies 28a and 28b. The anchor assembly 20 can include as many tensioning strands as desired that extend through one or both of the first and second actuation strands 38a and 38b. The first tensioning strand 380a defines a first end 380a', a second end 380a", and a middle portion 380a''' that extends between the first and second ends 380a' and 380a". Similarly, the second tensioning strand 380b defines a first end 380b', a second end 380b", and a middle portion 380b''' that extends between the first and second ends 380b' and 380b".

The first tensioning strand 380a can be stitched through the first actuation strand 38a, for instance through opposed ends of the first actuation strand 38a. For instance, the first tensioning stand 380a can be threaded onto a needle, which is driven through the first actuation strand 38a, so as to insert the first tensioning strand 380a through the first actuation strand 38a. The first tensioning strand 380a can extend through the first attachment portion 133a and the first actuation portion 131a of the first actuation strand 38a, and can loop back through the first actuation portion 131a and the first attachment portion 133a, at a location between the first and second anchor bodies 28a and 28b.

Similarly, the second tensioning strand 380b can be stitched through the second actuation strand 38b, for instance through opposed ends of the second actuation strand 380b. For instance, the second tensioning stand 380b can be threaded onto a needle, which is driven through the second actuation strand 38b so as to insert the second tensioning strand 380b through the second actuation strand 38b. The second tensioning strand 380b can extend through the first attachment portion 133b and the actuation portion 131b of the second actuation strand 38b, and can loop back through the second attachment portion 133b and the second actuation portion 131b at a location between the first and second anchor bodies 28a and 28b.

Figure 19A:
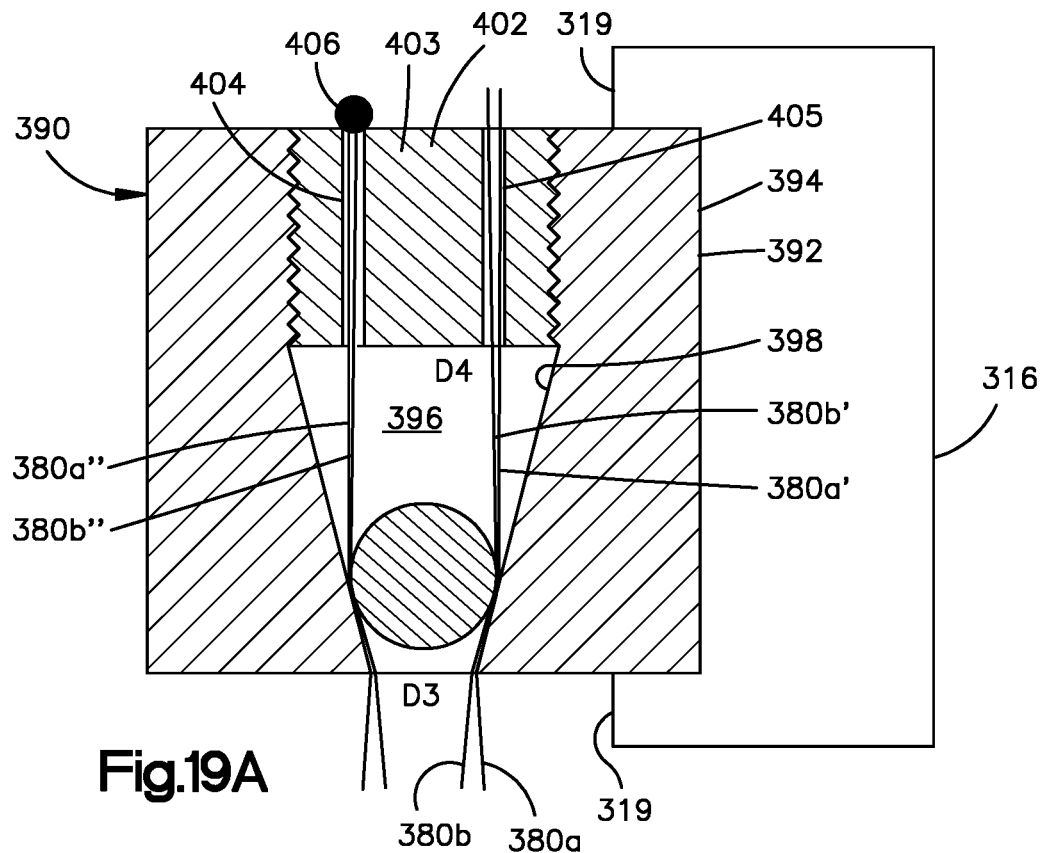
FIG. 19A is a schematic sectional side elevation view of a retention assembly of the insertion instrument constructed in accordance with another embodiment, shown in a locked configuration.
Figure 19B:
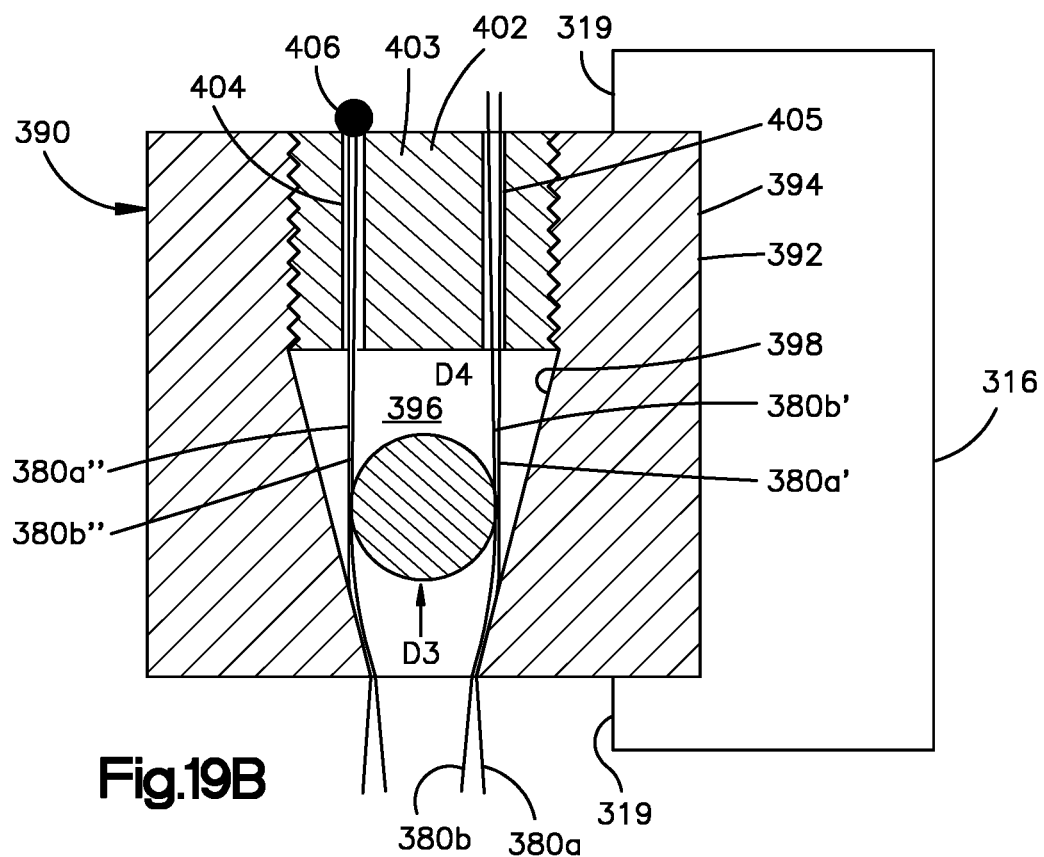
FIG. 19B is a schematic sectional side elevation view of a retention assembly of the insertion instrument illustrated in FIG. 19A, shown in an unlocked configuration.

Referring now to FIGS. 19A-B, the strand retention assembly 390 can be constructed in accordance with an alternative embodiment to releasably retain the at least one tensioning strand 380. Thus, while the strand retention assembly 390 illustrated in FIGS. 19A-B are illustrated as retaining the pair of first and second tensioning strands 380a and 380b, the retention assembly 390 can alternatively releasably retain a single tensioning strand, for instance as described above with respect to FIGS. 16-17. In accordance with the embodiment illustrated in FIGS. 19A-B, the retention assembly 390 retains the first and second ends 380a' and 380" and 380b' and 380b" of the first and second tensioning strands 380a and 380b. In accordance with one embodiment, the retention assembly 390 releasably retains the first and second tensioning strands 380a and 380b. As will now be described, the retention assembly 390 is translatably fixed to the first pusher assembly 317, and thus moves proximally and distally along the longitudinal direction L along with the plunger 316. Accordingly, after the second anchor body 28b has been ejected from the cannula 310, movement of the plunger 316 and the push rod 330 in the proximal direction causes the retention assembly 390 to move in the proximal direction, thereby applying the tensile actuation force to the second tensioning strand 380b, which communicates the actuation force to the second actuation portion 131b of the second actuation strand 38b, and causes the second anchor body 28b to expand. Similarly, after the first anchor body 28a has been ejected from the cannula 310, movement of the plunger 316 and the push rod 330 in the proximal direction causes the retention assembly 390 to move in the proximal direction, thereby applying the tensile actuation force to the first tensioning strand 380a, which communicates the actuation force to the first actuation portion 131a of the first actuation strand 38a, and causes the first anchor body 28a to expand.

The retention assembly 390 includes a retention housing 392 having a housing body 394 that is supported, directly or indirectly, by the casing 308. In accordance with the illustrated embodiment, the retention housing 392 is disposed in the interior 328 of the casing 308, though the retention housing 392 can alternatively be carried external of the casing 308, and can be attached to the plunger 316 or any suitable alternative structure of the insertion instrument 300 as desired. The retention housing 392 defines a bore 396 that extends longitudinally into the housing body 394 along the proximal direction. In accordance with the illustrated embodiment, the bore 396 extends longitudinally through the housing body 394. The housing body 394 can define at least one interior surface 398 that defines a perimeter of the bore 396. The interior surface 398 can slope (for instance linearly, curvilinearly, or along any suitable alternative shape) radially outward as it travels proximally along a direction from a distal end of the housing body 394 to a proximal end of the housing body 394. Thus, the bore 396 can define a first cross-sectional dimension D3 along a direction substantially perpendicular to the longitudinal axis 302 at its first or proximal end, and a second cross-sectional dimension D4 along a direction substantially perpendicular to the longitudinal axis 302 at its second or distal end. Because the bore 396 can be tapered, the first cross-sectional dimension D3 can be less than the second cross-sectional dimension D4. The bore 396 can be tapered, for instance linearly, curvilinearly, or along any suitable alternatively shape as desired.

The retention assembly 390 can further include a first locking member 400 that is disposed inside the bore 396. The first locking member 400 has a cross-sectional dimension D5, for instance along a direction substantially perpendicular to the longitudinal axis 302, that is between the first cross-sectional dimension D3 and the second cross-sectional dimension D4. The first locking member 400 can be substantially spherical as illustrated, or can alternatively define any shape as desired. The retention assembly 390 is configured to retain at least one strand between the first locking member 400 and the interior surface 398 of the housing body 394. For instance, the first end of at least one or both of the tensioning strands 380a' and 380b' can extend between the first locking member 400 and the interior surface 398. The first locking member 400 is configured to bear against the interior surface 398 during operation of the instrument, thereby capturing the first ends 380a' and 380b' between the first locking member 400 and the interior surface 398 of the housing body 394, and preventing relative movement between each of the first ends 380a' and 380b' and the retention housing 392. Thus, the first locking member 400 can present a first locking surface, and the interior surface 398 can present a second locking surface that cooperates with the first locking surface so as to retain the first ends 380a' and 380b' of the first and second retention strands 380a and 380b in the retention assembly 390.

The retention assembly 390 can further include a second locking member 402 that is configured to be attached to the first locking member 400. In particular, the second locking member 402 can include a threaded plug 403 that is threadedly inserted into the proximal end of the housing body 394. Accordingly, the second locking member 402 can be disposed adjacent the tapered inner surface 398, and can close the proximal end of the tapered bore 396. Alternatively, the second locking member 402 can be integral with the housing body 394. The second locking member 402 defines at least one opening, such as a longitudinal opening 404, that is configured to receive the end of the one or more tensioning strands that are opposite the end of the tensioning strands that are captured between the first locking member 400 and the interior surface 398 of the housing body 394. Accordingly, the second locking member 402 is configured to receive each of the second ends 380a" and 380b" of the first and second tensioning strands 380a and 380b. The second locking member 402 can thus be aligned with the tapered bore 396, such that the second end 380a" and 380b" of each of the first and second strands 380a and 380b extends through the tapered bore 396 and is attached to the second locking member 402.

In accordance with the illustrated embodiment, the longitudinal opening 404 extends longitudinally between the bore 396 and the exterior of the plug 403, which can be the interior 328 of the casing 308. Each or both of the second ends 380a" and 380b" can be tied in a knot 406 at the proximal end of the longitudinal opening 404, such that the knot 406 abuts the proximal end of the second locking member 402. Thus, the retention assembly 390 is configured to fix the first and second ends 380a' and 380a" of the first tensioning strand 380a, and is further configured to fix the first and second ends 380b' and 380b" of the second tensioning strand 380b. The second ends 380a" and 380b" can alternatively or additionally extend between the first locking member 400 and the interior surface 398, and can be captured between the first locking member 400 and the interior surface 398 as desired so as to retain the second ends 380a" and 380b" in the retention assembly 390. The second locking member 402 can further include a second longitudinal opening 405 that is spaced from the longitudinal opening 404. The second longitudinal opening 405 is configured to receive the remainder of the first ends 380a' and 380b' that are captured between the first locking member 400 and the interior surface 398.

Figure 19C:
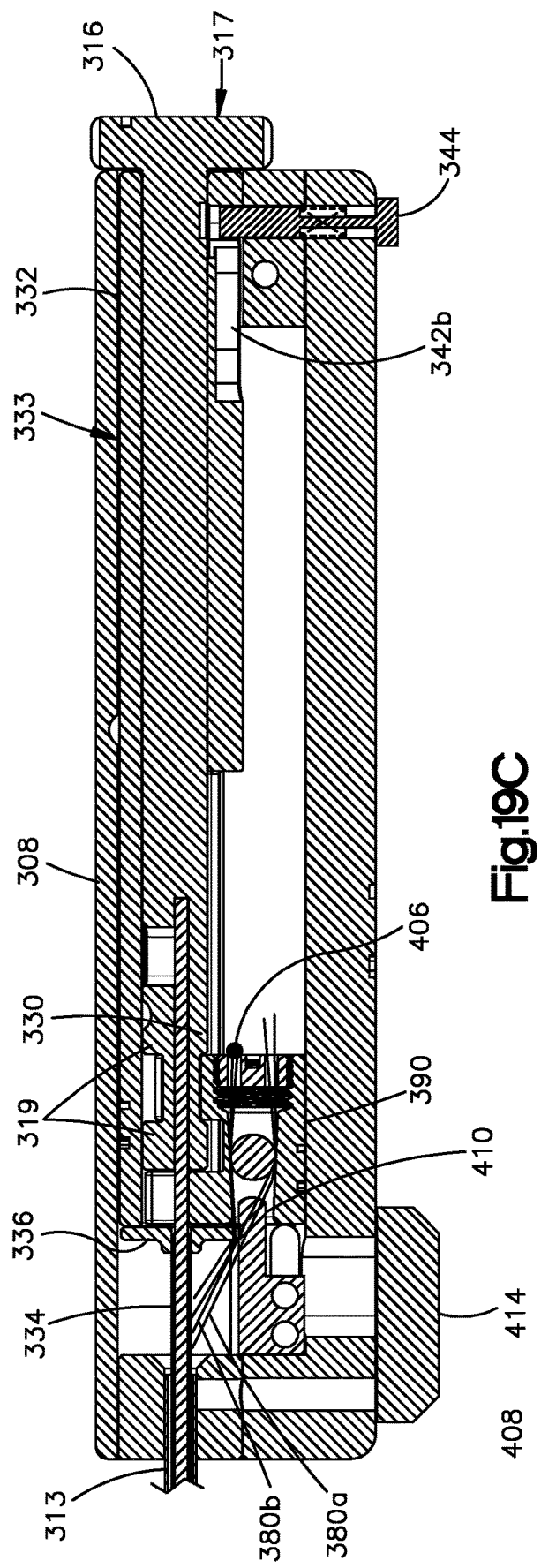
FIG. 19C is a sectional side elevation view of the casing of an insertion instrument similar to the insertion instrument as illustrated in FIG. 12C, but including a retention assembly constructed in accordance with an alternative embodiment.
Figure 22C:
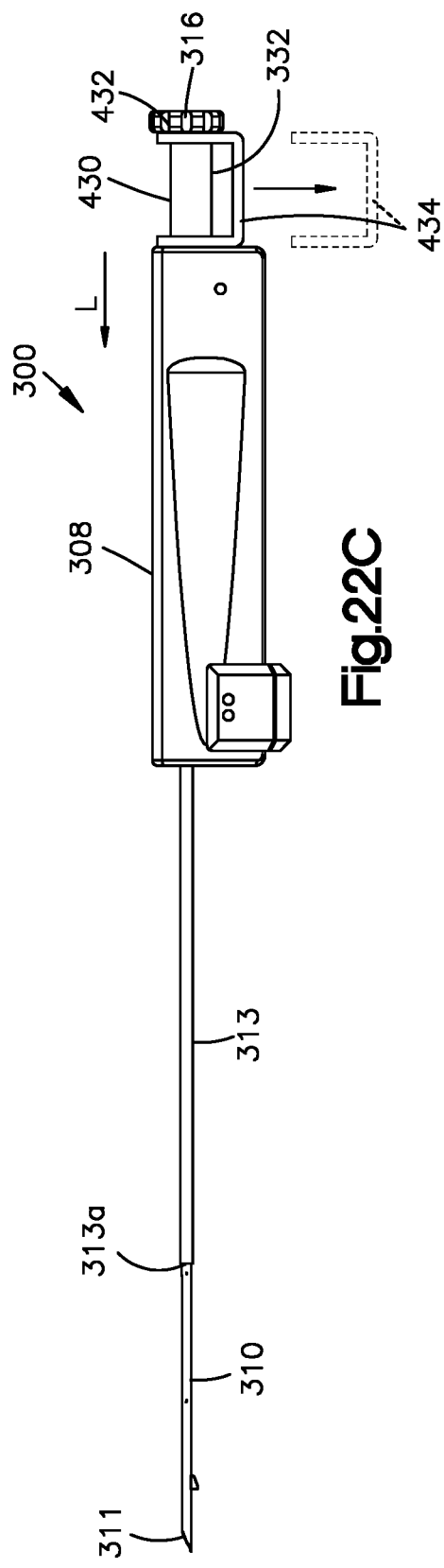
FIG. 22C is a side elevation view of the insertion instrument illustrated in FIG. 22B, but shown in a second position.
Figure 22D:
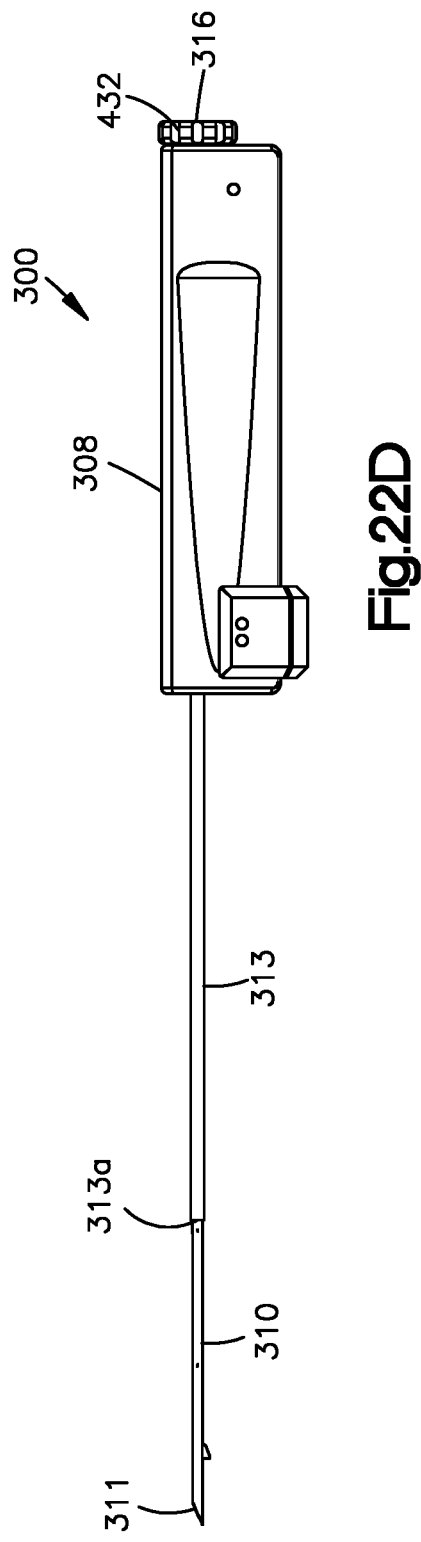
FIG. 22D is a side elevation view of the insertion instrument illustrated in FIG. 22C, but shown in a third position.

Referring to FIG. 19C, the first pusher assembly 317 can include a pair of flanges 319 that project out from the plunger 316 so as to define a gap 321 that extends between the flanges 319. The gap 321 can be sized to receive the housing body 394, such that each of the flanges 319 abuts the proximal and distal ends of the housing body 394, respectively. Accordingly, proximal movement of the plunger 316 causes the distal one of the flanges 319 to bias the housing body 394 and thus the retention assembly 390, to move proximally along with the plunger 316, and therefore also along with the push rod 330. Similarly, distal movement of the plunger 316 causes the proximal one of the flanges 319 to bias the housing body 394 and thus the retention assembly 390, to move distally along with the plunger 316, and therefore also along with the push rod 330.

During operation, because the plunger 316 and the push rod 330 move distally in tandem along the first stroke and the second stroke, and because the first and second anchor bodies 28a and 28b move distally along with the push rod 330, the retention assembly 390 likewise moves distally along with the first and second anchor bodies 28a and 28b. Accordingly, the retention assembly 290 can operate so as to not induce tension in either of the first and second tensioning strands 380a and 380b, and thus in the respective first and second actuation strands 38a and 38b, before the first and second anchor bodies 28a and 28b have been ejected from the cannula 310. However, as will now be described, the insertion instrument 300, and in particular the plunger 316, can be actuated so as to apply the respective first and second actuation forces to the first and second anchor bodies 28a and 28b after the first and second anchor bodies have been ejected from the cannula 310.

For instance, referring now to FIGS. 8A-D and FIGS. 19A-B, once the plunger 316 has traveled along the first stroke, thereby ejecting the second bone anchor 28b from the cannula 310 at a location behind the anatomical structure 24 and the second anatomical location 24b, the plunger 316 can be translated proximally such that the guide pin 344 rides along the first track portion 342a along the distal direction until contacting the collar 332, which provides stop surface at the distal end of the first track portion 342a, thereby preventing further proximal translation of the plunger. Because contact between the anatomical structure 24 and the second anchor body 28b prevents the second anchor body 28b from translating proximally along with the retention assembly 390, the retention assembly applies a tensile force to the tensioning strand 380b, which is communicated to the second actuation strand 38b as the actuation force that causes the second anchor body 28b to move from the first configuration illustrated in FIG. 9A to the expanded configuration illustrated in FIG. 9E.

For instance, referring now to FIGS. 9A-E and FIGS. 19A-B, once the plunger 316 has traveled along the first stroke, thereby ejecting the second bone anchor 28*b* from the cannula 310 at a location behind the anatomical structure 24 at the second anatomical location 24*b*, the insertion instrument 300 can be translated proximally as it is removed from the anatomical tissue 24 as described above. Because contact between the anatomical structure 24 and the second anchor body 28*b* prevents the second anchor body 28*b* from translating proximally along with the insertion instrument 300, the retention assembly 390 applies a tensile force to the tensioning strand 380*b*, which is communicated to the second actuation strand 38*b* as the actuation force that causes the second anchor body 28*b* to move from the first configuration illustrated in FIG. 9A to the expanded configuration illustrated in FIG. 9E.

Similarly, referring now to FIGS. 18A-E and FIGS. 19A-B, once the plunger 316 has traveled along the second portion of the second stroke, thereby ejecting the first bone anchor 28*a* from the cannula 310 at a location behind the anatomical structure 24 at the first anatomical location 24*a*, the insertion instrument 300 can be translated proximally as it is removed from the anatomical tissue 24. Because contact between the anatomical structure 24 and the first anchor body 28*a* prevents the first anchor body 28*a* from translating proximally along with the retention assembly 390, the retention assembly 390 applies a tensile force to the first tensioning strand 380*a*, which is communicated to the first actuation strand 38*a* as the actuation force that causes the first anchor body 28*a* to move from the first configuration illustrated in FIG. 12A to the expanded configuration illustrated in FIG. 12E.

Once the first and second anchor bodies 28*a* and 28*b* have been actuated to their expanded configurations, the tensioning strands 380*a* and 380*b* can be released from the retention assembly 390. For instance, as will now be described, the retention assembly 390 can configured to release at one of the ends of the tensioning strands 380*a* and 380*b*. Alternatively, as described in more detail below, the insertion instrument 300 can include a cutting blade that is configured to sever the first and second tensioning strands 380*a* and 380*b*. Referring to FIG. 19C, the insertion instrument 300 can include a release member 408 that is coupled to the retention assembly 390 and is configured to iterate the retention assembly 390 to an unlocked configuration. The release member 480 can include any suitable linkage 410 that can be aligned with the first locking member 400. The release member 408 can include an actuator 414 that is carried by the casing 308 and coupled to the linkage 410, such that a user can manipulate the actuator 414, for instance slide the actuator proximally, so as to cause the linkage 410 to contact the first locking member 400 and bias the first locking member 400 proximally along the direction of Arrow 401 to an unlocked configuration, which creates a gap 412 between the first locking member 400 and the interior surface 398, as illustrated in FIG. 19B. The gap can be greater than a cross-sectional dimension of the tensioning strands 380*a* and 380*b*.

When the second ends 380*a*" and 380*b*" are tied at the second locking member 402, proximal translation of the insertion instrument 300 relative to the implanted anchor bodies 28*a* and 28*b*, causes the first ends 380*a*' and 380*b*' of the first and second tensioning strands 380*a* and 380*b* to travel out the retention assembly 390 through the gap, and further draws the respective first and second tensioning strands 380*a* and 380*b* through the respective actuation strands 38*a* and 38*b*, thereby removing the first and second tensioning strands 380*a* and 380*b* from the actuation strands 38*a* and 38*b* as illustrated in FIGS. 18C-18D. Alternatively, if the first and second ends 380*a*" and 380*b*" are retained by the first locking member 400 and not the second locking member 402, proximal translation of the insertion instrument 300 relative to the implanted anchor bodies 28*a* and 28*b* removes the tensioning strands 380*a* and 380*b* from the insertion instrument 300. The user can then manually draw the tensioning strands 380*a* and 380*b* through the respective actuation strands 38*a* and 38*b* so as to remove the first and second tensioning strands 380*a* and 380*b* from the actuation strands 38*a* and 38*b*.

Referring now to FIG. 18D, once the tensioning strands 380*a* and 380*b* have been removed from the actuation strands 38*a* and 38*b*, the user can draw the connector 63 toward the anatomical structure. It should be appreciated that the connector 63 can be attached to the actuation strands 38*a* and 38*b* when the first and second anchor bodies 28*a* and 28*b* are loaded in the insertion instrument 300. Alternatively, the user can connect the actuation strands 38*a* and 38*b* after the first and second anchor bodies 28*a* and 28*b* have been ejected. While the connector member 63 illustrated in FIGS. 18C-E is configured as a knot of the type described above, the connector member 63 can be alternatively configured as desired. In accordance with the embodiment illustrated in FIGS. 18C-E, a tensile force can be applied to the free end 70, which causes the connector member to translate toward the anatomical structure, thereby applying an approximation force to the actuation strands 38*a* and 38*b*, thereby approximating the tissue gap 24*c*. The portion of the actuation strands 38*a* and 38*b* that extend out from the connector member 63 can then be severed as desired.

Referring now to FIGS. 20A-B, and as described above, the insertion instrument 300 can include a cutting assembly 416 that includes a cutting blade 418, and is movable between a disengaged position whereby the cutting blade 418 is spaced from one of the ends, such as the first ends 380*a*' and 380*b*' of the tensioning strands 380*a* and 380*b* that are retained by the retention assembly 390, and an engaged position whereby the cutting blade severs the first ends 380*a*' and 380*b*' of the tensioning strands 380. It should be appreciated that the retention assembly 390 illustrated in FIGS. 20A-B can be configured as illustrated in FIG. 17, and that the retention assembly 390 can be attached to a single tensioning strand, such that the cutting blade 418 is configured to cut a first end of the single tensioning strand, such that removal of the insertion instrument 300 from the anchor bodies 28*a* and 28*b* draws the tensioning strand through and away from actuation strands 38*a* and 38*b*.

The cutting assembly 416 can include a longitudinally elongate shaft 420, and a switch 422 that is pivotally coupled between the elongate shaft 420 and the cutting blade 418, thereby coupling the elongate shaft 420 to the cutting blade 418. The cutting blade 418 can be carried by a blade housing 424, such that the elongate shaft 420 and the switch 422 are indirectly coupled to the cutting blade 418. The proximal end of the longitudinally elongate shaft 420 can extend proximally out of the casing 408, and the longitudinal shaft can extend in a side wall of the casing 408. The shaft 420 is movable longitudinally in the distal direction from a disengaged position to an engaged position. Distal movement of the shaft 420 causes the switch to pivot, thereby driving the cutting blade 418 to translate proximally and into the first ends 380*a*' and 380*b*' of the first and second tensioning strands 380*a* and 380*b*, thereby severing the first ends 380*a*' and 380*b*'. Once the tensioning strands 380*a* and 380*b* have been severed, the instrument can be translated proximally with respect to the ejected anchor bodies 28*a* and 28*b* so as to remove the tensioning strands 380*a* and 380*b* from the respective actuation strands 38*a* and 38*b* in the manner described above.

Referring now to FIGS. 21A and 21B, it should be appreciated that the cutting assembly 416 can be constructed in accordance with any alternative embodiment as desired. For instance, the cutting assembly 416 can include an actuator 426 that extends laterally out the side wall of the casing 408 along a direction angularly offset with respect to the longitudinal direction L, and is movable radially inward from the disengaged position to the engaged position. The actuator 426 can carry the cutting blade 418. Accordingly, as the actuator 426 moves radially inward, the cutting blade 418 severs the first and second ends 380*a*' and 380*b*' of the actuation strands 380*a* and 380*b*. The insertion instrument 300 can include a divider wall 428 that separates the first and second ends of the actuation strands 380*a* and 380*b* and is aligned with the cutting blade 418. Accordingly, the cutting blade 418 drives into the divider wall 428 and does not sever the second ends of the first and second actuation strands 380*a* and 380*b*. Of course, it should be appreciated that a single tensioning strand can be coupled to the actuation strand 38 of the anchor assembly 20 as described above, such that the cutting blade 418 can cut one of the first and second ends of the single tensioning strand.

Referring now to FIGS. 22A-D generally, the insertion instrument 300 can be constructed substantially as described above with respect to FIG. 7A-21B, but can include the guide system 329 that operably couples the casing 308 and the push rod 330 so as to guide relative movement between the casing 308 and the push rod 330 in accordance with another embodiment. For instance, the guide track 342 can be defined in the collar 332 as described above, but extends substantially linearly along the longitudinal direction L. Accordingly, as the plunger translates distally along the first and second strokes, the guide track 342 translates linearly with respect to the guide pin 344. It should be appreciated in the embodiment illustrated in FIGS. 22A-D, the second recess 362 illustrated in FIGS. 13C-E can be longitudinally aligned with the first recess 354, such that the latch 370 moves from the first recess 354 into the second recess 362 so as to decouple the plunger 316 from the collar 332 without rotating the plunger 316. The plunger 316 can include a shaft portion 430 that defines a portion of the key 318 as described above, and a distal end cap that can define a grip portion 432 that extends radially out from the proximal end of the shaft portion 430. The collar 332 can extend at least partially around the shaft portion 430, and can extend radially out from the shaft portion 430 in accordance with the illustrated embodiment.

The insertion instrument 300 can further include a clip 434 that has a longitudinal length substantially equal to the longitudinal distance between the grip portion 432 of the plunger 316 and the proximal end of the collar 332 when the plunger 316 is in the first position. The clip 434 can be removably secured to the shaft portion 430 of the plunger 316. Thus, as the plunger 316 translates distally, the grip portion 432 biases the clip 434 against the collar 332, which causes the collar 332 to translate along with the plunger 316. It should therefore be appreciated that the clip 434 couples the plunger 316 and the collar 332 with respect to distal translation along the longitudinal direction L. Accordingly, during operation, the plunger 316 and collar 332 can be translated distally from the first position to the second position in tandem along the first stroke in the manner described above. As the plunger 316 and collar 332 move along the first stroke, the guide pin 344 translates proximally within the entire guide track 342. The plunger 316 and collar 332 reach the second position when the clip 434 abuts the casing 308, at which point the latch member 370 moves from the first recess 354 into the second recess 358 as described above with respect to FIGS. 14C-D. Next, the clip 434 can be removed from the plunger 316, and the plunger 316 can translate distally with respect to the collar 332 along the second stroke. It should be appreciated that the plunger 316 can translate along the entire second stroke independent of the collar 332.

Accordingly, the push tube 334 ejects the second anchor body 38*b* as described above with respect to FIGS. 9A-E after the plunger and collar 332 have moved along the first stroke from the first position to the second position. Thus, the plunger 316 can be depressed a first distance that causes the second anchor body 28*b* to be ejected from the insertion instrument, and the clip 434 abuts the casing 308 once the plunger 316 has been depressed the first distance so as to prevent the plunger 316 from being depressed a second distance greater than the first distance until the collar 434 is removed from the plunger 316. The push rod 330 can then eject the first anchor body 28*a* after the plunger 136 has moved from the second position to the third position along the second stroke in the manner described above with respect to FIGS. 12A-E. The guide pin 344 can abut the proximal end of the guide track 342 when the second stroke has been completed. Furthermore, the grip portion 432 of the plunger 316 can abut the casing 308 once the plunger 316 has completed the second stroke and has moved to the third position. It should be appreciated in the embodiment illustrated in FIGS. 22A-D that because the plunger 316 is rotatably keyed to the collar 332 and thus rotatably fixed to the collar 332, and because the latch 370 (described above) rotatably couples the collar 332 to the casing 308, the plunger 316 is unable to rotate with respect to the casing 308 as the plunger 316 translates along the second stroke. Alternatively, the insertion instrument can be configured to allow the plunger 316 to rotate as desired so as to align the latch 370 with the second recess 362, as described above.

Figure 23A:
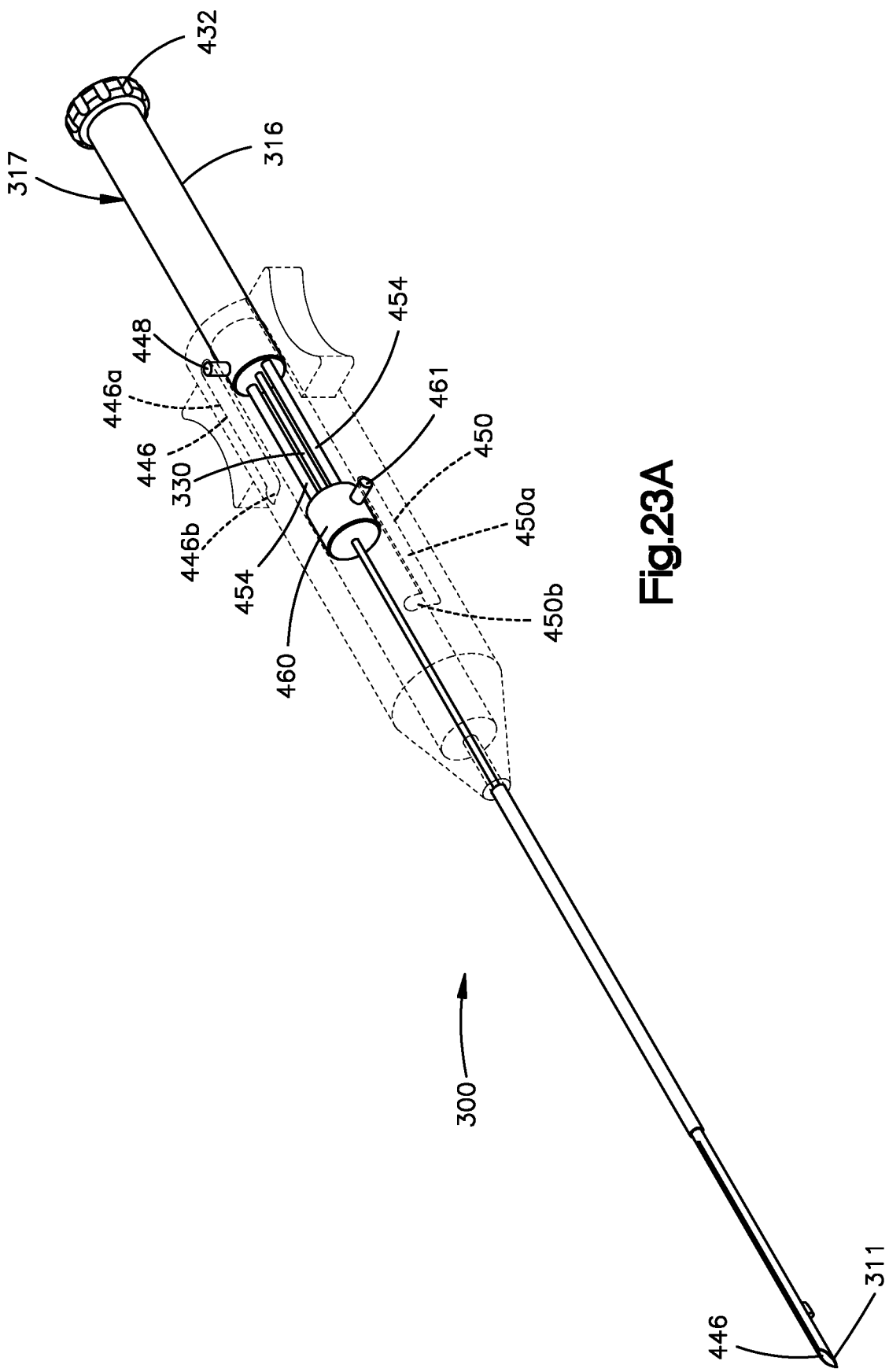
FIG. 23A is a perspective view of an insertion instrument constructed similar to the insertion instrument illustrated in FIG. 7A, but constructed in accordance with another embodiment, and shown in a first position.

As described above with respect to the insertion instrument illustrated in FIGS. 7A-13G, the guide track 342 can be carried by the casing 308, and the guide pin 344 can be carried by one of the pusher assemblies. Referring now to FIG. 23A, the insertion instrument 300 includes at least one guide track, such as a first guide track 446 that is carried by the casing 308, and at least a one guide member such as a first guide pin 448 carried by the pusher assembly 317, and in particular carried by the plunger 316, that rides in the first guide track 342.

As illustrated in FIG. 23B, the shaft portion 430 of the plunger 316 defines a distal surface 431, and further defines a first central aperture 440 that extends longitudinally into, or distally into, the distal surface 431. The shaft portion 430 of the plunger 316 further defines a radial aperture 435 that receives the guide pin 448. The first aperture 440 receives the push rod 330, such that the plunger 316 and the push rod 330 are coupled to each other with respect to both longitudinal translation and rotation. As illustrated in FIG. 23D, the push rod 330 extends from the plunger 316 and into the cannula 310, which is fixed to the casing 308 with respect to translation and rotation. Referring also to FIG. 23C, the tip 311 can be cannulated so as to define a distal ejection port 442 that is substantially aligned with the longitudinal axis 302, and thus also substantially aligned with the elongate opening 312 of the cannula 310. The push rod 330 is movable longitudinally inside the channel 312 in the manner described above. It should be appreciated that the insertion instrument 300 can alternatively define a side ejection port constructed substantially as described below. The cannula 310 can define a longitudinal slot 337, such that the attachment portions 133a and 133b of the actuation strands 38a and 38b (see FIG. 1A) that attach the first anchor body 28a to the second anchor body 28b can extend out the slot 337.

Referring now also to FIGS. 23D-E, the insertion instrument includes a guide system 444 that is configured to operably couple the casing 308 to the push rod 330 so as to guide relative movement between the casing 308 and the push rod 330. For instance, the guide system 444 includes the first guide member in the form of the first guide track 446 that is carried by the casing 308, and the second guide member illustrated as the first guide pin 448 that extends from the pusher assembly 317. The first guide track 446 can be configured as a slot that extends radially outward into the radially inner surface of the casing 308. Furthermore, in accordance with the illustrated embodiment, the first guide pin 448 extends radially out from the shaft portion 430 of the plunger 316, and rides within the first guide track 448. The first guide track 446 defines a first track portion 446a that extends substantially longitudinally, and an intermediate track portion 446b that extends circumferentially from the distal end of the first track portion 446a.

With continuing reference to FIG. 23E, the guide system 444 further includes a third guide member configured as a second guide track 450 that is carried by the casing 308, and is configured as a slot that extends radially outward into the inner surface of the casing 308. The second guide track 450 defines a first track portion 450a that extends substantially longitudinally, and an intermediate track portion 450b that extends circumferentially from the distal end of the second guide track 450b. The intermediate track portion 450b extends from the first track portion 450a the same direction that the intermediate track portion 446b extends from the first track portion 446a.

The first track portions 446a and 450a define a first stroke of movement for the plunger 316 that causes the push rod 330 to eject the second anchor out the ejection port 442. The intermediate track portions 446ba and 450b are configured such that the plunger is rotated so as to align a fifth guide member with a second track portion that is radially offset from the first track portions 446a and 450a. In particular, as illustrated in FIG. 23B, the insertion instrument 330 further includes a pair of apertures 452 that are disposed adjacent the central aperture 440 and extend longitudinally into the distal surface 431 of the shaft portion 430 of the plunger 416. The apertures 452 are each configured to receive respective fifth guide members configured as guide posts 454 (FIG. 23D) that extend distally from the plunger 416, and a sixth guide member illustrated as a guide housing 460 (FIG. 23E) that is disposed in the interior 328 of the casing 308 and fixed to the casing 308 with respect to translation. The guide housing 460 defines a seventh guide member configured as a radially outwardly extending second guide pin 461 that is configured to ride in the second guide track 450. The guide housing 460 further defines a guide member in the form of at least one aperture such as a pair of apertures that extend longitudinally through the guide housing 460 and define second track portions 462. The second track portions 462 are sized to receive the guide posts 454. The proximal end of the guide housing 460 can define a pair of recesses 464 that extend longitudinally into, but not through, the guide housing 460 at a location adjacent the second track portions 462. The recesses 464 can be arcuate shaped or alternatively shaped as desired.

Figure 23F:
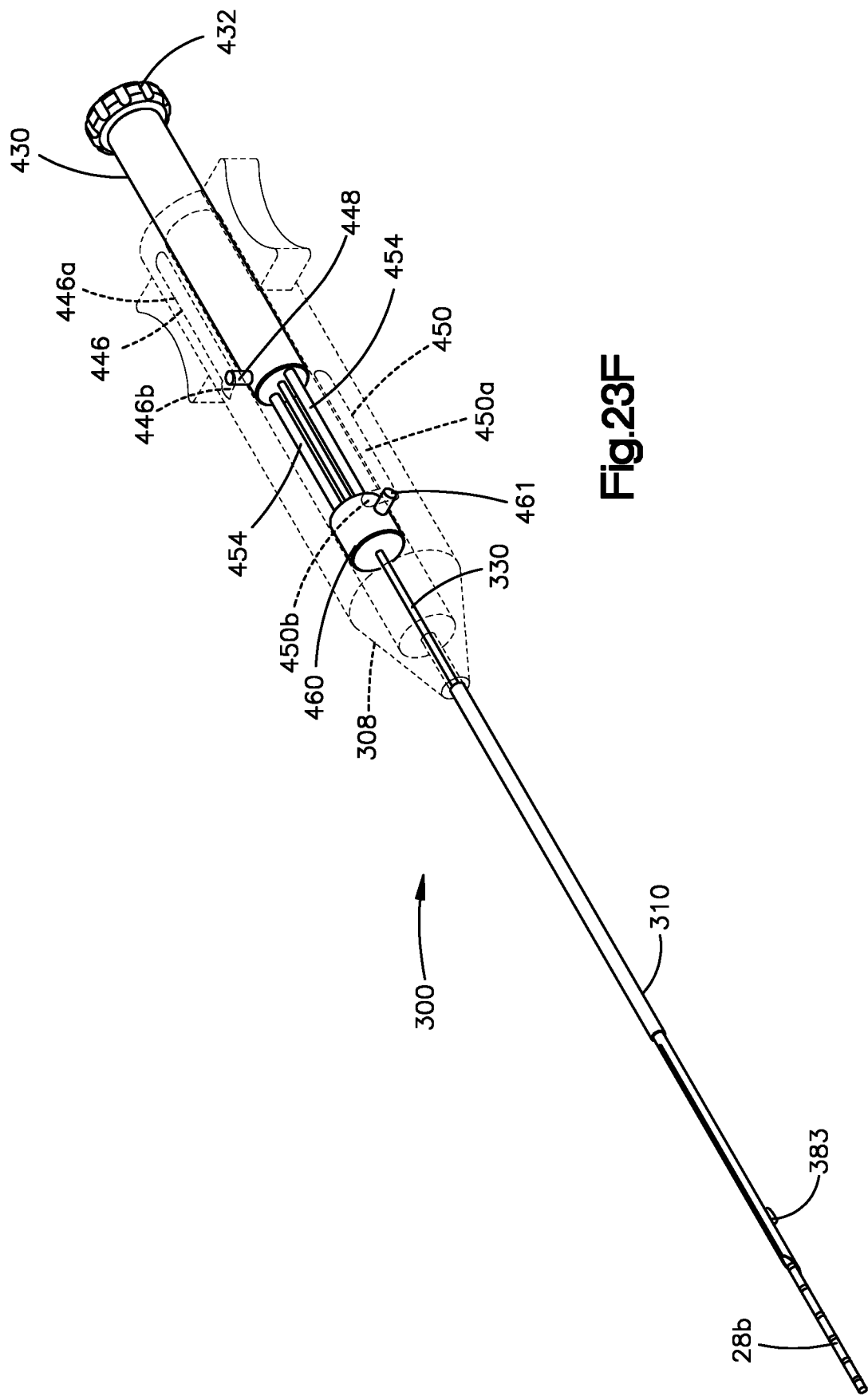
FIG. 23F is a perspective view of the insertion instrument illustrated in FIG. 23A, shown in a second position.

Referring now to FIGS. 23A and 23F, a distal biasing force can be applied to the plunger 316, which causes the plunger 316 and the push rod 330 to translate distally along the first stroke with respect to the casing 308 and thus the cannula 310 and the guide housing 460. The plunger 316 translates from the first position illustrated in FIG. 23A to the second position illustrated in FIG. 23F. As the plunger 316 translates distally from the first position to the second position, the first guide pin 448 translates distally along the first track portion 446a of the first guide track 446 until the first guide pin 448 is aligned with the intermediate track portion 446b of the first guide track 446. Likewise, as the plunger 316 translates distally from the first position to the second position, the second guide pin 461 translates distally in the first track portion 450a of the second guide track 450 until the second guide pin 461 is aligned with the intermediate track portion 450b of the second guide track 450. Once the plunger 316 has translated to the second position, the guide posts 454 are circumferentially offset from the respective second track portions 462, and abut the guide housing 460, for instance in the recesses 464.

Figure 23G:
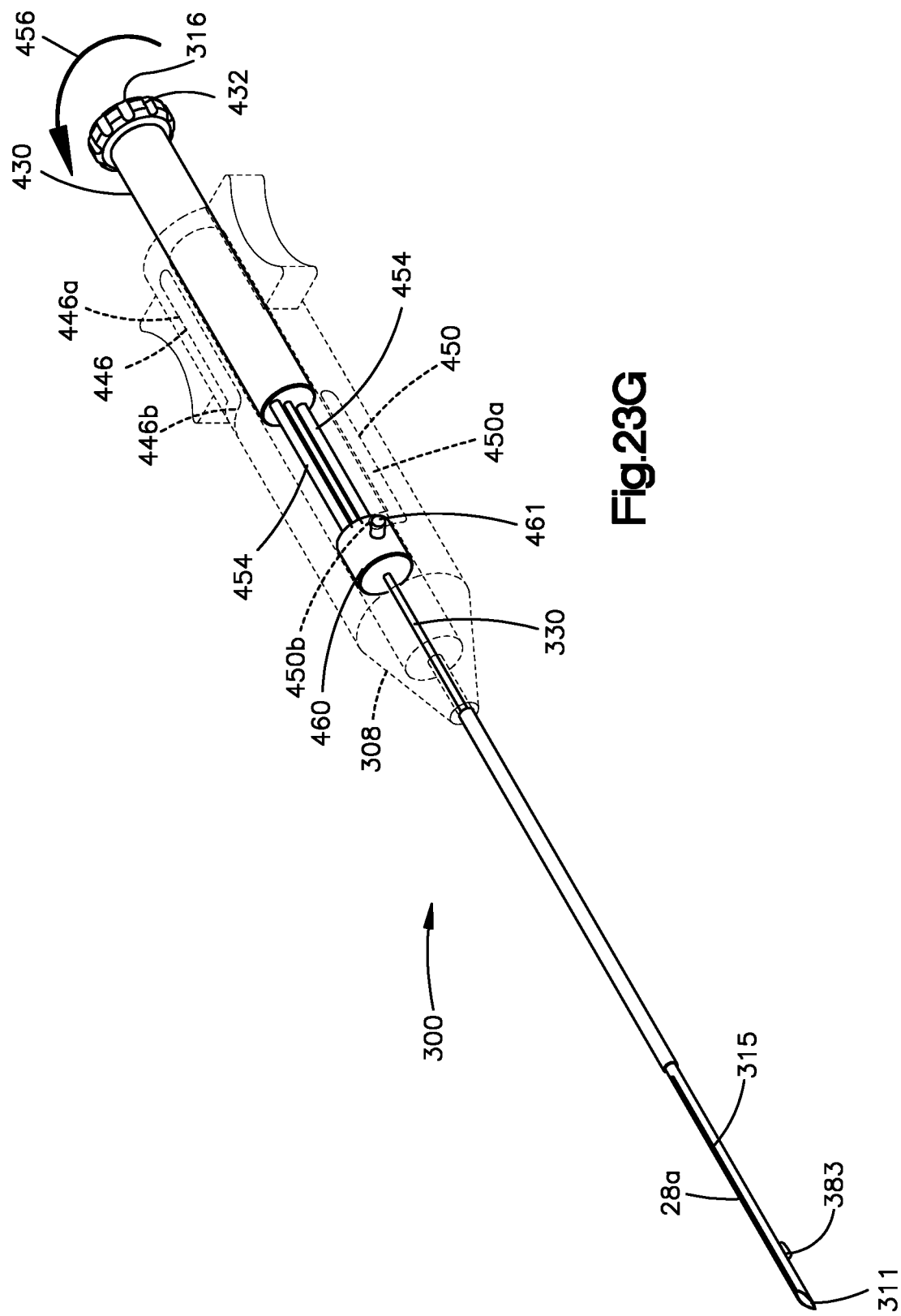
FIG. 23G is a perspective view of the insertion instrument illustrated in FIG. 23F, shown in an intermediate position.
Figure 23H:
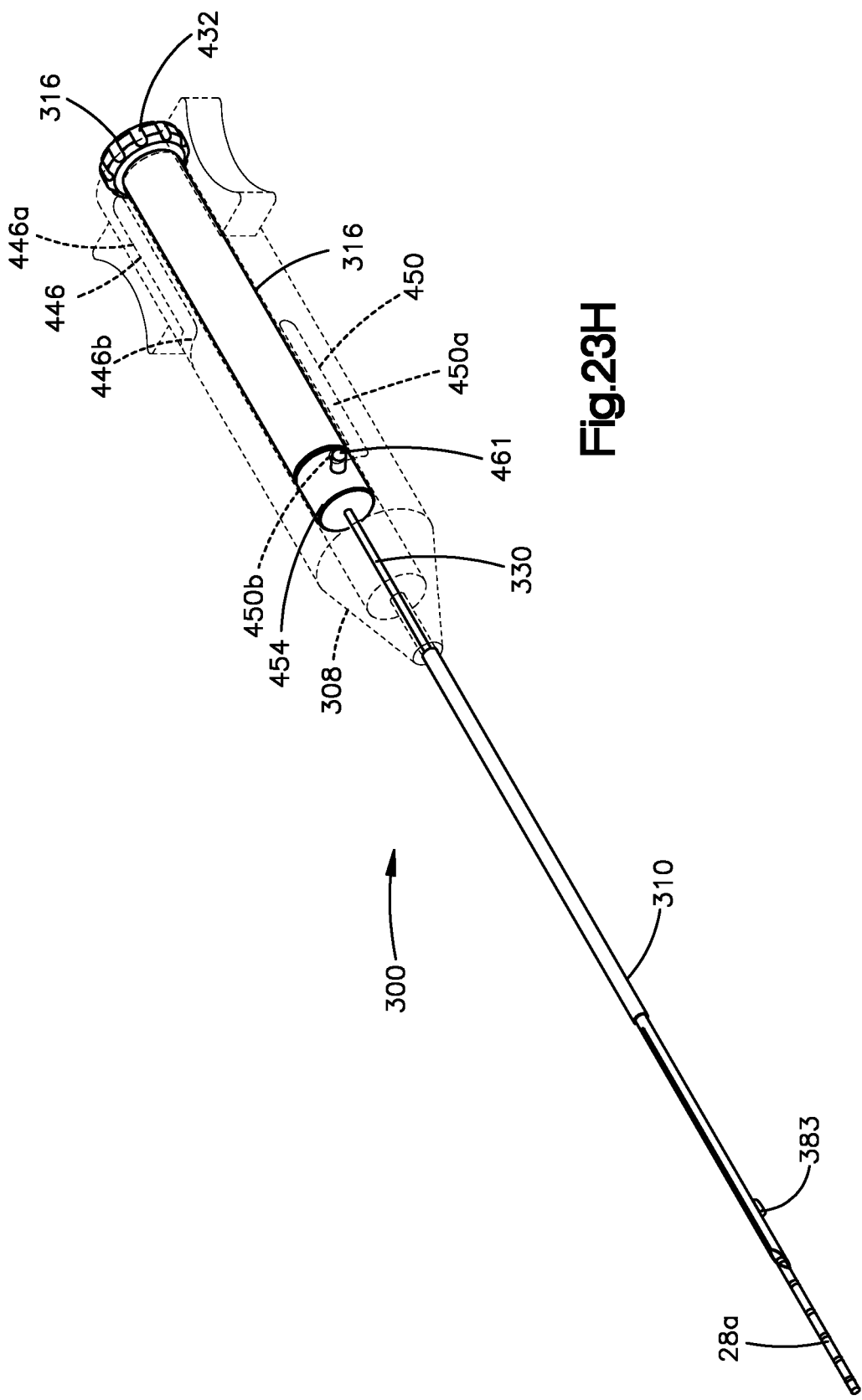
FIG. 23H is a perspective view of the insertion instrument illustrated in FIG. 23G, shown in a third position.

Referring now to FIG. 23G, the plunger 316 can be rotated along the direction of Arrow 456, which causes the first and second guide pins 448 and 461 to travel in the respective intermediate track portions 446b and 450b, until reaching the end of the intermediate track portions 446b and 450b, which define respective stops that prevent the plunger 316 from continuing to rotate relative to the casing 308, and further prevents the guide posts 454 from rotating relative to the guide housing 460. Once the plunger 316 has finished rotating, the guide posts 454 are aligned with the second track portions 462. Accordingly, as illustrated in FIG. 23H, the plunger 316 can be further translated distally along the second stroke from the second position to a third position, at which point the plunger 316 abuts the guide housing 460 and is prevented from traveling distally further. Thus, the guide housing 460 defines a stop that prevents the plunger 316 from translating distally beyond the third position.

As the plunger 316 translates along the second stroke, the push rod 330 translates distally within the channel 312 of the cannula 310, and ejects the first anchor body 28a out the ejection port 442. After each anchor body 28a and 28b has been ejected from the instrument to a location behind the anatomical structure 24 (see FIG. 1A), an actuation force can be applied to each anchor body 28a and 28b. For instance, the insertion instrument 330 can include a retention assembly of the type described above, such as the retention assembly 390 or any suitable alternatively constructed retention assembly. Alternatively, the user can manually apply the actuation force to the respective actuation strands 131a and 131b. A connector member can then attach the actuation strands 131a and 131b together in the manner described above.

Referring now to FIGS. 24A-25D generally, it should be appreciated that an insertion instrument can be configured having a first and second cannulas supported by the casing in a side-by-side orientation that retain first and second anchor bodies, and first and second pusher assemblies operatively associated with the first and second cannulas, respectively, so as to eject the first and second anchor bodies out the respective first and second cannulas. It can be desirable to ensure that a desired cannula from which the anchor body is to be ejected is distally disposed with respect to the other cannula, such that the desired cannula can be inserted into the underlying tissue without also inserting the other cannula.

Figure 24A:
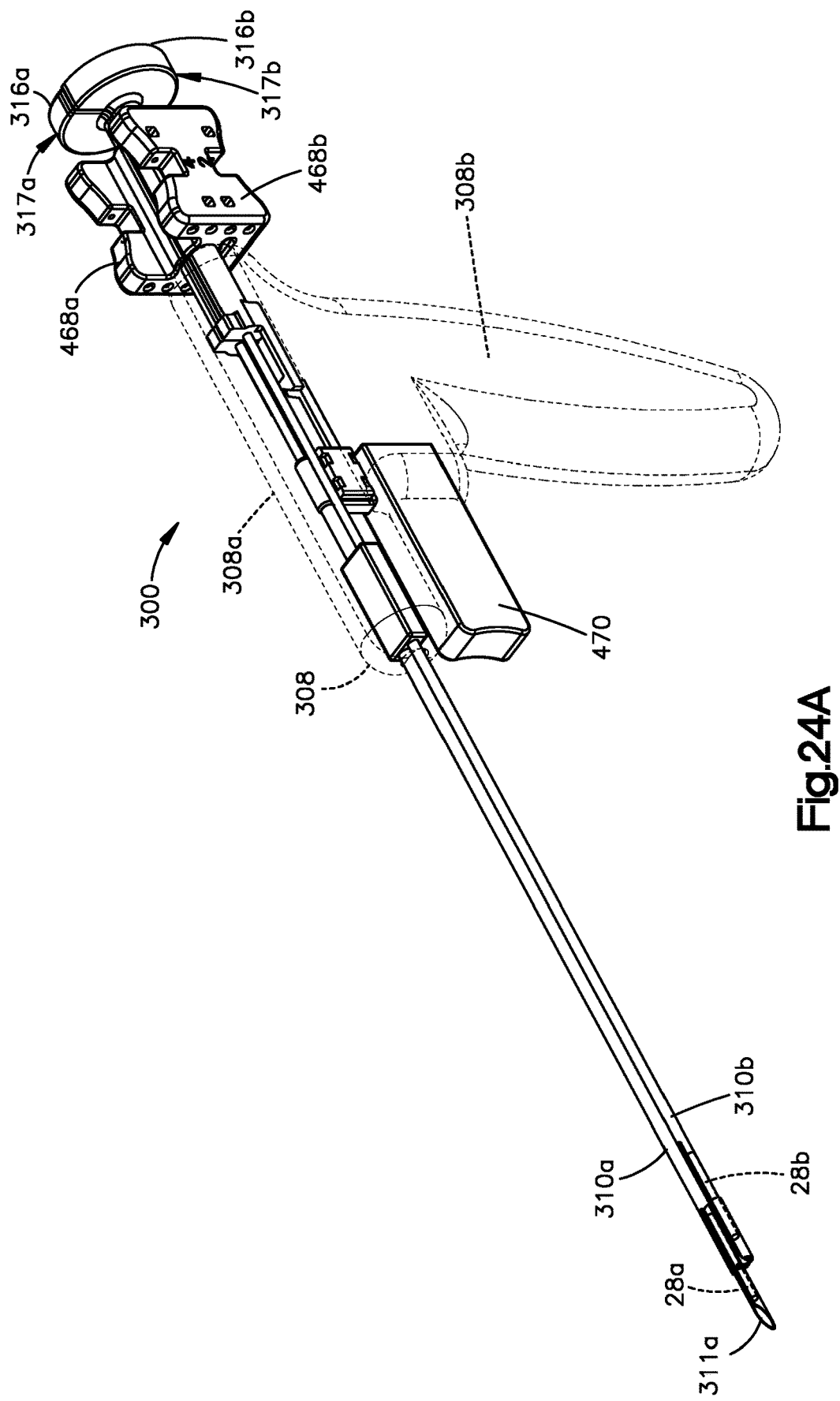
FIG. 24A is a perspective view of an insertion instrument including first and second pusher assemblies disposed in a side-by-side relationship, showing each of the pusher assemblies in a first position.

As illustrated in FIG. 24A, an insertion instrument 300 includes a casing 308 that includes a body portion 308a and a handle portion 308b that extends out from the body portion 308a. The insertion instrument 300 further includes a first cannula 310a that extends distally from the casing 308, and in particular from the body portion 308a, and a second cannula 310b that extends distally from the casing 308, and in particular from the body portion 308a, at a location adjacent the first cannula 310a. The first and second cannulas 310a and 310b can extend substantially parallel to each other as illustrated. Accordingly, the first and second cannulas 310a and 310b can be described as being in a side-by-side relationship. The first and second cannulas 310a and 310b can define respective longitudinally elongate channels 312a and 312b that retain respective first and second anchor bodies 28a and 28b.

The insertion instrument 300 can further include first and second pusher assemblies 317a and 317b operatively associated with the first and second cannulas 310a and 310b, respectively. Thus, the first pusher assembly 317a is configured to eject the first anchor body 28a out the first cannula 310a, and the second pusher assembly 317b is configured to eject the second anchor body 28b out the second cannula 310b. The first and second cannulas 310a and 310b can define respective first and second tapered tips 311a and 311b, and first and second distal ejection ports that extend longitudinally through the respective tips 311a and 311b.

Each of the first and second pusher assemblies 317a and 317b includes first and second plungers 316a and 316b, respectively, and first and second pusher rods 330a and 330b, respectively, that extend distally from the corresponding plungers 316a and 316b. Each of the plungers 316a and 316b define respective shaft portions 430a and 430b and respective end caps that can define first and second grip portion 432a and 432b that extends radially out from the proximal end of the corresponding shaft portions 430 and 430b. When the first and second plungers 316a and 316b are in their respective first positions, the first and second grip portions 432a and 432b are proximally spaced from the casing 308. The insertion instrument 300 can further include first and second lock-out tabs 468a and 468b that are removably attached to the first and second plungers 316a and 316b. For instance, in accordance with the illustrated embodiment, the first and second lock-out tabs 468a and 468b are attached to the respective first and second shaft portions 430a and 430b at a location longitudinally between the corresponding grip portions 432a and 432b and the casing 308. Accordingly, the first and second lock-out tabs 468a and 468b interfere with the respective grip portions 432a and 432b, and prevent the plungers 316 from translating distally relative to the casing 308 to a depth that would eject the respective first and second anchor bodies 28a and 28b.

The insertion instrument 330 can further include a swap actuator 470 in the form of a trigger that extends partially into the casing 308, and can extend out from the handle portion 308b. The swap actuator 470 is configured to be moved from a first position to an actuated position so as to reverse a relative position of the first and second tips 311a and 311b. The swap actuator 470 can be coupled to the first pusher assembly 317a, such that proximal translation of the actuator 470 causes the first pusher assembly 317a, including the first plunger 316a and the first cannula 310a, to translate proximally. As illustrated in FIG. 24A, the first tip 311a of the first cannula 310a is disposed distally with respect to the second tip 311b of the second cannula 310b. Furthermore, the distal end of the second push rod 330b can extend slightly out from the respective second tip 311b, such that the longitudinal distance between the distal end of the second push rod 330b and the distal end of the first tip 311a defines an insertion depth into underlying tissue. Otherwise stated, the second push rod 330b can define a depth stop for insertion of the first tip 311a into underlying tissue. It should thus be appreciated that the first tip 311a can be injected into underlying tissue, for instance at the first target anatomical location 24a (see FIG. 1A) without causing the second tip 311b to inject into the underlying tissue. As is described in more detail below, actuation of the swap actuator 470 from a first position to a second position causes the first tip 311a to move proximally with respect to the casing 308 and the second tip 311b, such that the second tip 311b can be injected into the underlying tissue, for instance at the second target anatomical location 24b (see FIG. 1B) without causing the first tip 311a to inject into the underlying tissue.

Figure 24B:
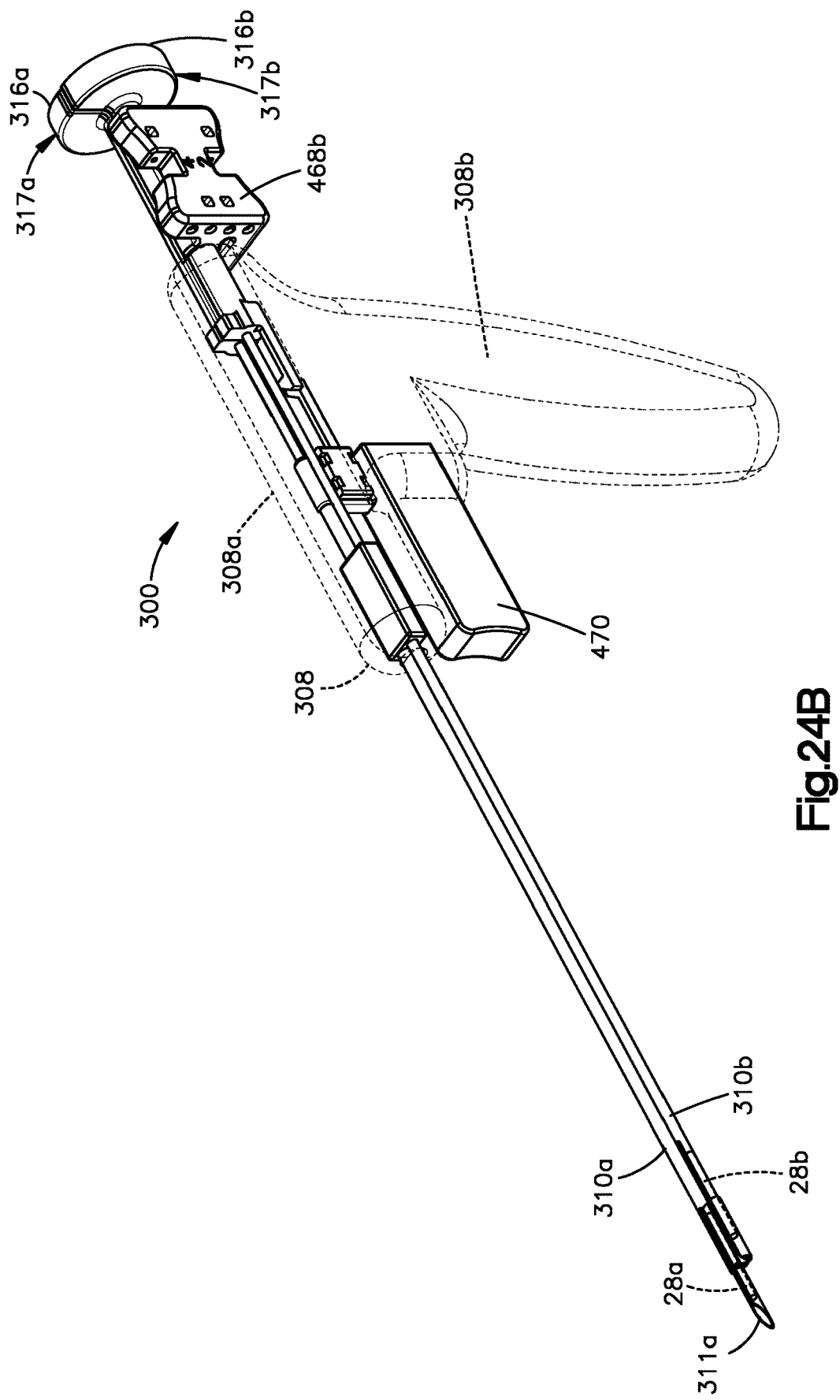
FIG. 24B is a perspective view of the insertion instrument illustrated in FIG. 24A, after removal of a first lockout tab from the first pusher assembly.
Figure 24C:
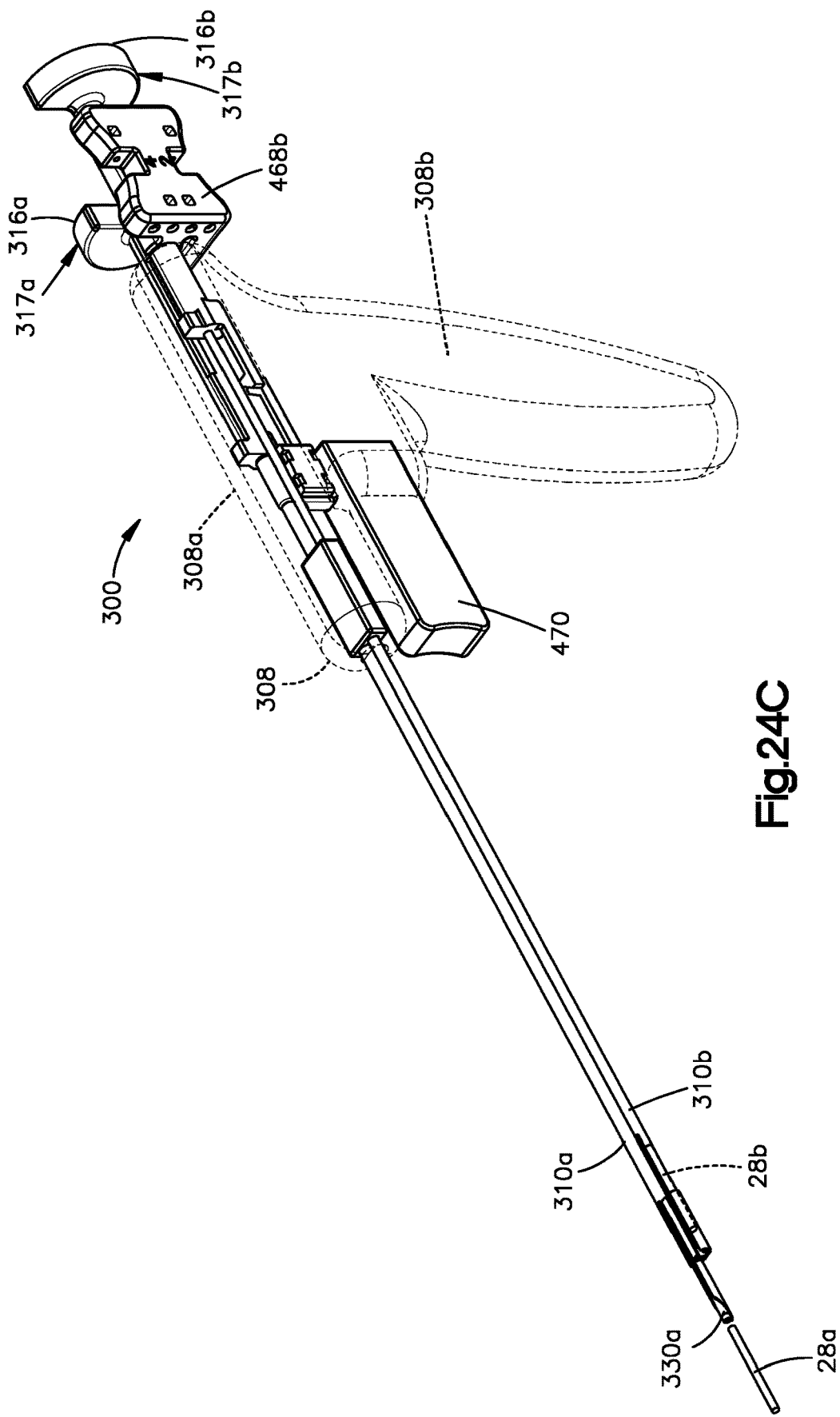
FIG. 24C is a perspective view of the insertion instrument illustrated in FIG. 24B, after actuation of the first pusher assembly to a second position.

During operation, referring to FIG. 24B, the first lock-out tab 468a can be removed from the first plunger 316a, such that the first plunger 316a can travel distally with respect to the casing 308 from the first position illustrated in FIG. 24A to a second position as illustrated in FIG. 24C, whereby the first grip portion 432a abuts the casing 308. Because the first push rod 330a is translatably fixed to the first plunger 316a, distal translation of the first plunger 316a causes the first push rod 330a to likewise translate in the first cannula 310a. The first push rod 330a abuts the first anchor body 28a, such that distal translation of the first push rod 330a ejects the first anchor body 28a out the first ejection port, for instance into the first target anatomical location.

Figure 24D:
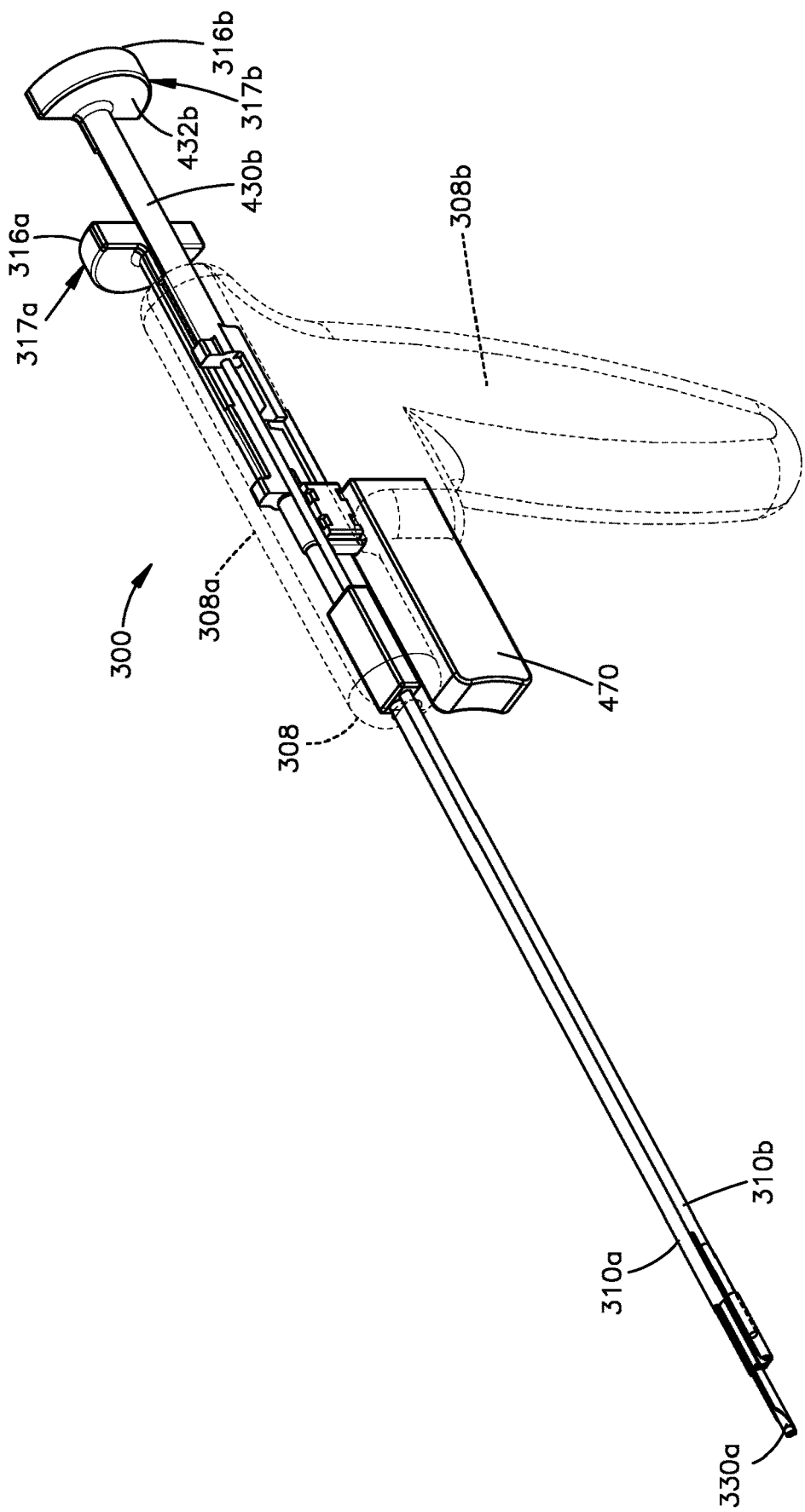
FIG. 24D is a perspective view of the insertion instrument illustrated in FIG. 24C, after removal of a second lockout tab from the second pusher assembly.
Figure 24E:
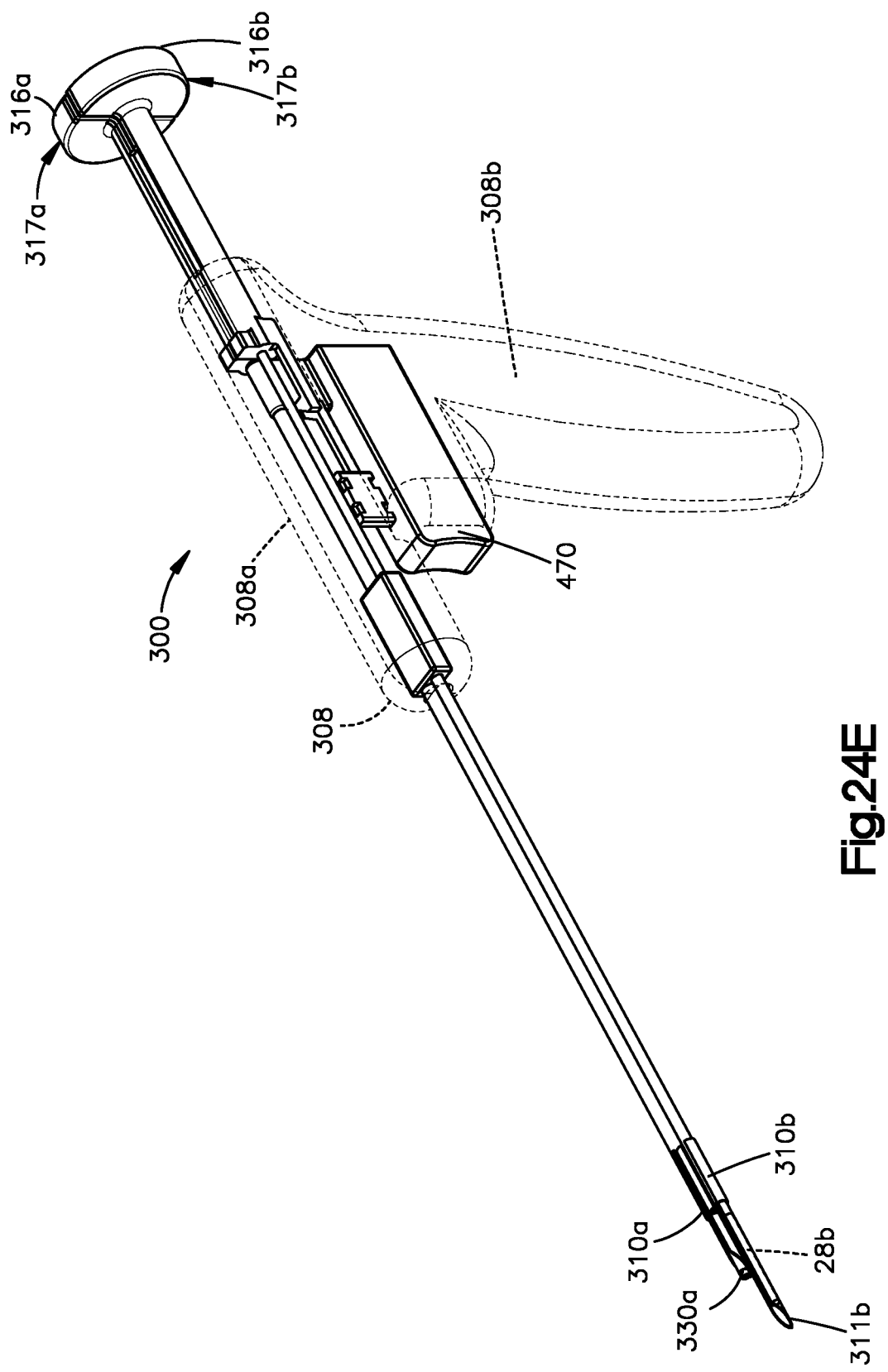
FIG. 24E is a perspective view of the insertion instrument illustrated in FIG. 24D, after actuation of a swap actuator.

Next, referring to FIG. 24D, the second lock-out tab 468b can be removed from the second plunger 316b, as illustrated in FIG. 24D. Referring to FIG. 24E, the swap actuator 470 can be actuated, for instance can be moved proximally, to retract the first tip 311a proximally with respect to the second cannula 310b until the first tip 311a is disposed proximally with respect to the second tip 311b. Furthermore, the distal end of the first push rod 330a can extend slightly out from the respective first tip 311a, such that the longitudinal distance between the distal end of the first push rod 330a and the distal end of the second tip 311b defines an insertion depth of the second tip 311b into the underlying anatomical structure. Otherwise stated, the first push rod 330a can define a depth stop for insertion of the second tip 311a into underlying tissue. It should thus be appreciated that the second tip 311b can be injected into underlying tissue, for instance at the second target anatomical location 24b (see FIG. 1A) without causing the first tip 311a to inject into the underlying tissue. In accordance with the illustrated embodiment, actuation of the swap actuator 470 further causes the first plunger 316a to translate proximally to the first position illustrated in FIG. 24A.

Figure 24F:
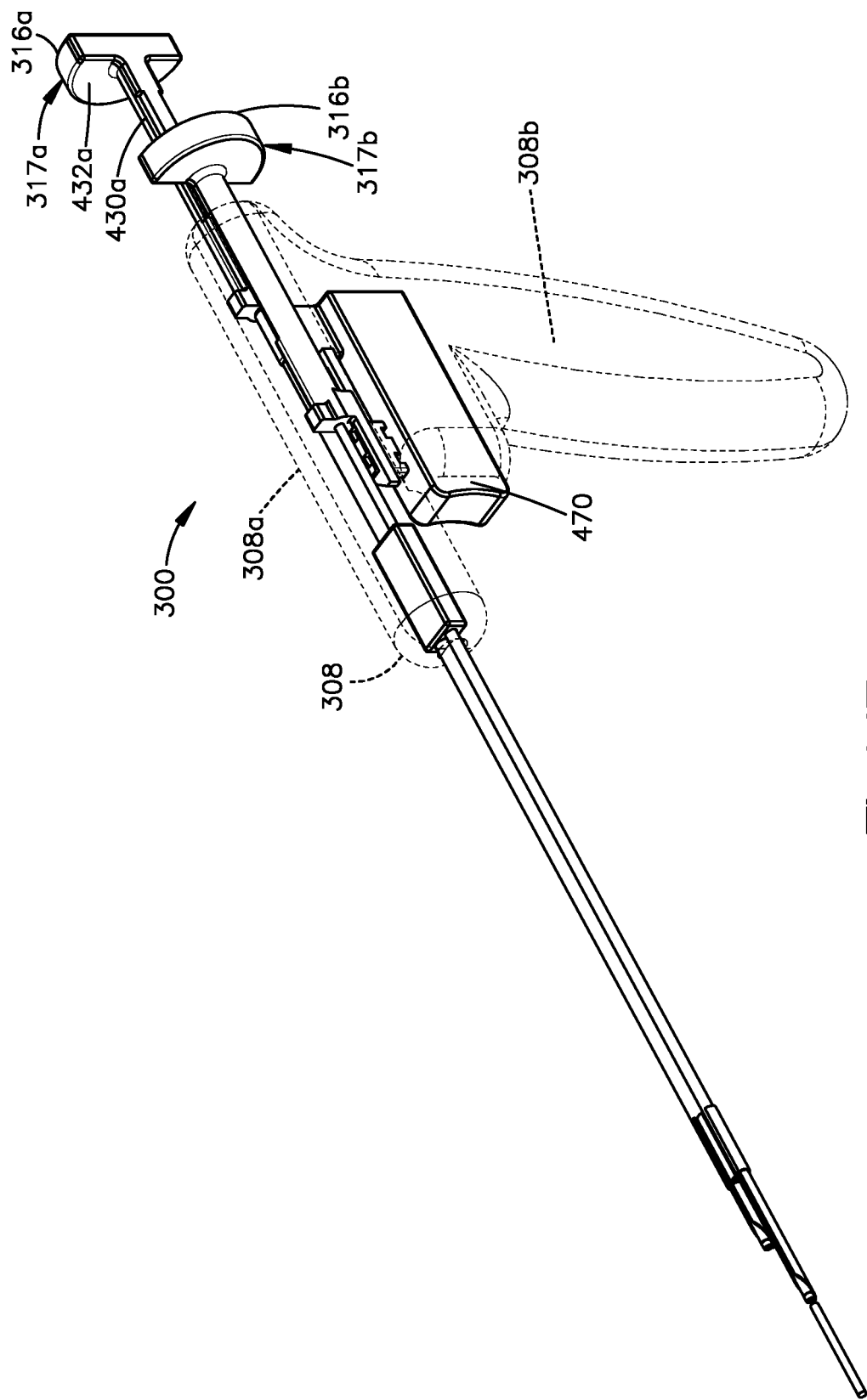
FIG. 24F is a perspective view of the insertion instrument illustrated in FIG. 24E, after actuation of the second pusher assembly to a second position.
Figure 25B:
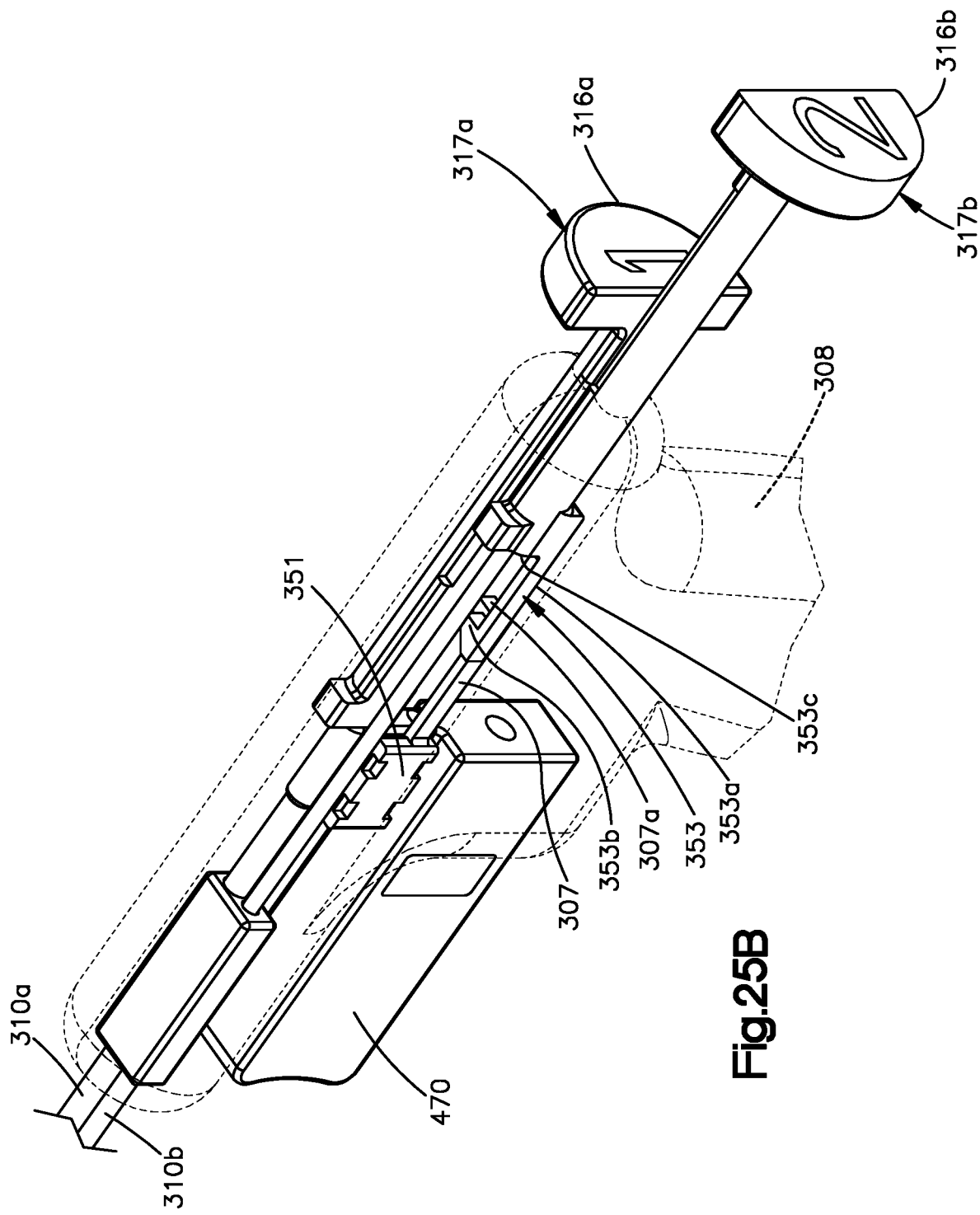
FIG. 25B is a perspective view of the components of the insertion instrument illustrated in FIG. 25A, after the first pusher assembly has been actuated to the second position.
Figure 25C:
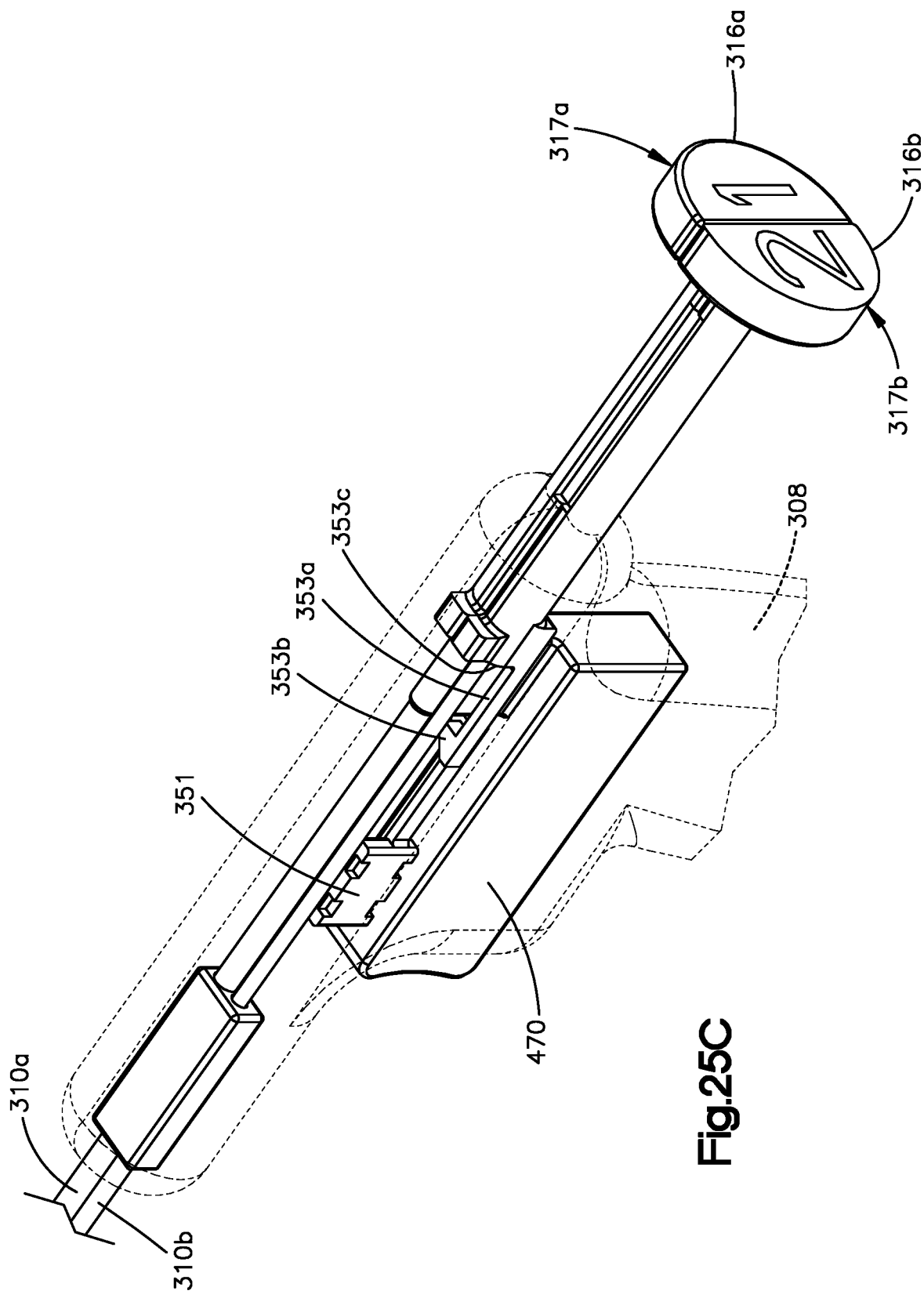
FIG. 25C is a perspective view of the components of the insertion instrument illustrated in FIG. 25B, after actuation of the swap actuator.
Figure 25D:
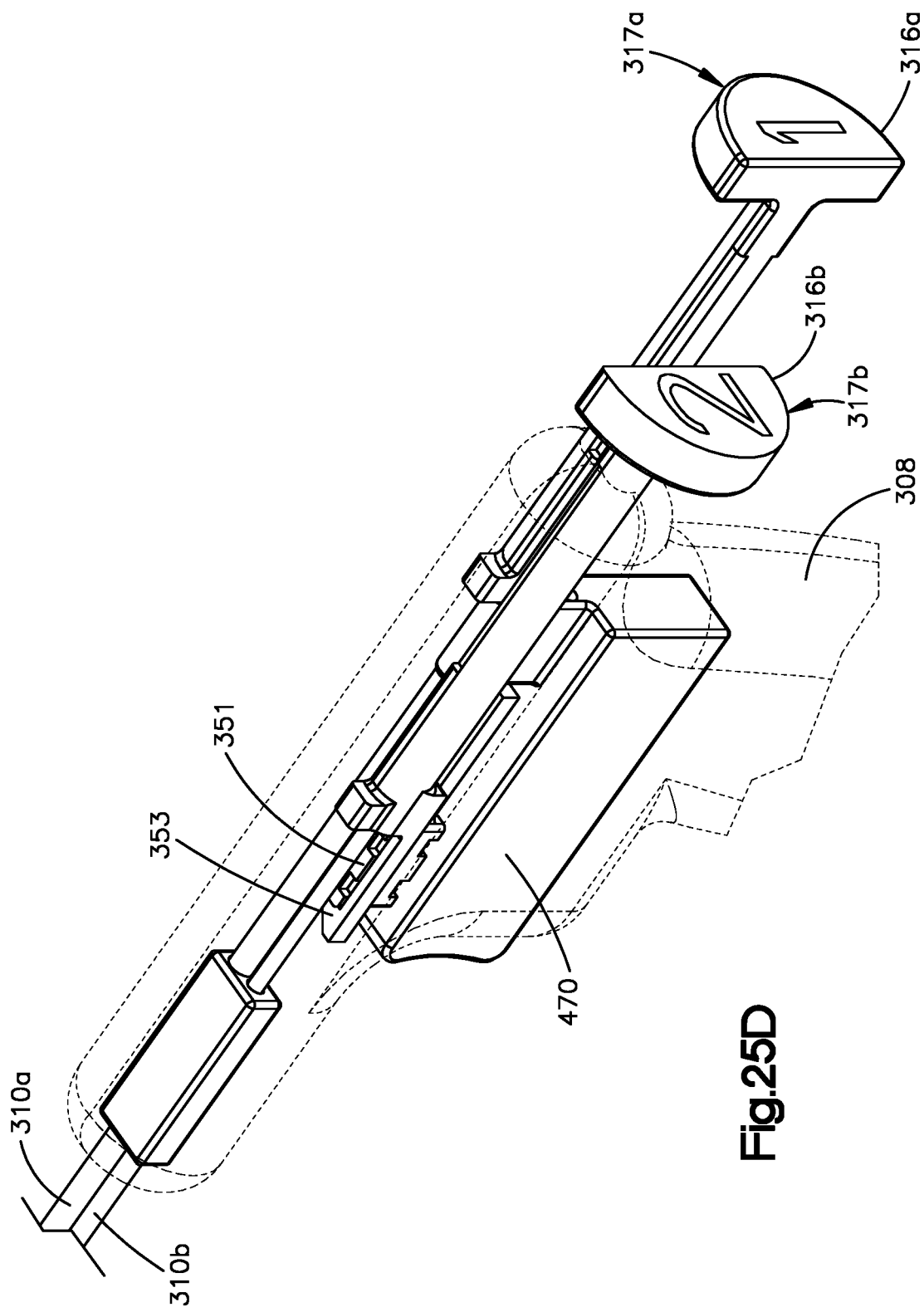
FIG. 25D is a perspective view of the components of the insertion instrument illustrated in FIG. 25C, after the second pusher assembly has been actuated to the second position.

Referring now to FIG. 24F, the second plunger 316b can travel distally with respect to the casing 308 from the first position illustrated in FIG. 24E to a second position as illustrated in FIG. 24F whereby the second grip portion 432b abuts the casing 308. Because the second push rod 330b is translatably fixed to the second plunger 316b, distal translation of the second plunger 316b causes the second push rod 330b to likewise translate in the second cannula 310b, thereby ejecting the second anchor body 28b out the second ejection port 442b and into the second target anatomical location.

Operation of the insertion instrument 300 illustrated in FIGS. 24A-25D will now be further described with particular reference to FIGS. 25A-D. In particular, the insertion instrument 300 includes at least one latch assembly such as a first latch assembly 305a, a second latch assembly 305b, and a third latch assembly 305c. The first latch assembly 305a is configured to lock the swap actuator 470 in its proximal position once it has been moved proximally from a first position illustrated in FIG. 24D to a second recessed position illustrated in FIG. 24E. For instance, the first latch assembly 305 can include a latch member 307 that is supported by the casing 308 extends proximally toward a proximal abutment surface 307a configured to abut the swap actuator 470 once the swap actuator 470 is in its second proximal position, thereby interfering with distal movement of the swap actuator 470 relative to the casing 308. As the swap actuator 470 moves proximally, the latch member 307 can deflect inwardly away from the swap actuator 470 so as to allow proximal translation of the swap member 470 relative to the latch member 307. Once the swap actuator 470 has been moved from its first initial position to its second proximal position relative to the casing 308, the latch member 307 moves outward under its spring force such that the proximal abutment surface 307a abuts the swap actuator 470 and prevents the swap actuator 407 from moving distally from its second position with respect to the casing 308.

The second latch assembly 305b includes a first latch member 347 carried by the swap actuator 470 and movable with the swap actuator 470, and a second latch member 349 that is carried by the first plunger 316a, and is movable with the first plunger 316a. The first latch member 347 is attached to the first cannula 310a, such that the first latch member 347 causes the first cannula 310a to translate with the swap actuator 470. The second latch member 349 includes a body 349a, a first attachment portion such as a hook at the distal end of the body 349a, and a second attachment portion such as an abutment surface at the proximal end of the body (the second latch member 349 can be constructed as the mirror image of the second latch member 353 of the third latch assembly 305c described below). Accordingly, as the first plunger 316a is translated from its first position illustrated in FIG. 24A to its second position illustrated in FIG. 24B, the hook deflects inwardly away from the first latch member and rides along and past the first latch member 347. Once the first plunger 316a is in its second position illustrated in FIG. 24B such that the first anchor body 28a has been ejected, the hook of the second latch member 349 moves outward under its spring force such that the hook is disposed distal of the first latch member 347, and the abutment surface of the second latch member is disposed proximal of the first latch member 347. Accordingly, the first latch member 347 is captured between the hook of the second latch member 349 and the abutment surface of the second latch member 349. Thus, the first and second latch members 349 are coupled with respect to translation.

Accordingly, once the first anchor body 28a has been ejected from the first cannula 310a, the second latch member 349 is attached to the first latch member 347, which translatably couples the first plunger 316a to the swap actuator 470 with respect to translation. Furthermore, because the first latch member 347 is carried by the swap actuator 470 and is further attached to the first cannula 310a, movement of the swap actuator 470 proximally causes both the first cannula 310a and the first plunger 316 to move proximally to a position whereby the first tip 311a and the first push rod 330a are disposed proximal with respect to the second tip 311b, while the first push rod 330a remains disposed distal of the first tip 311a. Furthermore, because the first plunger 316a is coupled to the swap actuator 470 with respect to relative translation both proximally and distally, and because the swap actuator 470 is coupled to the casing 308 with respect to at least proximal translation, the first plunger 316 is prevented from translating proximally with respect to the casing 308 once the first anchor body 28a has been ejected. The first push rod 330a can thus provide an insertion depth stop for the second tip 311b as described above.

The third latch assembly 305c includes a first latch member 351 carried by the casing 308, and a second latch member 353 carried by the second plunger 316b. The second latch member 353 includes a body 353a, a first attachment portion 353b such as a hook at the distal end of the body 353a, and a second attachment portion 353c such as an abutment surface disposed at the proximal end of the body 353a. When the second plunger 316b is translated distally from its first position illustrated in FIG. 24E to its second distal position illustrated in FIG. 24F, for instance when ejecting the second anchor body 28b, the hook can deflect inwardly, away from the first latch member 351 and ride along and move past the first latch member 351. Once the second plunger 316b is in its second position illustrated in FIG. 24F such that the second anchor body 28b has been ejected, the hook of the second latch member 353 moves outwardly under its spring force at a location distal of the first latch member 351, and the abutment surface of the second latch member 353 is disposed proximal of the first latch member 351. The first latch member 351 is thus captured between the hook of the second latch member 353 and the abutment surface of the second latch member 353. As a result, the second plunger 316b is prevented from moving proximally or distally with respect to the casing 308 once the second anchor body 28b has been ejected, and the blunt distal end of the second push rod 330b remains distal to the second tip 311b.

Once the anchor bodies 28a and 28b have been ejected, a tensile force can be applied to the actuation portions 131a and 131b (see FIG. 1A) so as to expand the anchor bodies 28a and 28b in the manner described above. For instance, first and second tensioning strands 380a and 380b (see FIGS. 18A-18B) can be attached between the respective actuation portions 131a and 131b, and the respective lock-out tabs 468a and 468b. Accordingly, after the lock-out tabs 468a and 468b have been removed from the respective plungers 316a and 316b and the respective first and second anchor bodies 28a and 28b have been ejected, proximal movement of the lock-out tabs 468a and 468b with respect to the anchor bodies 28a and 28b causes the tensile force to be applied to the corresponding tensioning strands 380a and 380b, which communicates the tensile force to the actuation portions 131a and 131b so as to expand the anchor bodies 28a and 28b. Alternatively, the tensioning strands 380a and 380b can be secured in the casing 308 in any manner described above.

Referring now to FIGS. 26A-B, the insertion instrument 300 can include a retention assembly 490 constructed in accordance with an alternative embodiment that is configured to apply an actuation force to the first and second actuation strands 38a and 38b (see FIG. 1A). For instance, the retention assembly 490 can retain the first and second actuation strands 38a and 38b directly. In accordance with the illustrated embodiment, the retention assembly 490 retains both the actuation portions 131a and 131b and the attachment portions 133a and 133b of the first and second anchor bodies 28a and 28b, respectively, for instance when the attachment portions 133a and 133b are not attached when loaded in the insertion instrument 300. Alternatively, if the attachment portions 133a and 133b are pre-attached to each other when loaded in the insertion instrument 300, the retention assembly can retain only the actuation portions 131a and 131b. Alternatively still, as described above, at least one tensioning strand can be stitched through the first and second actuation strands 38 and 38b, respectively, and can further be retained in the retention assembly 490. Regardless of the configuration, the retention assembly can be configured to apply an actuation force to the actuation strands 38a and 38b that causes the respective anchor bodies 28a and 28b to move to their expanded configurations.

In accordance with the illustrated embodiment, the retention assembly 490 can be mounted to either or both of the cannulas, such as the first cannula 310a as shown in FIG. 26A. The retention assembly 490 can include a first locking member such as a retention housing 492 that is mounted to the first cannula 310a and defines a lateral strand-receiving gap 493 extending therein. In particular, the retention housing includes a first or proximal housing portion 492a and a second or distal housing portion 492b, such that the gap 493 is disposed between the first and second housing portions 492a and 492b. The retention assembly 490 can further include a second locking member such as a pincher 494 that can be threadedly mounted to the retention housing 492, for instance to the first housing portion 492a at a location is aligned with the gap 493. Rotation of the pincher 494 relative to the retention housing 492 in a first direction causes the pincher 494 to translate into the gap 493 toward the second housing portion 492b. Rotation of the pincher 494 relative to the retention housing 492 in a second direction opposite the first direction causes the pincher 494 to translate out of the gap 493 and away from the second housing portion 492b.

Accordingly, during operation, one or more target strands 379, such as the actuation strand or strands 38a and 38b or at least one tensioning strand can be loaded into the gap 493, and the pincher 494 can be rotated in the first direction until the retention assembly 490 captures the target strands 379 between a distal end of the pincher 494 and the second housing portion 492b. Once the first and second anchor bodies 28a and 28b have been ejected into the respective first and second target anatomical locations (see FIG. 1A), the insertion instrument can be translated proximally away from the anatomical location, thereby applying the actuation force, either directly or indirectly, to the first and second actuation strands 38a and 38b, thereby actuating the anchor bodies 28a and 28b to their expanded configurations. The pincer 494 can then be rotated along the second direction so as to increase the gap 493 until the insertion instrument 300 can be pulled free from the target strands 379. Alternatively or additionally, for instance when the target strands 379 are provided as tensioning strands, the tensioning strands can be cut while captured in the retention assembly 490. Because the cannulas 310a and 310b can define longitudinal slots that extend through one side of the cannulas 310a and 310b, the actuation strands 38a and 38b can be freed from the respective cannula, for instance out the longitudinal slot, when the corresponding anchor bodies 28a and 28b are ejected from the cannula.

Referring now to FIGS. 27A-28B generally, the insertion instrument 300 can be configured having a first and second cannulas 310a and 310b supported by the casing 308 in a side-by-side orientation that retain first and second anchor bodies 28a and 28b, and first and second pusher assemblies 317a and 317b operatively associated with the first and second cannulas 310a and 310b, respectively, so as to eject the first and second anchor bodies 28a and 28b out the respective first and second cannulas 310a and 310b. Furthermore, as described above, it can be desirable to ensure that a desired cannula from which the anchor body is to be ejected is distally disposed with respect to the other cannula, such that the desired cannula can be inserted into the underlying tissue without also inserting the other cannula.

Figure 27A:
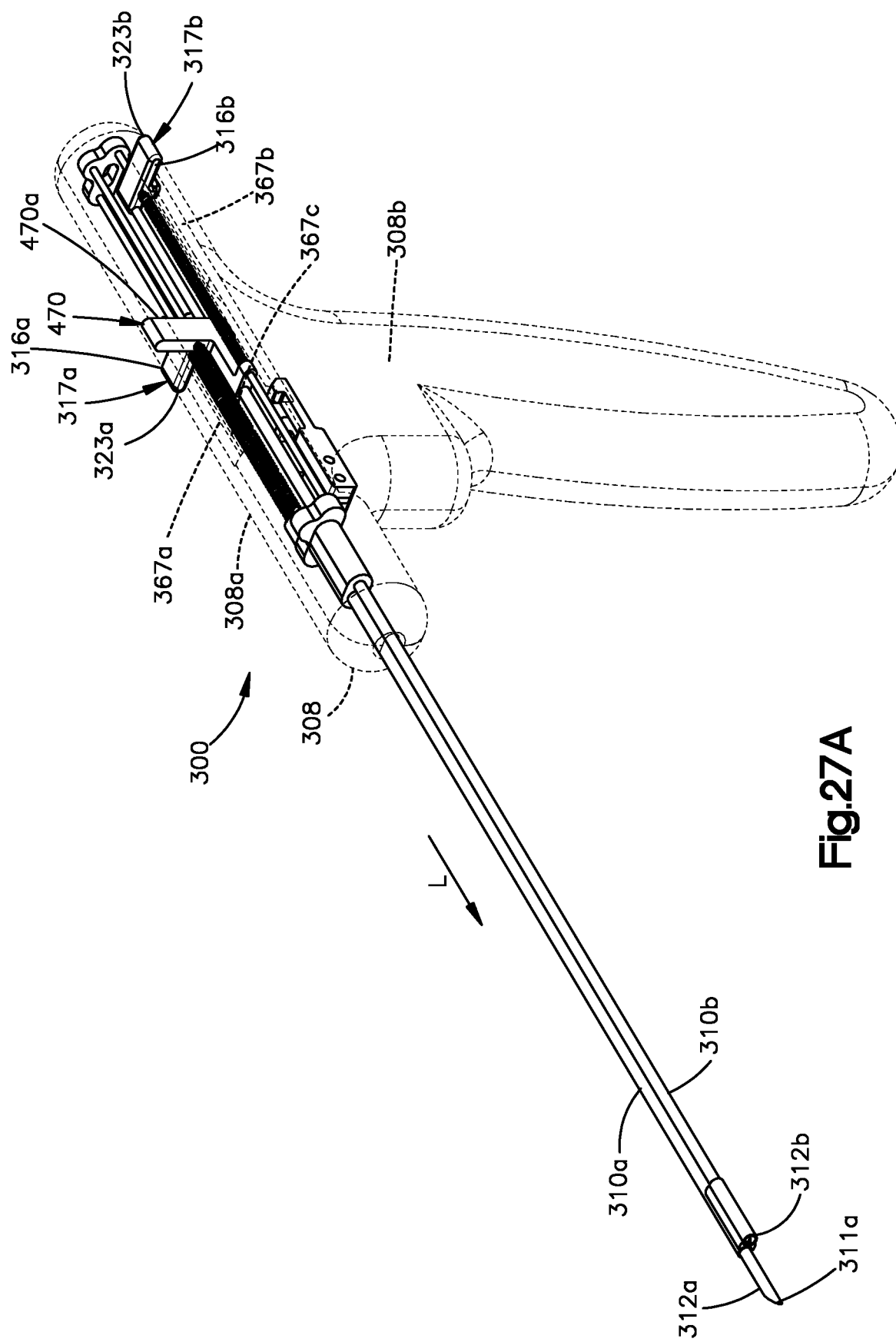
FIG. 27A is a perspective view of an insertion instrument constructed in accordance with another embodiment, the insertion instrument including first and second pusher assemblies disposed in a side-by-side relationship, showing each of the pusher assemblies in a first position.

As illustrated in FIG. 27A, the insertion instrument 300 includes a casing 308 that includes a body portion 308a and a handle portion 308b that extends out from the body portion 308a. The insertion instrument 300 further includes a first cannula 310a that extends distally from the casing 308, and in particular from the body portion 308a, and a second cannula 310b that extends distally from the casing 308, and in particular from the body portion 308a, at a location adjacent the first cannula 310a. The first and second cannulas 310a and 310b can extend substantially parallel to each other as illustrated. Accordingly, the first and second cannulas 310a and 310b can be described as being in a side-by-side relationship. The first and second cannulas 310a and 310b can define respective longitudinally elongate channels 312a and 312b that retain respective first and second anchor bodies 28a and 28b.

The insertion instrument 300 can further include first and second pusher assemblies 317a and 317b operatively associated with the first and second cannulas 310a and 310b, respectively. Thus, the first pusher assembly 317a is configured to eject the first anchor body 28a out the first cannula 310a, and the second pusher assembly 317b is configured to eject the second anchor body 28b out the second cannula 310b. The first and second cannulas 310a and 310b can define respective first and second tapered tips 311a and 311b, and first and second distal ejection ports 442a and 442b that extend longitudinally through the respective tips 311a and 311b.

Each of the first and second pusher assemblies 317a and 317b includes first and second plungers 316a and 316b, respectively, that extends out the casing 308, such as the body portion 308a of the casing 308. The first and second plungers 316a and 316b can extend proximally out the casing 308 as described above with respect to FIGS. 24A-F, or can extend out the casing along a direction angularly offset with respect to the longitudinal direction L so as to present respective tabs 323a and 323b that project out the casing 308. Each of the first and second pusher assemblies 317a and 317b can further include first and second pusher rods 330a and 330b, respectively, that extend distally from the corresponding plungers 316a and 316b. When the first and second plungers 316a and 316b are in their respective first positions (FIG. 27A), the first and second anchor bodies 28a and 28b are disposed in the respective cannulas 310a and 310b. The plungers 316a and 316b can be moved to respective second positions (FIG. 27D) so as to eject the respective first and second anchor bodies 28a and 28b out the respective cannulas 310a and 310b.

The insertion instrument 330 can further include a swap actuator 470 that can include a swap tab 470a that extends out from the casing 308, and can extend out from the body portion 308a at a location between the first and second tabs 323a and 323b. The casing 308 can defines slots 367a-c that extend through the upper end of the body portion 308 and are longitudinally elongate, and positioned such that the first and second tabs 323a and 323b extend out the first and second slots 367a and 367b, and the swap tab 470a extends out the third slot 367c at a location between the first and second tabs 323a and 323b. The slots 367a-c can thus provide tracks that define the longitudinal movement of the first and second pusher assemblies 317a and 317b and the swap actuator 470 as the tabs 323a-b and 470a ride in the respective slots 367a-c. The swap actuator 470 is configured to be moved from a first position to an actuated position so as to reverse a relative position of the first and second tips 311a and 311b. For instance, as illustrated in FIG. 27A, the first tip 311a of the first cannula 310a is disposed distally with respect to the second tip 311b of the second cannula 310b. It should thus be appreciated that the first tip 311a can be injected into underlying tissue, for instance at the first target anatomical location 24a (see FIG. 1A) without causing the second tip 311b to inject into the underlying tissue. As is described in more detail below, actuation of the swap actuator 470 from a first position (FIG. 27A) to a second position along the direction of Arrow 355 (FIG. 27C) causes the second tip 311b to move distally with respect to the first tip 311a, such that the second tip 311b can be injected into the underlying tissue, for instance at the second target anatomical location 24b (see FIG. 1B) without causing the first tip 311a to inject into the underlying tissue.

Figure 27B:
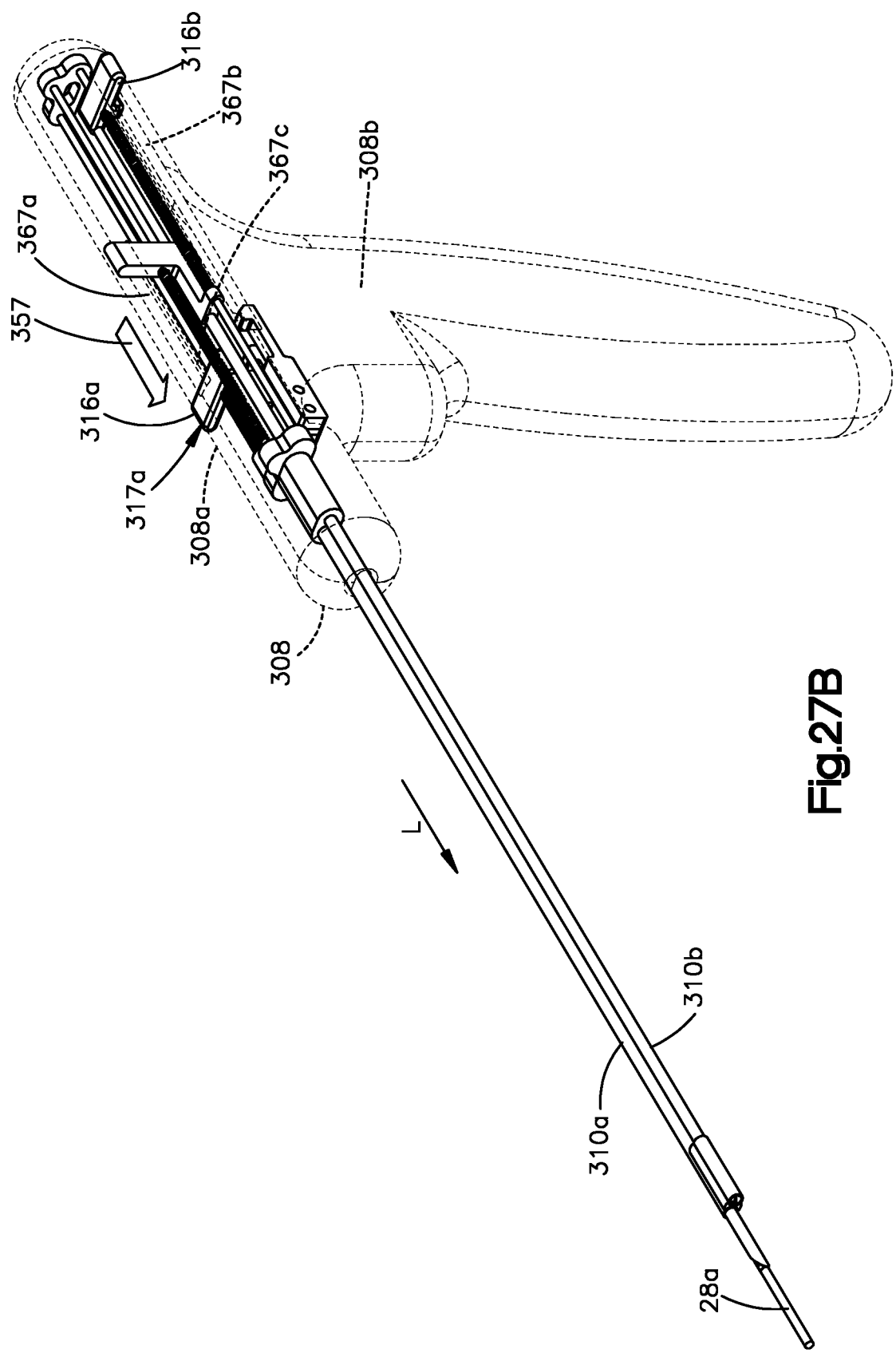
FIG. 27B is a perspective view of the insertion instrument illustrated in FIG. 27A, after actuation of the first pusher assembly to a position configuration.

During operation, referring to FIGS. 27A-B, the first plunger 316a can be translated distally along the direction of Arrow 357 from the first position to the second position, which causes the first push rod 330a to likewise translate distally in the first cannula 310a. The first push rod 330a abuts the first anchor body 28a, such that the first push rod 330a ejects the first anchor body 28a out the first cannula 310a, for instance into the first target anatomical location, as the first push rod 300a translates distally to the second position. The first plunger tab 323a abuts the casing 308 at the distal end of the first slot 367a when the first pusher assembly 317a is in the second position, whereby the first anchor body 28a has been ejected. Thus, when the first plunger tab 323a is in the second position, the plunger 316a is prevented from further distal translation. Thus, the user is provided with tactile feedback that the first anchor body 28a has been ejected.

Figure 27C:
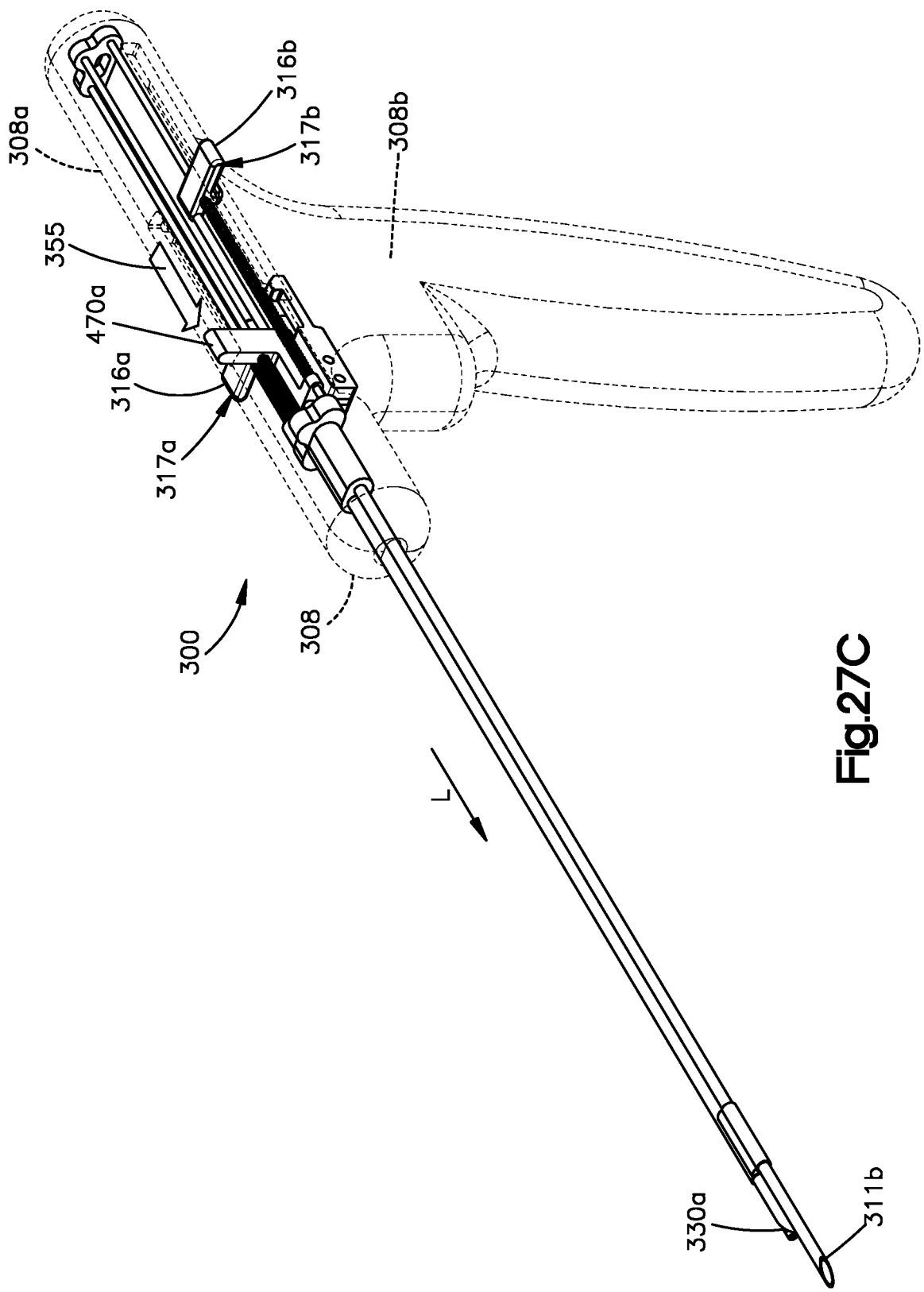
FIG. 27C is a perspective view of the components of the insertion instrument illustrated in FIG. 27B, after actuation of the swap actuator from a first position to an actuated position.

Next, referring to FIG. 27C, the swap actuator 470 can be actuated, for instance can be moved distally along the direction of Arrow 355, from the first position to the actuated position, which causes the second tip 311b to advance, or translate distally, with respect to the casing 308 and the first cannula 310a until the second tip 311b is disposed distally with respect to the first tip 311a. It should thus be appreciated that the second tip 311b can be injected into underlying tissue, for instance at the second target anatomical location 24b (see FIG. 1A) without causing the first tip 311a to inject into the underlying tissue. For instance, the distal end of the first push rod 330a, which is disposed distal with respect to the first tip 311a, can provide a depth stop for the insertion of the second tip 311b into the second target anatomical location. Thus, the second tip 311b can be injected until the first push rod 330a abuts the anatomical structure. In accordance with the illustrated embodiment, actuation of the swap actuator 470 further causes the second plunger 316b, and thus the second push rod 330b, to translate distally as illustrated in FIG. 27C. The swap tab 470a abuts the casing 308 at the distal end of the third slot 367c once the swap actuator 470 has been moved to the actuated position, such that the swap actuator 470 is prevented from further distal translation. Thus, the user is provided with tactile feedback that the swap actuator 470 has been actuated.

Figure 27D:
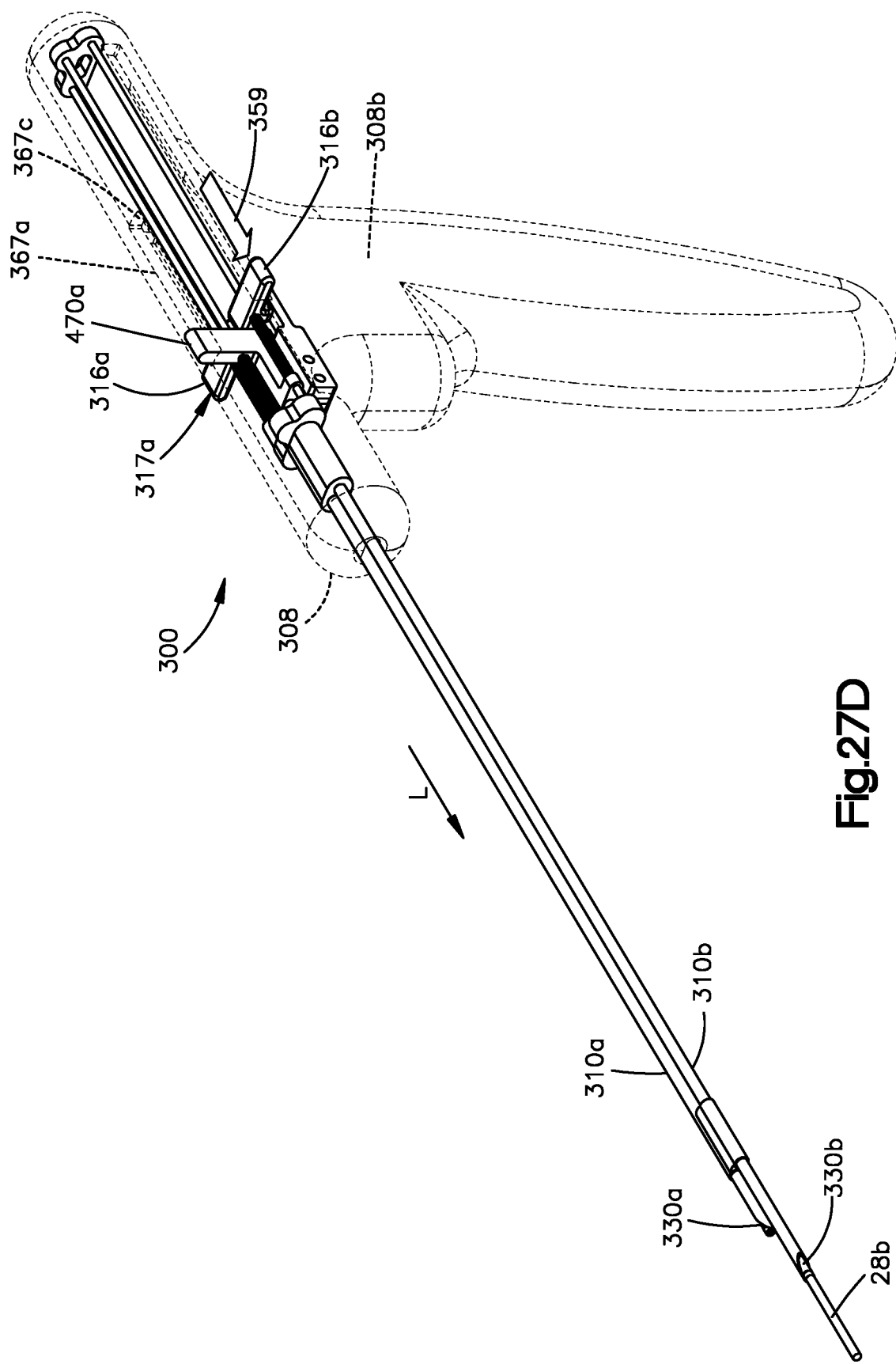
FIG. 27D is a perspective view of the insertion instrument illustrated in FIG. 27C, after actuation of the second pusher assembly to a second position.

Referring now to FIG. 27D, the second plunger 316b can be translated distally along the direction of Arrow 359 from the first position to the second position, which causes the second push rod 330b to likewise translate distally in the second cannula 310b. The second push rod 330b abuts the second anchor body 28b, such that the second push rod 330b ejects the second anchor body 28b out the second cannula 330b, for instance into the second target anatomical location, as the second push rod 300b translates distally to the second position. The second plunger tab 323b abuts the casing 308 at the distal end of the second slot 367b when the second pusher assembly 317b is in the second position, whereby the second anchor body 28b has been ejected. Thus, when the plunger tab 323b is in the second position, the plunger 316b is prevented from further distal translation. Thus, the user is provided with tactile feedback that the second anchor body 28b has been ejected.

Figure 28A:
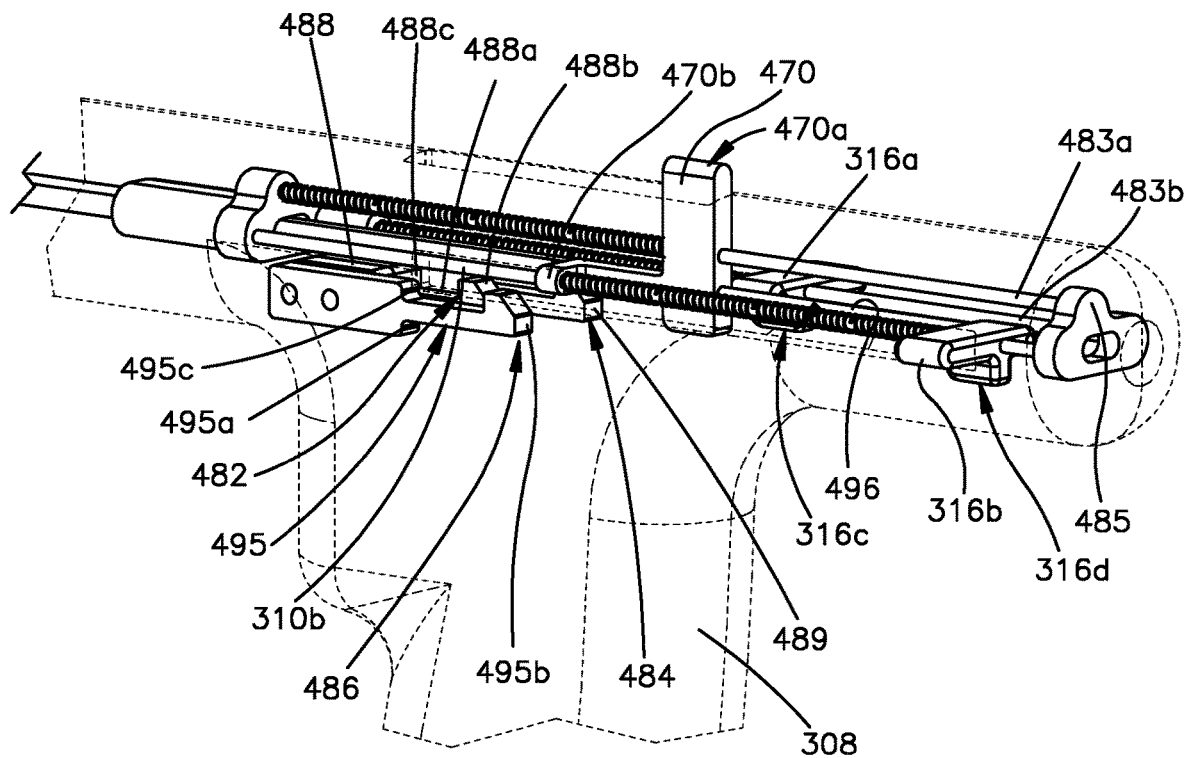
FIG. 28A is a perspective view of components of the insertion instrument illustrated in FIG. 27A, shown with the swap actuator in the first position.
Figure 28B:
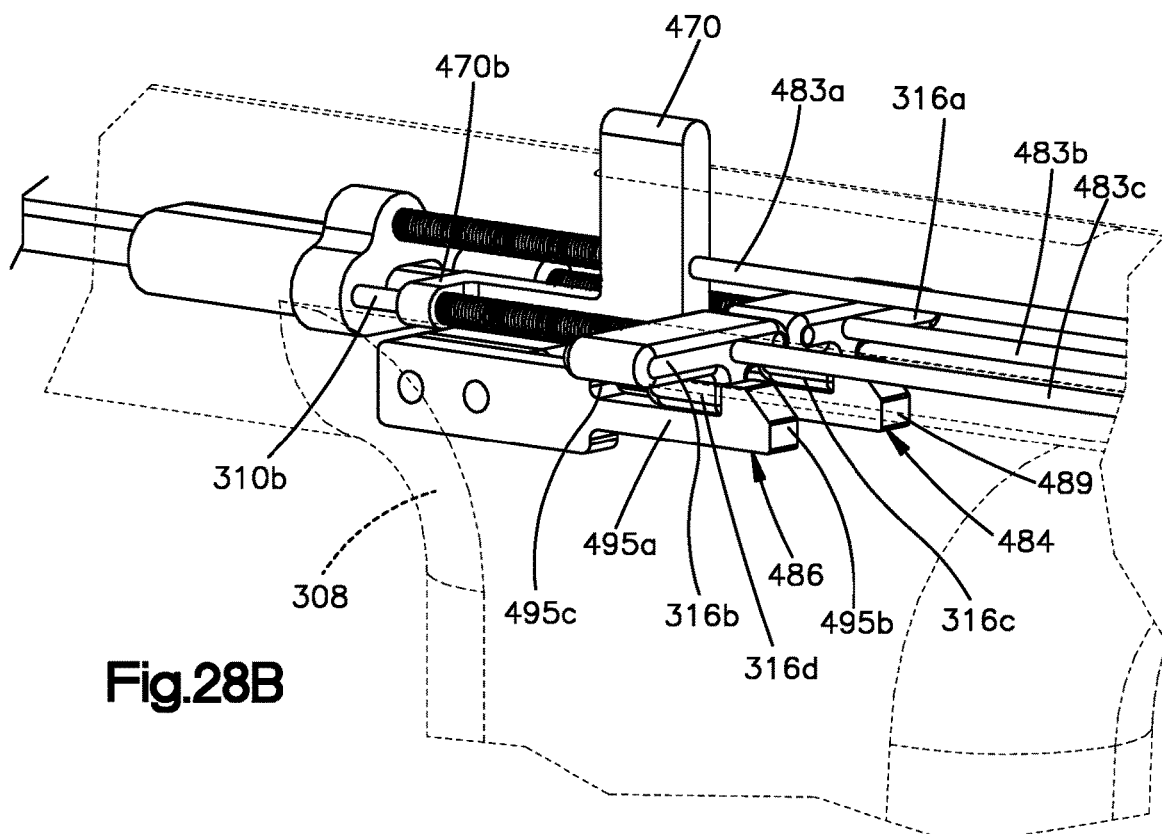
FIG. 28B is a perspective view of components of the insertion instrument illustrated in FIG. 28A, shown with the swap actuator in the second position.

Operation of the insertion instrument 300 illustrated in FIGS. 27A-28B will now be further described with particular reference to FIGS. 28A-B. In particular, the insertion instrument 300 includes at least one latch assembly such as a first latch assembly 482, a second latch assembly 484, and a third latch assembly 486. The first latch assembly 482 is configured to lock the swap actuator 470 in its distal position once it has been moved distally from a first position illustrated in FIG. 27B to a second recessed position illustrated in FIG. 27C. For instance, the first latch assembly 482 can include a latch member 488 that is supported by the casing 308 and configured to latch onto the swap actuator 470 so as to be coupled to the swap actuator 470 with respect to translation. The latch member 488 defines a body 488a, a first attachment portion 488b in the form of a hook carried by the body 488a, and a second attachment portion 488c in the form of an abutment surface carried by the body 488a disposed distal of the first attachment portion 488b. As the swap actuator 470 moves distally, the first attachment portion 488a can deflect inwardly away from the swap actuator 470 so as to allow distal translation of the swap member 470 relative to the latch member 488, such as an outwardly projecting tab 470a of the swap actuator 470. Once the swap actuator 470 has been moved from its first initial position to its second distal position relative to the casing 308, the swap actuator 470 contacts the abutment surface and the hook can deflect outward under the spring force of the body 488a, such that the swap actuator 470, for instance the tab 470a, becomes captured between the first and second attachment portions 488b and 488c. Accordingly, the latch member 488 prevents the swap actuator 470 from moving proximally and distally relative to the casing once the swap actuator 470 has been moved to its proximal position that advances the second pusher assembly 317b distally with respect to the first pusher assembly 316a.

The insertion instrument 300 can further include at least one first guide member 483a such as a guide wire that is translatably fixed to the casing 308. For instance, the insertion instrument 300 can include a mount 485 that is supported by the casing 308 and is attached to the first guide member 483a. The first guide member 483 can extend through the swap actuator 470 so as to guide the swap actuator to translate distally.

The second latch assembly 484 is configured to lock the first plunger 316a, and thus the first pusher assembly 317a, in its proximal position proximal position once it has been moved distally from a first position illustrated in FIG. 27A to a second distal position illustrated in FIG. 27B that causes the first push rod 330a to eject the first anchor body 28a. For instance, the second latch assembly 484 can include a latch member 489 that is supported by the casing 308 and configured to latch onto the first plunger 316a so as to be coupled to the first plunger 316a with respect to translation. The second latch member 489 can be constructed substantially identically with respect to the first latch member 488, and thus defines a body, a first attachment portion in the form of a hook carried by the body, and a second attachment portion in the form of an abutment surface carried by the body and disposed distal of the hook. As the first plunger 316a moves distally, the first attachment portion can deflect inwardly away from the first plunger 316a so as to allow distal translation of the first plunger 316a relative to the second latch member 489, such as an outwardly projecting tab 316c of the first plunger 316a. Once the first plunger 316a has been moved from its first initial position to its second distal position relative to the casing 308, the first plunger 316a contacts the abutment surface and the hook can deflect outward under the spring force of the body of the latch member 489, such that the first plunger 316a, for instance the tab 316c, becomes captured between the first and second attachment portions of the latch member 489. Accordingly, the latch member 489 prevents the first plunger 316a from moving proximally and distally relative to the casing 308 once the first plunger 316 has been moved to its distal position that ejects the first anchor body 28a from the first cannula 310a.

The insertion instrument 300 can further include at least one second guide member 483b such as a guide wire that is translatably fixed to the casing 308. For instance, the mount 485 can be attached to the second guide member 483b, which can extend distally through the first plunger 316a so as to guide the first plunger 316a to translate distally.

The third latch assembly 486 is configured to lock the second plunger 316b, and thus the second pusher assembly 317b, in its distal position proximal position once it has been moved distally from a first position illustrated in FIG. 27C to a second distal position illustrated in FIG. 27D that causes the second push rod 330b to eject the second anchor body 28b. For instance, the third latch assembly 486 can include a third latch member 495 that is supported by the casing 308 and configured to latch onto the second plunger 316b so as to be coupled to the second plunger 316b with respect to translation. The third latch member 495 can be constructed substantially identically with respect to the first and second latch members 488 and 489, and thus defines a body 495a, a first attachment portion 495b in the form of a hook carried by the body 495a, and a second attachment portion 495c in the form of an abutment surface carried by the body 495a at a location distal of the hook. As the second plunger 316b moves distally, the first attachment portion 495b can deflect inwardly away from the second plunger 316b so as to allow proximal translation of the second plunger 316b relative to the third latch member 495, such as an outwardly projecting tab 316d of the second plunger 316b. Once the second plunger 316b has been moved from its first initial position to its second proximal position relative to the casing 308, the second plunger 316b, for instance at the tab 316d, contacts the abutment surface 495c and the hook 495b can deflect outward under the spring force of the latch member body 495a, such that the second plunger 316b becomes captured between the first and second attachment portions of the latch member 495. Accordingly, the latch member 495 prevents the second plunger 316b from moving proximally and distally relative to the casing 308 once the second plunger 316b has been moved to its distal position that ejects the second anchor body 28b from the second cannula 310b.

The insertion instrument 300 can further include at least one third guide member 483c such as a guide wire that is translatably fixed to the casing 308. For instance, the mount 485 can be attached to the third guide member 483c, which can extend distally through the second plunger 316b so as to guide the second plunger 316b to translate distally. Furthermore, the insertion instrument 300 can include an attachment member 496 in the form of an attachment wire that attaches the second plunger 316b to the swap actuator 470 with respect to distal translation of the swap actuator 470. For instance, distal translation of the swap actuator 470 causes the second plunger 316b to translate distally along with the swap actuator 470. A distal force applied to the second plunger 316b can allow the second plunger 316b to translate distally relative to the swap actuator 470. In accordance with one embodiment, the attachment member 496 can be translatably fixed to the swap actuator 470, and can be attached to the second plunger 316b so that it interferes with the second plunger 316 with respect to proximal movement 316b of the second plunger 316b relative to the attachment member 493. The swap actuator 470 can include a second tab 470b that is attached to the second cannula 310b with respect to translation, such that distal translation of the swap actuator 470 causes the second cannula 310b to translate distally along with the swap actuator 470. Accordingly, distal translation of the swap actuator 470 causes the attachment member 496 to drag the second plunger 316b, the second cannula 310b, and the second push rod 330b distally until the second tip 311b is disposed distal of the first tip 311a. Because the first pusher rod 330a remains disposed distal of the first tip 311a after the first anchor body 28a has been ejected, the distal end of the first pusher rod 330a can define an insertion depth stop for the second tip 311b in the manner described above.

The attachment member 496 can extend at least partially through the second plunger 496b so as to allow the second plunger 496b to translate distally with respect to the attachment member 496 and therefore also with respect to the swap actuator 470. As a result, once the swap actuator 470 has been translated distally, thereby also translating the second cannula 310b and the second pusher assembly 317b distally, translation of the second plunger 316b causes the second push rod 330b to eject the second anchor body 28b from the second cannula 310b in the manner described above.

Referring now to FIGS. 29A-29G generally, the insertion instrument 300 can be configured having a first and second cannulas 310a and 310b supported by the casing 308 in a side-by-side orientation that retain first and second anchor bodies 28a and 28b, and first and second pusher assemblies 317a and 317b operatively associated with the first and second cannulas 310a and 310b, respectively, so as to eject the first and second anchor bodies 28a and 28b out the respective first and second cannulas 310a and 310b. Furthermore, as described above, it can be desirable to ensure that a desired cannula from which the anchor body is to be ejected is distally disposed with respect to the other cannula, such that the desired cannula can be inserted into the underlying tissue without also inserting the other cannula.

As illustrated in FIG. 29A, the insertion instrument 300 includes a casing 308 that includes a first casing portion 308a and a second casing portion 308b that is disposed adjacent the first casing portion 308b. The insertion instrument 300 further includes a first cannula 310a that extends distally from the first casing portion 308a, and a second cannula 310b that extends distally from the second casing portion 308b. The first and second casing portions 308a and 308b can extend substantially parallel to each other as illustrated. Accordingly, the first and second cannulas 310a and 310b can be described as being in a side-by-side relationship. The first and second cannulas 310a and 310b can define respective longitudinally elongate channels that retain respective first and second anchor bodies 28a and 28b in the manner described above. The first and second cannulas 310a and 310b can further include longitudinally elongate side slots 337a and 337b, respectively, that extend into one side of the cannulas and are in communication with the respective elongate channels. Accordingly, the attachment portions 133a-b of the actuation strands 38a and 38b can extend out the respective side slots 337a and 337b and attach to each other (see FIG. 1A) when the first and second anchor bodies 28a and 28b are loaded in the respective first and second cannulas 310a and 310b.

The insertion instrument 300 can further include first and second pusher assemblies 317a and 317b operatively associated with the first and second cannulas 310a and 310b, respectively. Thus, the first pusher assembly 317a is configured to eject the first anchor body 28a out the first cannula 310a, and the second pusher assembly 317b is configured to eject the second anchor body 28b out the second cannula 310b. The first and second cannulas 310a and 310b can define respective first and second tapered tips 311a and 311b, and first and second distal ejection ports that extend longitudinally through the respective tips 311a and 311b.

Each of the first and second pusher assemblies 317a and 317b includes first and second plungers 316a and 316b, respectively, that are disposed outside the respective first and second casing portions 308a and 308b at a location proximal with respect to the casing portions 308a and 308b as illustrated. Each of the first and second pusher assemblies 317a and 317b can further include first and second pusher rods 330a and 330b, respectively, that extend distally from the corresponding plungers 316a and 316b, through the respective first and second casing portions 308a and 308b, and into the respective first and second cannulas 310a and 310b. When the first and second plungers 316a and 316b are in their respective first positions (FIG. 29A), the first and second anchor bodies 28a and 28b are disposed in the respective cannulas 310a and 310b. The plungers 316a and 316b can be moved to respective second positions (FIG. 29F) so as to eject the respective first and second anchor bodies 28a and 28b out the respective cannulas 310a and 310b.

The insertion instrument 330 can further include a swap actuator 470 that can include a swap button 470a that extends laterally through the first casing portion 308a and into the second casing portion 308b. The swap actuator 470 is configured to selectively couple and decouple the first and second casing portions with respect to relative translation in the longitudinal direction L. For instance, as illustrated in FIGS. 29B and 29G, the first and second casing portions 308a and 308b can be slidably coupled along the longitudinal direction. For instance, one of the casing portions, such as the first casing portion 308a, can define a slot 375 extending along at least a portion of its longitudinal length. The other casing portion, such as the second casing portion 308b, can include a slider member such as a projection 377 that is configured to ride inside the slot so as to guide longitudinal movement of the first and second casing portions 308a and 308b relative to each other. The slot 375 and the projection 377 can flare angularly outward in a dovetail arrangement such that the first and second casing portions 308a and 308b are prevented from separating along a direction angularly offset from the longitudinal direction L. The swap actuator 470 is configured to move the first and second casing portions 308a and 308b relative to each other along the longitudinal direction such that the respective tips 311a and 311b move from a first relative position to a second relative position that is opposite the first relative position.

For instance, as illustrated in FIG. 29A, the first tip 311a of the first cannula 310a can be initially disposed distally with respect to the second tip 311b of the second cannula 310b. It should thus be appreciated that the first tip 311a can be injected into underlying tissue, for instance at the first target anatomical location 24a (see FIG. 1A) without causing the second tip 311b to inject into the underlying tissue. As is described in more detail below, actuation of the swap actuator 470 from a first position (FIG. 29D) to a second position causes the second tip 311b to move distally with respect to the first tip 311a such that the second tip 311b is positioned distal of the first tip 311a. Accordingly, the second tip 311b can be injected into the underlying tissue, for instance at the second target anatomical location 24b (see FIG. 1B) without causing the first tip 311a to inject into the underlying tissue.

Figure 29C:
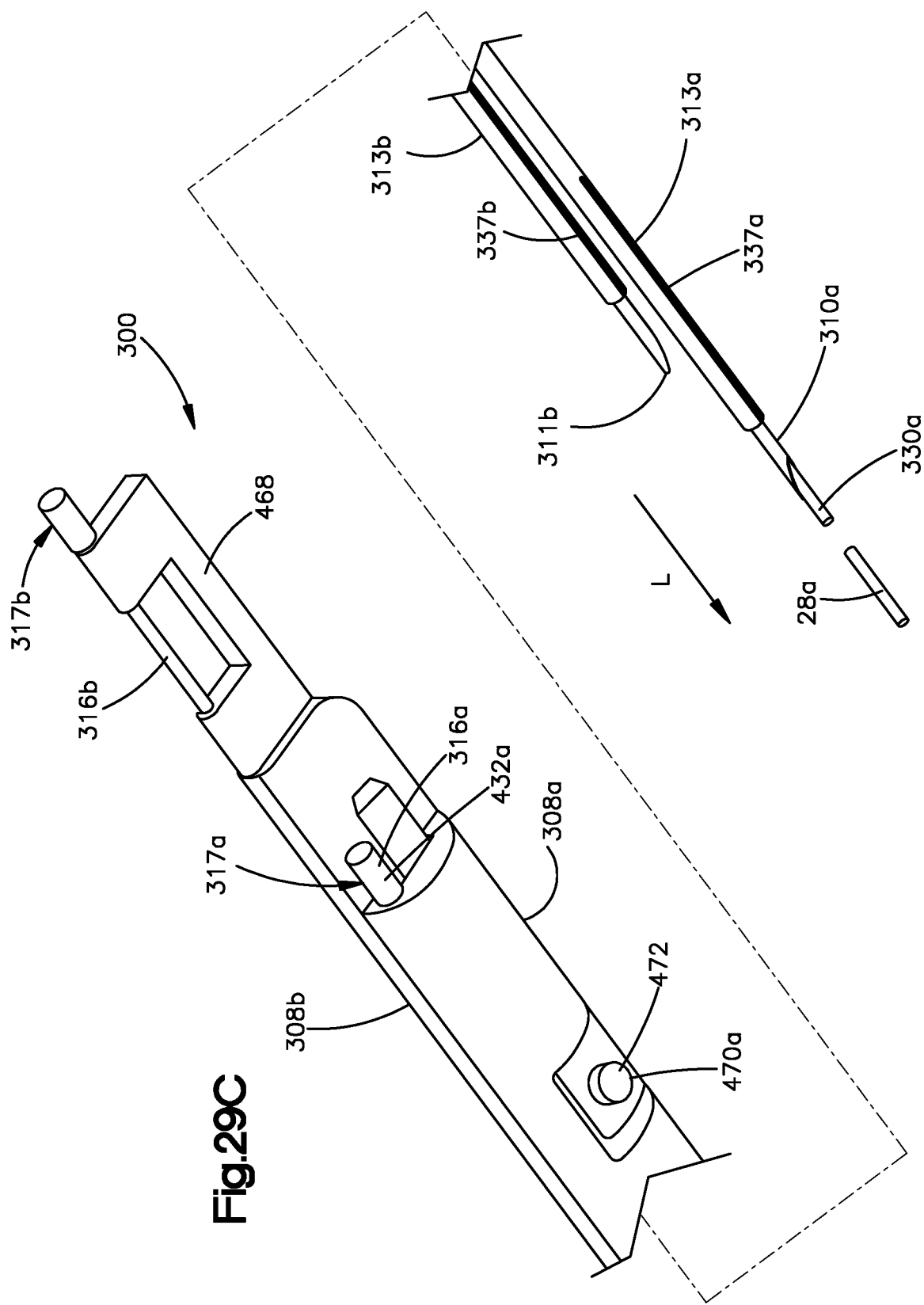
FIG. 29C is a perspective view of the insertion instrument illustrated in FIG. 29A, showing the first pusher assembly in a second position.

During operation, referring to FIG. 29C, the first plunger 316a can be translated distally from the first position to the second position, which causes the first push rod 330a to likewise translate distally in the first cannula 310a. The first push rod 330a abuts the first anchor body 28a, such that the first push rod 330a ejects the first anchor body 28a out the first cannula 310a, for instance into the first target anatomical location, as the first push rod 300a translates distally to the second position. The first plunger 316a can abuts the first casing portion 308a when the first pusher assembly 317a is in the second position, whereby the first anchor body 28a has been ejected. Thus, when the first plunger 316a is in the second position, the first plunger 316a is prevented from further distal translation. Thus, the user is provided with tactile feedback that the first anchor body 28a has been ejected.

Next, referring to FIGS. 29C, 29D, and 29G, the swap actuator 470 can be actuated so as to reverse the relative position of the first and second tips 311a and 311b in the manner described above. For instance, the swap actuator 470 can include a button 472 that extends laterally through the first casing portion 308a and into the second casing portion 308a. The second casing portion 308b can include a spring member 474 that biases the button 472 outward toward its first position. The button 472 can include at least one flange 476 that abuts a wall of the second casing portion 308b so as to prevent the force of the spring member 474 from ejecting the button 472 out the first casing portion 308a.

The first casing portion 308a can include a pair of apertures 478a-b sized to receive the button 472 such that the button 472 extends out the first casing portion 308a. The first aperture 478a is disposed proximal with respect to the second aperture 478b. When the button 472 extends through the first aperture 478a, the first tip 311a is disposed distal with respect to the second tip 311b. Furthermore, interference between the button 472 and the first casing portion 308a prevents the first casing portion 308a from translating longitudinally relative to the second casing portion 308b. When the button 472 is depressed into the slot 375, and thus into the projection 377, interference between the button 472 and the first casing portion 308a is removed, such that the first and second casing portions 308a and 308b are configured to translate longitudinally relative to each other. For instance, the second casing portion 308b, and thus the second cannula 310b, can slide distally with respect to the first casing portion 308a, and thus the first cannula 310a, until the button 472 is driven through the second aperture 478b as illustrated in FIG. 29D. When the button 472 extends through the second aperture 478b, the second tip 311b is disposed distal with respect to the first tip 311a. It should thus be appreciated that the second tip 311b can be injected into underlying tissue, for instance at the second target anatomical location 24b (see FIG. 1A) without causing the first tip 311a to inject into the underlying tissue.

Referring now to FIGS. 29D-E, the insertion instrument 300 can further include a lock-out tab 468 that is removably attached to the second push rod 330b at a location longitudinally between the corresponding plunger 316b and the second casing portion 308b. Accordingly, the lock-out tab 468 interferes with the distal translation of the plunger 316b relative to the second casing portion 308b to a depth that would eject the respective second anchor body 28b. The lock-out tab 468 can remain attached to the second push rod 330b until the first anchor body 28a has been ejected and the swap actuator 470 has been actuated. The insertion instrument 300 can further include a lock-out tab operatively associated with the first pusher assembly 317 in the manner described with respect to the second pusher assembly 317b.

Referring now to FIGS. 29E-F, once the lock-out tab 468 has been removed from the second push rod 430, the second plunger 316b can be translated distally from the first position to the second position, which causes the second push rod 330b to likewise translate distally in the second cannula 310b. The second push rod 330b abuts the second anchor body 28b, such that the second push rod 330b ejects the second anchor body 28b out the second cannula 330b, for instance into the second target anatomical location, as the second push rod 300b translates distally to the second position. The grip portion 432b of the second plunger 416b abuts the casing 308 at the distal end after the second anchor body 28b has been ejected, thereby providing the user with tactile feedback that the second anchor body 28b has been ejected.

Referring now to FIGS. 30A-D generally, the insertion instrument 300 can be configured having a first and second cannulas 310a and 310b supported by the casing 308 in a side-by-side orientation that retain first and second anchor bodies, respectively. Each of the first and second cannulas 310a and 310b is supported by the casing 308 so as to be translatably movable with respect to the casing 308. The insertion instrument 300 further includes a reciprocal motion assembly 500 that is configured to drive the first and second cannulas 310a and 310b in opposite directions. For instance, when the first cannula 310a is driven distally with respect to the casing 308, the reciprocal motion assembly 500 drives the second cannula 310b proximally with respect to the casing 308. Similarly, when the first cannula 310a is driven proximally with respect to the casing 308, the reciprocal motion assembly 500 drives the second cannula 310b distally with respect to the casing 308. Similarly, when the second cannula 310b is driven distally with respect to the casing 308, the reciprocal motion assembly 500 drives the first cannula 310a proximally with respect to the casing 308. Similarly, when the second cannula 310b is driven proximally with respect to the casing 308, the reciprocal motion assembly 500 drives the first cannula 310a distally with respect to the casing 308.

The insertion instrument 300 can include a pusher assembly 317 having a plunger 316 and first and second pusher members 330a and 330b. The first pusher member 330a extends into the first cannula 330a and is configured to eject a first anchor body out the first cannula 330a in the manner described above. Similarly, the second pusher member 330b extends into the second cannula 330b and is configured to eject a second anchor body 28b out the second cannula 330b in the manner described above. The insertion instrument further can include a selective plunger engagement assembly 502 that is operable so as to selectively engage the plunger between one of the first and second push rods 330a and 330b. Thus, the plunger 316 can be translatably coupled to the first push rod 330a, such that distal translation of the plunger 316 causes the push rod 330a to translate distally and eject the first anchor body 28a out of the respective first cannula 330a. The plunger 316 can be translatably coupled to the second push rod 330b, such that distal translation of the plunger 316 causes the push rod 330b to translate distally and eject the second anchor body 28b out of the respective first cannula 330b.

Figure 30C:
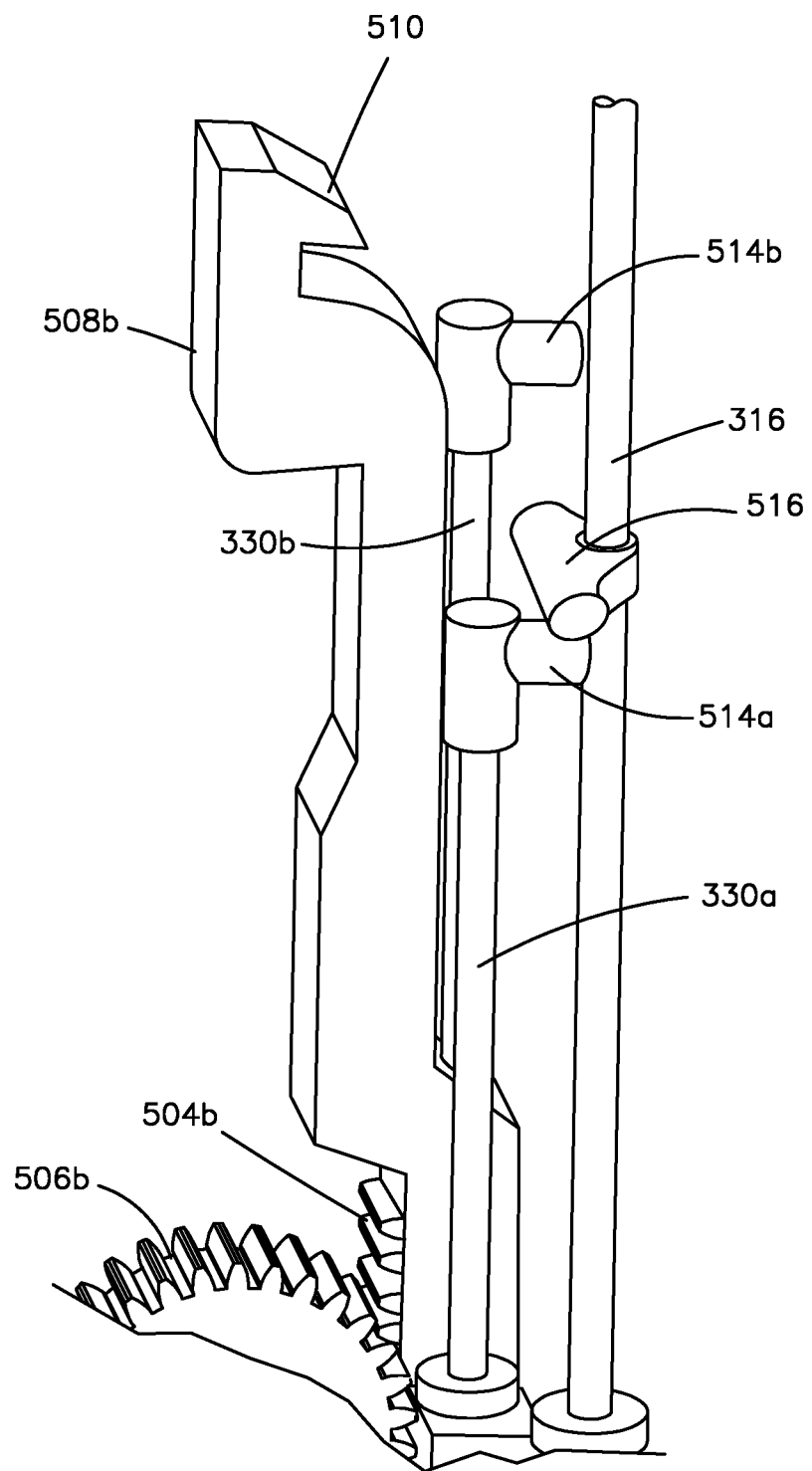

Referring now to FIGS. 30A-C, the reciprocal motion assembly 500 includes a first force transfer member, such as a toothed first rack 504a that is attached to the first cannula 310a and is translatably fixed to the first cannula 310a. The first rack 504a can be integral with the first cannula 310a or discretely attached to the first cannula 310a as desired. In accordance with the illustrated embodiment, the first rack 504a extends proximally from the first cannula 310a. The reciprocal motion assembly 500 can further include a second force transfer member such as a second toothed rack 504b that is attached to the second cannula 310b and is translatably fixed to the second cannula 310b. The second rack 504b can be integral with the second cannula 310b or discretely attached to the second cannula 310b as desired. In accordance with the illustrated embodiment, the second rack 504b extends proximally from the second cannula 310b.

The reciprocal motion assembly 500 can further include a third force transfer member such as a first gear 506a, which can be a spur gear, that mates with the first rack such that rotation of the first gear 506a drives the first rack 504a to translate substantially linearly, for instance proximally or distally. The first cannula 310a translates along with the first rack 504a. The reciprocal motion assembly 500 can further include a fourth force transfer member such as a second gear 506b, which can be a spur gear, that mates with the second rack 504b such that rotation of the second gear 506b drives the first rack 504a to translate substantially linearly, for instance proximally or distally. The second cannula 310b translates along with the second rack 504b. Furthermore, the first and second gears 506a and 506b are mated such that rotation of one of the first and second gears 506a and 506b in a first rotational direction along their respective axes of rotation 508a and 508b drives the other of the first and second gears 506a and 506b to rotate in a second rotational direction opposite the first rotational direction. The first and second gears 506a and 506b can be supported in the casing 308 such that the axes of rotation 508a and 508b remains stationary as the gears 506a and 506b rotate.

The second rack 504b can include a handle 508b that extends out the casing 308. During operation, for instance when the first cannula 310a extends distal with respect to the second cannula 310b, the handle 508b can be driven distally, which causes the second cannula 310b and the second rack 504b to translate distally, thereby rotating the second gear 506b along a direction of rotation. The second gear 506b drives the first gear 506a to rotate along an opposite direction of rotation, which causes the first cannula 310a to translate proximally toward the casing 308. Thus, as the second cannula 310b is driven distally, the reciprocal motion assembly drives the first cannula 310 in an opposite direction, such as proximally as illustrated.

When the second cannula 310b extends distal with respect to the first cannula 310a, the handle 508b can be driven proximally, which causes the second cannula 310b and the second rack 504b to translate proximally, thereby rotating the second gear 506b along a direction of rotation. The second gear 506b drives the first gear 506a to rotate along an opposite direction of rotation, which causes the first cannula 310a to translate distally away from the casing 308. Thus, as the second cannula 310b is driven proximally, the reciprocal motion assembly drives the first cannula 310a in an opposite direction, such as distally as illustrated.

The handle 508b can include a hook 510 that latches onto the casing 308 so as to provide a safety catch that prevents distal translation of the handle 508, and thus also distal translation of the second rack 504b. The hook 510 can be configured to latch onto the casing 308 when the second cannula 310b is retracted, and the first cannula 310a is extended and disposed distal with respect to the second cannula 310b.

Figure 30D:
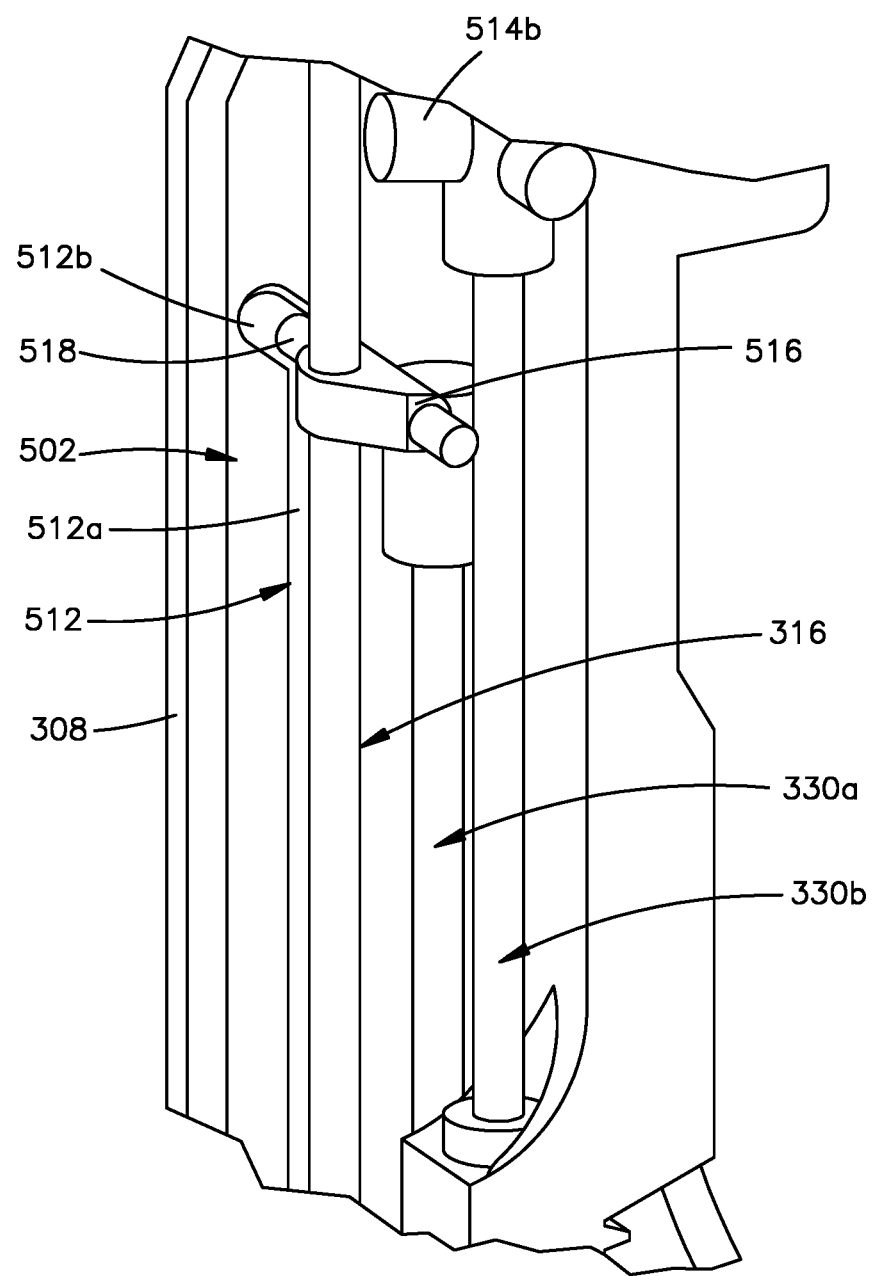

Referring now to FIGS. 30C-D, the selective plunger engagement assembly 502 includes a track 512 carried by the casing 308. The track 512 can extend radially outward into an inner wall of the casing 308. The track includes a first portion 512a that extends substantially longitudinally and parallel to the cannulas 310a and 310b and the push rods 330a and 330b. The track further includes a second portion 512b that extends from the first portion 512a, for instance from the proximal end of the first portion 512a, and extends proximally and outward, such as laterally outward, from the first portion 512b. Thus, it can be said that the second portion 512b is offset with respect to the first portion 512a. In accordance with the illustrated embodiment, the second portion 512b is angularly offset with respect to the first portion 512a.

The plunger 316 is configured to ride in the track 512, and is movable distally along the track 512 so as to drive a select one of the first and second push rods 330a and 330b distally within a respective one of the first and second cannulas 310a and 310b so as to eject the respective one of the first and second anchors out the insertion instrument. In accordance with the illustrated embodiment, the first and second push rods 330a and 330b carry first and second engagement members 514a and 514b. The engagement members 514a and 514b can be spaced from each other so as to provide clearance as the first and second cannulas 310a and 310b are driven reciprocally. It should be appreciated that because the first and second push rods 330a and 330b extend into the respective first and second cannulas 310a and 310b, the push rods 330a and 330b are likewise driven reciprocally during reciprocal movement of the cannulas 310a and 310b.

The plunger 316 carries a biasing member 516 that is longitudinally aligned with each of the engagement members 514a and 514b when the plunger 316 is disposed in the first track portion 512a. The plunger 316 further carries a follower 518 that is sized and shaped so as to ride in the track 512 and guide the travel path of the plunger 316 as the plunger is driven proximally and distally. The plunger 316 can include a proximal end that extends out, for instance proximally out, from the casing 308. Thus, the plunger 316 can be driven distally along the first track portion 512a and proximally along the first track portion 512a. The plunger can further be driven proximally along the second track portion 512b, which causes the biasing member 516 to move out of longitudinal alignment with the engagement members 514a and 514b. Thus, the cannulas 310a and 310b, and the respective push rods 330a and 330b, can move reciprocally without the engagement members 514a and 514b interfering with each other, and further without the engagement members 514a and 514b interfering with the biasing member 516 of the plunger 316.

When it is desired to eject one of the anchor bodies out of the respective cannula, for instance the first cannula 310a, the first push rod 330a can be placed into alignment with the plunger 316. For instance, the reciprocal motion assembly 500 can be actuated as desired so as to position the respective engagement member 514a distal of the proximal end of the first track portion 512a. Accordingly, the plunger 316 can be driven distally along the track 512. Once the plunger 512 travels distally along the first track portion 512a, the biasing member 516 engages the engagement member 514a, and drives the push rod 330a distally in the respective cannula 310a, thereby ejecting the anchor body out the cannula 310a as described above.

Once it is desired to eject the second anchor body from the second cannula 310b, the plunger 316 can be driven proximally onto the second track portion 512b until the biasing member 516 is out of longitudinal alignment with the engagement members 514a and 514b of the first and second push rods 330a and 330b. Next, the reciprocal motion assembly 500 can be actuated so as to drive the second cannula 310b and second push rod 330b distally, which causes the first cannula 310a and the first push rod 330a to translate proximally, until the first engagement member 514a is disposed proximal of the proximal end of the first track portion 512a, and the second engagement member 514b is disposed distal of the proximal end of the first track portion 512a. Thus, the second cannula 310b is disposed distal with respect to the first cannula 310a. Next, the plunger 316 can be driven distally, which causes the biasing member 516 to engage the second engagement member 514b, which drives the second push rod 330b distally in the second cannula 330b so as to eject the second anchor out the insertion instrument.

Figure 31:
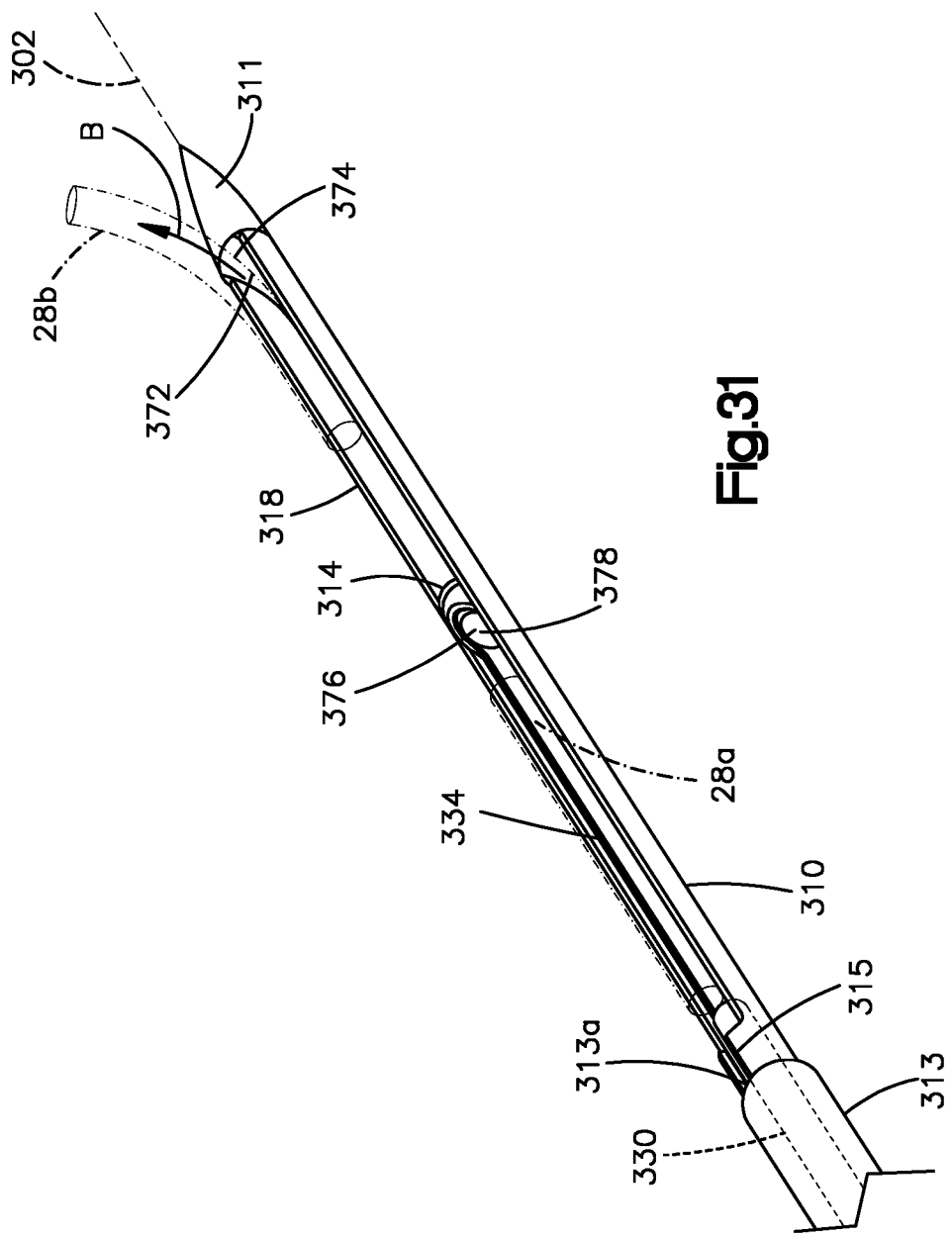

Referring now to FIG. 31, while various insertion instruments 300 have been described as including a distal ejection port 442, the insertion instruments 300 can define a side ejection port 318 as an alternative to the distal ejection port 442. For instance, the side ejection port 318 can be defined as a slot that extends radially through a distal portion of the cannula 310 at a location proximal with respect to the tip 311. The tip 311 can be closed so as to prevent the anchor bodies 28a and 28b from ejecting out the distal ejection port 442 that is defined by the tip 311. The side ejection port 318 can define a circumferential dimension at least substantially equal to or greater than the largest cross-sectional dimension of each of the first and second anchor bodies 28a and 28b, such that the anchor bodies 28a and 28b are sized to travel through the side ejection port 318. Furthermore, the side ejection port 318 can define a longitudinal length that is substantially equal to or greater than the longitudinal length of each of the first and second anchor bodies 28a and 28b. The longitudinal length of the side ejection port 318 can be slightly less than that of each of the first and second anchor bodies 28a and 28b, for instance, if the first and second anchor bodies 28a and 28b are angularly offset with respect to the longitudinal axis 302 as they are ejected out the side ejection port 318.

The tip 311 can define a ramp 372 at its proximal end. The ramp 372 can thus be disposed at the distal end of the side ejection port 318 and substantially aligned with the longitudinal axis 302. The ramp 372 can define a tapered ejection surface 374 that is angled radially outward toward the side ejection port 318 as it extends distally. Accordingly, as the plug 314 biases the second anchor body 28b distally from the elongate opening 312 of the cannula 310 onto the ejection surface 374 as the plunger 316 and push tube 334 collar 332 move from the first position to the second position, second anchor body 28b rides along the ejection surface 374, which directs the second anchor body 28b out the side ejection port 318 along the direction of Arrow B, thereby ejecting the second anchor body 28b out the insertion instrument 300 at the second target anatomical location 24b (see FIG. 1A). When the at least the distal portion of the side ejection port 318 is disposed behind the anatomical structure 24, the second anchor body 28b is ejected from the insertion instrument 300 at a location behind the anatomical structure 24, as further shown in FIG. 1A. The insertion instrument 300 can be configured such that the plug 314 is disposed proximal to and adjacent to the tip 311 when the push rod 330 and the push tube 334 become decoupled. Accordingly, translation of the push rod 330 relative to the push tube 334 causes the push rod to eject the first anchor 28a along the ramp surface 378 of the plug 314 in the manner described above, and out the side ejection port 318.

Referring now to FIGS. 32A-M, an example embodiment of an insertion instrument 600 configured to insert an anchor 22 into a target anatomical location 24 is illustrated. In accordance with the illustrated embodiment, the target anatomical location 24 is a bone, but the insertion instrument 600 can be used to insert an anchor 22 into any other suitable target anatomical location, as described herein elsewhere. The illustrated insertion instrument 600 can include components comprising an access assembly 602 and/or an anchor inserter assembly 604.

The access assembly 602 can be used to prepare a target anatomical location 24 for insertion of at least one, such as a plurality of anchors 22, as described in more detail below, and/or to provide access for one or more components of the anchor inserter assembly 604 to at least one, such as a plurality of target anatomical locations 24. The access assembly 602 can include an access member 606 and an opening creating member 608 configured to be disposed in the access member 606, such as the illustrated awl 609.

The illustrated access member 606 is elongate along the longitudinal direction L, and includes an access member body 610 that extends between a proximal end 610a and an opposed distal end 610b, which can define the distal end 610b of the insertion instrument 600. In this regard, reference made to the distal end 610b can be likewise made to the distal end of the insertion instrument 600, unless otherwise indicated. The access member 606 defines a cannulation 612 that extends therethrough along a longitudinal, or central axis C. The cannulation 612 can be sized to receive therein at least a portion of the awl 609, such that the access member 606 is configured to carry the awl 609. For example, the cannulation 612 can define a diameter D1 that is slightly larger than an outer diameter D2 of a complementary portion of the awl 609.

In accordance with the illustrated embodiment, the access member body 610 can be a two part body including a tubular portion 614 having opposed proximal and distal ends 614a, 614b and a holder portion 616 having opposed proximal and distal ends 616a, 616b. The holder portion 616 can define an outer diameter that is larger than the outer diameter of the tubular portion 614. The holder portion 616 can further define at least one, such as a plurality of axial bores extending into the holder portion. For example, the holder portion 616 can cleat define a first bore 616c that extends into the holder portion 616 from the distal end 616b thereof, the first bore 616c sized to secure the tubular portion 614 to the holder portion 616. Optionally, the holder portion 616 can further define a second bore 616d that extends into the holder portion 616 from the proximal end 616a thereof, the second bore 616d sized to receive an alternative embodiment of the anchor housing 634 in the form of a sleeve 660, as described in more detail below.

The proximal end 614a of the tubular portion 614 can be at least partially recessed in the distal end 616b of the holder portion 616. For example, the holder portion 616 can be overmolded onto the tubular portion 614. Alternatively, the tubular portion 614 can be otherwise attached to the holder portion 616. Alternatively still, the access member body 610 can be constructed monolithically, such that the tubular portion 614 and the holder portion 616 are integral with respect to each other. It should be appreciated that the access member body 610 is not limited to the cylindrical tubular and holder portions 614, 616, and that the access member body 610 can alternatively be constructed defining any other geometry, as desired.

The access member 606 can define a contact surface 618, for instance at the proximal end 610a of the access member 606. The contact surface 618 can be configured to abut a complementary contact surface defined by the awl 609, for instance when the awl 609 is fully inserted with respect to the access member 606. The access member can be configured to be at least partially inserted into an opening 25 defined at a target anatomical location 24 (see FIG. 32F). The opening 25 can be defined by the awl 609, as described in more detail below. The outer surface of the tubular portion 614 of the access member 606 can define at least one, such as a plurality of depth markings, the depth markings spaced at respective pre-determined distances relative to the distal end 610b of the access member 606. The depth markings can be used to determine the insertion depth of the distal end 610b of the access member 606 relative to the opening 25.

The awl 609 is elongate along the longitudinal direction L, and includes an opening creating member body 620 that extends between a proximal end 620a and an opposed distal end 620b. In accordance with the illustrated embodiment, the awl body 620 can include a shaft portion 622 having opposed proximal and distal ends 622a, 622b and a holder portion 624 having opposed proximal and distal ends 624a, 624b. The shaft portion 622 can define an outer diameter D2 that is slightly smaller than the diameter D1 of the cannulation 612, such that the awl 609 can be translated along the longitudinal direction L relative to the access member 606 when the awl 609 is carried by the access member 606.

The holder portion 624 can define an outer diameter that is larger than the outer diameter D2 of the shaft portion 622, and can be substantially equal to that of the holder portion 616 of the access member 606. It should be appreciated that the awl body 620 is not limited to the cylindrical tubular and holder portions 622, 624, and that the awl body 620 can alternatively be constructed defining any other geometry, as desired.

The shaft portion 622 of the awl 609 can have a length, as defined between the proximal and distal ends 622a, 622b, that is longer than the length of the access member 606, as defined between the proximal and distal ends 610a, 610b, such that at least a portion of the shaft portion 622 protrudes beyond the distal end 610b of the access member 606 when the awl 609 is fully inserted with respect to the access member 606. The protruding portion of the shaft portion 622 can be biased into a target anatomical location 24, so as to create an opening 25 at the target anatomical location 24, the opening sized to receive the anchor 22 therein.

The awl 609 can define a contact surface 626 that can be intermediate with respect to the proximal and distal ends 620a, 620b. For instance, the contact surface 626 can be defined at the distal end 624b of the holder portion 624 of the awl 609. The contact surface 626 can be configured to abut a complementary contact surface of the access member 606, such as the contact surface 618, for instance when the awl 609 is fully inserted with respect to the access member 606. The awl 609 can further define an impact surface 628, for instance at the proximal end 620a of the body 620, the impact surface 628 configured to receive one or more impaction forces, as described in more detail below.

In accordance with the illustrated embodiment, the awl 609 can further define a tip 630 at the distal end 620b of the body 620, the tip 630 configured to penetrate into tissue and/or bone at a target anatomical location 24. The illustrated tip 630 can define a conical shape that tapers distally at the distal end 620b of the body 620. The conical tip 630 can be configured to be biased into a target anatomical location 24, acting like an awl or punch to create an opening 25 at the target anatomical location 24, as described in more detail below. The base portion of the conical tip 630 can define a diameter that is slightly smaller than the outer diameter D2 of the awl 609, such that the distal end 620b of the body 620 defines a ledge 631 adjacent the base of the conical tip 630, the ledge 631 configured to core tissue and/or bone during creation of the opening 25. Coring tissue and/or bone displaced by the awl 609 during creation of the opening 25 can mitigate tissue collapse upon withdrawal of the awl 609 from the opening 25.

In accordance with an alternative embodiment, the opening creating member 608 can be configured as a drill 611 (see FIG. 32D). For example, the shaft portion 622 of the opening creating member 608 can define at least one, such as a plurality of boring flutes 632 that extend helically from the tip 630 along a direction toward the contact surface 626, the flutes 632 configured to create the opening 25 by boring material from the target anatomical location 24 when a rotational force is applied to the drill 611.

In a first portion of an example anchor insertion procedure, the access assembly 602 can be used to create an opening 25 at a target anatomical location 24. For example, in a first step the shaft portion 622 of the awl 609 can be inserted into the cannulation 612 of the access member 606 and distally advanced within the cannulation 612 until the contact surfaces 618 and 626 abut one another. The tip 630 of the awl 609 can then be placed at a desired penetration point at the target anatomical location 24. The awl 609 can then be biased into the target anatomical location 24 by applying at least one, such as a plurality, of impaction forces against the impaction surface 628 of the awl 609. As the shaft portion 622 advances into the target anatomical location 24, the opening 25 can be defined by the tip 630 and the ledge 631 of the shaft portion 622. As the access assembly 602 advances further into the target anatomical location 24, the distal end 614b of the shaft portion 614 of the access member 606 can be at least partially inserted into the opening 25 (see FIG. 32E), for example until one of the above-described depth markings is substantially aligned with an outer surface of the target anatomical location 24. At least partially inserting the access member 606 into the opening 25 can secure the access member 606 with respect to the opening 25. Once the access member 606 is secured within the opening 25, the awl 609 can be withdrawn from the access member 606 (see FIG. 32F). With the awl 609 removed, the access member 606 is configured to provide access to the target anatomical location 24, and more specifically the opening 25, by other components of the insertion instrument 600.

For example, the anchor inserter assembly 604 can then be used to insert and/or expand an anchor 22 within the opening 25, as described in more detail below. The illustrated anchor inserter assembly 604 includes the access member 606, an anchor housing 634 that releasably carries the anchor 22 and is configured to be inserted into the access member 606, and a pusher member 636 configured to be inserted into the anchor housing 634 and configured to eject the anchor 22 from the anchor housing 634.

The illustrated anchor housing 634 is elongate along the longitudinal direction L, and includes an anchor housing body 638 that extends between a proximal end 638a and an opposed distal end 638b. The anchor housing 634 defines a cannulation 640 that extends therethrough in the longitudinal direction L along the central axis C. The cannulation 640 can be sized to releasably carry the anchor 22 therein. For instance, the cannulation 640 can have a diameter D3 that is sufficiently narrow to support the anchor 22 within the cannulation 640 such that the anchor 22 will not fall out of the anchor housing 634, and sufficiently wide to allow the anchor to be translated within the cannulation 640 along the longitudinal direction L, for example responsive to a force applied to the anchor 22 by the pusher member 636.

In accordance with the illustrated embodiment, the anchor 22 is disposed at the distal end 638b of the anchor housing 634, with at least one or more actuation members 37 (for instance, at least one actuation strand 38, such as actuation strands 38 when the anchor includes a plurality (e.g., greater than two) actuation strands) extending freely within the cannulation 640 and out the proximal end 638a of the anchor housing 634. It should be appreciated that the anchor 22 could alternatively be disposed at a different location within the cannulation 640 as desired. The cannulation 640 can further be sized to receive therein at least a portion of the pusher member 636, such that the anchor housing 634 is configured to carry the pusher member 636. For example, the diameter D3 can be slightly larger than an outer diameter D4 of a complementary portion of the pusher member 636, such that the pusher member 636 can be translated longitudinally within the cannulation 640.

The anchor housing body 638 can be a two part body including a tubular portion 642 having opposed proximal and distal ends 642a, 642b and a holder portion 644 having opposed proximal and distal ends 644a, 644b. The holder portion 644 can define an outer diameter that is larger than the outer diameter of the tubular portion 642. The tubular portion 642 can have an outer diameter that is substantially equal to that of the awl 609. In other words, tubular portion 642 can have an outer diameter D2, such that the anchor housing 634 can be translated along the longitudinal direction L relative to the access member 606 when the anchor housing 634 is carried by the access member 606. The proximal end 642a of the tubular portion 642 can be at least partially recessed in the distal end 644b of the holder portion 644. For example, the holder portion 644 can be overmolded onto the tubular portion 642. Alternatively, the tubular portion 642 can be otherwise attached to the holder portion 644. Alternatively still, the anchor housing body 638 can be constructed monolithically, such that the tubular portion 642 and the holder portion 644 are integral with respect to each other. It should be appreciated that the anchor housing body 638 is not limited to the cylindrical tubular and holder portions 642, 644, and that the anchor housing body 638 can alternatively be constructed defining any other geometry, as desired.

In accordance with the illustrated embodiment, the anchor housing 634 can define at least one, such as a pair of contact surfaces, for example at opposed ends of the holder portion 644, the contact surfaces configured to abut complementary contact surfaces of the access member 606 and the pusher member 636. More specifically, the anchor housing 634 can define a first contact surface 646 that can be intermediate with respect to the proximal and distal ends 638a, 638b. For instance, the contact surface 646 can be defined at the distal end 644b of the holder portion 644. The contact surface 646 can be configured to abut a complementary contact surface of the access member 606, such as the contact surface 618, for instance when the anchor housing 634 is fully inserted with respect to the access member 606. The anchor housing 634 can further define a second contact surface 648, for instance at the proximal end 644a of the holder portion 644. The contact surface 648 can be configured to abut a complementary contact surface of the pusher member 636, such as the contact surface 658, for instance when the pusher member 636 is fully inserted with respect to the anchor housing 634.

The shaft portion 642 of the anchor housing body 638 can have a length, as defined between the distal end 644b of the holder portion 644 and the distal end 642b of the shaft portion 642, that is longer than the that of the access member 606, such that the distal end 638b of the anchor housing 634 protrudes beyond the distal end 610b of the access member 606 when the anchor housing 634 is fully inserted with respect to the access member 606 (see FIG. 32I). The anchor housing 634 is fully inserted with respect to the access member when the contact surface 646 abuts the contact surface 618.

The illustrated pusher member 636 is elongate along the longitudinal direction L, and includes a pusher member body 650 that extends between a proximal end 650a and an opposed distal end 650b. The pusher member 636 defines a cannulation 652 that extends therethrough in the longitudinal direction L along the central axis C. The cannulation 652 can be sized such that the pusher member 636 will cause the anchor 22 to eject from the anchor housing 634 and into the opening 25, as described in more detail below, and to carry the actuation strands 38 of the anchor 22 therein and out the proximal end 638a of the anchor housing 634.

In accordance with the illustrated embodiment, the pusher member body 650 can be a two part body including a tubular portion 654 having opposed proximal and distal ends 654a, 654b and a holder portion 656 having opposed proximal and distal ends 656a, 656b. The tubular portion 654 can have an outer diameter D4 that is slightly smaller than the diameter D3 of the cannulation 640 of the anchor housing 634, such that the pusher member 636 can be translated along the longitudinal direction L relative to the anchor housing 634 when the pusher member 636 is carried by the anchor housing 634. The holder portion 656 can define an outer diameter that is larger than the outer diameter of the tubular portion 654. The proximal end 654a of the tubular portion 654 can be at least partially recessed in the distal end 656b of the holder portion 656. For example, the holder portion 656 can be overmolded onto the tubular portion 654. Alternatively, the tubular portion 654 can be otherwise attached to the holder portion 656. Alternatively still, the pusher member body 650 can be constructed monolithically, such that the tubular portion 654 and the holder portion 656 are integral with respect to each other. It should be appreciated that the pusher member body 650 is not limited to the cylindrical tubular and holder portions 654, 656, and that the pusher member body 650 can alternatively be constructed defining any other geometry, as desired.

The pusher member 636 can define a contact surface 658 configured to abut a complementary contact surface of the anchor housing 634, for instance when the pusher member 636 is fully inserted with respect to the anchor housing 634. The contact surface 658 can be intermediate with respect to the proximal and distal ends 650a, 650b. For instance, the contact surface 658 can be defined at the distal end 656b of the holder portion 656. The contact surface 658 can be can be configured to abut a complementary contact surface of the anchor housing 634, such as the contact surface 648, for instance when the pusher member 636 is fully inserted with respect to the anchor housing 634.

The shaft portion 654 of the pusher member body 650 can have a length, as defined between the distal end 656b of the holder portion 656 and the distal end 654b of the shaft portion 654, that is longer than that of the access member 606 and the holder portion 644 of the anchor housing 634, such that the distal end 650b of the pusher member 636 protrudes from the distal end 610b of the access member 606 and the distal end 638b of the anchor housing 634 when the anchor housing 634 and the pusher member 636 are fully inserted with respect to the access member 606 (see FIG. 32K). The pusher member 636 is fully inserted with respect to the anchor housing 634 when the contact surface 658 abuts the contact surface 648.

In a second portion of the above described example anchor insertion procedure, once the access assembly 602 has been used to create an opening 25 at a target anatomical location 24, and to secure the access member 606 with respect to the opening 25, the anchor inserter assembly 604 can be used to insert an anchor 22 into the opening 25. For example, the shaft portion 642 of the anchor housing 634 can be inserted into the cannulation 612 of the access member 606 and distally advanced within the cannulation 612 until the contact surfaces 618 and 646 abut one another (see FIG. 32I). With the anchor housing 634 fully inserted with respect to the access member 606, the pusher member 636 can be used to eject the anchor 22 out the distal end 610b of the access member 606 and into the opening 25. For instance, the tubular portion 654 of the pusher member 636 can be inserted into the cannulation 640 of the anchor housing 634 and distally advanced within the cannulation 640. As the tubular portion 654 of the pusher member 636 advances within the cannulation 640, the distal end 650b of the pusher member 636 can come into contact with the anchor 22 and cause the anchor 22 to translate toward the distal end 610b of the access member 606 and to eject out the distal end 610b of the access member 606 (see FIG. 32K).

When the anchor 22 has been ejected out the distal end 610b of the access member 606 and into the opening 25, a tensile force can be applied to the actuation strands 38, thereby causing the anchor 22 to expand within the opening 25 and become secured with respect to the target anatomical location 24 (see FIG. 32L). During application of the tensile force to the actuation strands 38, a force can be applied to one or more of the components of the anchor inserter assembly 604, the force applied in a direction that is substantially opposed to the direction of the tensile force, for example in a direction toward the target anatomical location 24. When the anchor 22 has been expanded and secured within the opening 25, the components of the anchor inserter assembly 604 can be removed from the target anatomical location 24.

Referring now to FIG. 32M, the anchor housing can alternatively be provided as a sleeve 660, the sleeve configured to carry the anchor 22, to be disposed on the end of the pusher member 636 such that the pusher member 636 carries the sleeve 660, and to be inserted into the access member 606. The sleeve 660 can include a cylindrical sleeve body 664 that extends between a proximal end 664a and an opposed distal end 664b. The sleeve body 664 can be sized to be received in the second bore 616d of the access member

606. The sleeve body 664 can define a cannulation 662 configured to releasably carry the anchor 22. For instance, in accordance with the illustrated embodiment, the sleeve 660 is configured to carry the anchor 22 such that when the sleeve is carried by the pusher member 636, the distal end 650*b* of the pusher member 636 abuts the proximal end of the anchor 22. The sleeve 660 can further be sized such that when the anchor 22 is disposed in the sleeve 660, the anchor 22 will resist translation within the cannulation 662 until the sleeve is fully inserted with respect to the access member 606. The sleeve body 664 can further define a contact surface 666, for example at the proximal end 664*a*, the contact surface 666 configured to abut the contact surface 618 when the sleeve 660 is fully inserted with respect to the access member 606. The contact surface 666 of the illustrated sleeve 660 is defined by a flange 668 defined by the proximal end 664*a* of the sleeve body 664.

In operation, the sleeve 660 can be inserted into the cannulation 612 of the access member 606 and distally advanced within the cannulation 612 until the contact surfaces 666 and 618 abut one another. Alternatively, the sleeve 660 can be inserted into the cannulation 612 of the access member 606 and distally advanced within the cannulation 612 until the distal end 664*b* of the sleeve abuts the distal end 616*e* of the second bore 616*d*. In accordance with the illustrated embodiment, the anchor 22 will not translate within the cannulation 662 until the sleeve 660 is fully inserted with respect to the access member 606. Once the sleeve 660 is fully inserted with respect to the access member 606, further application of force to the pusher member 636 will cause the distal end 650*b* of the pusher member 636, thereby causing the anchor 22 to translate through the cannulation 662 of the sleeve 660 and through the cannulation 612, and to eject out the distal end 610*b* of the access member 606. Once the anchor 22 has been ejected out the distal end 610*b* of the access member 606 and into the opening 25, the anchor can be expanded and the components of the anchor inserter assembly 604 removed as described above.

Referring now to FIGS. 33A-C, an alternative embodiment of the insertion instrument 600' is illustrated. The insertion instrument 600' can include the access assembly 602, utilized for instance to create the opening 25. The insertion instrument 600' can further include an anchor inserter assembly 604' that can include components of the anchor inserter assembly 604, such as the access member 606 and the anchor housing 638 and/or the sleeve 660. The anchor inserter assembly 604' can further include a tension assembly, such as tension assembly 700, the tension assembly 700 configured to apply a predetermined tension force characteristic to the actuation strands 38 of an anchor 22.

In accordance with the illustrated embodiment, the tension assembly 700 includes a pusher member 702, a motion assembly that can include a first traveling member such as a translating member 704 that is configured to travel, such as translate a predetermined distance, with respect to the distal end 610*b* of the access member 606, and can further include a second traveling member, such as a rotatable member 706, that is operatively coupled to the pusher member 702 and the translating member 704, such that rotation of the rotatable member 706 causes the translating member 704 to translate the predetermined distance with respect to the distal end 610*b* of the access member 606 and further with respect to the pusher member 702. It will be appreciated from the description below that the tension assembly 700 likewise causes the actuation strand 38 to travel substantially the predetermined distance. In this regard, it should be appreciated that the tension force characteristic can be a predetermined distance.

The pusher member 702 can be constructed substantially the same as the pusher member 636, with the pusher member 702 further including at least one, such as a pair of coupling members 708, the coupling members 708 configured to interface with complementary coupling members 710 defined by the rotatable member 706, thereby operatively coupling the pusher member 702 to the rotatable member 706 such that the rotatable member 706 can rotate with respect to the pusher member 702. In accordance with the illustrated embodiment, the pusher member 702 can define a pair of coupling members 708 in the form of a pair of projections 712, the projections 712 extending from opposed sides of the pusher member 702 along a common rotation axis R that extends along the lateral direction A. The projections 712 can be configured to interface with complementary coupling members 710 defined by the rotatable member 706, such as apertures 714. The rotatable member 706 can be configured to be rotatable about the rotation axis R, such that the pusher member 702 can remain stationary with respect to the rotatable member 706 when the rotatable member 706 is rotated.

The translating member 704 can include at least one, such as a pair of coupling members 708, the coupling members 708 configured to interface with complementary coupling members 710 defined by the rotatable member 706, thereby operatively coupling the translating member 704 to the rotatable member 706. The translating member 704 can be configured to translate distally between a neutral position and an extended position with respect to the pusher member 702, for instance along the longitudinal direction L. For example, the translating member 704 can be configured to translate between the neutral and extended positions when the rotatable member 706 is rotated about the rotation axis R, thereby translating with respect to the distal end 610*b* of the access member 606.

The actuation strands 38 of the anchor 22 can be releasably attached to the translating member 704, for example by cleating the actuation strands 38 to the translating member 704, such that when the translating member 704 translates proximally with respect to the distal end 610*b* of the access member 606, the translating member 704 can apply a tensile force to the actuation strands 38 of the anchor 22, thereby causing the anchor 22 to expand within the opening 25. Thus, it should be appreciated that the translating member 704 can define a grip assembly that is configured to releasably attach to the actuation strand 38 so as to apply the tensile actuation force to the actuation strand when the translating member travels the predetermined distance. The degree to which the anchor 22 expands can be dependent upon the magnitude of the tensile force applied to the actuation strands 38 by the translating member 704. The magnitude of the tensile force can be dependent upon the distance between the neutral and extended positions through which the translating member 704 translates. Therefore, the magnitude of the tensile force that the translating member 704 will apply to the actuation strands 38 can be at least partially determined by the predetermined distance between the neutral and extended positions of the translating member 704.

The distance between the neutral and extended positions can be determined by the coupling members 708 defined by the translating member 704 and complementary coupling members 710 defined by the rotatable member 706. For example, in accordance with the illustrated embodiment, the translating member 704 can define a pair of coupling members 708 in the form of a pair of projections 716, the projections 716 extending from opposed sides of the translating member 704 along a common axis that extends along the lateral direction A. The projections 716 can be configured to interface with complementary coupling members 710 defined by the rotatable member 706, such as slots 718, each slot 718 extending between opposed proximal and distal slot ends 718a, 718b, respectively. The translating member 704 can be in the neutral position when the projections 716 are disposed at the proximal slot ends 718a, and can be in the extended position when the projections 716 are disposed at the distal slot ends 718b. Rotation of the rotatable member 706 about the rotation axis R can cause the projections 716 to translate in the slots 718 between the proximal and distal slot ends 718a, 718b, thereby causing the translating member 704 to translate between the neutral and extended positions.

The rotatable member 706 can include at least one, such as a pair of coupling members 710, the coupling members 710 configured to interface with complementary coupling members 708 defined by the pusher member 702 and/or the translating member 704, thereby operatively coupling the rotatable member 706 to the pusher member 702 and/or the translating member 704. In accordance with the illustrated embodiment, the rotatable member 706 includes a pair of plate like body members 720, the plate like members body 720 disposed on opposed sides of the pusher and translating members 702, 704. Each plate like body member 720 defines a first coupling member 710 in the form of an aperture 714 defined therethrough, the aperture 714 configured to receive a respective projection 712 of the pusher member 702, and a second coupling member 710 in the form of an elongated slot 718 defined therethrough, the slot 718 extending between proximal and distal slot ends 718a, 718b, the slot 718 configured to receive a respective projection 716 of the translating member 704. The illustrated slots 718 are linear between the proximal and distal slot ends 718a, 718b but the slots can alternatively define other geometries. For instance, the slots 718 could be curved. The plate like body members 720 can be coupled to each other, for example by a pair of bridging elements 722. In accordance with the illustrated embodiment, the translating member 704 can be translated from the neutral position to the extended position by rotating the rotatable member through substantially ninety degrees. It should be appreciated that the tension assembly 700 is not limited to the illustrated geometries of the various components thereof, and that one or more components of the tension assembly 700 can alternatively be constructed with any other suitable geometry as desired, for instance body members 720 having different geometries.

In accordance with an example anchor insertion procedure utilizing the insertion instrument 600', the access assembly 602 can be used to create an opening 25 at a target anatomical location 24 and/or to secure the access member with respect to the target anatomical location 24. Once the access member 606 is secured, the anchor inserter assembly 604' can be used to insert an anchor 22 into the opening 25. For example, the shaft portion 642 of the anchor housing 634 can be inserted into the cannulation 612 of the access member 606 and distally advanced within the cannulation 612 until the contact surfaces 618 and 646 abut one another. With the anchor housing 634 fully inserted with respect to the access member 606, the tension assembly 700 can be used to eject the anchor 22 out the distal end 610b of the access member 606 and into the opening 25. For instance, the tubular portion 654 of the pusher member 702 can be inserted into the cannulation 640 of the anchor housing 634 and distally advanced within the cannulation 640. As the tubular portion 654 of the pusher member 702 advances within the cannulation 640, the distal end 650b of the pusher member 702 can come into contact with the anchor 22 and cause the anchor 22 to translate toward the distal end 610b of the access member 606 and to eject out the distal end 610b of the access member 606.

When the anchor 22 has been ejected out the distal end 610b of the access member 606 and into the opening 25, the tension assembly 700 can be used to apply the tensile force to the actuation strands 38, thereby causing the anchor 22 to expand within the opening 25 and become secured with respect to the target anatomical location 24. The tensile force can be applied to the actuation strands 38 by applying a rotational force to the rotatable member 706, thereby causing the projections 716 to translate from the proximal slot ends 716a to the distal slot ends 716b, and causing the translating member 704 to translate from the neutral position to the extended position. As the translating member 704 translates from the neutral to the extended position, the translating member 704 can apply the tensile force to the actuation strands 38, thereby causing the anchor 22 to expand within the opening 25 and become secured with respect to the target anatomical location 24.

During rotation of the rotatable member 706, a force can be applied to one or more of the components of the anchor inserter assembly 604', the force applied in a direction that is substantially opposed to the direction of the tensile force exerted on the actuation strands 38, for example in a direction toward the target anatomical location 24. When the anchor 22 has been expanded and secured within the opening 25, the components of the anchor inserter assembly 604' can be removed from the target anatomical location 24.

Referring now to FIGS. 34A-C, still another alternative embodiment of the insertion instrument 600" is illustrated. The insertion instrument 600" can include the awl 609 of the access assembly 602, utilized for instance to create the opening 25. The insertion instrument 600" can further include an anchor inserter assembly 604" can include a variety of components, such as an access member 606", an anchor housing 638" and/or the sleeve 660 of the anchor inserter assembly 604. The anchor inserter assembly 604" can further include a tension assembly, such as tension assembly 800, the tension assembly 800 configured apply a tensile force to the actuation strands 38 of an anchor 22.

The access member 606" can be constructed substantially the same as the access member 606, with the access member 606" further defining at least one interlocking member 670, the interlocking member 670 configured to engage with a complementary interlocking member 670 defined by the anchor housing 634", such that when the interlocking members 670 are engaged with one another, the access member 606" and the anchor housing 634" are prevented from rotating with respect to each other about the central axis C. In accordance with the illustrated embodiment, the access member 606" defines a pair of interlocking members 670 in the form of a pair of notches 672 extending into the proximal end 610a of the access member 606" along the transverse direction T between the outer surface of the access member 606" and the tubular portion 614 thereof, the notches 672 configured to receive complementary interlocking members 670 defined by the anchor housing 634". The access member 606" can further define at least one bracing member 674, the bracing member 674 configured to allow the application of a counter rotation force to the access member 606", as described in more detail below. In accordance with the illustrated embodiment, the holder portion 616 of the access member 606" defines a pair of bracing members 674 in the form of tabs 676, the tabs 676 extending from opposed sides of the access member 606" along a common axis that extends along the lateral direction A.

The anchor housing 634" can be constructed substantially the same as the anchor housing 634, with the anchor housing 634" further defining at least one, such as a plurality of interlocking members 670, the interlocking members 670 configured to engage with respective complementary interlocking members 670 defined by the access member 606" and the pusher member 802 of the tension assembly 800, such that when the respective interlocking members 670 are engaged with one another, the access member 606", the anchor housing 634", and the pusher member 802 are prevented from rotating with respect to each other about the central axis C. In accordance with the illustrated embodiment, the anchor housing 634" defines a plurality of interlocking members 670 in the form of a pair of tabs 678 and a pair of notches, the pair of tabs 678 extending out from the distal end 644*b* of the holder portion 644 of the anchor housing 634" along the transverse direction T between the outer surface of the anchor housing 634" and the tubular portion 642 thereof, the tabs 678 configured to be received in corresponding ones of the notches 672 defined by the access member 606", and the pair of notches 672 extending into the proximal end 644*a* of the holder portion 644 of the anchor housing 634" along the transverse direction T between the outer surface of the anchor housing 634" and the tubular portion 642 thereof, the notches 672 configured to receive complementary interlocking members 670 defined by the pusher member 802.

In accordance with the illustrated embodiment, the tension assembly 800 includes a pusher member 802, a translating member 804 configured to translate with respect to the distal end 610*b* of the access member 606", and a rotatable member 806 operatively coupled to the pusher member 802 and the translating member 804, such that rotation of the rotatable member 806 causes the translating member 804 to translate with respect to the distal end 610*b* of the access member 606 and the with respect to the pusher member 802.

The pusher member 802 can be constructed substantially the same as the pusher member 702, with the pusher member 802 further including at least one guide member 808, the at least one guide member 808 configured to prevent rotation of the translating member 804 with respect to the rotatable member 806 as the translating member 804 translates between the neutral and extended positions. In accordance with the illustrated embodiment, the pusher member 802 defines guide members 808 in the form of a pair of rails 810, the rails 810 extending along the longitudinal direction L between the proximal end 802*a* of the pusher member 802 and the proximal end 806*a* of the rotatable member 806. The illustrated rails 810 can be spaced apart from each other along the longitudinal direction T.

The pusher member 802 can further define at least one, such as a plurality of interlocking members 670, the interlocking members 670 configured to engage with complementary interlocking members 670 defined by the anchor housing 634". In accordance with the illustrated embodiment, the pusher member 802 can define interlocking members 670 in the form of a pair of tabs 678, the tabs 678 extending out from the distal end 802*b* of the pusher member 802 along the transverse direction T between the outer surface of the pusher member 802 and the tubular portion 654 thereof, the tabs 678 configured to be received in corresponding ones of the notches 672 defined by the anchor housing 634".

The pusher member 802 can still further define at least one, such as a pair of coupling members 812, the coupling members 812 configured to interface with complementary coupling members 814 defined by the rotatable member 806, thereby operatively coupling the pusher member 802 to the rotatable member 806 such that the rotatable member 806 can rotate with respect to the pusher member 802. In accordance with the illustrated embodiment, the pusher member 802 can define a pair of coupling members 812 in the form of a pair of projections 816, the projections 816 extending from opposed sides of the pusher member 702 along a common axis that extends along the lateral direction A. The projections 816 can be configured to interface with at least one complementary coupling member 814 defined by the rotatable member 806, such as annular groove 828. The rotatable member 806 can be configured to be rotatable about the central axis C, such that the pusher member 802 can remain stationary with respect to the rotatable member 806 when the rotatable member 806 is rotated.

The translating member 804 can be constructed substantially the same as the translating member 704, with the translating member 804 further including a pair of apertures 818 extending longitudinally therethrough, each aperture 818 configured to receive a respective one of the rails 810, such that the translating member 804 rides along the rails 810 as it translates. The translating member 804 can further include at least one, such as a pair of coupling members 812, the coupling members 812 configured to interface with complementary coupling members 814 defined by the rotatable member 806, thereby operatively coupling the translating member 804 to the rotatable member 806. The translating member 804 can be configured to translate distally between a neutral position and an extended position with respect to the pusher member 802, for instance along the longitudinal direction L. For example, the translating member 804 can be configured to translate between the neutral and extended positions when the rotatable member 806 is rotated about the central axis C, thereby translating with respect to the distal end 610*b* of the access member 606".

The actuation strands 38 of the anchor 22 can be releasably attached to the translating member 804, for example by cleating the actuation strands 38 to the translating member 804, such that when the translating member 804 translates proximally with respect to the distal end 610*b* of the access member 606", the translating member 804 can apply a tensile force to the actuation strands 38 of the anchor 22, thereby causing the anchor 22 to expand within the opening 25. The degree to which the anchor 22 expands can be dependent upon the magnitude of the tensile force applied to the actuation strands 38 by the translating member 804. The magnitude of the tensile force can be dependent upon the distance between the neutral and extended positions through which the translating member 804 translates. Therefore, the magnitude of the tensile force that the translating member 804 will apply to the actuation strands 38 can be at least partially determined by the predetermined distance between the neutral and extended positions of the translating member 804.

The distance between the neutral and extended positions can be determined by the coupling members 812 defined by the translating member 804 and complementary coupling members 814 defined by the rotatable member 806. For example, in accordance with the illustrated embodiment, the translating member 804 can define a pair of coupling members 812 in the form of a pair of projections 820, the projections 820 extending from opposed sides of the translating member 804 along a common axis that extends along the lateral direction A. The projections 820 can be configured to interface with complementary coupling members 814 defined by the rotatable member 806, such as helical grooves 830, each helical groove 830 extending between opposed proximal and distal groove ends 830a, 830b, respectively. The translating member 804 can be in the neutral position when the projections 820 are disposed at the proximal groove ends 830a, and can be in the extended position when the projections 820 are disposed at the distal groove ends 830b. Rotation of the rotatable member 806 about the central axis C can cause the projections 820 to translate in the helical grooves 830 between the proximal and distal groove ends 830a, 830b, thereby causing the translating member 804 to translate between the neutral and extended positions.

The rotatable member 806 can include at least one, such as a pair of coupling members 814, the coupling members 814 configured to interface with complementary coupling members 812 defined by the pusher member 802 and/or the translating member 804, thereby operatively coupling the rotatable member 806 to the pusher member 802 and/or the translating member 804. In accordance with the illustrated embodiment, the rotatable member 806 includes a cylindrically shaped body 822, the body defining a cannulation 824 that extends therethrough along the central axis C. The cannulation 824 can be sized to receive the pusher member 802 and the translating member 804 therein. The cannulation defines an inner surface 826. The body 822 defines a plurality of coupling members 814 in the form of an annular groove 828 and a pair of opposed helical grooves 830, the annular groove 828 and the helical grooves 830 extending into the inner surface 826. The projections 816 can be captive in the annular groove 828, such that the pusher member 802 is prevented from translating with respect to the rotatable member 806 when the rotatable member 806 is rotated. Each of the projections 820 can be captive in a respective one of the helical grooves 830, such that the projections 820 translate within the respective helical grooves 830 when the rotatable member 806 is rotated, thereby causing the translating member 804 to translate from the neutral position to the extended position.

The helical grooves 830 extend between opposed proximal and distal groove ends 830a, 830b. In accordance with the illustrated embodiment, the helical grooves 830 can define corresponding variable groove pitches. The groove pitches can decrease between the respective proximal and distal groove ends 830a, 830b, such that for each unit of rotational displacement of the rotatable member 806, the magnitude of the tensile force applied by the translating member 804 to the actuation strands 38 increases with distance of the translating member 804 from the pusher member 802. It should be appreciated that the tension assembly 800 is not limited to the illustrated geometries of the various components thereof, and that one or more components of the tension assembly 800 can alternatively be constructed with any other suitable geometry as desired.

In accordance with an example anchor insertion procedure utilizing the insertion instrument 600″, the access member 606″ can be used with the awl 609 to create an opening 25 at a target anatomical location 24 and/or to secure the access member 606″ with respect to the target anatomical location 24. Once the access member 606″ is secured, the anchor inserter assembly 604″ can be used to insert an anchor 22 into the opening 25. For example, the shaft portion 642 of the anchor housing 634″ can be inserted into the cannulation 612 of the access member 606″ and distally advanced within the cannulation 612 until the contact surfaces 618 and 646 abut one another. With the anchor housing 634″ fully inserted with respect to the access member 606″, the tension assembly 800 can be used to eject the anchor 22 out the distal end 610b of the access member 606″ and into the opening 25. For instance, the tubular portion 654 of the pusher member 802 can be inserted into the cannulation 640 of the anchor housing 634 and distally advanced within the cannulation 640. As the tubular portion 654 of the pusher member 802 advances within the cannulation 640, the distal end 650b of the pusher member 802 can come into contact with the anchor 22 and cause the anchor 22 to translate toward the distal end 610b of the access member 606″ and to eject out the distal end 610b of the access member 606″.

When the anchor 22 has been ejected out the distal end 610b of the access member 606″ and into the opening 25, the tension assembly 800 can be used to apply the tensile force to the actuation strands 38, thereby causing the anchor 22 to expand within the opening 25 and become secured with respect to the target anatomical location 24. The tensile force can be applied to the actuation strands 38 by applying a rotational force to the rotatable member 806, thereby causing the projections 830 to translate from respective ones of the proximal groove ends 830a to the distal groove ends 830b, and causing the translating member 804 to translate the predetermined distance from the neutral position to the extended position. As the translating member 804 translates from the neutral to the extended position, the translating member 804 can apply the tensile force to the actuation strands 38, thereby causing the anchor 22 to expand within the opening 25 and become secured with respect to the target anatomical location 24.

During rotation of the rotatable member 806, a rotational force can be applied to at least one of the tabs 676, in a direction that substantially opposes the direction of the rotational force applied to the rotatable member 806, such that components of the anchor inserter assembly 604″ are prevented from rotating with respect to the target anatomical location 24. When the anchor 22 has been expanded and secured within the opening 25, the components of the anchor inserter assembly 604″ can be removed from the target anatomical location 24.

Referring now to FIG. 35, still another alternative embodiment of the insertion instrument 600‴ is illustrated. The insertion instrument 600‴ can include an access assembly 602‴ and an anchor inserter assembly 604‴. The access assembly 602‴ can include an awl 609‴ and an access member 606‴. The anchor inserter assembly 604‴ can include a variety of components, such as an access member 606‴, an anchor housing 638‴ and/or the sleeve 660 of the anchor inserter assembly 604. The anchor inserter assembly 604‴ can further include a tension assembly, such as tension assembly 900, the tension assembly 900 configured to apply a tensile force to the actuation strands 38 of an anchor 22. The tension assembly 900 can include a pusher member 902 configured to eject the anchor 22 out the distal end 610b of the access member 606‴, a translating member 904 configured to translate between a neutral position and an extended position, and a handle member 906 operatively coupled to the pusher member 902 and the translating member 904, such that translation of the handle member 906 causes the pusher member to eject the anchor 22 out the distal end 610b of the access member 606‴, and rotation of the handle member 906 causes the translating member 904 to translate from the neutral position to the extended position.

Referring now to FIGS. 36A-B, the access member 606‴ can be constructed substantially the same as the access member 606", with interlocking member 670 that can be configured to prevent rotation of the access member 606''' with respect to the awl 609''' or the anchor housing 634''', and to prevent translation of the access member 606''' with respect to the awl 609''' or the anchor housing 634". For example, in accordance with the illustrated embodiment, the interlocking member 670 can be provided in the form of a square plate body 680 disposed at the proximal end 610a of the access member 606''', the plate body 680 defining a proximal or upper surface 680a, an opposed distal or lower surface 680b, and four side surfaces 680c. The plate body 680 can be configured to be releasably retained by complementary interlocking members 670 defined by the awl 609''' and/or the anchor housing 634". For example, the plate body can define beveled edges 680d where the upper surface 680a of the plate body 680 intersects the side surfaces 680c thereof. The access member 606" can further define a neck 682 that extends between the lower surface 680b of the plate body 680 and the proximal end 610a of the access member 606''', such that a groove 684 is defined between the lower surface 680b of the plate body 680 and the proximal end 610a of the access member 606'''. It should be appreciated that the access member 606''' is not limited to the illustrated interlocking member 670, and that the access member 606''' can alternatively include any other suitable interlocking member as desired.

The awl 609''' can be constructed substantially the same as the awl 609, with the awl 609''' further defining at least one interlocking member 670, the interlocking member 670 configured to releasably engage with a complementary interlocking member 670 defined by the access member 606'''. For example, in accordance with the illustrated embodiment, the proximal end 620a of the awl 609''' can define an interlocking member 670 in the form of a pair of opposed latch members 686, the latch members 686 configured to be releasably retain the plate body 680. Each latching member 686 can include a resilient latch arm 688 that extends between a proximal end 688a and an opposed distal end 688b.

Each latch arm 688 can include a pivot member 690 about which the latch arm 688 can pivot, for example about a pivot axis substantially parallel to the transverse direction T. The distal end 688b of each latch arm 688 can define a projection 692, the projection 692 defining a proximal or upper surface 692a and a beveled distal or lower surface 690b, the upper surface 692a configured to abut the lower surface 680b of the plate body 680 when the latching member 682 is latched to the plate body 680.

In operation, when the awl 609''' in inserted into the access member 606''' such that the respective interlocking members of the awl 609''' and the access member 606''' engage, the lower surface 692b of each of the latch members 686 can abut a respective beveled edge 680d of the plate body 680 and ride along the beveled edge 680d, causing the distal ends 688b of the latch arms 688 to pivot outward with respect to the plate body 680 about respective pivot members 690. As the awl 609" is further advanced, the projections 692 ride along respective side surfaces 680c of the plate member 680 until the upper surfaces 692a of the projections pass the lower surface 680b of the plate body 680, at which point the projections enter the groove 684 and the latch arms 688 resiliently pivot back to their original positions, such that the latch arms 688 come to rest with the upper surfaces 692a of the projections 692 abutting the lower surface 680b of the plate body 680, thereby retaining the plate body 680. When the awl 609''' is latched with respect to the access member 606''', the awl 609''' is prevented from translating with respect to the access member 606''' along the longitudinal direction L and prevented from rotating with respect to the access member 606''' about the central axis C. It should be appreciated that the awl 609''' is not limited to the illustrated interlocking members 670, and that the awl 609''' can alternatively define any other suitable interlocking member as desired.

Referring now to FIG. 35 and FIGS. 37A-B, the anchor housing 634''' can be constructed substantially the same as the anchor housing 634", with the interlocking member 670 defined at the distal end 644b of the holder portion 644 including a pair of latch members 686 configured to engage with the plate body 308, as described above with reference to the awl 609''', such that when the anchor housing 634''' is latched with respect to the access member 606''', the anchor housing 634''' is prevented from translating with respect to the access member 606''' along the longitudinal direction L and prevented from rotating with respect to the access member 606''' about the central axis C. The anchor housing 634''' can further define second and third interlocking members 670, the second interlocking member configured to engage with a complementary interlocking member 670 defined by the tension assembly 900 so as to prevent rotation of the tension assembly 900 with respect to the anchor housing 634''', and the third interlocking member 670 configured engage with a complementary interlocking member 670 defined by the tension assembly 900 so as to prevent translation of the tension assembly with respect to the anchor housing 634''' along the longitudinal direction L, as described in more detail below.

The anchor housing 634''' can further define at least one guide member, the at least one guide member configured to prevent rotation of the translating member 904 with respect to the handle member 906 as the translating member 904 translates between the neutral and extended positions. In accordance with the illustrated embodiment, the anchor housing 634''' can define guide members in the form of a pair of rails 694, the rails 694 extending in a proximal direction that is substantially parallel with respect to the longitudinal direction L. The illustrated rails 694 can be spaced apart from each other along the lateral direction A.

In accordance with the illustrated embodiment, the tension assembly 900 includes a pusher member 902 configured to eject the anchor 22 out the distal end 610b of the access member 606''', a translating member 904 configured to translate with respect to the distal end 610b of the access member 606''' between a neutral position and an extended position, and a handle member 906 operatively coupled to the pusher member 902 and the translating member 904, such that translation of the handle member 906 causes the pusher member to eject the anchor 22 out the distal end 610b of the access member 606''', and rotation of the handle member 906 causes the translating member 904 to translate with respect to the distal end 610b of the access member 606''', thereby applying a tensile force to the actuation strands 38 of the anchor 22.

The pusher member 902 can include a tubular pusher member body 908 that extends between a proximal end 908a and an opposed distal end 908b. The pusher member body 908 can be sized as described above, such that the distal end 908b of the pusher member body 908 can contact the anchor 22 within the anchor housing 634''' and cause the anchor 22 to be ejected out the distal end 610b of the access member 606". The pusher member 902 can be coupled to the translation member 904, and in particular to the distal body portion 910b thereof.

The translation member 904 can define at least one, such as a pair of coupling members 914, the coupling members 914 configured to interface with complementary coupling members 916 defined by the handle member 906, thereby operatively coupling the translating member 904 to the rotatable member 906, such that the translating member 904 will translate proximally between a neutral position and an extended position with respect to the distal end 610*b* of the access member 606''', for instance along the longitudinal direction L, when the handle member 906 is rotated about the central axis C.

In accordance with the illustrated embodiment, the translating member 904 can define a pair of coupling members 914 in the form of a pair of projections 918, the projections 918 extending from opposed sides of the translating member 904 along a common axis that extends along the lateral direction A. The projections 918 can be configured to interface with complementary coupling members 916 defined by the handle member 906, such as the opposed helical grooves 920, each helical groove 920 extending between opposed proximal and distal groove ends 920*a*, 920*b*, respectively. The translating member 904 can be in the neutral position when the projections 918 are disposed at the distal groove ends 920*b*, and can be in the extended position when the projections 918 are disposed at the proximal groove ends 920*a*.

Referring now to FIGS. 37B-39, in accordance with the illustrated embodiment, the handle member 906 includes a handle body 922 that defines a central bore 924 therethrough along the central axis C. The bore 924 can be sized to receive the translating member 904 therein. The bore 924 defines an inner surface 926. The body 922 defines a plurality of coupling members 916 in the form of a pair of opposed helical grooves 920, the helical grooves 920 extending into the inner surface 926. Each of the projections 918 can be captive in a respective one of the helical grooves 920, such that the projections 918 translate within the respective helical grooves 920 when the rotatable member 906 is rotated, thereby causing the translating member 904 to translate from the neutral position to the extended position.

The helical grooves 920 extend between opposed proximal and distal groove ends 920*a*, 920*b*. In accordance with the illustrated embodiment, the helical grooves 920 can define corresponding variable groove pitches. The groove pitches can decrease between the respective proximal and distal groove ends 920*a*, 920*b*, such that for each unit of rotational displacement of the handle member 906, the magnitude of the tensile force applied by the translating member 904 to the actuation strands 38 increases with distance of the translating member 904 from the pusher member 902.

In accordance with the illustrated embodiment, the translating member 904 can be configured to act as a fuse member. For example, the translating member 904 can be configured to fail when a particular magnitude of tensile stress is applied to the translating member 904, thereby releasing the actuation strands 38. In an example embodiment of a translating member configured as a fuse member, the translating member 904 can have a two part translating member body 910 including a proximal body portion 910*a* and a proximal body portion 910*b*. The proximal and distal body portions 910*a*, 910*b* can be releasably coupled to one another such that the proximal and distal body portions 910*a*, 910*b* will translate together as one body 910 until a pre-determined magnitude of tensile force is applied to the translating member body 910, at which point the distal body portion 910*b* can separate from the proximal body portion 910*a*. In this regard, it should be appreciated that the predetermined tension force characteristic can include the pre-determined magnitude of tensile force. The pre-determined magnitude of tensile force applied to the at least one actuation strand 38 can be at least partially defined by distance of travel of the translating member 904 between the neutral and extended positions. The translating member body 910, in other words the proximal and distal body portions 910*a*, 910*b*, can define a pair of apertures 912 extending therethrough along the longitudinal direction L, the apertures 912 configured to receive the rails 694 therein such that the translating member body 910 can translate along the rails 694 in the longitudinal direction.

The actuation strands 38 of the anchor 22 can be releasably attached to the translating member 904, for example by sandwiching the actuation strands 38 between the proximal and distal body portions 910*a*, 910*b*, such that when the translating member 904 translates proximally with respect to the distal end 610*b* of the access member 606'', the translating member 904 can apply a tensile force to the actuation strands 38 of the anchor 22, thereby causing the anchor 22 to expand within the opening 25. For example, in accordance with the illustrated embodiment, the actuation strands 38 can be captured between the facing surfaces 911*a*, 911*b* of the proximal and distal body portions 910*a*, 910*b*, respectively. The degree to which the anchor 22 expands can be dependent upon the magnitude of the tensile force applied to the actuation strands 38 by the translating member 904. The tensile force applied to the actuation strands 38 can increase in magnitude with distance between the translating member 904 and the distal end 610*b* of the access member 606''.

Further in accordance with the illustrated embodiment, the proximal body portion 910*a* can define the projections 918, and the proximal end 902*a* of the pusher member 902 can be coupled to the distal body portion 910*b*. The proximal and distal body portions 910*a*, 910*b* can be releasably coupled to one another utilizing at least one failure member. For example, in the illustrated embodiment, the proximal body portion 910*a* defines a pair of opposed resilient flaps 928 that extend distally from the proximal body portion 910*a*, each flap 928 defining a failure member in the form of a shear tab 930. The distal body portion 910*b* can define a complementary pair of opposed ledges 932, each ledges 932 configured to receive a respective one of the shear tabs 930 therein when the proximal and distal body portions 910*a*, 910*b* are assembled with the actuation strands 38 sandwiched therebetween.

The bore 924 of the handle member 906 can be sized such that when the translating member is carried in the bore 924, the resilient flaps 928 are held secure against the distal body portion 910 such that the flaps 928 cannot bias outwardly. Therefore, when the translating member 904 is translated such that a tensile force is applied to the translating member 904, the shear tabs 930 can be biased against the ledges 932. The shear tabs 930 can be configured to resist shearing by the ledges until the magnitude of the tensile force equals the pre-determined release stress, for example when the translating member 904 translates to a distance from the distal end 610*b* of the access member 606'' such that the magnitude of the tensile force reaches the pre-determined release stress magnitude, at which point the shear tabs 930 can be shorn off by the ledges 932, allowing the proximal and distal body portions 910*a*, 910*b* to separate, thereby releasing the actuation strands 38 from the translating member 904. Preferably, the magnitude of the tensile force applied by the translating member 904 to the actuation strands 38 will exceed a pre-determined separation force value before the translating member 904 translates to the extended position.

Referring now to FIGS. 37A-39, the insertion instrument 600''' can be configured for operation in at least two distinct operational modes, dependent upon the longitudinal position of the handle member 906 with respect to the anchor housing 634'''. For example, in accordance with the illustrated embodiment, the insertion instrument 600''' is initially configured to operate in an anchor ejection mode, wherein the tension assembly 900 is in a retracted or proximal position with respect to the anchor housing 634'''. When the tension assembly 900 is in the retracted position, interlocking members 670 defined by the handle member 906 can be engaged with complementary second interlocking members 670 defined by the anchor housing 634'''. More specifically, the distal end 906b of the handle member 906 defines interlocking members 670 in the form of a pair of resilient tabs 934 on opposed sides of the handle member 906, the tabs 934 disposed in complementary interlocking members 670 defined by the anchor housing 634''' in the form of a pair of grooves 696 that extend into opposed sides of the anchor housing 634''' along the longitudinal direction L. The distal end 934b of each tab 934 can define a projection 936 that is configured to be received in a respective complementary notch 696b defined in the bottom surface 696a of the grooves 696, such that when the tension assembly 900 is in the retracted position with respect to the anchor housing 634''', it will remain in that position until a translational force sufficient to dislodge the projections 936 from the respective notches 696b is applied to the tension assembly 900.

When the tension assembly 900 is translated distally with respect to the anchor housing 634''', the pusher member 902 translates distally within the anchor housing 634''', causing the anchor 22 to be ejected from the distal end 610b of the access member 606'''. When the tension assembly 900 is fully translated distally with respect to the anchor housing 634''', the insertion instrument 600''' to be operated in the second operational mode.

The anchor housing 634''' can define third interlocking members 670 configured to enable the insertion instrument 600''' to be operated in the second operational mode. More specifically, the anchor housing 634''' can define a third interlocking member 670 in the form of an annular groove 698 disposed adjacent the distal end 644b of the holder portion 644 of the anchor housing 634''', the groove 698 sized to receive the projections 936 therein. When the projections 936 are received in the groove 698, such that the insertion instrument 600''' is operable in the second, anchor expanding mode, the handle member 906 is free to rotate with respect to the anchor housing 634'''. Therefore, when the insertion instrument 600''' is operable in the anchor expanding mode, the translating member 904 can be translated with respect to the distal end 610b of the access member 606''', thereby applying a tensile force to the actuation members and expanding the anchor within the opening 25. It should be appreciated that the anchor housing 634''' is not limited to the illustrated interlocking members 670, and that the anchor housing 634''' can alternatively define any other suitable interlocking member as desired. It should further be appreciated that the tension assembly 900 is not limited to the illustrated geometries of the various components thereof, and that one or more components of the tension assembly 900 can alternatively be constructed with any other suitable geometry as desired.

In accordance with an example anchor insertion procedure utilizing the insertion instrument 600''', the access member 606''' can be used with the awl 609''' to create an opening 25 at a target anatomical location 24 and/or to secure the access member 606''' with respect to the target anatomical location 24, as described herein elsewhere. Once the access member 606''' is secured the anchor inserter assembly 604''' can be used to insert an anchor 22 into the opening 25. For example, the shaft portion 642 of the anchor housing 634''' can be inserted into the cannulation 612 of the access member 606''' and distally advanced within the cannulation 612 until the latch members 686 engage the plate body 680, thereby securing the anchor housing 634''' with respect to the access member 606''. With the anchor housing 634''' fully inserted with respect to the access member 606''', the insertion instrument 600''' can be operated in the anchor ejection mode by translating the tension assembly 900 distally with respect to the anchor housing 634''' in order to eject the anchor 22 out the distal end 610b of the access member 606''' and into the opening 25.

When the anchor 22 has been ejected out the distal end 610b of the access member 606''' and the handle member 906 is fully translated with respect to the anchor housing 634''' such that the insertion instrument 600''' is operable in the anchor expansion mode, the handle member 906 can be rotated, thereby translating the translating member 904 and causing a tensile force to be applied to the actuation strands 38 of the anchor. When the magnitude of the tensile force reaches the pre-determined release force of the translating member 904, the proximal and distal body potions 910a, 910b of the translating member 904 can separate from one another, thereby releasing the actuation strands 38 from the tension assembly 900.

During rotation of the handle member 906, a rotational force can be applied to at least one of the tabs 676, in a direction that substantially opposes the direction of the rotational force applied to the handle member 906, such that components of the anchor inserter assembly 604''' are prevented from rotating with respect to the target anatomical location 24. When the anchor 22 has been expanded and secured within the opening 25, the components of the anchor inserter assembly 604''' can be removed from the target anatomical location 24.

Referring generally now to FIGS. 40A-43, alternative embodiments of translating members configured to act as fuse members are illustrated. More specifically, a first alternative translating member 1000 is depicted in FIG. 40A. In accordance with the illustrated embodiment, the translating member 1000 defines a two part translating member body 1002 including a base body portion 1002b configured to receive an insert body portion 1002a. The insert body portion 1002a can define a pair of resilient jaws 1004, each jaw 1004 carrying at least one tooth 1006, the teeth 1006 configured to interface with respect to one another to releasably capture the actuation strands 38 therebetween. The insert body portion 1002a can define a shear ledge 1008, the shear ledge 1008 configured to be shorn from the insert body portion 1002a by the base body portion 1002b when the magnitude of a tensile force applied to the translating member body 1002 exceeds a pre-determined release stress magnitude, such that the insert body portion 1002a is released from the base body portion 1002b. When the insert body portion 1002a is released from the base body portion 1002b, the resilient jaws 1004 can separate, thereby releasing the actuation strands 38. The insert body portion 1002a can further define coupling members in the form of a pair of projections 1012, the projections 1012 configured to interface with complementary coupling members defined by the handle member 906, such as the helical grooves 920.

Referring now to FIG. 40B, another alternative translating member 1100 is depicted. In accordance with the illustrated embodiment, the translating member 1100 defines a two part translating member body 1102 including a base body portion 1102a configured to receive an insert body portion 1102b. The insert body portion 1102b can define a pair of resilient jaws 1104, each jaw 1104 carrying at least one tooth 1106, the teeth 1106 configured to interface with respect to one another to releasably capture the actuation strands 38 therebetween. The body 1102 can define a bore 1108 that extends through at least a portion of the base body portion 1102a and extends into the insert body portion 1102b. The translating member 1100 can include a shear pin 1110 sized to be inserted into the bore 1108 and configured to be shorn between the insert body portion 1102b and the base body portion 1102a when the magnitude of a tensile force applied to the translating member body 1102 exceeds a pre-determined release stress magnitude, such that the insert body portion 1102b is released from the base body portion 1102a. When the insert body portion 1102b is released from the base body portion 1102a, the resilient jaws 1104 can separate, thereby releasing the actuation strands 38. The insert body portion 1102b can further define coupling members in the form of a pair of projections 1112, the projections 1112 configured to interface with complementary coupling members defined by the handle member 906, such as the helical grooves 920.

Referring now to FIGS. 41A-B, still another alternative translating member 1200 is depicted. In accordance with the illustrated embodiment, the translating member 1200 defines a two part translating member body 1202 including a base body portion 1202a configured to substantially enclose an insert body portion 1202b. The insert body portion 1202b can define a pair of resilient jaws 1204, each jaw 1204 carrying at least one tooth 1206, the teeth 1206 configured to interface with respect to one another to releasably capture the actuation strands 38 therebetween. The base body portion 1202a can define a shear ledge 1208, the shear ledge 1208 configured to be shorn from the base body portion 1202a by the insert body portion 1202b when the magnitude of a tensile force applied to the translating member body 1202 exceeds a pre-determined release stress magnitude, such that the insert body portion 1202b is released from the base body portion 1202a. When the insert body portion 1202b is released from the base body portion 1202a, the resilient jaws 1204 can separate, thereby releasing the actuation strands 38. The insert body portion 1202b can further define coupling members in the form of a pair of projections 1212, the projections 1212 configured to interface with complementary coupling members defined by the handle member 906, such as the helical grooves 920.

Referring now to FIG. 42, still another alternative translating member 1300 is depicted. In accordance with the illustrated embodiment, the translating member 1300 defines a two part translating member body 1302 including a base body portion 1302a configured to receive an insert body portion 1302b. The base body portion 1302a can define a spherical pocket 1304 configured to receive therein a complementary spherical member 1306 affixed to a neck 1308, the neck 1308 extending from the insert body portion 1302b. The spherical pocket 1304 can be configured to receive the spherical member 1306 in a resilient ball and socket press fit with the actuation members releasably captured 38 therebetween. The fit of the spherical member 1306 within the spherical pocket 1304 can be tuned such that when the magnitude of a tensile force applied to the translating member body 1302 exceeds a pre-determined release stress magnitude, spherical member 1306 is released from the spherical pocket 1304, thereby releasing the actuation strands 38. The insert body portion 1302b can further define coupling members in the form of a pair of projections 1310, the projections 1310 configured to interface with complementary coupling members defined by the handle member 906, such as the helical grooves 920.

Referring now to FIG. 43, still another alternative translating member 1400 is depicted. In accordance with the illustrated embodiment, the translating member 1400 defines a two part translating member including a distal portion 1402 and a proximal body portion 1404, the distal body portion 1402 defining a bore 1406 therethrough, the bore 1406 sized to receive at least a portion of the proximal body portion 1404 therein. The proximal body portion 1404 can further define at least one, such as a plurality of resilient legs 1408 that extend distally from the proximal body portion 1404, the legs 1408 defining respective distal ends 1408b that converge to define a head 1410 having a larger cross sectional dimension than that of the converged distal ends 1408b of the legs 1408, the head 1410 sized to be disposed within the bore 1406 in a press fit. Each of the distal leg ends 1408b can further define at least one tooth 1412, the teeth 1412 configured to interface with respect to one another to releasably capture the actuation strands 38 therebetween.

The distal body portion 1402 can further define coupling members in the form of a pair of projections 1414, the projections 1414 configured to interface with complementary coupling members defined by the handle member 906, such as the helical grooves 920. The translating member 1400 can further include a spring 1416, the spring 1416 disposed between the proximal and distal body portions 1402, 1404, respectively, the spring 1416 configured to bias the proximal and distal body portions 1402, 1404 away from each other along the longitudinal direction L.

In operation, when the translation member 1400 translates proximally with respect to the distal end 610b of the access member 606''', the distal body portion 1402 exerts a force against spring that along a substantially opposed direction relative to the tensile force applied by the proximal body portion 1404 to the actuation strands 38. The force exerted by the spring can be tuned such that when the magnitude of a tensile force applied to the distal body portion 1402 exceeds a pre-determined release stress magnitude, the head 1410 will be forced out the distal end of the distal body portion 1402, thereby allowing the distal ends 1408b of the legs 1408 to resiliently spread with respect to each other and releasing the actuation strands 38.

Referring to FIGS. 44A-C, a cleat 1500 configured to secure an actuation member 38, for instance to a translating member such as the above-described translating members 704, 804 is illustrated. In accordance with the illustrated embodiment, the cleat 1500 includes a cylindrically shaped cleat body 1502. The cleat body 1502 can define at least one radial slit 1504, the radial slit sized to receive at least a portion of an actuation member 38 therein. The illustrated defines a pair of interconnected radial slits 1504. In accordance with the illustrated embodiment, the illustrated actuation member 38 can be secured within the cleat by seating a first portion of the actuation member 38 in a first slit 1504 of the pair, and then seating a second portion of the actuation member 38 in the remaining slit 1504.

Referring now to FIG. 45, an insertion instrument 2000 constructed in accordance with an alternative embodiment is configured to deliver at least one anchor body, such as first and second anchor bodies 28a and 28b of the anchors 22a and 22b (see FIG. 1A), to a respective target anatomical structure 24 (see FIG. 1A). In accordance with the illustrated embodiment, the anatomical structure 24 can be bone or any alternative anatomical structure as desired. For instance, the bone can be cortical bone, cancellous portion, a medullary canal, or any combination thereof. Thus, the anchor bodies can be injected into a cortical wall of the bone, into the cancellous portion of the bone (either spaced from the cortical wall or against the cortical wall), and when the bone is a long bone, the anchors 22a-b can be injected into the medullary canal of the long bone.

The insertion instrument 2000 is illustrated as elongate along a longitudinal axis 2002 that extends substantially along a longitudinal direction L, and defines a proximal end 2004 and an opposed distal end 2006 that is spaced from the proximal end 2004 along the longitudinal axis 2002. Thus, it should be appreciated that the terms "distal" and "proximal" and derivatives thereof refer to a spatial orientation closer to the distal end 2006 and the proximal end 2004, respectively. Furthermore, the directional term "distally" and "proximally" and derivatives thereof refer to a downstream direction that extends from the proximal end 2004 toward the distal end 2006, and an upstream direction that extends from the distal end 2006 toward the proximal end 2004, respectively. The insertion instrument 2000 further extends along a lateral direction A that is substantially perpendicular to the longitudinal direction L, and a transverse direction T that is substantially perpendicular to the longitudinal direction L and the lateral direction A. The terms "outward" and "inward" and derivatives thereof refer to a direction away from and toward the longitudinal axis 2002, respectively, unless otherwise indicated.

The insertion instrument 2000 includes a housing 2007 that can include a first or inner body 2008 and a second or outer body 2010. In accordance with the illustrated embodiment, the inner body 2008 is supported by, or at least partially disposed in, the outer body 2010. For instance, the inner body 2008 can be slidably supported by the outer body 2010 such that the inner body 2008 is slidable both proximally and distally with respect to the outer body 2010. The inner body 2008 is configured to create the opening 23 at respective target locations 24a-b that are configured to receive the anchor bodies 28a and 28b, respectively. The outer body 2010 includes an access member, such as a cannula 2012, that defines a distal end 2014 that is configured to be at least partially inserted into the openings 23 of the respective target locations 24a and 24b selectively. The cannula 2012 is further configured to eject the anchor bodies 28a and 28b into the respective openings 23 in the respective anatomical structure 24.

The insertion instrument 2000 further includes an anchor housing 2015, which can be configured as an anchor cartridge 2016 that is supported by the housing 2007, such as the outer body 2010, and is configured to releasably carry at least a portion of the anchors 22a and 22b, such as the anchor bodies 28a and 28b. The cartridge 2016 can be movably supported by the outer body 2010 so as to selectively align the first and second anchor bodies 28a and 28b with the cannula 2012. The inner body 2008 includes a pusher member 2022 (see FIG. 46) that is operably aligned with the cannula 2012, such that the pusher member 2022 is configured to be inserted through the cannula 2012. For instance, in accordance with the illustrated embodiment, the pusher member 2022 is configured to be driven through the cartridge 2016 and to apply a biasing force to the aligned anchor so as to eject the aligned anchor from the cartridge 2016 and out the distal end 2014 of the cannula 2012.

The insertion instrument 2000 can further include a tension assembly 2020 that is supported by the housing 2007, such as the outer body 2010, and is configured to releasably attach selectively to at least one or both of the respective actuation strands 38a and 38b (see FIG. 1A), and apply a predetermined tensile force characteristic to the attached actuation strand so as to actuate the respective anchor body from its first configurations to its expanded configurations in the manner described above. For instance, the predetermined tension force characteristic can be at least partially defined by a predetermined distance of travel of the tension assembly 2020, which causes the tension assembly 2020 to apply a tensile actuation force to the first and second actuation strands 38a and 38b selectively (e.g., individually), thereby actuating the respective anchor bodies 28a and 28b from their respective first configurations to their respective expanded configurations.

The inner body 2008, the outer body 2010, the anchor housing 2015, and the tension assembly 2020 will now be described in more detail.

In particular, referring to FIGS. 46-48C, the inner body 2008 defines a proximal end 2008a and an opposed distal end 2008b, and includes the pusher member 2022 and a retractable opening creating member 2024. For instance, the opening creating member 2024 is movable with respect to the pusher member 2022 between a first or retracted position (FIG. 47C) and a second or extended position (FIG. 48C). The inner body 2008 thus includes an actuator 2009 that is configured to be releasably moved between a first position (FIG. 47C) that corresponds to the retracted position of the opening creating member 2024 and a second position (FIG. 48C) that corresponds to the extended position of the opening creating member 2024. Thus, as the actuator 2009 is moved between the first and second positions, the actuator 2009 causes the opening creating member 2024 to likewise move between the retracted position and the extended position.

The pusher member 2022 defines a proximal end 2022a and an opposed distal end 2022b, and the opening creating member 2024 defines a proximal end 2024a and an opposed distal end 2024b. As will be described in more detail below, when the opening creating member 2024 is in the retracted position, the distal end 2024b is disposed proximal with respect to the distal end 2022b of the pusher member 2022. Accordingly, the distal end 2022a of the pusher member 2022 defines the distal end 2008b of the inner body 2008, and is configured to push an anchor body out the outer body 2010. When the opening creating member 2024 is in the extended position, the distal end 2024b is disposed distal with respect to the distal end 2022a of the pusher member 2022, and thus defines the distal end 2008b of the inner body 2008. Thus, the distal end 2024b of the opening creating member 2024 is configured to create an opening 23 (see FIGS. 1A-B) at the target location 24.

The pusher member 2022 can include a pusher body, such as a cannula 2026, and a handle 2028 that extends proximally from the cannula 2026. For instance, the cannula 2026 can define a proximal end 2026a that is attached to the handle 2028, and a distal end that 2026b that can define the distal end 2022b of the pusher member 2022. The handle 2028 can define the proximal end 2004 of the insertion instrument 2000. In accordance with the illustrated embodiment, the handle 2028 can include a neck 2029 and at least one such as a pair of outer grip surfaces 2030 that extend out from the neck 2029 in opposed lateral directions A. The outer grip surfaces 2030 are configured to be engaged, for instance manually by a user when translating the inner body 2008 with respect to the outer body 2010, and further when actuating the opening creating member 2024 between the retracted and extended positions. It should be appreciated that the handle 2028 can be attached, for instance integrally or discretely, to the cannula 2026. In accordance with the illustrated embodiment, the pusher member 2022 includes an attachment member 2032, such as a pin, that extends laterally through at least a portion of the handle 2028, such as the neck 2029, and into the proximal end 2026a of the cannula 2026 so as to attach, fixedly, the handle 2028 to the cannula 2026. The pusher member 2022 can define a first engagement member, such as a slot 2034 that extends, for instance in the transverse direction T, into the cannula 2026, for instance at the distal end 2026b. The slot 2034 can have a length in the longitudinal direction L sufficient to allow the opening creating member 2024 to translate relative to the pusher member 2022 between the retracted position and the extended position.

The opening creating member 2024 includes a shaft 2036 that defines a proximal end 2036a and a distal end 2036b. The distal end 2036b can be tapered so as to define an opening tip 2038, which can be configured as an awl tip, a drill tip, a trocar tip, or any alternatively constructed opening tip. The shaft 2036 is sized so as to extend at least partially through the cannula 2026 of the pusher member 2022, such that the shaft 2036 is movable in the cannula 2026. The opening creating member 2024 further includes a slider 2040 that projects out, for instance in the transverse direction T, from the shaft 2036, and is sized to extend out through the slot 2034 of the pusher member 2022. The slot 2034 can define a thickness substantially equal to that of the slider 2040, such that the opening creating member 2024 is at least limited or prevented from rotating with respect to the pusher member 2022. The opening tip 2038 can be disposed distal with respect to the slider 2040.

As described above, the inner body 2008 includes an actuator 2009, movable between a first position and a second position, that causes the opening creating member 2024 to move between the retracted position and the extended position, respectively. In accordance with the illustrated embodiment, the opening creating member 2024 includes a first actuator member 2042 that extends from the proximal end 2036a of the shaft 2036. For instance, the first actuator member 2042 includes an actuator body 2044 and a first locking member in the form of a latch member that is configured as a tab 2046 that extends out from the actuator body 2044. The pusher member 2022 defines a second actuator member 2048 that is configured to selectively mate with the first actuator member 2042 in the respective first and second positions. In accordance with the illustrated embodiment, the second actuator member 2048 comprises a second locking member in the form of a catch member that is configured as a pocket 2050 that is defined by the pusher member 2022, for instance the handle 2028. The pocket is sized so as to receive the tab 2046.

The pocket 2050 includes a first or proximal portion 2050a, a second or distal portion 2050b, and a longitudinally elongate middle portion 2050c that extends between the proximal portion 2050a and the distal portion 2050b. The proximal and distal portions 2050a-b are offset from the middle portion 2050c, for instance along the lateral direction L, and can be aligned with each other. The proximal and distal portions 2050a-b and the middle portion 2050c are sized to receive the tab 2046 such that the tab 2046 is movable from the proximal portion 2050a to the middle portion 2050c, and is further movable from the middle portion 2050c to the distal portion 2050b. The tab 2046 is further movable from the distal portion 2050b to the middle portion 2050c, and is further movable from the middle portion 2050c to the proximal portion 2050a.

The tab 2046 is in mechanical communication with the slider 2040, such that contact between the slider 2040 and the cannula 2026 creates a spring force, which can be a torsion force, that biases the tab 2046 to rotate, or move laterally, along a direction from the middle portion 2050c toward the proximal and distal portions 2050a-b, and resists rotation of the shaft 2036 as the tab 2046 moves from the proximal and distal portions 2050a-b into the middle portion 2050c, and biases the shaft 2036 to rotate so as to cause the tab 2046 to move from the middle portion 2050c and selectively into the proximal and distal portions 2050a-b. The torsion force can at least partially depend on the stiffness of the shaft 2036, and the longitudinal length between the slider 2040 and the tab 2046. Thus, the inner body 2008 can define a spring member that biases the actuator 2009 into the first and second positions. The spring member can be integral with the pusher member 2022 and the opening creating member 2024 as illustrated, or can be a separate structure, such that the spring member is configured to selectively bias the tab 2046 from the middle portion 2050c of the pocket 2050 into the proximal and distal portions 2050a-b when the tab 2046 is aligned with the proximal and distal portions 2050a-b, respectively.

Referring now to FIGS. 47A-C in particular, when the tab 2046 is disposed in the proximal portion 2050a of the pocket 2050, the actuator 2009 is releasably locked in the first position, whereby the distal end 2036b of the shaft 2036, and thus the opening tip 2038, is recessed, or disposed proximal, with respect to the distal end 2026b of the cannula 2026 of the pusher member 2022. Accordingly, the distal end 2026b of the cannula 2026 defines the distal end 2008b of the inner body 2008. The tab 2046 can be biased along the direction of Arrow 2052 from the proximal portion 2050a of the pocket 2050 to the middle portion 2050c against the spring force defined by engagement between the slider 2040 and the cannula 2026. A distal biasing force can then be applied to the tab 2046 along the direction of Arrow 2054, which causes the tab 2046 to move distally along the middle portion 2050c from a first position aligned with the proximal portion 2050a to a second position aligned with the distal portion 2050b, thereby iterating the actuator 2009 to the first position. As the tab 2046 travels along the central portion 2050c, the slider 2040 travels along the slot 2034.

Referring now to FIGS. 48A-C, the spring force can bias the tab 2046 into the distal portion 2050b of the pocket 2050, such that the actuator 2009 is releasably locked in the second position. When the tab 2046 is disposed in the distal portion 2050b of the pocket 2050, the distal end 2036b of the shaft 2036, and thus the opening tip 2038, is extended, or disposed distal, with respect to the distal end 2026b of the cannula 2026 of the pusher member 2022. Accordingly, the opening tip 2038 defines the distal end 2008b of the inner body 2008. The tab 2046 can be biased along the direction of Arrow 2052 from the distal portion 2050b of the pocket 2050 to the middle portion 2050c against the spring force defined by engagement between the slider 2040 and the cannula 2026. A proximal biasing force can then be applied to the tab 2046 along the direction of Arrow 2058, which causes the tab 2046 to move proximally along the middle portion 2050c from the second position aligned with the distal portion 2050b to the second position aligned with the proximal portion 2050a, thereby iterating the actuator to the first position. The spring force can bias the tab 2046 into the proximal portion 2050*b* so as to releasably lock the actuator 2009 in the first position.

It should be appreciated that the actuator 2009 can be constructed in accordance with any suitable alternative embodiment as desired. For instance, while the first actuator member 2042 of the opening creating member 2024 is configured as a latch member and the second actuator member 2048 of the pusher member 2022 is configured as a catch member as described above, the first actuator member 2042 of the opening creating member 2024 can alternatively be configured as a catch member and the second actuator member 2048 of the pusher member 2022 can alternatively be configured as a latch member.

Referring again to FIG. 45, the outer body 2010 includes a support member 2060 and an access member, configured as the cannula 2012 that extends distally from the support member 2060. The support member 2060 can further include a handle 2059. As illustrated in FIG. 51A, the support member 2060 includes first or upper support member portion 2060*a* and a second or lower support member portion 2060*b* that is configured to be attached to the upper support member portion 2060*a*. One or both of the support member portions 2060*a-b* can define at least a portion of a cannula 2011 that extends along the longitudinal length of the support member 2060. The cannula 2011 is in alignment with the cannula 2012 of the outer body 2010. Thus, the cannula 2011 can be referred to as a first or proximal cannula of the outer body 2010, and the cannula 2012 can be referred to as a second or distal cannula of the outer body 2010 that is in alignment with the first cannula 2011. The cannula 2012 of the outer body 2010 is sized to receive the cannula 2026 of the pusher member 2022. The outer body 2010 further defines a slot 2034 that extends, for instance in the transverse direction T, into the cannula 2012. The slot 2034 is sized so as to receive the slider 2040 of the opening creating member 2024, such that the inner body 2008 is substantially rotatably fixed to the outer body 2010 with respect to relative rotational movement. For instance the torsional spring force defined by the shaft 2036 of the opening creating member 2024 and engagement between the slider 2040 and the slot 2034 resists rotational movement of the inner body 2008 with respect to the outer body 2010. The outer body further defines a pocket 2013 that extends at least into, for instance through, the support member 2060 along the lateral direction A. The pocket 2013 is sized to receive the cartridge 2016, such that the cartridge 2016 is movable with respect to the housing 2007, and in particular the outer body 2010, so as to selectively align the first and second anchor bodies 28*a* and 28*b* with the pusher member 2022 of the inner body 2008 and the cannula 2012 of the outer body 2010.

Referring now to FIGS. 49A-B the cartridge 2016 includes a cartridge housing 2064 that is configured to be supported in a pocket 2013 (see FIG. 50A) of the outer body 2010 at a location between the first and second cannulas 2011 and 2012. The cartridge housing 2064 can define at least one receptacle such as a plurality of receptacles 2066*a-c* that extend longitudinally through the cartridge housing 2064. The first receptacle 2066*a* is configured to retain one of the anchor bodies 28*a* and 28*b*, and retains the first anchor body 28*a* during operation in accordance with the illustrated embodiment. The second receptacle 2066*b* is laterally outwardly disposed with respect to the first receptacle 2066*a*, and is configured to retain the other of the anchor bodies 28*a* and 28*b*, and thus retains the second anchor body 28*b* during operation in accordance with the illustrated embodiment. It should be appreciated that the cartridge 2016 can include as many receptacles as desired that are configured to retain respective anchor bodies, such that the insertion instrument 2000 is configured to selectively eject the retained anchor bodies to a respective target location, and subsequently actuate the ejected anchor to its expanded configuration in the manner described herein. The receptacles 2066*a-c* further includes a third or blank receptacle 2066*c* is a blank receptacle laterally inwardly disposed with respect to the first receptacle 2066*a*, and can be sized to receive one of the anchor bodies 28*a* and 28*b*, but does not in fact retain an anchor body during operation in accordance with the illustrated embodiment. The first receptacle 2066*a* is disposed between the second and blank receptacles 2066*b* and 2066*c*.

As will be appreciated from the description below, the cartridge 2016 is movable from an initial position whereby the blank receptacle 2066*c* is aligned with the cannula 2012, to a first position whereby the first receptacle 2066*a*, and the retained first anchor body 28*a*, is aligned with the cannula 2012, to a second position whereby the second receptacle 2066*b*, and the retained second anchor body 28*b*, is aligned with the cannula 2012. When the blank receptacle 2066*c* is aligned with the cannula 2012, the cannula 2026 of the pusher member 2022 is translatable through the blank receptacle 2066*c* and further through the cannula 2012 such that the opening tip 2038 of the inner body 2008 can create a first opening in a first target location that is configured to receive the first anchor body 22*a*. When the first receptacle 2066*a* is aligned with the cannula 2012, the cannula 2026 of the pusher member 2022 is translatable through the first receptacle 2066*a* and further through the cannula 2012 such that the pusher member 2022 can bias the first anchor body 28*a* through the cartridge 2016 and the cannula 2012 and into the created first opening in the first target location. In certain alternative embodiments, the cartridge 2016 can be devoid of the blank receptacle 2066*c*, and the cartridge 2016 can be attached to the outer body 2010 such that the first receptacle 2066*a* is aligned with the cannula 2012 after the inner body 2008 has created the first opening in the first target location.

It should be appreciated that once the first anchor body 28*a* has been removed from the first receptacle 2066*a*, the first receptacle 2066*a* defines a blank receptacle that can receive the cannula 2026 of the pusher member 2022, such that the pusher member 2022 is further translatable through the cannula 2012 such that the opening tip 2038 of the inner body 2008 can create a second opening in a second target location that is configured to receive the second anchor body 22*b*. When the second receptacle 2066*b* is aligned with the cannula 2012, the pusher member 2022 is translatable through the second receptacle 2066*b* and further through the cannula 2012 such that the pusher member 2022 can bias the second anchor body 28*b* through the cartridge 2016 and the cannula 2012 and into the created second opening in the second target location.

The cartridge 2016 can further include a stop clip 2068 that is releasably coupled to the cartridge housing 2064 and is disposed laterally outward with respect to the first receptacle 2066*a*. For instance, the stop clip 2068 can include a pair of arms 2069 that extend out from a base 2071 and are configured to clip onto opposed ends of the cartridge housing 2064. The stop clip 2068 is configured to abut the housing 2007, and in particular the outer body 2010, when the first receptacle 2066*a* is aligned with the cannula 2012 so as to assist in alignment of the first receptacle 2066*a* with the cannula 2012. The stop clip 2068 is removable from the cartridge housing 2064, so as to permit the cartridge 2016 to move along the lateral direction A with respect to the outer body 2010 so as to align the second receptacle 2066*b* with the cannula 2012. The stop clip 2068 can include a pull tab 2070 that can be engaged, for instance manually, so as remove one of the arms 2069 from engagement with the cartridge hosing 2064, thereby providing an ergonomically friendly removal of the stop clip 2068 from the cartridge housing 2064.

Referring now to FIG. 49B in particular, the first and second anchors 22*a* and 22*b* include the first and second anchor bodies 28*a* and 28*b* that are retained in the first and second receptacles 2066*a-b*, respectively, and respective actuation strands 38*a-b* that are attached to the corresponding anchor bodies 28*a* and 28*b*. The actuation strands 38*a* and 38*b* can be integral with each other so as to define a common strand, or can be separate from each other and attached to each other as desired. For instance, each actuation strand 38*a* and 38*b* can include a respective actuation portion 131*a* and 131*b*, and a respective attachment portion 133*a* and 133*b*. The attachment portions 133*a* and 133*b* can be attached to each other, either integrally or they can be separate from each other and attached in any manner desired. While each anchor 22*a* and 22*b* is illustrated as including a single respective actuation strand 38*a* and 38*b* that is attached to the corresponding anchor body 28, it should be appreciated that the anchors 22*a* and 22*b* can include as many actuation strands 38*a* and 38*b* as desired that are attached to the anchor bodies 28*a* and 28*b* in any manner described herein. For instance, each anchor 22*a* and 22*b* can include a pair of respective actuation strands 38*a* and 38*b* that are attached to the anchor bodies 28*a* and 28*b*, respectively.

The cartridge 2016 can further include a canister 2072 supported relative to the cartridge housing 2064, and a guide assembly 2074 supported relative to the canister 2072 and the cartridge housing 2064. For instance, the canister 2072 can be attached to the cartridge housing 2064, and the guide assembly 2074 can be attached to the canister 2072. In accordance with the illustrated embodiment, the cartridge housing 2064, the canister 2072, and the guide assembly 2074 are integral with each other. The guide assembly 2074 can be disposed proximal with respect to the cartridge housing 2064, and substantially in longitudinal alignment with the cartridge housing 2064, such that the cartridge 2016 defines a void 2076 that extends longitudinally between the cartridge hosing 2064 and the guide assembly 2074. The guide assembly 2074 includes a base 2078 and at least one guide tooth 2080 such as a plurality of guide teeth 2080 that extend from the base 2078.

In accordance with the illustrated embodiment, the actuation portion 131*a* and the attachment portion 133*a* of the actuation strand 28*a* of the first anchor 22*a* extend distally between a first pair of adjacent ones of the guide teeth 2080, loop around the first pair of the adjacent guide teeth 2080, and extend proximally between a second pair of adjacent ones of the guide teeth 2080 and into the canister 2072. Similarly, the actuation portion 131*b* and the attachment portion 133*a* of the actuation strand 38*b* of the second anchor 22*b* extend distally between a third pair of adjacent ones of the guide teeth 2080, loop around the third pair of the adjacent guide teeth 2080, and extend proximally between a fourth pair of adjacent ones of the guide teeth 2080 and into the canister 2072. It should be appreciated that the first, second, third, and fourth pairs of guide teeth 2080 can include one of the guide teeth 2080 in common. It should be further appreciated that the canister 2072 is configured to releasably retain an excess of the actuation strands 38*a* and 38*b*. The excess of the attachment portions 133*a* and 133*b* can have a sufficient length so as to allow for sufficient clearance between the first and second anchor bodies 28*a-b* as they are implanted in the respective target locations 24*a-b* (see FIGS. 1A-1B). It should be appreciated that the insertion instrument 2000 can include the anchors 22*a-b* preloaded in the cartridge 2016. Furthermore, the cartridge 2016 can be provided separate from the insertion instrument 2000 such that the cartridge 2016 can be loaded prior to use, or the cartridge can be permanently supported by the housing 2007 as desired.

Operation of the cartridge 2016 will now be described with reference to FIGS. 50A-H. In particular, referring to FIG. 50A, the cartridge 2016 is in the initial position whereby the blank receptacle 2066*c* is aligned with the first and second cannulas 2011 and 2012, such that a portion of the inner body can extend through the blank receptacle 2066*c*, and through the second cannula 2012. The opening tip 2038 of the opening creating member 2024 can extend distal of the cannula 2026 in the manner described above so as to create a first opening in a first target location. For instance, the cannula 2026 of the pusher member 2022 can extend through the first cannula 2011, through the blank receptacle 2066*c*, and through the second cannula 2012. The opening tip 2038 of the opening creating member 2024 can be in the extended position as described above so as to create a first opening in a first target location.

Next, as illustrated in FIG. 50B, the cannula 2026 of the pusher member 2022 can be retracted to a position proximal of the pocket 2013, and the opening tip 2038 can be retracted such that the distal end 2026*b* of the cannula 2026 defines the distal end 2008*b* of the inner body 2008. As illustrated in FIG. 50C, the cartridge housing 2064 can be translated, for instance laterally, with respect to the housing 2007, and in particular with respect to the inner and outer bodies 2008 and 2010 in the pocket 2013, to a first position whereby the first receptacle 2066*a*, and thus the first anchor body 28*a*, is aligned with the first and second cannulas 2011 and 2012 and the pusher member 2022. The stop clip 2068 can abut the cartridge housing 2064 when the first receptacle 2066*a* is in the first position. As illustrated in FIG. 50D, the cannula 2026 of the pusher member 2022 can be driven through the first receptacle 2066*a*, such that the cannula 2026 biases the first anchor body 22*a* distally through the second cannula 2012 and into the created first opening. The opening tip 2038 can then be extended again so as to define the distal end 2008*b* of the inner body 2008, and can create a second opening in a second target location. Alternatively, the opening tip 2038 can create the second opening when the cannula 2026 extends through the blank receptacle 2066*c* when the cartridge housing 2064 is in the initial position illustrated in FIG. 50A.

Referring now to FIG. 50E, once the first anchor body 28*a* has been ejected and the second opening has been created, the opening creating member 2024 can again be retracted such that the opening tip 2038 is disposed proximal of the pocket 2013 as described above. The opening tip 2038 can be retracted such that the distal end 2026*b* of the cannula 2026 defines the distal end 2008*b* of the inner body 2008. As illustrated in FIG. 50F, the stop clip 2068 can be removed from the cartridge housing 2064. Referring to FIG. 50G, the cartridge housing 2064 can be translated, for instance laterally, with respect to the housing 2007, and in particular with respect to the inner and outer bodies 2008 and 2010 in the pocket 2013, to a second position whereby the second receptacle 2066*b*, and thus the second anchor body 28*b*, is aligned with the first and second cannulas 2011 and 2012 and the pusher member 2022. As illustrated in FIG. 50H, the cannula 2026 of the pusher member 2022 can be driven through the second receptacle 2066b, such that the cannula 2026 biases the second anchor body 22b distally through the second cannula 2012.

Referring now to FIGS. 51A-D, the insertion instrument 2000 can further include a tension assembly 2020 that is configured to releasably attach selectively to the respective actuation strands 38a and 38b, and apply the predetermined tension force characteristic to the actuation strands 38a and 38b, for instance upon actuation by the user, that causes the respective anchor bodies 28a and 28b to expand from their first respective configuration to their respective expanded configuration. The tension assembly 2020 includes grip assembly 2021 configured to selectively releasably engage the actuation strands 38a and 38b of the anchors 22a and 22b, and a motion assembly 2023 that is configured to move the grip assembly 2021 a predetermined distance from a first position to a second position that causes the grip assembly 2021 to apply the tensile actuation force to the actuation strands 38a and 38b, respectively. The tension assembly 2020, and in particular the motion assembly 2023, can include an actuator that can be configured as a lever 2082 that defines a first or proximal end 2082a and an opposed second or distal end 2082b. The proximal end 2082a is configured to be pivotally connected to the outer body 2010, for instance at a joint 2017 disposed at a location proximal of the pocket 2013. In accordance with the illustrated embodiment, the motion assembly 2023 further includes a first pivot member, such as a first pivot pin 2083, that extends at least into the outer body 2010 and the distal end 2082b f the lever 2082, and defines a first pivot axis 2084 that extends in the lateral direction A. As is described in more detail below, the lever 2082 is configured to pivot about the first pivot axis 2084 so as to actuate the tension assembly 2020 from a first or disengaged configuration whereby the grip assembly 2021 is not attached to one of the actuation strands 38a and 38b, to a second or engaged configuration whereby the grip assembly 2021 is selectively attached to one of the actuation strands 38a and 38b (e.g., the grip assembly can be attached to the actuation strands 38a and 38b individually as opposed to simultaneously), to a third or tensioned configuration, whereby the grip assembly 2021 applies a tensile force to the selectively attached one of the actuation strands 38a and 38b, thereby actuating the respective anchor body 28a or 28b from its first configuration to its expanded configuration.

The motion assembly 2023 can further include a force transfer member such as an arm 2086 that defines a first or proximal end 2086a and a second or distal end 2086b. The arm 2086 can be configured as a pair of struts 2087 that are spaced from each other along the lateral direction A. The distal end 2086b of the arm 2086 is configured to be pivotally connected to the lever 2082 at a joint 2085. In accordance with the illustrated embodiment, the motion assembly 2023 includes a second pivot member, such as a such as a second pivot pin 2088, that extends at least into the outer body arm 2086 at the proximal end 2086a and the lever 2082, and defines a second pivot axis 2090 that extends in the lateral direction A. As is described in more detail below, the arm 2086 is configured to pivot about the pivot axis 2084 so as to translate the proximal end 2086a proximally as the lever 2082 is actuated from the disengaged configuration toward the tensioned configuration. As described in more detail below, the proximal end 2086a of the arm 2086 defines a cam member 2090 that is configured to bias the tension assembly 2020 between the disengaged configuration and the engaged configuration. The cam member 2090 defines an outer cam surface 2091, for instance carried by at least one or both of the forks 2087.

With continuing reference to FIGS. 51A-D, the grip assembly 2021 includes a first engagement member 2081, such as a first grip member 2090 configured as a latch 2092 that defines a first or outer end and 2092a and a second or inner end 2092b that is spaced from the first end 2092a. The first end 2092a is configured to be pivotally connected to the arm 2086 at a joint 2089. In accordance with the illustrated embodiment, the tension assembly 2020 includes a third pivot member, such as a third pivot pin 2094, that extends at least into the latch 2092, for instance at the first end 2092a, and further into the arm 2086, for instance at the distal end 2086b at a location adjacent the cam member 2090. For example, the proximal end 2092 of the latch 2092 can be disposed between the adjacent struts 2087, and the third pivot pin 2094 can extend through the struts 2087 and the first end 2092a of the latch 2092. The third pivot pin 2094 extends in the lateral direction A and defines a third pivot axis 2096. In accordance with the illustrated embodiment, the outer cam surface 2091 is eccentrically disposed with respect to the third pivot axis 2096. It should thus be appreciated that the lever 2082, the arm 2086, and the latch 2092 are pivotally coupled with respect to each other, and the first, second, and third pivot axes 2084, 2090, and 2096 can be substantially parallel to each other, such that the lever 2082, the arm 2086, and the latch 2092 can pivot in a common plane that is defined by the transverse and longitudinal directions T and L.

Referring now to FIG. 51D in particular, the first end 2092a of the latch 2092 defines a first cross-sectional dimension D1 along at least one or both of the lateral and longitudinal directions A and L. The first end 2092a can define any shape as desired. The second end 2092b of the latch 2092 defines a second cross sectional dimension D2 along at least one or both of the lateral and longitudinal directions A and L. The second cross sectional dimension D2 can be substantially parallel with respect to the first cross-sectional dimension D1, and can be greater than D1 in accordance with the illustrated embodiment. The latch 2092 further defines a first slot 2098 that extends into the second end 2092b, such that the latch 2092 includes a first engagement surface 2100 that at least partially defines a first or lower end of the slot first 2098.

The grip assembly 2021 further includes a second engagement member 2079 configured to engage the first engagement member 2081 so as to releasably selectively capture actuation strands 38a and 38b. The second engagement member 2079 can include a second grip member 2102 that can define a traveling member, such as a translating member, that is slidably supported relative to the outer body 2010, such as the support member 2060, and is configured to translate relative to the distal end 2014 of the cannula 2012 upon actuation of the motion assembly 2023. For instance, the second engagement member includes a base 2104 that supports the second grip member 2102. The base 2104 can be movably supported, for instance translatably supported, both proximally and distally along the longitudinal direction L, by the support member at a location proximal with respect to the pocket 2013 (see FIG. 45). In accordance with the illustrated embodiment, the support member 2060 defines at least one first guide member such as a pair of laterally opposed first guide members that are carried by the support member 2060. The base 2104 of the second grip member 2102 includes at least one second guide member such as a pair of laterally opposed second guide members that mate with the first guide members so as to allow the second grip member 2102 to translate along the longitudinal direction L with respect to the outer body 2010. For instance, the first guide members can be configured as longitudinally elongate slots 2106 that are recessed laterally inward in opposed laterally outer surfaces 2061 of the support member 2060. The second guide members can be configured as longitudinally elongate rails 2108 that extend from the base 2104 and into the slots 2106, such that the rails 2108 are slidably in the slots 2106 so as to translate the second grip member 2102 proximally and distally relative to the outer body 2010. The base 2104 is configured to abut a stop member 2063 of the outer body 2010, for instance at the support member 2060, in a first distal-most position so as to define the disengaged configuration of the tension assembly 2020.

The second grip member 2102 can be configured as a clip 2103 that defines a first or outer end 2103a and a second or inner end 2103b that is spaced from the first end 2103a so as to define a cavity 2110. The cavity 2110 defines a third cross-sectional dimension D3 that extends substantially parallel to the first and second cross-sectional dimensions and is sized substantially equal to or slightly greater than the second cross-sectional dimension D2. Furthermore, the cavity 2110 has a thickness in the transverse direction T that is greater than the thickness of the second end 2092b of the latch 2092, such that the second end 2092b is translatable, for instance along the transverse direction, relative to the clip 2103. The clip further defines an aperture 2112 that extends through the first end 2103a into the cavity 2110. The aperture 2112 defines a fourth cross-sectional dimension D4 that extends substantially parallel to the first, second, and third cross-sectional dimensions D1-D3, and is less than the third cross-sectional dimension D3. For instance, the fourth cross-sectional dimension D4 can be substantially equal to or slightly greater than the first cross-sectional dimension D1 and less than the second cross-sectional dimension D2. Accordingly, the first end 2092a of the latch 2092 is slidable in the aperture 2112, and the first end 2103a clip 2102 interferes with the second end 2092b of the latch 2092 so as to prevent the second end 2092b from traveling through the aperture 2112.

The clip 2103 further defines a second slot 2114 that extends laterally between the first end 2103a and the second end 2103b, and is in alignment with the cavity 2110. The clip 2103 includes a second engagement surface 2115 that at least partially defines the second slot 2114. The second engagement surface 2115 is opposite the first engagement surface 2100 of the latch 2098, for instance along the transverse direction, so as to define a variable sized gap 2116 that extends between the first and second engagement surfaces 2100 and 2115, as will now be described.

With continuing reference to FIGS. 51A-D, when the tension assembly 2020 is in the disengaged configuration, the second engagement member, for instance at the base 2104, is in a distal-most position whereby the base 2104 abuts the stop member 2063, and the lever 2082 is in an extended position. The tension assembly 2020 can include a spring member 2118 that is configured to bias the tension assembly 2020 to its disengaged configuration. For instance, the spring member 2118 can be a torsion spring disposed proximate to the joint 2085 disposed between the lever 2082 and the arm 2086. The spring member 2118 biases the lever 2082 toward its extended position, and further biases the base 2104 to its distal-most position. When the tension assembly 2020 is in the disengaged configuration, the variable sized gap 2116 is greater than the thickness of the actuation strand 38, such that the actuation strand is slidable between the first and second engagement surfaces 2100 and 2115.

Referring now to FIGS. 51E-F, the motion assembly 2023 can be actuated, for instance, by actuating the lever 2082, such as depressing the lever 2082 toward the outer body 2010 against the force of the spring member 2118, movement of the latch 2092 biases the arm 2086 proximally with respect to the outer body 2010, which causes the clip 2103 to translate proximally with respect to the outer body 2010 in the manner described above. In particular, the proximal end 2086a of the arm 2086 is driven to pivot about the third pivot axis 2096, which brings the outer cam surface 2091 of the cam member 2090 into engagement with the first end 2103a of the clip 2103. As the cam surface 2091 rides along the first end 2103a of the clip 2103, the proximal end 2086a of the arm 2086 moves transversely away from the outer body 2010, which causes the third pivot pin 2094 to likewise moves transversely away from the outer body 2010. As described above, the third pivot pin 2094 is coupled to the first end 2092a of the latch 2092. Accordingly, as the third pivot pin 2094 moves away from the outer body 2010, the third pivot pin 2094 causes the latch 2092 to move away from the outer body 2010, which draws the first and second engagement surfaces 2100 and 2115 together. It can therefore be said that at least one of the first and second engagement surfaces 2100 and 2115 is movable with respect to the other engagement surfaces so as to decrease the variable sized gap 2116. The tension assembly 2020 is thus movable to the engaged position whereby the second grip member 2102 is spaced proximally from the stop surface 2063 and the first and second engagement surfaces 2100 and 2115 are brought into engagement with the actuation strand 38, including the actuation and attachment portions, so as to capture the actuation strand 38 in the variable sized gap 2116. Thus, the actuation strand 38 is movable proximally with the grip assembly 2021.

Referring to FIGS. 51G-H, as the lever 2082 is further actuated, for instance depressed further down toward the outer body 2010 against the force of the spring member 2118, movement of the latch 2092 biases the arm 2086 further proximally with respect to the outer body 2010, which causes the clip 2103 to translate further proximally with respect to the outer body 2010 in the manner described above. In particular, the proximal end 2086a of the arm 2086 is driven to further pivot about the third pivot axis 2096, which brings the outer cam surface 2091 of the cam member 2090 further into engagement with the first end 2103a of the clip 2103. As the cam surface 2091 further rides along the first end 2103a of the clip 2103, the proximal end 2086a of the arm 2086 moves further transversely away from the outer body 2010, which causes the third pivot pin 2094 to likewise further move transversely away from the outer body 2010, which in turn causes the latch 2092 to move further away from the outer body 2010, which draws the first and second engagement surfaces 2100 and 2115 closer together and further decreases the variable sized gap 2116, which causes the actuation strand 38 to be further captured between the first and second engagement surfaces 2100 and 2115. As the grip assembly 2021 translates further proximally in response to further actuation of the latch 2092 after the first and second engagement surfaces 2100 and 2115 have captured the actuation strand, the tension assembly 2020 iterates to the tensioned configuration whereby the grip assembly 2021, applies a tensile actuation force to the actuation strand 38, including the actuation portion 131 and the attachment portion 133 that causes the respective anchor body to expand from its first configuration to its expanded configuration.

The motion assembly 2023 is configured to cause the grip assembly 2021 to translate proximally a predetermined distance between the engaged configuration and the tensioned configuration. The predetermined distance can be been calibrated so as to cause the anchor bodies 28a and 28b to expand without causing the tension assembly 2020 to apply unnecessary forces to the anchor bodies 28a and 28b that bias the anchor bodies 28a and 28b along a direction out of their respective target locations or jeopardize the structural integrity of the anchor bodies 28a and 28b. Therefore, in accordance with the illustrated embodiment, the resulting tension of the tension assembly 2020 can be defined by a distance of travel of the grip assembly 2021. It should be appreciated, however, that the grip assembly 2021 can be configured in accordance with any suitable alternative embodiment described herein, such that the predetermined tension force characteristic of the tension assembly 2020 can be a predetermined force, or a combination of a predetermined force and a predetermined distance. Once the anchor body 28 has expanded to its expanded configuration, the lever 2082 can be released, which causes the spring member 2118 to bias the tension assembly 2020 to its disengaged configuration as described above. It should be appreciated that as the tension assembly 2020 iterates to its disengaged configuration, at least one or both of the engagement surfaces 2100 and 2115 moves away from the other engagement surface so as to increase the sized gap 2116 greater than the thickness of the actuation strand 38. The actuation strand can then be removed from the tension assembly 2020.

Operation of the insertion instrument 2000 will now be described with reference to FIGS. 52A-55F. It should be appreciated that the method steps identified below need not take place in the order set forth below, unless otherwise indicated, and that all method steps identified below need not be performed to implant first and second anchor bodies 28a and 28b in the respective target location 24a and 24b.

Referring to FIGS. 52A-D, the insertion instrument 2000 is configured to create a first opening 23a that is configured to receive a respective first knot anchor body 28a. For instance, as illustrated in FIG. 52A, the insertion instrument 2000, for instance the cannula 2012, can be aligned with the first target location 22a, and the cartridge 2016 can be in the initial position, such that the blank receptacle 2066c is aligned with the cannula 2012. The actuator 2009 can be moved to its second position in the manner described above with respect to FIGS. 48A-C. Accordingly, the tab 2046 is moved from the proximal portion 2050a of the pocket 2050 to the middle portion 2050c of the pocket 2050 against the spring force that can be defined by engagement between the shaft 2036 of the opening creating member 2024 and the cannula 2026 of the pusher member 2022. Once the tab 2046 is in the middle portion 2050c, the tab 2046 can be translated distally to a position in alignment with the distal portion 2050b of the pocket, such that the spring force biases the tab 2046 into the distal portion 2050b. As the tab 2046 travels distally, the shaft 2036, and thus the opening tip 2038, also travels distally. When the tab 2046 is aligned with, and disposed in, the distal portion 2050b, the actuator 2009 is in the second position. When the actuator 2009 is in the second position and the inner body 2008 is in a distal position, for instance such that the handle 2028 abuts the handle 2059, the cannula 2026 can extend through the blank receptacle 2066c while the opening creating member 2024 is in the extended position, such that the opening tip 2038 extends distally out from the distal end 2014 of the cannula 2012.

Next, referring to FIG. 52B, the opening tip 2038 can create the first opening 23a in the first target location 24a. For instance, the proximal end 2004 of the insertion instrument 2000 can be tapped with a mallet so as to impart a distal driving force onto the opening tip 2038. Alternatively or additionally, and awling motion can be imparted onto the insertion instrument 2002 so as to impart a distal driving force onto the opening tip 2038. Alternatively still, a drilling motion can be imparted onto the shaft 2036, for instance via the insertion instrument 2000, and thus onto the opening tip 2038 so as to impart a distal driving force onto the opening tip 2038. When the opening tip 2038 is aligned with the first target location 24a, the distal driving force causes the opening tip 2038 to create the first opening 23a in the first target location 24a, such that at least the distal end 2014 of the cannula 2012 is disposed in the first opening 23a.

Referring to FIG. 52C, once the first opening 23a has been created in the first target location 24a, the actuator 2009 can be iterated from the second position to the first position while at least the distal end 2014 of the cannula 2012 remains positioned in the first opening 23a. Once the actuator 2009 has been iterated to the first position, the opening tip 2038 is recessed with respect to the distal end 2026b of the cannula 2026. For instance, as described above with respect to FIGS. 47A-C, the tab 2046 can be actuated from the distal portion 2050b to the middle portion 2050c against the spring force defined by engagement between the shaft 2036 of the opening creating member 2024 and the cannula 2026 of the pusher member 2022, and translated proximally to a position in alignment with the proximal portion 2050a of the pocket, such that the spring force biases the tab 2046 into the proximal portion 2050a. Once the actuator 2009 is in the first position, the opening creating member 2024 is in the retracted position, such that the opening tip 2038 is disposed proximal from the distal end of the cannula 2026b. When the inner body 2008 is in its first or distal position, the distal end of the cannula 2026b can extend to a position at least substantially flush with or distal from the distal end 2014 of the cannula 1012, such that the distal end of the cannula 2026b defines the distal end of the insertion instrument 2000.

Referring now to FIG. 52D, once the first opening 23a has been created in the first target location 24a, the inner body 2008 can be retracted to a second or proximal position whereby the distal end 2008b of the inner body 2008 (see FIG. 46) is disposed proximal with respect to the pocket 2013. For instance, the distal end 2008b can be disposed in the cannula 2011 that is defined by the support member 2060. It should be appreciated that the actuator 2009 can be moved from its second position prior to or after retracting the inner body 2008 to the proximal position.

Next, referring to FIGS. 53A-E, the first anchor body 28a can be implanted in the first opening 23a in its first configuration, and subsequently expended to its expanded configuration. For instance, as illustrated in FIG. 53A, and as described above with respect to FIGS. 50B-C, once the inner body 2008 is in the proximal position, the cartridge 2016 can be actuated to place the first receptacle 2066a, and the retained anchor body 28a, in operable alignment with the cannula 2026 of the pusher member 2022. Accordingly, the cartridge 2016 can be translated laterally in the pocket 2013 to a first position whereby the first receptacle 2066a, and thus the first anchor body 28a, is operably aligned with the pusher member 2022 and the cannulas 2011 and 2012. In accordance with one embodiment, the cartridge 2016 can be translated laterally until the stop clip 2068 abuts the housing 2007, for instance at the outer body 2010, at which point the anchor body 28a is operably aligned with the pusher member 2022 and the cannulas 2011 and 2012. It should be appreciated that when the cartridge 2016 is in the first position, the at least one first actuation strand 38a (it being appreciated that the first anchor 22a can include more than one first actuation strand 38a, such as two first actuation strands 38a woven through the same openings of the first anchor body 28a or through different openings as desired), extends through the slots 2098 and 2114 of the grip assembly 2021, and of the latch 2092 and the clip 2103, respectively, in accordance with the illustrated embodiment.

Referring now to FIG. 53B, once the cartridge is in the first position, the pusher member 2022 can be translated distally from the proximal position to the distal position, whereby the inner member 2008 abuts the outer member 2010. As the pusher member 2022 translates distally, the distal end 2026b of the cannula 2026 travels along the cannula 2011, enters the first receptacle 2060a, and drives the first anchor body 28a through the cannula 2012 and out the distal end 2014 into the first opening 23a. As described above, when the pusher member is in the distal position, the distal end 2026b of the cannula 2026 can extend to a position at least substantially flush with or distal from the distal end 2014 of the cannula 2012 to ensure that the first anchor body 28a is ejected out the cannula 2012. It should be appreciated that the first actuation strand 38a remains extended through the slots 2098 and 2114 of the grip assembly 2021.

Accordingly, referring now to FIG. 53C, and as described above with respect to FIGS. 51A-51I, the tension assembly 2020 can be actuated from the first or disengaged configuration whereby the at least one actuation strand 38a is slidable in the grip assembly 2021, for instance in the slots 2098 and 2114, to the second or engaged configuration whereby the grip assembly 2021 is attached to the at least one actuation strand 38a, which can include the actuation portion 131a and the attachment portion 133a, to the third or tensioned configuration, whereby the grip assembly 2021 applies the tensile actuation force to the at least one actuation strand 38a in the manner described above, thereby actuating the respective anchor body 28a from its first configuration to its expanded configuration. For instance, the lever 2082 can be depressed from a first or neutral position to a second actuated position that causes the motion assembly to translate the grip assembly 2021 proximally, thereby actuating the grip assembly to move the at least one of the first and second engagement surfaces 2100 and 2115 is movable with respect to the other engagement surfaces so as to decrease the variable sized gap 2116. In accordance with the illustrated embodiment, the first engagement surface 2100 is movable toward the second engagement surface 2115 to decrease the variable sized gap 2116 and capture the at least one actuation strand 38a. Further actuation of the motion assembly 2023 causes the grip assembly 2021 to travel a predetermined distance and apply the tensile actuation force to the at least one captured actuation strand 38a. Referring to FIG. 53D, once the first anchor body 28a has expanded, the lever 2082 can be returned to its neutral position, for instance under the force of the spring member 2118 (see FIGS. 51A-51I), as described above. As illustrated in FIG. 53E, the insertion instrument 2000 can be removed from the first target location 24a, for instance by applying a proximal force to the outer body 2010 that causes the cannula 2012 to be removed from the first opening 23a.

Once the first anchor body 28a has been implanted at the first target location 24a and expanded, the insertion instrument 2000 is configured to implant and actuate the second anchor body 28b at the second target location 24b as will now be described with respect to FIGS. 54A-55F. For instance, referring to FIGS. 54A-D generally, the insertion instrument 2000 is configured to create the second opening 23b that is configured to receive the respective second knot anchor body 28b. For instance, as illustrated in FIG. 54A, the insertion instrument 2000, such as the cannula 2012, can be aligned with the second target location 24b, and the cartridge 2016 can be disposed in its first position such that the first receptacle 2066a, which is devoid of any anchor bodies, is aligned with the cannula 2012. The actuator 2009 can be is moved to its second position in the manner described above with respect to FIGS. 48A-C. Accordingly, the tab 2046 is moved from the proximal portion 2050a of the pocket 2050 to the middle portion 2050c of the pocket 2050 against the spring force that can be defined by engagement between the shaft 2036 of the opening creating member 2024 and the cannula 2026 of the pusher member 2022. Once the tab 2046 is disposed in the middle portion 2050c, the tab 2046 can be translated distally to a position in alignment with the distal portion 2050b of the pocket, such that the spring force biases the tab 2046 into the distal portion 2050b. As the tab 2046 travels distally, the shaft 2036, and thus the opening tip 2038, also travels distally. When the tab 2046 is aligned with, and disposed in, the distal portion 2050b, the actuator 2009 is in the second position. When the actuator 2009 is in the second position and the inner body 2008 is in a distal position, for instance such that the handle 2028 abuts the handle 2059, the opening creating member 2024 is in the extended position, whereby the opening tip 2038 extends distally out from the distal end 2014 of the cannula 2012.

Next, referring to FIG. 54B, the opening tip 2038 can create the second opening 23b in the second target location 24b. For instance, the proximal end 2004 of the insertion instrument 2000 can be tapped with a mallet so as to impart a distal driving force onto the opening tip 2038. Alternatively or additionally, and awling motion can be imparted onto the insertion instrument 2002 so as to impart a distal driving force onto the opening tip 2038. Alternatively still, a drilling motion can be imparted onto the shaft 2036, for instance via the insertion instrument 2000, and thus onto the opening tip 2038 so as to impart a distal driving force onto the opening tip 2038. When the opening tip 2038 is aligned with the first target location 24a, the distal driving force causes the opening tip 2038 to create the second opening 23b in the second target location 24b, such that at least the distal end 2014 of the cannula 2012 is disposed in the second opening 23b.

Referring to FIG. 54C, once the second opening 23b has been created in the second target location 24b, the actuator 2009 can be iterated from the second position to the first position such that at least the distal end 2014 of the cannula 2012 remains positioned in the second opening 23b. Once the actuator 2009 has been iterated to the first position, the opening tip 2038 is recessed with respect to the distal end 2026b of the cannula 2026. For instance, as described above with respect to FIGS. 47A-C, the tab 2046 can be actuated from the distal portion 2050b to the middle portion 2050c against the spring force defined by engagement between the shaft 2036 of the opening creating member 2024 and the cannula 2026 of the pusher member 2022, and translated proximally to a position in alignment with the proximal portion 2050a of the pocket, such that the spring force biases the tab 2046 into the proximal portion 2050a. Once the actuator 2009 is in the first position, the opening creating member 2024 is in the retracted position, such that the opening tip 2038 is disposed proximal from the distal end of the cannula 2026b. When the inner body 2008 is in its first or distal position, the distal end of the cannula 2026b can extend to a position at least substantially flush with or distal from the distal end 2014 of the cannula 1012, such that the distal end of the cannula 2026b defines the distal end of the insertion instrument 2000.

Referring now to FIG. 54D, once the second opening 23b has been created in the second target location 24b, the inner body 2008 can be retracted to a second or proximal position whereby the distal end 2008b of the inner body 2008 (see FIG. 46) is disposed proximal with respect to the pocket 2013. For instance, the distal end 2008b can be disposed in the cannula 2011 that is defined by the support member 2060. It should be appreciated that the actuator 2009 can be moved from its second position prior to or after retracting the inner body 2008 to the proximal position.

Next, referring to FIGS. 55A-F generally, the second anchor body 28b can be implanted in the second opening 23b in its first configuration, and subsequently expended to its expanded configuration. For instance, as illustrated in FIG. 55A, and as described above with respect to FIGS. 50B-C, once the inner body 2008 is in the proximal position, the cartridge 2016 can be actuated to place the second receptacle 2066b, and the retained second anchor body 28b, in operable alignment with the cannula 2026 of the pusher member 2022. Accordingly, the cartridge 2016 can be translated laterally in the pocket 2013 to a second position whereby the second receptacle 2066b, and thus the second anchor body 28b, is operably aligned with the pusher member 2022 and the cannulas 2011 and 2012. For instance, as illustrated in FIGS. 55A-F, the stop clip 2068 can be removed from the cartridge housing 2064 in the manner described above.

Next, referring to FIG. 55B, in accordance with one embodiment, the cartridge 2016 can be translated laterally until the cartridge 2016 is in the second position, whereby the second receptacle 2066b, and thus the second anchor body 28b is operably aligned with the pusher member 2022 and the cannulas 2011 and 2012. It should be appreciated that when the cartridge 2016 is in the second position, the at least one second actuation strand 38b (it being appreciated that the second anchor 22b can include more than one second actuation strand 38b, such as two second actuation strands 38b woven through the same openings of the second anchor body 28b or through different openings as desired), extends through the slots 2098 and 2114 of the grip assembly 2021, and of the latch 2092 and the clip 2103, respectively, in accordance with the illustrated embodiment. It should be appreciated that the at least one first actuation strand 38a, including the actuation portion 131a and the attachment portion 131b can be manually freed from the cartridge 2016 prior to moving the cartridge 2016 to its second position.

Referring now to FIG. 55C, once the cartridge 2016 is in the second position, the pusher member 2022 can be translated distally from the proximal position to the distal position, whereby the inner member 2008 abuts the outer member 2010. As the pusher member 2022 translates distally, the distal end 2026b of the cannula 2026 travels along the cannula 2011, enters the second receptacle 2060b, and drives the second anchor body 28b through the cannula 2012 and out the distal end 2014 into the second opening 23b. As described above, when the pusher member 2022 is in the distal position, the distal end 2026b of the cannula 2026 can extend to a position at least substantially flush with or distal from the distal end 2014 of the cannula 2012 to ensure that the second anchor body 28b is ejected out the cannula 2012. It should be appreciated that the second actuation strand 38b remains extended through the slots 2098 and 2114 of the grip assembly 2021.

Accordingly, referring now to FIG. 55D, and as described above with respect to FIGS. 51A-51I, the tension assembly 2020 can be actuated from the first or disengaged configuration whereby the at least one second actuation strand 38b is slidable in the grip assembly 2021, for instance in the slots 2098 and 2114, to the second or engaged configuration whereby the grip assembly 2021 is attached to the at least one second actuation strand 38b, which can include the actuation portion 131b and the attachment portion 133b, to the third or tensioned configuration, whereby the grip assembly 2021 applies the tensile actuation force to the at least one second actuation strand 38b in the manner described above, thereby actuating the second anchor body 28b from its first configuration to its expanded configuration. For instance, the lever 2082 can be depressed from a first or neutral position to a second actuated position that causes the motion assembly to translate the grip assembly 2021 proximally, thereby actuating the grip assembly to move the at least one of the first and second engagement surfaces 2100 and 2115 is movable with respect to the other engagement surfaces so as to decrease the variable sized gap 2116. In accordance with the illustrated embodiment, the first engagement surface 2100 is movable toward the second engagement surface 2115 to decrease the variable sized gap 2116 and capture the at least one second actuation strand 38b. Further actuation of the motion assembly 2023 causes the grip assembly 2021 to travel a predetermined distance and apply the tensile actuation force to the at least one captured actuation strand 38b. Referring to FIG. 55E, once the second anchor body 28b has expanded, the lever 2082 can be returned to its neutral position, for instance under the force of the spring member 2118 (see FIGS. 51A-51I), as described above. As illustrated in FIG. 53E, the insertion instrument 2000 can be removed from the second target location 24b, for instance by applying a proximal force to the outer body 2010 that causes the cannula 2012 to be removed from the second opening 23b.

Once the first and second anchor bodies 28a and 28b have been inserted and expanded at the respective target locations 24a and 24b, the first and second actuation portions 131a and 131b and the first and second attachment portions 133a and 133b can be removed from the canister 2072. The first and second attachment portions 133a and 133b can be attached to each other in any manner desired. An approximation force can be applied to the actuation strands 38a and 38b to reduce the gap 24c prior to locking the attachment portions together (or to other members as shown in FIG. 33) to maintain gap 24c in approximation. For instance, FIGS. 52-55 show a gap 24c in a bone (such as a fracture) being approximated; however, a similar method could be used whereby the suture strands are first passed trans-tendonously through soft tissue prior to being driven into bone in order to approximate a gap between tissue and bone. It should be appreciated in accordance with an alternative embodiment that the insertion instrument 2000 can be configured to implant the first and second anchor bodies 28a and 28b in the respective openings 23a and 23b, and subsequently actuate the anchor bodies 28a and 28b to their expanded configurations either individually or simultaneously, for instance by attaching both actuation strands 38a and 38b to the grip assembly 2021 simultaneously, and actuating the motion assembly 2023.

Referring now to FIGS. 56A-B, it should be appreciated that the anchors 22 can be constructed in accordance with any suitable embodiment as desired. For instance, the anchor 22 can include an anchor body 28 that is constructed as described below with respect to FIGS. 57A-60D. For instance, the anchor body 28 defines an expandable portion 36, and a connector member 63 such as at least one eyelet 90 that extends from the expandable portion 36, and an actuation member 37 (see FIG. 1A) such as an actuation strand 38 that is configured to actuate the expandable portion 36, and thus the anchor body 28, from a first configuration illustrated in FIG. 56A, in which the anchor body 28 can initially be inserted in the target location (which, for instance, can be bone, soft tissue, or an auxiliary structure as described above), to an expanded configuration as illustrated in FIG. 56B, whereby the anchor body 28 can be secured to the target location as described above. In accordance with the illustrated embodiment, the actuation strand 38 be configured as an auxiliary strand 33 that is separate from the anchor body 28, and attached to the anchor body 28. The actuation strand 38 can define an actuation portion 131 and an attachment portion 133. It should be appreciated from the description below that the actuation strand 38 can be further attached to a second anchor body, so as to define an integral actuation strand that attaches first and second anchors together in the manner described above. The actuation strand 38, for instance the actuation portion 131 and the attachment portion 133, are configured to receive a tensile actuation force F that causes the anchor body 28 to actuate from the first configuration to the expanded configuration.

With continuing reference to FIGS. 56A-B, the anchor body 28, and also the expandable portion 36, is elongate along a central axis 29, and defines a first or proximal end 30 and a second or distal end 32 that is spaced from the proximal end 30 substantially along the central axis 29. The central axis 29 can define any shape, or portions having any shape as desired. For instance, the central axis 29, or portions of the central axis 29, can be linear, substantially linear, nonlinear, including regularly, irregularly, otherwise curved, or can be otherwise shaped as desired. In accordance with the illustrated embodiment, the central axis 29 is substantially linear. Accordingly, the anchor body 28 can define a direction of elongation 34 that extends substantially linearly between the first and second ends 30 and 32. It should be appreciated, for instance when the central axis 29 is substantially linear, that the direction of elongation 34 can be substantially coincident with the central axis 29. It should be further appreciated, for instance when the central axis 29 is nonlinear that the direction of elongation 34 at least partially or substantially entirely spaced from the central axis 29. The expandable portion 36 that has a first or proximal end 39a and a second or distal end 39b. The proximal end 39a of the expandable portion 36 can be coincident with or different than (for instance recessed with respect to) the proximal end 30 of the anchor body 28, and the distal end 39b of the expandable portion 36 can be coincident or different than (for instance recessed with respect to) the distal end 32 of the anchor body 28

The expandable portion 36 of the anchor body 28 extends along the direction of elongation 34 such that the expandable portion 36 defines an initial distance D1 along the direction of elongation 34 when in the first configuration. The initial distance D1 can be any length as desired, such within a range having a lower end that can be defined by approximately 5 mm, alternatively approximately 10 mm, alternatively still approximately 20 mm, and alternatively still approximately 24.5 mm, and having an upper end that can be defined by approximately 50 mm, alternatively approximately 40 mm, alternatively still approximately 30 mm, and alternatively still approximately 25.5 mm.

Furthermore, when in the first configuration, the expandable portion 36 defines an initial maximum thickness T1 that extends in a second direction 35 that is substantially perpendicular, with respect to the direction of elongation 34. The initial maximum thickness T1 can be sized as desired. As illustrated in FIG. 1B, when the expandable portion 36 in the expanded configuration, the expandable portion 36 is collapsed, for instance compressed or tangled, along the direction of elongation 34 to a second distance D2 as measured from the proximal end 39a to the distal end 39b along the direction of elongation 34. The second distance D2 can be less than the initial distance D1. As the expandable portion 36 collapses along the direction of elongation, for instance as it is actuated from the first configuration to the expanded configuration, the expandable portion 36 expands along the second direction 35 to a second maximum thickness T2 that is greater than the initial maximum thickness T1. The second maximum thickness T2 extends along the second direction 35 which is substantially perpendicular to the direction of elongation 34.

The maximum thicknesses T1 and T2 in the second direction 35 can be defined such the anchor body 28 does not define a thickness in the second direction 35 that is greater than the maximum thicknesses T1 and T2, respectively. It should be appreciated that the proximal and distal ends 39a and 39b can change locations on the expandable portion 36 as the expandable portion 36 actuates to the expanded configuration, for instance due to configuration of the expandable portion 36 when in the expanded configuration. However, when the expandable portion 36 is in the expanded configuration, the proximal and distal ends 39a and 39b continue to define the proximal-most and distal-most ends of the expandable portion 36, such that the distance D2 along the direction of elongation 34 is defined linearly between the proximal and distal ends 39a and 39b of the expandable portion 36 when the expandable portion 36 is in the expanded configuration.

The expandable portion 36 can define a plurality of substantially concentric loops 31 that can be integral with each other and at least partially defined by a plurality of knots 49 that define first and second knots 49a and 49b alternatingly arranged along the length of the expandable portion 36 along the central axis 29, such that adjacent first and second knots 49a and 49b defines at least a pair 51 of knots 49 that in turn at least partially defines one of the loops 31. Each knot 49a and 49b of at least one of the pairs 51, such as a plurality of the pairs 51, up to all of the pairs 51, is offset with respect to the other knot 49a and 49b. For instance, the knots 49a and 49b of each pair 51 can be disposed on opposite sides of the central axis 29. In accordance with one embodiment, the knots 49a and 49b of each pair 51 are disposed substantially opposite each other, such that the central axis 29 can be disposed substantially linearly between the knots 49a and 49b of each pair 51. For instance, it should be appreciated that the knots 49a and 49b of each pair can be angularly offset as desired, for instance between and including approximately 90 degrees and approximately 270 degrees offset with respect to each other, including between and including approximately 135 degrees 225 degrees offset with respect to each other. In accordance with one embodiment, the knots 49a and 49b of each pair 51 can be disposed approximately 180 degrees offset with respect to each other.

The loops 31 can define respective openings 40 (such as at least two openings 40), which can be configured as central openings, such that the central axis 29 extends along the openings 40. Accordingly, the loops 31, and thus the respective openings 40, can be aligned with each other along the direction of elongation 34. Therefore, when the anchor body 28 is actuated to its expanded configuration, the loops 31 travel toward each other and can stack against each other. The loops 31 can define a distal loop 31a, a proximal loop 31b, and at least one intermediate loop 31c disposed between the proximal and distal loops 31a-b. The actuation strand 38 is configured to extend through at least one of the openings 40, including a plurality of the openings 40 (for instance at least two up to all of the openings 40). Accordingly, when an actuation force F is applied to the actuation strand 38 substantially along the direction of elongation 34, the actuation strand 38 can bias the expandable portion 36, and thus the anchor body 28, to collapse along the direction of elongation 34 and expand along the second direction 35, thereby expanding the anchor from the first configuration to the expanded configuration. The force F can be a tensile force, including a pure tensile force or a force that can be offset from a pure tensile force but has a component that is a pure tensile force. It should thus be appreciated that the force F can be applied to the respective actuation strand 38 substantially along the direction of elongation 34, such that the force F can have a directional component that is parallel to or coincident with the direction of elongation 34, or can be entirely parallel to or coincident with the direction of elongation 34.

With continuing reference to FIGS. 56A-B, the anchor body 22 can be in the form of a substrate 42, which in one embodiment can be a strand, such as a suture strand or any alternatively constructed strand, that defines an anchor body strand 44. The anchor body strand 44, along with the other components of the anchor assembly 20, can be resorbable as desired. The anchor body strand 44 can have any suitable USP (United States Pharmacopia) size (or diameter) as desired, for instance between and including USP 7-0 and USP 5, such as between and including USP 2-0 and USP 5, for instance USP 2. The anchor body strand 44 can be woven and porous so as to defining openings, or can be nonwoven and devoid of openings as desired. Whether the anchor body strand 44 is woven or nonwoven, the anchor body strand 44 can be braided as desired so as to define the openings 40, as is described in more detail below with respect to FIGS. 57A-60D. The actuation strand 38 can have any suitable USP (United States Pharmacopia) size (or diameter) as desired, for instance between and including USP 7-0 and USP 5, such as between and including USP 2-0 and USP 5.

A method for constructing the anchor 22 illustrated in FIGS. 56A-B will now be described. For instance, referring to FIG. 57A, the anchor body strand 44 defines at least one eyelet 90 and a closure location 113 that can define base of the eyelet 90. The eyelet 90 can be constructed in accordance with any number of embodiments as desired. For instance, as illustrated in FIGS. 57B-C, the eyelet 90 can be constructed by folding the anchor body strand 44 so as to define a first and second segments 92a and 92b that are shaped so as to define a loop 91. The loop 91 can be wrapped around the first and second segments 92a and 92b so as to define an opening, and the loop 91 can be fed through the opening so as to define a knot at the closure location 113.

Alternatively, referring to FIG. 57D, the second segment 92b can be welded, for instance heated or via an adhesive, to the first segment 92a so as to close the loop 91 and define the closure location 113 of the eyelet 90. Alternatively still, referring to FIG. 57E, the terminal second segment 92b can be stitched to the first segment 92a at the closure location 113 so as to close the loop 90 and define the base of the eyelet 90. For instance, a strand, such as at least one suture strand 75, can be stitched through the first and second segments 92a and 92b so as to join the first and second segments 92a and 92b to each other.

Figure 57G:
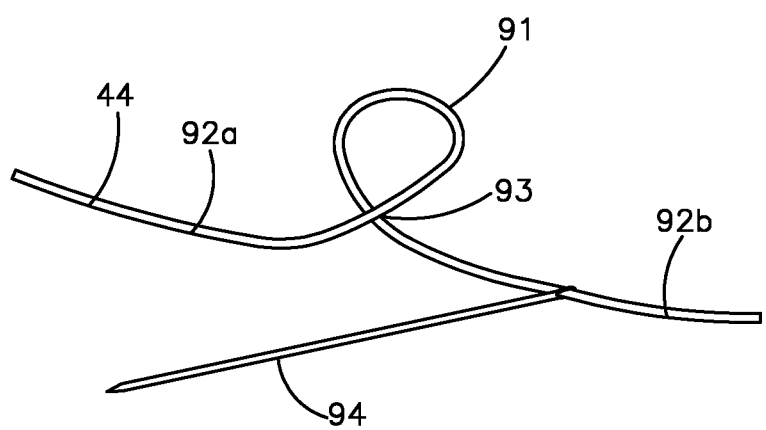
Figure 57H:
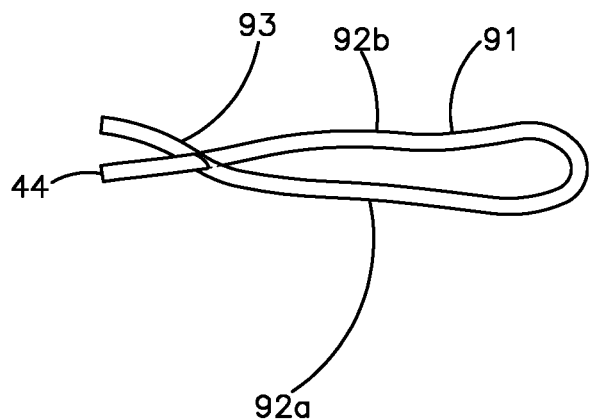
Figure 57:
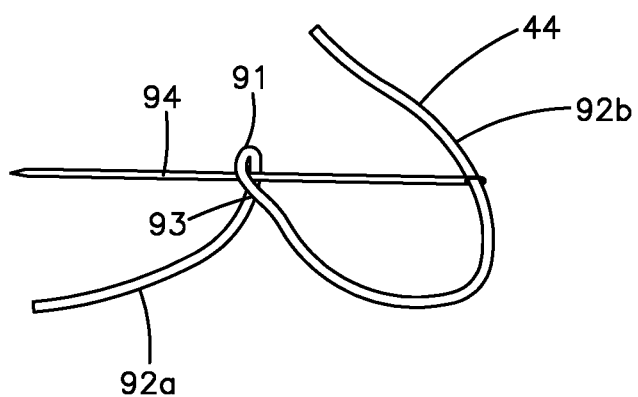

Alternatively, referring to FIGS. 57F-L, the anchor body strand 44 can be woven to itself so as to define the eyelet 90. In accordance with one embodiment, referring to FIGS. 57F-G generally, the anchor body strand 44 can be folded and stitched through itself so as to define a loop 91, and first and second segments 92a and 92b, respectively, that extend from opposed sides of the loop 91. The tip of a needle 94 can be inserted through the first segment 92a so as to define a first channel that extends through the first segment 92a. The second segment 92b can be fed through the eyelet of the needle 94 at the trailing end of the needle 94. The needle 94 can then be translated forward through the first segment 92a such that the second segment 92b is drawn through the channel in the first segment 92a as created by the needle 94, thereby closing the loop 91 as illustrated in FIG. 57G and defining a first stitch 93. The loop 91 extends distally from the first stitch 93. As illustrated in FIG. 57H, the second segment 92b can be translated in opposite directions through the first segment 92a so as to adjust the size of the loop 91 as desired. In accordance with one embodiment, the loop 91 can be adjusted to a length of approximately 5 mm when pulled taught.

Figure 57J:
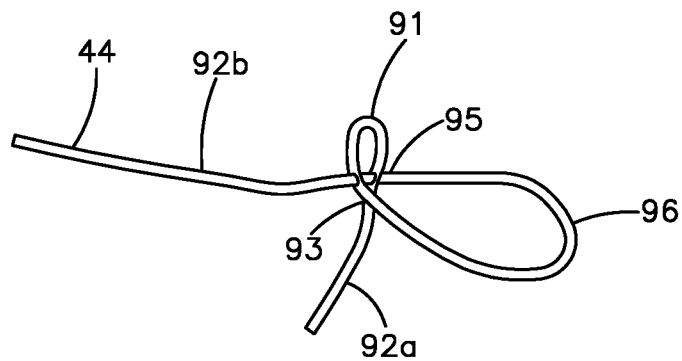

Next, referring to FIGS. 57I-J, the anchor body strand 44 can be stitched through itself a second time. For instance, the tip of the needle 94 can be driven through both segments 92a and 92b of the anchor body strand 44 at a location distal of the first stitch 93, thereby creating second and third channels that extend through the first and second segments 92a and 92b, respectively, at a location distal of the first stitch 93. As illustrated in FIG. 57J, the second segment 92b can be fed through the eyelet of the needle 94, and the needle 94 can then be translated forward through the second and third channels such that the second segment 92b is drawn through itself at one side of the loop 91, and further drawn through the first segment 92a at the opposite side of the loop 91 so as to define a second stitch 95 at a location distal of the first stitch 93. The first and second stitches 93 and 95 can define a base of the loop 91. The second segment 92b further defines a loop 96 that extends from the first and second stitches 93 and 95. It is appreciated that the size of the loop 91 is therefore decreased, for instance by approximately 1 mm, after the second stitch 95 is created.

Figure 57K:
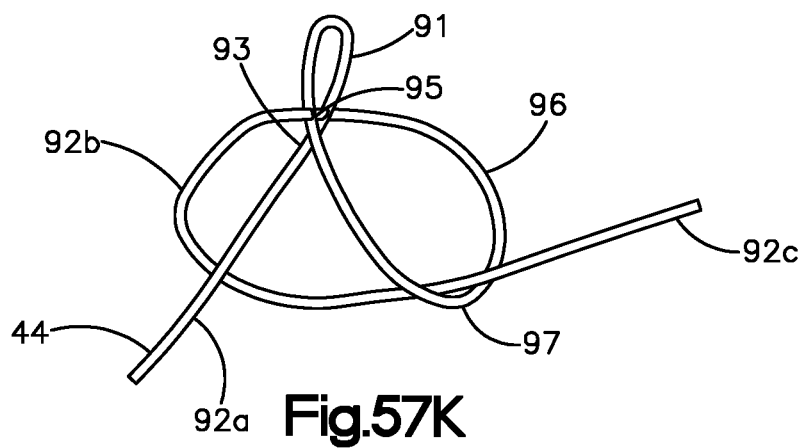
Figure 57L:
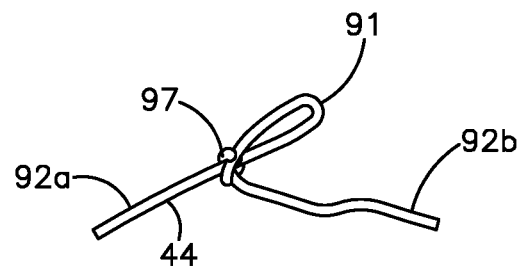

Referring to FIGS. 57K-L, the anchor body strand 44 can be tied in a knot 97 at the first and second stitches 93 and 95 to fix the size of the loop 91, which defines the eyelet 90. For instance, the second segment 92b can define a free end 92c that extends from the third channel of the second segment 92b through the loop 96, and is subsequently tightened so as to define the knot 97. Thus, the knot 97 is disposed at the base of the loop. It should be appreciated that the second segment 92b can be stitched through the loop 91 as many times as desired prior to creating the knot 97 so as to fix the loop 91. Thus, it should be appreciated that the eyelet 90 can be created by stitching the anchor body strand 44 through itself so as to create at least one stitch, for instance two stitches, thereby define a loop, and subsequently tying a knot 97 about the base of the loop so as to fix the eyelet 90.

One method of constructing the expandable portion 36 includes braiding the actuation strand 44 as will now be described with reference to FIGS. 58A-F. For instance as illustrated in FIG. 58A-B, the anchor body strand 44 is placed against a mandrel 79, such that the first and second segments 92a and 92b extend out from the base of the eyelet 90. The first and second segments 92a and 92b can be tied in any suitable knot 49 which can define a first knot 49a. At least the first knot 49a up to all of the knots 49 can be tied in any manner desired, such as a square knot as illustrated, an overhand knot (see FIG. 59), or any suitably constructed alternative knot. The first knot 49a is positioned such that the mandrel 79 is disposed or captured between the base of the eyelet 90 and the first knot 49. The base of the eyelet 90 and the first knot 49a can be joined by the first and second segments 92a and 92b, respectively.

Referring now to FIGS. 58C-D, the first and second segments 92a and 92b are tied to each other so as to define a second knot 49b that can be disposed substantially opposite the first knot 49a so as to define a first pair 51a of knots 49a and 49b that are joined by the first and second segments 92 and 92b about the mandrel 79 so as to define a first or distal loop 31a of the loops 31. The first loop 31a defines a corresponding first central opening 40 that is occupied by the mandrel 79. The mandrel 79, and thus the shape of the openings 40 of the loops 31, can be substantially cylindrical or any suitable alternative shape as desired. While the knots 49a and 49b are substantially disposed 180 degrees opposite each other as illustrated, it should be appreciated that the knots 49a and 49b can alternatively be offset as desired about the perimeter of the mandrel 79. Furthermore, while the loop 31 include a pair 51 of knots 49, it should be appreciated that each loop 31 can include as many knots as desired, such as at least one or a plurality, which includes a pair, of knots 49. Thus, it can be said that the loop 31 includes a group, such as a pair 51, of knots 49, which can include first and second knots 49a and 9b, that are joined by the first and second segments 92a and 92b of the anchor body strand 44.

As illustrated in FIG. 58E-F, the first and second segments 92a and 92b can be tied together to define a first knot 49a of a second pair 51b of knots, for instance at a location substantially opposite the second knot 49b of the adjacent first pair 51a, and the first and second segments 92a and 92b can be further tied together to define a second knot 49b of the second pair, for instance at a location substantially opposite the first knot 49a of the second pair 51b. Thus, the first and second knots 49a and 49b of the second pair 51b are joined by the first and second segments so as to define a second loop of the plurality of loops 31. In accordance with the illustrated embodiment, the second loop is disposed adjacent the first loop 31a along the central axis 23. The second loop can be spaced apart from the first loop 31a, or can substantially abut the first loop 31a as desired. The first and second strands 92a and 92b can be subsequently tied so as to define any suitable number of pairs 51 of first and second knots 49a and 49b as desired, so as to thereby define as many corresponding loops 31 as desired that are spaced from each other along a direction substantially parallel to the central axis 23. In accordance with one embodiment, the anchor body 28, for instance the expandable portion 36 of the anchor body 28, can define a five pairs 51 of first and second knots 49a and 49b. It should be appreciated, however, that the anchor body strand 44 can be woven as many times as desired, such that the anchor body 28, and in particular the expandable portion 36, defines at least two pairs 51 of first and second knots 49a and 49b that at least partially define at least a pair of loops 31 that, in turn, define a corresponding pair of openings 40 aligned along the central axis 23, such that the central axis 23 can extend through the openings 40. As illustrated in FIG. 58G, excess lengths of the first and second segments 92a and 92b can be trimmed to a location proximate to the final loop, and can be singed or melted to each other or, alternatively or additionally, melted to the adjacent loop 31 so as to define the proximal end 30 of the anchor body 28.

Next, referring to FIG. 58H, the actuation strand 38, can be fed through the eyelet 90, such that the actuation strand 38 slidably extends through the eyelet 90 so as to define a first segment 59a and a second segment 59b that extend out from substantially opposite sides of the eyelet 90. The first and second segments 59a and 59b can define opposed respective free ends of the actuation strand 38 that can be fed through an eyelet of the mandrel 79, which can be configured as a needle. The mandrel 79 can then be drawn proximally through the openings 40 along the central axis 23 so as to draw the first and second segments 59a and 59b proximally through the openings 40 substantially along the central axis 23. The first and second segments 59a and 59b can thus define the actuation portion 131 and the attachment portion 133 of the anchor 22, respectively.

It should be appreciated that the proximal-most loop 31 can be engaged so as to provide a brace to draw the actuation strand 38 through the expandable portion 36, which causes the loops 31 to compress against each other. As a result, the actuation strand 38 can drive the eyelet 90 proximally so that the eyelet extends proximally from the first loop 31a substantially along the central axis 23. Depending for instance on the length of the eyelet 90 and the number of loops 31 of the expandable portion, the eyelet 90 can extend through at least one of the openings 40, such as a plurality of the openings 40, up to all of the openings 40 so as to extend proximally out the proximal end 39a of the expandable portion 36. Thus, the anchor 22 can be in an expanded configuration after the actuation strand 38 has been drawn through the expandable portion. Accordingly, referring again to FIG. 56A, the expandable portion 36 can be extended along the actuation strand 38 to its first configuration, whereby the eyelet 90 can be embedded in the expandable portion 36.

It should be appreciated that the base of the eyelet 90 can abut the first loop 31a. Accordingly, when the actuation force F is applied to the actuation strand 38, mechanical interference between the base of the eyelet 90 and the first or distal loop 31a prevents the base of the eyelet 90 from traveling proximally through the expandable portion 36. Accordingly, as the anchor body 28 actuates to the expanded configuration, the loops 31 stack and compress against each other along a direction substantially parallel to the central axis 23, which causes the loops 31 to expand radially, thereby causing the expandable portion 36, and thus the anchor body 28, to expand along the second direction 35 to a second maximum thickness T2. Furthermore, the eyelet 90 can extend through the expandable portion 36, which can cause the openings 40 to expand radially as the eyelet 90 adds structural rigidity to the expandable potion 36 along the direction of elongation 34.

It should be appreciated that as the loops 31 compress against each other during actuation of the expandable portion 36 from the first configuration to the expanded configuration, the length of the expandable portion 36 decreases, and can decrease to a length less than that of the eyelet 90, such that the eyelet 90 can extend out the proximal end 39a of the expandable portion 36 when the anchor body 28 has been actuated to the expanded configuration. The actuation strand 38 can thus be freely slidable through the eyelet 90 when the anchor body 28 is expanded. It can thus be said that the eyelet 90 extends proximally at least into the expandable portion 36 along a first length of the expandable portion 36 (for instance a first number of loops 31) when the expandable portion 36 is in the first configuration, and extends proximally at least into, for instance through, the expandable portion 36 along a second length of the expandable portion (for instance a second number of loops 31) when the expandable portion 36 is in the expanded configuration, wherein the second length is greater than the first length (for instance, the second number of loops 31 is greater than the first number of loops 31). It should be appreciated that the first length can equal zero, for instance if the eyelet extends distally from the distal end 39b of the expandable portion 36 when the expandable portion is in the first configuration.

As described above, the anchor body 28 can include at least one eyelet 90. For instance, referring to FIGS. 60A-D, the anchor body 28 can define a pair of eyelets 90a and 90b that extends from the expandable portion 36. For instance, as illustrated in FIG. 60C, the anchor body strand 44 can be folded twice so as to define first and second loops 91a and 91b that are disposed in a side-by-side relationship so as to define a substantial "W shape." Thus, the actuation strand 44 can define first and second segments 92a and 92b that extend out from the first and second loops 91a and 91b, respectively, and a joining segment 92d that extends between the first and second loops. The first and second segments can be attached to the joining segment 92d so as to define a common base for the first and second loops 91a and 91b that can be closed in any manner described above so as to define respective first and second eyelets 90a and 90b. For instance, the first and second segments 92a and 92b and the joining segment 92d can be tied to each other so as to define the common base. The first and second segments 92a and 92b can extend out from the common base so as to define the expandable portion 36 as described above. It should be appreciated that the eyelets 90 of the type described herein can be integral with the anchor body strand 44 as described herein, or can be separate from the anchor body strand 44 and attached to the anchor body strand 44 in any suitable manner as desired.

The embodiments described in connection with the illustrated embodiments have been presented by way of illustration, and the present invention is therefore not intended to be limited to the disclosed embodiments. Furthermore, the various structures, features, and methodologies associated with any embodiment described herein can apply to any other embodiment as described herein, unless otherwise indicated. For instance, unless otherwise indicated, any insertion instrument described herein can include a tensioning assembly as described herein in accordance with any suitable alternative embodiment. As one example, any of the insertion instruments described herein can include a fuse element of any type described above as suitable, a predetermined distance of travel of any type described above as suitable, or combinations thereof as suitable. Accordingly, those skilled in the art will realize that the invention is intended to encompass all modifications and alternative arrangements included within the spirit and scope of the invention, for instance as set forth by the appended claims.

We claim:

1. A method of deploying at least one anchor at a target location, the method comprising:
   at least partially inserting a distal end of an access member into the target location, wherein the access member is elongate along a longitudinal direction;
   advancing an anchor housing that releasably carries the at least one anchor through a cannulation of the access member; and
   applying a predetermined tension force characteristic to an actuation member that extends substantially along a direction of elongation from an anchor body of the at least one anchor, thereby reducing a dimension of the anchor body along the direction of elongation and increasing a dimension of the anchor body along a second direction that is angularly offset relative to the direction of elongation,
   wherein the applying step comprises translating a translating member of a tension assembly from a neutral position to an extended position with respect to the distal end of the access member while the tension assembly is connected to the anchor housing.

2. The method of claim 1, wherein the advancing step comprises advancing a cannulation of the anchor housing through the cannulation of the access member, and the at least one anchor is releasably carried within the cannulation of the anchor housing.

3. The method of claim 2, wherein the advancing step concludes by abutting a contact surface defined by the anchor housing against a contact surface at a proximal end of the access member.

4. The method of claim 1, further comprising advancing a pusher member through a cannulation of the anchor housing, thereby ejecting the at least one anchor from the anchor housing and out the distal end of the access member at the target location.

5. The method of claim 4, wherein the step of advancing the pusher member concludes by abutting a contact surface defined by pusher member against another contact surface at a proximal end of the anchor housing.

6. The method of claim 4, further comprising:
   abutting a portion of the translating member against a proximal end of the pusher member while the translating member is in the neutral position; and
   applying the predetermined tension force characteristic to the actuation member as the translating member translates from the neutral position to the extended position, wherein the tension force characteristic is a tensile force.

7. The method of claim 6, wherein the translating step comprises rotating a rotatable member of the tension assembly, thereby causing the translating member to translate from the neutral position to the extended position.

8. The method of claim 7, wherein the rotating step comprises rotating the rotatable member about a longitudinal axis oriented along the longitudinal direction.

9. The method of claim 8, wherein the rotatable member includes a body that defines a bore extending therethrough along the longitudinal direction, the bore defines an inner surface, the bore sized to receive the translating member and at least a portion of the pusher member therein.

10. The method of claim 9, wherein:
    the translating member defines at least one projection extending along a third direction that is substantially perpendicular to the direction of elongation; and
    the bore of the body of the rotatable member further defines at least one helical groove that extends into the inner surface, the at least one helical groove extending between opposed proximal and distal groove ends, and the at least one projection is captive in the at least one helical groove such that, during the rotating step, the translating member translates within the rotatable member.

11. The method of claim 10, wherein the at least one helical groove has a variable groove pitch that becomes shallower between the proximal and distal groove ends.

12. The method of claim 10, wherein the pusher member defines at least one projection that resides in an annular groove that extends into the inner surface of the bore of the body of the rotatable member.

13. The method of claim 4, wherein the pusher member defines a cannulation extending therethrough along the longitudinal direction and sized to receive at least a portion of the actuation member therein, and a diameter of the cannulation of the pusher member is less than the dimension of the anchor body along the second direction prior to the applying step, such that, during the step of advancing a pusher member, a distal end of the pusher member causes the at least one anchor to translate along the longitudinal direction through the cannulation of the anchor housing.

14. The method of claim 1, further comprising, before the advancing step, inserting a shaft of an opening creating member through the cannulation of the access member such that a tip at a distal end of the shaft advances beyond the distal end of the access member and engages tissue at the target location, thereby creating an opening in the tissue at the target location.

15. The method of claim 14, wherein the tip is conically shaped.

16. The method of claim 14, wherein the shaft defines at least one boring flute that extends helically from the tip toward a proximal end of the opening creating member.

17. A method of deploying an anchor at a target location, the method comprising:
　　at least partially inserting a distal end of an access member into the target location, wherein the access member is elongate along a longitudinal direction;
　　advancing an anchor housing that releasably carries the anchor through a cannulation of the access member, the anchor comprising an anchor body and an actuation member, the actuation member comprising suture strands extending from the anchor body substantially along a direction of elongation; and
　　applying a predetermined tension force characteristic to the suture strands, thereby reducing a dimension of the anchor body along the direction of elongation and increasing a dimension of the anchor body along a second direction that is angularly offset relative to the direction of elongation,
　　　wherein the applying step comprises translating a translating member of a tension assembly from a neutral position to an extended position with respect to the distal end of the access member.

18. The method of claim 17, further comprising advancing a pusher member through a cannulation of the anchor housing, thereby ejecting the anchor from the anchor housing and out the distal end of the access member at the target location.

19. The method of claim 17, wherein the translating step comprises rotating a rotatable member of the tension assembly about a longitudinal axis oriented along the longitudinal direction, thereby causing the translating member to translate from the neutral position to the extended position.

20. The method of claim 17, further comprising, before the advancing step, inserting a shaft of an opening creating member through the cannulation of the access member such that a tip at a distal end of the shaft advances beyond the distal end of the access member and engages tissue at the target location, thereby creating an opening in the tissue at the target location.

* * * * *